(12) United States Patent
Dyckman et al.

(10) Patent No.: US 11,739,098 B2
(45) Date of Patent: Aug. 29, 2023

(54) SUBSTITUTED INDOLE COMPOUNDS

(71) Applicant: BRISTOL-MYERS SQUIBB COMPANY, Princeton, NJ (US)

(72) Inventors: Alaric J. Dyckman, Lawrenceville, NJ (US); Dharmpal S. Dodd, San Diego, CA (US); Christopher P. Mussari, Princeton, NJ (US); Trevor C. Sherwood, West Windsor, NJ (US); John L. Gilmore, Yardley, PA (US); Tasir Shamsul Haque, Yardley, PA (US); Brian K. Whiteley, Lebanon, NJ (US); David R. Tortolani, Skillman, NJ (US); Shoshana L. Posy, Highland Park, NJ (US); John E. Macor, Washington Crossing, PA (US); Louis J. Lombardo, Belle Mead, NJ (US); Ramesh Kumar Sistla, Bangalore (IN); Anupama Kandhi Ramachandra Reddy, Bangalore (IN); Subramanya Hegde, Bangalore (IN); Laxman Pasunoori, Warangal (IN); Sreekantha Ratna Kumar, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 17/699,944

(22) Filed: Mar. 21, 2022

(65) Prior Publication Data

US 2023/0098244 A1 Mar. 30, 2023

Related U.S. Application Data

(63) Continuation of application No. 16/763,670, filed as application No. PCT/US2018/060590 on Nov. 13, 2018, now abandoned.

(60) Provisional application No. 62/585,733, filed on Nov. 14, 2017.

(51) Int. Cl.
| | |
|---|---|
| *C07D 401/14* | (2006.01) |
| *C07D 405/14* | (2006.01) |
| *C07D 413/14* | (2006.01) |
| *C07D 417/14* | (2006.01) |
| *C07D 471/04* | (2006.01) |
| *C07D 487/04* | (2006.01) |
| *C07D 495/04* | (2006.01) |
| *C07D 498/04* | (2006.01) |
| *C07D 513/04* | (2006.01) |

(52) U.S. Cl.
CPC ......... *C07D 498/04* (2013.01); *C07D 401/14* (2013.01); *C07D 405/14* (2013.01); *C07D 413/14* (2013.01); *C07D 417/14* (2013.01); *C07D 471/04* (2013.01); *C07D 487/04* (2013.01); *C07D 495/04* (2013.01); *C07D 513/04* (2013.01)

(58) Field of Classification Search
CPC .. C07D 401/14; C07D 405/14; C07D 413/14; C07D 417/14; C07D 471/04; C07D 487/04; C07D 495/04; C07D 498/04; C07D 513/04
See application file for complete search history.

(56) References Cited

U.S. PATENT DOCUMENTS

| | | | |
|---|---|---|---|
| 6,187,777 B1 | 2/2001 | Norman et al. |
| 6,306,874 B1 | 10/2001 | Fraley et al. |
| 6,867,200 B1 | 3/2005 | Allen et al. |
| 7,410,975 B2 | 8/2008 | Lipford et al. |
| 8,138,187 B2 | 3/2012 | Zemolka et al. |
| 8,354,400 B2 | 1/2013 | Zheng et al. |
| 9,126,996 B2 | 9/2015 | Lipford et al. |
| 9,126,999 B2 | 9/2015 | Bolvin et al. |
| 9,241,991 B2 | 1/2016 | Ji et al. |

(Continued)

FOREIGN PATENT DOCUMENTS

| | | |
|---|---|---|
| EP | 2738172 A1 | 6/2014 |
| WO | 2003057696 A1 | 7/2003 |

(Continued)

OTHER PUBLICATIONS

Bobko, M. et al., "Synthesis of 2,5-disubstituted-3-cyanoindoles", Tetrahedron Letters, 53 (2012) 200-202.

(Continued)

*Primary Examiner* — Laura L Stockton
(74) *Attorney, Agent, or Firm* — Gary Greenblatt

(57) ABSTRACT

Disclosed are compounds of Formula (I)

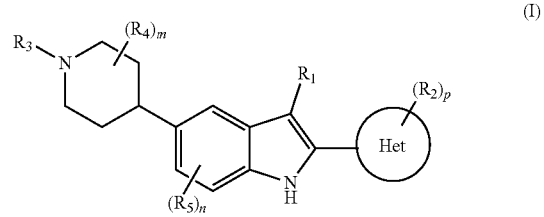

or salts thereof, wherein Ring Het, $R_1$, $R_2$, $R_3$, $R_4$, $R_5$, m, n, and p are defined herein. Also disclosed are methods of using such compounds as inhibitors of signaling through Toll-like receptor 7, or 8, or 9, and pharmaceutical compositions comprising such compounds. These compounds are useful in treating inflammatory and autoimmune diseases.

12 Claims, No Drawings

(56) References Cited

U.S. PATENT DOCUMENTS

| | | |
|---|---|---|
| 9,353,115 B2 | 5/2016 | Lipford et al. |
| 9,376,398 B2 | 6/2016 | Hori et al. |
| 9,428,495 B2 | 8/2016 | Carlson et al. |
| 9,643,967 B2 | 5/2017 | Kaul et al. |
| 2006/0235037 A1* | 10/2006 | Purandare ............ C07D 401/14 514/304 |
| 2010/0160314 A1 | 6/2010 | Lipford et al. |
| 2010/0197657 A1 | 8/2010 | Chang et al. |
| 2011/0015219 A1 | 1/2011 | Trawick et al. |
| 2011/0071150 A1 | 3/2011 | Alam et al. |
| 2011/0105427 A1 | 5/2011 | Daun et al. |
| 2011/0183967 A1 | 7/2011 | Zheng et al. |
| 2011/0275631 A1 | 11/2011 | Abeywardane et al. |
| 2013/0045986 A1 | 2/2013 | Nagarathnam et al. |
| 2013/0324547 A1 | 12/2013 | Boivin et al. |
| 2014/0066432 A1 | 3/2014 | Howbert et al. |
| 2014/0088085 A1 | 3/2014 | Burgess et al. |
| 2014/0242121 A1 | 8/2014 | Lipford et al. |
| 2015/0231142 A1 | 8/2015 | van Goor et al. |
| 2017/0008885 A1 | 1/2017 | Koul et al. |
| 2017/0273983 A1 | 9/2017 | Ding et al. |
| 2018/0000790 A1 | 1/2018 | Dyckman et al. |

FOREIGN PATENT DOCUMENTS

| | | |
|---|---|---|
| WO | 2006113458 A1 | 10/2006 |
| WO | 2007115306 A2 | 10/2007 |
| WO | 2008065198 A1 | 6/2008 |
| WO | 2008152471 A1 | 12/2008 |
| WO | 2009030996 A1 | 3/2009 |
| WO | 2010149769 A1 | 12/2010 |
| WO | 2013010904 A1 | 1/2013 |
| WO | 2013181579 A2 | 12/2013 |
| WO | 2015088045 A1 | 6/2015 |
| WO | 2016029077 A1 | 2/2016 |
| WO | 2018005586 A1 | 1/2018 |
| WO | 2018026620 A1 | 2/2018 |
| WO | 2018049089 A1 | 3/2018 |

OTHER PUBLICATIONS

International Preliminary Report on Patentability for PCT/US2018/060590, dated May 19, 2020.

International Search Report for PCT/US2018/060590, filed Nov. 13, 2018.

Kawai, T., et al., "The Role of Pattern-Recognition Receptors in Innate Immunity: Update on Toll-like Receptors", Nature Immunol., 2011, 11, 373-384.

Lamphier, M. et al., "Novel Small Molecule Inhibitors of TLR7 and TLR9: Mechanism of Action and Efficacy in Vivo", Mol Pharmacol, 2014, 85:429-440.

Patra, Mahesh Chandra, et al., "Recent Progress in the Development of Toll-like Receptor (TLR) antagonists", Exp. Opin. On Therapeutic Patents, 2016, vol. 26, No. 6, 719-730.

Roy, et al., "Design and developmen of benzoxazole derivatives with toll-like receptor 9 antagonism", Eur J Med Chem, 2017, vol. 134, 334-347.

Sims, et al., "The IL-1 Family: Regulators of Immunity", Nature Rev. Immunol., 2010, 10, 89-102.

* cited by examiner

SUBSTITUTED INDOLE COMPOUNDS

CROSS REFERENCE

This application is a continuation application of U.S. Application No. 16,763,670, filed May 13, 2020, which is a national phase application under 35 U.S.C. § 371 of International Patent Application No. PCT/US2018/060590, filed Nov. 13, 2018, which claims priority to U.S. Provisional Application Ser. No. 62/585,733, filed Nov. 14, 2017, the contents of which are specifically incorporated fully herein by reference.

The present invention generally relates to substituted indole compounds useful as inhibitors of signaling through Toll-like receptor 7, 8, or 9 (TLR7, TLR8, TLR9) or combinations thereof. Provided herein are substituted indole compounds, compositions comprising such compounds, and methods of their use. The invention further pertains to pharmaceutical compositions containing at least one compound according to the invention that are useful for the treatment of conditions related to TLR modulation, such as inflammatory and autoimmune diseases, and methods of inhibiting the activity of TLRs in a mammal.

Toll/IL-1 receptor family members are important regulators of inflammation and host resistance. The Toll-like receptor family recognizes molecular patterns derived from infectious organisms including bacteria, fungi, parasites, and viruses (reviewed in Kawai, T. et al., Nature Immunol., 11:373-384 (2010)). Ligand binding to the receptor induces dimerization and recruitment of adaptor molecules to a conserved cytoplasmic motif in the receptor termed the Toll/IL-1 receptor (TIR) domain. With the exception of TLR3, all TLRs recruit the adaptor molecule MyD88. The IL-1 receptor family also contains a cytoplasmic TIR motif and recruits MyD88 upon ligand binding (reviewed in Sims, J. E. et al., Nature Rev. Immunol., 10:89-102 (2010)).

Toll-like receptors (TLRs) are a family of evolutionarily conserved, transmembrane innate immune receptors that participate in the first-line defense. As pattern recognition receptors, the TLRs protect against foreign molecules, activated by pathogen associated molecular patterns (PAMPs), or from damaged tissue, activated by danger associated molecular patterns (DAMPs). A total of 13 TLR family members have been identified, 10 in human, that span either the cell surface or the endosomal compartment. TLR7-9 are among the set that are endosomally located and respond to single-stranded RNA (TLR7 and TLR8) or unmethylated single-stranded DNA containing cytosine-phosphate-guanine (CpG) motifs (TLR9).

Activation of TLR7/8/9 can initiate a variety of inflammatory responses (cytokine production, B cell activation and IgG production, Type I interferon response). In the case of autoimmune disorders, the aberrant sustained activation of TLR7/8/9 leads to worsening of disease states. Whereas overexpression of TLR7 in mice has been shown to exacerbate autoimmune disease, knockout of TLR7 in mice was found to be protective against disease in lupus-prone MRL/lpr mice. Dual knockout of TLR7 and 9 showed further enhanced protection.

As numerous conditions may benefit by treatment involving modulation of cytokines, IFN production and B cell activity, it is immediately apparent that new compounds capable of modulating TLR7 and/or TLR8 and/or TLR9 and methods of using these compounds could provide substantial therapeutic benefits to a wide variety of patients.

The present invention relates to a new class of substituted indole compounds found to be effective inhibitors of signaling through TLR7/8/9. These compounds are provided to be useful as pharmaceuticals with desirable stability, bioavailability, therapeutic index, and toxicity values that are important to their drugability.

SUMMARY OF THE INVENTION

The present invention provides compounds of Formula (I) that are useful as inhibitors of signaling through Toll-like receptor 7, 8, or 9 and are useful for the treatment of proliferative diseases, allergic diseases, autoimmune diseases and inflammatory diseases, or stereoisomers, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of Toll-like receptor 7, 8, or 9 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method of treating a disease or disorder associated with Toll-like receptor 7, 8, or 9 activity, the method comprising administering to a mammal in need thereof, at least one of the compounds of Formula (I) or salts, solvates, and prodrugs thereof.

The present invention also provides processes and intermediates for making the compounds of Formula (I) including salts, solvates, and prodrugs thereof.

The present invention also provides at least one of the compounds of Formula (I) or salts, solvates, and prodrugs thereof, for use in therapy.

The present invention also provides the use of at least one of the compounds of Formula (I) or salts, solvates, and prodrugs thereof, for the manufacture of a medicament for the treatment of prophylaxis of Toll-like receptor 7, 8, or 9 related conditions, such as allergic disease, autoimmune diseases, inflammatory diseases, and proliferative diseases.

The compound of Formula (I) and compositions comprising the compounds of Formula (I) may be used in treating, preventing, or curing various Toll-like receptor 7, 8, or 9 related conditions. Pharmaceutical compositions comprising these compounds are useful for treating, preventing, or slowing the progression of diseases or disorders in a variety of therapeutic areas, such as allergic disease, autoimmune diseases, inflammatory diseases, and proliferative diseases.

These and other features of the invention will be set forth in expanded form as the disclosure continues.

DETAILED DESCRIPTION

The first aspect of the present invention provides at least one compound of Formula (I):

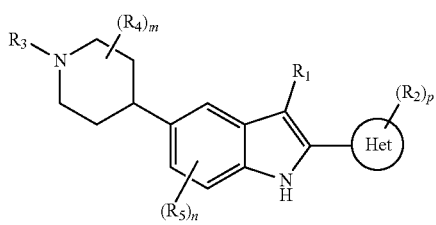
or a salt thereof, wherein:
Ring Het is a:
(i) 9-membered heterocyclic ring selected from:
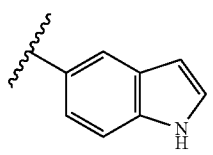 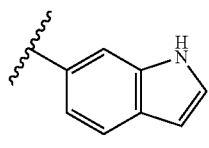
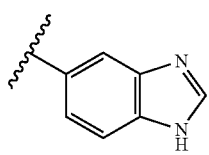 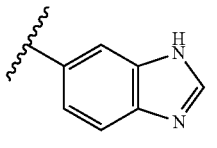
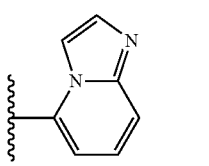 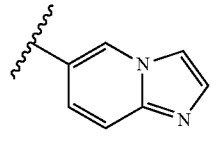
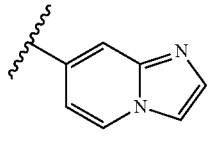 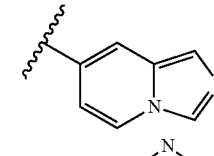
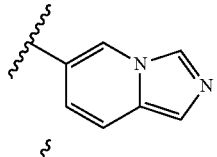 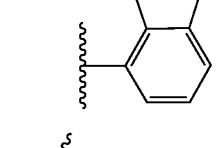
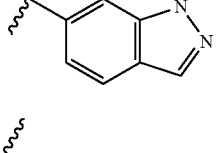 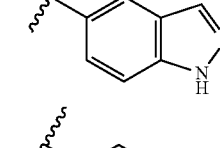
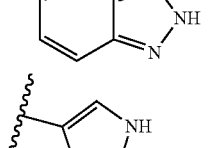 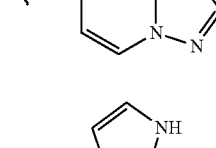
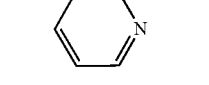 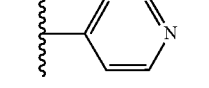
-continued
 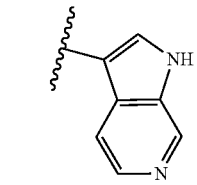
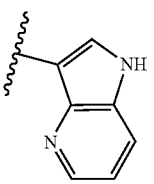

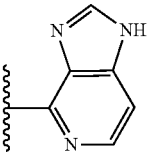
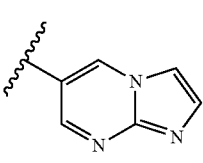
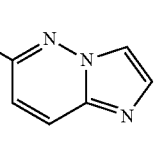
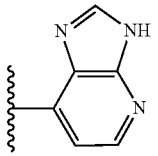
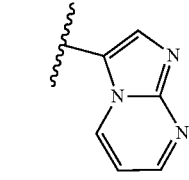

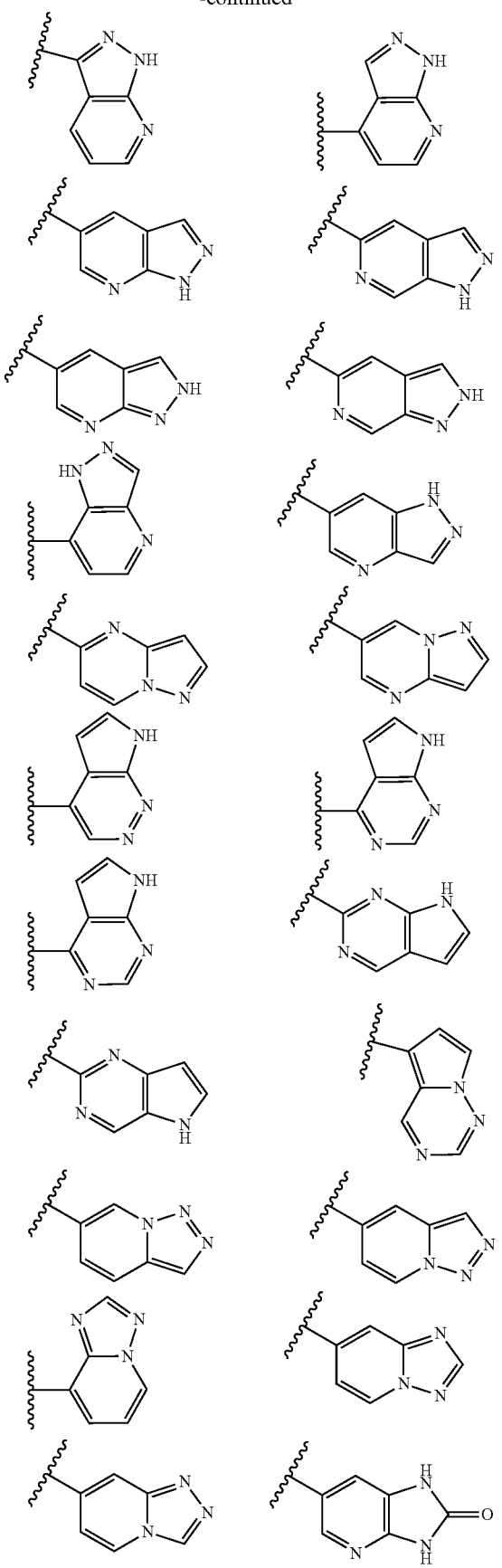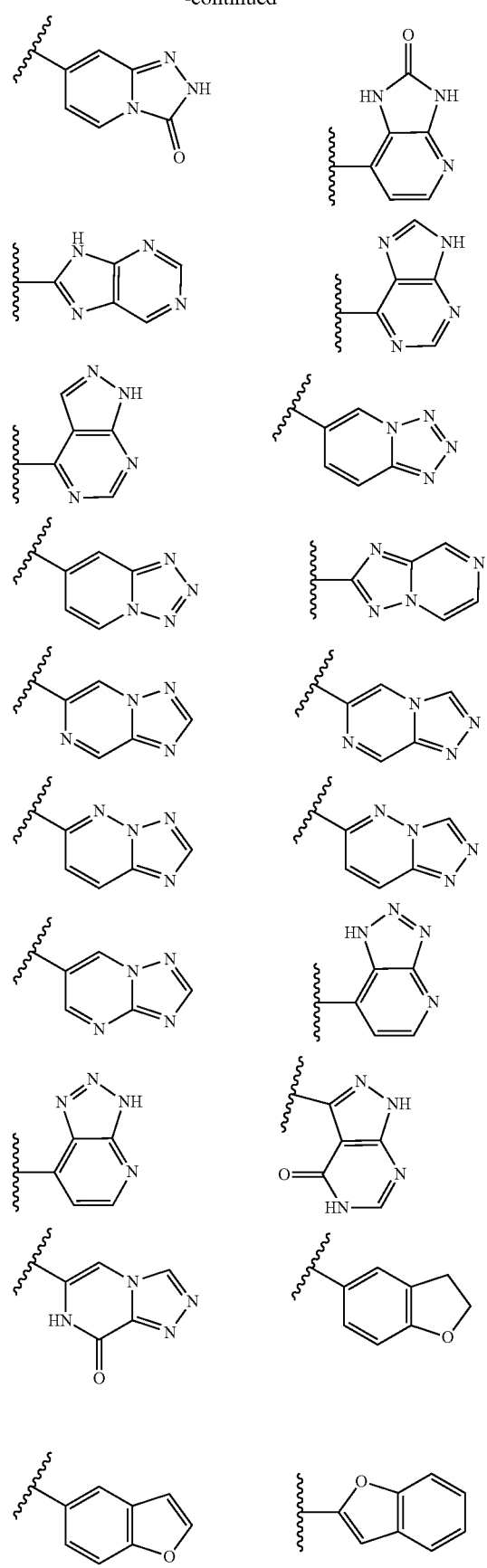

-continued

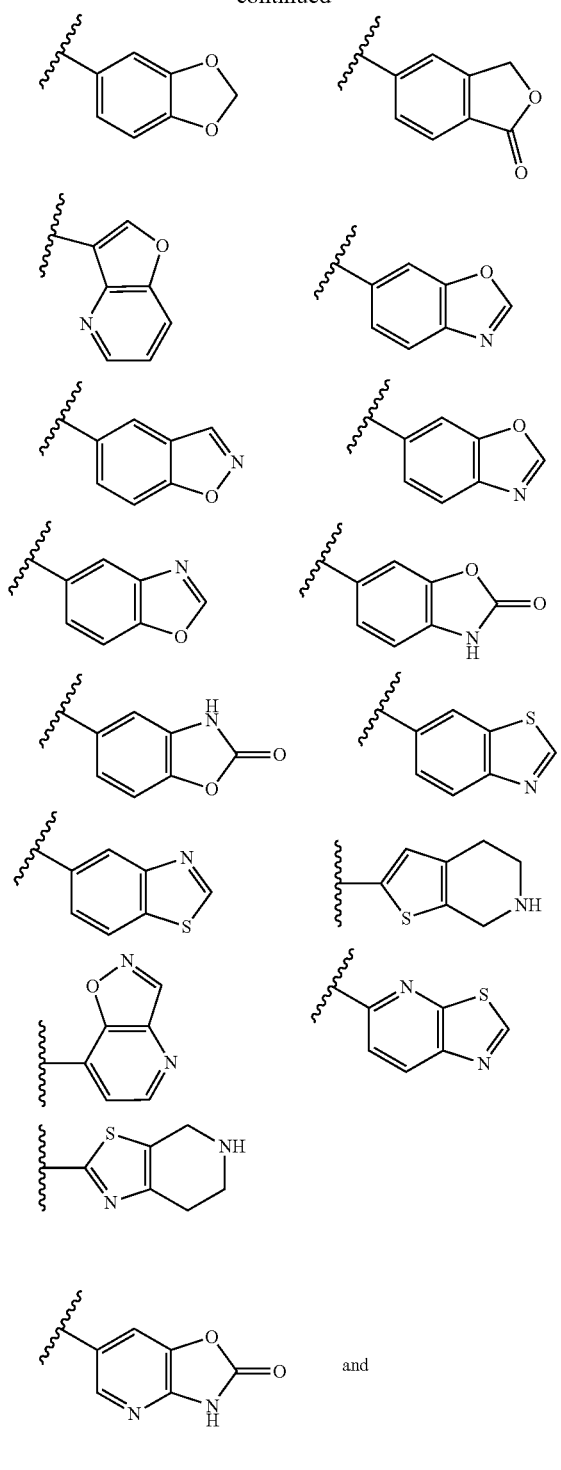

or
(ii) 10-membered heterocyclic ring selected from:

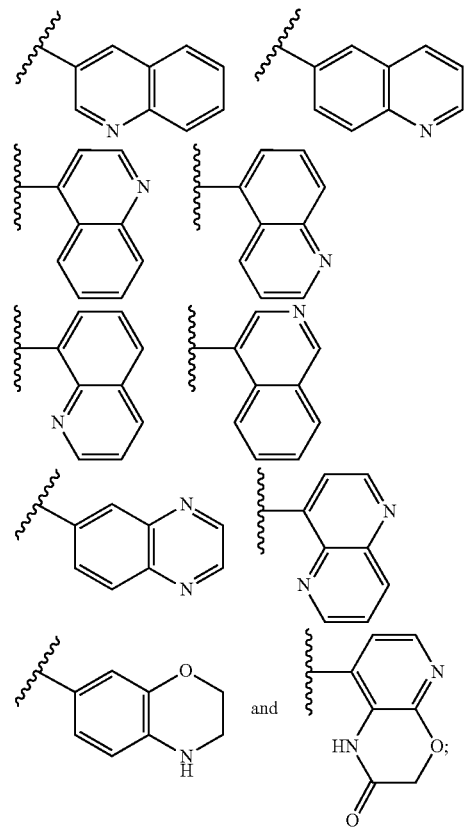

R₁ is H, Cl, —CN, $C_{1-4}$ alkyl, $C_{1-3}$ fluoroalkyl, $C_{1-3}$ hydroxyalkyl, $C_{1-3}$ hydroxy-fluoroalkyl, —CR$_z$=CH$_2$, $C_{3-6}$ cycloalkyl, —CH$_2$($C_{3-6}$ cycloalkyl), —C(O)O ($C_{1-3}$ alkyl), or tetrahydropyranyl;

each R₂ is independently halo, —CN, —OH, —NO$_2$, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, —O(CH$_2$)$_{1-2}$OH, —(CH$_2$)$_{0-4}$O ($C_{1-4}$ alkyl), $C_{1-3}$ fluoroalkoxy, —(CH$_2$)$_{1-4}$O($C_{1-3}$ alkyl), —O(CH$_2$)$_{1-2}$OC(O)($C_{1-3}$ alkyl), —O(CH$_2$)$_{1-2}$NR$_x$R$_x$, —C(O)O($C_{1-3}$ alkyl), —C(O)NR$_y$R$_y$, —C(O)NR$_x$($C_{1-5}$ hydroxyalkyl), —C(O)NR$_x$ ($C_{2-6}$ alkoxyalkyl), —C(O)NR$_x$($C_{3-6}$ cycloalkyl), —NR$_y$R$_y$, —NR$_y$($C_{1-3}$ fluoroalkyl), —NR$_y$($C_{1-4}$ hydroxyalkyl), —NR$_x$CH$_2$(phenyl), —NR$_x$S(O)$_2$($C_{3-6}$ cycloalkyl), —NR$_x$C(O)($C_{1-3}$ alkyl), —NR$_x$(CH$_2$-cyclopropyl), —S(O)$_2$($C_{1-3}$ alkyl), $C_{3-6}$ cycloalkyl, phenyl, morpholinyl, dioxothiomorpholinyl, dimethyl pyrazolyl, methylpiperidinyl, methylpiperazinyl, amino-oxadiazolyl, imidazolyl, triazolyl, or —C(O) (thiazolyl);

R₃ is:
(a) -L$_1$-A; or
(b) H, $C_{1-6}$ alkyl, $C_{1-3}$ fluoroalkyl, $C_{1-3}$ cyanoalkyl, $C_{1-6}$ hydroxyalkyl, $C_{1-3}$ hydroxy-fluoroalkyl, —CR$_x$R$_x$CR$_x$ (OH)CR$_x$=CR$_x$R$_x$, —C=N(NR$_x$R$_x$), —(CR$_x$R$_x$)$_{1-4}$O ($C_{1-3}$ alkyl), —(CR$_x$R$_x$)$_{1-4}$O(CR$_x$R$_x$)$_{1-3}$O($C_{1-3}$ alkyl), —CH$_2$CH(OH)CH$_2$O($C_{1-3}$ alkyl), —(CR$_x$R$_x$)$_{1-3}$S($C_{1-3}$ alkyl), —(CH$_2$)$_{1-3}$C(O)OC(CH$_3$)$_3$, —(CR$_x$R$_x$)$_{0-3}$ NR$_x$R$_y$, —(CR$_x$R$_x$)$_{0-3}$NR$_x$($C_{1-4}$ hydroxyalkyl), —CH$_2$CH(OH)CH$_2$NR$_x$R$_y$, —C(O)H, —C(O)($C_{1-6}$ alkyl), —C(O)($C_{1-4}$ hydroxyalkyl), —C(O)($C_{1-3}$ fluoroalkyl), —C(O)(C$_{1-3}$ chloroalkyl), —C(O)(C$_{1-3}$ cyanoalkyl), —(CR$_x$R$_x$)$_{0-3}$C(O)OH, —C(O)(CH$_2$)$_{0-2}$O(C$_{1-4}$ alkyl), —C(O)(CR$_x$R$_x$)$_{0-2}$O(CR$_x$R$_x$)$_{1-2}$O(C$_{1-3}$ alkyl), —C(O)(CR$_x$R$_x$)$_{0-2}$O(CR$_x$R$_x$)$_{1-2}$NR$_y$R$_y$, —C(O)CR$_x$R$_x$S(O)$_2$(C$_{1-3}$ alkyl), —C(O)CR$_x$R$_x$NR$_x$S(O)$_2$(C$_{1-3}$ alkyl), —C(O)CR$_x$R$_x$OC(O)(C$_{1-3}$ alkyl), —C(O)(CR$_x$R$_x$)$_{0-3}$NR$_y$R$_y$, —C(O)(CR$_x$R$_x$)$_{0-1}$NR$_x$(C$_{1-3}$ cyanoalkyl), —C(O)(CR$_x$R$_x$)$_{0-2}$NR$_y$(C$_{1-6}$ hydroxyalkyl), —C(O)(CR$_x$R$_x$)$_{0-2}$NR$_x$(C$_{1-3}$ fluoroalkyl), —C(O)(CR$_x$R$_x$)$_{0-1}$NR$_x$(C$_{1-5}$ hydroxy-fluoroalkyl), —C(O)(CR$_x$R$_x$)$_{0-1}$NR$_x$(CH$_2$)$_{1-2}$O(C$_{1-3}$ hydroxyalkyl), —C(O)(CR$_x$R$_x$)$_{0-1}$NR$_x$(CH$_2$)$_{1-2}$NR$_x$C(O)(C$_{1-2}$ alkyl), —C(O)(CR$_x$R$_x$)$_{0-2}$NR$_x$((CR$_x$R$_x$)$_{1-2}$O(C$_{1-2}$ alkyl)), —C(O)(CR$_x$R$_x$)$_{0-2}$N((CR$_x$R$_x$)$_{1-2}$O(C$_{1-2}$ alkyl))$_2$, —C(O)(CR$_x$R$_x$)$_{0-2}$NR$_x$(CR$_x$R$_x$)$_{1-3}$NR$_x$R$_x$, —C(O)CR$_x$(NH$_2$)(CR$_x$R$_x$)$_{1-4}$NR$_x$R$_x$, —C(O)CR$_x$(NH$_2$)(CR$_x$R$_x$)$_{1-4}$NR$_x$C(O)NR$_x$R$_x$, —C(O)(CR$_x$R$_x$)$_{0-3}$NR$_x$(CH$_2$)$_{0-1}$C(O)(C$_{1-3}$ alkyl), —C(O)(CR$_x$R$_x$)$_{0-3}$N((CH$_2$)$_{0-1}$C(O)(C$_{1-3}$ alkyl))$_2$, —C(O)(CR$_x$R$_x$)$_{0-1}$NR$_x$(CH$_2$)$_{0-1}$C(O)(C$_{1-3}$ cyanoalkyl), —C(O)(CR$_x$R$_x$)$_{0-2}$NR$_x$(CH$_2$)$_{1-2}$C(O)NR$_y$R$_y$, —C(O)(CR$_x$R$_x$)$_{1-3}$C(O)NR$_y$R$_y$, —C(O)(CR$_x$R$_x$)$_{1-3}$S(O)$_2$NR$_y$R$_y$, —C(O)(CR$_x$R$_x$)$_{0-2}$NR$_x$(CHR$_y$(CH$_2$OH)), —(CR$_x$R$_x$)$_{1-2}$C(O)NR$_y$R$_y$, —CH(CN)C(O)NR$_y$R$_y$, —(CR$_x$R$_x$)$_{1-2}$C(O)NR$_y$(C$_{1-3}$ fluoroalkyl), —(CR$_x$R$_x$)$_{1-2}$C(O)NR$_y$(C$_{1-4}$ hydroxyalkyl), —(CR$_x$R$_x$)$_{1-2}$C(O)NR$_y$(C$_{1-3}$ cyanoalkyl), —(CR$_x$R$_x$)$_{1-2}$C(O)NR$_x$(CH$_2$)$_{1-2}$O(C$_{1-3}$ alkyl), —(CR$_x$R$_x$)$_{1-2}$C(O)NR$_x$CH(C$_{1-4}$ alkyl)(C$_{1-3}$ hydroxyalkyl), —(CR$_x$R$_x$)$_{1-2}$C(O)NR$_x$CH(C$_{1-3}$ hydroxyalkyl)(C$_{3-6}$ cycloalkyl), —(CH$_2$)$_{1-2}$C(O)NR$_x$(CH$_2$)$_{1-2}$C(O)NR$_x$R$_x$, —(CH$_2$)$_{1-2}$C(O)NR$_x$(CH$_2$)$_{1-2}$S(C$_{1-3}$ alkyl), —(CH$_2$)$_{1-2}$C(O)NR$_x$(CH$_2$)$_{1-2}$S(O)$_2$OH, —(CH$_2$)$_{1-2}$C(O)NR$_x$(CH$_2$)$_{1-2}$NR$_x$C(O)(C$_{1-3}$ alkyl), —(CH$_2$)$_{1-2}$C(O)NR$_x$(CH$_2$)$_{1-3}$NR$_x$R$_x$, —(CH$_2$)$_{1-2}$C(O)N(CH$_2$CH$_3$)(CH$_2$)$_{1-3}$NR$_x$R$_x$, —(CR$_x$R$_x$)$_{0-3}$S(O)$_2$(C$_{1-4}$ alkyl), —(CH$_2$)$_{0-2}$S(O)$_2$(C$_{1-3}$ fluoroalkyl), —(CR$_x$R$_x$)$_{0-2}$S(O)$_2$NR$_y$R$_y$, —(CR$_x$R$_x$)$_{0-2}$NR$_x$S(O)$_2$(C$_{1-3}$ alkyl), —C(O)C(O)OH, —C(O)C(O)NR$_y$R$_y$, or —C(O)C(O)NR$_y$(CR$_x$R$_x$)$_{1-2}$NR$_y$R$_y$;

L$_1$ is a bond, —(CR$_x$R$_x$)$_{1-2}$—, —(CR$_x$R$_x$)$_{1-2}$CR$_x$(OH)—, —(CR$_x$R$_x$)$_{1-2}$O—, —CR$_x$R$_x$C(O)—, —(CR$_x$R$_x$)$_2$NR$_x$(CR$_x$R$_x$)$_{0-1}$—, —CR$_x$R$_x$C(O)NR$_x$(CR$_x$R$_x$)$_{0-4}$—, —C(O)(CR$_x$R$_x$)$_{0-3}$—, —C(O)(CR$_x$R$_x$)$_{0-2}$NR$_x$(CR$_x$R$_x$)$_{0-2}$—, —C(O)(CR$_x$R$_x$)$_{0-2}$N(C$_{1-2}$ hydroxyalkyl)(CR$_x$R$_x$)$_{0-2}$—, —C(O)(CR$_x$R$_x$)$_{0-2}$NR$_x$(CR$_x$R$_x$)$_{1-2}$CR$_x$(OH)—, —C(O)(CR$_x$R$_x$)$_{1-2}$C(O)NR$_x$—, —(CR$_x$R$_x$)$_{0-2}$C(O)NR$_x$(CR$_x$R$_x$)$_{1-2}$CR$_x$(OH)—, —(CR$_x$R$_x$)$_{0-2}$C(O)N(C$_{1-2}$ hydroxyalkyl)(CR$_x$R$_x$)$_{1-2}$—, —C(O)(CR$_x$R$_x$)$_{0-1}$O—, —C(O)(CR$_x$R$_x$)$_{1-2}$NHS(O)$_2$—, —C(O)CR$_x$(NH$_2$)CR$_x$R$_x$—, —C(O)C(O)(CR$_x$R$_x$)$_{0-2}$—, —C(O)NR$_x$(CR$_x$R$_x$)$_{1-2}$—, or —S(O)$_2$—;

A is 3-oxa-8-azabicyclo[3.2.1]octanyl, 8-oxa-3-azabicyclo[3.2.1]octanyl, 1,1-dioxidothiomorpholinyl, 1,2-dioxotetrahydro-2H-thiopyranyl, 1,4-diazepanyl, 2-azabicyclo[3.1.0]hexanyl, azabicyclo[3.2.1]octanyl, 2-oxa-6-azaspiro[3.3]heptanyl, azepanyl, C$_{3-7}$ cycloalkyl, imidazo[1,2-a]pyridinyl, imidazo[1,5-a]pyridinyl, imidazolyl, isoxazolyl, morpholinyl, oxadiazolyl, oxazolyl, oxetanyl, phenyl, piperazinonyl, piperazinyl, piperidinonyl, piperidinyl, pyrazinyl, pyrazolyl, pyridazinyl, pyridinyl, pyrimidinyl, pyrrolidinonyl, pyrrolidinyl, pyrrolyl, quinolinyl, tetrahydrofuranyl, tetrahydropyranyl, tetrahydrothiopyranyl, tetrazolyl, thiadiazolyl, thiazolyl, or triazolyl, each substituted with zero to 4 substituents independently selected from F, Cl, —OH, —CN, C$_{1-6}$ alkyl, C$_{1-3}$ fluoroalkyl, C$_{1-5}$ hydroxyalkyl, —CH$_2$NR$_x$R$_x$, C$_{1-3}$ alkoxy, —O(CH$_2$)$_{1-3}$NR$_x$R$_x$, —O(CH$_2$)$_{1-3}$NR$_x$(pyridinyl), —C(O)(C$_{1-3}$ alkyl), —C(O)O(C$_{1-3}$ alkyl), —C(O)NR$_y$R$_y$, —NR$_x$R$_x$, —NR$_x$C(O)(C$_{1-3}$ alkyl), —O(pyrimidinyl), C$_{3-6}$ cycloalkyl, morpholinyl, phenyl, methyl piperazinyl, pyridinyl, and pyrrolidinyl;

each R$_x$ is independently H or —CH$_3$;

each R$_y$ is independently H or C$_{1-6}$ alkyl;

each R$_4$ is independently F, —OH, C$_{1-2}$ alkyl, or —OCH$_3$; or two R$_4$ attached to the same carbon atom form =O; or wherein when m is at least 2, two R$_4$, each attached to a different carbon atom adjacent to the nitrogen atom in the piperidinyl ring, can form a —CH$_2$CH$_2$— bridge;

each R$_5$ is independently F, Cl, —CN, C$_{1-2}$ alkyl, C$_{1-2}$ fluoroalkyl, or —OCH$_3$;

m is zero, 1, 2, 3, or 4;

n is zero, 1, or 2; and p is zero, 1, 2, 3, or 4.

One embodiment provides a compound of Formula (I) or a salt thereof, wherein Ring Het is a 9-membered heterocyclic ring selected from:

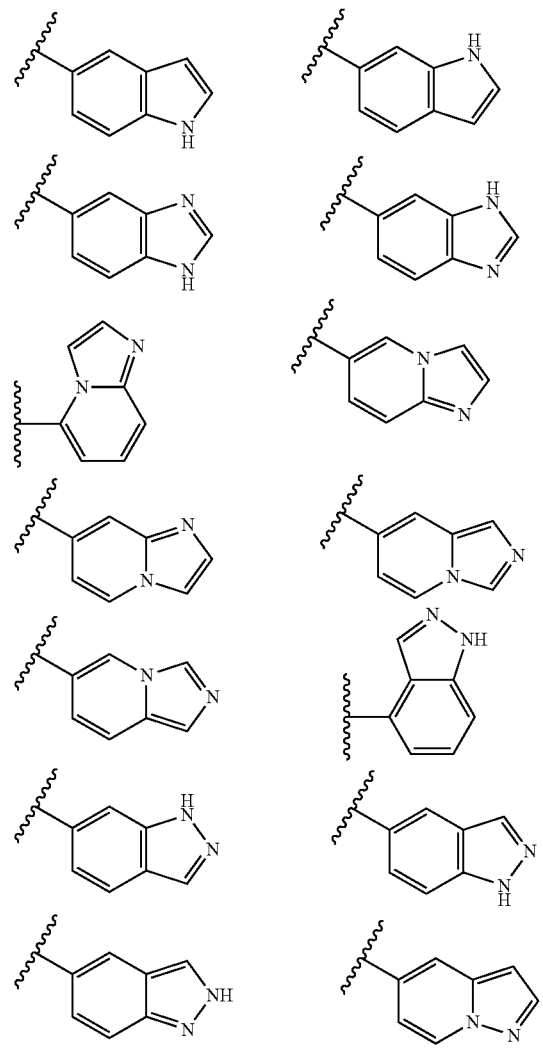

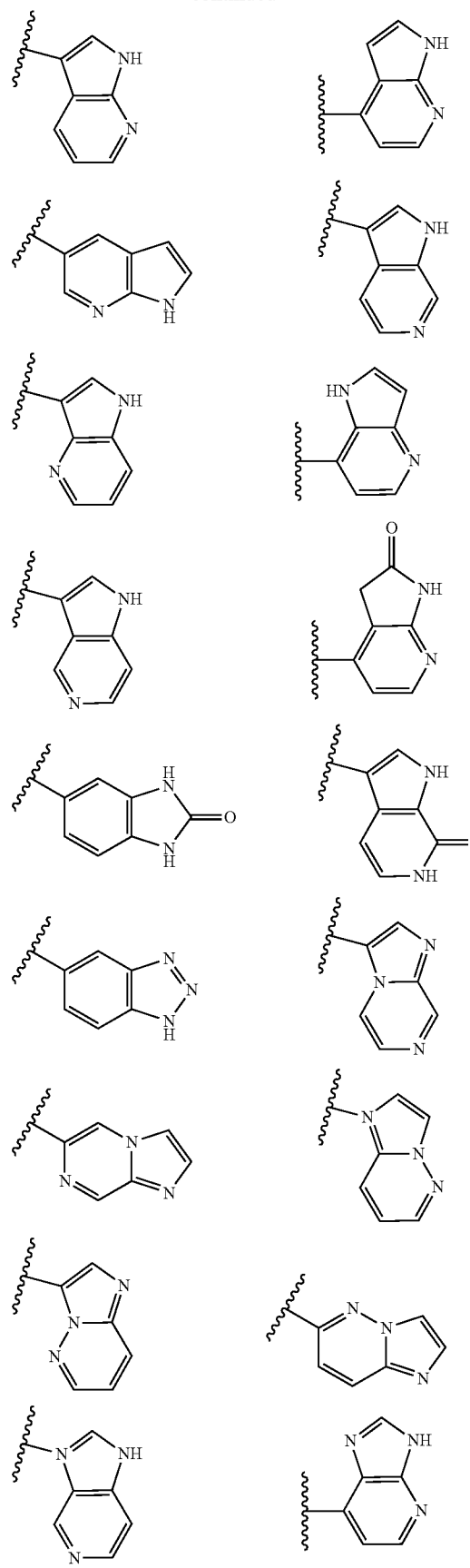
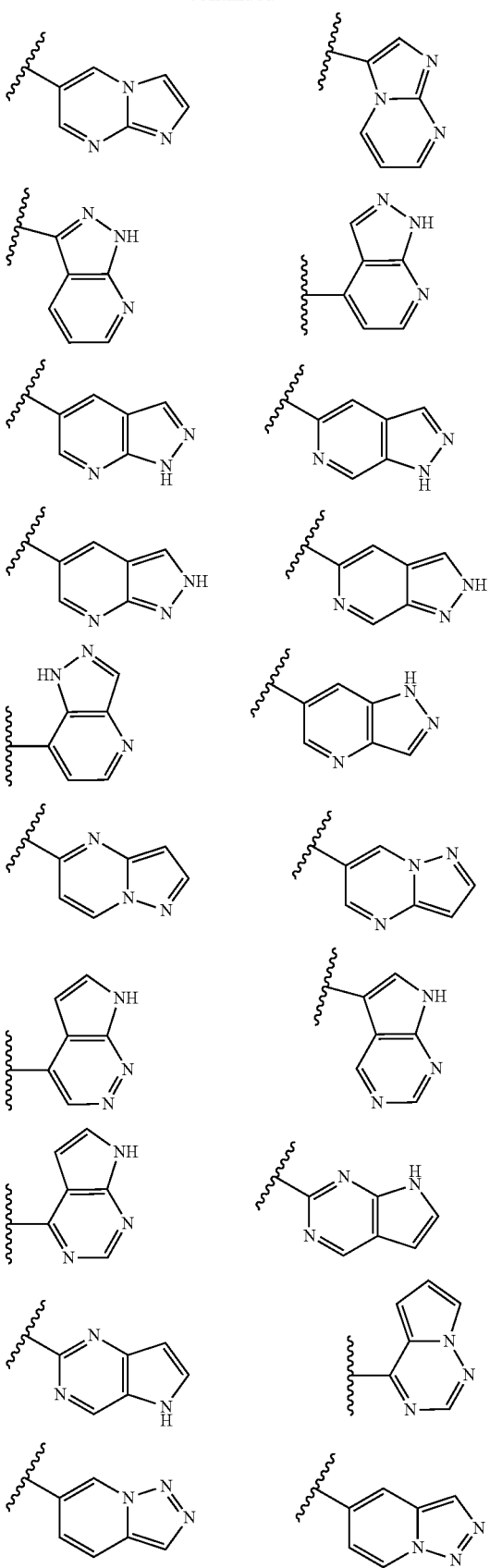

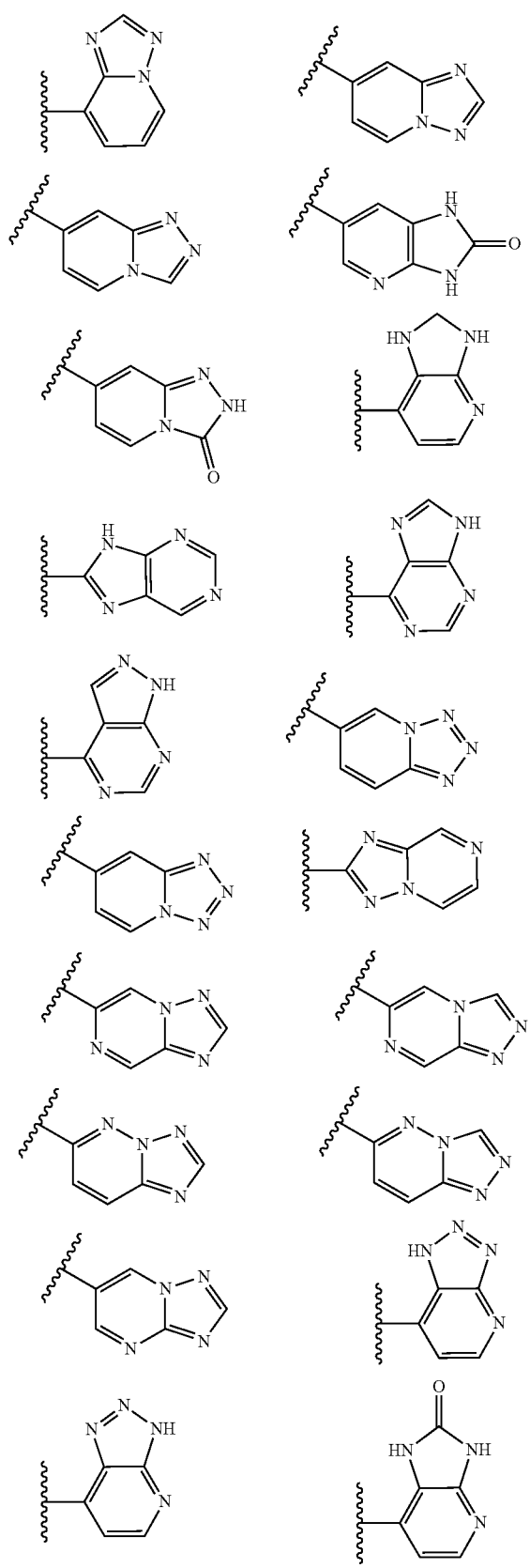
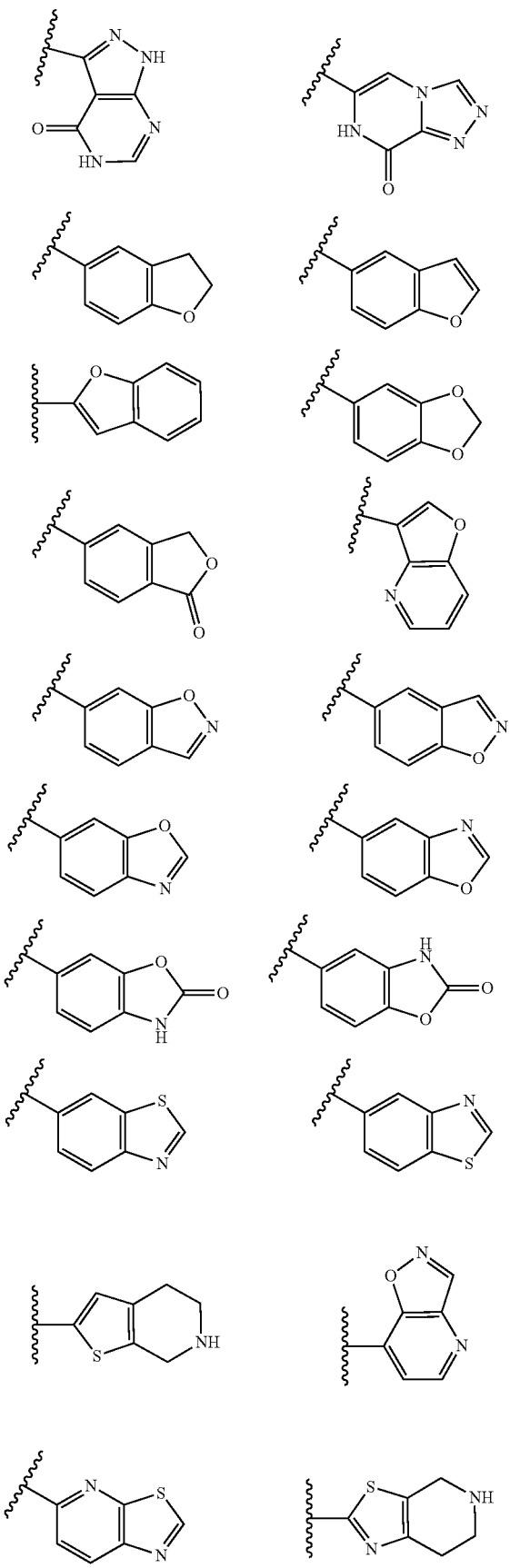

-continued

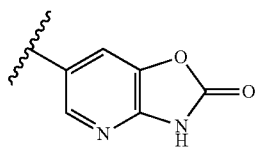 and 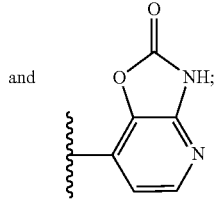

and R₁, R₂, R₃, R₄, R₅, m, n, and p are defined in the first aspect.

One embodiment provides a compound of Formula (I) or a salt thereof, wherein Ring Het is a 10-membered heterocyclic ring selected from:

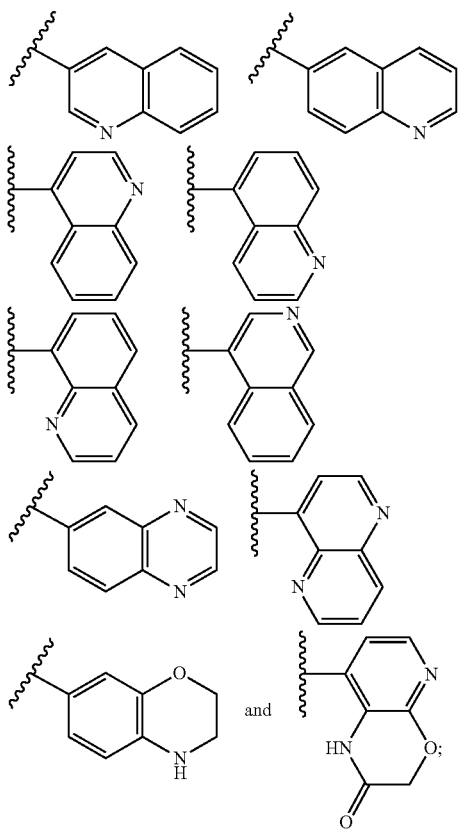

and R₁, R₂, R₃, R₄, R₅, m, n, and p are defined in the first aspect.

One embodiment provides a compound of Formula (I) or a salt thereof, wherein Ring Het is a 9-membered heterocyclic ring having one nitrogen heteroatom, wherein said Ring Het is

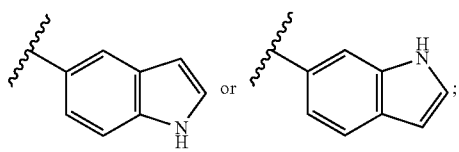 [SMILES: *c1ccc2[nH]ccc2c1 ; *c1ccc2cc[nH]c2c1]

and R₁, R₂, R₃, R₄, R₅, m, n, and p are defined in the first aspect.

One embodiment provides a compound of Formula (I) or a salt thereof, wherein Ring Het is a 9-membered heterocyclic ring having two nitrogen heteroatoms, wherein said Ring Het is:

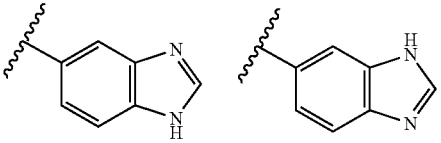
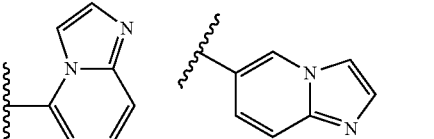
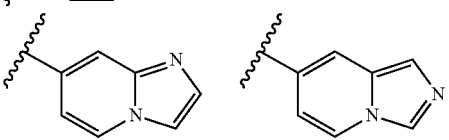
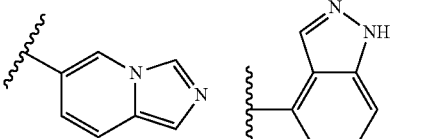
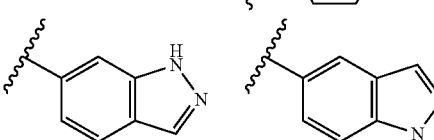
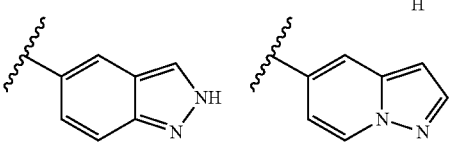
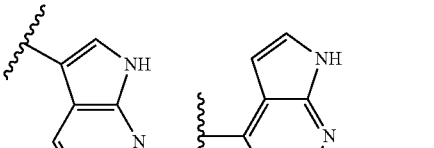
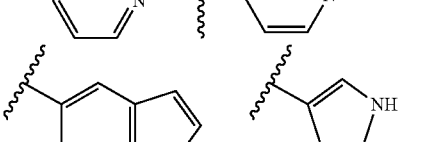
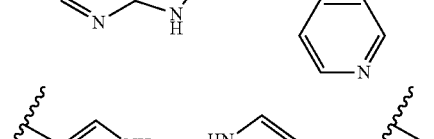
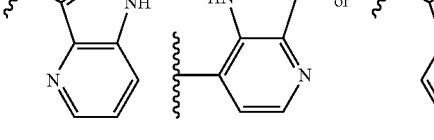

and R₁, R₂, R₃, R₄, R₅, m, n, and p are defined in the first aspect.

One embodiment provides a compound of Formula (I) or a salt thereof, wherein Ring Het is a 9-membered heterocyclic ring having two nitrogen heteroatoms and is substituted with =O, wherein said Ring Het is:

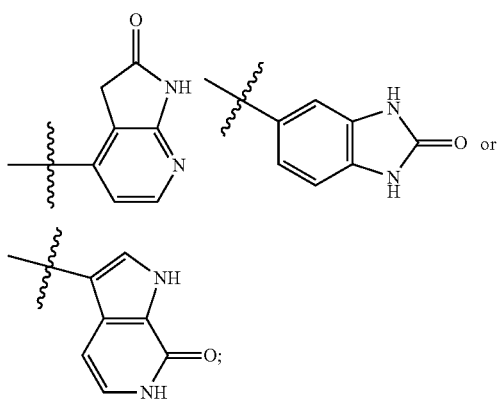

and $R_1$, $R_2$, $R_3$, $R_4$, $R_5$, m, n, and p are defined in the first aspect.

One embodiment provides a compound of Formula (I) or a salt thereof, wherein Ring Het is a 9-membered heterocyclic ring having three nitrogen heteroatoms, wherein said Ring Het is:

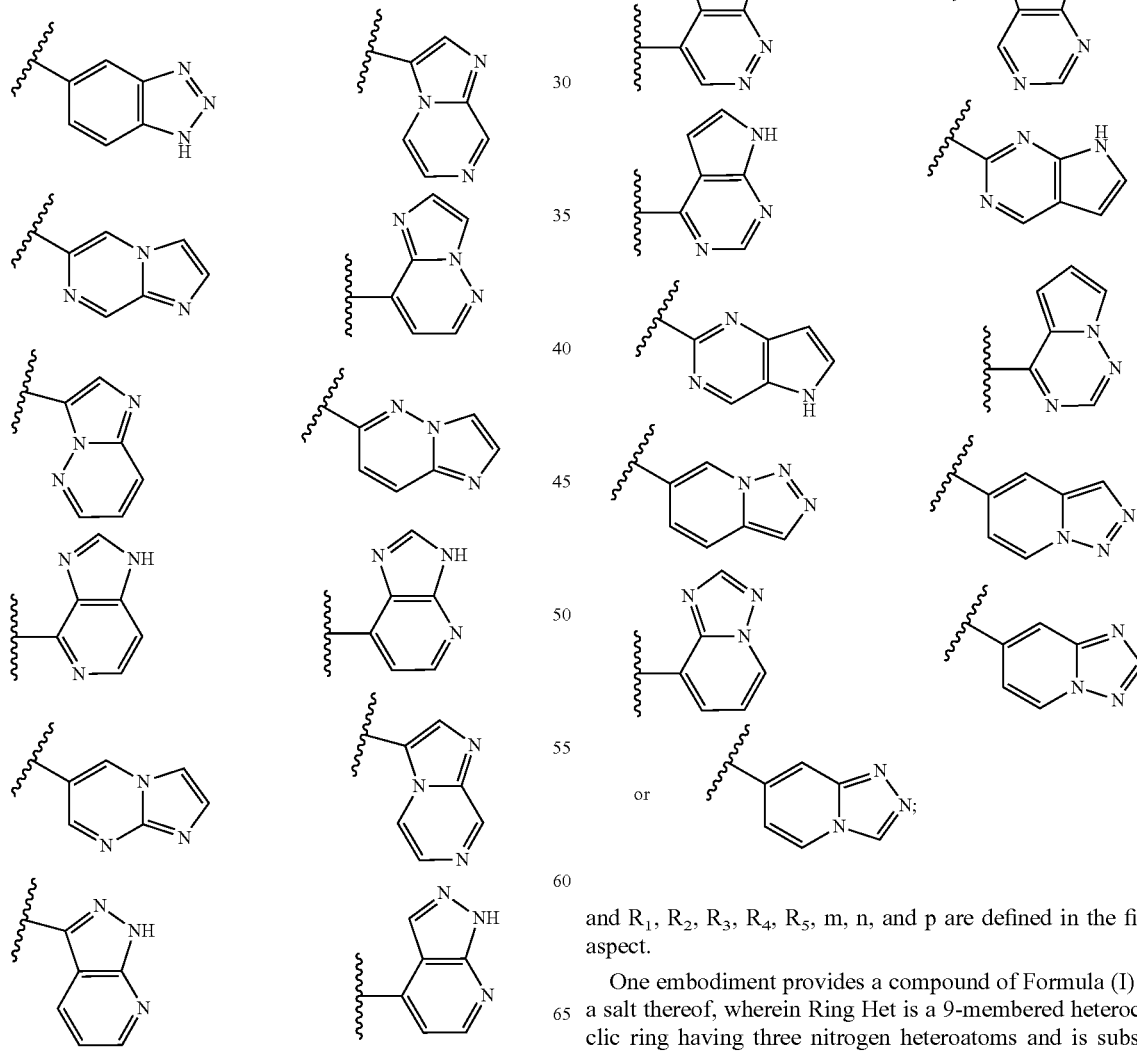

and $R_1$, $R_2$, $R_3$, $R_4$, $R_5$, m, n, and p are defined in the first aspect.

One embodiment provides a compound of Formula (I) or a salt thereof, wherein Ring Het is a 9-membered heterocyclic ring having three nitrogen heteroatoms and is substituted with =O, wherein said Ring Het is:

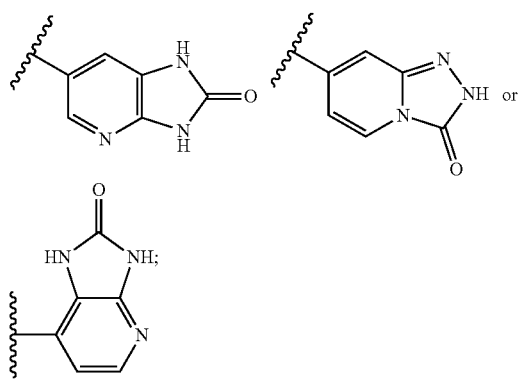

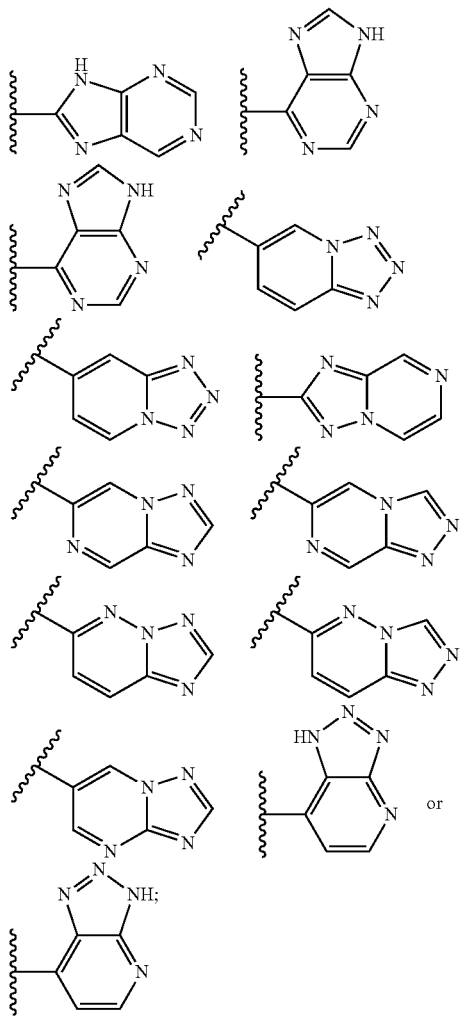

and R$_1$, R$_2$, R$_3$, R$_4$, R$_5$, m, n, and p are defined in the first aspect.

One embodiment provides a compound of Formula (I) or a salt thereof, wherein Ring Het is a 9-membered heterocyclic ring having four nitrogen heteroatoms, wherein said Ring Het is:

One embodiment provides a compound of Formula (I) or a salt thereof, wherein Ring Het is a 9-membered heterocyclic ring having four nitrogen heteroatoms and is substituted with =O, wherein said Ring Het is:

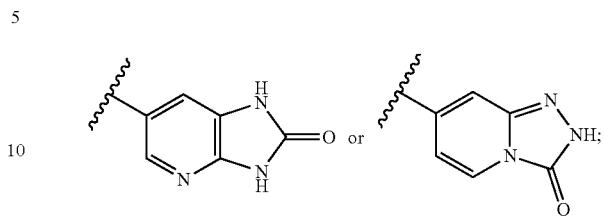

and R$_1$, R$_2$, R$_3$, R$_4$, R$_5$, m, n, and p are defined in the first aspect.

One embodiment provides a compound of Formula (I) or a salt thereof, wherein Ring Het is a 9-membered heterocyclic ring having one or two oxygen heteroatoms and optionally, is substituted with =O, wherein said Ring Het is:

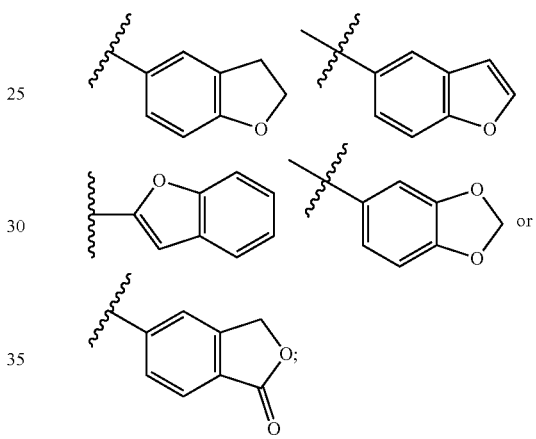

and R$_1$, R$_2$, R$_3$, R$_4$, R$_5$, m, n, and p are defined in the first aspect.

One embodiment provides a compound of Formula (I) or a salt thereof, wherein Ring Het is a 9-membered heterocyclic ring having one nitrogen heteroatom and one oxygen heteroatom and optionally, is substituted with =O, wherein said Ring Het is:

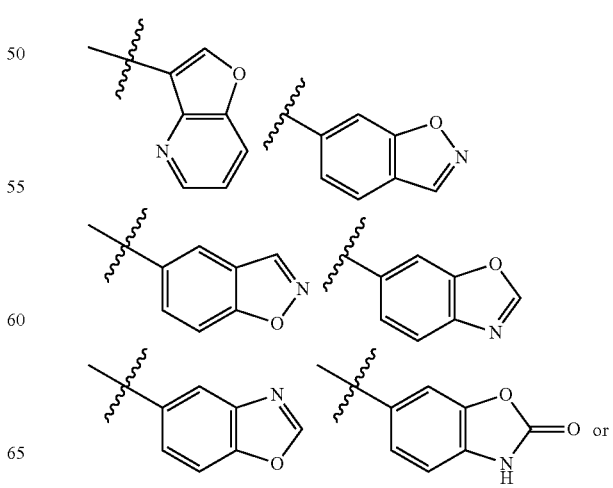

and R$_1$, R$_2$, R$_3$, R$_4$, R$_5$, m, n, and p are defined in the first aspect.

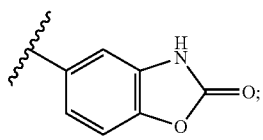

and $R_1$, $R_2$, $R_3$, $R_4$, $R_5$, m, n, and p are defined in the first aspect.

One embodiment provides a compound of Formula (I) or a salt thereof, wherein Ring Het is a 9-membered heterocyclic ring having one or two nitrogen heteroatoms and one sulfur heteroatom, wherein said Ring Het is:

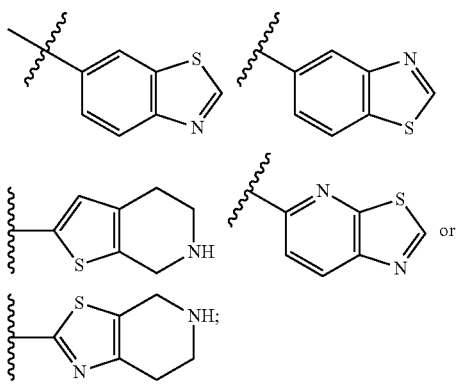

and $R_1$, $R_2$, $R_3$, $R_4$, $R_5$, m, n, and p are defined in the first aspect.

One embodiment provides a compound of Formula (I) or a salt thereof, wherein Ring Het is a 9-membered heterocyclic ring having two nitrogen heteroatoms and one oxygen heteroatom, and is substituted with =O, wherein said Ring Het is:

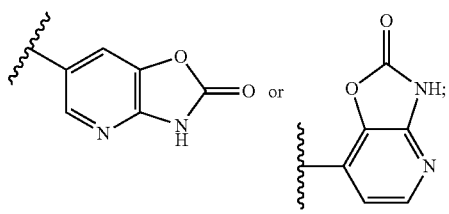 [SMILES: *c1cnc2[nH]c(=O)oc2c1 ; *c1ccnc2[nH]c(=O)oc12]

and $R_1$, $R_2$, $R_3$, $R_4$, $R_5$, m, n, and p are defined in the first aspect.

One embodiment provides a compound of Formula (I) or a salt thereof, wherein Ring Het is a 10-membered heterocyclic ring having one nitrogen heteroatom, wherein said Ring Het is:

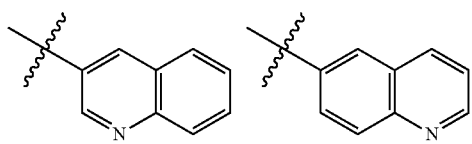

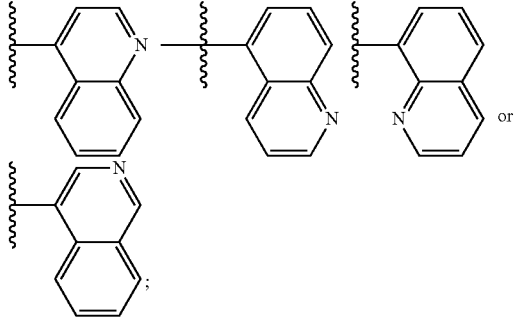

and $R_1$, $R_2$, $R_3$, $R_4$, $R_5$, m, n, and p are defined in the first aspect.

One embodiment provides a compound of Formula (I) or a salt thereof, wherein Ring Het is a 10-membered heterocyclic ring having two nitrogen heteroatoms, wherein said Ring Het is:

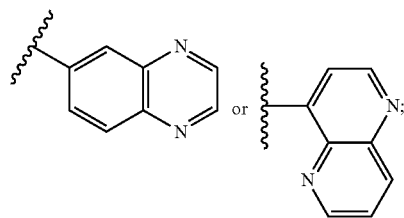

and $R_1$, $R_2$, $R_3$, $R_4$, $R_5$, m, n, and p are defined in the first aspect.

One embodiment provides a compound of Formula (I) or a salt thereof, wherein Ring Het is a 10-membered heterocyclic ring having one or two nitrogen heteroatoms and one oxygen heteroatom, and is optionally substituted with =O, wherein said Ring Het is:

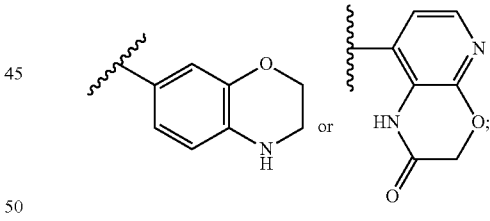

and $R_1$, $R_2$, $R_3$, $R_4$, $R_5$, m, n, and p are defined in the first aspect.

One embodiment provides a compound of Formula (I) or a salt thereof, wherein $R_1$ is H, Cl, —CN, $C_{1-4}$ alkyl, $C_{1-3}$ fluoroalkyl, $C_{1-3}$ hydroxyalkyl, —$CR_z$=$CH_2$, $C_{3-6}$ cycloalkyl, —$CH_2(C_{3-6}$ cycloalkyl), —C(O)O($C_{1-3}$ alkyl), or tetrahydropyranyl; and Ring Het, $R_2$, $R_3$, $R_4$, $R_5$, m, n, and p are defined in the first aspect. Included in this embodiment are compounds in which $R_1$ is H, Cl, —CN, $C_{1-4}$ alkyl, $C_{1-2}$ fluoroalkyl, $C_{1-2}$ hydroxyalkyl, or —C(O)O($C_{1-2}$ alkyl). Also included in this embodiment are compounds in which $R_1$ is —$CH_3$, —$CH_2CH_3$, —$CH(CH_3)_2$, —$CH_2OH$, —$CH_2CHF_2$, or —C(O)O$CH_3$.

One embodiment provides a compound of Formula (I) or a salt thereof, wherein p is 1, 2, 3, or 4; and each $R_2$ is independently F, Cl, —CN, —OH, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, —$(CH_2)_{0-4}O(C_{1-4}$ alkyl), $C_{1-3}$ fluoroalkoxy, —$(CH_2)_{1-3}O$ $(C_{1-2}$ alkyl), —$O(CH_2)_{1-2}OC(O)(C_{1-2}$ alkyl), —$O(CH_2)_{1-2}$ $NR_xR_x$, —$C(O)O(C_{1-2}$ alkyl), —$C(O)NR_yR_y$, —$C(O)NR_x$ $(C_{1-4}$ hydroxyalkyl), —$C(O)NR_x(C_{2-4}$ alkoxyalkyl), —$C(O)$ $NR_x(C_{3-6}$ cycloalkyl), —$NR_yR_y$, —$NR_y(C_{1-3}$ fluoroalkyl), —$NR_y(C_{1-3}$ hydroxyalkyl), —$NR_xCH_2(phenyl)$, —$NR_xS$ $(O)_2(C_{3-6}$ cycloalkyl), —$NR_xC(O)(C_{1-3}$ alkyl), —$NR_x(CH_2$-cyclopropyl), —$S(O)_2(C_{1-3}$ alkyl), $C_{3-6}$ cycloalkyl, morpholinyl, dioxothiomorpholinyl, methylpiperidinyl, methylpiperazinyl, amino-oxadiazolyl, imidazolyl, triazolyl, or —$C(O)(thiazolyl)$; and $R_1$, $R_3$, $R_4$, $R_5$, $R_x$, $R_y$, m, and n are defined in the first aspect. Included in this embodiment are compounds in which each $R_2$ is independently F, Cl, —CN, —OH, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, $C_{1-4}$ alkoxy, —$NR_yR_y$, —$C(O)NR_yR_y$, —$C(O)NR_x(C_{1-4}$ hydroxyalkyl), —$C(O)$ $NR_x(C_{2-4}$ alkoxyalkyl), —$C(O)NR_x(C_{3-6}$ cycloalkyl), —$S(O)_2(C_{1-3}$ alkyl), $C_{3-6}$ cycloalkyl, morpholinyl, phenyl, or dimethyl pyrazolyl. Also included in this embodiment are compounds in which each $R_2$ is independently F, Cl, —CN, —OH, —$CH_3$, —$CH_2CH_3$, —$CH(CH_3)_2$, —$CH_2$ $CH(CH_3)_2$, —$CF_3$, —$CH_2OH$, —$C(CH_3)_2OH$, —$OCH_3$, —$OCH_2CH_3$, —$NH_2$, —$NH(CH_3)$, —$C(O)NH_2$, —$C(O)$ $NH(CH_3)$, —$C(O)N(CH_3)_2$, —$C(O)NH(CH_2CH_2OH)$, —$C(O)NH(CH_2CH_2OCH_3)$, —$C(O)NH(CH_2C(CH_3)_2OH)$, —$C(O)NH(cyclopropyl)$, —$C(O)N(CH_3)(CH_2CH_3)$, —$C(O)N(CH_3)(CH_2CH_2OH)$, —$S(O)_2CH_3$, phenyl, or dimethyl pyrazolyl.

One embodiment provides a compound of Formula (I) or a salt thereof, wherein p is 1, 2, 3, or 4; and each $R_2$ is independently halo, —CN, —OH, —$NO_2$, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, —$O(CH_2)_{1-2}OH$, —$(CH_2)_{0-4}O(C_{1-4}$ alkyl), $C_{1-3}$ fluoroalkoxy, —$(CH_2)_{1-4}O(C_{1-3}$ alkyl), —$O(CH_2)_{1-2}OC(O)$ $(C_{1-3}$ alkyl), —$O(CH_2)_{1-2}NR_xR_x$, —$C(O)O(C_{1-3}$ alkyl), —$C(O)NR_yR_y$, —$C(O)NR_x(C_{1-5}$ hydroxyalkyl), —$C(O)$ $NR_x(C_{2-6}$ alkoxyalkyl), —$C(O)NR_x(C_{3-6}$ cycloalkyl), —$NR_yR_y$, —$NR_y(C_{1-3}$ fluoroalkyl), —$NR_y(C_{1-4}$ hydroxyalkyl), —$NR_xCH_2(phenyl)$, —$NR_xS(O)_2(C_{3-6}$ cycloalkyl), —$NR_xC(O)(C_{1-3}$ alkyl), —$NR_x(CH_2$-cyclopropyl), or —$S(O)_2(C_{1-3}$ alkyl); and $R_1$, $R_3$, $R_4$, $R_5$, $R_x$, $R_y$, m, and n are defined in the first aspect. Included in this embodiment are compounds in which each $R_2$ is independently F, Cl, —CN, —OH, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, $C_{1-4}$ alkoxy, —$NR_yR_y$, —$C(O)NR_yR_y$, —$C(O)NR_x(C_{1-4}$ hydroxyalkyl), —$C(O)$ $NR_x(C_{2-4}$ alkoxyalkyl), —$C(O)NR_x(C_{3-6}$ cycloalkyl), or —$S(O)_2(C_{1-3}$ alkyl). Also included are compounds in which each $R_2$ is independently F, Cl, —CN, —OH, —$CH_3$, —$CH_2CH_3$, —$CH(CH_3)_2$, —$CH_2CH(CH_3)_2$, —$CF_3$, —$CH_2OH$, —$C(CH_3)_2OH$, —$OCH_3$, —$OCH_2CH_3$, —$NH_2$, —$NH(CH_3)$, —$C(O)NH_2$, —$C(O)NH(CH_3)$, —$C(O)N(CH_3)_2$, —$C(O)NH(CH_2CH_2OH)$, —$C(O)NH(CH_2CH_2OCH_3)$, —$C(O)NH(CH_2C(CH_3)_2OH)$, —$C(O)NH(cyclopropyl)$, —$C(O)N(CH_3)(CH_2CH_3)$, —$C(O)N(CH_3)(CH_2CH_2OH)$, or —$S(O)_2CH_3$.

One embodiment provides a compound of Formula (I) or a salt thereof, wherein p is 1 or 2; and each $R_2$ is independently $C_{3-6}$ cycloalkyl, phenyl, morpholinyl, dioxothiomorpholinyl, dimethyl pyrazolyl, methylpiperidinyl, methylpiperazinyl, amino-oxadiazolyl, imidazolyl, triazolyl, or —$C(O)(thiazolyl)$; and $R_1$, $R_3$, $R_4$, $R_5$, m, and n are defined in the first aspect. Included in this embodiment are compounds in which $C_{3-6}$ cycloalkyl, morpholinyl, phenyl, or dimethyl pyrazolyl. Also included in this embodiment are compounds in which phenyl, or dimethyl pyrazolyl. Additionally, included in this embodiment are compounds in which p is 1.

One embodiment provides a compound of Formula (I) or a salt thereof, wherein $R_1$ is —$CH_3$, —$CH_2CH_3$, —$CH(CH_3)_2$, —$CH_2OH$, —$CH_2CHF_2$, or —$C(O)OCH_3$; each $R_2$ is independently F, Cl, —CN, —OH, —$CH_3$, —$CH_2CH_3$, —$CH(CH_3)_2$, —$CH_2CH(CH_3)_2$, —$CF_3$, —$CH_2OH$, —$C(CH_3)_2OH$, —$OCH_3$, —$OCH_2CH_3$, —$NH_2$, —$NH(CH_3)$, —$C(O)NH_2$, —$C(O)NH(CH_3)$, —$C(O)N(CH_3)_2$, —$C(O)NH(CH_2CH_2OH)$, —$C(O)NH(CH_2CH_2OCH_3)$, —$C(O)NH(CH_2C(CH_3)_2OH)$, —$C(O)NH(cyclopropyl)$, —$C(O)N(CH_3)(CH_2CH_3)$, —$C(O)N(CH_3)(CH_2CH_2OH)$, —$S(O)_2CH_3$, phenyl, or dimethyl pyrazolyl; and $R_3$, $R_4$, $R_5$, m, n, and p are defined in the first aspect.

One embodiment provides a compound of Formula (I) or a salt thereof, wherein $R_3$ is (a) -$L_1$-A; or (b) H, $C_{1-6}$ alkyl, $C_{1-3}$ fluoroalkyl, $C_{1-3}$ cyanoalkyl, $C_{1-6}$ hydroxyalkyl, $C_{1-2}$ hydroxy-fluoroalkyl, —$(CR_xR_x)_{1-3}O(C_{1-3}$ alkyl), —$(CR_xR_x)_{1-4}O(CR_xR_x)_{1-3}O(C_{1-3}$ alkyl), —$CH_2CH(OH)$ $CH_2O(C_{1-3}$ alkyl), —$(CR_xR_x)_{1-3}S(C_{1-3}$ alkyl), —$(CH_2)_{1-3}C$ $(O)OC(CH_3)_3$, —$(CR_xR_x)_{0-3}NR_yR_y$, —$(CR_xR_x)_{0-3}NR_x(C_{1-4}$ hydroxyalkyl), —$CH_2CH(OH)CH_2NR_xR_y$, —$C(O)(C_{1-6}$ alkyl), —$C(O)(C_{1-4}$ hydroxyalkyl), —$C(O)(C_{1-3}$ fluoroalkyl), —$C(O)(C_{1-3}$ chloroalkyl), —$C(O)(C_{1-3}$ cyanoalkyl), —$(CR_xR_x)_{0-3}C(O)OH$, —$C(O)(CH_2)_{0-2}O(C_{1-4}$ alkyl), —$C(O)(CR_xR_x)_{0-2}O(CR_xR_x)_{1-2}O(C_{1-3}$ alkyl), —$C(O)$ $(CR_xR_x)_{0-2}O(CR_xR_x)_{1-2}NR_yR_y$, —$C(O)CR_xR_xS(O)_2(C_{1-3}$ alkyl), —$C(O)CR_xR_xNR_xS(O)_2(C_{1-3}$ alkyl), —$C(O)$ $CR_xR_xOC(O)(C_{1-3}$ alkyl), —$C(O)(CR_xR_x)_{0-3}NR_yR_y$, —$C(O)(CR_xR_x)_{0-1}NR_x(C_{1-3}$ cyanoalkyl), —$C(O)$ $(CR_xR_x)_{0-2}NR_x(C_{1-6}$ hydroxyalkyl), —$C(O)(CR_xR_x)_{0-2}NR_x$ $(C_{1-3}$ fluoroalkyl), —$C(O)(CR_xR_x)_{0-1}NR_x(C_{1-5}$ hydroxy-fluoroalkyl), —$C(O)(CR_xR_x)_{0-1}NR_x(CH_2)_{1-2}O(C_{1-3}$ hydroxyalkyl), —$C(O)(CR_xR_x)_{0-2}NR_x(CH_2)_{1-2}NR_xC(O)$ $(C_{1-2}$ alkyl), —$C(O)(CR_xR_x)_{0-2}NR_x((CR_xR_x)_{1-2}O(C_{1-2}$ alkyl)), —$C(O)(CR_xR_x)_{0-2}N((CR_xR_x)_{1-2}O(C_{1-2}$ alkyl))$_2$, —$C(O)(CR_xR_x)_{0-2}NR_x(CR_xR_x)_{1-3}NR_xR_x$, —$C(O)CR_x$ $(NH_2)(CR_xR_x)_{1-4}NR_xR_x$, —$C(O)CR_x(NH_2)(CR_xR_x)_{1-4}$ $NR_xC(O)NR_xR_x$, —$C(O)(CR_xR_x)_{0-3}NR_x(CH_2)_{0-1}C(O)(C_{1-3}$ alkyl), —$C(O)(CR_xR_x)_{0-3}N((CH_2)_{0-1}C(O)(C_{1-3}$ alkyl))$_2$, —$C(O)(CR_xR_x)_{0-1}NR_x(CH_2)_{0-1}C(O)(C_{1-3}$ cyanoalkyl), —$C(O)(CR_xR_x)_{0-2}NR_x(CH_2)_{1-2}C(O)NR_yR_y$, —$C(O)$ $(CR_xR_x)_{1-3}C(O)NR_yR_y$, —$C(O)(CR_xR_x)_{1-3}S(O)_2NR_yR_y$, —$C(O)(CR_xR_x)_{0-2}NR_x(CHR_y(CH_2OH))$, —$(CR_xR_x)_{1-2}C$ $(O)NR_yR_y$, —$CH(CN)C(O)NR_yR_y$, —$(CR_xR_x)_{1-2}C(O)NR_y$ $(C_{1-3}$ fluoroalkyl), —$(CR_xR_x)_{1-2}C(O)NR_y(C_{1-4}$ hydroxyalkyl), —$(CR_xR_x)_{1-2}C(O)NR_y(C_{1-3}$ cyanoalkyl), —$(CR_xR_x)_{1-2}C(O)NR_x(CH_2)_{1-2}O(C_{1-3}$ alkyl), —$(CR_xR_x)_{1-2}C(O)NR_xCH(C_{1-4}$ alkyl)$(C_{1-3}$ hydroxyalkyl), —$(CR_xR_x)_{1-2}C(O)NR_xCH(C_{1-3}$ hydroxyalkyl)$(C_{3-6}$ cycloalkyl), —$(CH_2)_{1-2}C(O)NR_x(CH_2)_{1-2}C(O)NR_xR_x$, —$(CH_2)_{1-2}C(O)NR_x(CH_2)_{1-2}S(C_{1-3}$ alkyl), —$(CH_2)_{1-2}C(O)$ $NR_x(CH_2)_{1-2}S(O)_2OH$, —$(CH_2)_{1-2}C(O)NR_x(CH_2)_{1-2}NR_xC$ $(O)(C_{1-3}$ alkyl), —$(CH_2)_{1-2}C(O)NR_x(CH_2)_{1-3}NR_xR_x$, —$(CH_2)_{1-2}C(O)N(CH_2CH_3)(CH_2)_{1-3}NR_xR_x$, —$(CR_xR_x)_{0-3}$ $S(O)_2(C_{1-4}$ alkyl), —$(CH_2)_{0-2}S(O)_2(C_{1-3}$ fluoroalkyl), —$(CR_xR_x)_{0-2}S(O)_2NR_yR_y$, —$(CR_xR_x)_{0-2}NR_xS(O)_2(C_{1-3}$ alkyl), or —$C(O)C(O)NR_y(CR_xR_x)_{1-2}NR_yR_y$; and $R_1$, $R_2$, $R_4$, $R_5$, $R_x$, $R_y$, $L_1$, A, m, n, and p are defined in the first embodiment. Included in this embodiment are compounds in which (a) -$L_1$-A; or (b) H, $C_{1-6}$ alkyl, $C_{1-3}$ fluoroalkyl, $C_{1-3}$ cyanoalkyl, $C_{1-5}$ hydroxyalkyl, —$(CR_xR_x)_{1-2}O(C_{1-2}$ alkyl), —$(CR_xR_x)_{1-4}O(CR_xR_x)_{1-3}O(C_{1-3}$ alkyl), —$CH_2CH(OH)$ $CH_2O(C_{1-3}$ alkyl), —$(CR_xR_x)_{1-3}S(C_{1-3}$ alkyl), —$(CH_2)_{1-3}C$ $(O)OC(CH_3)_3$, —$(CR_xR_x)_{0-3}NR_yR_y$, —$(CR_xR_x)_{0-3}NR_x(C_{1-4}$ hydroxyalkyl), —$CH_2CH(OH)CH_2NR_xR_y$, —$C(O)(C_{1-6}$ alkyl), —$C(O)(C_{1-4}$ hydroxyalkyl), —$C(O)(C_{1-3}$ fluoroalkyl), —C(O)($C_{1-3}$ chloroalkyl), —C(O)($C_{1-3}$ cyanoalkyl), —($CR_xR_x$)$_{0-3}$C(O)OH, —C(O)($CH_2$)$_{0-2}$O($C_{1-4}$ alkyl), —C(O)($CR_xR_x$)$_{0-2}$O($CR_xR_x$)$_{1-2}$($C_{1-3}$ alkyl), —C(O)($CH_2$)$_{0-2}$O($CH_2$)$_{1-2}$$NR_yR_y$, —C(O)$CR_xR_xS(O)_2$($C_{1-2}$ alkyl), —C(O)$CR_xR_xNR_xS(O)_2$($C_{1-2}$ alkyl), —C(O) $CR_xR_xOC(O)(C_{1-3}$ alkyl), —C(O)($CR_xR_x$)$_{0-2}$$NR_yR_y$, —C(O)($CR_xR_x$)$_{0-2}$$NR_x$($C_{1-2}$ cyanoalkyl), —C(O)($CR_xR_x$)$_{0-2}$$NR_x$($C_{1-2}$ hydroxyalkyl), —C(O)($CR_xR_x$)$_{0-2}$$NR_x$($C_{1-3}$ fluoroalkyl), —C(O)($CR_xR_x$)$_{0-1}$$NR_x$($C_{1-5}$ hydroxy-fluoroalkyl), —C(O)($CR_xR_x$)$_{0-1}$$NR_x$(($CR_xR_x$)$_{1-2}$O($C_{1-2}$ alkyl)), —C(O)($CR_xR_x$)$_{0-1}$$NR_x$($CH_2$)$_{1-2}$O($C_{1-3}$ hydroxyalkyl), —C(O)($CR_xR_x$)$_{0-1}$$NR_x$($CH_2$)$_{1-2}$$NR_xC(O)(C_{1-2}$ alkyl), —C(O)($CR_xR_x$)$_{0-2}$$NR_x$(($CR_xR_x$)$_{1-2}$($C_{1-2}$ alkyl)), —C(O)($CR_xR_x$)$_{0-1}$$NR_x$($CR_xR_x$)$_{1-3}$$NR_xR_x$, —C(O)$CR_x$(NH$_2$)($CR_xR_x$)$_{1-4}$$NR_xR_x$, —C(O)$CR_x$(NH$_2$)($CR_xR_x$)$_{1-4}$$NR_xC(O)NR_xR_x$, —C(O)($CR_xR_x$)$_{0-3}$$NR_x$($CH_2$)$_{0-1}$C(O)($C_{1-3}$ alkyl), —C(O)($CR_xR_x$)$_{0-1}$$NR_x$($CH_2$)$_{0-1}$C(O)($C_{1-3}$ cyanoalkyl), —C(O)($CR_xR_x$)$_{0-2}$$NR_x$($CH_2$)$_{1-2}$C(O)$NR_yR_y$, —C(O)($CR_xR_x$)$_{0-2}$$NR_x$(CHR$_y$(CH$_2$OH)), —($CR_xR_x$)$_{1-2}$C(O)$NR_yR_y$, —($CR_xR_x$)$_{1-2}$C(O)$NR_y$($C_{1-3}$ fluoroalkyl), —($CR_xR_x$)$_{1-2}$C(O)$NR_y$($C_{1-4}$ hydroxyalkyl), —($CR_xR_x$)$_{1-2}$C(O)$NR_x$($C_{1-3}$ cyanoalkyl), —CH(CN)C(O)$NR_yR_y$, —($CR_xR_x$)$_{1-2}$C(O)$NR_x$($CH_2$)$_{1-2}$O($C_{1-3}$ alkyl), —($CR_xR_x$)$_{1-2}$C(O)$NR_x$CH($C_{1-4}$ alkyl)($C_{1-3}$ hydroxyalkyl), —($CH_2$)$_{1-2}$C(O)$NR_x$($CH_2$)$_{1-2}$C(O)$NR_xR_x$, —($CH_2$)$_{1-2}$S(O)$_2$$NR_x$($CH_2$)$_{1-2}$S($C_{1-2}$ alkyl), —($CH_2$)$_{1-2}$C(O)$NR_x$($CH_2$)$_{1-2}$S(O)$_2$OH, —($CH_2$)$_{1-2}$C(O)$NR_x$($CH_2$)$_{1-2}$$NR_xC(O)(C_{1-3}$ alkyl), —($CH_2$)$_{1-2}$C(O)$NR_x$($CH_2$)$_{1-3}$$NR_xR_x$, —($CH_2$)$_{1-2}$C(O)N(CH$_2$CH$_3$)(CH$_2$)$_{1-3}$$NR_xR_x$, —($CR_xR_x$)$_{1-3}$S(O)$_2$($C_{1-4}$ alkyl), —($CH_2$)$_{0-2}$S(O)$_2$($C_{1-3}$ fluoroalkyl), —($CH_2$)$_{1-2}$S(O)$_2$$NR_yR_y$, or —C(O)C(O)$NR_y$($CR_xR_x$)$_{1-2}$$NR_yR_y$. Also included in this embodiment are compounds in which R$_3$ is: (a) -L$_1$-A; or (b) H, —CH$_3$, —CH(CH$_3$)$_2$, —CH$_2$CH$_2$CH$_3$, —CH$_2$CH(CH$_3$)$_2$, —CH$_2$CH$_2$CF$_3$, —CH$_2$CH$_2$CH$_2$CF$_3$, —CH$_2$CN, —CH$_2$CH$_2$CN, —CH$_2$C(CH$_3$)$_2$OH, —CH(CH$_2$OH)$_2$, —CH$_2$CH$_2$OCH$_3$, —CH(CH$_2$OH)(CH$_2$OCH$_3$), —CH$_2$CH$_2$NH$_2$, —CH$_2$CH$_2$NH(CH$_3$), —CH$_2$CH$_2$N(CH$_2$CH$_3$)$_2$, —CH$_2$CH$_2$CH$_2$N(CH$_3$)$_2$, —CH$_2$CH(CH$_3$)CH$_2$N(CH$_3$)$_2$, —CH$_2$C(CH$_3$)$_2$CH$_2$N(CH$_3$)$_2$, —CH$_2$CH$_2$NH(S(O)$_2$CH$_3$, —CH$_2$CH$_2$S(O)$_2$CH$_3$, —CH$_2$CH$_2$CH$_2$S(O)$_2$CH$_3$, —CH$_2$CH$_2$S(O)$_2$NH$_2$, —CH$_2$C(O)NH$_2$, —CH$_2$C(O)NH(CH$_3$), —CH$_2$C(O)N(CH$_3$)$_2$, —CH$_2$C(O)NH(CF$_3$), —C(O)CH$_2$CH(CH$_3$)OH, —C(O)CH$_2$C(CH$_3$)$_2$OH, —C(O)CH$_2$NH$_2$, —C(O)CH$_2$NH(CH$_3$), —C(O)CH$_2$NH(CH(CH$_3$)$_2$), —C(O)CH$_2$N(CH$_3$)$_2$, —C(O)CH$_2$N(CH$_3$)(CH(CH$_3$)$_2$), —C(O)CH$_2$NH(CH$_2$C(CH$_3$)$_3$), —C(O)CH$_2$NH(CH(CH$_3$)CH$_2$CH$_3$), —C(O)CH$_2$NH(CH$_2$CH$_2$CH$_2$N(CH$_3$)$_2$), —C(O)CH$_2$N(CH$_3$)(CH$_2$CH(CH$_3$)$_2$), —C(O)CH$_2$CH$_2$N(CH$_3$)$_2$, —C(O)CH$_2$CH$_2$N(CH$_3$)(CH$_2$CH$_3$), —C(O)CH$_2$CH$_2$N(CH$_3$)(CH(CH$_3$)$_2$), —C(O)CH$_2$CH(CH$_3$)NH$_2$, —C(O)CH$_2$NHC(O)CH$_3$, —C(O)CH$_2$CH$_2$C(O)N(CH$_3$)$_2$, —C(O)CH$_2$NH(CH$_2$CH$_2$NHC(O)CH$_3$), —C(O)CH$_2$S(O)$_2$CH$_3$, —S(O)$_2$CH$_2$CH$_2$OH, or —S(O)$_2$CH$_2$CH$_2$N(CH$_3$)$_2$.

One embodiment provides a compound of Formula (I) or a salt thereof, wherein R$_3$ is -L$_1$-A; and R$_1$, R$_2$, R$_4$, R$_5$, L$_1$, A, m, n, and p are defined in the first aspect. Included in this embodiment are compounds in which L$_1$ is a bond, —($CR_xR_x$)$_{1-2}$—, —($CR_xR_x$)$_{1-2}$$CR_x$(OH)—, —($CR_xR_x$)$_{1-2}$O—, —$CR_xR_x$C(O)—, —($CR_xR_x$)$_2$$NR_x$($CR_xR_x$)$_{0-1}$—, —$CR_xR_x$C(O)$NR_x$($CR_xR_x$)$_{0-4}$—, —C(O)($CR_xR_x$)$_{0-3}$—, —C(O)($CR_xR_x$)$_{0-2}$$NR_x$($CR_xR_x$)$_{0-2}$—, —C(O)($CR_xR_x$)$_{0-2}$N($C_{1-2}$ hydroxyalkyl)($CR_xR_x$)$_{0-2}$—, —C(O)($CR_xR_x$)$_{0-2}$$NR_x$($CR_xR_x$)$_{1-2}$$CR_x$(OH)—, —C(O)($CR_xR_x$)$_{1-2}$C(O)$NR_x$—, —($CR_xR_x$)$_{0-2}$C(O)$NR_x$($CR_xR_x$)$_{1-2}$$CR_x$(OH)—, —($CR_xR_x$)$_{0-2}$C(O)N($C_{1-2}$ hydroxyalkyl)($CR_xR_x$)$_{1-2}$—, —C(O)($CR_xR_x$)$_{0-1}$O—, —C(O)($CR_xR_x$)$_{1-2}$NHS(O)$_2$—, —C(O)$CR_x$(NH$_2$)$CR_xR_x$—, —C(O)C(O)($CR_xR_x$)$_{0-2}$—, —C(O)$NR_x$($CR_xR_x$)$_{1-2}$—, or —S(O)$_2$—. Also included in this embodiment are compounds in which L$_1$ is a bond, —CH$_2$—, —CH$_2$CH$_2$—, —CH$_2$CH$_2$CH$_2$—, —CH$_2$C(O)—, —C(O)—, —C(O)CH$_2$—, —C(O)CH$_2$CH$_2$—, —C(O)CH$_2$NH—, —C(O)CH$_2$N(CH$_3$)—, —C(O)CH$_2$CH$_2$N(CH$_3$)—, or —C(O)CH$_2$NHCH$_2$C(CH$_3$)$_2$—.

One embodiment provides a compound of Formula (I) or a salt thereof, wherein R$_3$ is -L$_1$-A; L$_1$ is a bond, —CH$_2$—, —CH$_2$CH$_2$—, —CH$_2$CH$_2$CH$_2$—, —CH$_2$C(O)—, —C(O)—, —C(O)CH$_2$—, —C(O)CH$_2$CH$_2$—, —C(O)CH$_2$NH—, —C(O)CH$_2$N(CH$_3$)—, —C(O)CH$_2$CH$_2$N(CH$_3$)—, or —C(O)CH$_2$NHCH$_2$C(CH$_3$)$_2$—; A is (1R,5S)-3-oxa-8-azabicyclo[3.2.1]octanyl, (1R,5S)-8-oxa-3-azabicyclo[3.2.1]octanyl, 1,1-dioxidothiomorpholinyl, 1,2-dioxotetrahydro-2H-thiopyranyl, 1,4-diazepanyl, 2-azabicyclo[3.1.0]hexanyl, azabicyclo[3.2.1]octanyl, 2-oxa-6-azaspiro[3.3]heptanyl, azepanyl, cyclohexyl, cyclopropyl, imidazo[1,2-a]pyridinyl, imidazo[1,5-a]pyridinyl, imidazolyl, isoxazolyl, morpholinyl, oxadiazolyl, oxazolyl, oxetanyl, phenyl, piperazinonyl, piperazinyl, piperidinonyl, piperidinyl, pyrazolyl, pyridinyl, pyrimidinyl, pyrrolidinonyl, pyrrolidinyl, quinolinyl, tetrahydropyranyl, thiadiazolyl, thiazolyl, or triazolyl, each substituted with zero to 4 substituents independently selected from F, Cl, —OH, —CH$_3$, —CH$_2$H$_3$, —CH(CH$_3$)$_2$, —CH$_2$CH$_2$CH$_3$, —CH$_2$CH(CH$_3$)$_2$, —CH$_2$OH, —CH$_2$N(CH$_3$)$_2$, —OCH$_3$, —OCH$_2$CH$_2$CH$_2$N(CH$_3$)$_2$, —OCH$_2$CH$_2$N(CH$_3$)(pyridinyl), —C(O)CH$_3$, —C(O)OCH$_3$, —C(O)OCH$_2$CH$_3$, —C(O)NH$_2$, —C(O)N(CH$_2$CH$_3$)$_2$, —NH$_2$, —N(CH$_3$)$_2$, —NHC(O)CH$_3$, —O(pyrimidinyl), morpholinyl, phenyl, methyl piperazinyl, pyridinyl, and pyrrolidinyl; and R$_1$, R$_2$, R$_4$, R$_5$, m, n, and p are defined in the first aspect.

One embodiment provides a compound of Formula (I) or a salt thereof, wherein R$_3$ is -L$_1$-A; L$_1$ is a bond, —CH$_2$—, —CH$_2$CH$_2$—, —CH$_2$CH$_2$CH$_2$—, —CH$_2$C(O)—, —C(O)—, —C(O)CH$_2$—, —C(O)CH$_2$CH$_2$—, —C(O)CH$_2$NH—, —C(O)CH$_2$N(CH$_3$)—, —C(O)CH$_2$CH$_2$N(CH$_3$)—, or —C(O)CH$_2$NHCH$_2$C(CH$_3$)$_2$—; A is azepanyl, cyclohexyl, cyclopropyl, imidazo[1,2-a]pyridinyl, imidazo[1,5-a]pyridinyl, imidazolyl, isoxazolyl, morpholinyl, oxadiazolyl, oxazolyl, oxetanyl, phenyl, piperazinonyl, piperazinyl, piperidinonyl, piperidinyl, pyrazolyl, pyridinyl, pyrimidinyl, pyrrolidinonyl, pyrrolidinyl, quinolinyl, tetrahydropyranyl, thiadiazolyl, thiazolyl, or triazolyl, each substituted with zero to 4 substituents independently selected from F, Cl, —OH, —CH$_3$, —CH$_2$H$_3$, —CH(CH$_3$)$_2$, —CH$_2$CH$_2$CH$_3$, —CH$_2$CH(CH$_3$)$_2$, —CH$_2$OH, —CH$_2$N(CH$_3$)$_2$, —OCH$_3$, —OCH$_2$CH$_2$CH$_2$N(CH$_3$)$_2$, —OCH$_2$CH$_2$N(CH$_3$)(pyridinyl), —C(O)CH$_3$, —C(O)OCH$_3$, —C(O)OCH$_2$CH$_3$, —C(O)NH$_2$, —C(O)N(CH$_2$CH$_3$)$_2$, —NH$_2$, —N(CH$_3$)$_2$, —NHC(O)CH$_3$, —O(pyrimidinyl), morpholinyl, phenyl, methyl piperazinyl, pyridinyl, and pyrrolidinyl; and R$_1$, R$_2$, R$_4$, R$_5$, m, n, and p are defined in the first aspect.

One embodiment provides a compound of Formula (I) or a salt thereof, wherein each R$_4$ is independently F, —OH, $C_{1-2}$ alkyl, or —OCH$_3$; and R$_1$, R$_2$, R$_3$, R$_5$, m, n, and p are defined in the first aspect. Included in this embodiment are compounds in which each R$_4$ is independently F or —OH.

One embodiment provides a compound of Formula (I) or a salt thereof, wherein two R$_4$ attached to the same carbon atom form =O; and R$_1$, R$_2$, R$_3$, R$_5$, n, and p are defined in the first aspect.

One embodiment provides a compound of Formula (I) or a salt thereof, wherein m is at least 2; two R$_4$, each attached to a different carbon atom adjacent to the nitrogen atom in the piperidinyl ring, form a —CH$_2$CH$_2$— bridge; and R$_1$, R$_2$, R$_3$, R$_5$, n, and p are defined in the first aspect.

One embodiment provides a compound of Formula (I) or a salt thereof, wherein each $R_5$ is independently F, Cl, —CN, $C_{1-2}$ alkyl, —$CF_3$, or —$OCH_3$; and $R_1$, $R_2$, $R_3$, $R_4$, m, n, and p are defined in the first aspect. Included in this embodiment are compounds in which each $R_5$ is independently F, Cl, —CN, $C_{1-2}$ alkyl, or —$OCH_3$. Also included in this embodiment are compounds in which each $R_5$ is independently F, Cl, —$CH_3$, —$CF_3$, or —$OCH_3$.

One embodiment provides a compound of Formula (I) or a salt thereof, wherein m is zero, 1, 2, or 3; and $R_1$, $R_2$, $R_3$, $R_4$, $R_5$, n, and p are defined in the first aspect. Included in this embodiment are compounds in which m is zero, 1, or 2. Also included are compounds in which m is zero or 1. Additionally, included in this embodiment are compounds in which m is zero.

One embodiment provides a compound of Formula (I) or a salt thereof, wherein n is zero, 1, or 2; and $R_1$, $R_2$, $R_3$, $R_4$, $R_5$, m, and p are defined in the first aspect. Included in this embodiment are compounds in which n is zero or 1. Additionally, included in this embodiment are compounds in which n is zero.

One embodiment provides a compound of Formula (I) or a salt thereof, wherein p is zero, 1, 2, or 3; and $R_1$, $R_2$, $R_3$, $R_4$, $R_5$, m, and n are defined in the first aspect. Included in this embodiment are compounds in which p is zero, 1, or 2. Also included are compounds in which p is zero or 1. Additionally, included in this embodiment are compounds in which p is zero.

One embodiment provides a compound of Formula (I) or a salt thereof, wherein m is zero or 1; n is zero or 1; and $R_1$, $R_2$, $R_3$, $R_4$, $R_5$, and p are defined in the first aspect. Included in this embodiment are compounds in which m is zero and n is zero.

One embodiment provides a compound of Formula (I) or a salt thereof, wherein said compound is selected from 4-(3-isopropyl-5-(piperidin-4-yl)-1H-indol-2-yl)-1H-pyrrolo[2,3-b]pyridine (1); 4-(3-methyl-5-(piperidin-4-yl)-1H-indol-2-yl)-1H-pyrrolo[2,3-b]pyridine (2); 4-(3-isopropyl-5-(piperidin-4-yl)-1h-indol-2-yl)-1-(methylsulfonyl)-1h-pyrrolo[2,3-b] pyridine (3); 3-methyl-4-(3-methyl-5-(piperidin-4-yl)-1H-indol-2-yl)-1H-pyrrolo[2,3-b] pyridine (4); 6-(3-isopropyl-5-(piperidin-4-yl)-1H-indol-2-yl)benzo[d]isoxazol-3-ol (5); 6-(3-isopropyl-5-(piperidin-4-yl)-1H-indol-2-yl)-2-methylbenzo[d]oxazole (6); 5-(3-isopropyl-5-(piperidin-4-yl)-1H-indol-2-yl)benzo[d]isoxazol-3-amine (7); 8-(3-isopropyl-5-(piperidin-4-yl)-1H-indol-2-yl)-9H-purin-6-amine (8); 6-(3-isopropyl-5-(piperidin-4-yl)-1H-indol-2-yl) benzo[d]thiazole (9); 6-(3-isopropyl-5-(piperidin-4-yl)-1H-indol-2-yl)benzo[d]oxazol-2(3H)-one (10); 5-(3-isopropyl-5-(piperidin-4-yl)-1H-indol-2-yl)benzo[d]oxazol-2(3H)-one (11); 5-(3-isopropyl-5-(piperidin-4-yl)-1H-indol-2-yl)benzo[d]thiazole (12); 5-(3-isopropyl-5-(piperidin-4-yl)-1H-indol-2-yl)-7H-pyrrolo[2,3-d]pyrimidine (13); 3-(3-isopropyl-5-(piperidin-4-yl)-1H-indol-2-yl)-1H-pyrrolo[3,2-c]pyridine (14); 3-(3-isopropyl-5-(piperidin-4-yl)-1H-indol-2-yl)-1H-pyrrolo[2,3-c]pyridine (15); 6-(3-isopropyl-5-(piperidin-4-yl)-1H-indol-2-yl)oxazolo[4,5-b]pyridin-2(3H)-one (16); 3-(3-isopropyl-5-(piperidin-4-yl)-1H-indol-2-yl)-1H-pyrrolo[2,3-b]pyridine (17); 3-(3-isopropyl-5-(piperidin-4-yl)-1H-indol-2-yl)-1H-pyrazolo[3,4-b]pyridine (18); 3-(3-isopropyl-5-(piperidin-4-yl)-1H-indol-2-yl)-1H-pyrrolo[3,2-b]pyridine (19); 3-(3-isopropyl-5-(piperidin-4-yl)-1H-indol-2-yl)furo[3,2-b] pyridine (20); 3-(3-isopropyl-5-(piperidin-4-yl)-1H-indol-2-yl)-1,5-dihydro-4H-pyrazolo[3,4-d]pyrimidin-4-one (21); 4-(3-isopropyl-5-(piperidin-4-yl)-1H-indol-2-yl)-1,5-naphthyridine (22); 7-(3-methyl-5-(piperidin-4-yl)-1H-indol-2-yl)-1H-pyrrolo[3,2-b]pyridine (23); 6-(3-isopropyl-5-(piperidin-4-yl)-1H-indol-2-yl)imidazo[1,2-b]pyridazin-2-amine (24); 3-(3-ethyl-5-(piperidin-4-yl)-1H-indol-2-yl)-5-methoxyimidazo[1,2-a]pyrazine (25); 6-(3-ethyl-5-(piperidin-4-yl)-1H-indol-2-yl)-[1,2,4]triazolo[1,5-a]pyrimidine (26); 6-(3-isopropyl-5-(piperidin-4-yl)-1H-indol-2-yl)imidazo[1,2-b]pyridazine (27); 3-(3-ethyl-5-(piperidin-4-yl)-1H-indol-2-yl)imidazo[1,2-a]pyrazine (28); 3-(3-ethyl-5-(piperidin-4-yl)-1H-indol-2-yl)imidazo[1,2-a]pyrimidine (29); 6-(3-isopropyl-5-(piperidin-4-yl)-1H-indol-2-yl)-8-methyl-[1,2,4]triazolo[1,5-b]pyridazine (30); 6-(3-isopropyl-5-(piperidin-4-yl)-1H-indol-2-yl)-7-methyl-[1,2,4]triazolo[1,5-b]pyridazine (31); 6-(3-isopropyl-5-(piperidin-4-yl)-1H-indol-2-yl)-7,8-dimethyl-[1,2,4]triazolo[1,5-b]pyridazine (32); 6-(3-isopropyl-5-(piperidin-4-yl)-1H-indol-2-yl)-8-methoxy-7-methyl-[1,2,4]triazolo[1,5-b]pyridazine (33); 6-(3-isopropyl-5-(piperidin-4-yl)-1H-indol-2-yl)-[1,2,4]triazolo[4,3-a]pyrazin-8-ol (34); 3-(3-isopropyl-5-(piperidin-4-yl)-1H-indol-2-yl)-1,4-dimethyl-1H-pyrrolo[2,3-b]pyridine (35); 3-(3-isopropyl-5-(piperidin-4-yl)-1H-indol-2-yl)-4-methyl-1H-pyrrolo[2,3-b]pyridine (36); 3-(3-isopropyl-5-(piperidin-4-yl)-1H-indol-2-yl)-1,2-dimethyl-1H-pyrrolo[2,3-b]pyridine (37); 6-(3-isopropyl-5-(piperidin-4-yl)-1H-indol-2-yl)-8-methoxy-[1,2,4]triazolo[1,5-b]pyridazine (38); 3-chloro-4-(3-ethyl-5-(piperidin-4-yl)-1H-indol-2-yl)-1H-pyrrolo[2,3-b]pyridine (39); 7-(3-isopropyl-5-(piperidin-4-yl)-1H-indol-2-yl)-2,5-dimethyl-1H-pyrrolo[3,2-b]pyridine (40); 7-(3-ethyl-5-(piperidin-4-yl)-1H-indol-2-yl)-1-methyl-1H-pyrazolo[4,3-b]pyridine (41); 7-(3-isopropyl-5-(piperidin-4-yl)-1H-indol-2-yl)-1-methyl-1H-pyrazolo[4,3-b]pyridine (42); 7-(3-isopropyl-5-(piperidin-4-yl)-1H-indol-2-yl)-1-methyl-1H-pyrazolo[4,3-b]pyridine (43); 7-(3-isopropyl-5-(piperidin-4-yl)-1H-indol-2-yl)-3-methyl-3H-imidazo[4,5-b]pyridine (44); 7-(3-isopropyl-5-(piperidin-4-yl)-1H-indol-2-yl)-3-methyl-3H-imidazo[4,5-b]pyridine (45); 4-(3-isopropyl-5-(piperidin-4-yl)-1H-indol-2-yl)-5-methyl-1H-pyrazolo[3,4-b]pyridine (46); 6-(3-isopropyl-5-(piperidin-4-yl)-1H-indol-2-yl)-8-methoxy-[1,2,4]triazolo[1,5-a]pyrazine (47); 3-(3-isopropyl-5-(piperidin-4-yl)-1H-indol-2-yl)-1-methyl-1H-pyrrolo[2,3-b]pyridine (48); 7-(3-isopropyl-5-(piperidin-4-yl)-1H-indol-2-yl)-5-methyl-1H-pyrazolo[4,3-b]pyridine (49); 5-(3-isopropyl-5-(piperidin-4-yl)-1H-indol-2-yl)-1H-benzo[d]imidazole (50); 5-(3-isopropyl-5-(piperidin-4-yl)-1H-indol-2-yl)-1H-benzo[d][1,2,3]triazole (51); 5-(3-methyl-5-(piperidin-4-yl)-1H-indol-2-yl)-1H-benzo[d][1,2,3]triazole (52); 5-(3-ethyl-5-(piperidin-4-yl)-1H-indol-2-yl)-1H-pyrazolo[3,4-b]pyridine (53); 7-(3-isopropyl-5-(piperidin-4-yl)-1H-indol-2-yl)-1H-pyrazolo[4,3-b]pyridine (54); 7-(3-methyl-5-(piperidin-4-yl)-1H-indol-2-yl)-1H-pyrazolo [4,3-b]pyridine (55); 7-(3-ethyl-5-(piperidin-4-yl)-1H-indol-2-yl)-1H-[1,2,3]triazolo [4,5-b] pyridine (56); 7-(3-isopropyl-5-(piperidin-4-yl)-1H-indol-2-yl)-1,3-dihydro-2H-imidazo[4,5-b]pyridin-2-one (57); 7-(3-isopropyl-5-(piperidin-4-yl)-1H-indol-2-yl)oxazolo[4,5-b]pyridin-2(3H)-one (58); 7-(3-ethyl-5-(piperidin-4-yl)-1H-indol-2-yl)-3H-imidazo[4,5-b]pyridine (59); 7-(3-methyl-5-(piperidin-4-yl)-1H-indol-2-yl)-3H-imidazo[4,5-b]pyridine (60); 7-(3-isopropyl-5-(piperidin-4-yl)-1H-indol-2-yl)-3H-imidazo[4,5-b]pyridine (61); 6-(3-ethyl-5-(piperidin-4-yl)-1H-indol-2-yl)-1H-pyrazolo[4,3-b]pyridine (62); 6-(3-isopropyl-5-(piperidin-4-yl)-1H-indol-2-yl)-1H-pyrazolo[4,3-b]pyridine (63); 3-(3-isopropyl-5-(piperidin-4-yl)-1H-indol-2-yl)imidazo[1,2-a]pyrimidine (64); 3-isopropyl-5-(piperidin-4-yl)-1H,1'H-2,6'-biindole (65); 3-isopropyl-5-(piperidin-4-yl)-1H,1'H-2,5'-biindole (66); 2-(benzofuran-5-yl)-3-isopropyl-5-(piperidin-4-yl)-1H-indole (67); 8-(3-isopropyl-5-(piperidin-4-yl)-1H-indol-2-yl)-

1H-pyrido[2,3-b][1,4]oxazin-2(3H)-one (68); 4-(3-isopropyl-5-(piperidin-4-yl)-1H-indol-2-yl)-1,3-dihydro-2H-pyrrolo[2,3-b]pyridin-2-one (69); 6-(3-isopropyl-5-(piperidin-4-yl)-1H-indol-2-yl)-4-methyl-[1,2,3]triazolo[1,5-a]pyridine (70); (6-(3-isopropyl-5-(piperidin-4-yl)-1H-indol-2-yl)tetrazolo[1,5-a]pyridin-8-yl)methanol (71); 6-(3-isopropyl-5-(piperidin-4-yl)-1H-indol-2-yl)-5-methyltetrazolo[1,5-a]pyridine (72); 6-(3-isopropyl-5-(piperidin-4-yl)-1H-indol-2-yl)-7,8-dimethyltetrazolo[1,5-a]pyridine (73); 6-(3-isopropyl-5-(piperidin-4-yl)-1H-indol-2-yl)-5,8-dimethyltetrazolo[1,5-a]pyridine (74); 6-(3-isopropyl-5-(piperidin-4-yl)-1H-indol-2-yl)-8-methyltetrazolo[1,5-a]pyridine (75); 6-(3-isopropyl-5-(piperidin-4-yl)-1H-indol-2-yl)-7-methyltetrazolo[1,5-a]pyridine (76); 5-(3-isopropyl-5-(piperidin-4-yl)-1H-indol-2-yl)-3-methyl-[1,2,3]triazolo[1,5-a]pyridine (77); 5-(3-isopropyl-5-(piperidin-4-yl)-1H-indol-2-yl)-7-methyl-[1,2,3]triazolo[1,5-a]pyridine (78); 6-(3-isopropyl-5-(piperidin-4-yl)-1H-indol-2-yl)-[1,2,3]triazolo[1,5-a]pyridine (79); 6-(3-isopropyl-5-(piperidin-4-yl)-1H-indol-2-yl)tetrazolo[1,5-a]pyridine (80); 5-(3-isopropyl-5-(piperidin-4-yl)-1H-indol-2-yl)-[1,2,3]triazolo[1,5-a]pyridine (81); 7-(3-isopropyl-5-(piperidin-4-yl)-1H-indol-2-yl)tetrazolo[1,5-a]pyridine (82); 7-(3-isopropyl-5-(piperidin-4-yl)-1H-indol-2-yl)-[1,2,4]triazolo[4,3-a]pyridine (83); 6-(3-isopropyl-5-(piperidin-4-yl)-1H-indol-2-yl)-1H-indazol-3-amine (84); 6-(3-ethyl-5-(piperidin-4-yl)-1H-indol-2-yl)-1H-indazol-3-ol (85); 6-(3-isopropyl-5-(piperidin-4-yl)-1H-indol-2-yl)benzo[d]isoxazol-3-amine (86); 6-(3-isopropyl-5-(piperidin-4-yl)-1H-indol-2-yl)-8-methylquinoxalin-2-ol (87); 7-(3-isopropyl-5-(piperidin-4-yl)-1H-indol-2-yl)-5-methylquinoxaline (88); 6-(3-isopropyl-5-(piperidin-4-yl)-1H-indol-2-yl)-3-methylbenzo[d]oxazol-2(3H)-one (89); 5-(3-isopropyl-5-(piperidin-4-yl)-1H-indol-2-yl)-3,7-dimethylbenzo[d]oxazol-2(3H)-one (90); 5-(3-isopropyl-5-(piperidin-4-yl)-1H-indol-2-yl)-7-methylbenzo[d]oxazol-2(3H)-one (91); 5-(3-isopropyl-5-(piperidin-4-yl)-1H-indol-2-yl)-2,7-dimethylbenzo[d]oxazole (92); 5-(3-isopropyl-5-(piperidin-4-yl)-1H-indol-2-yl)-1H-indazol-3-amine (93); 5-(3-isopropyl-5-(piperidin-4-yl)-1H-indol-2-yl)-1,4-dimethyl-1H-indazole (94); 5-(3-ethyl-5-(piperidin-4-yl)-1H-indol-2-yl)benzo[d]isoxazol-3-amine (95); 5-(3-isopropyl-5-(piperidin-4-yl)-1H-indol-2-yl)-1-methyl-1H-pyrazolo[3,4-b]pyridine (96); 5-(3-ethyl-5-(piperidin-4-yl)-1H-indol-2-yl)-1-methyl-1H-pyrazolo[3,4-c]pyridine (97); 5-(3-ethyl-5-(piperidin-4-yl)-1H-indol-2-yl)-2-methyl-2H-pyrazolo[3,4-c]pyridine (98); 5-(3-isopropyl-5-(piperidin-4-yl)-1H-indol-2-yl)-1H-pyrazolo[3,4-b]pyridin-3-amine (99); 4-(3-ethyl-5-(piperidin-4-yl)-1H-indol-2-yl)-1-methyl-1H-indazole (100); 5-(3-isopropyl-5-(piperidin-4-yl)-1H-indol-2-yl)-7-methylthiazolo[5,4-b]pyridine (101); 6-(3-ethyl-5-(piperidin-4-yl)-1H-indol-2-yl)imidazo[1,2-b]pyridazine-3-carbonitrile (102); 6-(3-ethyl-5-(piperidin-4-yl)-1H-indol-2-yl)-3-methylimidazo[1,2-b]pyridazine (103); 4-(3-isopropyl-5-(piperidin-4-yl)-1H-indol-2-yl)-2-methylquinoline (104); 4-(3-isopropyl-5-(piperidin-4-yl)-1H-indol-2-yl)-2-methoxyquinoline (105); 7-chloro-4-(3-isopropyl-5-(piperidin-4-yl)-1H-indol-2-yl)-1H-indazole (106); 4-hydroxy-6-(3-isopropyl-5-(piperidin-4-yl)-1H-indol-2-yl)-8-methylquinoline-3-carbonitrile (107); 3-(3-ethyl-5-(piperidin-4-yl)-1H-indol-2-yl)-7-methylimidazo[1,2-b]pyridazine (108); 5-(3-isopropyl-5-(piperidin-4-yl)-1H-indol-2-yl)quinoline-8-carbonitrile (109); 6-(3-isopropyl-5-(piperidin-4-yl)-1H-indol-2-yl)-7-methylimidazo[1,2-a]pyridine (110); 6-(3-isopropyl-5-(piperidin-4-yl)-1H-indol-2-yl)-5-methylimidazo[1,2-a]pyridine (111); 6-(3-isopropyl-5-(piperidin-4-yl)-1H-indol-2-yl)-8-methylimidazo[1,2-a]pyridine (112); 6-(3-isopropyl-5-(piperidin-4-yl)-1H-indol-2-yl)-7-methylimidazo[1,2-a]pyridine (113); 6-(3-isopropyl-5-(piperidin-4-yl)-1H-indol-2-yl)-3-methylimidazo[1,2-a]pyridine (114); 6-(3-isopropyl-5-(piperidin-4-yl)-1H-indol-2-yl)-2-methylimidazo[1,2-a]pyridine (115); 6-(3-isopropyl-5-(piperidin-4-yl)-1H-indol-2-yl)imidazo[1,2-a]pyridin-2-amine (116); 6-(3-isopropyl-5-(piperidin-4-yl)-1H-indol-2-yl)imidazo[1,2-a]pyridin-8-amine (117); 8-fluoro-6-(3-isopropyl-5-(piperidin-4-yl)-1H-indol-2-yl)imidazo[1,2-a]pyridine (118); 6-(3-isopropyl-5-(piperidin-4-yl)-1H-indol-2-yl)imidazo[1,2-a]pyridine-3-carbonitrile (119); 6-(3-isopropyl-5-(piperidin-4-yl)-1H-indol-2-yl)-2,8-dimethylimidazo[1,2-a]pyridine (120); 6-(3-isopropyl-5-(piperidin-4-yl)-1H-indol-2-yl)-3,8-dimethylimidazo[1,2-a]pyridine (121); 6-(3-isopropyl-5-(piperidin-4-yl)-1H-indol-2-yl)-2,7-dimethylimidazo[1,2-a]pyridine (122); 6-(3-isopropyl-5-(piperidin-4-yl)-1H-indol-2-yl)-2,5-dimethylimidazo[1,2-a]pyridine (123); (6-(3-isopropyl-5-(piperidin-4-yl)-1H-indol-2-yl)imidazo[1,2-a]pyridin-8-yl)methanol (124); 6-(3-isopropyl-5-(piperidin-4-yl)-1H-indol-2-yl)-8-methoxyimidazo[1,2-a]pyridine (125); 8-fluoro-6-(3-isopropyl-5-(piperidin-4-yl)-1H-indol-2-yl)-2-methylimidazo[1,2-a]pyridine (126); 7-chloro-5-(3-isopropyl-5-(piperidin-4-yl)-1H-indol-2-yl)imidazo[1,2-a]pyridine (127); 7-chloro-6-(3-isopropyl-5-(piperidin-4-yl)-1H-indol-2-yl)imidazo[1,2-a]pyridine (128); 6-(3-(2,2-difluoroethyl)-5-(piperidin-4-yl)-1H-indol-2-yl)-2-methylimidazo[1,2-a]pyridine (129); 6-(3-isopropyl-5-(piperidin-4-yl)-1H-indol-2-yl)-8-methylimidazo[1,2-a]pyridine-3-carbonitrile (130); 6-(3-(2,2-difluoroethyl)-5-(piperidin-4-yl)-1H-indol-2-yl)-8-fluoroimidazo[1,2-a]pyridine (131); 6-(3-isopropyl-5-(piperidin-4-yl)-1H-indol-2-yl)-2,3,8-trimethylimidazo[1,2-a]pyridine (132); 8-chloro-6-(3-isopropyl-5-(piperidin-4-yl)-1H-indol-2-yl)-7-methylimidazo[1,2-a]pyridine (133); 2-(6-(3-isopropyl-5-(piperidin-4-yl)-1H-indol-2-yl) imidazo[1,2-a]pyridin-8-yl)propan-2-ol (134); 6-(3-isopropyl-5-(piperidin-4-yl)-1H-indol-2-yl)-7-(trifluoromethyl)imidazo[1,2-a]pyridine (135); 6-(3-isopropyl-5-(piperidin-4-yl)-1H-indol-2-yl)-8-(trifluoromethyl)imidazo[1,2-a]pyridine (136); 6-(3-isopropyl-5-(piperidin-4-yl)-1H-indol-2-yl)-2-methyl-8-(trifluoromethyl)imidazo[1,2-a]pyridine (137); 5-(3-isopropyl-5-(piperidin-4-yl)-1H-indol-2-yl)-2,7-dimethyl-2H-indazole (138); 8-chloro-6-(3-isopropyl-5-(piperidin-4-yl)-1H-indol-2-yl)quinoline (139); 6-(3-isopropyl-5-(piperidin-4-yl)-1H-indol-2-yl)-7-methylquinoline (140); 6-(3-isopropyl-5-(piperidin-4-yl)-1H-indol-2-yl)-8-methylquinoline (141); 5-(3-isopropyl-5-(piperidin-4-yl)-1H-indol-2-yl)-2,7-dimethylpyrazolo[1,5-a]pyridine (142); 5-(3-isopropyl-5-(piperidin-4-yl)-1H-indol-2-yl)-7-methylpyrazolo[1,5-a]pyridine (143); 7-isobutyl-5-(3-isopropyl-5-(piperidin-4-yl)-1H-indol-2-yl)-2-methylpyrazolo[1,5-a]pyridine (144); 5-(3-isopropyl-5-(piperidin-4-yl)-1H-indol-2-yl)-2-methylpyrazolo[1,5-a]pyridine (145); 3-fluoro-5-(3-isopropyl-5-(piperidin-4-yl)-1H-indol-2-yl)-2-methylpyrazolo[1,5-a]pyridine (146); 6-fluoro-5-(3-isopropyl-5-(piperidin-4-yl)-1H-indol-2-yl)pyrazolo[1,5-a]pyrimidine (147); 6-fluoro-5-(3-isopropyl-5-(piperidin-4-yl)-1H-indol-2-yl)-2-methylpyrazolo[1,5-a]pyrimidine (148); 5-(3-isopropyl-5-(piperidin-4-yl)-1H-indol-2-yl)-2-methylpyrazolo[1,5-a]pyrimidine (149); 3-fluoro-5-(3-isopropyl-5-(piperidin-4-yl)-1H-indol-2-yl)-2-methylpyrazolo[1,5-a]pyrimidine (150); 8-(3-isopropyl-5-(piperidin-4-yl)-1H-indol-2-yl)-2,5-dimethyl-[1,2,4]triazolo[1,5-a]pyridine (151); 8-(3-isopropyl-5-(piperidin-4-yl)-1H-indol-2-yl)-5-methyl-[1,2,4]triazolo[1,5-a]pyridine (152); 8-(3-isopropyl-5-(piperidin-4- yl)-1H-indol-2-yl)-2-methyl-[1,2,4]triazolo[1,5-a]pyridine (153); 7-(3-isopropyl-5-(piperidin-4-yl)-1H-indol-2-yl)-5-methyl-[1,2,4]triazolo[1,5-a]pyridine (154); 7-(3-isopropyl-5-(piperidin-4-yl)-1H-indol-2-yl)-5-methoxy-2-methyl-[1,2,4]triazolo [1,5-a]pyridine (155); 7-(3-isopropyl-5-(piperidin-4-yl)-1H-indol-2-yl)-2-methyl-[1,2,4] triazolo[1,5-a]pyridine (156); 5-ethoxy-7-(3-isopropyl-5-(piperidin-4-yl)-1H-indol-2-yl)-[1,2,4]triazolo[1,5-a]pyridine (157); 7-(3-isopropyl-5-(piperidin-4-yl)-1H-indol-2-yl)-5-methoxy-[1,2,4]triazolo[1,5-a]pyridine (158); 6-(3-isopropyl-5-(piperidin-4-yl)-1H-indol-2-yl)-2-methylimidazo[1,2-a]pyrimidine (159); 7-(3-isopropyl-5-(piperidin-4-yl)-1H-indol-2-yl)-2,5-dimethylimidazo[1,2-a]pyridine (160); 7-(3-isopropyl-5-(piperidin-4-yl)-1H-indol-2-yl)-5-methylimidazo[1,2-a]pyridine (161); 7-(3-isopropyl-5-(piperidin-4-yl)-1H-indol-2-yl)-5-methoxy-2-methylimidazo[1,2-a]pyridine (162); 7-(3-isopropyl-5-(piperidin-4-yl)-1H-indol-2-yl)-5-methoxyimidazo[1,2-a]pyridine (163); 7-(3-isopropyl-5-(piperidin-4-yl)-1H-indol-2-yl)-5-methylimidazo[1,5-a]pyridine (164); 6-(3-isopropyl-5-(piperidin-4-yl)-1H-indol-2-yl)quinoxaline (165); 5-(3-ethyl-5-(piperidin-4-yl)-1H-indol-2-yl)-1,3-dihydro-2H-benzo[d]imidazol-2-one (166); 6-(3-ethyl-5-(piperidin-4-yl)-1H-indol-2-yl)benzo[d]oxazol-2(3H)-one (167); 5-(3-ethyl-5-(piperidin-4-yl)-1H-indol-2-yl)benzo[d]oxazol-2(3H)-one (168); 5-(3-isopropyl-5-(piperidin-4-yl)-1H-indol-2-yl)-1H-indazole (169); 6-(3-isopropyl-5-(piperidin-4-yl)-1H-indol-2-yl)-[1,2,4]triazolo[1,5-a]pyrimidine (170); 4-(5-(3-fluoropiperidin-4-yl)-3-isopropyl-1H-indol-2-yl)-1H-pyrazolo[3,4-b]pyridine (171); 4-(5-(3-fluoropiperidin-4-yl)-3-isopropyl-1H-indol-2-yl)-1H-pyrazolo[3,4-b]pyridine (172); 4-(3-ethyl-5-(3-fluoropiperidin-4-yl)-1H-indol-2-yl)-1H-pyrazolo[3,4-b]pyridine (173); methyl 5-(piperidin-4-yl)-2-(1H-pyrazolo[3,4-b]pyridin-4-yl)-1H-indole-3-carboxylate (174); 4-(3-ethyl-2-(1H-pyrazolo[3,4-b]pyridin-4-yl)-1H-indol-5-yl)piperidin-3-ol (175); (5-(piperidin-4-yl)-2-(1H-pyrazolo[3,4-b]pyridin-4-yl)-1H-indol-3-yl)methanol (176); 4-(3-ethyl-5-(3-fluoropiperidin-4-yl)-1H-indol-2-yl)-1H-pyrazolo[3,4-b]pyridine (177); 4-(3-(2,2-difluoroethyl)-5-(piperidin-4-yl)-1H-indol-2-yl)-1H-pyrazolo[3,4-b]pyridine (178); 5-(3-isopropyl-5-(piperidin-4-yl)-1H-indol-2-yl)-1H-pyrazolo[3,4-c]pyridine (179); 6-(3-ethyl-5-(piperidin-4-yl)-1H-indol-2-yl)-1,3-dihydro-2H-imidazo[4,5-b]pyridin-2-one (180); 6-(3-isopropyl-5-(piperidin-4-yl)-1H-indol-2-yl)pyrazolo[1,5-a]pyrimidine (181); 4-(3-ethyl-5-(piperidin-4-yl)-1H-indol-2-yl)-1H-indazole (182); 6-(3-isopropyl-5-(piperidin-4-yl)-1H-indol-2-yl)imidazo[1,5-a]pyridine (183); 6-(3-ethyl-5-(piperidin-4-yl)-1H-indol-2-yl)-[1,2,4] triazolo[4,3-b]pyridazine (184); 6-(3-isopropyl-5-(piperidin-4-yl)-1H-indol-2-yl)-[1,2,4] triazolo[4,3-b]pyridazine (185); 2-(benzofuran-2-yl)-3-ethyl-5-(piperidin-4-yl)-1H-indole (186); 3-(3-ethyl-5-(piperidin-4-yl)-1H-indol-2-yl)imidazo[1,2-b]pyridazine (187); 6-(3-isopropyl-5-(piperidin-4-yl)-1H-indol-2-yl)imidazo[1,2-a]pyridine (188); 7-(3-(2,2-difluoroethyl)-5-(piperidin-4-yl)-1H-indol-2-yl)imidazo[1,2-a]pyridine (189); 6-(3-isopropyl-5-(piperidin-4-yl)-1H-indol-2-yl)quinoline (190); 4-(3-isopropyl-5-(piperidin-4-yl)-1H-indol-2-yl)pyrrolo[2,1-f][1,2,4]triazine (191); 5-(3-isopropyl-5-(piperidin-4-yl)-1H-indol-2-yl) pyrazolo[1,5-a]pyridine (192); 5-(3-isopropyl-5-(piperidin-4-yl)-1H-indol-2-yl)pyrazolo[1,5-a]pyrimidine (193); 3-(3-isopropyl-5-(piperidin-4-yl)-1H-indol-2-yl)imidazo[1,2-a]pyrazine (194); 2-(3-isopropyl-5-(piperidin-4-yl)-1H-indol-2-yl)-[1,2,4]triazolo[1,5-a]pyrazine (195); 8-(3-isopropyl-5-(piperidin-4-yl)-1H-indol-2-yl)-[1,2,4]triazolo[1,5-a]pyridine (196); 7-(3-isopropyl-5-(piperidin-4-yl)-1H-indol-2-yl)-[1,2,4]triazolo[1,5-a]pyridine (197); 7-(3-ethyl-5-(piperidin-4-yl)-1H-indol-2-yl)-[1,2,4]triazolo[1,5-a]pyridine (198); 7-(3-isopropyl-5-(piperidin-4-yl)-1H-indol-2-yl)-[1,2,4]triazolo[4,3-a]pyridin-3(2H)-one (199); 6-(3-isopropyl-5-(piperidin-4-yl)-1H-indol-2-yl)imidazo[1,2-a]pyrimidine (200); 6-(3-ethyl-5-(piperidin-4-yl)-1H-indol-2-yl)imidazo[1,2-a]pyrazine (201); 7-(3-ethyl-5-(piperidin-4-yl)-1H-indol-2-yl)imidazo[1,2-a]pyridine (202); 7-(3-isopropyl-5-(piperidin-4-yl)-1H-indol-2-yl)imidazo[1,2-a]pyridine (203); 7-(3-ethyl-5-(piperidin-4-yl)-1H-indol-2-yl)-[1,2,4]triazolo[4,3-a]pyridine (204); 4-(3-(2,2-difluoroethyl)-5-(piperidin-4-yl)-1H-indol-2-yl)-1H-pyrrolo[2,3-b]pyridine (205); 4-(3-ethyl-5-(piperidin-4-yl)-1H-indol-2-yl)-7H-pyrrolo[2,3-d] pyrimidine (206); 2-(3-isopropyl-5-(piperidin-4-yl)-1H-indol-2-yl)-4,5,6,7-tetrahydrothieno [2,3-c]pyridine (207); 2-(3-isopropyl-5-(piperidin-4-yl)-1H-indol-2-yl)-4,5,6,7-tetrahydrothiazolo[5,4-c]pyridine (208); 5-(3-isopropyl-5-(piperidin-4-yl)-1H-indol-2-yl) thiazolo[5,4-b]pyridine (209); N-methyl-4-(3-methyl-5-(piperidin-4-yl)-1H-indol-2-yl)-1H-pyrrolo[2,3-b]pyridin-3-amine (210); 4-(3-methyl-5-(piperidin-4-yl)-1H-indol-2-yl)-1H-pyrrolo[2,3-b]pyridin-3-amine (211); 4-(3-methyl-5-(piperidin-4-yl)-1H-indol-2-yl)-1H-pyrrolo[2,3-b]pyridin-3-ol (212); 3-methoxy-4-(3-methyl-5-(piperidin-4-yl)-1H-indol-2-yl)-1H-pyrrolo[2,3-b]pyridine (213); 3-isopropyl-4-(3-methyl-5-(piperidin-4-yl)-1H-indol-2-yl)-1H-pyrrolo[2,3-b]pyridine (214); 4-(3-isopropyl-5-(piperidin-4-yl)-1H-indol-2-yl)-3-methyl-1H-pyrrolo[2,3-b]pyridine (215); 4-(3-isopropyl-5-(piperidin-4-yl)-1H-indol-2-yl)-1H-pyrrolo[2,3-b]pyridin-3-ol (216); 4-(3-ethyl-5-(piperidin-4-yl)-1H-indol-2-yl)-3-methyl-1H-pyrrolo[2,3-b]pyridine (217); 3-methyl-4-(3-methyl-5-(piperidin-4-yl)-1H-indol-2-yl)-1H-pyrazolo[3,4-b]pyridine (218); 4-(3-methyl-5-(piperidin-4-yl)-1H-indol-2-yl)-3-ethyl-1H-pyrrolo[2,3-b]pyridine (219); 3-ethyl-4-(3-ethyl-5-(piperidin-4-yl)-1H-indol-2-yl)-1H-pyrrolo[2,3-b]pyridine (220); 4-(3-ethyl-5-(piperidin-4-yl)-1H-indol-2-yl)-3-isopropyl-1H-pyrrolo[2,3-b]pyridine (221); 3-ethyl-4-(3-isopropyl-5-(piperidin-4-yl)-1H-indol-2-yl)-1H-pyrrolo[2,3-b]pyridine (222); 4-(3-methyl-5-(piperidin-4-yl)-1H-indol-2-yl)-3-phenyl-1H-pyrrolo[2,3-b]pyridine (223); 3-ethyl-4-(3-ethyl-5-(piperidin-4-yl)-1H-indol-2-yl)-1H-pyrazolo[3,4-b]pyridine (224); 3-(1,3-dimethyl-1H-pyrazol-5-yl)-4-(3-methyl-5-(piperidin-4-yl)-1H-indol-2-yl)-1H-pyrrolo[2,3-b]pyridine (225); 4-(3-ethyl-5-(piperidin-4-yl)-1H-indol-2-yl)-3-methyl-1H-pyrazolo[3,4-b]pyridine (226); 4-(3-isopropyl-5-(piperidin-4-yl)-1H-indol-2-yl)-3-methyl-1H-pyrazolo[3,4-b]pyridine (227); 7-(3-isopropyl-5-(piperidin-4-yl)-1H-indol-2-yl)-3H-imidazo[4,5-b]pyridin-5-amine (228); 4-(3-ethyl-5-(piperidin-4-yl)-1H-indol-2-yl)-1H-pyrazolo[3,4-b]pyridine (229); 4-(3-isopropyl-5-(piperidin-4-yl)-1H-indol-2-yl)-1H-pyrazolo[3,4-b]pyridine (230); 4-(3-methyl-5-(piperidin-4-yl)-1H-indol-2-yl)-1H-pyrazolo[3,4-b]pyridine (231); 2-methyl-7-(3-methyl-5-(piperidin-4-yl)-1H-indol-2-yl)-3H-imidazo[4,5-b]pyridine (232); 7-(3-methyl-5-(piperidin-4-yl)-1H-indol-2-yl)-3H-[1,2,3]triazolo[4,5-b]pyridine (233); 6-(3-isopropyl-5-(piperidin-4-yl)-1H-indol-2-yl)-4-methylbenzo[d]oxazole (234); 4-(3-isopropyl-5-(piperidin-4-yl)-1H-indol-2-yl)-1H-indazole-7-carbonitrile (235); 4-(3-ethyl-5-(piperidin-4-yl)-1H-indol-2-yl)-1H-pyrrolo[2,3-b]pyridine (236); 6-(3-isopropyl-5-(piperidin-4-yl)-1H-indol-2-yl)-7-methyl-[1,2,4]triazolo[4,3-a] pyrazin-8(7H)-one (237); 7-(3-ethyl-5-(piperidin-4-yl)-1H-indol-2-yl)-1H-pyrazolo[4,3-b] pyridin-3-amine (238); 7-(3-ethyl-5-(piperidin-4-yl)-1H-indol-2-yl)isoxazolo[4,5-b]pyridin-3-amine (239); 6-(3-ethyl-5-(piperidin-4-yl)-1H-indol-2-yl)-1H-pyrazolo[4,3-b]pyridin-3-amine (240); 5-(3-ethyl-5-(piperidin-4-yl)-1H-indol-2-yl)-7H-pyrrolo[2,3-d]

pyrimidine (241); 6-(3-isopropyl-5-(piperidin-4-yl)-1H-indol-2-yl)-[1,2,4]triazolo[1,5-b]pyridazine (242); 3-(3-ethyl-5-(piperidin-4-yl)-1H-indol-2-yl)-1H-pyrrolo[2,3-b]pyridine (243); 3-(3-ethyl-5-(piperidin-4-yl)-1H-indol-2-yl)-1H-pyrazolo[3,4-b]pyridine (244); 4-(3-ethyl-5-(piperidin-4-yl)-1H-indol-2-yl)-7H-pyrrolo[2,3-c]pyridazine (245); 4-(3-ethyl-5-(piperidin-4-yl)-1H-indol-2-yl)-5-methyl-1H-pyrrolo[2,3-b]pyridine (246); 4-(3-isopropyl-5-(piperidin-4-yl)-1H-indol-2-yl)-5-methyl-1H-pyrrolo[2,3-b]pyridine (247); 4-(3-isopropyl-2-(1H-pyrazolo[3,4-b]pyridin-4-yl)-1H-indol-5-yl)piperidin-2-one (248); 4-(3-isopropyl-5-(piperidin-4-yl)-6-(trifluoromethyl)-1H-indol-2-yl)-1H-pyrazolo[3,4-b]pyridine (249); 4-(3-isopropyl-6-methyl-5-(piperidin-4-yl)-1H-indol-2-yl)-1H-pyrazolo[3,4-b]pyridine (250); 4-(3-ethyl-7-fluoro-5-(piperidin-4-yl)-1H-indol-2-yl)-1H-pyrazolo[3,4-b]pyridine (251); 4-(6-chloro-3-isopropyl-5-(piperidin-4-yl)-1H-indol-2-yl)-1H-pyrazolo[3,4-b]pyridine (252); 4-(6-fluoro-3-isopropyl-5-(piperidin-4-yl)-1H-indol-2-yl)-1H-pyrazolo[3,4-b]pyridine (253); 4-(3-ethyl-4-methyl-5-(piperidin-4-yl)-1H-indol-2-yl)-1H-pyrazolo[3,4-b]pyridine (254); 4-(3-isopropyl-6-methoxy-5-(piperidin-4-yl)-1H-indol-2-yl)-1H-pyrazolo[3,4-b]pyridine (255); 4-(3,4-dimethyl-5-(piperidin-4-yl)-1H-indol-2-yl)-1H-pyrazolo[3,4-b]pyridine (256); 6-(3-ethyl-4,6-difluoro-5-(piperidin-4-yl)-1H-indol-2-yl)imidazo[1,2-a]pyridine (257); 6-(4-fluoro-3-isopropyl-5-(piperidin-4-yl)-1H-indol-2-yl)imidazo[1,2-a]pyridine (258); 4-(4-fluoro-3-isopropyl-5-(piperidin-4-yl)-1H-indol-2-yl)-1H-pyrazolo[3,4-b]pyridine (259); 8-isopropyl-6-(3-isopropyl-5-(piperidin-4-yl)-1H-indol-2-yl)imidazo[1,2-a]pyridine (260); 6-(3-isopropyl-5-(piperidin-4-yl)-1H-indol-2-yl)-8-methylimidazo[1,2-a]pyridine-3-carboxamide (261); N-cyclopropyl-6-(3-isopropyl-5-(piperidin-4-yl)-1H-indol-2-yl)-8-methylimidazo[1,2-a]pyridine-2-carboxamide (262); 6-(3-isopropyl-5-(piperidin-4-yl)-1H-indol-2-yl)-8-methoxy-N,N-dimethylimidazo[1,2-a]pyridine-2-carboxamide (263); 6-(3-isopropyl-5-(piperidin-4-yl)-1H-indol-2-yl)-N,8-dimethylimidazo[1,2-a]pyridine-2-carboxamide (264); 6-(3-isopropyl-5-(piperidin-4-yl)-1H-indol-2-yl)-N,N,8-trimethylimidazo[1,2-a]pyridine-2-carboxamide (265); N-ethyl-6-(3-isopropyl-5-(piperidin-4-yl)-1H-indol-2-yl)-N,8-dimethylimidazo[1,2-a]pyridine-2-carboxamide (266); N-(2-hydroxyethyl)-6-(3-isopropyl-5-(piperidin-4-yl)-1H-indol-2-yl)-8-methylimidazo[1,2-a]pyridine-2-carboxamide (267); N-(2-hydroxyethyl)-6-(3-isopropyl-5-(piperidin-4-yl)-1H-indol-2-yl)-N,8-dimethylimidazo[1,2-a]pyridine-2-carboxamide (268); 6-(3-isopropyl-5-(piperidin-4-yl)-1H-indol-2-yl)-N-(2-methoxyethyl)-8-methylimidazo[1,2-a]pyridine-2-carboxamide (269); N-(2-hydroxy-2-methylpropyl)-6-(3-isopropyl-5-(piperidin-4-yl)-1H-indol-2-yl)-8-methylimidazo[1,2-a]pyridine-2-carboxamide (270); 6-(3-isopropyl-5-(piperidin-4-yl)-1H-indol-2-yl)-7,8-dimethylimidazo[1,2-a]pyridine (271); 8-ethyl-6-(3-isopropyl-5-(piperidin-4-yl)-1H-5 indol-2-yl)-7-methylimidazo[1,2-a]pyridine (272); 8-isopropyl-6-(3-isopropyl-5-(piperidin-4-yl)-1H-indol-2-yl)-7-methylimidazo[1,2-a]pyridine (273); 5-(3-isopropyl-5-(piperidin-4-yl)-1H-indol-2-yl)-N,7-dimethylpyrazolo[1,5-a]pyridine-3-carboxamide (274); 5-(3-isopropyl-5-(piperidin-4-yl)-1H-indol-2-yl)-N,N,7-trimethylpyrazolo[1,5-a]pyridine-3-carboxamide (275); 2-(4-(3-isopropyl-2-(1H-pyrazolo[3,4-b]pyridin-4-yl)-1H-indol-5-yl)piperidin-1-yl)-N-methylacetamide (276); 2-(4-(2-([1,2,4]triazolo[1,5-b]pyridazin-6-yl)-3-isopropyl-1H-indol-5-yl)piperidin-1-yl)-N-methylacetamide (277); 2-(4-(2-([1,2,4]triazolo[1,5-b]pyridazin-6-yl)-3-isopropyl-1H-indol-5-yl)piperidin-1-yl)-N,N-dimethylacetamide (278); 2-(4-(2-(7,8-dimethyl-[1,2,4]triazolo[1,5-b]pyridazin-6-yl)-3-isopropyl-1H-indol-5-yl)piperidin-1-yl)-N-methylacetamide (279); 2-(4-(2-(7,8-dimethyl-[1,2,4]triazolo[1,5-b]pyridazin-6-yl)-3-isopropyl-1H-indol-5-yl)piperidin-1-yl)-N,N-dimethylacetamide (280); 2-(4-(3-isopropyl-2-(8-methoxy-7-methyl-[1,2,4]triazolo[1,5-b]pyridazin-6-yl)-1H-indol-5-yl)piperidin-1-yl)-N-methylacetamide (281); 2-(4-(3-isopropyl-2-(8-methoxy-7-methyl-[1,2,4]triazolo[1,5-b]pyridazin-6-yl)-1H-indol-5-yl)piperidin-1-yl)-N,N-dimethylacetamide (282); 2-(4-(3-isopropyl-2-(8-methoxy-[1,2,4]triazolo[1,5-b]pyridazin-6-yl)-1H-indol-5-yl)piperidin-1-yl)-N,N-dimethylacetamide (283); 2-(4-(3-isopropyl-2-(8-methoxy-[1,2,4]triazolo[1,5-b]pyridazin-6-yl)-1H-indol-5-yl)piperidin-1-yl)acetamide (284); 2-(4-(2-(1,4-dimethyl-1H-pyrrolo[2,3-b]pyridin-3-yl)-3-isopropyl-1H-indol-5-yl)piperidin-1-yl)-N,N-dimethylacetamide (285); 2-(4-(2-(1,2-dimethyl-1H-pyrrolo[2,3-b]pyridin-3-yl)-3-isopropyl-1H-indol-5-yl)piperidin-1-yl)-N,N-dimethylacetamide (286); 2-(4-(3-isopropyl-2-(4-methyl-1H-benzo[d]imidazol-6-yl)-1H-indol-5-yl)piperidin-1-yl)-N,N-dimethylacetamide (287); 2-(4-(2-(benzo[d]oxazol-6-yl)-3-isopropyl-1H-indol-5-yl)piperidin-1-yl)-N,N-dimethylacetamide (288); 2-(4-(3-ethyl-2-(1H-pyrazolo[3,4-b]pyridin-4-yl)-1H-indol-5-yl)piperidin-1-yl)acetamide (289); 2-(4-(2-(imidazo[1,2-a]pyrimidin-3-yl)-3-isopropyl-1H-indol-5-yl)piperidin-1-yl)-N,N-dimethylacetamide (290); 2-(4-(3-isopropyl-2-(4-methylbenzo[d]oxazol-6-yl)-1H-indol-5-yl)piperidin-1-yl)-N,N-dimethylacetamide (291); 2-(4-(3-isopropyl-2-(8-methoxy-[1,2,4]triazolo[1,5-a]pyrazin-6-yl)-1H-indol-5-yl)piperidin-1-yl)-N,N-dimethylacetamide (292); 2-(4-(3-isopropyl-2-(1-methyl-1H-pyrrolo[2,3-b]pyridin-3-yl)-1H-indol-5-yl)piperidin-1-yl)-N-methylacetamide (293); 2-(4-(3-isopropyl-2-(1-methyl-1H-pyrrolo[2,3-b]pyridin-3-yl)-1H-indol-5-yl)piperidin-1-yl)-1-morpholinoethan-1-one (294); 2-(4-(3-isopropyl-2-(1-methyl-1H-pyrrolo[2,3-b]pyridin-3-yl)-1H-indol-5-yl) piperidin-1-yl)-N,N-dimethylacetamide (295); 2-(4-(3-isopropyl-2-(1-methyl-1H-pyrrolo [2,3-b]pyridin-3-yl)-1H-indol-5-yl)piperidin-1-yl)acetamide (296); 2-(4-(2-(1,6-dimethyl-7-oxo-6,7-dihydro-1H-pyrrolo[2,3-c]pyridin-3-yl)-3-isopropyl-1H-indol-5-yl)piperidin-1-yl)-N,N-dimethylacetamide (297); 2-(4-(2-(benzo[d]thiazol-6-yl)-3-isopropyl-1H-indol-5-yl) piperidin-1-yl)-N,N-dimethylacetamide (298); 2-(4-(2-([1,2,3]triazolo[1,5-a]pyridin-6-yl)-3-isopropyl-1H-indol-5-yl)piperidin-1-yl)-N,N-dimethylacetamide (299); 2-(4-(2-([1,2,3]triazolo[1,5-a]pyridin-6-yl)-3-isopropyl-1H-indol-5-yl)piperidin-1-yl)-N-methylacetamide (300); 2-(4-(3-isopropyl-2-(tetrazolo[1,5-a]pyridin-6-yl)-1H-indol-5-yl)piperidin-1-yl)-N,N-dimethylacetamide (301); 2-(4-(2-([1,2,3]triazolo[1,5-a]pyridin-5-yl)-3-isopropyl-1H-indol-5-yl)piperidin-1-yl)-N,N-dimethylacetamide (302); 2-(4-(2-([1,2,3]triazolo[1,5-a]pyridin-5-yl)-3-isopropyl-1H-indol-5-yl)piperidin-1-yl)-N-methylacetamide (303); 2-(4-(3-isopropyl-2-(tetrazolo[1,5-a]pyridin-7-yl)-1H-indol-5-yl)piperidin-1-yl)-N,N-dimethylacetamide (304); 2-(4-(2-([1,2,4]triazolo[4,3-a]pyridin-7-yl)-3-isopropyl-1H-indol-5-yl)piperidin-1-yl)-N,N-dimethylacetamide (305); 2-(4-(2-([1,2,4]triazolo[4,3-a]pyridin-7-yl)-3-isopropyl-1H-indol-5-yl)piperidin-1-yl)-N-methylacetamide (306); 2-(4-(3-isopropyl-2-(4-methyl-[1,2,3]triazolo [1,5-a]pyridin-6-yl)-1H-indol-5-yl)piperidin-1-yl)-N,N-dimethylacetamide (307); 2-(4-(3-isopropyl-2-(5-methyltetrazolo[1,5-a]pyridin-6-yl)-1H-indol-5-yl) piperidin-1-yl)-N,N-dimethylacetamide (308); 2-(4-(2-(7,8-dimethyltetrazolo[1,5-a]pyridin-6-yl)-3-isopropyl-1H-indol-5-yl)piperidin-1-yl)-N,N-dimethylacetamide (309); 2-(4-(2-(5,8-dimethyltetrazolo[1,5-a]pyridin-6-yl)-3-isopropyl-1H-indol-5-yl)piperidin-1-yl)-N,N-dimethylacetamide (310); 2-(4-(3-isopropyl-2-(8-methyltetrazolo[1,5-a]pyridin-6-yl)-1H-indol-5-yl)piperidin-1-yl) acetamide (311); 2-(4-(3-isopropyl-2-(8-methyltetrazolo[1,5-a]pyridin-6-yl)-1H-indol-5-yl) piperidin-1-yl)-N-methylacetamide (312); 2-(4-(3-isopropyl-2-(8-methyltetrazolo[1,5-a] pyridin-6-yl)-1H-indol-5-yl)piperidin-1-yl)-N,N-dimethylacetamide (313); 2-(4-(3-isopropyl-2-(7-methyltetrazolo[1,5-a]pyridin-6-yl)-1H-indol-5-yl)piperidin-1-yl)-N,N-dimethylacetamide (314); 2-(4-(3-isopropyl-2-(7-methyltetrazolo[1,5-a]pyridin-6-yl)-1H-indol-5-yl)piperidin-1-yl)acetamide (315); 2-(4-(3-isopropyl-2-(7-methyltetrazolo[1,5-a] pyridin-6-yl)-1H-indol-5-yl)piperidin-1-yl)-N-methylacetamide (316); 2-(4-(3-isopropyl-2-(3-methyl-[1,2,3]triazolo[1,5-a]pyridin-5-yl)-1H-indol-5-yl)piperidin-1-yl)acetamide (317); 2-(4-(3-isopropyl-2-(3-methyl-[1,2,3]triazolo[1,5-a]pyridin-5-yl)-1H-indol-5-yl)piperidin-1-yl)-N,N-dimethylacetamide (318); 2-(4-(3-isopropyl-2-(3-methyl-[1,2,3]triazolo[1,5-a] pyridin-5-yl)-1H-indol-5-yl)piperidin-1-yl)-N-methylacetamide (319); 2-(4-(3-isopropyl-2-(7-methyl-[1,2,3]triazolo[1,5-a]pyridin-5-yl)-1H-indol-5-yl)piperidin-1-yl)-N-methylacetamide (320); 2-(4-(3-isopropyl-2-(7-methyl-[1,2,3]triazolo[1,5-a]pyridin-5-yl)-1H-indol-5-yl)piperidin-1-yl)acetamide (321); 2-(4-(3-isopropyl-2-(2-methylpyrazolo[1,5-a] pyridin-5-yl)-1H-indol-5-yl)piperidin-1-yl)-N-methylacetamide (322); 2-(4-(3-isopropyl-2-(2-methylpyrazolo[1,5-a]pyridin-5-yl)-1H-indol-5-yl)piperidin-1-yl)-N,N-dimethylacetamide (323); 2-(4-(3-isopropyl-2-(5-methyl-[1,2,4]triazolo[1,5-a]pyridin-7-yl)-1H-indol-5-yl) piperidin-1-yl)-N,N-dimethylacetamide (324); 2-(4-(3-isopropyl-2-(5-methyl-[1,2,4]triazolo[1,5-a]pyridin-7-yl)-1H-indol-5-yl)piperidin-1-yl)-N-methylacetamide (325); 2-(4-(3-isopropyl-2-(2-methyl-[1,2,4]triazolo[1,5-a]pyridin-7-yl)-1H-indol-5-yl)piperidin-1-yl)-N,N-dimethylacetamide (326); 2-(4-(3-isopropyl-2-(2-methylquinolin-4-yl)-1H-indol-5-yl) piperidin-1-yl)-N,N-dimethylacetamide (327); 2-(4-(3-isopropyl-2-(2-methylquinolin-4-yl)-1H-indol-5-yl)piperidin-1-yl)-N-methylacetamide (328); 2-(4-(2-(8-(hydroxymethyl)imidazo[1,2-a]pyridin-6-yl)-3-isopropyl-1H-indol-5-yl)piperidin-1-yl)-N,N-dimethylacetamide (329); 6-(5-(1-(2-(dimethylamino)-2-oxoethyl)piperidin-4-yl)-3-isopropyl-1H-indol-2-yl)-N-methylimidazo[1,2-a]pyridine-2-carboxamide (330); 2-(4-(3-isopropyl-2-(2-methyl-[1,2,4] triazolo[1,5-a]pyridin-7-yl)-1H-indol-5-yl)piperidin-1-yl)-N-methylacetamide (331); 2-(4-(3-isopropyl-2-(5-methoxy-[1,2,4]triazolo[1,5-a]pyridin-7-yl)-1H-indol-5-yl)piperidin-1-yl)-N-methylacetamide (332); 2-(4-(3-isopropyl-2-(5-methoxy-[1,2,4]triazolo[1,5-a]pyridin-7-yl)-1H-indol-5-yl)piperidin-1-yl)-N,N-dimethylacetamide (333); 2-(4-(3-isopropyl-2-(5-methoxy-2-methylimidazo[1,2-a]pyridin-7-yl)-1H-indol-5-yl)piperidin-1-yl)-N,N-dimethylacetamide (334); 2-(4-(3-isopropyl-2-(5-methoxy-2-methylimidazo[1,2-a]pyridin-7-yl)-1H-indol-5-yl)piperidin-1-yl)-N-methylacetamide (335); 2-(4-(2-(3,7-dimethyl-2-oxo-2,3-dihydrobenzo[d]oxazol-5-yl)-3-isopropyl-1H-indol-5-yl)piperidin-1-yl)-N-methylacetamide (336); 2-(4-(3-isopropyl-2-(7-methyl-2-oxo-2,3-dihydrobenzo[d]oxazol-5-yl)-1H-indol-5-yl) piperidin-1-yl)-N-methylacetamide (337); 2-(4-(2-(2,7-dimethylbenzo [d]oxazol-5-yl)-3-isopropyl-1H-indol-5-yl) piperidin-1-yl)-N,N-dimethylacetamide (338); 2-(4-(2-(2,7-dimethylbenzo[d]oxazol-5-yl)-3-isopropyl-1H-indol-5-yl) piperidin-1-yl)-N-methylacetamide (339); 2-(4-(3-isopropyl-2-(2-5 methoxyquinolin-4-yl)-1H-indol-5-yl) piperidin-1-yl)-N,N-dimethylacetamide (340); 2-(4-(2-(8-(hydroxymethyl)-6-imidazo[1,2-a] pyridin-6-yl)-3-isopropyl-1H-indol-5-yl)piperidin-1-yl)-N-methylacetamide (341); 2-(4-(2-(8-(2-hydroxypropan-2-yl)imidazo[1,2-a] pyridin-6-yl)-3-isopropyl-1H-indol-5-yl)piperidin-1-yl)-N-methylacetamide (342); 2-(4-(2-(8-(2-hydroxypropan-2-yl)imidazo[1,2-a]pyridin-6-yl)-3-isopropyl-1H-indol-5-yl)piperidin-1-yl)-N,N-dimethylacetamide (343); 6-(5-(1-(2-(dimethylamino)-2-oxoethyl)piperidin-4-yl)-3-isopropyl-1H-indol-2-yl)-N-(2-hydroxyethyl)-N,8-dimethylimidazo [1,2-a]pyridine-2-carboxamide (344); N-(2-hydroxyethyl)-6-(3-isopropyl-5-(1-(2-(methylamino)-2-oxoethyl)piperidin-4-yl)-1H-indol-2-yl)-N,8-dimethylimidazo[1,2-a]pyridine-2-carboxamide (345); 6-(5-(1-(2-(dimethylamino)-2-oxoethyl)piperidin-4-yl)-3-isopropyl-1H-indol-2-yl)-N,8-dimethylimidazo[1,2-a]pyridine-2-carboxamide (346); 2-(4-(3-isopropyl-2-(5-methoxy-2-methyl-[1,2,4]triazolo[1,5-a]pyridin-7-yl)-1H-indol-5-yl)piperidin-1-yl)-N-methylacetamide (347); 2-(4-(3-isopropyl-2-(5-methoxy-2-methyl-[1,2,4]triazolo[1,5-a]pyridin-7-yl)-1H-indol-5-yl)piperidin-1-yl)-N,N-dimethylacetamide (348); 2-(4-(2-(5-ethoxy-2-methyl-[1,2,4]triazolo[1,5-a]pyridin-7-yl)-3-isopropyl-1H-indol-5-yl)piperidin-1-yl)-N-methylacetamide (349); 2-(4-(2-(5-ethoxy-[1,2,4] triazolo[1,5-a]pyridin-7-yl)-3-isopropyl-1H-indol-5-yl)piperidin-1-yl)-N,N-dimethylacetamide (350); 2-(4-(2-(5-ethoxy-[1,2,4] triazolo[1,5-a]pyridin-7-yl)-3-isopropyl-1H-indol-5-yl)piperidin-1-yl)-N-methylacetamide (351); 2-(4-(2-(2,5-dimethylimidazo[1,2-a] pyridin-7-yl)-3-isopropyl-1H-indol-5-yl)piperidin-1-yl)-N-methylacetamide (352); 2-(4-(2-(2,5-dimethylimidazo[1,2-a]pyridin-7-yl)-3-isopropyl-1H-indol-5-yl)piperidin-1-yl)-N,N-dimethylacetamide (353); 2-(4-(3-isopropyl-2-(5-methylimidazo[1,2-a]pyridin-7-yl)-1H-indol-5-yl)piperidin-1-yl)-N,N-dimethylacetamide (354); 2-(4-(3-isopropyl-2-(5-methylimidazo[1,2-a]pyridin-7-yl)-1H-indol-5-yl)piperidin-1-yl)-N-methylacetamide (355); 2-(4-(3-isopropyl-2-(5-methoxyimidazo[1,2-a]pyridin-7-yl)-1H-indol-5-yl) piperidin-1-yl)-N-methylacetamide (356); 2-(4-(3-isopropyl-2-(5-methoxyimidazo[1,2-a]pyridin-7-yl)-1H-indol-5-yl)piperidin-1-yl)-N,N-dimethylacetamide (357); 2-(4-(3-isopropyl-2-(pyrazolo[1,5-a]pyrimidin-6-yl)-1H-indol-5-yl)piperidin-1-yl)-N,N-dimethylacetamide (359); 2-(4-(3-isopropyl-2-(pyrazolo[1,5-a]pyrimidin-6-yl)-1H-indol-5-yl)piperidin-1-yl)-N-methylacetamide (360); 2-(4-(2-([1,2,4]triazolo[1,5-a]pyridin-8-yl)-3-isopropyl-1H-indol-5-yl)piperidin-1-yl)-N-methylacetamide (361); 2-(4-(2-5 ([1,2,4]triazolo[1,5-a]pyridin-8-yl)-3-isopropyl-1H-indol-5-yl) piperidin-1-yl)-N,N-dimethylacetamide (362); 2-(4-(2-(imidazo[1,2-a]pyrimidin-6-yl)-3-isopropyl-1H-indol-5-yl) piperidin-1-yl)-N,N-dimethylacetamide (363); 2-(4-(2-(1,7-dimethyl-1H-indazol-5-yl)-3-isopropyl-1H-indol-5-yl) piperidin-1-yl)-N-methylacetamide (364); 2-(4-(2-(1,4-dimethyl-1H-indazol-5-yl)-3-isopropyl-1H-indol-5-yl) piperidin-1-yl)-N-methylacetamide (365); 2-(4-(3-isopropyl-2-(1-methyl-1H-pyrazolo[3,4-b]pyridin-5-yl)-1H-indol-5-yl)piperidin-1-yl)-N-methylacetamide (366); 2-(4-(3-isopropyl-2-(1-methyl-1H-pyrazolo[3,4-b]pyridin-5-yl)-1H-indol-5-yl) piperidin-1-yl)-N,N-dimethylacetamide (367); 2-(4-(3-isopropyl-2-(2-methyl-2H-pyrazolo[3,4-b]pyridin-5-yl)-1H-indol-5-yl)piperidin-1-yl)-N-methylacetamide (368); 2-(4-(2-(8-cyanoquinolin-5-yl)-3-isopropyl-1H-indol-5-yl)piperidin-1-yl)acetamide (369); 2-(4-(2-(8-cyanoquinolin-5-yl)-3-isopropyl-1H-indol-5-yl)piperidin-1-yl)-N,N-dimethylacetamide (370); 2-(4-(2-(8-cyanoquinolin-5-yl)-3-isopropyl-1H-indol-5-yl)piperidin-1-yl)-N-methylacetamide (371); 2-(4-(3-isopropyl-2-(8-(trifluoromethyl)imidazo[1,2-a]pyridin-6-yl)-1H-indol-5-yl)piperidin-1-yl)-N,N-dimethylacetamide (372); 2-(4-(3-isopropyl-2-(8-(trifluoromethyl)imidazo[1,2-a]pyridin-6-yl)-1H-indol-5-yl)piperidin-1-yl)-N-methylacetamide (373); 2-(4-(2-(2,7-dimethylimidazo[1,2-a]pyridin-6-yl)-3-isopropyl-1H-indol-5-yl)piperidin-1-yl)-N-methylacetamide (374); 2-(4-(2-(2,7-dimethylimidazo[1,2-a] pyridin-6-yl)-3-isopropyl-1H-indol-5-yl)piperidin-1-yl)-N,N-dimethylacetamide (375); 2-(4-(3-isopropyl-2-(2-methyl-8-(trifluoromethyl)imidazo[1,2-a]pyridin-6-yl)-1H-indol-5-yl) piperidin-1-yl)-N,N-dimethylacetamide (376); 2-(4-(3-isopropyl-2-(2-methyl-8-(trifluoromethyl)imidazo[1,2-a] pyridin-6-yl)-1H-indol-5-yl)piperidin-1-yl)-N-methylacetamide (377); 2-(4-(2-(2,7-dimethyl-2H-indazol-5-yl)-3-isopropyl-1H-indol-5-yl)piperidin-1-yl)-N-methylacetamide (378); 2-(4-(2-(2,7-dimethyl-2H-indazol-5-yl)-3-isopropyl-1H-indol-5-yl)piperidin-1-yl)-N,N-dimethylacetamide (379); 2-(4-(2-(8-chloroquinolin-6-yl)-3-isopropyl-1H-indol-5-yl)piperidin-1-yl)-N,N-dimethylacetamide (380); 2-(4-(2-(8-chloroquinolin-6-yl)-3-isopropyl-1H-indol-5-yl)piperidin-1-yl)-N-methylacetamide (381); 2-(4-(2-(1,4-dimethyl-1H-indazol-5-yl)-3-isopropyl-1H-indol-5-yl) piperidin-1-yl)-N,N-dimethylacetamide (382); 2-(4-(2-(2,5-dimethyl-[1,2,4]triazolo[1,5-a] pyridin-8-yl)-3-isopropyl-1H-indol-5-yl) piperidin-1-yl)-N-methylacetamide (383); 2-(4-(2-(2,5-dimethyl-[1,2,4]triazolo[1,5-a]pyridin-8-yl)-3-isopropyl-1H-indol-5-yl)piperidin-1-yl)-N,N-dimethylacetamide (384); 2-(4-(3-isopropyl-2-(5-methyl-[1,2,4]triazolo[1,5-a] pyridin-8-yl)-1H-indol-5-yl)piperidin-1-yl)-N,N-dimethylacetamide (385); 2-(4-(3-isopropyl-2-(5-methyl-[1,2,4]triazolo[1,5-a]pyridin-8-yl)-1H-indol-5-yl)piperidin-1-yl)-N-methylacetamide (386); 2-(4-(3-(2,2-difluoroethyl)-2-(1H-pyrazolo[3,4-b]pyridin-4-yl)-1H-indol-5-yl) piperidin-1-yl)-N-methylacetamide (387); 2-(4-(3-ethyl-2-(1H-indazol-4-yl)-1H-indol-5-yl) piperidin-1-yl)-N-methylacetamide (388); 2-(4-(3-ethyl-2-(1H-indazol-4-yl)-1H-indol-5-yl) piperidin-1-yl)-N,N-dimethylacetamide (389); 2-(4-(2-(3-cyanoimidazo[1,2-a]pyridin-6-yl)-3-isopropyl-1H-indol-5-yl)piperidin-1-yl)-N-methylacetamide (390); 2-(4-(2-(2,8-dimethylimidazo[1,2-a]pyridin-6-yl)-3-isopropyl-1H-indol-5-yl)piperidin-1-yl)-N-methylacetamide (391); 2-(4-(2-(7-isobutyl-2-methylpyrazolo[1,5-a]pyridin-5-yl)-3-isopropyl-1H-indol-5-yl)piperidin-1-yl)-N-methylacetamide (392); 2-(4-(2-(7-isobutyl-2-methylpyrazolo[1,5-a]pyridin-5-yl)-3-isopropyl-1H-indol-5-yl)piperidin-1-yl)-N,N-dimethylacetamide (393); 2-(4-(3-isopropyl-2-(8-methylquinoxalin-6-yl)-1H-indol-5-yl) piperidin-1-yl)-N-methylacetamide (394); 2-(4-(3-isopropyl-2-(8-methylquinoxalin-6-yl)-1H-indol-5-yl)piperidin-1-yl)-N,N-dimethylacetamide (395); 2-(4-(3-isopropyl-2-(2,3,8-trimethylimidazo[1,2-a]pyridin-6-yl)-1H-indol-5-yl)piperidin-1-yl)-N,N-dimethylacetamide (396); 2-(4-(3-isopropyl-2-(8-methylimidazo[1,2-a]pyridin-6-yl)-1H-indol-5-yl)piperidin-1-yl)-N-methylacetamide (397); 2-(4-(3-isopropyl-2-(8-methylimidazo[1,2-a]pyridin-6-yl)-1H-indol-5-yl) piperidin-1-yl)-N,N-dimethylacetamide (398); 2-(4-(2-(3-fluoro-2-methylpyrazolo[1,5-a]pyridin-5-yl)-3-isopropyl-1H-indol-5-yl)piperidin-1-yl)-N,N-dimethylacetamide (399); 2-(4-(2-(3-fluoro-2-methylpyrazolo[1,5-a]pyrimidin-5-yl)-3-isopropyl-1H-indol-5-yl) piperidin-1-yl)-N,N-dimethylacetamide (400); 2-(4-(2-(imidazo[1,2-a]pyridin-6-yl)-3-isopropyl-1H-indol-5-yl)piperidin-1-yl)-N-(2,2,2-trifluoroethyl)acetamide (401); 2-(4-(2-(imidazo[1,2-a]pyridin-6-yl)-3-isopropyl-1H-indol-5-yl)piperidin-1-yl)-N-isopropylacetamide (402); 2-(4-(2-(imidazo[1,2-a]pyridin-6-yl)-3-isopropyl-1H-indol-5-yl) piperidin-1-yl)-N-methylacetamide (403); 2-(4-(2-(5-ethoxy-2-methyl-[1,2,4]triazolo[1,5-a] pyridin-7-yl)-3-isopropyl-1H-indol-5-yl) piperidin-1-yl)-N,N-dimethylacetamide (404); 2-(4-(3-isopropyl-2-(pyrazolo[1,5-a]pyridin-5-yl)-1H-indol-5-yl) piperidin-1-yl)-N-methylacetamide (405); 2-(4-(3-isopropyl-2-(7-methylthiazolo[5,4-b]pyridin-5-yl)-1H-indol-5-yl)piperidin-1-yl)-N-methylacetamide (406); 2-(4-(3-isopropyl-2-(7-methylthiazolo[5,4-b] pyridin-5-yl)-1H-indol-5-yl)piperidin-1-yl)-N,N-dimethylacetamide (407); 2-(4-(2-(8-fluoroimidazo[1,2-5a]pyridin-6-yl)-3-isopropyl-1H-indol-5-yl)piperidin-1-yl)-N,N-dimethylacetamide (408); 2-(4-(3-(2,2-difluoroethyl)-2-(8-fluoroimidazo[1,2-a]pyridin-6-yl)-1H-indol-5-yl)piperidin-1-yl)-N,N-dimethylacetamide (409); 2-(4-(2-(8-fluoroimidazo[1,2-a] pyridin-6-yl)-3-isopropyl-1H-indol-5-yl)piperidin-1-yl)-N-methylacetamide (410); 2-(4-(3-(2,2-difluoroethyl)-2-(8-fluoroimidazo[1,2-a]pyridin-6-yl)-1H-indol-5-yl)piperidin-1-yl)-N-methylacetamide (411); 2-(4-(2-(7,8-dimethylimidazo[1,2-a]pyridin-6-yl)-3-isopropyl-1H-indol-5-yl)piperidin-1-yl)-N,N-dimethylacetamide (412); 2-(4-(2-(7,8-dimethylimidazo[1,2-a]pyridin-6-yl)-3-isopropyl-1H-indol-5-yl)piperidin-1-yl)-N-methylacetamide (413); 2-(4-(2-(8-chloro-7-methylimidazo[1,2-a]pyridin-6-yl)-3-isopropyl-1H-indol-5-yl)piperidin-1-yl)-N-methylacetamide (414); 2-(4-(2-(8-chloro-7-methylimidazo[1,2-a]pyridin-6-yl)-3-isopropyl-1H-indol-5-yl)piperidin-1-yl)-N,N-dimethylacetamide (415); 2-(4-(3-(2,2-difluoroethyl)-2-(2-methylimidazo[1,2-a]pyridin-6-yl)-1H-indol-5-yl)piperidin-1-yl)-N,N-dimethylacetamide (416); 2-(4-(3-(2,2-difluoroethyl)-2-(2-methylimidazo[1,2-a]pyridin-6-yl)-1H-indol-5-yl) piperidin-1-yl)-N-methylacetamide (417); 2-(4-(2-(8-ethyl-7-methylimidazo[1,2-a]pyridin-6-yl)-3-isopropyl-1H-indol-5-yl)piperidin-1-yl)-N-methylacetamide (418); 2-(4-(2-(2,7-dimethylpyrazolo[1,5-a]pyridin-5-yl)-3-isopropyl-1H-indol-5-yl)piperidin-1-yl)-N-methylacetamide (419); 2-(4-(2-(2,7-dimethylpyrazolo[1,5-a]pyridin-5-yl)-3-isopropyl-1H-indol-5-yl)piperidin-1-yl)-N,N-dimethylacetamide (420); 2-(4-(3-isopropyl-2-(5-methoxy-[1,2,4]triazolo[1,5-a]pyridin-7-yl)-1H-indol-5-yl) piperidin-1-yl)-N,N-dimethylacetamide (421); 2-(4-(2-([1,2,4]triazolo[1,5-a]pyrimidin-6-yl)-3-isopropyl-1H-indol-5-yl)piperidin-1-yl)-N,N-dimethylacetamide (422); 2-(4-(2-([1,2,4]triazolo[1,5-a]pyrimidin-6-yl)-3-isopropyl-1H-indol-5-yl)piperidin-1-yl)-N-methylacetamide (423); 2-(4-(3-isopropyl-2-(pyrrolo[2,1-f][1,2,4]triazin-4-yl)-1H-indol-5-yl)piperidin-1-yl)-N,N-dimethylacetamide (424); 2-(4-(3-isopropyl-2-(pyrazolo[1,5-a]pyrimidin-5-yl)-1H-indol-5-yl)piperidin-1-yl)-N,N-dimethylacetamide (425); 2-(4-(2-(imidazo[1,2-a]pyrazin-3-yl)-3-isopropyl-1H-indol-5-yl)piperidin-1-yl)-N,N-dimethylacetamide (426); 2-(4-(3-isopropyl-2-(7-(trifluoromethyl) imidazo[1,2-a]pyridin-6-yl)-1H-indol-5-yl)piperidin-1-yl)-N,N-dimethylacetamide (427); 2-(4-(2-(7-chloroimidazo[1,2-a]pyridin-6-yl)-3-isopropyl-1H-indol-5-yl)piperidin-1-yl)-N,N-dimethylacetamide (428); 2-(4-(3-isopropyl-2-(2,3,8-trimethylimidazo[1,2-a]pyridin-6-yl)-1H-indol-5-yl)piperidin-1-yl)-N-methylacetamide (429); 2-(4-(2-(3-cyano-8-methylimidazo[1,2-a]pyridin-6-yl)-3-isopropyl-1H-indol-5-yl)piperidin-1-yl)-N,N-dimethylacetamide (430); 2-(4-(3-isopropyl-2-(7-methylimidazo[1,2-a]pyridin-6-yl)-1H-indol-5-yl)piperidin-1-yl)-N,N-dimethylacetamide (431); 6-(5-(1-(2-(dimethylamino)-2-oxoethyl)piperidin-4-yl)-3-isopropyl-1H-indol-2-yl)-8-methoxy-N,N-dimethylimidazo[1,2-a] pyridine-2-carboxamide (432); 2-(4-(3-isopropyl-2-(8-methoxyimidazo[1,2-a]pyridin-6-yl)-1H-indol-5-yl) piperidin-1-yl)-N,N-dimethylacetamide (433); 2-(4-(3-isopropyl-2-(8-methoxyimidazo[1,2-a]pyridin-6-yl)-1H-indol-5-yl)piperidin-1-yl)-N-methylacetamide (434); 2-(4-(3-isopropyl-2-(8-methylquinolin-6-yl)-1H-indol-5-yl) piperidin-1-yl)-N,N-dimethylacetamide (435); 2-(4-(3-isopropyl-2-(8-methylquinolin-6-yl)-1H-indol-5-yl)

piperidin-1-yl)acetamide (436); 2-(4-(3-isopropyl-2-(8-methylquinolin-6-yl)-1H-indol-5-yl)piperidin-1-yl)-N-methylacetamide (437); 2-(4-(2-(6-fluoro-2-methylpyrazolo[1,5-a]pyrimidin-6-yl)-3-isopropyl-1H-indol-5-yl)piperidin-1-yl)-N,N-dimethylacetamide (438); 2-(4-(3-isopropyl-2-(5-methylimidazo[1,5-a] pyridin-7-yl)-1H-indol-5-yl)piperidin-1-yl)-N,N-dimethylacetamide (439); 2-(4-(3-isopropyl-2-(5-methylimidazo[1,5-a]pyridin-7-yl)-1H-indol-5-yl)piperidin-1-yl)-N-methylacetamide (440); 2-(4-(3-isopropyl-2-(pyrazolo[1,5-a]pyridin-5-yl)-1H-indol-5-yl)piperidin-1-yl)-N,N-dimethylacetamide (441); 2-(4-(3-isopropyl-2-(7-methylpyrazolo[1,5-a]pyridin-5-yl)-1H-indol-5-yl)piperidin-1-yl)-N,N-dimethylacetamide (442); 2-(4-(3-isopropyl-2-(7-methylpyrazolo[1,5-a]pyridin-5-yl)-1H-indol-5-yl)piperidin-1-yl)-N-methylacetamide (443); 2-(4-(2-(imidazo[1,2-a]pyridin-6-yl)-3-isopropyl-1H-indol-5-yl)piperidin-1-yl)-N,N-dimethylacetamide (444); 2-(4-(3-(2,2-difluoroethyl)-2-(imidazo[1,2-a]pyridin-7-yl)-1H-indol-5-yl)piperidin-1-yl)-N,N-dimethylacetamide (445); 2-(4-(3-(2,2-difluoroethyl)-2-(imidazo[1,2-a]pyridin-7-yl)-1H-indol-5-yl)piperidin-1-yl)-N-methylacetamide (446); 2-(4-(3-isopropyl-2-(8-methylimidazo[1,2-b]pyridazin-6-yl)-1H-indol-5-yl)piperidin-1-yl)-N,N-dimethylacetamide (447); 2-(4-(3-isopropyl-2-(8-methylimidazo[1,2-b]pyridazin-6-yl)-1H-indol-5-yl)piperidin-1-yl)-N-methylacetamide (448); 2-(dimethylamino)-1-(4-(3-isopropyl-2-(1H-pyrazolo[3,4-b]pyridin-4-yl)-1H-indol-5-yl)piperidin-1-yl) ethanone (449); 2-(dimethylamino)-1-(4-(3-isopropyl-2-(1-(methylsulfonyl)-1H-pyrrolo[2,3-b]pyridin-4-yl)-1H-indol-5-yl)piperidin-1-yl)ethanone (450); 2-(dimethylamino)-1-(4-(3-isopropyl-2-(8-methoxy-7-methyl-[1,2,4]triazolo[1,5-b]pyridazin-6-yl)-1H-indol-5-yl)piperidin-1-yl)ethan-1-one (451); 1-(4-(2-([1,2,4]triazolo[1,5-b]pyridazin-6-yl)-3-isopropyl-1H-indol-5-yl) piperidin-1-yl)-2-(dimethylamino) ethan-1-one (452); 1-(4-(2-(7,8-dimethyl-[1,2,4]triazolo[1,5-b]pyridazin-6-yl)-3-isopropyl-1H-indol-5-yl)piperidin-1-yl)-2-(dimethylamino)ethan-1-one (453); 2-(dimethylamino)-1-(4-(3-isopropyl-2-(8-methyl-[1,2,4]triazolo[1,5-b]pyridazin-6-yl)-1H-indol-5-yl)piperidin-1-yl)ethan-1-one (454); 2-(dimethylamino)-1-(4-(3-isopropyl-2-(7-methyl-[1,2,4]triazolo[1,5-b]pyridazin-6-yl)-1H-indol-5-yl)piperidin-1-yl)ethan-1-one (455); 2-(dimethylamino)-1-(4-(3-isopropyl-2-(7-methyl-7H-pyrrolo[2,3-d]pyrimidin-5-yl)-1H-indol-5-yl)piperidin-1-yl)ethan-1-one (456); 1-(4-(2-(1,4-dimethyl-1H-pyrrolo[2,3-b] pyridin-3-yl)-3-isopropyl-1H-indol-5-yl)piperidin-1-yl)-2-(dimethylamino)ethan-1-one (457); 2-(dimethylamino)-1-(4-(3-isopropyl-2-(4-methyl-1H-pyrrolo[2,3-b]pyridin-3-yl)-1H-indol-5-yl)piperidin-1-yl)ethan-1-one (458); 1-(4-(2-(1,2-dimethyl-1H-pyrrolo[2,3-b]pyridin-3-yl)-3-isopropyl-1H-indol-5-yl)piperidin-1-yl)-2-(dimethylamino)ethan-1-one (459); 2-(dimethylamino)-1-(4-(3-isopropyl-2-(8-methoxy-[1,2,4]triazolo[1,5-b]pyridazin-6-yl)-1H-indol-5-yl)piperidin-1-yl)ethan-1-one (460); 2-amino-1-(4-(3-ethyl-2-(1H-pyrazolo[3,4-b] pyridin-4-yl)-1H-indol-5-yl)piperidin-1-yl)ethan-1-one (461); 1-(4-(3-ethyl-2-(1H-pyrazolo [3,4-b]pyridin-4-yl)-1H-indol-5-yl)piperidin-1-yl)-2-(methylamino)ethan-1-one (462); 2-(dimethylamino)-1-(4-(3-isopropyl-2-(1-methyl-1H-pyrrolo[2,3-b]pyridin-3-yl)-1H-indol-5-yl)piperidin-1-yl)ethan-1-one (463); 1-(4-(2-([1,2,3]triazolo[1,5-a]pyridin-6-yl)-3-isopropyl-1H-indol-5-yl)piperidin-1-yl)-2-(dimethylamino)ethan-1-one (464); 1-(4-(2-([1,2,3]triazolo [1,5-a]pyridin-5-yl)-3-isopropyl-1H-indol-5-yl)piperidin-1-yl)-2-(dimethylamino)ethan-1-one (465); 1-(4-(2-([1,2,4]triazolo[4,3-a]pyridin-7-yl)-3-isopropyl-1H-indol-5-yl)piperidin-1-yl)-2-(dimethylamino)ethan-1-one (466); 2-(dimethylamino)-1-(4-(3-isopropyl-2-(4-methyl-[1,2,3]triazolo[1,5-a]pyridin-6-yl)-1H-indol-5-yl)piperidin-1-yl)ethan-1-one (467); 2-(dimethylamino)-1-(4-(2-(7,8-dimethyltetrazolo[1,5-a]pyridin-6-yl)-3-isopropyl-1H-indol-5-yl)piperidin-1-yl)ethan-1-one (468); 2-(dimethylamino)-1-(4-(2-(5,8-dimethyltetrazolo[1,5-a] pyridin-6-yl)-3-isopropyl-1H-indol-5-yl)piperidin-1-yl)ethan-1-one (469); 1-(4-(3-isopropyl-2-(8-methyltetrazolo[1,5-a]pyridin-6-yl)-1H-indol-5-yl)piperidin-1-yl)-2-(pyrrolidin-1-yl) ethan-1-one (470); 1-(4-(3-isopropyl-2-(8-methyltetrazolo[1,5-a] pyridin-6-yl)-1H-indol-5-yl) piperidin-1-yl)-2-(2-oxa-6-azaspiro[3.3]heptan-6-yl)ethan-1-one (471); 1-(4-(3-isopropyl-2-(8-methyltetrazolo[1,5-a]pyridin-6-yl)-1H-indol-5-yl)piperidin-1-yl)-2-(piperidin-1-yl)ethan-1-one (472); 1-(4-(3-isopropyl-2-(8-methyltetrazolo[1,5-a]pyridin-6-yl)-1H-indol-5-yl) piperidin-1-yl)-2-(2,2,6,6-tetramethylmorpholino)ethan-1-one (473); 2-(4-fluoropiperidin-1-yl)-1-(4-(3-isopropyl-2-(8-methyltetrazolo[1,5-a]pyridin-6-yl)-1H-indol-5-yl)piperidin-1-yl) ethan-1-one (474); 2-(ethyl(methyl)amino)-1-(4-(3-isopropyl-2-(8-methyltetrazolo[1,5-a] pyridin-6-yl)-1H-indol-5-yl)piperidin-1-yl) ethan-1-one (475); 1-(4-(3-isopropyl-2-(8-methyltetrazolo [1,5-a]pyridin-6-yl)-1H-indol-5-yl)piperidin-1-yl)-2-morpholinoethan-1-one (476); 2-(dimethylamino)-1-(4-(3-isopropyl-2-(8-methyltetrazolo[1,5-a]pyridin-6-yl)-1H-indol-5-yl)piperidin-1-yl)ethan-1-one (477); 2-(3,3-difluoropyrrolidin-1-yl)-1-(4-(3-isopropyl-2-(8-methyltetrazolo[1,5-a]pyridin-6-yl)-1H-indol-5-yl) piperidin-1-yl)ethan-1-one (478); 2-((1R,5S)-3-oxa-8-azabicyclo[3.2.1]octan-8-yl)-1-(4-(3-isopropyl-2-(8-methyltetrazolo[1,5-a]pyridin-6-yl)-1H-indol-5-yl) piperidin-1-yl)ethan-1-one (479); 2-(isopropyl(methyl) amino)-1-(4-(3-isopropyl-2-(8-methyltetrazolo[1,5-a] pyridin-6-yl)-1H-indol-5-yl)piperidin-1-yl)ethan-1-one (480); 2-(tert-butyl(methyl)amino)-1-(4-(3-isopropyl-2-(8-methyltetrazolo[1,5-a]pyridin-6-yl)-1H-indol-5-yl)piperidin-1-yl)ethan-1-one (481); 2-(4,4-difluoropiperidin-1-yl)-1-(4-(3-isopropyl-2-(8-methyltetrazolo[1,5-a]pyridin-6-yl)-1H-indol-5-yl)piperidin-1-yl)ethan-1-one (482); 2-(cyclopropyl(methyl)amino)-1-(4-(3-isopropyl-2-(8-methyltetrazolo[1,5-a]pyridin-6-yl)-1H-indol-5-yl)piperidin-1-yl)ethan-1-one (483); 2-((1R,5S)-8-oxa-3-azabicyclo[3.2.1]octan-3-yl)-1-(4-(3-isopropyl-2-(8-methyltetrazolo [1,5-a]pyridin-6-yl)-1H-indol-5-yl)piperidin-1-yl)ethan-1-one (484); 2-(1,1-dioxidothiomorpholino)-1-(4-(3-isopropyl-2-(8-methyltetrazolo[1,5-a]pyridin-6-yl)-1H-indol-5-yl)piperidin-1-yl)ethan-1-one (485); 2-(dimethylamino)-1-(4-(3-isopropyl-2-(7-methyltetrazolo[1,5-a]pyridin-6-yl)-1H-indol-5-yl)piperidin-1-yl)ethan-1-one (486); 2-(dimethylamino)-1-(4-(3-isopropyl-2-(3-methyl-[1,2,3]triazolo[1,5-a]pyridin-5-yl)-1H-indol-5-yl) piperidin-1-yl)ethan-1-one (487); 2-(dimethylamino)-1-(4-(3-isopropyl-2-(7-methyl-[1,2,3]triazolo[1,5-a]pyridin-5-yl)-1H-indol-5-yl)piperidin-1-yl)ethan-1-one (488); 5-(5-(1-(dimethylglycyl)piperidin-4-yl)-3-isopropyl-1H-indol-2-yl)-3,7-dimethylbenzo[d]oxazol-2(3H)-one (489); 5-(5-(1-(dimethylglycyl)piperidin-4-yl)-3-isopropyl-1H-indol-2-yl)-7-methylbenzo[d]oxazol-2(3H)-one (490); 2-(dimethylamino)-1-(4-(2-(2,7-dimethylbenzo[d] oxazol-5-yl)-3-isopropyl-1H-indol-5-yl)piperidin-1-yl)ethan-1-one (491); 2-(dimethylamino)-1-(4-(2-(8-(hydroxymethyl)imidazo[1,2-a]pyridin-6-yl)-3-isopropyl-1H-indol-5-yl)piperidin-1-yl)ethan-1-one (492); 2-(dimethylamino)-1-(4-(2-(8-(2-hydroxypropan-2-yl)imidazo[1,2-a]pyridin-6-yl)-3-isopropyl-1H-indol-5-yl)piperidin-1-yl) ethan-1-one (493); 6-(5-(1-(dimethylglycyl)piperidin-4-yl)-3-isopropyl-1H-indol-2-yl)-N-(2-hydroxyethyl)-N,8-dimethylimidazo[1,2-a] pyridine-2-carboxamide (494); 6-(5-(1-(dimethylglycyl)piperidin-4-yl)-3-isopropyl-1H-indol-2-yl)-N,8-dimethylimidazo[1,2-a] pyridine-2-carboxamide (495); 2-(dimethylamino)-1-(4-(3-isopropyl-2-(5-methoxy-2-methyl-[1,2,4]triazolo[1,5-a]pyridin-7-yl)-1H-indol-5-yl)piperidin-1-yl)ethan-1-one (496); 2-(dimethylamino)-1-(4-(2-(5-ethoxy-2-methyl-[1,2,4]triazolo[1,5-a]pyridin-7-yl)-3-isopropyl-1H-indol-5-yl)piperidin-1-yl)ethan-1-one (497); 2-(dimethylamino)-1-(4-(2-(5-ethoxy-[1,2,4]triazolo[1,5-a]pyridin-7-yl)-3-isopropyl-1H-indol-5-yl)piperidin-1-yl)ethan-1-one (498); 2-(dimethylamino)-1-(4-(2-(2,5-dimethylimidazo[1,2-a]pyridin-7-yl)-3-isopropyl-1H-indol-5-yl)piperidin-1-yl)ethan-1-one (499); 2-(dimethylamino)-1-(4-(3-isopropyl-2-(5-methylimidazo[1,2-a]pyridin-7-yl)-1H-indol-5-yl)piperidin-1-yl)ethan-1-one (500); 2-(dimethylamino)-1-(4-(3-isopropyl-2-(5-methoxyimidazo[1,2-a]pyridin-7-yl)-1H-indol-5-yl)piperidin-1-yl)ethan-1-one (501); 2-(dimethylamino)-1-(4-(3-isopropyl-2-(pyrazolo[1,5-a]pyrimidin-6-yl)-1H-indol-5-yl)piperidin-1-yl)ethan-1-one (502); 1-(4-(3-isopropyl-2-(pyrazolo[1,5-a]pyrimidin-6-yl)-1H-indol-5-yl)piperidin-1-yl)-2-(methylamino)ethan-1-one (503); 2-(dimethylamino)-1-(4-(3-isopropyl-2-(1-methyl-1H-pyrazolo[3,4-b]pyridin-5-yl)-1H-indol-5-yl)piperidin-1-yl)ethan-1-one (504); 2-(dimethylamino)-1-(4-(3-isopropyl-2-(2-methyl-2H-pyrazolo[3,4-b]pyridin-5-yl)-1H-indol-5-yl)piperidin-1-yl)ethan-1-one (505); 5-(5-(1-(dimethylglycyl)piperidin-4-yl)-3-isopropyl-1H-indol-2-yl)quinoline-8-carbonitrile (506); 2-(dimethylamino)-1-(4-(3-isopropyl-2-(8-(trifluoromethyl)imidazo[1,2-a]pyridin-6-yl)-1H-indol-5-yl)piperidin-1-yl)ethan-1-one (507); 1-(4-(3-isopropyl-2-(8-(trifluoromethyl)imidazo[1,2-a]pyridin-6-yl)-1H-indol-5-yl)piperidin-1-yl)-2-(methylamino)ethan-1-one (508); 2-(dimethylamino)-1-(4-(2-(2,8-dimethylimidazo[1,2-a]pyridin-6-yl)-3-isopropyl-1H-indol-5-yl)piperidin-1-yl)ethan-1-one (509); 1-(4-(2-(2,7-dimethylimidazo[1,2-a]pyridin-6-yl)-3-isopropyl-1H-indol-5-yl)piperidin-1-yl)-2-(methylamino)ethan-1-one (510); 2-(dimethylamino)-1-(4-(3-isopropyl-2-(2-methyl-8-(trifluoromethyl)imidazo[1,2-a]pyridin-6-yl)-1H-indol-5-yl)piperidin-1-yl)ethan-1-one (511); 1-(4-(2-(8-chloroquinolin-6-yl)-3-isopropyl-1H-indol-5-yl)piperidin-1-yl)-2-(dimethylamino)ethan-1-one (512); ((2R,3R)-3-hydroxypyrrolidin-2-yl)(4-(3-isopropyl-2-(pyrazolo[1,5-a]pyrimidin-6-yl)-1H-indol-5-yl) piperidin-1-yl)methanone (513); 1-(4-(2-([1,2,4]triazolo[1,5-a]pyridin-8-yl)-3-isopropyl-1H-indol-5-yl)piperidin-1-yl)-2-(dimethylamino)ethan-1-one (514); 1-(4-(2-(2,5-dimethyl-[1,2,4]triazolo[1,5-a]pyridin-8-yl)-3-isopropyl-1H-indol-5-yl)piperidin-1-yl)-2-(dimethylamino)ethan-1-one (515); 2-(dimethylamino)-1-(4-(3-isopropyl-2-(5-methyl-[1,2,4]triazolo[1,5-a]pyridin-8-yl)-1H-indol-5-yl)piperidin-1-yl)ethan-1-one (516); 1-(4-(3-(2,2-difluoroethyl)-2-(1H-pyrazolo[3,4-b]pyridin-4-yl)-1H-indol-5-yl)piperidin-1-yl)-2-(dimethylamino)ethan-1-one (517); 2-(dimethylamino)-1-(4-(3-isopropyl-2-(8-methylquinoxalin-6-yl)-1H-indol-5-yl)piperidin-1-yl)ethan-1-one (518); 2-(((1s,4s)-4-aminocyclohexyl)amino)-1-(4-(3-ethyl-2-(1-methyl-1H-indazol-4-yl)-1H-indol-5-yl)piperidin-1-yl)ethan-1-one (519); 2-(dimethylamino)-1-(4-(3-ethyl-2-(1-methyl-1H-indazol-4-yl)-1H-indol-5-yl)piperidin-1-yl)ethan-1-one (520); 1-(4-(3-ethyl-2-(1-methyl-1H-indazol-4-yl)-1H-indol-5-yl)piperidin-1-yl)-2-(4-methyl-1,4-diazepan-1-yl)ethan-1-one (521); 2-(dimethylamino)-1-(4-(3-isopropyl-2-(3-methylimidazo[1,2-a]pyridin-6-yl)-1H-indol-5-yl) piperidin-1-yl)ethan-1-one (522); 2-(dimethylamino)-1-(4-(3-isopropyl-2-(2-methylimidazo [1,2-a]pyridin-6-yl)-1H-indol-5-yl)piperidin-1-yl)ethan-1-one (523); 2-(dimethylamino)-1-(4-(2-(7-isobutyl-2-methylpyrazolo[1,5-a]pyridin-5-yl)-3-isopropyl-1H-indol-5-yl)piperidin-1-yl)ethan-1-one (524); 2-(dimethylamino)-1-(4-(3-isopropyl-2-(1H-pyrazolo[4,3-b]pyridin-6-yl)-1H-indol-5-yl)piperidin-1-yl)ethan-1-one (526); 2-(dimethylamino)-1-(4-(3-isopropyl-2-(2,3,8-trimethylimidazo[1,2-a]pyridin-6-yl)-1H-indol-5-yl)piperidin-1-yl)ethan-1-one (527); 2-(dimethylamino)-1-(4-(3-isopropyl-2-(8-methylimidazo[1,2-a]pyridin-6-yl)-1H-indol-5-yl)piperidin-1-yl)ethan-1-one (528); 2-(dimethylamino)-1-(4-(3-isopropyl-2-(8-methylquinolin-6-yl)-1H-indol-5-yl) piperidin-1-yl) ethan-1-one (529); 1-(4-(3-isopropyl-2-(5-methylimidazo[1,5-a]pyridin-7-yl)-1H-indol-5-yl)piperidin-1-yl)-2-(methylamino)ethan-1-one (530); 2-(dimethylamino)-1-(4-(3-isopropyl-2-(5-methylimidazo[1,5-a]pyridin-7-yl)-1H-indol-5-yl)piperidin-1-yl)ethan-1-one (531); 2-(dimethylamino)-1-(4-(3-isopropyl-2-(5-methoxy-[1,2,4]triazolo[1,5-a]pyridin-7-yl)-1H-indol-5-yl)piperidin-1-yl)ethan-1-one (532); 2-(dimethylamino)-1-(4-(3-isopropyl-2-(2-methylquinolin-4-yl)-1H-indol-5-yl)piperidin-1-yl)ethan-1-one (533); 1-(4-(3-isopropyl-2-(2-methylquinolin-4-yl)-1H-indol-5-yl)piperidin-1-yl)-2-(methylamino)ethan-1-one (534); 2-(dimethylamino)-1-(4-(3-isopropyl-2-(2-methylpyrazolo[1,5-a]pyridin-5-yl)-1H-indol-5-yl) piperidin-1-yl)ethan-1-one (535); 2-(dimethylamino)-1-(4-(3-isopropyl-2-(5-methyl-[1,2,4]triazolo[1,5-a]pyridin-7-yl)-1H-indol-5-yl)ethan-1-one (536); ((2S,4R)-4-hydroxypyrrolidin-2-yl)(4-(3-isopropyl-2-(5-methyl-[1,2,4]triazolo[1,5-a]pyridin-7-yl)-1H-indol-5-yl)piperidin-1-yl)methanone (537); 2-(dimethylamino)-1-(4-(3-isopropyl-2-(2-methyl-[1,2,4]triazolo[1,5-a]pyridin-7-yl)-1H-indol-5-yl)piperidin-1-yl)ethan-1-one (538); ((2S,4R)-4-hydroxypyrrolidin-2-yl)(4-(3-isopropyl-2-(5-methylimidazo[1,2-a]pyridin-7-yl)-1H-indol-5-yl)piperidin-1-yl)methanone (539); ((2S,4R)-4-hydroxypyrrolidin-2-yl)(4-(3-isopropyl-2-(2-methyl-[1,2,4]triazolo[1,5-a]pyridin-7-yl)-1H-indol-5-yl)piperidin-1-yl) methanone (540); 2-(dimethylamino)-1-(4-(3-isopropyl-2-(5-methoxy-2-methylimidazo[1,2-a]pyridin-7-yl)-1H-indol-5-yl)piperidin-1-yl)ethan-1-one (541); 2-(dimethylamino)-1-(4-(3-isopropyl-2-(pyrazolo[1,5-a]pyridin-5-yl)-1H-indol-5-yl)piperidin-1-yl)ethan-1-one (542); 2-(dimethylamino)-1-(4-(3-isopropyl-2-(7-methylthiazolo[5,4-b]pyridin-5-yl)-1H-indol-5-yl) piperidin-1-yl)ethan-1-one (543); 2-(dimethylamino)-1-(4-(2-(8-fluoroimidazo[1,2-a]pyridin-6-yl)-3-isopropyl-1H-indol-5-yl)piperidin-1-yl)ethan-1-one (544); 1-(4-(3-(2,2-difluoroethyl)-2-(8-fluoroimidazo[1,2-a]pyridin-6-yl)-1H-indol-5-yl)piperidin-1-yl)-2-(methylamino)ethan-1-one (545); 1-(4-(3-(2,2-difluoroethyl)-2-(8-fluoroimidazo[1,2-a] pyridin-6-yl)-1H-indol-5-yl)piperidin-1-yl)-2-(dimethylamino)ethan-1-one (546); 1-(4-(2-(8-fluoroimidazo[1,2-a]pyridin-6-yl)-3-isopropyl-1H-indol-5-yl)piperidin-1-yl)-2-(methylamino) ethan-1-one (547); 1-(4-(2-(7,8-dimethylimidazo[1,2-a]pyridin-6-yl)-3-isopropyl-1H-indol-5-yl)piperidin-1-yl)-2-(methylamino)ethan-1-one (548); 2-(dimethylamino)-1-(4-(2-(7,8-dimethylimidazo[1,2-a]pyridin-6-yl)-3-isopropyl-1H-indol-5-yl)piperidin-1-yl)ethan-1-one (549); 1-(4-(3-(2,2-difluoroethyl)-2-(2-methylimidazo[1,2-a] pyridin-6-yl)-1H-indol-5-yl)piperidin-1-yl)-2-(methylamino)ethan-1-one (550); 1-(4-(3-(2,2-difluoroethyl)-2-(2-methylimidazo[1,2-a]pyridin-6-yl)-1H-indol-5-yl)piperidin-1-yl)-2-(dimethylamino)ethan-1-one (551); 2-(dimethylamino)-1-(4-(2-(2,7-dimethylpyrazolo[1,5-a] pyridin-5-yl)-3-isopropyl-1H-indol-5-yl)piperidin-1-yl)ethan-1-one (552); 1-(4-(3-isopropyl-2-(5-methoxy-[1,2,4]triazolo[1,5-a]pyridin-7-yl)-1H-indol-5-yl)piperidin-1-yl)-2-(methylamino)ethan-1-one (553); 1-(4-(2-([1,2,4]triazolo[1,5-a]pyrimidin-6-yl)-3-isopropyl-1H-indol-5-yl)piperidin-1-yl)-2-(dimethylamino)

ethan-1-one (554); 1-(4-(2-([1,2,4]triazolo [1,5-a]pyrimidin-6-yl)-3-isopropyl-1H-indol-5-yl)piperidin-1-yl)-2-(methylamino)ethan-1-one (555); 1-(4-(2-(7-chloro-1H-indazol-4-yl)-3-isopropyl-1H-indol-5-yl)piperidin-1-yl)-2-(dimethylamino)ethan-1-one (556); 1-(4-(3-isopropyl-2-(8-methylimidazo[1,2-a]pyridin-6-yl)-1H-indol-5-yl) piperidin-1-yl)-2-(methylamino)ethan-1-one (557); 2-(dimethylamino)-1-(4-(3-isopropyl-2-(8-methoxyimidazo [1,2-a]pyridin-6-yl)-1H-indol-5-yl)piperidin-1-yl) ethan-1-one (558); 1-(4-(3-isopropyl-2-(8-methoxyimidazo[1,2-a]pyridin-6-yl)-1H-indol-5-yl)piperidin-1-yl)-2-(methylamino)ethan-1-one (559); 1-(4-(3-isopropyl-2-(8-methylquinolin-6-yl)-1H-indol-5-yl)piperidin-1-yl)-2-(methylamino)ethan-1-one (560); 2-(dimethylamino)-1-(4-(3-isopropyl-2-(1H-pyrazolo[3,4-b]pyridin-5-yl)-1H-indol-5-yl)piperidin-1-yl)ethan-1-one (562); 2-(dimethylamino)-1-(4-(3-isopropyl-2-(1H-pyrrolo[2,3-b]pyridin-5-yl)-1H-indol-5-yl) piperidin-1-yl)ethan-1-one (563); 2-(dimethylamino)-1-(4-(3-isopropyl-2-(1H-pyrrolo[2,3-b]pyridin-4-yl)-1H-indol-5-yl)piperidin-1-yl)ethan-1-one (564); 2-(1H-imidazol-1-yl)-1-(4-(3-isopropyl-2-(1H-pyrazolo[3,4-b]pyridin-4-yl)-1H-indol-5-yl)piperidin-1-yl) ethan-1-one (565); (S)-1-(2-(4-(3-isopropyl-2-(1H-pyrazolo [3,4-b]pyridin-4-yl)-1H-indol-5-yl)piperidine-1-carbonyl) pyrrolidin-1-yl)ethan-1-one (566); N-(2-(4-(3-isopropyl-2-(1H-pyrazolo[3,4-b] pyridin-4-yl)-1H-indol-5-yl)piperidin-1-yl)-2-oxoethyl)acetamide (567); N,N-diethyl-1-(2-(4-(3-isopropyl-2-(1H-pyrrolo[2,3-b]pyridin-4-yl)-1H-indol-5-yl) piperidin-1-yl)-2-oxoethyl) piperidine-3-carboxamide (568); N,N-diethyl-1-(2-(4-(3-isopropyl-2-(1H-pyrrolo[2,3-b] pyridin-4-yl)-1H-indol-5-yl)piperidin-1-yl)-2-oxoethyl) piperidine-3-carboxamide (569); 2-(dimethylamino)-1-(4-(3-isopropyl-2-(7-methylpyrazolo[1,5-a]pyridin-5-yl)-1H-indol-5-yl) piperidin-1-yl)ethan-1-one (570); 1-(4-(3-(2,2-difluoroethyl)-2-(imidazo[1,2-a]pyridin-7-yl)-1H-indol-5-yl)piperidin-1-yl)-2-(dimethylamino)ethan-1-one (571); 2-(dimethylamino)-1-(4-(2-(imidazo[1,2-a]pyridin-6-yl)-3-isopropyl-1H-indol-5-yl)piperidin-1-yl)ethan-1-one (572); N-(2-((2-(4-(3-isopropyl-2-(1H-pyrazolo[3,4-b]pyridin-4-yl)-1H-indol-5-yl)piperidin-1-yl)-2-oxoethyl)amino)ethyl) acetamide (573); 2-(4-acetylpiperazin-1-yl)-1-(4-(3-isopropyl-2-(1H-pyrazolo[3,4-b]pyridin-4-yl)-1H-indol-5-yl) piperidin-1-yl)ethan-1-one (574); 2-((3-(dimethylamino) propyl)amino)-1-(4-(3-isopropyl-2-(1H-pyrazolo[3,4-b] pyridin-4-yl)-1H-indol-5-yl)piperidin-1-yl)ethan-1-one (575); 2-(4-(hydroxymethyl)piperidin-1-yl)-1-(4-(3-isopropyl-2-(1H-pyrazolo[3,4-b]pyridin-4-yl)-1H-indol-5-yl)piperidin-1-yl)ethan-1-one (576); 1-(4-(3-isopropyl-2-(1H-pyrazolo[3,4-b]pyridin-4-yl)-1H-indol-5-yl)piperidin-1-yl)-2-(4-methyl-1,4-diazepan-1-yl)ethan-1-one (577); 1-(4-(3-isopropyl-2-(1H-pyrazolo[3,4-b] pyridin-4-yl)-1H-indol-5-yl)piperidin-1-yl)-2-(isopropylamino)ethan-1-one (578); (R)-2-(3-hydroxypyrrolidin-1-yl)-1-(4-(3-isopropyl-2-(1H-pyrazolo[3,4-b]pyridin-4-yl)-1H-indol-5-yl)piperidin-1-yl) ethan-1-one (579); 1-(4-(3-isopropyl-2-(1H-pyrazolo[3,4-b] pyridin-4-yl)-1H-indol-5-yl)piperidin-1-yl)-2-((2-methyl-2-morpholinopropyl)amino)ethan-1-one (580); (S)—N-(1-(2-(4-(3-isopropyl-2-(1H-pyrazolo[3,4-b]pyridin-4-yl)-1H-indol-5-yl)piperidin-1-yl)-2-oxoethyl)pyrrolidin-3-yl) acetamide (581); (R)-2-(3-(dimethylamino)pyrrolidin-1-yl)-1-(4-(3-isopropyl-2-(1H-pyrazolo[3,4-b]pyridin-4-yl)-1H-indol-5-yl)piperidin-1-yl)ethan-1-one (582); 2-(sec-butylamino)-1-(4-(3-isopropyl-2-(1H-pyrazolo[3,4-b] pyridin-4-yl)-1H-indol-5-yl)piperidin-1-yl)ethan-1-one (583); (S)-1-(2-(4-(3-isopropyl-2-(1H-pyrazolo[3,4-b]pyridin-4-yl)-1H-indol-5-yl)piperidin-1-yl)-2-oxoethyl)pyrrolidine-2-carboxamide (584); 2-(isopropyl(methyl)amino)-1-(4-(3-isopropyl-2-(1H-pyrazolo[3,4-b]pyridin-4-yl)-1H-indol-5-yl)piperidin-1-yl)ethan-1-one (585); 2-(4-acetyl-1, 4-diazepan-1-yl)-1-(4-(3-isopropyl-2-(1H-pyrazolo[3,4-b] pyridin-4-yl)-1H-indol-5-yl)piperidin-1-yl)ethan-1-one (586); 4-(2-(4-(3-isopropyl-2-(1H-pyrazolo[3,4-b]pyridin-4-yl)-1H-indol-5-yl)piperidin-1-yl)-2-oxoethyl) piperazin-2-one (587); N,N-diethyl-1-(2-(4-(3-isopropyl-2-(1H-pyrazolo[3,4-b]pyridin-4-yl)-1H-indol-5-yl)piperidin-1-yl)-2-oxoethyl)piperidine-3-carboxamide (588); 1-(4-(3-isopropyl-2-(1H-pyrazolo[3,4-b]pyridin-4-yl)-1H-indol-5-yl)piperidin-1-yl)-2-(neopentylamino)ethan-1-one (589); (S)-2-(3-(dimethylamino)pyrrolidin-1-yl)-1-(4-(3-isopropyl-2-(1H-pyrazolo [3,4-b]pyridin-4-yl)-1H-indol-5-yl)piperidin-1-yl)ethan-1-one (590); 1-(4-(3-isopropyl-2-(1H-pyrazolo[3,4-b]pyridin-4-yl)-1H-indol-5-yl)piperidin-1-yl)-2-(4-(pyridin-4-yl)piperazin-1-yl)ethan-1-one (591); 1-(4-(3-isopropyl-2-(1H-pyrazolo[3,4-b]pyridin-4-yl)-1H-indol-5-yl) piperidin-1-yl)ethan-1-one (592); (S)-3-hydroxy-1-(4-(3-isopropyl-2-(8-methyltetrazolo[1,5-a]pyridin-6-yl)-1H-indol-5-yl)piperidin-1-yl)butan-1-one (593); (R)-3-hydroxy-1-(4-(3-isopropyl-2-(8-methyltetrazolo[1,5-a] pyridin-6-yl)-1H-indol-5-yl)piperidin-1-yl)butan-1-one (594); (S)-3-hydroxy-1-(4-(3-isopropyl-2-(pyrazolo[1,5-a] pyrimidin-6-yl)-1H-indol-5-yl) piperidin-1-yl)butan-1-one (595); 1-(4-(2-(2,7-dimethylimidazo[1,2-a]pyridin-6-yl)-3-isopropyl-1H-indol-5-yl)piperidin-1-yl)-3-hydroxybutan-1-one (596); 1-(4-(2-(2,7-dimethylimidazo[1,2-a]pyridin-6-yl)-3-isopropyl-1H-indol-5-yl)piperidin-1-yl)-3-hydroxy-3-methylbutan-1-one (597); (S)-1-(4-(2-(2,5-dimethyl-[1,2,4] triazolo[1,5-a]pyridin-8-yl)-3-isopropyl-1H-indol-5-yl) piperidin-1-yl)-3-hydroxybutan-1-one (598); (S)-3-hydroxy-1-(4-(3-isopropyl-2-(5-methyl-[1,2,4]triazolo[1,5-a]pyridin-8-yl)-1H-indol-5-yl)piperidin-1-yl)butan-1-one (599); (S)-3-hydroxy-1-(4-(3-isopropyl-2-(5-methyl-[1,2,4] triazolo[1,5-a]pyridin-7-yl)-1H-indol-5-yl)piperidin-1-yl) butan-1-one (600); 3-hydroxy-1-(4-(3-isopropyl-2-(2-methyl-[1,2,4]triazolo[1,5-a]pyridin-7-yl)-1H-indol-5-yl) piperidin-1-yl)-3-methylbutan-1-one (601); (S)-3-hydroxy-1-(4-(3-isopropyl-2-(2-methyl-[1,2,4]triazolo[1,5-a] pyridin-7-yl)-1H-indol-5-yl)piperidin-1-yl)butan-1-one (602); (R)-1-(4-(3-(2,2-difluoroethyl)-2-(8-fluoroimidazo [1,2-a]pyridin-6-yl)-1H-indol-5-yl)piperidin-1-yl)-3-hydroxybutan-1-one (603); (S)-1-(4-(2-(8-fluoroimidazo[1,2-a]pyridin-6-yl)-3-isopropyl-1H-indol-5-yl)piperidin-1-yl)-3-hydroxybutan-1-one (604); (R)-1-(4-(2-(8-fluoroimidazo [1,2-a]pyridin-6-yl)-3-isopropyl-1H-indol-5-yl)piperidin-1-yl)-3-hydroxybutan-1-one (605); 1-(4-(3-(2,2-difluoroethyl)-2-(8-fluoroimidazo[1,2-a]pyridin-6-yl)-1H-indol-5-yl)piperidin-1-yl)-3-hydroxy-3-methylbutan-1-one (606); 1-(4-(3-(2,2-difluoroethyl)-2-(2-methylimidazo[1,2-a]pyridin-6-yl)-1H-indol-5-yl)piperidin-1-yl)-3-hydroxy-3-methylbutan-1-one (607); (S)-1-(4-(3-(2,2-difluoroethyl)-2-(2-methylimidazo[1,2-a]pyridin-6-yl)-1H-indol-5-yl) piperidin-1-yl)-3-hydroxybutan-1-one (608); (R)-1-(4-(3-(2, 2-difluoroethyl)-2-(2-methylimidazo[1,2-a]pyridin-6-yl)-1H-indol-5-yl)piperidin-1-yl)-3-hydroxybutan-1-one (609); (4-(3-isopropyl-2-(1H-pyrazolo[3,4-b]pyridin-4-yl)-1H-indol-5-yl)piperidin-1-yl)(1H-pyrazol-4-yl)methanone (610); (4-(3-isopropyl-2-(1H-pyrazolo[3,4-b]pyridin-4-yl)-1H-indol-5-yl)piperidin-1-yl)(thiazol-4-yl)methanone (611); 2-(1H-imidazol-4-yl)-1-(4-(3-isopropyl-2-(1H-pyrazolo[3, 4-b]pyridin-4-yl)-1H-indol-5-yl)piperidin-1-yl)ethan-1-one (612); 4-(4-(3-isopropyl-2-(1H-pyrazolo[3,4-b]pyridin-4-yl)-1H-indol-5-yl)piperidin-1-yl)-N,N-dimethyl-4-oxobutanamide (613); 1-(4-(3-isopropyl-2-(1H-pyrazolo[3,4-b] pyridin-4-yl)-1H-indol-5-yl)piperidin-1-yl)-2-(methylsulfonyl)ethan-1-one (614); (4-(3-isopropyl-2-(1H- pyrazolo[3,4-b]pyridin-4-yl)-1H-indol-5-yl)piperidin-1-yl)(1H-pyrazol-3-yl)methanone (615); 2-((4-(3-isopropyl-2-(8-methyltetrazolo[1,5-a]pyridin-6-yl)-1H-indol-5-yl)piperidin-1-yl)sulfonyl)ethan-1-ol (616); 2-((4-(3-isopropyl-2-(8-methyltetrazolo[1,5-a]pyridin-6-yl)-1H-indol-5-yl)piperidin-1-yl)sulfonyl)-N,N-dimethylethan-1-amine (617); 1-(4-(3-isopropyl-2-(8-methyltetrazolo[1,5-a]pyridin-6-yl)-1H-indol-5-yl)piperidin-1-yl)-3-(pyrrolidin-1-yl)propan-1-one (618); 1-(4-(2-(7,8-dimethyltetrazolo[1,5-a]pyridin-6-yl)-3-isopropyl-1H-indol-5-yl)piperidin-1-yl)-3-morpholinopropan-1-one (619); 3-(dimethylamino)-1-(4-(3-isopropyl-2-(8-methyltetrazolo[1,5-a]pyridin-6-yl)-1H-indol-5-yl)piperidin-1-yl)propan-1-one (620); 1-(4-(3-isopropyl-2-(8-methyltetrazolo[1,5-a]pyridin-6-yl)-1H-indol-5-yl)piperidin-1-yl)-3-(2,2,6,6-tetramethylmorpholino)propan-1-one (621); 3-((1R,5S)-8-oxa-3-azabicyclo[3.2.1]octan-3-yl)-1-(4-(3-isopropyl-2-(8-methyltetrazolo[1,5-a]pyridin-6-yl)-1H-indol-5-yl)piperidin-1-yl)propan-1-one (622); 3-(cyclopropyl(methyl)amino)-1-(4-(3-isopropyl-2-(8-methyltetrazolo[1,5-a]pyridin-6-yl)-1H-indol-5-yl)piperidin-1-yl)propan-1-one (623); 3-(isopropyl(methyl)amino)-1-(4-(3-isopropyl-2-(8-methyltetrazolo[1,5-a]pyridin-6-yl)-1H-indol-5-yl)piperidin-1-yl)propan-1-one (624); 3-(ethyl(methyl)amino)-1-(4-(3-isopropyl-2-(8-methyltetrazolo[1,5-a]pyridin-6-yl)-1H-indol-5-yl)piperidin-1-yl)propan-1-one (625); 3-(3,3-difluoropyrrolidin-1-yl)-1-(4-(3-isopropyl-2-(8-methyltetrazolo[1,5-a]pyridin-6-yl)-1H-indol-5-yl)piperidin-1-yl)propan-1-one (626); 1-(4-(3-isopropyl-2-(8-methyltetrazolo[1,5-a]pyridin-6-yl)-1H-indol-5-yl)piperidin-1-yl)-3-morpholinopropan-1-one (627); 3-(4,4-difluoropiperidin-1-yl)-1-(4-(3-isopropyl-2-(8-methyltetrazolo[1,5-a]pyridin-6-yl)-1H-indol-5-yl)piperidin-1-yl)propan-1-one (628); 1-(4-(3-isopropyl-2-(8-methyltetrazolo[1,5-a]pyridin-6-yl)-1H-indol-5-yl)piperidin-1-yl)-3-(piperidin-1-yl)propan-1-one (629); 1-(4-(3-isopropyl-2-(8-methyltetrazolo[1,5-a]pyridin-6-yl)-1H-indol-5-yl)piperidin-1-yl)-3-(2-oxa-6-azaspiro[3.3]heptan-6-yl)propan-1-one (631); 3-(2-azabicyclo[3.1.0]hexan-2-yl)-1-(4-(3-isopropyl-2-(8-methyltetrazolo[1,5-a]pyridin-6-yl)-1H-indol-5-yl)piperidin-1-yl)propan-1-one (632); 3-(4-fluoropiperidin-1-yl)-1-(4-(3-isopropyl-2-(8-methyltetrazolo[1,5-a]pyridin-6-yl)-1H-ndol-5-yl)piperidin-1-yl)propan-1-one (633); 3-(1,1-dioxidothiomorpholino)-1-(4-(3-isopropyl-2-(8-methyltetrazolo[1,5-a]pyridin-6-yl)-1H-indol-5-yl)piperidin-1-yl)propan-1-one (634); 3-((1R,5S)-3-oxa-8-azabicyclo[3.2.1]octan-8-yl)-1-(4-(3-isopropyl-2-(8-methyltetrazolo[1,5-a]pyridin-6-yl)-1H-indol-5-yl)piperidin-1-yl)propan-1-one (635); (4-(3-isopropyl-2-(1H-pyrazolo[3,4-b]pyridin-4-yl)-1H-indol-5-yl)piperidin-1-yl)(piperidin-3-yl)methanone (636); (S)-3-amino-1-(4-(3-isopropyl-2-(1H-pyrazolo[3,4-b]pyridin-4-yl)-1H-indol-5-yl)piperidin-1-yl)butan-1-one (637); 4-(4-(3-isopropyl-2-(2-methylquinolin-4-yl)-1H-indol-5-yl)piperidine-1-carbonyl)-1-methylpyrrolidin-2-one (638); (R)-(4-(2-(imidazo[1,2-a]pyridin-6-yl)-3-isopropyl-1H-indol-5-yl)piperidin-1-yl)(piperidin-3-yl)methanone (639); (S)-(4-(2-(imidazo[1,2-a]pyridin-6-yl)-3-isopropyl-1H-indol-5-yl)piperidin-1-yl)(piperidin-3-yl)methanone (640); 1-(4-(3-isopropyl-2-(1H-pyrazolo[3,4-b]pyridin-4-yl)-1H-indol-5-yl)piperidin-1-yl)-3-(piperidin-1-yl)propan-1-one (641); 3-(1H-imidazol-1-yl)-1-(4-(3-isopropyl-2-(1H-pyrazolo[3,4-b]pyridin-4-yl)-1H-indol-5-yl)piperidin-1-yl)propan-1-one (642); 3-(dimethylamino)-1-(4-(3-isopropyl-2-(1H-pyrazolo[3,4-b]pyridin-4-yl)-1H-indol-5-yl)piperidin-1-yl)propan-1-one (643); 4-(4-(3-(2,2-difluoroethyl)-2-(imidazo[1,2-a]pyridin-6-yl)-1H-indol-5-yl)piperidine-1-carbonyl)-1-methylpyrrolidin-2-one (644); 4-(4-(2-(imidazo[1,2-a]pyridin-6-yl)-3-isopropyl-1H-indol-5-yl)piperidine-1-carbonyl)-1-methylpyrrolidin-2-one (645); 1-(4-(4-(3-isopropyl-2-(1H-pyrazolo[3,4-b]pyridin-4-yl)-1H-indol-5-yl)piperidine-1-carbonyl)piperidin-1-yl)ethan-1-one (646); (4-(3-ethyl-2-(1H-pyrazolo[3,4-b]pyridin-4-yl)-1H-indol-5-yl)piperidin-1-yl)(piperidin-4-yl)methanone (647); (4-(3-ethyl-2-(1H-pyrazolo[3,4-b]pyridin-4-yl)-1H-indol-5-yl)piperidin-1-yl)(1-methylpiperidin-4-yl)methanone (648); (4-(3-isopropyl-2-(1H-pyrazolo[3,4-b]pyridin-4-yl)-1H-indol-5-yl)piperidin-1-yl)(piperidin-4-yl)methanone (649); 2-(4-(3-isopropyl-2-(1H-pyrazolo[3,4-b]pyridin-4-yl)-1H-indol-5-yl)piperidin-1-yl)-N-methylethanamine dihydrochloride (650); 2-(4-(2-([1,2,4]triazolo[1,5-b]pyridazin-6-yl)-3-methyl-1H-indol-5-yl)piperidin-1-yl)-N-methylethan-1-amine (651); N-(2-(4-(3-isopropyl-2-(8-methoxy-[1,2,4]triazolo[1,5-b]pyridazin-6-yl)-1H-indol-5-yl)piperidin-1-yl)ethyl)methanesulfonamide (652); 4-(5-([1,3'-bipiperidin]-4-yl)-3-isopropyl-1H-indol-2-yl)-1H-pyrazolo[3,4-b]pyridine (653); 2-(4-(3-ethyl-2-(1H-pyrazolo[3,4-b]pyridin-4-yl)-1H-indol-5-yl)piperidin-1-yl)-N-methylethan-1-amine (654); 2-(4-(3-isopropyl-2-(1H-pyrazolo[3,4-b]pyridin-4-yl)-1H-indol-5-yl)piperidin-1-yl)ethan-1-amine (655); 2-(4-(3-ethyl-2-(1H-pyrazolo[3,4-b]pyridin-4-yl)-1H-indol-5-yl)piperidin-1-yl)ethan-1-amine (656); 1-((4-(3-ethyl-2-(1H-pyrazolo[3,4-b]pyridin-4-yl)-1H-indol-5-yl)piperidin-1-yl)methyl)cyclopropan-1-amine (657); 2-(4-(3-isopropyl-2-(1H-pyrazolo[3,4-b]pyridin-4-yl)-1H-indol-5-yl)piperidin-1-yl)-N-methylethan-1-amine (658); N-methyl-2-(4-(3-methyl-2-(quinoxalin-6-yl)-1H-indol-5-yl)piperidin-1-yl)ethan-1-amine (659); 2-(4-(2-(benzo[d]thiazol-5-yl)-3-methyl-1H-indol-5-yl)piperidin-1-yl)-N-methylethan-1-amine (659); 4-(5-(1-(2-(azepan-1-yl)ethyl)piperidin-4-yl)-3-isopropyl-1H-indol-2-yl)-1H-pyrazolo[3,4-b]pyridine (660); N,N-diethyl-2-(4-(3-isopropyl-2-(1H-pyrazolo[3,4-b]pyridin-4-yl)-1H-indol-5-yl)piperidin-1-yl)ethan-1-amine (661); N-methyl-2-(4-(3-methyl-2-(quinolin-8-yl)-1H-indol-5-yl)piperidin-1-yl)ethan-1-amine (662); 2-(4-(2-(isoquinolin-4-yl)-3-methyl-1H-indol-5-yl)piperidin-1-yl)-N-methylethan-1-amine (663); N-methyl-2-(4-(3-methyl-2-(quinolin-3-yl)-1H-indol-5-yl)piperidin-1-yl)ethan-1-amine (664); 2-(4-(2-(isoquinolin-4-yl)-3-methyl-1H-indol-5-yl)piperidin-1-yl)-N-methylethan-1-amine (665); N-methyl-2-(4-(3-methyl-2-(quinolin-6-yl)-1H-indol-5-yl)piperidin-1-yl)ethan-1-amine (666); N-methyl-2-(4-(3-methyl-1H,1'H-[2,5'-biindol]-5-yl)piperidin-1-yl)ethan-1-amine (667); N-methyl-2-(4-(3-methyl-2-(1H-pyrrolo[2,3-b]pyridin-4-yl)-1H-indol-5-yl)piperidin-1-yl)ethan-1-amine (668); 2-(4-(2-(2,3-dihydrobenzofuran-5-yl)-3-methyl-1H-indol-5-yl)piperidin-1-yl)-N-methylethan-1-amine (669); 2-(4-(2-(benzo[d][1,3]dioxol-5-yl)-3-methyl-1H-indol-5-yl)piperidin-1-yl)-N-methylethan-1-amine (670); 2-(4-(2-(5-methoxybenzofuran-2-yl)-3-methyl-1H-indol-5-yl)piperidin-1-yl)-N-methylethan-1-amine (671); 2-(4-(1',3-dimethyl-1H,1'H-[2,5'-biindol]-5-yl)piperidin-1-yl)-N-methylethan-1-amine (672); N-methyl-2-(4-(3-methyl-2-(4-methyl-3,4-dihydro-2H-benzo[b][1,4]oxazin-7-yl)-1H-indol-5-yl)piperidin-1-yl)ethan-1-amine (673); 2-(3,3-difluoro-4-(3-isopropyl-2-(1H-pyrazolo[3,4-b]pyridin-4-yl)-1H-indol-5-yl)piperidin-1-yl)-N-methylethan-1-amine (674); 2-(3-fluoro-4-(3-isopropyl-2-(1H-pyrazolo[3,4-b]pyridin-4-yl)-1H-indol-5-yl)piperidin-1-yl)-N-methylethan-1-amine (675); 2-(4-(3-isopropyl-2-(2-methylimidazo[1,2-a]pyridin-6-yl)-1H-indol-5-yl)piperidin-1-yl)-N-methylethan-1-amine (676); 2-(3-fluoro-4-(3-isopropyl-2-(1H-pyrazolo[3,4-b]pyridin-4-yl)-1H-indol-5-yl)piperidin- 1-yl)-N-methylethan-1-amine (677-679); 2-(4-(2-(imidazo[1,2-a]pyridin-6-yl)-3-isopropyl-1H-indol-5-yl)piperidin-1-yl)-N-methylethan-1-amine (680); 2-(4-(3-(2,2-difluoroethyl)-2-(imidazo[1,2-a]pyridin-6-yl)-1H-indol-5-yl)piperidin-1-yl)-N-methylethan-1-amine (681); 4-(3-isopropyl-5-(1-(tetrahydro-2H-pyran-4-yl)piperidin-4-yl)-1H-indol-2-yl)-1H-pyrazolo[3,4-b]pyridine (682); 6-(3-isopropyl-5-(1-(tetrahydro-2H-pyran-4-yl)piperidin-4-yl)-1H-indol-2-yl)-[1,2,4]triazolo[1,5-b]pyridazine (683); 6-(3-isopropyl-5-(1-(tetrahydro-2H-pyran-4-yl)piperidin-4-yl)-1H-indol-2-yl)-7,8-dimethyl-[1,2,4]triazolo[1,5-b]pyridazine (684); 6-(3-isopropyl-5-(1-(tetrahydro-2H-pyran-4-yl)piperidin-4-yl)-1H-indol-2-yl)-8-methoxy-7-methyl-[1,2,4]triazolo[1,5-b]pyridazine (685); 6-(3-isopropyl-5-(1-(tetrahydro-2H-pyran-4-yl)piperidin-4-yl)-1H-indol-2-yl)-8-methyl-[1,2,4]triazolo[1,5-b]pyridazine (686); 6-(3-isopropyl-5-(1-(tetrahydro-2H-pyran-4-yl)piperidin-4-yl)-1H-indol-2-yl)-7-methyl-[1,2,4]triazolo[1,5-b]pyridazine (687); 5-(3-isopropyl-5-(1-(tetrahydro-2H-pyran-4-yl)piperidin-4-yl)-1H-indol-2-yl)-7-methyl-7H-pyrrolo[2,3-d]pyrimidine (688); 3-(3-isopropyl-5-(1-(tetrahydro-2H-pyran-4-yl)piperidin-4-yl)-1H-indol-2-yl)-1,4-dimethyl-1H-pyrrolo[2,3-b]pyridine (689); 3-(3-isopropyl-5-(1-(tetrahydro-2H-pyran-4-yl)piperidin-4-yl)-1H-indol-2-yl)-4-methyl-1H-pyrrolo[2,3-b]pyridine (690); 3-(3-isopropyl-5-(1-(tetrahydro-2H-pyran-4-yl)piperidin-4-yl)-1H-indol-2-yl)-1,2-dimethyl-1H-pyrrolo[2,3-b]pyridine (691); 6-(3-isopropyl-5-(1-(tetrahydro-2H-pyran-4-yl)piperidin-4-yl)-1H-indol-2-yl)-8-methoxy-[1,2,4]triazolo[1,5-b]pyridazine (692); 6-(3-isopropyl-5-(1-(tetrahydro-2H-pyran-4-yl)piperidin-4-yl)-1H-indol-2-yl)-7-methylimidazo[1,2-a]pyridine (693); 3-(3-isopropyl-5-(1-(tetrahydro-2H-pyran-4-yl)piperidin-4-yl)-1H-indol-2-yl)-1-methyl-1H-pyrrolo[2,3-b]pyridine (694); 6-(3-isopropyl-5-(1-(tetrahydro-2H-pyran-4-yl)piperidin-4-yl)-1H-indol-2-yl)-[1,2,3]triazolo[1,5-a]pyridine (695); 5-(3-isopropyl-5-(1-(tetrahydro-2H-pyran-4-yl)piperidin-4-yl)-1H-indol-2-yl)-[1,2,3]triazolo[1,5-a]pyridine (696); 7-(3-isopropyl-5-(1-(tetrahydro-2H-pyran-4-yl)piperidin-4-yl)-1H-indol-2-yl)-[1,2,4]triazolo[4,3-a]pyridine (697); 6-(3-isopropyl-5-(1-(tetrahydro-2H-pyran-4-yl)piperidin-4-yl)-1H-indol-2-yl)-8-methyltetrazolo[1,5-a]pyridine (698); 6-(3-isopropyl-5-(1-(tetrahydro-2H-pyran-4-yl)piperidin-4-yl)-1H-indol-2-yl)-7-methyltetrazolo[1,5-a]pyridine (699); 5-(3-isopropyl-5-(1-(tetrahydro-2H-pyran-4-yl)piperidin-4-yl)-1H-indol-2-yl)-3-methyl-[1,2,3]triazolo[1,5-a]pyridine (700); 5-(3-isopropyl-5-(1-(tetrahydro-2H-pyran-4-yl)piperidin-4-yl)-1H-indol-2-yl)-[1,2,3]triazolo[1,5-a]pyridine (701); 8-(3-isopropyl-5-(1-(tetrahydro-2H-pyran-4-yl)piperidin-4-yl)-1H-indol-2-yl)-[1,2,4]triazolo[1,5-a]pyridine (702); 6-(3-isopropyl-5-(1-(tetrahydro-2H-pyran-4-yl)piperidin-4-yl)-1H-indol-2-yl)-8-methylquinoline (703); 6-(3-isopropyl-5-(1-(tetrahydro-2H-pyran-4-yl)piperidin-4-yl)-1H-indol-2-yl)-8-methylquinoline (704); 6-(3-isopropyl-5-(1-(tetrahydro-2H-pyran-4-yl)piperidin-4-yl)-1H-indol-2-yl)-8-methylimidazo[1,2-a]pyridine (705); 6-(3-isopropyl-5-(1-(tetrahydro-2H-pyran-4-yl)piperidin-4-yl)-1H-indol-2-yl)-8-methoxyimidazo[1,2-a]pyridine (706); 7-(3-isopropyl-5-(1-(tetrahydro-2H-pyran-4-yl)piperidin-4-yl)-1H-indol-2-yl)-5-methylimidazo[1,5-a]pyridine (707); 5-(3-isopropyl-5-(1-(oxetan-3-yl)piperidin-4-yl)-1H-indol-2-yl)-7-methylbenzo[d]oxazol-2(3H)-one (708); 5-(3-isopropyl-5-(1-(oxetan-3-yl)piperidin-4-yl)-1H-indol-2-yl)-2,7-dimethylbenzo[d]oxazole (709); 7-(3-isopropyl-5-(1-(oxetan-3-yl)piperidin-4-yl)-1H-indol-2-yl)-5-methoxy-[1,2,4]triazolo[1,5-a]pyridine (710); 7-(3-isopropyl-5-(1-(oxetan-3-yl)piperidin-4-yl)-1H-indol-2-yl)-5-methylimidazo[1,2-a]pyridine (711); 7-(3-isopropyl-5-(1-(oxetan-3-yl)piperidin-4-yl)-1H-indol-2-yl)-5-methoxyimidazo[1,2-a]pyridine (712); 6-(3-isopropyl-5-(1-(oxetan-3-yl)piperidin-4-yl)-1H-indol-2-yl)pyrazolo[1,5-a]pyrimidine (713); 5-(3-isopropyl-5-(1-(oxetan-3-yl)piperidin-4-yl)-1H-indol-2-yl)quinoline-8-carbonitrile (714); 8-(3-isopropyl-5-(1-(oxetan-3-yl)piperidin-4-yl)-1H-indol-2-yl)-[1,2,4]triazolo[1,5-a]pyridine (715); 7-isobutyl-5-(3-isopropyl-5-(1-(oxetan-3-yl)piperidin-4-yl)-1H-indol-2-yl)-2-methylpyrazolo[1,5-a]pyridine (716); 6-(3-isopropyl-5-(1-(oxetan-3-yl)piperidin-4-yl)-1H-indol-2-yl)-2,8-dimethylimidazo[1,2-a]pyridine (717); 5-(3-isopropyl-5-(1-(oxetan-3-yl)piperidin-4-yl)-1H-indol-2-yl)-7-methylthiazolo[5,4-b]pyridine (718); 6-(3-isopropyl-5-(1-(oxetan-3-yl)piperidin-4-yl)-1H-indol-2-yl)-8-methylimidazo[1,2-a]pyridine (719); 5-(3-isopropyl-5-(1-(oxetan-3-yl)piperidin-4-yl)-1H-indol-2-yl)-7-methylpyrazolo[1,5-a]pyridine (720); 6-(3-isopropyl-5-(1-(oxetan-3-yl)piperidin-4-yl)-1H-indol-2-yl)-[1,2,4]triazolo[1,5-a]pyrimidine (721); 6-(3-isopropyl-5-(1-(oxetan-3-yl)piperidin-4-yl)-1H-indol-2-yl)-8-methoxyimidazo[1,2-a]pyridine (722); 6-(3-isopropyl-5-(1-(oxetan-3-yl)piperidin-4-yl)-1H-indol-2-yl)-8-methylquinoline (723); 7-(3-isopropyl-5-(1-(oxetan-3-yl)piperidin-4-yl)-1H-indol-2-yl)-5-methylimidazo[1,5-a]pyridine (724); 4-(3-isopropyl-5-(1-(oxetan-3-yl)piperidin-4-yl)-1H-indol-2-yl)-2-methylquinoline (725); 5-(3-isopropyl-5-(1-(oxetan-3-yl)piperidin-4-yl)-1H-indol-2-yl)-2-methylpyrazolo[1,5-a]pyridine (726); 7-(3-isopropyl-5-(1-(oxetan-3-yl)piperidin-4-yl)-1H-indol-2-yl)-5-methyl-[1,2,4]triazolo[1,5-a]pyridine (727); 7-(3-isopropyl-5-(1-(oxetan-3-yl)piperidin-4-yl)-1H-indol-2-yl)-2-methyl-[1,2,4]triazolo[1,5-a]pyridine (728); 6-(3-isopropyl-5-(1-(oxetan-3-yl)piperidin-4-yl)-1H-indol-2-yl)-[1,2,4]triazolo[1,5-b]pyridazine (729); 6-(3-isopropyl-5-(1-(oxetan-3-yl)piperidin-4-yl)-1H-indol-2-yl)-7,8-dimethyl-[1,2,4]triazolo[1,5-b]pyridazine (730); 6-(3-isopropyl-5-(1-(oxetan-3-yl)piperidin-4-yl)-1H-indol-2-yl)-8-methoxy-7-methyl-[1,2,4]triazolo[1,5-b]pyridazine (731); 6-(3-isopropyl-5-(1-(oxetan-3-yl)piperidin-4-yl)-1H-indol-2-yl)-8-methoxy-[1,2,4]triazolo[1,5-b]pyridazine (732); 3-(3-isopropyl-5-(1-(oxetan-3-yl)piperidin-4-yl)-1H-indol-2-yl)-1-methyl-1H-pyrrolo[2,3-b]pyridine (733); 6-(3-isopropyl-5-(1-(oxetan-3-yl)piperidin-4-yl)-1H-indol-2-yl)-[1,2,3]triazolo[1,5-a]pyridine (734); 5-(3-isopropyl-5-(1-(oxetan-3-yl)piperidin-4-yl)-1H-indol-2-yl)-[1,2,3]triazolo[1,5-a]pyridine (735); 7-(3-isopropyl-5-(1-(oxetan-3-yl)piperidin-4-yl)-1H-indol-2-yl)-[1,2,4]triazolo[4,3-a]pyridine (736); 6-(3-isopropyl-5-(1-(oxetan-3-yl)piperidin-4-yl)-1H-indol-2-yl)-4-methyl-[1,2,3]triazolo[1,5-a]pyridine (737); (6-(3-isopropyl-5-(1-(oxetan-3-yl)piperidin-4-yl)-1H-indol-2-yl)tetrazolo[1,5-a]pyridin-8-yl)methanol (738); 6-(3-isopropyl-5-(1-(oxetan-3-yl)piperidin-4-yl)-1H-indol-2-yl)-7,8-dimethyltetrazolo[1,5-a]pyridine (739); 6-(3-isopropyl-5-(1-(oxetan-3-yl)piperidin-4-yl)-1H-indol-2-yl)-5,8-dimethyltetrazolo[1,5-a]pyridine (740); 6-(3-isopropyl-5-(1-(oxetan-3-yl)piperidin-4-yl)-1H-indol-2-yl)-8-methyltetrazolo[1,5-a]pyridine (741); 6-(3-isopropyl-5-(1-(oxetan-3-yl)piperidin-4-yl)-1H-indol-2-yl)-7-methyltetrazolo[1,5-a]pyridine (742); 5-(3-isopropyl-5-(1-(oxetan-3-yl)piperidin-4-yl)-1H-indol-2-yl)-3-methyl-[1,2,3]triazolo[1,5-a]pyridine (743); 5-(3-isopropyl-5-(1-(oxetan-3-yl)piperidin-4-yl)-1H-indol-2-yl)-7-methyl-[1,2,3]triazolo[1,5-a]pyridine (744); 1-(4-(3-isopropyl-2-(8-methyltetrazolo[1,5-a]pyridin-6-yl)-1H-indol-5-yl)piperidin-1-yl)-2-methylpropan-2-ol, TFA (745); 1-(4-(2-([1,2,4]triazolo[1,5-b]pyridazin-6-yl)-3-isopropyl-1H-indol-5-yl)piperidin-1-yl)-2-methylpropan-2-ol (746); 1-(4-

(2-(7,8-dimethyl-[1,2,4]triazolo[1,5-b]pyridazin-6-yl)-3-isopropyl-1H-indol-5-yl)piperidin-1-yl)-2-methylpropan-2-ol (747); 1-(4-(3-isopropyl-2-(8-methoxy-7-methyl-[1,2,4]triazolo[1,5-b]pyridazin-6-yl)-1H-indol-5-yl)piperidin-1-yl)-2-methylpropan-2-ol (748); 1-(4-(3-isopropyl-2-(8-methoxy-[1,2,4]triazolo[1,5-b]pyridazin-6-yl)-1H-indol-5-yl)piperidin-1-yl)-2-methylpropan-2-ol (749); 1-(4-(3-isopropyl-2-(1-methyl-1H-pyrrolo[2,3-b]pyridin-3-yl)-1H-indol-5-yl)piperidin-1-yl)-2-methylpropan-2-ol (750); 1-(4-(3-isopropyl-2-(2-methylquinolin-4-yl)-1H-indol-5-yl)piperidin-1-yl)-2-methylpropan-2-ol (752); 1-(4-(3-isopropyl-2-(2-methyl-[1,2,4]triazolo[1,5-a]pyridin-7-yl)-1H-indol-5-yl)piperidin-1-yl)-2-methylpropan-2-ol (753); 2-(4-(3-isopropyl-2-(5-methylimidazo[1,2-a]pyridin-7-yl)-1H-indol-5-yl)piperidin-1-yl)-3-methoxypropan-1-ol (754); 2-(4-(3-isopropyl-2-(5-methylimidazo[1,2-a]pyridin-7-yl)-1H-indol-5-yl)piperidin-1-yl)propane-1,3-diol (755); 1-(4-(3-isopropyl-2-(5-methyl-[1,2,4]triazolo[1,5-a]pyridin-7-yl)-1H-indol-5-yl)piperidin-1-yl)-2-methylpropan-2-ol (756); 1-(4-(3-isopropyl-2-(5-methylimidazo[1,2-a]pyridin-7-yl)-1H-indol-5-yl)piperidin-1-yl)-2-methylpropan-2-ol (757); 1-(4-(3-isopropyl-2-(5-methoxyimidazo[1,2-a]pyridin-7-yl)-1H-indol-5-yl)piperidin-1-yl)-2-methylpropan-2-ol (758); 1-(4-(3-isopropyl-2-(pyrazolo[1,5-a]pyrimidin-6-yl)-1H-indol-5-yl)piperidin-1-yl)-2-methylpropan-2-ol (759); 1-(4-(2-([1,2,4]triazolo[1,5-a]pyridin-8-yl)-3-isopropyl-1H-indol-5-yl)piperidin-1-yl)-2-methylpropan-2-ol (760); 1-(4-(2-(imidazo[1,2-a]pyrimidin-6-yl)-3-isopropyl-1H-indol-5-yl)piperidin-1-yl)-2-methylpropan-2-ol (761); 1-(4-(2-(1,7-dimethyl-1H-indazol-5-yl)-3-isopropyl-1H-indol-5-yl)piperidin-1-yl)-2-methylpropan-2-ol (762); 1-(4-(2-(1,4-dimethyl-1H-indazol-5-yl)-3-isopropyl-1H-indol-5-yl)piperidin-1-yl)-2-methylpropan-2-ol (763); 1-(4-(3-isopropyl-2-(1-methyl-1H-pyrazolo[3,4-b]pyridin-5-yl)-1H-indol-5-yl)piperidin-1-yl)-2-methylpropan-2-ol (764); 1-(4-(3-isopropyl-2-(2-methyl-2H-pyrazolo[3,4-b]pyridin-5-yl)-1H-indol-5-yl)piperidin-1-yl)-2-methylpropan-2-ol (765); 5-(5-(1-(2-hydroxy-2-methylpropyl)piperidin-4-yl)-3-isopropyl-1H-indol-2-yl)quinoline-8-carbonitrile (766); 1-(4-(2-(8-chloroquinolin-6-yl)-3-isopropyl-1H-indol-5-yl)piperidin-1-yl)-2-methylpropan-2-ol (767); 1-(4-(2-(2,5-dimethyl-[1,2,4]triazolo[1,5-a]pyridin-8-yl)-3-isopropyl-1H-indol-5-yl)piperidin-1-yl)-2-methylpropan-2-ol (768); 1-(4-(3-isopropyl-2-(5-methyl-[1,2,4]triazolo[1,5-a]pyridin-8-yl)-1H-indol-5-yl)piperidin-1-yl)-2-methylpropan-2-ol (769); 1-(4-(2-(7-isobutyl-2-methylpyrazolo[1,5-a]pyridin-5-yl)-3-isopropyl-1H-indol-5-yl)piperidin-1-yl)-2-methylpropan-2-ol (770); 1-(4-(3-isopropyl-2-(8-methylquinolin-6-yl)-1H-indol-5-yl)piperidin-1-yl)-2-methylpropan-2-ol (771); 1-(4-(2-(8-chloro-7-methylimidazo[1,2-a]pyridin-6-yl)-3-isopropyl-1H-indol-5-yl)piperidin-1-yl)-2-methylpropan-2-ol (772); 1-(4-(2-([1,2,4]triazolo[1,5-a]pyrimidin-6-yl)-3-isopropyl-1H-indol-5-yl)piperidin-1-yl)-2-methylpropan-2-ol (773); 1-(4-(3-isopropyl-2-(8-methylimidazo[1,2-a]pyridin-6-yl)-1H-indol-5-yl)piperidin-1-yl)-2-methylpropan-2-ol (774); 1-(4-(3-isopropyl-2-(8-methoxyimidazo[1,2-a]pyridin-6-yl)-1H-indol-5-yl)piperidin-1-yl)-2-methylpropan-2-ol (775); 1-(4-(3-isopropyl-2-(8-methylimidazo[1,2-a]pyridin-6-yl)-1H-indol-5-yl)piperidin-1-yl)-2-methylpropan-2-ol (776); 1-(4-(2-(8-ethyl-7-methylimidazo[1,2-a]pyridin-6-yl)-3-isopropyl-1H-indol-5-yl)piperidin-1-yl)-2-methylpropan-2-ol (777); 5-(3-isopropyl-5-(1-(2-methoxyethyl)piperidin-4-yl)-1H-indol-2-yl)quinoline-8-carbonitrile (778); 7-(3-isopropyl-5-(1-(2-methoxyethyl)piperidin-4-yl)-1H-indol-2-yl)-5-methyl-[1,2,4]triazolo[1,5-a]pyridine (779); 7-(3-isopropyl-5-(1-(2-methoxyethyl)piperidin-4-yl)-1H-indol-2-yl)-5-methoxy-[1,2,4]triazolo[1,5-a]pyridine (780); (6-(3-isopropyl-5-(1-((3-methyloxetan-3-yl)methyl)piperidin-4-yl)-1H-indol-2-yl)tetrazolo[1,5-a]pyridin-8-yl)methanol (781); 6-(3-isopropyl-5-(1-(2-(methylsulfonyl)ethyl)piperidin-4-yl)-1H-indol-2-yl)-8-methoxy-[1,2,4]triazolo[1,5-b]pyridazine (782); 2-(4-(3-isopropyl-2-(1-methyl-1H-pyrrolo[2,3-b]pyridin-3-yl)-1H-indol-5-yl)piperidin-1-yl)ethane-1-sulfonamide (783); 4-(4-(3-isopropyl-2-(1-methyl-1H-pyrrolo[2,3-b]pyridin-3-yl)-1H-indol-5-yl)piperidin-1-yl)tetrahydro-2H-thiopyran 1,1-dioxide (784); 6-(3-isopropyl-5-(1-(2-(methylsulfonyl)ethyl)piperidin-4-yl)-1H-indol-2-yl)-4-methyl-[1,2,3]triazolo[1,5-a]pyridine (785); 6-(3-isopropyl-5-(1-(2-(methylsulfonyl)ethyl)piperidin-4-yl)-1H-indol-2-yl)-7,8-dimethyltetrazolo[1,5-a]pyridine (786); 6-(3-isopropyl-5-(1-(3-(methylsulfonyl)propyl)piperidin-4-yl)-1H-indol-2-yl)-8-methyltetrazolo[1,5-a]pyridine (787); 4-(4-(3-isopropyl-2-(8-methyltetrazolo[1,5-a]pyridin-6-yl)-1H-indol-5-yl)piperidin-1-yl)tetrahydro-2H-thiopyran 1,1-dioxide (788); 6-(3-isopropyl-5-(1-(2-(methylsulfonyl)ethyl)piperidin-4-yl)-1H-indol-2-yl)-8-methyltetrazolo[1,5-a]pyridine (789); 6-(3-isopropyl-5-(1-(2-(methylsulfonyl)ethyl)piperidin-4-yl)-1H-indol-2-yl)-7-methyltetrazolo[1,5-a]pyridine (790); 4-(4-(3-isopropyl-2-(7-methyltetrazolo[1,5-a]pyridin-6-yl)-1H-indol-5-yl)piperidin-1-yl)tetrahydro-2H-thiopyran 1,1-dioxide (791); 4-(4-(3-isopropyl-2-(3-methyl-[1,2,3]triazolo[1,5-a]pyridin-5-yl)-1H-indol-5-yl)piperidin-1-yl)tetrahydro-2H-thiopyran 1,1-dioxide (792); 5-(3-isopropyl-5-(1-(2-(methylsulfonyl)ethyl)piperidin-4-yl)-1H-indol-2-yl)-3-methyl-[1,2,3]triazolo[1,5-a]pyridine (793); 4-(4-(3-isopropyl-2-(7-methyl-[1,2,3]triazolo[1,5-a]pyridin-5-yl)-1H-indol-5-yl)piperidin-1-yl)tetrahydro-2H-thiopyran 1,1-dioxide (794); 5-(3-isopropyl-5-(1-(2-(methylsulfonyl)ethyl)piperidin-4-yl)-1H-indol-2-yl)-7-methyl-[1,2,3]triazolo[1,5-a]pyridine (795); 5-(3-isopropyl-5-(1-(2-(methylsulfonyl)ethyl)piperidin-4-yl)-1H-indol-2-yl)quinoline-8-carbonitrile (796); 7-(3-isopropyl-5-(1-(2-(methylsulfonyl)ethyl)piperidin-4-yl)-1H-indol-2-yl)-5-methoxy-[1,2,4]triazolo[1,5-a]pyridine (797); 4-(4-(2-([1,2,4]triazolo[1,5-a]pyrimidin-6-yl)-3-isopropyl-1H-indol-5-yl)piperidin-1-yl)tetrahydro-2H-thiopyran 1,1-dioxide (798); 4-(4-(3-isopropyl-2-(8-methylimidazo[1,2-a]pyridin-6-yl)-1H-indol-5-yl)piperidin-1-yl)tetrahydro-2H-thiopyran 1,1-dioxide (799); 4-(4-(3-isopropyl-2-(8-methylquinolin-6-yl)-1H-indol-5-yl)piperidin-1-yl)tetrahydro-2H-thiopyran 1,1-dioxide (800); 6-(3-isopropyl-5-(1-(2-(methylsulfonyl)ethyl)piperidin-4-yl)-1H-indol-2-yl)-8-methoxyimidazo[1,2-a]pyridine (801); 5-(3-isopropyl-5-(1'-methyl-[1,4'-bipiperidin]-4-yl)-1H-indol-2-yl)-1H-pyrrolo[2,3-b]pyridine (802); 6-(3-isopropyl-5-(1'-isopropyl-[1,4'-bipiperidin]-4-yl)-1H-indol-2-yl)imidazo[1,2-a]pyridine (803); 4-(3-isopropyl-2-(1H-pyrazolo[3,4-b]pyridin-4-yl)-1H-indol-5-yl)-[1,4'-bipiperidin]-3'-ol (804); 4-(5-(1'-isopropyl-[1,4'-bipiperidin]-4-yl)-3-methyl-1H-indol-2-yl)-1H-imidazo[4,5-c]pyridine (805); 4-(5-(1'-isopropyl-[1,4'-bipiperidin]-4-yl)-3-methyl-1H-indol-2-yl)pyrrolo[2,1-f][1,2,4]triazine (806); 8-(5-(1'-isopropyl-[1,4'-bipiperidin]-4-yl)-3-methyl-1H-indol-2-yl)imidazo[1,2-b]pyridazine (807); 2-(5-(1'-isopropyl-[1,4'-bipiperidin]-4-yl)-3-methyl-1H-indol-2-yl)-5H-pyrrolo[3,2-d]pyrimidine (808); 2-(5-(1'-isopropyl-[1,4'-bipiperidin]-4-yl)-3-methyl-1H-indol-2-yl)-7H-pyrrolo[2,3-d]pyrimidine (809); 4-(3-methyl-5-(1'-methyl-[1,4'-bipiperidin]-4-yl)-1H-indol-2-yl)-1H-pyrrolo[2,3-b]pyridine (810); 4-(5-(1'-ethyl-[1,4'-bipiperidin]-4-yl)-3-methyl-1H-indol-2-yl)-1H-pyrrolo[2,3-b]pyridine (811); 4-(5-(1'-isobutyl-[1,4'-bipiperidin]-4-yl)-3-methyl-1H-indol-2-yl)-1H-pyrrolo[2,3-b]pyridine (812); 4-(5-(1'-isopropyl-[1,4'-bipiperidin]-4-yl)-3-methyl-1H-indol-2-yl)-

1H-pyrrolo[2,3-b]pyridine (813); 4-(5-(1'-isopropyl-[1,4'-bipiperidin]-4-yl)-3-methyl-1H-indol-2-yl)-7H-pyrrolo[2,3-d]pyrimidine (814); 6-(5-(1'-isopropyl-[1,4'-bipiperidin]-4-yl)-3-methyl-1H-indol-2-yl)-9H-purine (815); 4-(5-(1'-isopropyl-[1,4'-bipiperidin]-4-yl)-3-methyl-1H-indol-2-yl)-1H-pyrazolo[3,4-d]pyrimidine (816); 6-(5-(1'-isopropyl-[1,4'-bipiperidin]-4-yl)-3-methyl-1H-indol-2-yl)-9-methyl-9H-purine (817); 4-(5-(1'-isopropyl-[1,4'-bipiperidin]-4-yl)-3-methyl-1H-indol-2-yl)-1-methyl-1H-pyrazolo[3,4-d]pyrimidine (818); 5-(3-ethyl-5-(1'-isopropyl-[1,4'-bipiperidin]-4-yl)-1H-indol-2-yl)-1H-pyrazolo[3,4-b]pyridine (819); 4-(3-isopropyl-5-(2'-methyl-[1,4'-bipiperidin]-4-yl)-1H-indol-2-yl)-1H-pyrazolo[3,4-b]pyridine (820); 4-(3-isopropyl-5-(1'-isopropyl-[1,4'-bipiperidin]-4-yl)-1H-indol-2-yl)-1H-pyrazolo[3,4-b]pyridine (821); 4-(3-isopropyl-2-(1H-pyrazolo[3,4-b]pyridin-4-yl)-1H-indol-5-yl)-[1,4'-bipiperidin]-2'-one (822); 1-(4-(3-isopropyl-2-(1H-pyrazolo[3,4-b]pyridin-4-yl)-1H-indol-5-yl)-[1,4'-bipiperidin]-1'-yl)ethan-1-one (823); 4-(3-ethyl-5-(1'-isopropyl-[1,4'-bipiperidin]-4-yl)-1H-indol-2-yl)-1H-pyrazolo[3,4-b]pyridine (824); methyl 4-(3-isopropyl-2-(1H-pyrazolo[3,4-b]pyridin-4-yl)-1H-indol-5-yl)-[1,4'-bipiperidine]-2'-carboxylate (825); 4-(3-isopropyl-5-(1'-isopropyl-[1,4'-bipiperidin]-4-yl)-6-methyl-1H-indol-2-yl)-1H-pyrazolo[3,4-b]pyridine (826); 4-(5-(3'-fluoro-[1,4'-bipiperidin]-4-yl)-3-isopropyl-1H-indol-2-yl)-1H-pyrazolo[3,4-b]pyridine (827); 4-(5-(1-(azepan-4-yl)piperidin-4-yl)-3-isopropyl-1H-indol-2-yl)-1H-pyrazolo[3,4-b]pyridine (828); 4-(3-isopropyl-5-(1-((1R,5S)-8-methyl-8-azabicyclo[3.2.1]octan-3-yl)piperidin-4-yl)-1H-indol-2-yl)-1H-pyrazolo[3,4-b]pyridine (829); 4-(6-fluoro-3-isopropyl-5-(1'-isopropyl-[1,4'-bipiperidin]-4-yl)-1H-indol-2-yl)-1H-pyrazolo[3,4-b]pyridine (830); methyl 4-(3-isopropyl-2-(1H-pyrazolo[3,4-b]pyridin-4-yl)-1H-indol-5-yl)-[1,4'-bipiperidine]-2'-carboxylate (831); 4-(5-([1,4'-bipiperidin]-4-yl)-3-isopropyl-1H-indol-2-yl)-1H-pyrazolo[3,4-b]pyridine (832); 4-(5-(1'-isopropyl-[1,4'-bipiperidin]-4-yl)-3-methyl-1H-indol-2-yl)-1H-pyrazolo[3,4-b]pyridine (833); 4-(3-isopropyl-5-(3'-methyl-[1,4'-bipiperidin]-4-yl)-1H-indol-2-yl)-1H-pyrazolo[3,4-b]pyridine (834); ethyl 4-(3-isopropyl-2-(1H-pyrazolo[3,4-b]pyridin-4-yl)-1H-indol-5-yl)-3'-methyl-[1,4'-bipiperidine]-1'-carboxylate (835); 6-(3-ethyl-5-(1'-isopropyl-[1,4'-bipiperidin]-4-yl)-1H-indol-2-yl)-1H-pyrazolo[4,3-b]pyridine (836); 4-(3-ethyl-5-(1'-ethyl-[1,4'-bipiperidin]-4-yl)-1H-indol-2-yl)-1H-pyrrolo[2,3-b]pyridine (837); 4-(3-ethyl-5-(2',2',6',6'-tetramethyl-[1,4'-bipiperidin]-4-yl)-1H-indol-2-yl)-1H-pyrrolo[2,3-b]pyridine (838); 4-(3-ethyl-5-(1'-methyl-[1,4'-bipiperidin]-4-yl)-1H-indol-2-yl)-1H-pyrrolo[2,3-b]pyridine (839); 4-(3-ethyl-5-(1'-isopropyl-[1,4'-bipiperidin]-4-yl)-6-methyl-1H-indol-2-yl)-1H-pyrrolo[2,3-b]pyridine (840); 6-(3-isopropyl-5-(1'-isopropyl-[1,4'-bipiperidin]-4-yl)-1H-indol-2-yl)-7-methylimidazo[1,2-a]pyridine (841); 3-chloro-4-(3-ethyl-5-(1'-isopropyl-[1,4'-bipiperidin]-4-yl)-1H-indol-2-yl)-1H-pyrrolo[2,3-b]pyridine (842); 4-(5-(1'-isobutyl-[1,4'-bipiperidin]-4-yl)-3-methyl-1H-indol-2-yl)-1-methyl-1H-pyrrolo[2,3-b]pyridine (843); 4-(5-(1'-isopropyl-[1,4'-bipiperidin]-4-yl)-3-methyl-1H-indol-2-yl)-1-methyl-1H-pyrrolo[2,3-b]pyridine (844); 3-(4-(3-isopropyl-2-(1H-pyrazolo[3,4-b]pyridin-4-yl)-1H-indol-5-yl)piperidin-1-yl)-N,N-dimethylpropan-1-amine (845); 3-(4-(3-isopropyl-2-(1H-pyrazolo[3,4-b]pyridin-4-yl)-1H-indol-5-yl)piperidin-1-yl)-N,N,2-trimethylpropan-1-amine (846); 3-(4-(3-isopropyl-2-(1H-pyrazolo[3,4-b]pyridin-4-yl)-1H-indol-5-yl)piperidin-1-yl)-N,N,2,2-tetramethylpropan-1-amine (847); 4-(3-isopropyl-5-(1-(3-(piperidin-1-yl)propyl)piperidin-4-yl)-1H-indol-2-yl)-1H-pyrazolo[3,4-b]pyridine (848); 4-(3-ethyl-5-(1'-isobutyl-[1,4'-bipiperidin]-4-yl)-1H-indol-2-yl)-1H-pyrrolo[2,3-b]pyridine (849); 4-(3-ethyl-5-(1'-isopropyl-[1,4'-bipiperidin]-4-yl)-1H-indol-2-yl)-1H-pyrrolo[2,3-b]pyridine (850); 4-(3-isopropyl-5-(1-(pyrrolidin-3-ylmethyl)piperidin-4-yl)-6-(trifluoromethyl)-1H-indol-2-yl)-1H-pyrazolo[3,4-b]pyridine (851); 4-(6-fluoro-3-isopropyl-5-(1-((1-isopropylpyrrolidin-3-yl)methyl)piperidin-4-yl)-1H-indol-2-yl)-1H-pyrazolo[3,4-b]pyridine (852); 4-(6-fluoro-3-isopropyl-5-(1-(pyrrolidin-3-ylmethyl)piperidin-4-yl)-1H-indol-2-yl)-1H-pyrazolo[3,4-b]pyridine (853); 4-(3-isopropyl-5-(1-((1-isopropylpyrrolidin-3-yl)methyl)piperidin-4-yl)-6-(trifluoromethyl)-1H-indol-2-yl)-1H-pyrazolo[3,4-b]pyridine (854); 3-(4-(6-fluoro-3-isopropyl-2-(1H-pyrazolo[3,4-b]pyridin-4-yl)-1H-indol-5-yl)piperidin-1-yl)-N,N-dimethylpropan-1-amine (855); 3-(4-(3-isopropyl-2-(7-methylimidazo[1,2-a]pyridin-6-yl)-1H-indol-5-yl)piperidin-1-yl)-N,N-dimethylpropan-1-amine (856); 4-(3-(4-(3-isopropyl-2-(1H-pyrazolo[3,4-b]pyridin-4-yl)-1H-indol-5-yl)piperidin-1-yl)propyl)morpholine (857); 4-(3-(4-(3-isopropyl-2-(1H-pyrazolo[3,4-b]pyridin-4-yl)-1H-indol-5-yl)piperidin-1-yl)propyl)morpholine (858); 4-((4-(3-ethyl-2-(1H-pyrazolo[3,4-b]pyridin-4-yl)-1H-indol-5-yl)piperidin-1-yl)methyl)-2-isopropylthiazole (859); 6-(5-(1-((1H-1,2,3-triazol-5-yl)methyl)piperidin-4-yl)-3-isopropyl-1H-indol-2-yl)-8-methoxy-[1,2,4]triazolo[1,5-b]pyridazine (860); 7-(3-isopropyl-5-(1-((4-methyl-1H-imidazol-5-yl)methyl)piperidin-4-yl)-1H-indol-2-yl)-3H-imidazo[4,5-b]pyridine (861); 4-(5-(1-(imidazo[1,2-a]pyridin-2-ylmethyl)piperidin-4-yl)-3-isopropyl-1H-indol-2-yl)-1H-pyrazolo[3,4-b]pyridine (862); 4-(5-(1-((1H-imidazol-5-yl)methyl)piperidin-4-yl)-3-ethyl-1H-indol-2-yl)-1H-pyrazolo[3,4-b]pyridine (863); 4-(3-isopropyl-5-(1-((4-methyl-1H-imidazol-5-yl)methyl)piperidin-4-yl)-1H-indol-2-yl)-1H-pyrazolo[3,4-b]pyridine (864); 4-(3-isopropyl-5-(1-((1-methyl-1H-1,2,4-triazol-3-yl)methyl)piperidin-4-yl)-1H-indol-2-yl)-1H-pyrazolo[3,4-b]pyridine (865); 4-(3-isopropyl-5-(1-(pyridin-2-ylmethyl)piperidin-4-yl)-1H-indol-2-yl)-1H-pyrazolo[3,4-b]pyridine (866); 2-((4-(3-ethyl-2-(1H-pyrazolo[3,4-b]pyridin-4-yl)-1H-indol-5-yl)piperidin-1-yl)methyl)oxazole (867); 4-(3-isopropyl-5-(1-((3-methylimidazo[1,5-a]pyridin-1-yl)methyl)piperidin-4-yl)-1H-indol-2-yl)-1H-pyrazolo[3,4-b]pyridine (868); 4-(3-isopropyl-5-(1-((2-methyl-1H-imidazol-5-yl)methyl)piperidin-4-yl)-1H-indol-2-yl)-1H-pyrazolo[3,4-b]pyridine (869); 4-(5-(1-((1H-imidazol-4-yl)methyl)piperidin-4-yl)-3-isopropyl-1H-indol-2-yl)-1H-pyrazolo[3,4-b]pyridine (870); 4-(3-ethyl-5-(1-((1-methyl-1H-pyrrol-2-yl)methyl)piperidin-4-yl)-1H-indol-2-yl)-1H-pyrrolo[2,3-b]pyridine (871); 4-(3-isopropyl-5-(1-((2-methyl-1H-imidazol-5-yl)methyl)piperidin-4-yl)-1H-indol-2-yl)-3-methyl-1H-pyrazolo[3,4-b]pyridine (872); 4-(5-(1-((1H-imidazol-5-yl)methyl)piperidin-4-yl)-3-ethyl-1H-indol-2-yl)-3-methyl-1H-pyrazolo[3,4-b]pyridine (873); 4-(3-isopropyl-5-(1-((4-methyl-1H-imidazol-5-yl)methyl)piperidin-4-yl)-1H-indol-2-yl)-3-methyl-1H-pyrazolo[3,4-b]pyridine (874); 4-(5-(1-((1H-imidazol-5-yl)methyl)piperidin-4-yl)-3-isopropyl-1H-indol-2-yl)-3-methyl-1H-pyrazolo[3,4-b]pyridine (875); 3-(3-isopropyl-5-(1-((2-methylpyrimidin-5-yl)methyl)piperidin-4-yl)-1H-indol-2-yl)-1-methyl-1H-pyrrolo[2,3-b]pyridine (876); 3-(5-(1-((1H-1,2,3-triazol-5-yl)methyl)piperidin-4-yl)-3-isopropyl-1H-indol-2-yl)-1-methyl-1H-pyrrolo[2,3-b]pyridine (877); 3-(3-isopropyl-5-(1-((1-methyl-1H-1,2,4-triazol-3-yl)methyl)piperidin-4-yl)-1H-indol-2-yl)-1-methyl-1H-pyrrolo[2,3-b]pyridine (878); 6-(3-isopropyl-5-(1-((1-methyl-1H-1,2,4-triazol-3-yl)methyl)piperidin-4-yl)-1H-indol-2-yl)-[1,2,3]triazolo[1,5-a]pyridine (879); 7-(3-isopropyl-5-(1-((1-methyl-1H-1,2,4-triazol-3-yl)methyl)piperidin-4-yl)-1H-indol-2-yl)-[1,2,4]triazolo[4,3-a]pyridine (880); 6-(3-isopropyl-5-(1-((1-methyl-1H-1,2,4-triazol-3-yl)methyl)piperidin-4-yl)-1H-indol-2-yl)-4-methyl-[1,2,3]triazolo[1,5-a]pyridine (881); 6-(3-isopropyl-5-(1-((1-methyl-1H-pyrazol-3-yl)methyl)piperidin-4-yl)-1H-indol-2-yl)-4-methyl-[1,2,3]triazolo[1,5-a]pyridine (882); 6-(5-(1-((1H-1,2,3-triazol-5-yl)methyl)piperidin-4-yl)-3-isopropyl-1H-indol-2-yl)-8-methyltetrazolo[1,5-a]pyridine (883); 6-(3-isopropyl-5-(1-((1-methyl-1H-pyrazol-3-yl)methyl)piperidin-4-yl)-1H-indol-2-yl)-8-methyltetrazolo[1,5-a]pyridine (884); 6-(3-isopropyl-5-(1-((1-methyl-1H-1,2,4-triazol-3-yl)methyl)piperidin-4-yl)-1H-indol-2-yl)-8-methyltetrazolo[1,5-a]pyridine (885); 6-(3-isopropyl-5-(1-((1-methyl-1H-1,2,4-triazol-3-yl)methyl)piperidin-4-yl)-1H-indol-2-yl)-7-methyltetrazolo[1,5-a]pyridine (886); 6-(3-isopropyl-5-(1-((1-methyl-1H-pyrazol-3-yl)methyl)piperidin-4-yl)-1H-indol-2-yl)-7-methyltetrazolo[1,5-a]pyridine (887); 5-(3-isopropyl-5-(1-((1-methyl-1H-pyrazol-3-yl)methyl)piperidin-4-yl)-1H-indol-2-yl)-3-methyl-[1,2,3]triazolo[1,5-a]pyridine (888); 5-(3-isopropyl-5-(1-((1-methyl-1H-1,2,4-triazol-3-yl)methyl)piperidin-4-yl)-1H-indol-2-yl)-3-methyl-[1,2,3]triazolo[1,5-a]pyridine (889); 5-(3-isopropyl-5-(1-((1-methyl-1H-1,2,4-triazol-3-yl)methyl)piperidin-4-yl)-1H-indol-2-yl)-7-methyl-[1,2,3]triazolo[1,5-a]pyridine (890); 5-(3-isopropyl-5-(1-((1-methyl-1H-pyrazol-3-yl)methyl)piperidin-4-yl)-1H-indol-2-yl)-7-methyl-[1,2,3]triazolo[1,5-a]pyridine (891); 4-(5-(1-((2H-1,2,3-triazol-4-yl)methyl)piperidin-4-yl)-3-ethyl-1H-indol-2-yl)-1H-pyrazolo[3,4-b]pyridine (892); 4-((4-(3-ethyl-2-(1H-pyrazolo[3,4-b]pyridin-4-yl)-1H-indol-5-yl)piperidin-1-yl)methyl)-3,5-dimethylisoxazole (893); N-(2-(4-((4-(3-isopropyl-2-(1H-pyrazolo[3,4-b]pyridin-4-yl)-1H-indol-5-yl)piperidin-1-yl)methyl)phenoxy)ethyl)-N-methylpyridin-2-amine (894); 3-((4-(3-isopropyl-2-(1H-pyrazolo[3,4-b]pyridin-4-yl)-1H-indol-5-yl)piperidin-1-yl)methyl)quinoline (895); 4-(5-(1-((2-butyl-4-chloro-1H-imidazol-5-yl)methyl)piperidin-4-yl)-3-isopropyl-1H-indol-2-yl)-1H-pyrazolo[3,4-b]pyridine (896); 3-((4-(3-ethyl-2-(1H-pyrazolo[3,4-b]pyridin-4-yl)-1H-indol-5-yl)piperidin-1-yl)methyl)-5-phenylisoxazole (897); 4-((4-(3-ethyl-2-(1H-pyrazolo[3,4-b]pyridin-4-yl)-1H-indol-5-yl)piperidin-1-yl)methyl)-2,5-dimethyloxazole (898); 4-(3-isopropyl-5-(1-(4-(pyrimidin-2-yloxy)benzyl)piperidin-4-yl)-1H-indol-2-yl)-1H-pyrazolo[3,4-b]pyridine (899); 4-(3-ethyl-5-(1-((3-methyl-1H-pyrazol-5-yl)methyl)piperidin-4-yl)-1H-indol-2-yl)-1H-pyrazolo[3,4-b]pyridine (900); 4-(3-ethyl-5-(1-((1-methyl-1H-pyrazol-4-yl)methyl)piperidin-4-yl)-1H-indol-2-yl)-1H-pyrazolo[3,4-b]pyridine (901); 2-chloro-3-((4-(3-isopropyl-2-(1H-pyrazolo[3,4-b]pyridin-4-yl)-1H-indol-5-yl)piperidin-1-yl)methyl)-6-methoxyquinoline (902); 4-(3-isopropyl-5-(1-(pyrazin-2-ylmethyl)piperidin-4-yl)-1H-indol-2-yl)-1H-pyrazolo[3,4-b]pyridine (903); 4-(5-(1-((1H-imidazol-5-yl)methyl)piperidin-4-yl)-3-ethyl-1H-indol-2-yl)-1H-pyrazolo[3,4-b]pyridine (904); 4-(3-isopropyl-5-(1-(4-(pyrrolidin-1-yl)benzyl)piperidin-4-yl)-1H-indol-2-yl)-1H-5 pyrazolo[3,4-b]pyridine (905); 4-(3-isopropyl-5-(1-((1-methyl-1H-imidazol-4-yl)methyl)piperidin-4-yl)-1H-indol-2-yl)-1H-pyrazolo[3,4-b]pyridine (906); 4-(3-isopropyl-5-(1-(pyridin-3-ylmethyl)piperidin-4-yl)-1H-indol-2-yl)-1H-pyrazolo[3,4-b]pyridine (907); 4-(3-ethyl-5-(1-((2-phenyl-1H-imidazol-4-yl)methyl)piperidin-4-yl)-1H-indol-2-yl)-1H-pyrazolo[3,4-b]pyridine (908); 4-(3-isopropyl-5-(1-((2-methoxypyrimidin-5-yl)methyl)piperidin-4-yl)-1H-indol-2-yl)-1H-pyrazolo[3,4-b]pyridine (909); 1-((4-(3-isopropyl-2-(1H-pyrazolo[3,4-b]pyridin-4-yl)-1H-indol-5-yl)piperidin-1-yl)methyl)isoquinoline (910); 4-(3-ethyl-5-(1-((1-methyl-1H-imidazol-5-yl)methyl)piperidin-4-yl)-1H-indol-2-yl)-1H-pyrazolo[3,4-b]pyridine (911); 4-(4-((4-(3-isopropyl-2-(1H-pyrazolo[3,4-b]pyridin-4-yl)-1H-indol-5-yl)piperidin-1-yl)methyl)phenyl)morpholine (912); 4-(5-(1-((2-chloro-5-fluoropyridin-3-yl)methyl)piperidin-4-yl)-3-isopropyl-1H-indol-2-yl)-1H-pyrazolo[3,4-b]pyridine (913); 4-(5-(1-((1H-imidazol-2-yl)methyl)piperidin-4-yl)-3-isopropyl-1H-indol-2-yl)-1H-pyrazolo[3,4-b]pyridine (914); 4-(3-ethyl-5-(1-((2-ethyl-1H-imidazol-5-yl)methyl)piperidin-4-yl)-1H-indol-2-yl)-1H-pyrazolo[3,4-b]pyridine (915); 4-(3-ethyl-5-(1-((4-methyl-1H-imidazol-5-yl)methyl)piperidin-4-yl)-1H-indol-2-yl)-1H-pyrazolo[3,4-b]pyridine (916); 4-((4-(3-ethyl-2-(1H-pyrazolo[3,4-b]pyridin-4-yl)-1H-indol-5-yl)piperidin-1-yl)methyl)-2-methyloxazole (917); 4-(5-(1-((1H-imidazol-4-yl)methyl)piperidin-4-yl)-3-isopropyl-1H-indol-2-yl)-1H-pyrazolo[3,4-b]pyridine (918); 4-(3-isopropyl-5-(1-(4-(4-methylpiperazin-1-yl)benzyl)piperidin-4-yl)-1H-indol-2-yl)-1H-pyrazolo[3,4-b]pyridine (919); 4-((4-(3-ethyl-2-(1H-pyrazolo[3,4-b]pyridin-4-yl)-1H-indol-5-yl)piperidin-1-yl)methyl)oxazole (920); 3-(2-((4-(3-isopropyl-2-(1H-pyrazolo[3,4-b]pyridin-4-yl)-1H-indol-5-yl)piperidin-1-yl)methyl)phenoxy)-N,N-dimethylpropan-1-amine (921); 2-chloro-3-((4-(3-isopropyl-2-(1H-pyrazolo[3,4-b]pyridin-4-yl)-1H-indol-5-yl)piperidin-1-yl)methyl)-8-methylquinoline (922); 4-(5-(1-((3-chloropyridin-4-yl)methyl)piperidin-4-yl)-3-isopropyl-1H-indol-2-yl)-1H-pyrazolo[3,4-b]pyridine (923); 4-((dimethylamino)methyl)-2-((4-(3-isopropyl-2-(1H-pyrazolo[3,4-b]pyridin-4-yl)-1H-indol-5-yl)piperidin-1-yl)methyl)-6-methoxyphenol (924); 4-((4-(3-isopropyl-2-(1H-pyrazolo[3,4-b]pyridin-4-yl)-1H-indol-5-yl)piperidin-1-yl)methyl)thiazol-2-amine (925); 5-((4-(3-isopropyl-2-(1H-pyrazolo[3,4-b]pyridin-4-yl)-1H-indol-5-yl)piperidin-1-yl)methyl)thiazol-2-amine (926); 4-((4-(3-ethyl-2-(1H-pyrazolo[3,4-b]pyridin-4-yl)-1H-indol-5-yl)piperidin-1-yl)methyl)thiazole (927); 5-((4-(3-ethyl-2-(1H-pyrazolo[3,4-b]pyridin-4-yl)-1H-indol-5-yl)piperidin-1-yl)methyl)thiazole (928); 2-((4-(3-ethyl-2-(1H-pyrazolo[3,4-b]pyridin-4-yl)-1H-indol-5-yl)piperidin-1-yl)methyl)thiazole (929); 4-((4-(3-ethyl-2-(1H-pyrazolo[3,4-b]pyridin-4-yl)-1H-indol-5-yl)piperidin-1-yl)methyl)-1,2,3-thiadiazole (930); 5-((4-(3-ethyl-2-(1H-pyrazolo[3,4-b]pyridin-4-yl)-1H-indol-5-yl)piperidin-1-yl)methyl)thiazol-2-amine (931); 6-(3-isopropyl-5-(1-((1-methyl-1H-pyrazol-4-yl)methyl)piperidin-4-yl)-1H-indol-2-yl)pyrazolo[1,5-a]pyrimidine (932); 6-(3-isopropyl-5-(1-((1-methyl-1H-pyrazol-4-yl)methyl)piperidin-4-yl)-1H-indol-2-yl)-8-(trifluoromethyl)imidazo[1,2-a]pyridine (933); 6-(3-isopropyl-5-(1-((1-methyl-1H-pyrazol-4-yl)methyl)piperidin-4-yl)-1H-indol-2-yl)-2-methyl-8-(trifluoromethyl)imidazo[1,2-a]pyridine (934); 6-(3-isopropyl-5-(1-((6-methoxypyridin-3-yl)methyl)piperidin-4-yl)-1H-indol-2-yl)imidazo[1,2-a]pyridine (935); 6-(5-(1-((1H-imidazol-4-yl)methyl)piperidin-4-yl)-3-isopropyl-1H-indol-2-yl)-2-methylimidazo[1,2-a]pyridine (936); 6-(3-isopropyl-5-(1-((2-methyl-1H-imidazol-4-yl)methyl)piperidin-4-yl)-1H-indol-2-yl)-2-methylimidazo[1,2-a]pyridine (937); 6-(3-isopropyl-5-(1-((2-methyl-1H-imidazol-4-yl)methyl)piperidin-4-yl)-1H-indol-2-yl)imidazo[1,2-a]pyridine (938); 6-(3-(2,2-difluoroethyl)-5-(1-((2-methyl-1H-imidazol-4-yl)methyl)piperidin-4-yl)-1H-indol-2-yl)imidazo[1,2-a]pyridine (939); 6-(5-(1-((1H-imidazol-4-yl)methyl)piperidin-4-yl)-3-isopropyl-1H-indol-2-yl)imidazo[1,2-a]pyridine (940); 6-(5-(1-((1H-imidazol-4-yl)methyl)piperidin-4-yl)-3-(2,2-difluoroethyl)-1H-indol-2-yl)imidazo[1,2-a]pyridine (941); 6-(3-isopropyl-5-(1-isopropylpiperidin-4-yl)-1H-indol-2-yl)-8-(trifluoromethyl)imidazo[1,2-a]pyridine (942); 6-(3- isopropyl-5-(1-isopropylpiperidin-4-yl)-1H-indol-2-yl)-2-methyl-8-(trifluoromethyl)imidazo[1,2-a]pyridine (943); 6-(3-isopropyl-5-(1-isopropylpiperidin-4-yl)-1H-indol-2-yl)pyrazolo[1,5-a]pyrimidine (944); 6-(3-isopropyl-5-(1-isopropylpiperidin-4-yl)-1H-indol-2-yl)-2-methylimidazo[1,2-a]pyridine (945); 6-(3-isopropyl-5-(1-isopropylpiperidin-4-yl)-1H-indol-2-yl)imidazo[1,2-a]pyridine (946); 6-(3-isopropyl-5-(1-methylpiperidin-4-yl)-1H-indol-2-yl)imidazo[1,2-a]pyridine (947); 6-(3-(2,2-difluoroethyl)-5-(1-isopropylpiperidin-4-yl)-1H-indol-2-yl)imidazo[1,2-a]pyridine (948); 5-(3-isopropyl-5-(1-isopropylpiperidin-4-yl)-1H-indol-2-yl)quinoline-8-carbonitrile (949); 2-(4-(3-isopropyl-2-(8-methoxyimidazo[1,2-a]pyridin-6-yl)-1H-indol-5-yl)piperidin-1-yl)acetonitrile (950); 2-(4-(3-isopropyl-2-(8-methylimidazo[1,2-a]pyridin-6-yl)-1H-indol-5-yl)piperidin-1-yl)acetonitrile (951); 6-(3-isopropyl-5-(1-propylpiperidin-4-yl)-1H-indol-2-yl)-8-methoxy-[1,2,4]triazolo[1,5-b]pyridazine (952); 5-(3-isopropyl-5-(1-propylpiperidin-4-yl)-1H-indol-2-yl)isobenzofuran-1(3H)-one (953); 6-(3-isopropyl-5-(1-propylpiperidin-4-yl)-1H-indol-2-yl)-1,4-dimethyl-1H-benzo[d]imidazole (954); 6-(5-(1-isobutylpiperidin-4-yl)-3-isopropyl-1H-indol-2-yl)-4-methyl-1H-benzo[d]imidazole (955); 5-(3-isopropyl-5-(1-propylpiperidin-4-yl)-1H-indol-2-yl)-1,7-dimethyl-1H-benzo[d]imidazole (956); 4-(3-ethyl-5-(1-isopropylpiperidin-4-yl)-1H-indol-2-yl)-1H-pyrazolo[3,4-b]pyridine (957); 2-(4-(3-isopropyl-2-(1-methyl-1H-pyrrolo[2,3-b]pyridin-3-yl)-1H-indol-5-yl)piperidin-1-yl)acetonitrile (958); 3-(4-(3-isopropyl-2-(1-methyl-1H-pyrrolo[2,3-b]pyridin-3-yl)-1H-indol-5-yl)piperidin-1-yl)propanenitrile (959); 6-(3-isopropyl-5-(1-(4,4,4-trifluorobutyl)piperidin-4-yl)-1H-indol-2-yl)-4-methyl-[1,2,3]triazolo[1,5-a]pyridine (960); 2-(4-(3-isopropyl-2-(8-methyltetrazolo[1,5-a]pyridin-6-yl)-1H-indol-5-yl)piperidin-1-yl)acetonitrile (961); 6-(3-isopropyl-5-(1-(3,3,3-trifluoropropyl)piperidin-4-yl)-1H-indol-2-yl)-8-methyltetrazolo[1,5-a]pyridine (962); 6-(3-isopropyl-5-(1-(4,4,4-trifluorobutyl)piperidin-4-yl)-1H-indol-2-yl)-8-methyltetrazolo[1,5-a]pyridine (963); 2-(4-(3-isopropyl-2-(7-methyl-[1,2,3]triazolo[1,5-a]pyridin-5-yl)-1H-indol-5-yl)piperidin-1-yl)acetonitrile (964); 3-(4-((4-(3-isopropyl-2-(1H-pyrazolo[3,4-b]pyridin-4-yl)-1H-indol-5-yl)piperidin-1-yl)methyl)phenoxy)-N,N-dimethylpropan-1-amine (965); 4-(6-fluoro-3-isopropyl-5-(1-((1-isopropylpiperidin-4-yl)methyl)piperidin-4-yl)-1H-indol-2-yl)-1H-pyrazolo[3,4-b]pyridine (966); and 4-(4-fluoro-3-isopropyl-5-(1-((1-isopropylpiperidin-4-yl)methyl)piperidin-4-yl)-1H-indol-2-yl)-1H-pyrazolo[3,4-b]pyridine (967).

The present invention may be embodied in other specific forms without departing from the spirit or essential attributes thereof. The invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group —$NH_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "chloroalkyl" as used herein is intended to include both branched and straight-chain saturated aliphatic hydrocarbon groups substituted with one or more chlorine atoms. For example, "$C_{1-4}$ chloroalkyl" is intended to include $C_1$, $C_2$, $C_3$, and $C_4$ alkyl groups substituted with one or more chlorine atoms. Representative examples of fluoroalkyl groups include, but are not limited to, —$CCl_3$ and —$CH_2CCl_3$.

The term "cyanoalkyl" includes both branched and straight-chain saturated alkyl groups substituted with one or more cyano groups. For example, "cyanoalkyl" includes —$CH_2CN$, —$CH_2CH_2CN$, and $C_{1-4}$ cyanoalkyl.

The term "aminoalkyl" includes both branched and straight-chain saturated alkyl groups substituted with one or more amine groups. For example, "aminoalkyl" includes —$CH_2NH_2$, —$CH_2CH_2NH_2$, and $C_{1-4}$ aminoalkyl.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and $C_{1-4}$ hydroxyalkyl.

The term "hydroxy-fluoroalkyl" includes both branched and straight-chain saturated alkyl groups substituted with one or more hydroxyl groups and one or more fluorine atoms. For example, "hydroxy-fluoroalkyl" includes —$CHFCH_2OH$, —$CH_2CHFC(CH_3)_2OH$, and $C_{1-4}$ hydroxy-fluoroalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_3$-$C_6$ cycloalkyl" denotes cycloalkyl groups with three to six carbon atoms.

The term "alkoxy," as used herein, refers to an alkyl group attached to the parent molecular moiety through an oxygen atom, for example, methoxy group (—$OCH_3$). For example, "$C_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "alkoxyalkyl," as used herein, refers to an alkoxy group attached through its oxygen atom to an alkyl group, which is attached to the parent molecular moiety, for example, methoxymethyl group (—$CH_2OCH_3$). For example, "$C_{2-4}$ alkoxyalkyl" denotes alkoxyalkyl groups with two to four carbon atoms, such as —$CH_2OCH_3$, —$CH_2CH_2OCH_3$, —$CH_2OCH_2CH_3$, and —$CH_2CH_2OCH_2CH_3$.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to TLR7/8/9, or effective to treat or prevent autoimmune and/or inflammatory disease states, such as SLE, IBD, multiple sclerosis (MS), and Sjögren's syndrome, and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Utility

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease.

The compounds of the invention inhibit signaling through Toll-like receptor 7, or 8, or 9 (TLR7, TLR8, TLR9) or combinations thereof. Accordingly, compounds of Formula (I) have utility in treating conditions associated with the inhibition of signaling through one or more of TLR7, TLR8, or TLR9. Such conditions include TLR7, TLR8, or TLR9 receptor associated diseases in which cytokine levels are modulated as a consequence of intracellular signaling.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of TLR7, TLR8, or TLR9, compounds of Formula (I) are useful in treating TLR7, TLR8, or TLR9 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, lupus nephritis, cutaneous lupus, psoriasis; auto-inflammatory diseases including Cryopyrin-Associated Periodic Syndromes (CAPS), TNF Receptor Associated Periodic Syndrome (TRAPS), Familial Mediterranean Fever (FMF), adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Included in this embodiment are methods of treatment in which the condition is selected from lupus including lupus nephritis and systemic lupus erythematosus (SLE), Crohn's disease, ulcerative colitis, allograft rejection, rheumatoid arthritis, psoriasis, ankylosing spondylitis, psoriatic arthritis, and pemphigus vulgaris. Also included are methods of treatment in which the condition is selected from ischemia reperfusion injury, including cerebral ischemia reperfusions injury arising from stroke and cardiac ischemia reperfusion injury arising from myocardial infarction. Another method of treatment is one in which the condition is multiple myeloma.

In one embodiment, the compounds of Formula (I) are useful in treating cancer, including Waldenstrom's Macroglobulinemia (WM), diffuse large B cell lymphoma (DLBCL), chronic lymphocytic leukemia (CLL), cutaneous diffuse large B cell lymphoma, and primary CNS lymphoma.

In addition, the TLR7, TLR8, or TLR9 inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional TLR7/8/9 associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

The present invention thus provides methods for treating such conditions, comprising administering to a subject in need thereof a therapeutically-effective amount of at least one compound of Formula (I) or a salt thereof "Therapeutically effective amount" is intended to include an amount of a compound of the present invention that is effective when administered alone or in combination to inhibit autoimmune disease or chronic inflammatory disease.

The methods of treating TLR7, TLR8, or TLR9 associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit TLR7, TLR8, or TLR9 and/or treat diseases associated with TLR7, TLR8, or TLR9.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating TLR7/8/9 receptor-associated conditions, including IL-1 family receptor-mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition (1985), which is incorporated herein by reference in its entirety.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parenterally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, anti-oxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). In one embodiment, the package insert specifically recites the indications for which the pharmaceutical composition has been approved. The package insert may be made of any material on which a person can read information contained therein or thereon. For example, the package insert is a printable material (e.g., paper, plastic, cardboard, foil, adhesive-backed paper or plastic, etc.) on which the desired information has been formed (e.g., printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

Abbreviations

Ac acetyl
ACN acetonitrile
anhyd. anhydrous
aq. aqueous
Bn benzyl
Boc-anhydride di-tert-butyl dicarbonate
Bu butyl
Boc tert-butoxycarbonyl
CV Column Volumes
DCE dichloroethane
DCM dichloromethane
DMAP dimethylaminopyridine
DMF dimethylformamide
DMSO dimethylsulfoxide
EtOAc ethyl acetate
Et ethyl
$Et_3N$ triethylamine
H or $H_2$ hydrogen
h, hr or hrs hour(s)
hex hexane
i iso
HCl hydrochloric acid
HPLC high pressure liquid chromatography
LC liquid chromatography
LCMS liquid chromatography-mass spectroscopy
$LiAlH_4$ lithium aluminum hydride
M molar
mM millimolar
Me methyl
MeOH methanol
MHz megahertz
min. minute(s)

mins minute(s)
M+1 (M+H)+
MS mass spectrometry
n or N normal
NBS n-bromosuccinimide
NCS n-chlorosuccinimide
nm nanometer
nM nanomolar
NMP N-methylpyrrolidinone
Pd/C palladium on carbon
$PdCl_2$(dppf) [1,1'-bis(diphenylphosphino)ferrocene]dichloropalladium(II)
Ph phenyl
Pr propyl
PSI pounds per square inch
Ret Time retention time
sat. saturated
SFC supercritical fluid chromatography
TEA triethylamine
TFA trifluoroacetic acid
THF tetrahydrofuran
XPhos Precatalyst chloro(2-dicyclohexylphosphino-2',4',6'-triisopropyl-1,1'-biphenyl)[2-(2'-amino-1,1'-biphenyl)]palladium(II)

Analytical and Preparative HPLC Conditions:

QC-ACN-AA-XB: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

QC-ACN-TFA-XB: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Method A1: L3 Acquity: Column: (LCMS) UPLC BEH C18, 2.1×50 mm, 1.7 μm particles; Mobile Phase: (A) water; (B) acetonitrile; Buffer: 0.05% TFA; Gradient Range: 2%-98% B (0 to 1 min) 98% B (to 1.5 min) 98%-2% B (to 1.6 min); Gradient Time: 1.6 min; Flow Rate: 0.8 mL/min; Analysis Time: 2.2 min; Detection: Detector 1: UV at 220 nm; Detector 2: MS (ESI+).

Method B1: L2 Aquity; Column: (LCMS) UPLC BEH C18, 2.1×50 mm, 1.7 μm particles; Mobile Phase: (A) water; (B) acetonitrile; Buffer: 0.05% TFA; Gradient Range: 2%-98% B (0 to 1 min), 98%-2% B (to 1.5 min); Gradient Time: 1.8 min; Flow Rate: 0.8 mL/min; Analysis Time: 2.2 min; Detection: Detector 1: UV at 220 nm; Detector 2: MS (ESI+).

Method C1 SCP: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate. Temperature: 50° C.; Gradient: 0-100% B over 3 minutes, then a 0.75-minute hold at 100% B; Flow: 1.11 mL/min; Detection: UV at 220 nm.

Method D1 SCP: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm.

Method D2 SCP: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min. Detection: UV at 220 nm.

Method D3 SCP: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 6-46% B over 20 minutes, then a 4-minute hold at 100% B; Flow: 20 mL/min. Detection: UV at 220 nm.

Method E1 iPAC: Column: Waters Xbridge C18 4.6×50 mm 5 um particles; Mobile Phase A: 5:95 acetonitrile:water with 10 mM ammonium acetate; Mobile Phase B: 95:5 acetonitrile:water with 10 mM ammonium acetate. Temperature: 50° C.; Gradient: 0-100% B over 1 minute; Flow: 4 mL/min; Detection: UV at 220 nm.

Method F1 iPAC: Column: Waters Acquity BEH C18 2.1×50 mm 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 2.20 minutes; Flow: 0.800 mL/min; Detection: UV at 220 nm.

(A): Column-Ascentis Express C18 (50×2.1 mm-2.7 μm) Mphase A: 10 mM $NH_4COOH$ in water:ACN (98:02); Mphase B: 10 mM $NH_4COOH$ in water:ACN (02:98), Gradient: 0-100% B over 3 minutes, Flow=1 mL/min.

(B): Waters Acquity BEH C18 (2.1×50 mm) 1.7 micron; Buffer: 5 mM ammonium acetate pH 5 adjusted with HCOOH, Solvent A: Buffer:ACN (95:5), Solvent B: Buffer:ACN (5:95), Method:% B: 0 min-5%: 1.1 min -95%: 1.7 μmin-95%, Flow: 0.8 mL/min.

(C): Column-Ascentis Express C18 (50×2.1 mm-2.7 μm) Mobile phase A: 0.1% HCOOH in water; Mobile phase B: ACN. Temperature: 50° C.; Gradient: 0-100% B over 3 minutes; Flow rate: 1.0 mL/min.

(D): Kinetex XB-C18 (75×3 mm) 2.6 micron; Solvent A: 10 mM ammonium formate in water:acetonitrile (98:02); Mobile Phase B: 10 mM ammonium formate in water:acetonitrile (02:98); Temperature: 50° C.; Gradient: 0-100% B over 3 minutes; Flow rate: 1.1 mL/min; Detection: UV at 220 nm.

(E): Column: Ascentis Express C18 (50×2.1) mm, 2.7 μm; Mobile Phase A: 5:95 acetonitrile:water with 10 mM $NH_4OAc$; Mobile Phase B: 95:5 acetonitrile:water with 10 mM $NH_4OAc$; Temperature: 50° C.; Gradient: 0-100% B over 3 minutes; Flow: 1.1 mL/min.

(F): Column: Ascentis Express C18 (50×2.1) mm, 2.7 μm; Mobile Phase A: 5:95 acetonitrile:water with 0.1% TFA; Mobile Phase B: 95:5 acetonitrile:water with 0.1% TFA; Temperature: 50° C.; Gradient: 0-100% B over 3 minutes; Flow: 1.1 mL/min.

(G): Column: Waters Acquity UPLC BEH C18 (2.1×50 mm), 1.7 micron; Solvent A=100% water with 0.05% TFA; Solvent B=100% acetonitrile with 0.05% TFA; gradient=2-98% B over 1 minute, then a 0.5-minute hold at 98% B; Flow rate: 0.8 mL/min; Detection: UV at 220 nm.

(H): Column: Acentis Express C18 (50×2.1 mm) 1.7 μm, Acentis C8 $NH_4COOH$ 5 min. M, Mobile Phase A: –10 mM ammonium formate:ACN (98:2), Mobile Phase B: –10 mM ammonium formate:ACN (2:98), gradient: 20%-100% B (0-4 min); 100% B (4-4.6 min); Flow: 1 ml/min (I) Column: Sunfire C18 (4.6×150) mm, 3.5 μm; Mobile Phase A: 5:95 acetonitrile:water with 0.05% TFA; Mobile Phase B: 95:5 acetonitrile:water with 0.05% TFA; Temperature: 50° C.; Gradient: 10-100% B over 12 minutes; Flow: 1 ml/min.

(J) Column: Sunfire C18 (4.6×150) mm, 3.5 μm; Mobile Phase A: 5:95 acetonitrile:water with 0.05% TFA; Mobile Phase B: 95:5 acetonitrile:water with 0.05% TFA;

(K) Waters Acquity SDS
Mobile Phase: A: water B: ACN; 5%-95% B in 1 min; Gradient Range: 50%-98% B (0-0.5 min); 98% B (0.5 min-1 min); 98%-2% B (1-1.1 min); Run time: 1.2 min; Flow Rate: 0.7 mL/min; Analysis Time: 1.7 μmin; Detection: Detector 1: UV at 220 nm; Detector 2: MS (ES+).

(L) Acquity UPLC BEH C18 (3.0×50 mm) 1.7 μm. Buffer: 5 mM ammonium acetate Mobile phase A: Buffer:ACN (95:5); Mobile phase B: Buffer:ACN (5:95) Method: % B: 0 min-20%: 1.1 min—90%: 1.7 μmin-90%. Run time: 2.25 min; Flow Rate: 0.7 mL/min; Detection: Detector 1: UV at 220 nm; Detector 2: MS (ES$^+$).

(M): Kinetex SBC18 (4.6×50 mm) 5 micron; Solvent A: 10 mM ammonium formate in water:acetonitrile (98:02); Mobile Phase B: 10 mM ammonium formate in water:acetonitrile (02:98); Temperature: 50° C.; Gradient: 30-100% B (0-4 min), 100% B (4-4.6 min), 100-30% B (4.6-4.7 min), 30% B (4.7-5.0 min); Flow rate: 1.5 mL/min; Detection: UV at 220 nm.

(N): Column-Ascentis Express C18 (50×2.1 mm-2.7 μm) Mphase A: 10 mM NH$_4$COOH in water:ACN (98:02); Mphase B: 10 mM NH$_4$COOH in water:ACN (02:98), Gradient: 0-100% B (0-1.7 μminutes); 100% B (1.7-3.4 minutes). Flow=1 mL/min.

(O) Waters Acquity SDS Column BEH C18 (2.1×50 mm) 1.7μ. Phase A: buffer in water; Mphase B: buffer in ACN, Gradient: 20-98% B (0-1.25 minutes); 98% B (1.25-1.70 minutes); 98%-2% B (1.70-1.75 minutes); Flow=0.8 mL/min.

Templates

Template 1: tert-butyl 4-(2-bromo-3-isopropyl-1H-indol-5-yl)piperidine-1-carboxylate

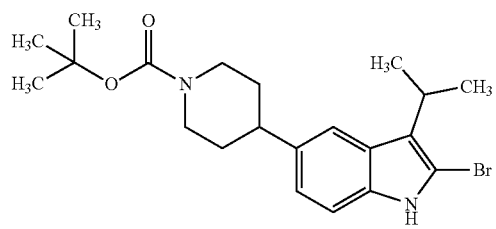

(T-1)

Intermediate T-1A: 5-bromo-3-isopropyl-1H-indole

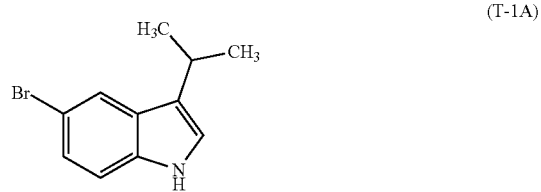

(T-1A)

A 250 mL round bottom flask was charged with triethylsilane (8.90 g, 77 mmol), trichloroacetic acid (6.25 g, 38.3 mmol) and toluene (50 mL). The solution was heated to 70° C., then a solution of 5-bromo-1H-indole (5.0 g, 25.5 mmol) and acetone (2.247 mL, 30.6 mmol) in toluene (30 mL) was added drop wise via an addition funnel. The resulting brown solution was heated at 70° C. for 1.5 h. The solution was cooled to 10° C. The reaction was quenched with 10% sodium bicarbonate. The solution was diluted with diethyl ether. The organic layer was separated, dried, and concentrated under vacuum to afford crude compound. The crude was purified using silica gel chromatography eluting with 5% ethyl acetate in hexanes to afford 5-bromo-3-isopropyl-1H-indole (5.5 g, 23.10 mmol 95% yield) as an oil. MS (M−1) m/z: 236.3 (MH$^-$). LC retention time 1.55 min [L]. $^1$H NMR (400 MHz, DMSO-d$_6$) δ 10.96 (br s, 1H), 7.70 (d, J=2.0 Hz, 1H), 7.31 (d, J=8.6 Hz, 1H), 7.18 (d, J=2.0 Hz, 1H), 7.15 (t, J=2.1 Hz, 1H), 3.12 (dtd, J=13.8, 6.8, 0.7 Hz, 1H), 1.29 (d, J=6.8 Hz, 6H).

Intermediate T-1B: tert-butyl 4-(3-isopropyl-1H-indol-5-yl)-5,6-dihydropyridine-1(2H)-carboxylate

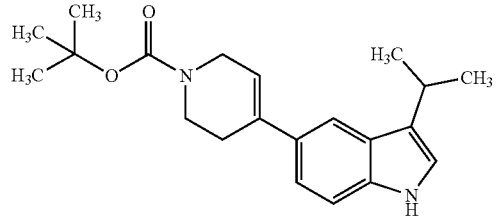

(T-1B)

To a mixture of 5-bromo-3-isopropyl-1H-indole (5.5 g, 23.10 mmol), tert-butyl 4-(4,4,5,5-tetramethyl-1,3,2-dioxaborolan-2-yl)-5,6-dihydropyridine-1(2H)-carboxylate (7.50 g, 24.25 mmol) in a 250 mL round bottom flask were added THF (50 mL) followed by an aqueous solution of potassium phosphate, tribasic (12.07 g, 69.3 mmol, 20 mL). The reaction mixture was degassed for 10 minutes with nitrogen gas, then PdCl$_2$(dppf)-CH$_2$Cl$_2$ adduct, (0.472 g, 0.577 mmol) was added. The mixture was degassed again for 5 min. The resulting reaction mixture was heated at 75° C. for 18 hours. The reaction mixture was diluted with ethyl acetate (100 mL), poured into a separate funnel and was washed with water (2×50 mL), brine (50 mL), dried over sodium sulfate, and concentrated to afford crude product. The crude material was purified using silica gel chromatography, eluting with 15% ethyl acetate in hexane. The fractions were collected and concentrated to afford tert-butyl 4-(3-isopropyl-1H-indol-5-yl)-5,6-dihydropyridine-1(2H)-carboxylate (6.5 g, 19.09 mmol, 83% yield) as an oil. MS (M$^{+1}$) m/z: 341.2 (MH$^+$). LC retention time 1.21 min [L]. $^1$H NMR (400 MHz, CHLOROFORM-d) δ 7.94 (br. s., 1H), 7.67-7.61 (m, 1H), 7.33 (dd, J=8.6, 0.5 Hz, 1H), 7.27 (dd, J=8.6, 1.7 Hz, 1H), 6.98 (dd, J=2.3, 0.7 Hz, 1H), 6.02 (br. s., 1H), 4.12 (d, J=2.0 Hz, 2H), 3.70 (t, J=5.7 Hz, 2H), 3.24 (sptd, J=6.8, 0.7 Hz, 1H), 2.66 (br. s., 2H), 1.53 (s, 9H), 1.39 (d, J=6.8 Hz, 6H).

Intermediate T-1C: tert-butyl 4-(3-isopropyl-1H-indol-5-yl)piperidine-1-carboxylate

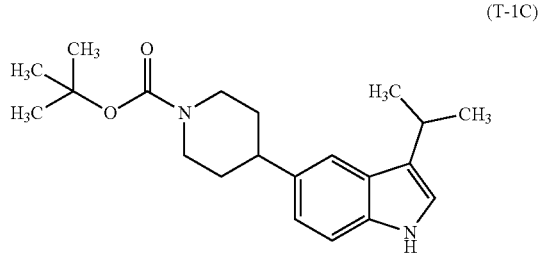 [SMILES: CC(C)c1c[nH]c2ccc(C3CCN(C(=O)OC(C)(C)C)CC3)cc12]

(T-1C)

To a solution of tert-butyl 4-(3-isopropyl-1H-indol-5-yl)-5,6-dihydropyridine-1(2H)-carboxylate (7.9 g, 23.20 mmol) in ethyl acetate (150 mL), under a nitrogen atmosphere, was added 10% palladium on carbon (0.617 g, 0.580 mmol). The vessel was pump/purged three times with nitrogen gas, and then evacuated. Hydrogen gas was introduced via a balloon and the mixture was stirred at room temperature for 5 hours. The suspension was filtered through celite and the filtrate was concentrated to afford crude compound. The crude residue was purified by ISCO using a 40 g silica column, eluting with 15% ethyl acetate in hexane. The combined fractions were collected and concentrated to afford tert-butyl 4-(3-isopropyl-1H-indol-5-yl)piperidine-1-carboxylate (6.5 g, 18.98 mmol, 82% yield) as a white solid. MS (M−1) m/z: 341.2 (MH$^-$). LC retention time 2.48 min [N]. $^1$H NMR (400 MHz, CHLOROFORM-d) δ 7.88 (br. s., 1H), 7.48 (s, 1H), 7.31 (d, J=8.3 Hz, 1H), 7.06 (dd, J=8.3, 1.6 Hz, 1H), 6.97 (d, J=1.8 Hz, 1H), 4.29 (br. s., 2H), 3.22 (sptd, J=6.8, 0.5 Hz, 1H), 2.86 (t, J=12.3 Hz, 2H), 2.77 (tt, J=12.1, 3.7 Hz, 1H), 1.91 (d, J=13.0 Hz, 2H), 1.73 (qd, J=12.8, 4.6 Hz, 2H), 1.52 (s, 9H), 1.38 (d, J=7.0 Hz, 6H).

Template 1: tert-butyl 4-(2-bromo-3-isopropyl-1H-indol-5-yl)piperidine-1-carboxylate

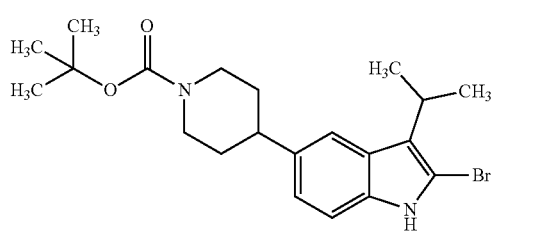

(T-1)

To a solution of tert-butyl 4-(3-isopropyl-1H-indol-5-yl) piperidine-1-carboxylate (6.3 g, 18.40 mmol) in DCE (60 mL) was added NBS (3.27 g, 18.40 mmol) dissolved in DCE (50 mL) dropwise via an addition funnel over 10 min at 0° C. The resulting brown solution was stirred at room temperature for 20 min. The reaction was quenched with sodium sulfite solution (15 mL). The volatiles were removed and the residue was taken up in DCM (50 mL) and the aqueous layer was separated. The organic layer was dried over Na$_2$SO$_4$ and concentrated to afford crude compound. The crude material was purified by ISCO using 40 g silica column. The compound eluted in 15% ethyl acetate in petroleum ether, the fractions were collected and concentrated to afford tert-butyl 4-(2-bromo-3-isopropyl-1H-indol-5-yl) piperidine-1-carboxylate (6.4 g, 15.19 mmol, 83% yield) as a white solid. MS (M$^{+1}$) m/z: 367.2 (MH$^+$-tertbutyl). LC retention time 2.59 min [N]. $^1$H NMR (400 MHz, CHLOROFORM-d) δ 7.88 (br. s., 1H), 7.48 (s, 1H), 7.31 (d, J=8.3 Hz, 1H), 7.06 (dd, J=8.3, 1.6 Hz, 1H), 6.97 (d, J=1.8 Hz, 1H), 4.29 (br. s., 2H), 3.22 (sptd, J=6.8, 0.5 Hz, 1H), 2.86 (t, J=12.3 Hz, 2H), 2.77 (tt, J=12.1, 3.7 Hz, 1H), 1.91 (d, J=13.0 Hz, 2H), 1.73 (qd, J=12.8, 4.6 Hz, 2H), 1.52 (s, 9H), 1.38 (d, J=7.0 Hz, 6H).

Template 2: tert-butyl 4-(3-isopropyl-2-(4,4,5,5-tetramethyl-1,3,2-dioxaborolan-2-yl)-1H-indol-5-yl) piperidine-1-carboxylate

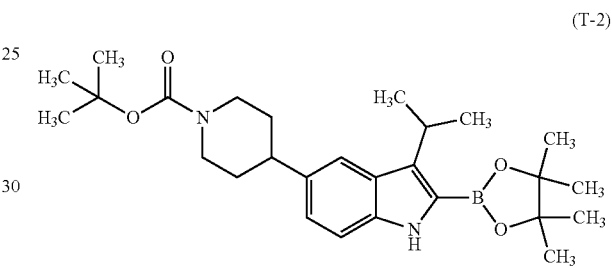

(T-2)

Dioxane (10 mL) was added to a mixture of tert-butyl 4-(2-bromo-3-isopropyl-1H-indol-5-yl)piperidine-1-carboxylate (1.0 g, 2.373 mmol), 2-dicyclohexyphosphino-2',6'-dimethoxybiphenyl (0.117 g, 0.285 mmol) and bis(benzonitrile)palladium(II) chloride (0.027 g, 0.071 mmol) in a 50 mL reaction tube. The reaction mixture was degassed for 10 min and then pinacolborane (0.456 g, 3.56 mmol) was added followed by dropwise the addition of TEA (0.992 mL, 7.12 mmol). The solution was again degassed for 5 min. The resulting reaction mixture was heated at 85° C. for 3 h. The reaction mixture was concentrated and the crude residue was dissolved in ethyl acetate (100 mL), poured into a separatory funnel and was washed thoroughly with water (2×250 mL). The organic layer was dried over Na$_2$SO$_4$, filtered and the filtrate was concentrated under vacuum to afford the crude product. The residue was taken up in DCM (3 mL). The crude was purified by combiflash system by eluting with 12% EtOAc/Pet ether. Following concentration of the fractions, the product was isolated as a white gummy material (0.75 g, 1.601 mmol, 67.5% yield). MS (M$^{+1}$) m/z: 413.2 (MH$^+$-tertbutyl). LC retention time 4.27 min [H]. $^1$H NMR (400 MHz, DMSO-d$_6$) δ 10.65 (s, 1H), 7.50 (s, 1H), 7.29 (d, J=8.4 Hz, 1H), 6.99 (dd, J=8.5, 1.3 Hz, 1H), 4.09 (br d, J=11.1 Hz, 2H), 3.71-3.61 (m, 1H), 2.91-2.66 (m, 3H), 1.77 (br d, J=11.7 Hz, 2H), 1.59-1.46 (m, 2H), 1.43 (s, 9H), 1.36 (d, J=7.1 Hz, 6H), 1.32 (s, 12H).

Template 3: tert-butyl 5-(1-(tert-butoxycarbonyl)piperidin-4-yl)-3-isopropyl-1H-indole-1-carboxylate

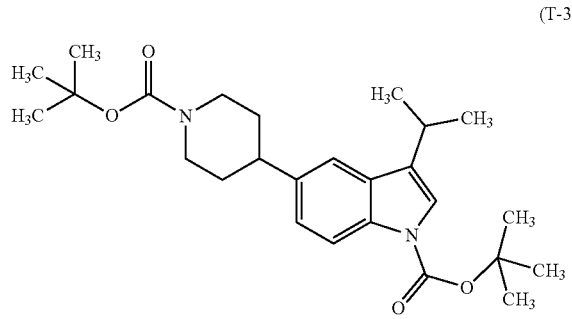

(T-3)

Tert-butyl 4-(3-isopropyl-1H-indol-5-yl)piperidine-1-carboxylate (328 mg, 0.958 mmol) (T-1C) was dissolved in THF (7662 μl) in a 50 mL recovery flask containing a Teflon-covered stir bar. Di-tert-butyl dicarbonate (298 μl, 1.245 mmol) was added to the flask, followed by 4-dimethylaminopyridine (11.70 mg, 0.096 mmol). The flask was capped and stirred at room temperature for 16 h. Excess solvent was evaporated from the reaction mixture under reduced pressure. The residue was taken up in DCM (~3 mL) and purified by flash chromatography on a 24 g SiO$_2$ column, eluting with 0%-50% gradient using EtOAc and hexanes, on an ISCO Rf instrument to afford tert-butyl 5-(1-(tert-butoxycarbonyl) piperidin-4-yl)-3-isopropyl-1H-indole-1-carboxylate (313.7 mg, 0.702 mmol, 73.3% yield) as a colorless foam. MS (M$^{+1}$) m/z: 331.1 (MH$^+$-2tertbutyl). LC retention time 1.51 min [O]. $^1$H NMR (400 MHz, CHLOROFORM-d) δ 8.05 (d, J=6.2 Hz, 1H), 7.39 (d, J=1.6 Hz, 1H), 7.33 (br. s., 1H), 7.17 (dd, J=8.6, 1.7 Hz, 1H), 4.29 (br. s., 2H), 3.13 (sptd, J=6.8, 0.9 Hz, 1H), 2.86 (t, J=12.3 Hz, 2H), 2.77 (tt, J=12.0, 3.5 Hz, 1H), 1.90 (d, J=12.7 Hz, 2H), 1.80-1.70 (m, 2H), 1.68 (s, 9H), 1.52 (s, 9H), 1.36 (d, J=7.0 Hz, 6H).

Template 4: tert-butyl 4-(2-bromo-3-methyl-1H-indol-5-yl)piperidine-1-carboxylate

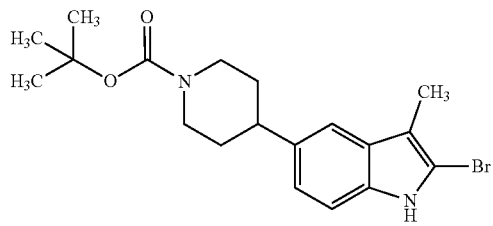

(T-4)

Template 4A: 5-bromo-3-methyl-1H-indole

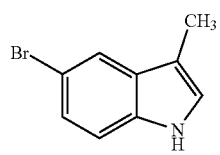

(T-4A)

A solution of 5-bromo-1H-indole-3-carbaldehyde (13.12 g, 58.6 mmol) in THF (100 mL) was added to a refluxing mixture of LiAlH$_4$ (4.89 g, 129 mmol) in THF (100 mL) (reflux condenser fitted to a two neck flask) over 30 min. The reaction mixture was refluxed for 8 hours, cooled to room temperature and treated with diethyl ether (~50 mL). The reaction mixture was acidified to ~pH 3 with 1 N HCl, while cooling in an ice bath. The reaction mixture was diluted with ethyl acetate (125 mL), poured into a separatory funnel and washed with water (2×50 mL) and saturated aqueous sodium chloride solution (50 mL), dried over anhydrous sodium sulfate and filtered. The filtrate was concentrated in vacuo to give crude product. The crude product was dissolved in a small amount of DCM and charged to an ISCO silica gel (80 g) column, which was eluted over 15 minutes using a gradient of 0-50% ethyl acetate/heptane. The combined fractions were concentrated to give 5-bromo-3-methyl-1H-indole (5.5 g, 26.2 mmol, 44.7% yield). MS (M$^{+1}$) m/z: 211.9 (MH$^+$). LC retention time 1.00 min [A1].

T-4B: tert-butyl 4-(3-methyl-1H-indol-5-yl)-3,6-dihydropyridine-1(2H)-carboxylate

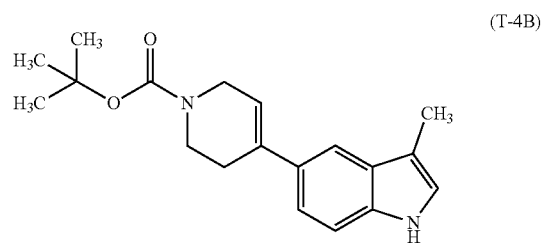 [SMILES: Cc1c[nH]c2ccc(C3=CCN(C(=O)OC(C)(C)C)CC3)cc12]

(T-4B)

To a mixture of 5-bromo-3-methyl-1H-indole (0.417 g, 1.985 mmol), PdCl$_2$(dppf)-CH$_2$Cl$_2$ adduct (0.041 g, 0.050 mmol), and tert-butyl 4-(4,4,5,5-tetramethyl-1,3,2-dioxaborolan-2-yl)-5,6-dihydropyridine-1(2H)-carboxylate (0.675 g, 2.183 mmol) in a 40 mL reaction vial were added THF (10 mL) followed by a 3 M aqueous solution of tripotassium phosphate (1.985 mL, 5.95 mmol). The vial was fitted with a Teflon-lined septum cap. The system was evacuated under vacuum (via a needle from a nitrogen/vacuum manifold line) and back-filled with nitrogen gas. The procedure was repeated three times. The needle was removed and the vial was heated at 75° C. for 18 hours. The reaction mixture was cooled to room temperature and diluted with ethyl acetate (125 mL). The mixture was poured into a separatory funnel and washed with water (2×50 mL) and saturated aqueous sodium chloride solution (50 mL), dried over anhydrous sodium sulfate and filtered. The filtrate was concentrated in vacuo to give crude product. The crude product was dissolved in a small amount of DCM and charged to an ISCO silica gel (24 g) column, which was eluted over 20 minutes using a gradient of 0-50% ethyl acetate/heptane. The combined fractions were concentrated to give tert-butyl 4-(3-methyl-1H-indol-5-yl)-5,6-dihydropyridine-1(2H)-carboxylate (0.510 g, 1.632 mmol, 82% yield) as a tan oil. MS (M$^{+1}$) m/z: 257.1 (MH$^+$-tertbutyl). LC retention time 1.08 min [A1].

T-4C: tert-butyl 4-(3-methyl-1H-indol-5-yl)piperidine-1-carboxylate

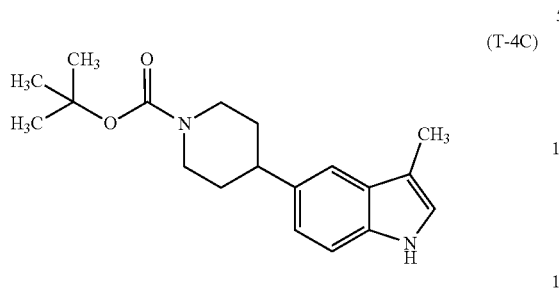
(T-4C)

To a 250 mL round bottom flask were added tert-butyl 4-(3-methyl-1H-indol-5-yl)-5,6-dihydropyridine-1(2H)-carboxylate (1.300 g, 4.16 mmol) and ethyl acetate (20 mL). The flask was purged with nitrogen gas and Pd/C (10%, 0.310 g, 0.291 mmol) was added. Following pump/purging with nitrogen gas three times, hydrogen gas was introduced via a balloon. The reaction mixture was stirred at room temperature overnight. The flask was evacuated and filled with nitrogen gas. The suspension was filtered through fluted filter paper and the filtrate was concentrated in vacuo to afford tert-butyl 4-(3-methyl-1H-indol-5-yl)piperidine-1-carboxylate (1.15 g, 3.66 mmol, 88% yield) as an off-white solid. MS ($M^{+1}$) m/z: 259.1 ($MH^+$-tertbutyl). LC retention time 1.15 min [A1].

Template 5: tert-butyl 4-(2-bromo-3-methyl-1H-indol-5-yl)piperidine-1-carboxylate

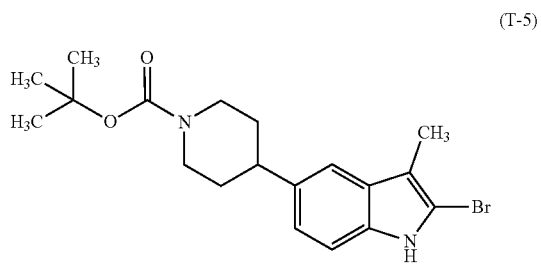 [SMILES: Cc1c(Br)[nH]c2ccc(C3CCN(C(=O)OC(C)(C)C)CC3)cc12]
(T-5)

In a 100 mL round bottom flask were added tert-butyl 4-(3-methyl-1H-indol-5-yl) piperidine-1-carboxylate (1.100 g, 3.50 mmol) and DCE (20 mL). NBS (0.560 g, 3.15 mmol) was dissolved in 15 mL of DCE and the solution was added drop-wise to the reaction mixture via an addition funnel over a 15 minute period. Following this addition, the reaction mixture was stirred at room temperature for 15 minutes. The reaction was quenched with a 10% aqueous sodium sulfite solution (1.0 mL). The mixture was diluted with DCM (100 mL), poured into a separatory funnel and washed with water (2×50 mL) and then, saturated aqueous sodium chloride solution (50 mL), dried over anhydrous sodium sulfate and filtered. The filtrate was concentrated in vacuo to give crude product. The crude product was dissolved in a small amount of DCM and charged to an ISCO silica gel column (40 g), which was eluted over a 30 min gradient with 0%-50% EtOAc/hexanes to afford tert-butyl 4-(2-bromo-3-methyl-1H-indol-5-yl)piperidine-1-carboxylate (1.05 g, 2.67 mmol, 76% yield) as a white solid. MS ($M^{+1}$) m/z: 339.1 ($MH^+$-tertbutyl). LC retention time 1.16 min [A1].

Template 6: tert-butyl 4-(2-bromo-3-ethyl-1H-indol-5-yl)piperidine-1-carboxylate

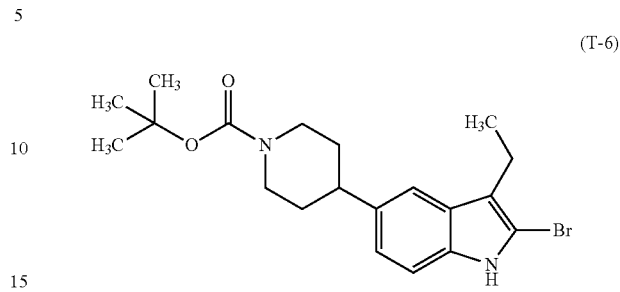
(T-6)

T-6A: 5-bromo-3-ethyl-1H-indole

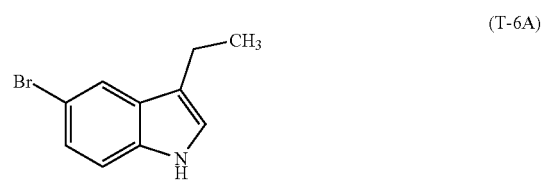
(T-6A)

5-bromo-1H-indole (2.80 g, 14.28 mmol), Shvo's Catalyst (0.155 g, 0.143 mmol), potassium carbonate (0.099 g, 0.714 mmol) and diethylamine (2.089 g, 28.6 mmol) were added in a 30 mL pressure tube. The reaction mixture was purged with nitrogen and heated to 155° C. for 20 hours. The reaction mixture was diluted with dichloromethane and washed with 1 N HCl. The organic phase was dried over $Na_2SO_4$, filtered and concentrated. The residue was purified using silica gel chromatography eluting with 0-50% ethyl acetate/hexane. The product fractions were combined and concentrated to provide white solid product (2.1 g, 9.37 mmol, 65.6% yield). MS ($M^{+1}$) m/z: 225.8 ($MH^+$). LC retention time 1.06 min [A1].

T-6B: tert-butyl 4-(3-ethyl-1H-indol-5-yl)-3,6-dihydropyridine-1(2H)-carboxylate

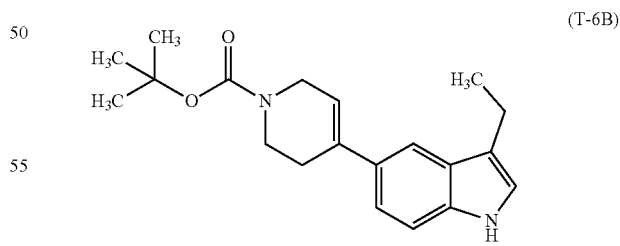
(T-6B)

THF (35 mL) was added to a mixture of 5-bromo-3-ethyl-1H-indole (1.950 g, 8.70 mmol), $PdCl_2$(dppf)-$CH_2Cl_2$ adduct (0.178 g, 0.218 mmol) and tert-butyl 4-(4,4,5,5-tetramethyl-1,3,2-dioxaborolan-2-yl)-5,6-dihydropyridine-1(2H)-carboxylate (2.83 g, 9.14 mmol) in a 100 mL round bottom flask. An aqueous solution of 3 M tripotassium phosphate (8.70 mL, 26.1 mmol) was added to the reaction mixture. The vial was fitted with a Teflon lined septum cap.

The system was evacuated under vacuum (via a needle from a nitrogen/vacuum manifold line) and backfilled with nitrogen gas. The procedure was repeated three times. The needle was removed and the vial was heated at 75° C. for 18 hours. The reaction mixture was diluted with ethyl acetate (100 mL) and poured into a separatory funnel. The mixture was washed with water (2×50 mL) and saturated aqueous NaCl solution (50 mL), dried ($Na_2SO_4$) and filtered. The filtrate was concentrated in vacuum to give crude product. The crude product was purified with silica gel chromatography eluting with 0%-50% ethyl acetate/hexanes over 20 minutes to afford tert-butyl 4-(3-ethyl-1H-indol-5-yl)-5,6-dihydropyridine-1(2H)-carboxylate (2.3 g, 7.05 mmol, 81% yield). MS ($M^{+1}$) m/z: 271.0 ($MH^+$-tertbutyl). LC retention time 1.12 min [A1].

T-6C: tert-butyl 4-(3-ethyl-1H-indol-5-yl)piperidine-1-carboxylate

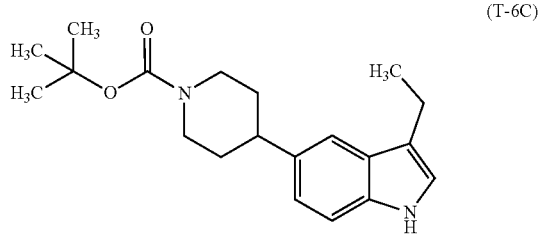 [SMILES: CCc1c[nH]c2ccc(C3CCN(C(=O)OC(C)(C)C)CC3)cc12]

(T-6C)

Tert-butyl 4-(3-ethyl-1H-indol-5-yl)-5,6-dihydropyridine-1(2H)-carboxylate (2.100 g, 6.43 mmol) and ethyl acetate (20 mL) were added to a 250 mL round-bottom flask. The flask was purged with nitrogen gas. Pd/C (0.479 g, 0.450 mmol) was added to the reaction flask, followed by pump/purging with nitrogen gas, three times. Hydrogen gas was introduced via a balloon. The reaction mixture was stirred at room temperature overnight. The flask was evacuated and back-filled with nitrogen gas. The suspension was filtered through fluted filter paper and the filtrate was concentrated. The residue was purified with flash chromatography (ISCO) eluting with 0-40% ethyl acetate/hexane. The product fractions were combined and concentrated to provide the product as a white solid (1.15 g, 3.50 mmol, 54.4% yield). MS ($M^{+1}$) m/z: 273.0 ($MH^+$-tertbutyl). LC retention time 1.13 min [A1].

Template 6: tert-butyl 4-(2-bromo-3-ethyl-1H-indol-5-yl)piperidine-1-carboxylate

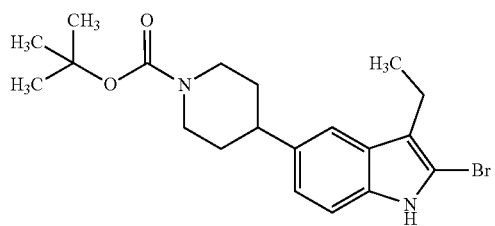

(T-6)

Tert-butyl 4-(3-ethyl-1H-indol-5-yl)piperidine-1-carboxylate (1.820 g, 5.54 mmol) and DCE (10 mL) were added to a 100 mL round-bottom flask. NBS (0.986 g, 5.54 mmol) was dissolved in 10 mL of DCE and the suspension was added to the reaction mixture drop-wise via an addition funnel over 15 minutes. The reaction was quenched with 5 mL of a 10% sodium sulfite solution. The volatiles were removed. The residue was taken up in dichloromethane (5 mL), filtered and loaded onto a silica gel column. The column was eluted with 0-50% ethyl acetate/heptanes. The product fractions were combined and concentrated to provide the product as white foam (1.95 g, 4.79 mmol, 86% yield). MS ($M^{+1}$) m/z: 353.0 ($MH^+$-tertbutyl). LC retention time 1.20 min [A1].

Template 7: tert-butyl 5-(1-(tert-butoxycarbonyl)piperidin-4-yl)-3-isopropyl-2-(4,4,5,5-tetramethyl-1,3,2-dioxaborolan-2-yl)-1H-indole-1-carboxylate

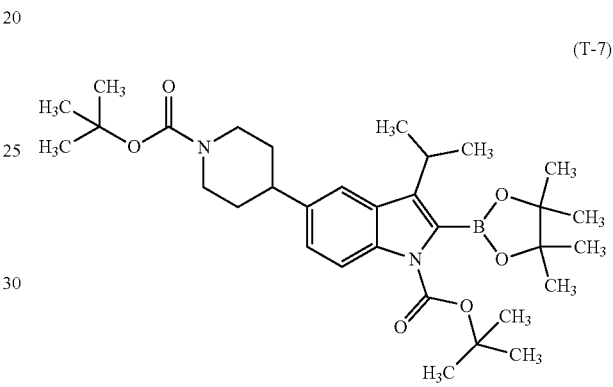

(T-7)

Tert-butyl 5-(1-(tert-butoxycarbonyl)piperidin-4-yl)-3-isopropyl-1H-indole-1-carboxylate (100 mg, 0.226 mmol) and 2-isopropoxy-4,4,5,5-tetramethyl-1,3,2-dioxaborolane (73.8 μl, 0.362 mmol) were dissolved in THF (1808 μl) in a 2-dram vial containing a Teflon-covered stir bar. The vial was cooled to −20° C. (dry ice/NMP bath) under an $N_2$ atmosphere. Lithium diisopropylamide (169 μl, 0.339 mmol) was added dropwise to the vial (via a syringe through the septum cap) over ~15 min. The reaction mixture was stirred at −20° C. for 1 h, then allowed to slowly warm to 10° C. The reaction was quenched by addition of 1 M $KHSO_4$ (2 mL). The mixture was extracted with EtOAc (3×2 mL). The combined organic exacts were dried over $Na_2SO_4$, and filtered. Excess solvent was evaporated off under an $N_2$ stream. The residue was taken up in DCM (2.5 mL) and purified by flash chromatography on a 4 g $SiO_2$ column, eluting with 0%-50% gradient using EtOAc and hexanes, on an ISCO Rf instrument to afford tert-butyl 5-(1-(tert-butoxycarbonyl)piperidin-4-yl)-3-isopropyl-2-(4,4,5,5-tetramethyl-1,3,2-dioxaborolan-2-yl)-1H-indole-1-carboxylate (112.9 mg, 0.189 mmol, 83% yield) as a colorless foam. MS ($M^{+1}$) m/z: 457.2 ($MH^+$-2tertbutyl). LC retention time 1.57 min [0]. $^1$H NMR (400 MHz, CHLOROFORM-d) δ 7.79 (d, J=8.6 Hz, 1H), 7.42 (d, J=1.5 Hz, 1H), 7.09 (dd, J=8.6, 1.6 Hz, 1H), 4.28 (br. s., 2H), 3.20 (spt, J=7.1 Hz, 1H), 2.85 (t, J=12.2 Hz, 2H), 2.74 (tt, J=12.1, 3.5 Hz, 1H), 1.89 (d, J=12.7 Hz, 2H), 1.75-1.69 (m, 2H), 1.68 (s, 9H), 1.51 (s, 9H), 1.44 (s, 12H), 1.42 (d, J=7.1 Hz, 6H).

Example 1

4-(3-isopropyl-5-(piperidin-4-yl)-1H-indol-2-yl)-1H-pyrrolo[2,3-b]pyridine

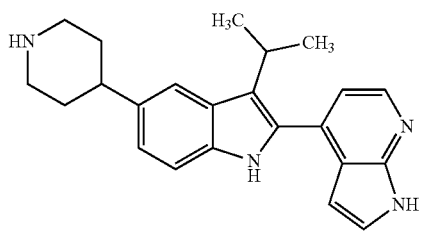

(1)

In a 2 dram vial, tert-butyl 4-(2-bromo-3-isopropyl-1H-indol-5-yl)piperidine-1-carboxylate (0.157 g, 0.373 mmol) was mixed in THF (2 mL), 4-(4,4,5,5-tetramethyl-1,3,2-dioxaborolan-2-yl)-1H-pyrrolo[2,3-b]pyridine (0.109 g, 0.447 mmol), [1,1'-bis(di-tert-butylphosphino)ferrocene]dichloropalladium(II) (0.012 g, 0.019 mmol), and potassium phosphate solution (0.373 mL, 1.118 mmol). The vial was capped and pump/purged with $N_2$ three times. The reaction mixture was heated at 70° C. for 3 hours. LC showed complete reaction. The mixture was concentrated and purified to afford 0.144 g of a tan solid. To 0.020 g of the resulting solid was added DCM and 1 mL of 4 M HCl/dioxane. The mixture was stirred at room temperature for 30 minutes, then concentrated to dryness. The product was diluted with MeOH/water and the crude material was purified via preparative LC/M to afford 4-(3-isopropyl-5-(piperidin-4-yl)-1H-indol-2-yl)-1H-pyrrolo[2,3-b]pyridine (125 mg, 0.349 mmol, 94% yield). MS ($M^{+1}$) m/z: 359.3 ($MH^+$). LC retention time 1.11 min [QC-ACN-AA-XB]. $^1H$ NMR (500 MHz, DMSO-$d_6$) δ 11.09-10.94 (m, 1H), 8.29-8.24 (m, 1H), 7.62-7.56 (m, 1H), 7.54-7.48 (m, 1H), 7.41-7.35 (m, 1H), 7.11-7.07 (m, 1H), 7.07-7.00 (m, 1H), 6.47-6.42 (m, 1H), 3.39-3.30 (m, 2H), 3.28-3.17 (m, 1H), 3.03-2.93 (m, 2H), 2.90-2.85 (m, 1H), 1.98-1.90 (m, 2H), 1.90-1.78 (m, 2H), 1.42-1.30 (m, 6H).

Example 2

4-(3-methyl-5-(piperidin-4-yl)-1H-indol-2-yl)-1H-pyrrolo[2,3-b]pyridine

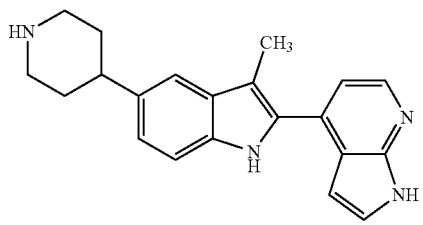

(2)

To a mixture of tert-butyl 4-(2-bromo-3-methyl-1H-indol-5-yl)piperidine-1-carboxylate (150 mg, 0.381 mmol), 4-(4,4,5,5-tetramethyl-1,3,2-dioxaborolan-2-yl)-1H-pyrrolo[2,3-b]pyridine (102 mg, 0.420 mmol), and Pd(dppf)Cl$_2$ (13.95 mg, 0.019 mmol) in a screw cap vial were added THF (3 mL) followed by aqueous solution of tripotassium phosphate (0.381 mL, 1.144 mmol). The vial was fitted with a Teflon lined septum cap. The vial was evacuated under vacuum (via a needle from a nitrogen/vacuum manifold line) and backfilled with nitrogen gas. The procedure was repeated three times. The needle was removed and the vial was heated at 65° C. for 1 h. The reaction mixture was diluted with ethyl acetate (10 mL). Saturated aqueous NaCl solution (2 mL) was added. The organic layer was isolated and the aqueous layer was extracted with additional ethyl acetate (2×3 mL). To the combined extracts was added 5 g of silica and the mixture was concentrated in vacuo, solid loaded and purified on 12 g ISCO column silica gel cartridge which was eluted with a 10 minute gradient from 0%-5% MeOH/DCM to afford tert-butyl 4-(3-methyl-2-(1H-pyrrolo[2,3-b]pyridin-4-yl)-1H-indol-5-yl)piperidine-1-carboxylate (160 mg, 0.372 mmol, 97% yield), m/e (431, $M^{+1}$).

tert-Butyl 4-(3-methyl-2-(1H-pyrrolo[2,3-b]pyridin-4-yl)-1H-indol-5-yl)piperidine-1-carboxylate (160 mg, 0.372 mmol) was suspended in HCl (4 N in dioxane) (3 mL, 99 mmol) and stirred for 30 min to afford 4-(3-methyl-5-(piperidin-4-yl)-1H-indol-2-yl)-1H-pyrrolo[2,3-b]pyridine, 2 HCl. The reaction mixture was concentrated in vacuo. m/e (331, $M^{+1}$). LCMS $MH^+$: 331 HPLC Ret. Time 0.56 min. Method: Method B1.

Alternative Preparation:

To a 40 mL reaction vial was added tert-butyl 2-bromo-5-(1-(tert-butoxycarbonyl) piperidin-4-yl)-3-methyl-1H-indole-1-carboxylate (0.6 g, 1.216 mmol) was taken in THF (7 mL). Next, 4-(4,4,5,5-tetramethyl-1,3,2-dioxaborolan-2-yl)-1H-pyrrolo[2,3-b]pyridine (0.356 g, 1.459 mmol), [1,1'-bis(di-tert-butylphosphino)ferrocene]dichloropalladium(II) (0.040 g, 0.061 mmol), and potassium phosphate solution (1.216 mL, 3.65 mmol) were added. The vial was capped and pump/purged with $N_2$ three times. The reaction mixture was heated at 70° C. for 1 hour. LC showed complete reaction. The mixture was concentrated. The crude residue was diluted with DCM and purified on a 24G ISCO column using 0-100% ethyl acetate/hexane. Following concentration of fractions, the Boc protected intermediate was collected as a tan/yellow solid. The isolated intermediate (20 mg) was treated with 0.1 mL DCM, followed by the addition of 0.5 mL of TFA. The reaction mixture was stirred at room temperature for 30 minutes and then concentrated to dryness. The product was diluted with MeOH/water and purified with prep HPLC to provide 4-(3-methyl-5-(piperidin-4-yl)-1H-indol-2-yl)-1H-pyrrolo[2,3-b] pyridine (406 mg, 1.229 mmol, 101% yield). MS ($M^{+1}$) m/z: 331.2 ($MH^+$). LC retention time 0.97 min [QC-ACN-AA-XB]. $^1H$ NMR (500 MHz, DMSO-$d_6$) δ 11.10 (s, 1H), 8.30 (d, J=5.0 Hz, 1H), 7.55 (d, J=3.0 Hz, 1H), 7.43-7.31 (m, 2H), 7.18 (d, J=5.0 Hz, 1H), 7.06 (br d, J=8.4 Hz, 1H), 6.54 (d, J=3.4 Hz, 1H), 3.59 (br d, J=8.1 Hz, 1H), 3.21 (br d, J=11.1 Hz, 2H), 2.87-2.76 (m, 3H), 2.36 (s, 3H), 1.94-1.68 (m, 4H).

Example 3

4-(3-isopropyl-5-(piperidin-4-yl)-1h-indol-2-yl)-1-(methylsulfonyl)-1H-pyrrolo[2,3-b]pyridine

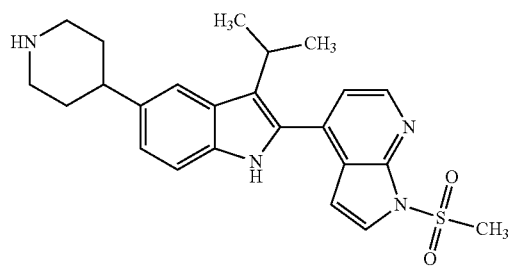

(3)

Intermediate 3A: tert-butyl 4-(3-isopropyl-2-(1-(methylsulfonyl)-1H-pyrrolo[2,3-b]pyridin-4-yl)-1H-indol-5-yl)piperidine-1-carboxylate

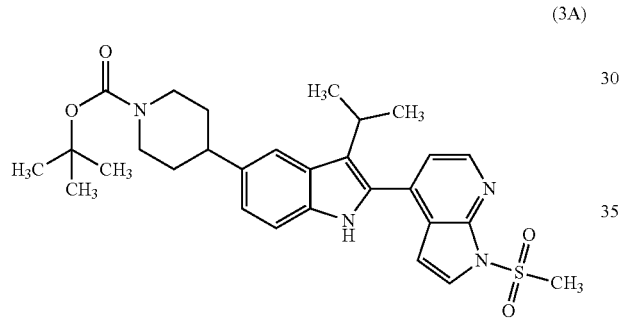

(3A)

To a solution of tert-butyl 4-(3-isopropyl-2-(4,4,5,5-tetramethyl-1,3,2-dioxaborolan-2-yl)-1H-indol-5-yl)piperidine-1-carboxylate (0.15 g, 0.320 mmol), 4-bromo-1-(methylsulfonyl)-1H-pyrrolo[2,3-b]pyridine (0.106 g, 0.384 mmol), and potassium carbonate (0.111 g, 0.801 mmol) in a 10 mL sealed tube were added dioxane (1 mL) and water (0.1 mL). The reaction mixture was degassed for 10 min. Next, PdCl$_2$(dppf)-CH$_2$Cl$_2$ adduct (0.026 g, 0.032 mmol) was added and the reaction mixture was degassed again for 5 min. The resulting reaction mixture was heated at 90° C. for 4 hours. The TLC showed formation of a polar spot and absence of starting material. The reaction mixture was concentrated. The crude material was dissolved in ethyl acetate and water washed. The organic layer was dried over Na$_2$SO$_4$ and concentrated. The residue was taken up in DCM (3 mL). The crude material was purified by combiflash by eluting with 25% ethyl acetate/pet ether. Following concentration of fractions, tert-butyl 4-(3-isopropyl-2-(1-(methylsulfonyl)-1H-pyrrolo[2,3-b] pyridin-4-yl)-1H-indol-5-yl)piperidine-1-carboxylate (90 mg, 0.168 mmol, 52.4% yield) was collected as a white solid. MS (M$^{+1}$) m/z: 537.3 (MH$^+$). LC retention time 1.17 min [E].

Example 3

To a solution of tert-butyl 4-(3-isopropyl-2-(1-(methylsulfonyl)-1H-pyrrolo[2,3-b]pyridin-4-yl)-1H-indol-5-yl)piperidine-1-carboxylate (0.08 g, 0.149 mmol) in DCM was added hydrochloric acid in dioxane (0.559 mL, 2.236 mmol) dropwise. The reaction mixture was stirred at 25° C. for 1 hr. The solvent was removed under vacuum and the green-colored solid product formed was washed with diethyl ether to remove non polar impurities. The crude material was purified via preparative LC/MS. Fractions containing the desired product were combined and dried via centrifugal evaporation to afford 4-(3-isopropyl-5-(piperidin-4-yl)-1H-indol-2-yl)-1-(methylsulfonyl)-1H-pyrrolo[2,3-b]pyridine (5 mg, 0.011 mmol, 7.68% yield). MS (M$^{+1}$) m/z: 437.3 (MH$^+$). LC retention time 1.13 min [E]. $^1$H NMR (400 MHz, DMSO-d$_6$) δ=11.15 (s, 1H), 8.53 (d, J=5.0 Hz, 1H), 7.82 (d, J=4.0 Hz, 1H), 7.59 (s, 1H), 7.40-7.32 (m, 2H), 7.05 (dd, J=8.5, 1.5 Hz, 1H), 6.75 (d, J=4.5 Hz, 1H), 3.80 (s, 3H), 3.24-3.15 (m, 3H), 3.08 (d, J=12.0 Hz, 2H), 2.72-2.61 (m, 2H), 2.33 (dt, J=3.6, 1.9 Hz, 1H), 1.88 (s, 3H), 1.75 (d, J=12.5 Hz, 2H), 1.61 (dd, J=12.3, 3.8 Hz, 2H), 1.42 (d, J=7.0 Hz, 6H).

Example 4

3-methyl-4-(3-methyl-5-(piperidin-4-yl)-1H-indol-2-yl)-1H-pyrrolo[2,3-b]pyridine

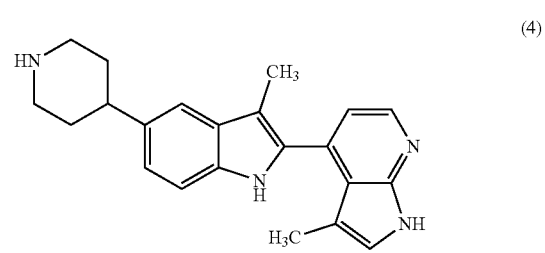 [SMILES: Cc1c(-c2ccnc3[nH]cc(C)c23)[nH]c2ccc(C3CCNCC3)cc12]

(4)

Intermediate 4A: tert-butyl 3-bromo-4-(1-(tert-butoxycarbonyl)-5-(1-(tert-butoxycarbonyl) piperidin-4-yl)-3-methyl-1H-indol-2-yl)-1H-pyrrolo[2,3-b]pyridine-1-carboxylate

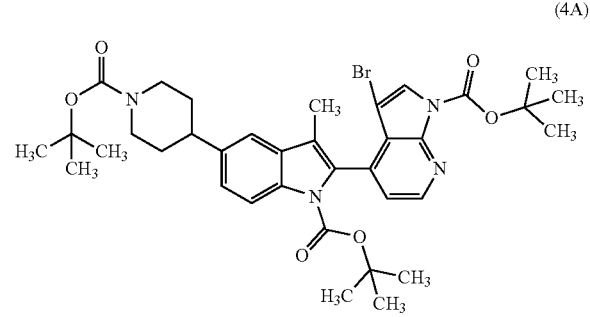 [SMILES: Cc1c(-c2ccnc3c2c(Br)cn3C(=O)OC(C)(C)C)n(C(=O)OC(C)(C)C)c2ccc(C3CCN(C(=O)OC(C)(C)C)CC3)cc12]

(4A)

In a 40 mL reaction vial were added tert-butyl 5-(1-(tert-butoxycarbonyl) piperidin-4-yl)-3-methyl-2-(1H-pyrrolo[2,3-b]pyridin-4-yl)-1H-indole-1-carboxylate (0.740 g, 1.394 mmol), DCM and drop-wise in 5 mL of DCM, NBS (0.248 g, 1.394 mmol). The dark solution was stirred for 5 minutes. The reaction was quenched with 10% NaSO$_3$ solution. DCM was added and the layers were separated. The organic was washed with water, then brine and dried over Na$_2$SO$_4$ and filtered and concentrated. The product was further purified on a 40 g ISCO column using 0-100% ethyl acetate/hexane. Following concentration, the intermediate was collected as a yellow solid, tert-butyl 2-(3-bromo-1H-pyrrolo[2,3-b]pyridin-4-yl)-5-(1-(tert-butoxycarbonyl)piperidin-4-yl)-3-methyl-1H-indole-1-carboxylate.

In a 40 mL reaction vial were added tert-butyl 2-(3-bromo-1H-pyrrolo[2,3-b]pyridin-4-yl)-5-(1-(tert-butoxycarbonyl)piperidin-4-yl)-3-methyl-1H-indole-1-carboxylate followed by the addition of THF (10 mL), DMAP (1.704 mg, 0.014 mmol) and Boc-anhydride (0.809 mL, 3.49 mmol). The reaction mixture was stirred for 2 hours at room temperature then quenched with water and 10% 1N HCl. To this was added ethyl acetate and the layers were separated. The organics were washed with brine, dried over $Na_2SO_4$, filtered and concentrated to afford tert-butyl 3-bromo-4-(1-(tert-butoxycarbonyl)-5-(1-(tert-butoxycarbonyl)piperidin-4-yl)-3-methyl-1H-indol-2-yl)-1H-pyrrolo[2,3-b]pyridine-1-carboxylate (655 mg, 0.923 mmol, 66.2% yield) as yellow solid. MS ($M^{+1}$) m/z: 710.0/711.6 ($MH^+$). LC retention time 1.34 min [B1].

Example 4

To mixture of tert-butyl 3-bromo-4-(1-(tert-butoxycarbonyl)-5-(1-(tert-butoxycarbonyl)piperidin-4-yl)-3-methyl-1H-indol-2-yl)-1H-pyrrolo[2,3-b]pyridine-1-carboxylate (220 mg, 0.310 mmol), $Pd(dppf)Cl_2$ (11.34 mg, 0.016 mmol) and $K_2CO_3$ (129 mg, 0.930 mmol) in a 40 mL vial was added DMF (1 mL). The vial was fitted with a Teflon-lined septum and pump-purged vial a needle and dimethylzinc (1 M in heptane) (620 μl, 0.620 mmol) was added. The needle was removed and the reaction mixture was sealed and heated at 95° C. for 4 h. LCMs analysis showed product along with some de-brominated material and product in which the tert-butyloxycarbonyl group has been removed. The reaction mixture was cooled to room temperature, diluted with ethyl acetate (10 mL), and washed with saturated $NH_4C_1$ solution (2×10 mL), 10% aqueous LiCl (2×20 mL) and saturated aqueous NaCl solution, dried ($Na_2SO_4$) and concentrated in vacuo. The crude product was dissolved in a small amount of DCM and purified on 24 g ISCO Column silica gel cartridge which was eluted with 0-75% ethyl acetate/hexane to afford the product as a tan oil. The resulting oil was dissolved in DCM (10 mL) and treated with TFA (10 mL). The solvents were evaporated and the residue was placed under vacuum to provide 3-methyl-4-(3-methyl-5-(piperidin-4-yl)-1H-indol-2-yl)-1H-pyrrolo[2,3-b]pyridine (2.1 mg, 0.006 mmol). MS ($M^{+1}$) m/z: 345.3 ($MH^+$). LC retention time 1.05 min [QC-ACN-AA-XB]. $^1H$ NMR (500 MHz, DMSO-$d_6$) δ 11.65-11.54 (m, 1H), 11.26-11.12 (m, 1H), 8.73-8.57 (m, 1H), 8.47-8.22 (m, 2H), 7.46-7.28 (m, 3H), 7.09-6.94 (m, 2H), 3.63-3.34 (m, 2H), 3.12-2.87 (m, 3H), 2.24-2.16 (m, 3H), 2.06-1.96 (in 2H), 1.95-1.81 (m, 5H).

The following examples were prepared according to the general procedures for Examples 1-4.

TABLE 1

| Ex. No. | Structure | LCMS $MH^+$ | Ret Time (min) | HPLC Method |
|---|---|---|---|---|
| 5 | 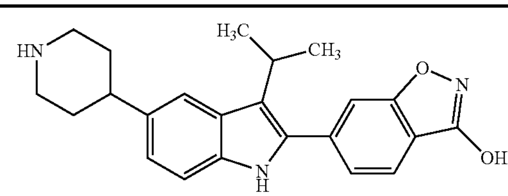 | 376.1 | 0.95 | QC-ACN-AA-XB |
| 6 | 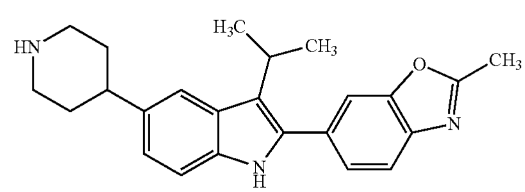 [SMILES: Cc1nc2ccc(-c3[nH]c4ccc(C5CCNCC5)cc4c3C(C)C)cc2o1] | 374.2 | 1.52 | QC-ACN-TFA-XB |
| 7 | 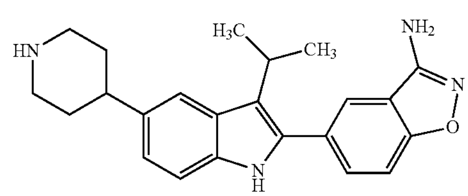 [SMILES: CC(C)c1c(-c2ccc3onc(N)c3c2)[nH]c2ccc(C3CCNCC3)cc12] | 375.1 | 1.3 | QC-ACN-TFA-XB |
| 8 | 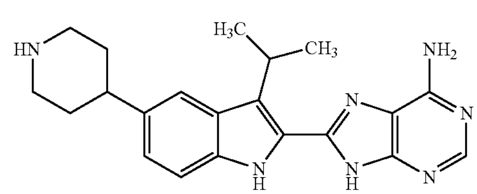 [SMILES: CC(C)c1c(-c2nc3c(N)ncnc3[nH]2)[nH]c2ccc(C3CCNCC3)cc12] | 376.2 | 0.98 | QC-ACN-AA-XB |

TABLE 1-continued
| Ex. No. | Structure | LCMS MH+ | Ret Time (min) | HPLC Method |
|---|---|---|---|---|
| 9 | 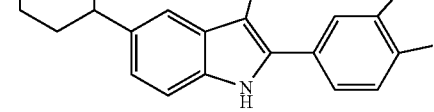 | 376.2 | 1.5 | QC-ACN-AA-XB |
| 10 | 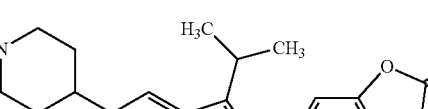 | 376.2 | 1.31 | QC-ACN-TFA-XB |
| 11 | 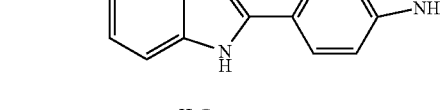 | 376.2 | 1.41 | QC-ACN-TFA-XB |
| 12 | 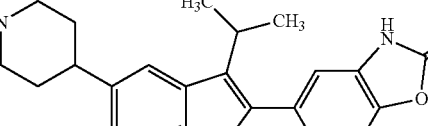 | 376.1 | 1.55 | QC-ACN-AA-XB |
| 13 | 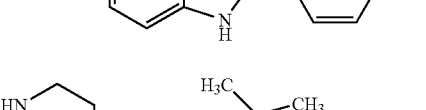 | 360.2 | 1.1 | QC-ACN-AA-XB |
| 14 | 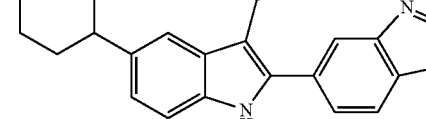 | 359.2 | 1.02 | QC-ACN-TFA-XB |
| 15 | 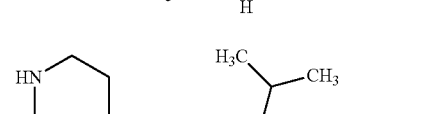 | 359.2 | 1.12 | QC-ACN-AA-XB |

TABLE 1-continued

| Ex. No. | Structure | LCMS MH+ | Ret Time (min) | HPLC Method |
|---|---|---|---|---|
| 16 | 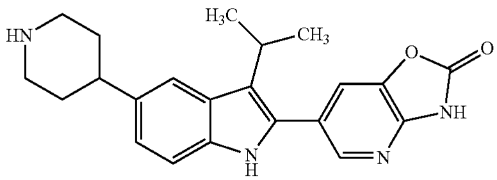 [SMILES: CC(C)c1c(-c2cnc3[nH]c(=O)oc3c2)[nH]c2ccc(C3CCNCC3)cc12] | 377.2 | 1.09 | QC-ACN-AA-XB |
| 17 | 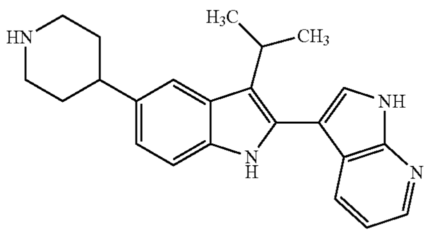 [SMILES: CC(C)c1c(-c2c[nH]c3ncccc23)[nH]c2ccc(C3CCNCC3)cc12] | 359.2 | 1.28 | QC-ACN-AA-XB |
| 18 | 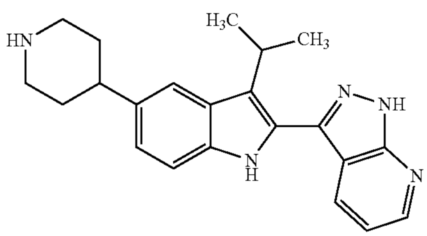 [SMILES: CC(C)c1c(-c2n[nH]c3ncccc23)[nH]c2ccc(C3CCNCC3)cc12] | 360.2 | 1.21 | QC-ACN-AA-XB |
| 19 | 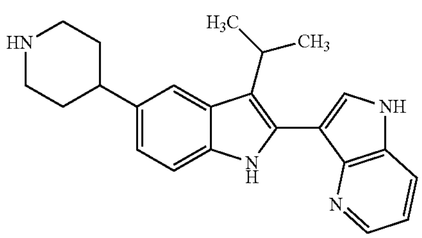 [SMILES: CC(C)c1c(-c2c[nH]c3cccnc23)[nH]c2ccc(C3CCNCC3)cc12] | 359.2 | 1.38 | QC-ACN-AA-XB |
| 20 | 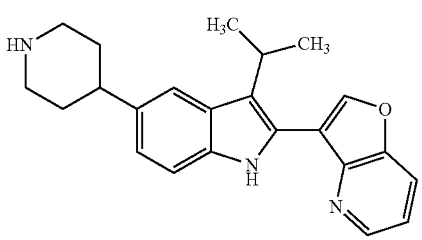 [SMILES: CC(C)c1c(-c2coc3cccnc23)[nH]c2ccc(C3CCNCC3)cc12] | 360.2 | 1.52 | QC-ACN-TFA-XB |
| 21 | 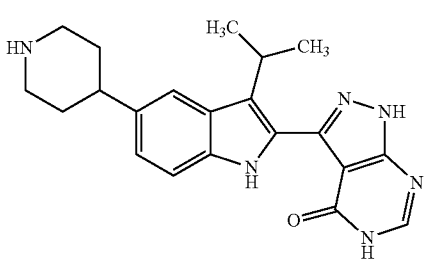 [SMILES: CC(C)c1c(-c2n[nH]c3nc[nH]c(=O)c23)[nH]c2ccc(C3CCNCC3)cc12] | 377.1 | 1.04 | QC-ACN-AA-XB |

TABLE 1-continued
| Ex. No. | Structure | LCMS MH+ | Ret Time (min) | HPLC Method |
|---|---|---|---|---|
| 22 | 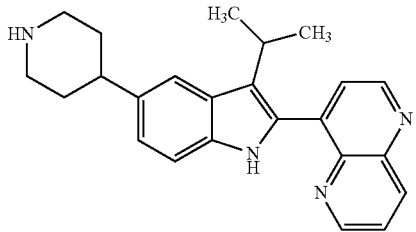 [SMILES: CC(C)c1c(-c2ccnc3cccnc23)[nH]c2ccc(C3CCNCC3)cc12] | 370.93 | | QC-ACN-TFA-XB |
| 23 | 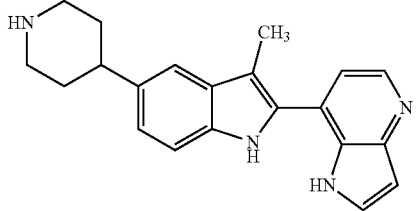 [SMILES: Cc1c(-c2ccnc3cc[nH]c23)[nH]c2ccc(C3CCNCC3)cc12] | 359.4 | 1.01 | QC-ACN-AA-XB |
| 24 | 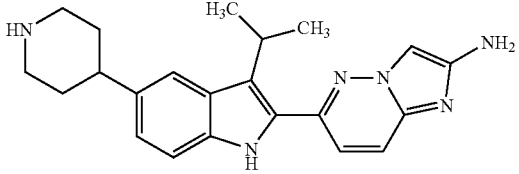 [SMILES: CC(C)c1c(-c2ccc3nc(N)cn3n2)[nH]c2ccc(C3CCNCC3)cc12] | 375.2 | | QC-ACN-TFA-XB |
| 25 | 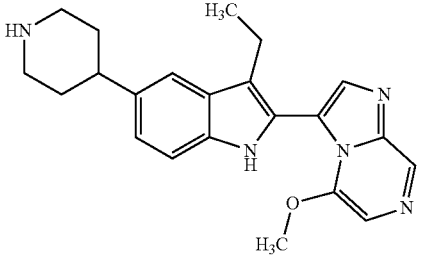 [SMILES: CCc1c(-c2cnc3cncc(OC)n23)[nH]c2ccc(C3CCNCC3)cc12] | 376.2 | 0.95 | QC-ACN-AA-XB |
| 26 | 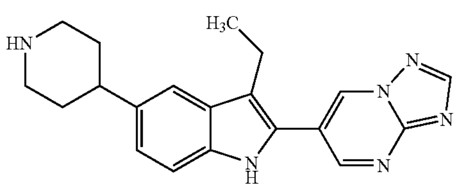 [SMILES: CCc1c(-c2cnc3ncnn3c2)[nH]c2ccc(C3CCNCC3)cc12] | 347.2 | 0.85 | QC-ACN-TFA-XB |
| 27 | 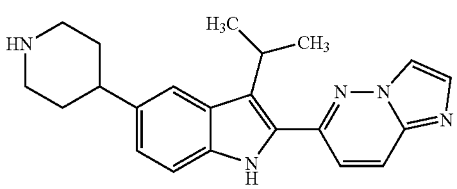 [SMILES: CC(C)c1c(-c2ccc3nccn3n2)[nH]c2ccc(C3CCNCC3)cc12] | 360 | 1.06 | QC-ACN-AA-XB |
| 28 | 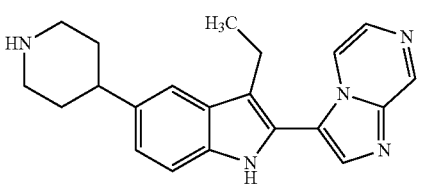 [SMILES: CCc1c(-c2cnc3cnccn23)[nH]c2ccc(C3CCNCC3)cc12] | 346.2 | 0.74 | QC-ACN-TFA-XB |

TABLE 1-continued

| Ex. No. | Structure | LCMS MH+ | Ret Time (min) | HPLC Method |
|---|---|---|---|---|
| 29 | 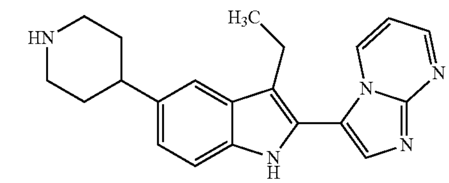 [SMILES: CCc1c(-c2cnc3ncccn23)[nH]c2ccc(C3CCNCC3)cc12] | 346.2 | 0.86 | QC-ACN-AA-XB |
| 30 | 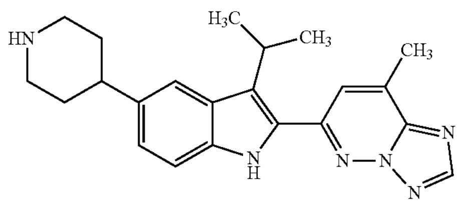 [SMILES: Cc1cc(-c2[nH]c3ccc(C4CCNCC4)cc3c2C(C)C)nn2ncnc12] | 375.2 | 0.63 | B1 |
| 31 | 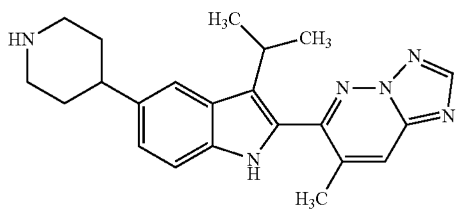 [SMILES: Cc1cc2ncnn2nc1-c1[nH]c2ccc(C3CCNCC3)cc2c1C(C)C] | 375.0 | 0.62 | A1 |
| 32 | 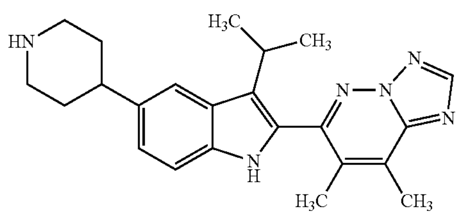 [SMILES: Cc1c(-c2[nH]c3ccc(C4CCNCC4)cc3c2C(C)C)nn2ncnc2c1C] | 389.1 | 0.65 | A1 |
| 33 | 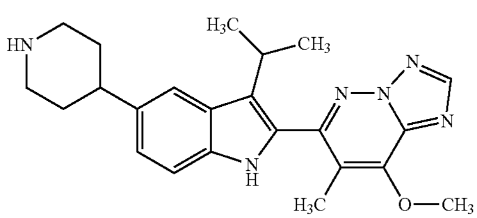 [SMILES: COc1c(C)c(-c2[nH]c3ccc(C4CCNCC4)cc3c2C(C)C)nn2ncnc12] | 405.2 | 0.71 | K |
| 34 | 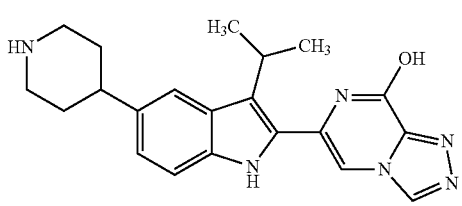 [SMILES: CC(C)c1c(-c2cn3cnnc3c(O)n2)[nH]c2ccc(C3CCNCC3)cc12] | 377.2 | 0.93 | QC-ACN-AA-XB |
| 35 | 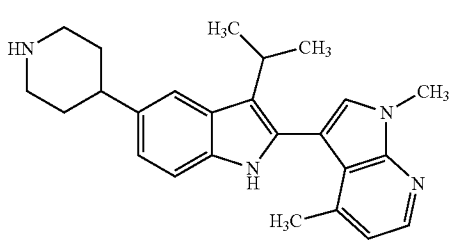 [SMILES: Cc1ccnc2c1c(-c1[nH]c3ccc(C4CCNCC4)cc3c1C(C)C)cn2C] | 387 | 1.56 | QC-ACN-AA-XB |

TABLE 1-continued
| Ex. No. | Structure | LCMS MH+ | Ret Time (min) | HPLC Method |
|---|---|---|---|---|
| 36 | 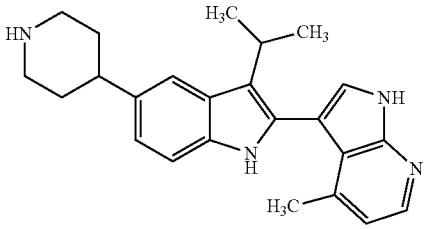 [SMILES: Cc1ccnc2[nH]cc(-c3[nH]c4ccc(C5CCNCC5)cc4c3C(C)C)c12] | 373.2 | 1.24 | QC-ACN-AA-XB |
| 37 | 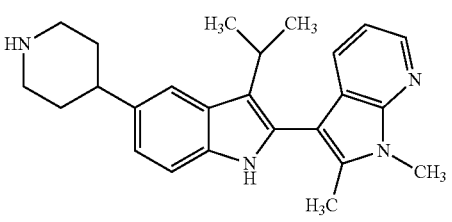 [SMILES: Cc1c(-c2[nH]c3ccc(C4CCNCC4)cc3c2C(C)C)c2cccnc2n1C] | 386.9 | 1.15 | QC-ACN-TFA-XB |
| 38 | 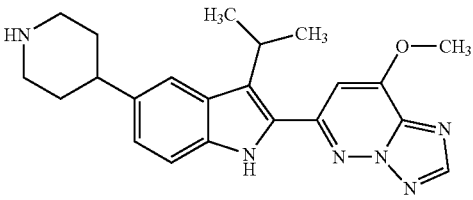 [SMILES: COc1cc(-c2[nH]c3ccc(C4CCNCC4)cc3c2C(C)C)nn2ncnc12] | 391.2 | 0.64 | A1 |
| 39 | 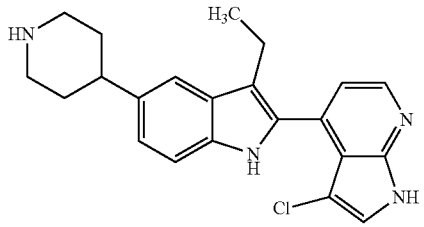 [SMILES: CCc1c(-c2ccnc3[nH]cc(Cl)c23)[nH]c2ccc(C3CCNCC3)cc12] | 379 | 0.86 | QC-ACN-TFA-XB |
| 40 | 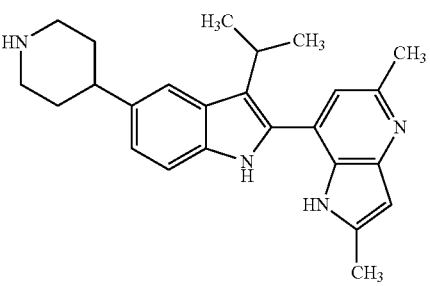 [SMILES: Cc1cc(-c2[nH]c3ccc(C4CCNCC4)cc3c2C(C)C)c2[nH]c(C)cc2n1] | 387 | 1.28 | QC-ACN-AA-XB |
| 41 | 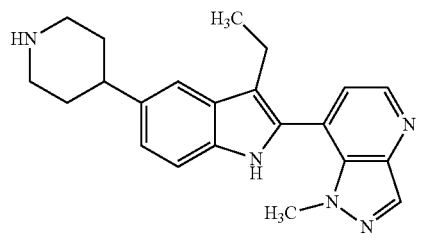 [SMILES: CCc1c(-c2ccnc3cnn(C)c23)[nH]c2ccc(C3CCNCC3)cc12] | 360.2 | 1.06 | QC-ACN-AA-XB |

TABLE 1-continued

| Ex. No. | Structure | LCMS MH+ | Ret Time (min) | HPLC Method |
|---|---|---|---|---|
| 42 | 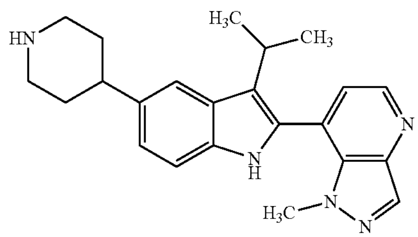 [SMILES: CC(C)c1c(-c2ccnc3cnn(C)c23)[nH]c2ccc(C3CCNCC3)cc12] | 374.2 | 1.22 | QC-ACN-AA-XB |
| 43 | 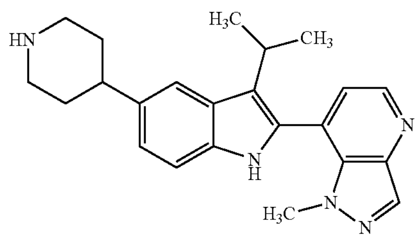 [SMILES: CC(C)c1c(-c2ccnc3cnn(C)c23)[nH]c2ccc(C3CCNCC3)cc12] | 374.2 | 1.21 | QC-ACN-AA-XB |
| 44 | 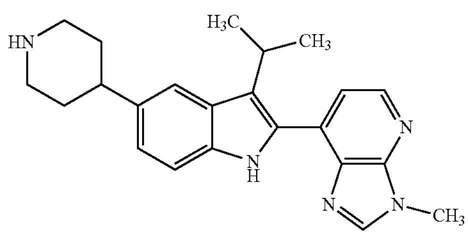 [SMILES: CC(C)c1c(-c2ccnc3c2ncn3C)[nH]c2ccc(C3CCNCC3)cc12] | 374.3 | 1.04 | QC-ACN-AA-XB |
| 45 | 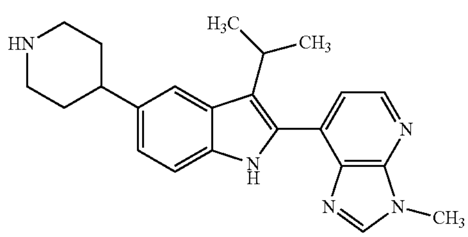 [SMILES: CC(C)c1c(-c2ccnc3c2ncn3C)[nH]c2ccc(C3CCNCC3)cc12] | 374.2 | 0.78 | QC-ACN-TFA-XB |
| 46 | 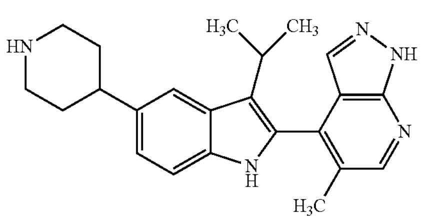 [SMILES: Cc1cnc2[nH]ncc2c1-c1[nH]c2ccc(C3CCNCC3)cc2c1C(C)C] | 374.1 | 0.96 | QC-ACN-TFA-XB |
| 47 | 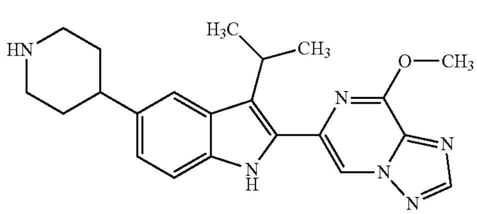 [SMILES: COc1nc(-c2[nH]c3ccc(C4CCNCC4)cc3c2C(C)C)cn2ncnc12] | 391.2 | 0.86 | QC-ACN-AA-XB |

TABLE 1-continued

| Ex. No. | Structure | LCMS MH+ | Ret Time (min) | HPLC Method |
|---|---|---|---|---|
| 48 | 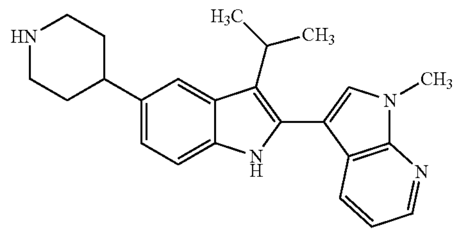 [SMILES: CC(C)c1c(-c2cn(C)c3ncccc23)[nH]c2ccc(C3CCNCC3)cc12] | 373.3 | 1.42 | QC-ACN-AA-XB |
| 49 | 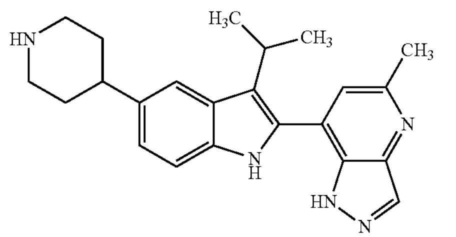 [SMILES: Cc1cc(-c2[nH]c3ccc(C4CCNCC4)cc3c2C(C)C)c2[nH]ncc2n1] | 374.3 | 1.02 | QC-ACN-AA-XB |
| 50 | 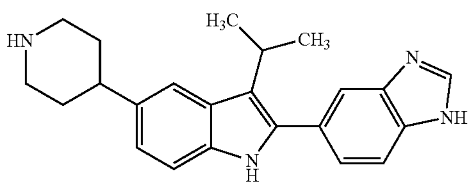 [SMILES: CC(C)c1c(-c2ccc3[nH]cnc3c2)[nH]c2ccc(C3CCNCC3)cc12] | 359.2 | 0.81 | QC-ACN-AA-XB |
| 51 | 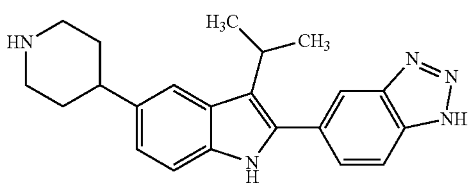 [SMILES: CC(C)c1c(-c2ccc3[nH]nnc3c2)[nH]c2ccc(C3CCNCC3)cc12] | 360.3 | 0.95 | QC-ACN-AA-XB |
| 52 | 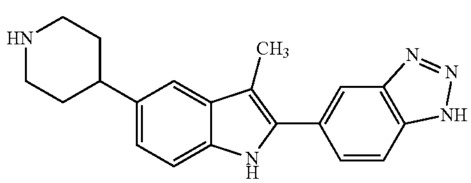 [SMILES: Cc1c(-c2ccc3[nH]nnc3c2)[nH]c2ccc(C3CCNCC3)cc12] | 332.2 | 0.89 | QC-ACN-AA-XB |
| 53 | 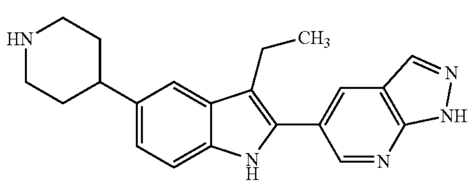 [SMILES: CCc1c(-c2cnc3[nH]ncc3c2)[nH]c2ccc(C3CCNCC3)cc12] | 346.2 | 0.91 | QC-ACN-AA-XB |
| 54 | 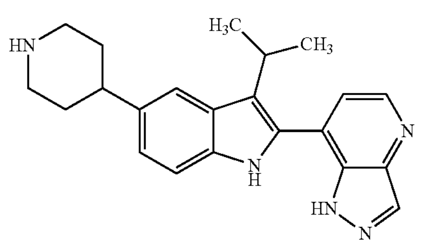 [SMILES: CC(C)c1c(-c2ccnc3cn[nH]c23)[nH]c2ccc(C3CCNCC3)cc12] | 360.2 | 0.8 | QC-ACN-TFA-XB |

TABLE 1-continued

| Ex. No. | Structure | LCMS MH+ | Ret Time (min) | HPLC Method |
|---|---|---|---|---|
| 55 | 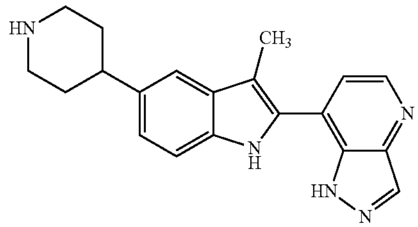 [SMILES: Cc1c(-c2ccnc3cn[nH]c23)[nH]c2ccc(C3CCNCC3)cc12] | 332.2 | 0.83 | QC-ACN-AA-XB |
| 56 | 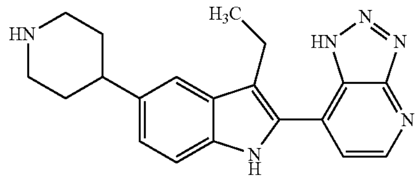 [SMILES: CCc1c(-c2ccnc3nn[nH]c23)[nH]c2ccc(C3CCNCC3)cc12] | 347.1 | 0.85 | QC-ACN-AA-XB |
| 57 | 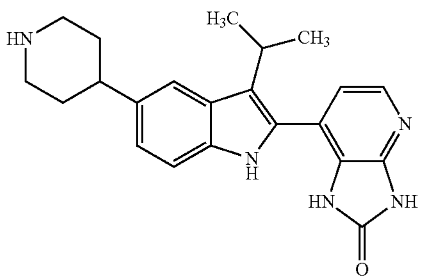 [SMILES: CC(C)c1c(-c2ccnc3[nH]c(=O)[nH]c23)[nH]c2ccc(C3CCNCC3)cc12] | 376.4 | 0.83 | QC-ACN-TFA-XB |
| 58 | 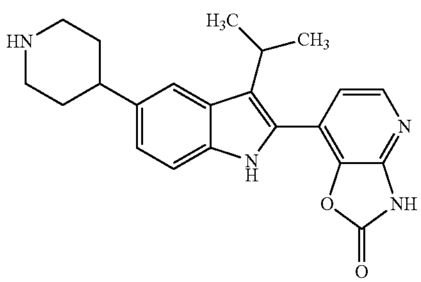 [SMILES: CC(C)c1c(-c2ccnc3[nH]c(=O)oc23)[nH]c2ccc(C3CCNCC3)cc12] | 377.2 | 0.81 | QC-ACN-AA-XB |
| 59 | 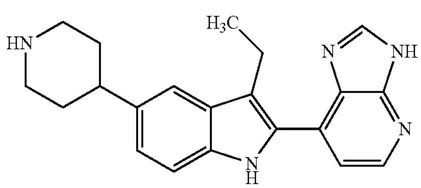 [SMILES: CCc1c(-c2ccnc3[nH]cnc23)[nH]c2ccc(C3CCNCC3)cc12] | 346.4 | 0.93 | QC-ACN-AA-XB |
| 60 | 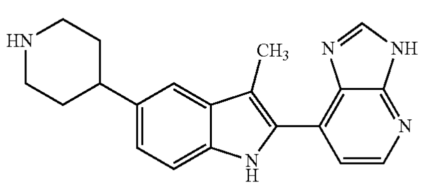 [SMILES: Cc1c(-c2ccnc3[nH]cnc23)[nH]c2ccc(C3CCNCC3)cc12] | 332.3 | 0.55 | QC-ACN-TFA-XB |

TABLE 1-continued

| Ex. No. | Structure | LCMS MH+ | Ret Time (min) | HPLC Method |
|---|---|---|---|---|
| 61 | 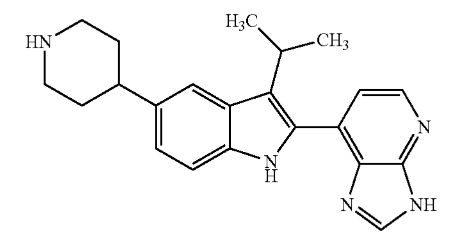 [SMILES: CC(C)c1c(-c2ccnc3[nH]cnc23)[nH]c2ccc(C3CCNCC3)cc12] | 360.4 | 0.83 | QC-ACN-AA-XB |
| 62 | 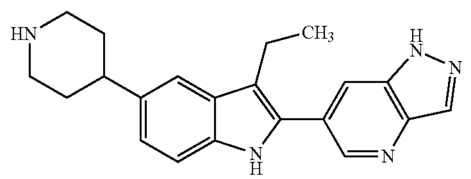 [SMILES: CCc1c(-c2cnc3cn[nH]c3c2)[nH]c2ccc(C3CCNCC3)cc12] | 346.3 | 0.82 | QC-ACN-TFA-XB |
| 63 | 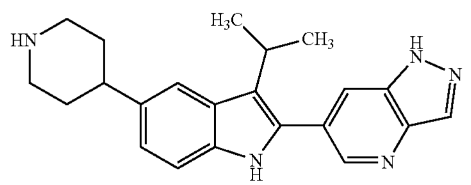 [SMILES: CC(C)c1c(-c2cnc3cn[nH]c3c2)[nH]c2ccc(C3CCNCC3)cc12] | 360.3 | 0.9 | QC-ACN-TFA-XB |
| 64 | 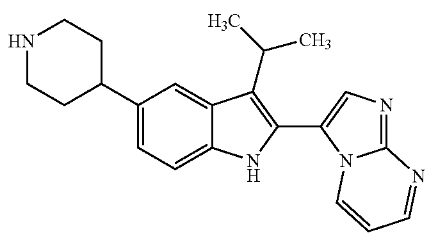 [SMILES: CC(C)c1c(-c2cnc3ncccn23)[nH]c2ccc(C3CCNCC3)cc12] | 360.1 | 0.93 | QC-ACN-AA-XB |
| 65 | 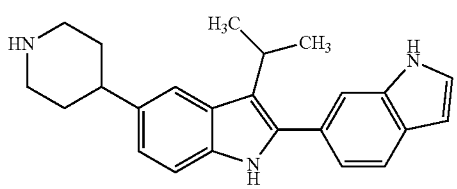 [SMILES: CC(C)c1c(-c2ccc3cc[nH]c3c2)[nH]c2ccc(C3CCNCC3)cc12] | 358.4 | 1.31 | QC-ACN-AA-XB |
| 66 | 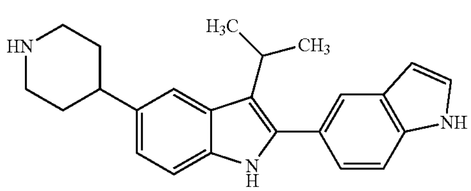 [SMILES: CC(C)c1c(-c2ccc3[nH]ccc3c2)[nH]c2ccc(C3CCNCC3)cc12] | 358.3 | 1.46 | QC-ACN-AA-XB |
| 67 | 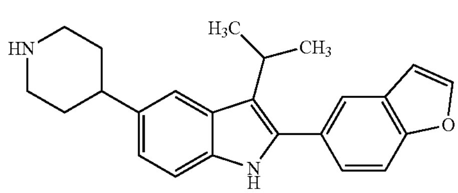 [SMILES: CC(C)c1c(-c2ccc3occc3c2)[nH]c2ccc(C3CCNCC3)cc12] | 359.1 | 1.51 | QC-ACN-TFA-XB |

TABLE 1-continued

| Ex. No. | Structure | LCMS MH+ | Ret Time (min) | HPLC Method |
|---|---|---|---|---|
| 68 | 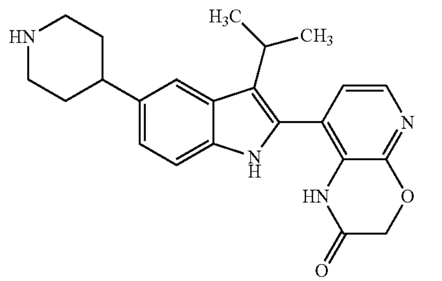 [SMILES: CC(C)c1c(-c2ccnc3c2NC(=O)CO3)[nH]c2ccc(C3CCNCC3)cc12] | 391.2 | 1.0 | QC-ACN-TFA-XB |
| 69 | 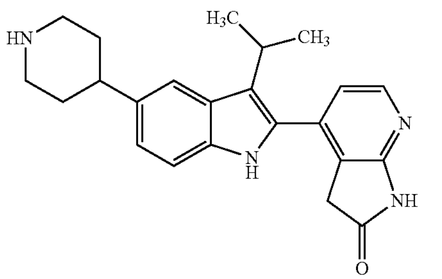 [SMILES: CC(C)c1c(-c2ccnc3c2CC(=O)N3)[nH]c2ccc(C3CCNCC3)cc12] | 375.2 | 0.93 | QC-ACN-TFA-XB |
| 70 | 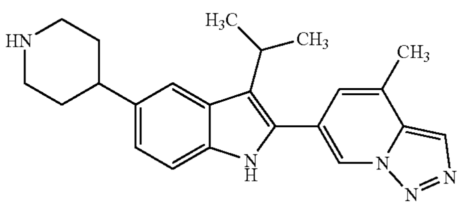 [SMILES: Cc1cc(-c2[nH]c3ccc(C4CCNCC4)cc3c2C(C)C)cn2nncc12] | 374 | 1.45 | QC-ACN-AA-XB |
| 71 | 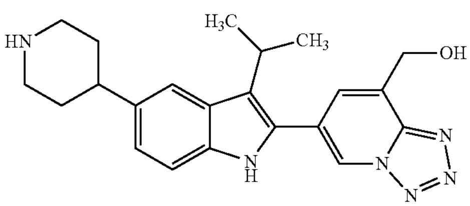 [SMILES: CC(C)c1c(-c2cc(CO)c3nnnn3c2)[nH]c2ccc(C3CCNCC3)cc12] | 391 | 1.11 | QC-ACN-AA-XB |
| 72 | 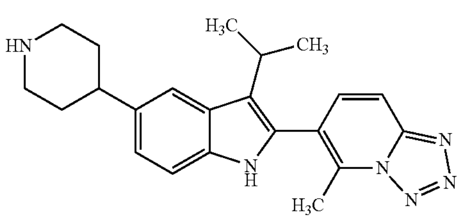 [SMILES: Cc1c(-c2[nH]c3ccc(C4CCNCC4)cc3c2C(C)C)ccc2nnnn12] | 375 | 1.44 | QC-ACN-AA-XB |
| 73 | 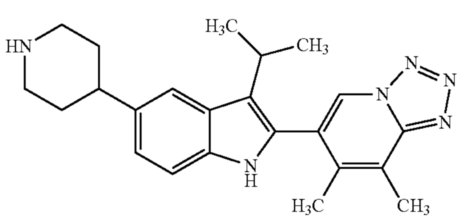 [SMILES: Cc1c(-c2[nH]c3ccc(C4CCNCC4)cc3c2C(C)C)cn2nnnc2c1C] | 389.2 | 1.33 | QC-ACN-AA-XB |

TABLE 1-continued

| Ex. No. | Structure | LCMS MH+ | Ret Time (min) | HPLC Method |
|---|---|---|---|---|
| 74 | 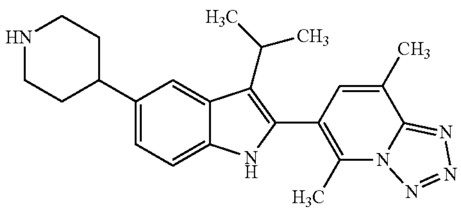 [SMILES: Cc1cc(-c2[nH]c3ccc(C4CCNCC4)cc3c2C(C)C)c(C)n2nnnc12] | 389.2 | 1.25 | QC-ACN-AA-XB |
| 75 | 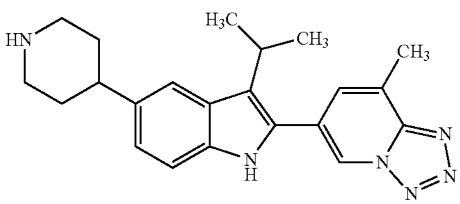 [SMILES: Cc1cc(-c2[nH]c3ccc(C4CCNCC4)cc3c2C(C)C)cn2nnnc12] | 375.2 | 1.31 | QC-ACN-AA-XB |
| 76 | 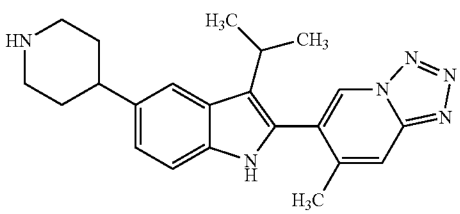 [SMILES: Cc1cc2nnnn2cc1-c1[nH]c2ccc(C3CCNCC3)cc2c1C(C)C] | 375.1 | 1.22 | QC-ACN-TFA-XB |
| 77 | 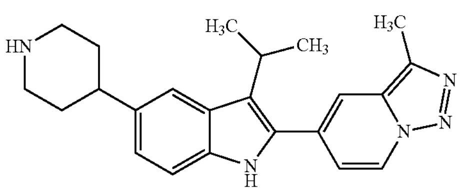 [SMILES: Cc1nnn2ccc(-c3[nH]c4ccc(C5CCNCC5)cc4c3C(C)C)cc12] | 374.2 | 1.18 | QC-ACN-AA-XB |
| 78 | 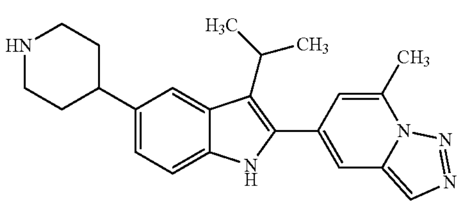 [SMILES: Cc1cc(-c2[nH]c3ccc(C4CCNCC4)cc3c2C(C)C)cc2cnnn12] | 374.3 | 1.31 | QC-ACN-AA-XB |
| 79 | 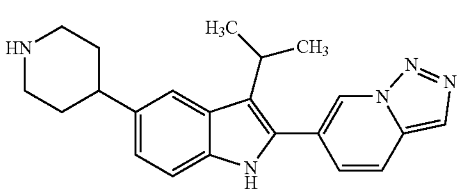 [SMILES: CC(C)c1c(-c2ccc3cnnn3c2)[nH]c2ccc(C3CCNCC3)cc12] | 360.1 | 1.14 | QC-ACN-AA-XB |
| 80 | 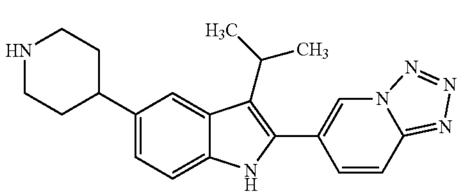 [SMILES: CC(C)c1c(-c2ccc3nnnn3c2)[nH]c2ccc(C3CCNCC3)cc12] | 361.3 | 1.12 | QC-ACN-AA-XB |

TABLE 1-continued

| Ex. No. | Structure | LCMS MH+ | Ret Time (min) | HPLC Method |
|---|---|---|---|---|
| 81 | 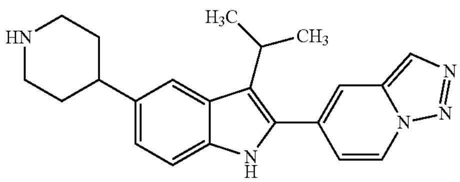 [SMILES: CC(C)c1c(-c2ccn3nncc3c2)[nH]c2ccc(C3CCNCC3)cc12] | 360.1 | 1.05 | QC-ACN-TFA-XB |
| 82 | 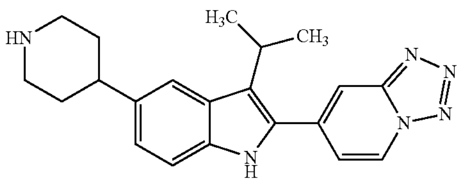 [SMILES: CC(C)c1c(-c2ccn3nnnc3c2)[nH]c2ccc(C3CCNCC3)cc12] | 361.3 | 1.1 | QC-ACN-AA-XB |
| 83 | 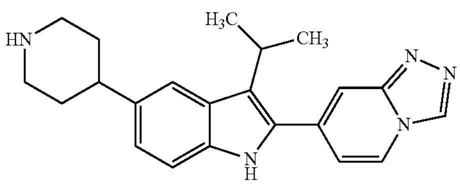 [SMILES: CC(C)c1c(-c2ccn3cnnc3c2)[nH]c2ccc(C3CCNCC3)cc12] | 360.1 | 0.89 | QC-ACN-AA-XB |

The following examples were prepared according to the general procedures for Examples 1-4.

TABLE 2

| Ex. No. | Structure | Obs. MS Ion | RT | HPLC Method |
|---|---|---|---|---|
| 84 | 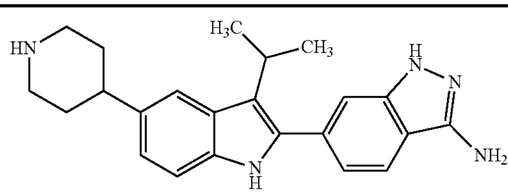 | 374.3 | 0.84 | E |
| 85 | 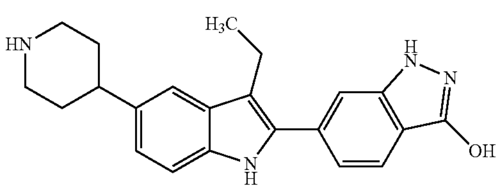 [SMILES: CCc1c(-c2ccc3c(O)n[nH]c3c2)[nH]c2ccc(C3CCNCC3)cc12] | 361.3 | 0.884 | E |
| 86 | 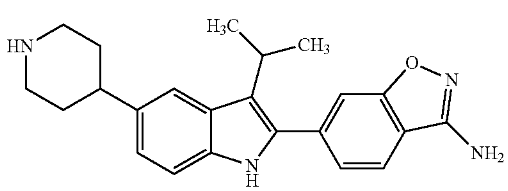 [SMILES: CC(C)c1c(-c2ccc3c(N)noc3c2)[nH]c2ccc(C3CCNCC3)cc12] | 375 | 1.08 | E |
| 87 | 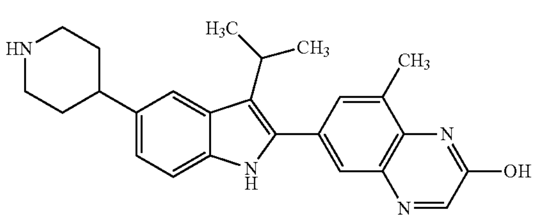 [SMILES: Cc1cc(-c2[nH]c3ccc(C4CCNCC4)cc3c2C(C)C)cc2ncc(O)nc12] | 401.1 | 1.43 | E |

TABLE 2-continued

| Ex. No. | Structure | Obs. MS Ion | RT | HPLC Method |
|---|---|---|---|---|
| 88 | 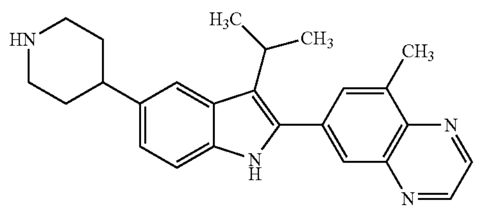 [SMILES: Cc1cc(-c2[nH]c3ccc(C4CCNCC4)cc3c2C(C)C)cc2nccnc12] | 385.1 | 1.57 | E |
| 89 | 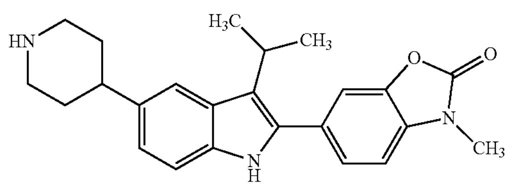 [SMILES: CC(C)c1c(-c2ccc3c(c2)oc(=O)n3C)[nH]c2ccc(C3CCNCC3)cc12] | 390 | 1.29 | E |
| 90 | 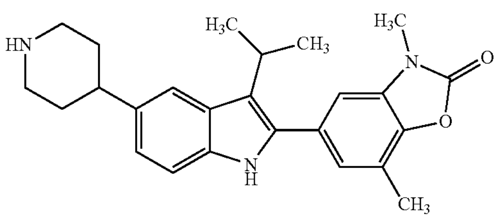 [SMILES: Cc1cc(-c2[nH]c3ccc(C4CCNCC4)cc3c2C(C)C)cc2c1oc(=O)n2C] | 404.2 | 1.571 | E |
| 91 | 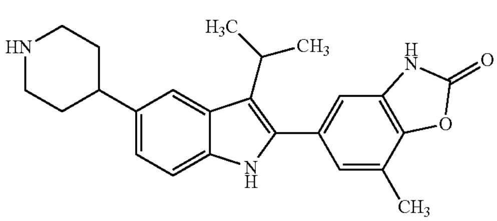 [SMILES: Cc1cc(-c2[nH]c3ccc(C4CCNCC4)cc3c2C(C)C)cc2[nH]c(=O)oc12] | 390.1 | 1.499 | E |
| 92 | 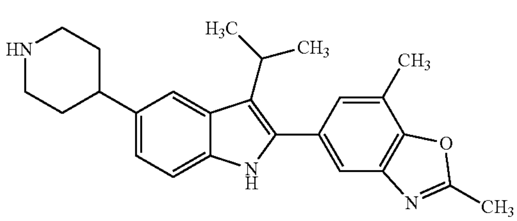 [SMILES: Cc1nc2cc(-c3[nH]c4ccc(C5CCNCC5)cc4c3C(C)C)cc(C)c2o1] | 388.2 | 1.702 | E |
| 93 | 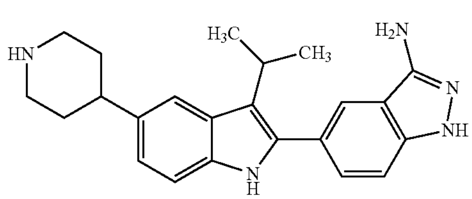 [SMILES: CC(C)c1c(-c2ccc3[nH]nc(N)c3c2)[nH]c2ccc(C3CCNCC3)cc12] | 374 | 0.92 | E |
| 94 | 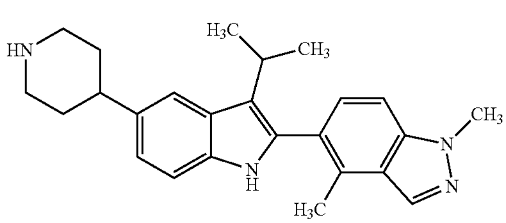 [SMILES: Cc1c(-c2[nH]c3ccc(C4CCNCC4)cc3c2C(C)C)ccc2c1cnn2C] | 387.2 | 1.61 | E |

TABLE 2-continued

| Ex. No. | Structure | Obs. MS Ion | RT | HPLC Method |
|---|---|---|---|---|
| 95 | 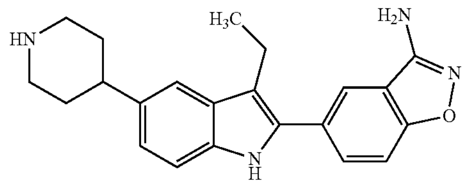 [SMILES: CCc1c(-c2ccc3onc(N)c3c2)[nH]c2ccc(C3CCNCC3)cc12] | 361.3 | 0.854 | E |
| 96 | 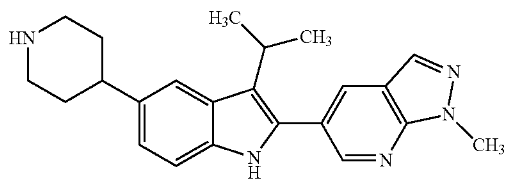 [SMILES: CC(C)c1c(-c2cnc3c(cnn3C)c2)[nH]c2ccc(C3CCNCC3)cc12] | 374.2 | 1.344 | E |
| 97 | 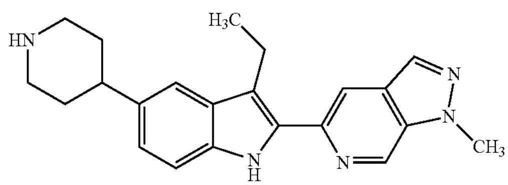 [SMILES: CCc1c(-c2cc3cnn(C)c3cn2)[nH]c2ccc(C3CCNCC3)cc12] | 360 | 1.182 | E |
| 98 | 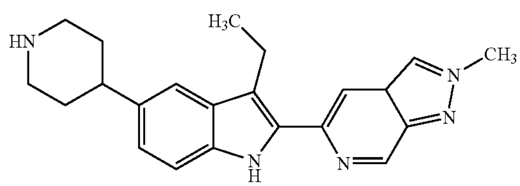 | 360 | 1.029 | E |
| 99 | 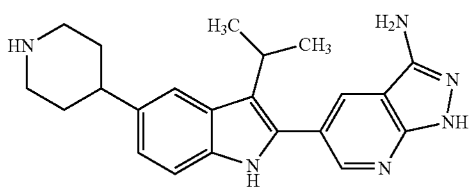 [SMILES: CC(C)c1c(-c2cnc3[nH]nc(N)c3c2)[nH]c2ccc(C3CCNCC3)cc12] | 375 | 0.84 | E |
| 100 | 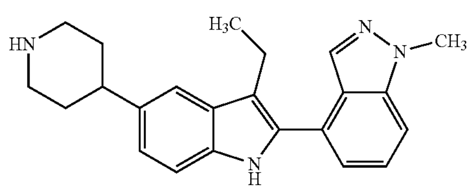 [SMILES: CCc1c(-c2cccc3c2cnn3C)[nH]c2ccc(C3CCNCC3)cc12] | 359 | 2.17 | E |
| 101 | 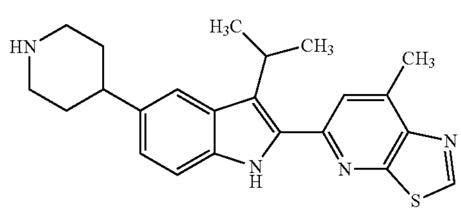 [SMILES: Cc1cc(-c2[nH]c3ccc(C4CCNCC4)cc3c2C(C)C)nc2scnc12] | 391.1 | 1.569 | E |
| 102 | 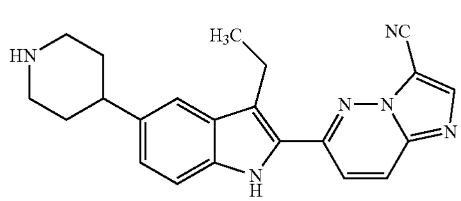 [SMILES: CCc1c(-c2ccc3ncc(C#N)n3n2)[nH]c2ccc(C3CCNCC3)cc12] | 371 | 1.002 | E |

TABLE 2-continued

| Ex. No. | Structure | Obs. MS Ion | RT | HPLC Method |
|---|---|---|---|---|
| 103 | 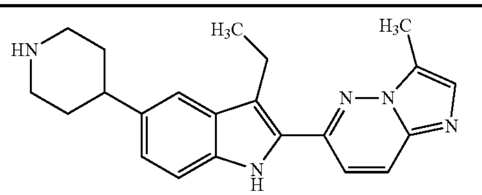 | 360 | 1 | E |
| 104 | 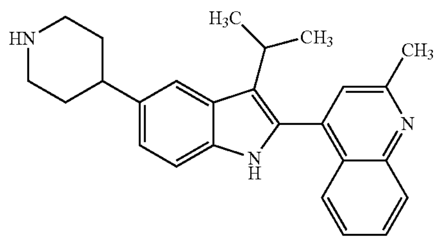 [SMILES: Cc1cc(-c2[nH]c3ccc(C4CCNCC4)cc3c2C(C)C)c2ccccc2n1] | 384.2 | 1.51 | E |
| 105 | 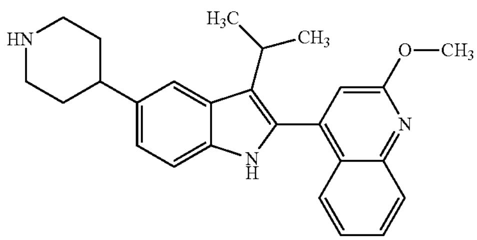 [SMILES: COc1cc(-c2[nH]c3ccc(C4CCNCC4)cc3c2C(C)C)c2ccccc2n1] | 400.2 | 1.76 | F |
| 106 | 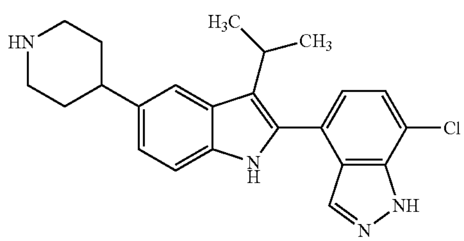 [SMILES: CC(C)c1c(-c2ccc(Cl)c3[nH]ncc23)[nH]c2ccc(C3CCNCC3)cc12] | 393 | 1.22 | E |
| 107 | 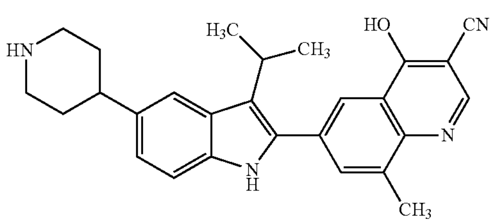 [SMILES: Cc1cc(-c2[nH]c3ccc(C4CCNCC4)cc3c2C(C)C)cc2c(O)c(C#N)cnc12] | 425.1 | 1.29 | E |
| 108 | 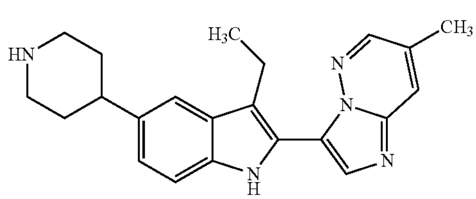 [SMILES: CCc1c(-c2cnc3cc(C)cnn23)[nH]c2ccc(C3CCNCC3)cc12] | 360 | 1.11 | E |
| 109 | 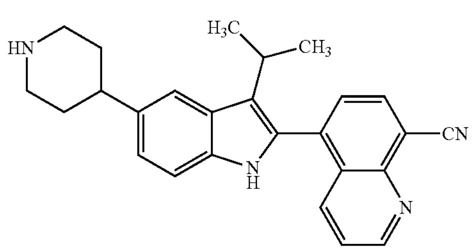 [SMILES: CC(C)c1c(-c2ccc(C#N)c3ncccc23)[nH]c2ccc(C3CCNCC3)cc12] | 395.3 | 1.262 | E |

TABLE 2-continued

| Ex. No. | Structure | Obs. MS Ion | RT | HPLC Method |
|---|---|---|---|---|
| 110 | 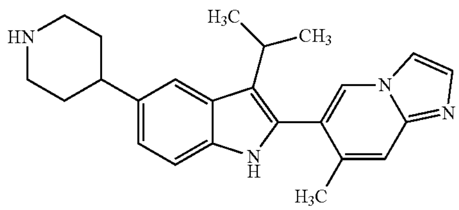 [SMILES: Cc1cc2nccn2cc1-c1[nH]c2ccc(C3CCNCC3)cc2c1C(C)C] | 373.2 | 0.81 | QC-ACN-TFA-XB |
| 111 | 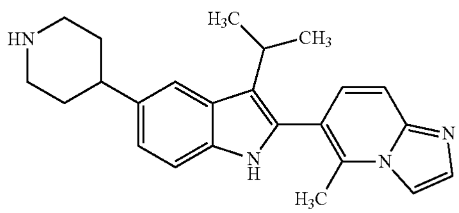 [SMILES: Cc1c(-c2[nH]c3ccc(C4CCNCC4)cc3c2C(C)C)ccc2nccn12] | 373.3 | 1 | F |
| 112 | 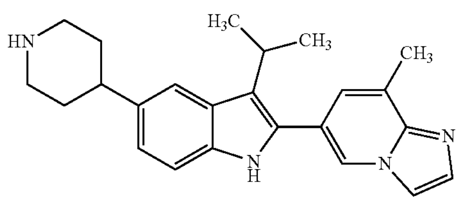 [SMILES: Cc1cc(-c2[nH]c3ccc(C4CCNCC4)cc3c2C(C)C)cn2ccnc12] | 373.3 | 1.1 | E |
| 113 | 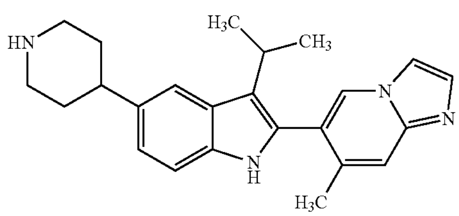 | 373.1 | 1.28 | E |
| 114 | 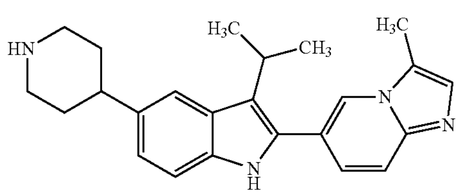 [SMILES: Cc1cnc2ccc(-c3[nH]c4ccc(C5CCNCC5)cc4c3C(C)C)cn12] | 373.3 | 1.06 | F |
| 115 | 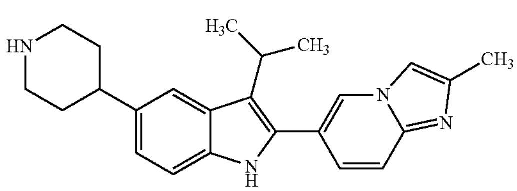 | 373.3 | 1.09 | F |
| 116 | 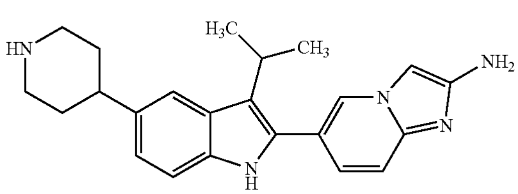 [SMILES: CC(C)c1c(-c2ccc3nc(N)cn3c2)[nH]c2ccc(C3CCNCC3)cc12] | 374 | 0.881 | E |

TABLE 2-continued

| Ex. No. | Structure | Obs. MS Ion | RT | HPLC Method |
|---|---|---|---|---|
| 117 | 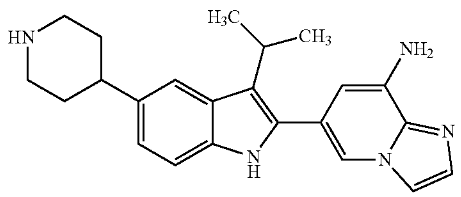 [SMILES: CC(C)c1c(-c2cc(N)c3nccn3c2)[nH]c2ccc(C3CCNCC3)cc12] | 374.2 | 1.201 | E |
| 118 | 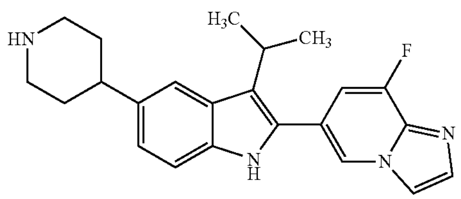 [SMILES: CC(C)c1c(-c2cc(F)c3nccn3c2)[nH]c2ccc(C3CCNCC3)cc12] | 377.2 | 1.47 | E |
| 119 | 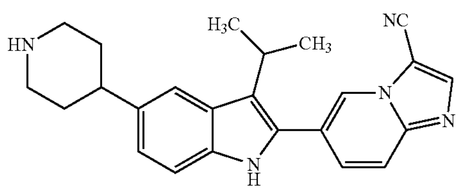 [SMILES: CC(C)c1c(-c2ccc3ncc(C#N)n3c2)[nH]c2ccc(C3CCNCC3)cc12] | 384.2 | 1.3 | E |
| 120 | 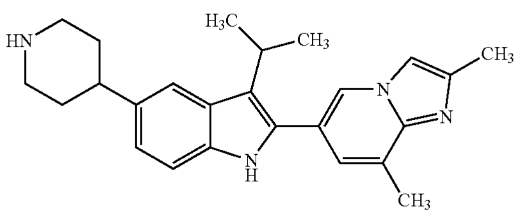 [SMILES: Cc1cn2cc(-c3[nH]c4ccc(C5CCNCC5)cc4c3C(C)C)cc(C)c2n1] | 387.3 | 1.17 | F |
| 121 | 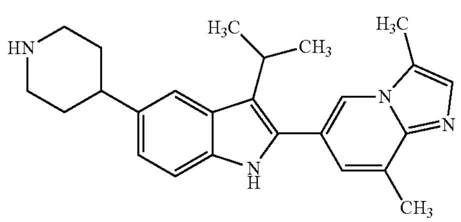 [SMILES: Cc1cc(-c2[nH]c3ccc(C4CCNCC4)cc3c2C(C)C)cn2c(C)cnc12] | 387.2 | 1.41 | E |
| 122 | 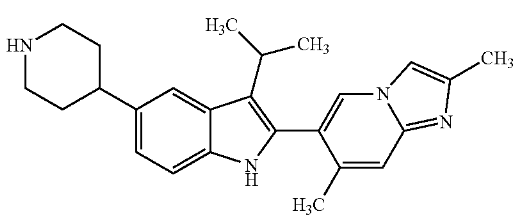 [SMILES: Cc1cn2cc(-c3[nH]c4ccc(C5CCNCC5)cc4c3C(C)C)c(C)cc2n1] | 387.3 | 1.09 | F |
| 123 | 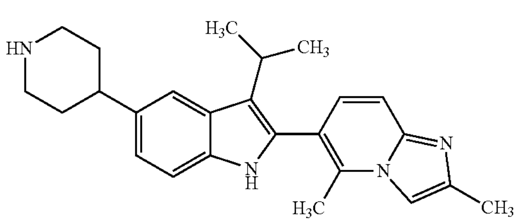 | 387.2 | 1.06 | F |

TABLE 2-continued

| Ex. No. | Structure | Obs. MS Ion | HPLC RT | Method |
|---|---|---|---|---|
| 124 | 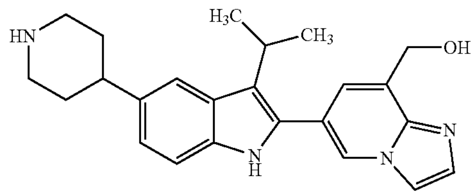 [SMILES: CC(C)c1c(-c2cc(CO)c3nccn3c2)[nH]c2ccc(C3CCNCC3)cc12] | 389.2 | 1.09 | E |
| 125 | 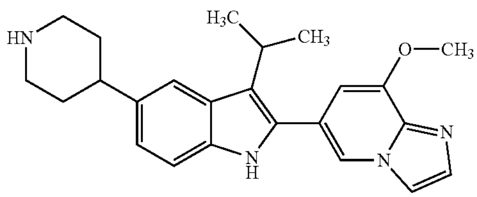 [SMILES: COc1cc(-c2[nH]c3ccc(C4CCNCC4)cc3c2C(C)C)cn2ccnc12] | 389 | 1.08 | E |
| 126 | 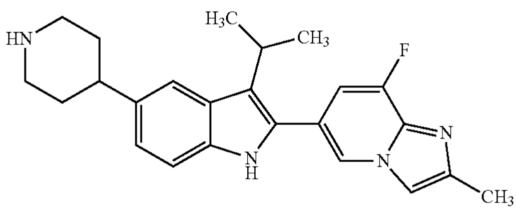 | 391.2 | 1.4 | E |
| 127 | 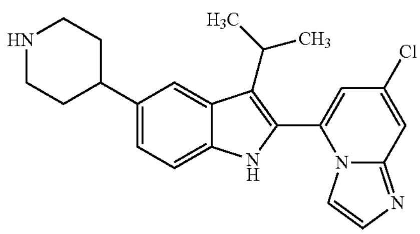 [SMILES: CC(C)c1c(-c2cc(Cl)cc3nccn23)[nH]c2ccc(C3CCNCC3)cc12] | 393 | 1.44 | E |
| 128 | 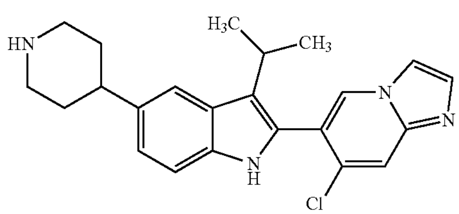 [SMILES: CC(C)c1c(-c2cn3ccnc3cc2Cl)[nH]c2ccc(C3CCNCC3)cc12] | 393 | 1.32 | E |
| 129 | 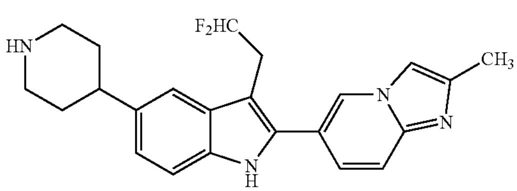 [SMILES: Cc1cn2cc(-c3[nH]c4ccc(C5CCNCC5)cc4c3CC(F)F)ccc2n1] | 395.2 | 1.007 | E |
| 130 | 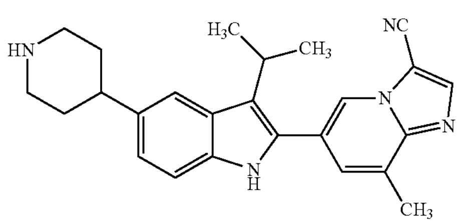 [SMILES: Cc1cc(-c2[nH]c3ccc(C4CCNCC4)cc3c2C(C)C)cn2c(C#N)cnc12] | 398 | 1.46 | E |

TABLE 2-continued
| Ex. No. | Structure | Obs. MS Ion | HPLC RT | Method |
|---|---|---|---|---|
| 131 | 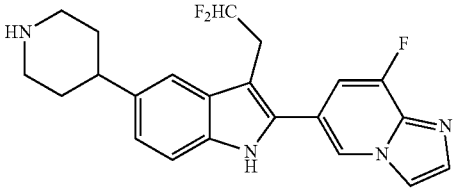 [SMILES: Fc1cc(-c2[nH]c3ccc(C4CCNCC4)cc3c2CC(F)F)cn2ccnc12] | 399.1 | 1.08 | E |
| 132 | 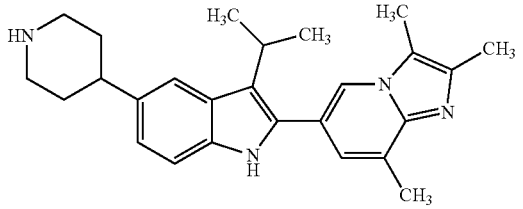 [SMILES: Cc1nc2c(C)cc(-c3[nH]c4ccc(C5CCNCC5)cc4c3C(C)C)cn2c1C] | 401.1 | 1.45 | E |
| 133 | 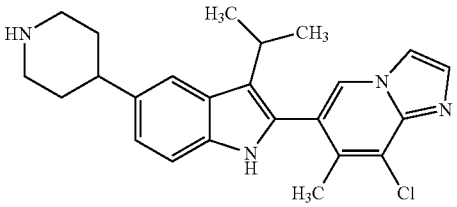 [SMILES: Cc1c(-c2[nH]c3ccc(C4CCNCC4)cc3c2C(C)C)cn2ccnc2c1Cl] | 407.2 | 1.388 | E |
| 134 | 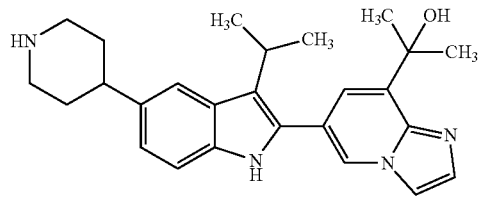 [SMILES: CC(C)c1c(-c2cc(C(C)(C)O)c3nccn3c2)[nH]c2ccc(C3CCNCC3)cc12] | 417.2 | 1.385 | E |
TABLE 3
| Ex. No. | Structure | Obs. MS Ion | HPLC RT | Method |
|---|---|---|---|---|
| 135 | 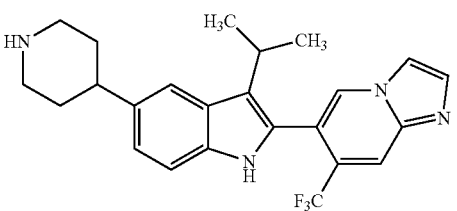 | 427.1 | 1.44 | E |
| 136 | 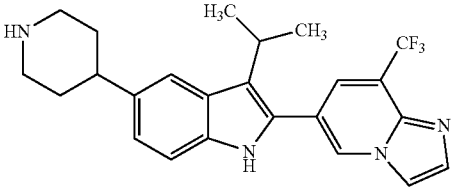 [SMILES: CC(C)c1c(-c2cc(C(F)(F)F)c3nccn3c2)[nH]c2ccc(C3CCNCC3)cc12] | 427 | 1.375 | E |

TABLE 3-continued

| Ex. No. | Structure | Obs. MS Ion | RT | HPLC Method |
|---|---|---|---|---|
| 137 | 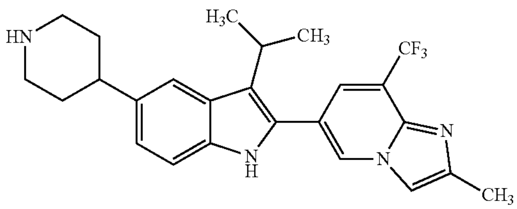 [SMILES: Cc1cn2cc(-c3[nH]c4ccc(C5CCNCC5)cc4c3C(C)C)cc(C(F)(F)F)c2n1] | 441 | 1.5 | E |
| 138 | 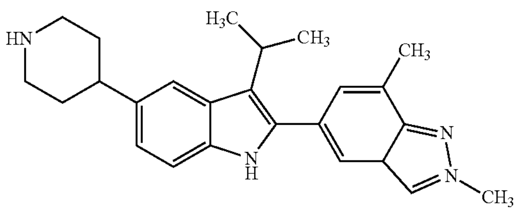 | 387.2 | 1.5 | E |
| 139 | 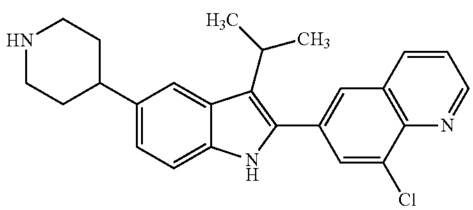 [SMILES: CC(C)c1c(-c2cc(Cl)c3ncccc3c2)[nH]c2ccc(C3CCNCC3)cc12] | 404 | 1.5 | E |
| 140 | 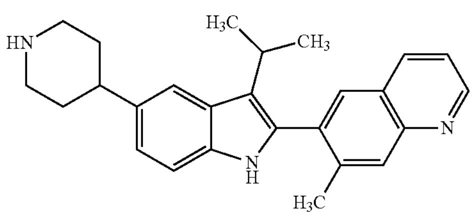 [SMILES: Cc1cc2ncccc2cc1-c1[nH]c2ccc(C3CCNCC3)cc2c1C(C)C] | 384.1 | 1.53 | E |
| 141 | 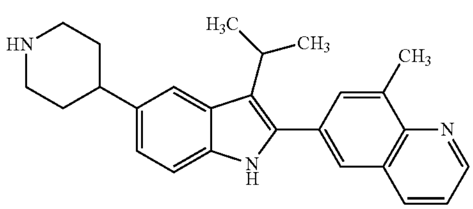 [SMILES: Cc1cc(-c2[nH]c3ccc(C4CCNCC4)cc3c2C(C)C)cc2cccnc12] | 384 | 1.47 | E |
| 142 | 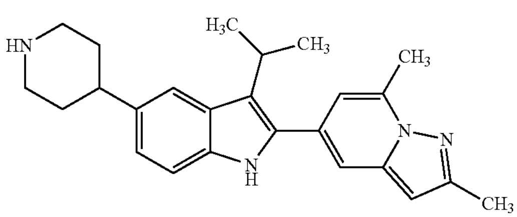 [SMILES: Cc1cc2cc(-c3[nH]c4ccc(C5CCNCC5)cc4c3C(C)C)cc(C)n2n1] | 387.3 | 1.697 | E |
| 143 | 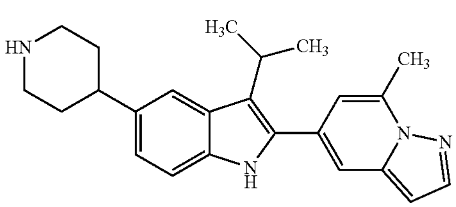 [SMILES: Cc1cc(-c2[nH]c3ccc(C4CCNCC4)cc3c2C(C)C)cc2ccnn12] | 373 | 1.328 | E |

TABLE 3-continued
| Ex. No. | Structure | Obs. MS Ion | HPLC RT | Method |
|---|---|---|---|---|
| 144 | 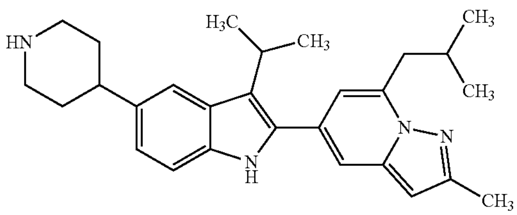 [SMILES: Cc1cc2cc(-c3[nH]c4ccc(C5CCNCC5)cc4c3C(C)C)cc(CC(C)C)n2n1] | 430.2 | 1.99 | E |
| 145 | 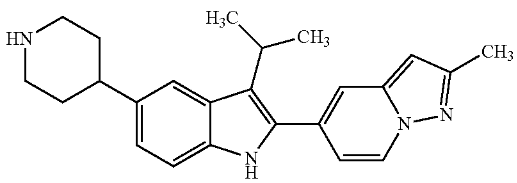 [SMILES: Cc1cc2cc(-c3[nH]c4ccc(C5CCNCC5)cc4c3C(C)C)ccn2n1] | 373.2 | 1.612 | E |
| 146 | 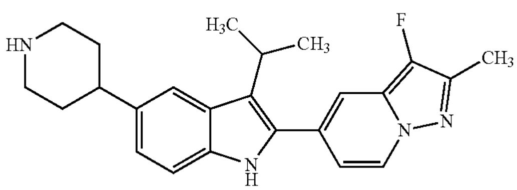 [SMILES: Cc1nn2ccc(-c3[nH]c4ccc(C5CCNCC5)cc4c3C(C)C)cc2c1F] | 391.2 | 1.62 | E |
| 147 | 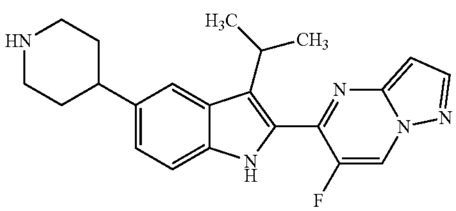 [SMILES: CC(C)c1c(-c2nc3ccnn3cc2F)[nH]c2ccc(C3CCNCC3)cc12] | 378 | 1.31 | E |
| 148 | 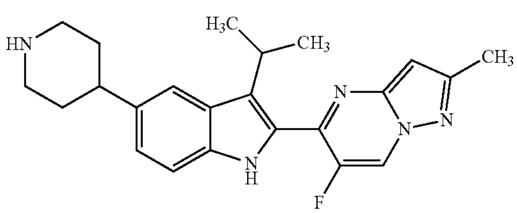 [SMILES: Cc1cc2nc(-c3[nH]c4ccc(C5CCNCC5)cc4c3C(C)C)c(F)cn2n1] | 392.2 | 1.53 | E |
| 149 | 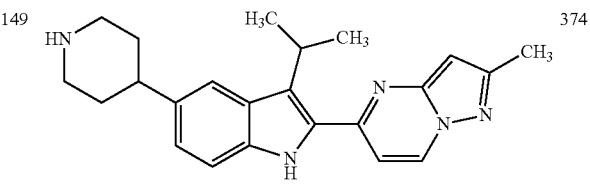 | 374 | 1.4 | E |
| 150 | 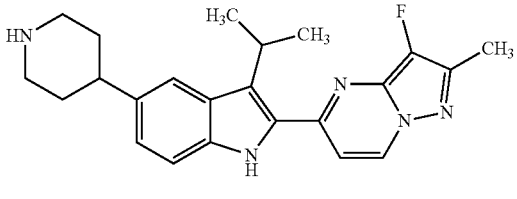 [SMILES: Cc1nn2ccc(-c3[nH]c4ccc(C5CCNCC5)cc4c3C(C)C)nc2c1F] | 392.2 | 1.47 | E |

TABLE 3-continued

| Ex. No. | Structure | Obs. MS Ion | HPLC RT | Method |
|---|---|---|---|---|
| 151 | 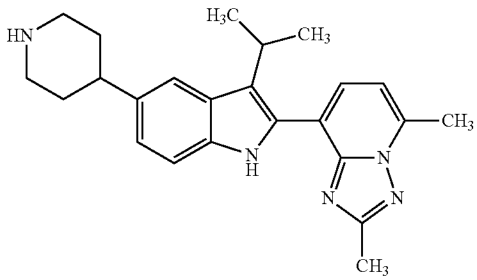 [SMILES: Cc1nc2c(-c3[nH]c4ccc(C5CCNCC5)cc4c3C(C)C)ccc(C)n2n1] | 388.3 | 1.328 | E |
| 152 | 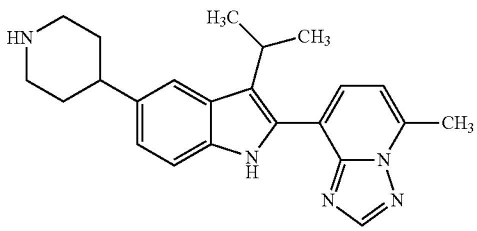 [SMILES: Cc1ccc(-c2[nH]c3ccc(C4CCNCC4)cc3c2C(C)C)c2ncnn12] | 374.3 | 1.14 | E |
| 153 | 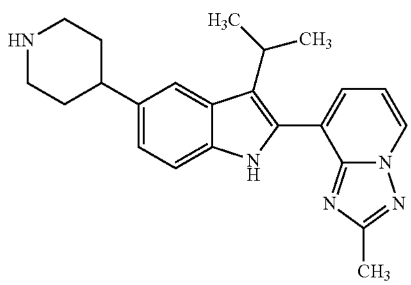 [SMILES: Cc1nc2c(-c3[nH]c4ccc(C5CCNCC5)cc4c3C(C)C)cccn2n1] | 374.2 | 1.609 | E |
| 154 | 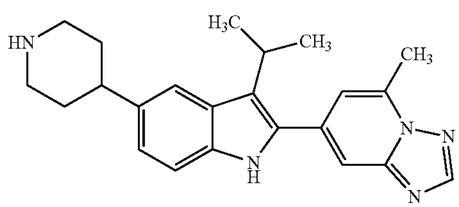 [SMILES: Cc1cc(-c2[nH]c3ccc(C4CCNCC4)cc3c2C(C)C)cc2ncnn12] | 374.2 | 1.306 | E |
| 155 | 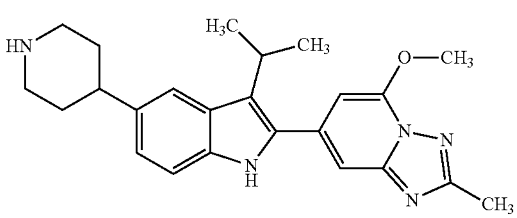 [SMILES: COc1cc(-c2[nH]c3ccc(C4CCNCC4)cc3c2C(C)C)cc2nc(C)nn12] | 404.3 | 0.993 | E |
| 156 | 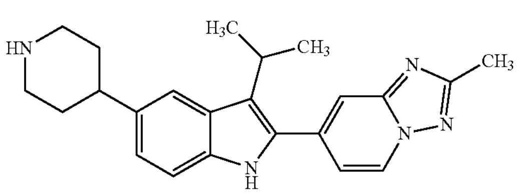 [SMILES: Cc1nc2cc(-c3[nH]c4ccc(C5CCNCC5)cc4c3C(C)C)ccn2n1] | 374 | 1.272 | E |

TABLE 3-continued

| Ex. No. | Structure | Obs. MS Ion | RT | HPLC Method |
|---|---|---|---|---|
| 157 | 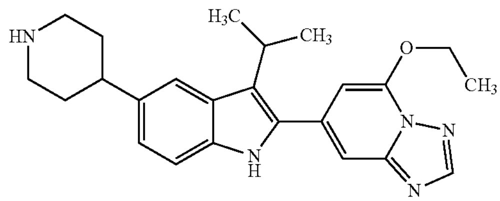 [SMILES: CCOc1cc(-c2[nH]c3ccc(C4CCNCC4)cc3c2C(C)C)cc2ncnn12] | 404.2 | 1.322 | E |
| 158 | 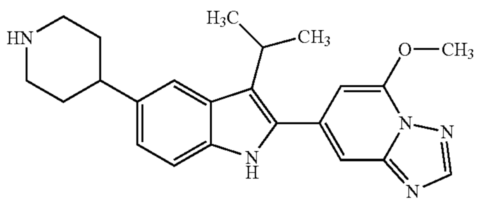 [SMILES: COc1cc(-c2[nH]c3ccc(C4CCNCC4)cc3c2C(C)C)cc2ncnn12] | 390.3 | 0.955 | E |
| 159 | 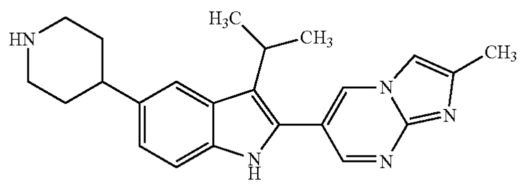 [SMILES: Cc1cn2cc(-c3[nH]c4ccc(C5CCNCC5)cc4c3C(C)C)cnc2n1] | 374.3 | 1.07 | E |
| 160 | 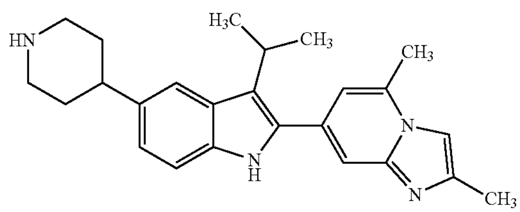 [SMILES: Cc1cn2c(C)cc(-c3[nH]c4ccc(C5CCNCC5)cc4c3C(C)C)cc2n1] | 387.1 | 1.428 | E |
| 161 | 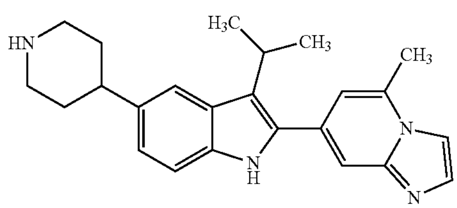 [SMILES: Cc1cc(-c2[nH]c3ccc(C4CCNCC4)cc3c2C(C)C)cc2nccn12] | 373 | 1.316 | E |
| 162 | 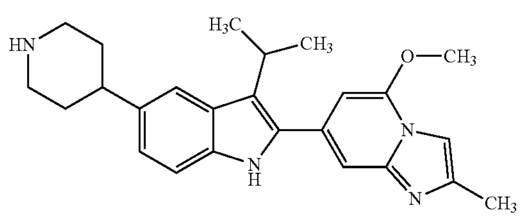 | 403.2 | 1.514 | E |
| 163 | 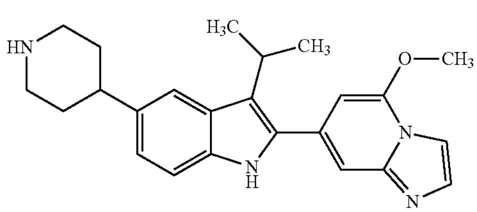 [SMILES: COc1cc(-c2[nH]c3ccc(C4CCNCC4)cc3c2C(C)C)cc2nccn12] | 389.1 | 1.381 | E |

TABLE 3-continued
| Ex. No. | Structure | Obs. MS Ion | RT | HPLC Method |
|---|---|---|---|---|
| 164 | 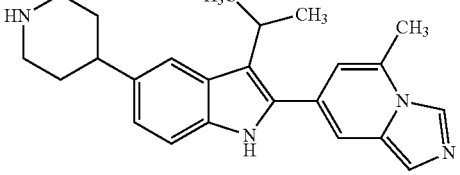 | 373.2 | 1.37 | E |
| 165 | 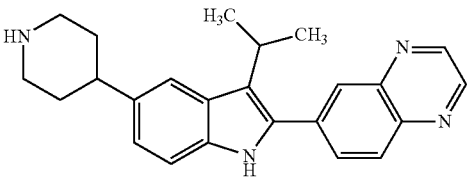 [SMILES: CC(C)c1c(-c2ccc3nccnc3c2)[nH]c2ccc(C3CCNCC3)cc12] | 371 | 1.35 | E |
| 166 | 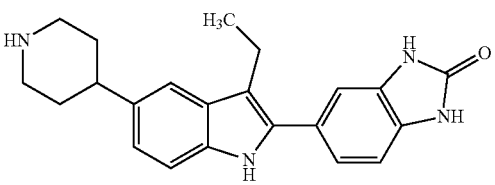 | 361.3 | 0.914 | F |
| 167 | 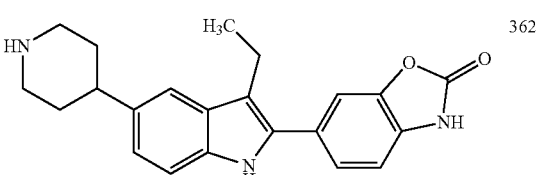 | 362 | 1.1 | E |
| 168 | 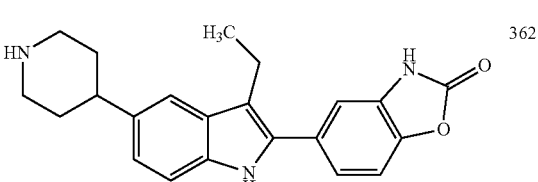 | 362 | 1.16 | F |
| 169 | 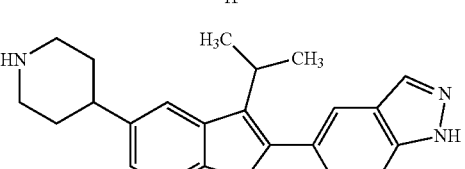 | 359 | 1.17 | E |
| 170 | 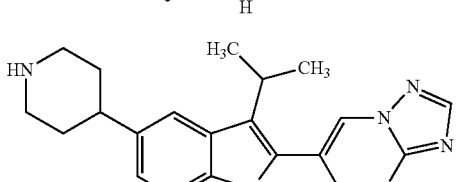 | 361.2 | 1.18 | F |
| 171 | 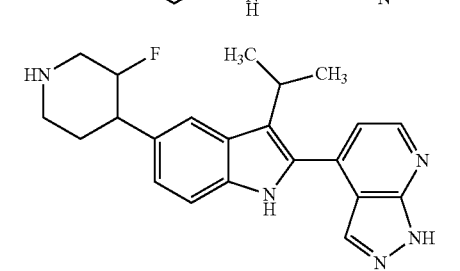 | 378 | 1.39 | E |

TABLE 3-continued

| Ex. No. | Structure | Obs. MS Ion | RT | HPLC Method |
|---|---|---|---|---|
| 172 | 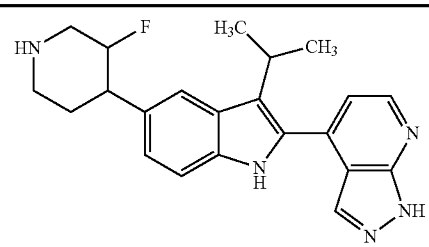 | 378.1 | 1.2 | E |
| 173 | 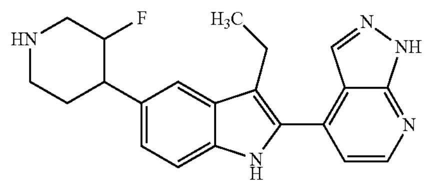 [SMILES: CCc1c(-c2ccnc3[nH]ncc23)[nH]c2ccc(C3CCNCC3F)cc12] | 364 | 0.97 | E |
| 174 | 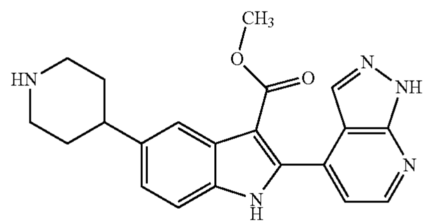 [SMILES: COC(=O)c1c(-c2ccnc3[nH]ncc23)[nH]c2ccc(C3CCNCC3)cc12] | 376 | 0.86 | E |
| 175 | 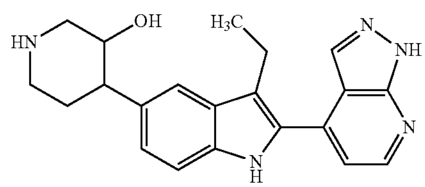 [SMILES: CCc1c(-c2ccnc3[nH]ncc23)[nH]c2ccc(C3CCNCC3O)cc12] | 362 | 1.1 | F |
| 176 | 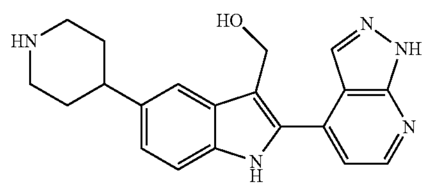 [SMILES: OCc1c(-c2ccnc3[nH]ncc23)[nH]c2ccc(C3CCNCC3)cc12] | 346 | 3.86 | H |
| 177 | 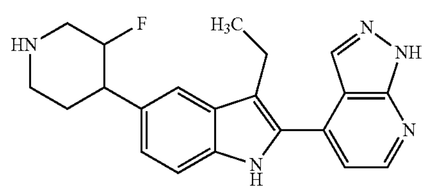 [SMILES: CCc1c(-c2ccnc3[nH]ncc23)[nH]c2ccc(C3CCNCC3F)cc12] | 364 | 1.1 | E |
| 178 | 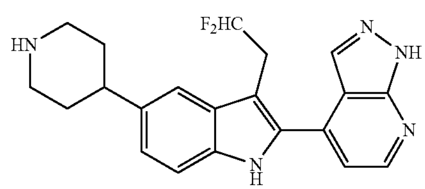 [SMILES: FC(F)Cc1c(-c2ccnc3[nH]ncc23)[nH]c2ccc(C3CCNCC3)cc12] | 382.3 | 0.9 | E |
| 179 | 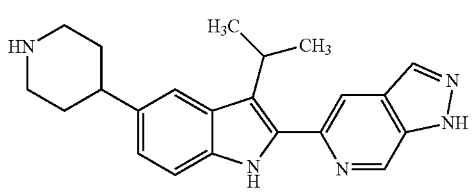 [SMILES: CC(C)c1c(-c2cc3cn[nH]c3cn2)[nH]c2ccc(C3CCNCC3)cc12] | 360 | 0.89 | E |

TABLE 3-continued

| Ex. No. | Structure | Obs. MS Ion | RT | HPLC Method |
|---|---|---|---|---|
| 180 | 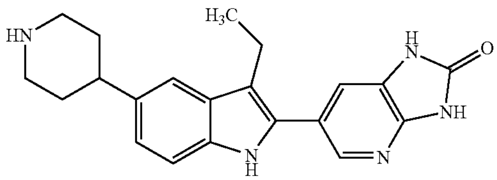 [SMILES: CCc1c(-c2cnc3[nH]c(=O)[nH]c3c2)[nH]c2ccc(C3CCNCC3)cc12] | 362.3 | 0.853 | F |
| 181 | 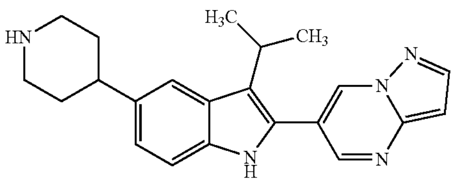 [SMILES: CC(C)c1c(-c2cnc3ccnn3c2)[nH]c2ccc(C3CCNCC3)cc12] | 360 | 1.281 | E |
| 182 | 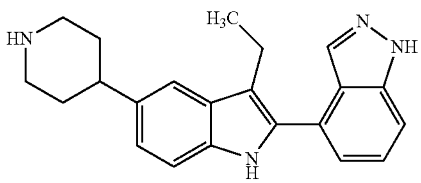 [SMILES: CCc1c(-c2cccc3[nH]ncc23)[nH]c2ccc(C3CCNCC3)cc12] | 345 | 1.2 | E |
| 183 | 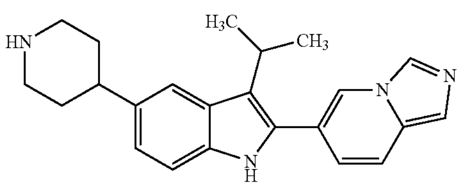 [SMILES: CC(C)c1c(-c2ccc3cncn3c2)[nH]c2ccc(C3CCNCC3)cc12] | 359.2 | 1.37 | E |
| 184 | 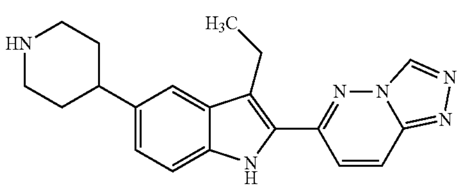 [SMILES: CCc1c(-c2ccc3nncn3n2)[nH]c2ccc(C3CCNCC3)cc12] | 347 | 0.708 | F |

TABLE 4

| Ex. No. | Structure | Obs. MS Ion | RT | HPLC Method |
|---|---|---|---|---|
| 185 | 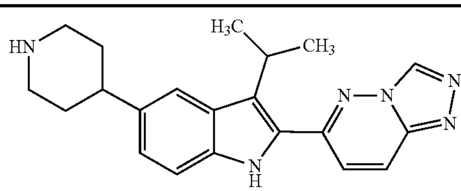 | 361 | 0.87 | E |
| 186 | 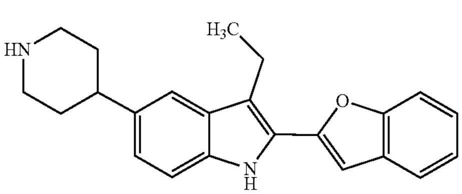 [SMILES: CCc1c(-c2cc3ccccc3o2)[nH]c2ccc(C3CCNCC3)cc12] | 345.3 | 1.69 | E |

TABLE 4-continued
| Ex. No. | Structure | Obs. MS Ion | RT | HPLC Method |
|---|---|---|---|---|
| 187 | 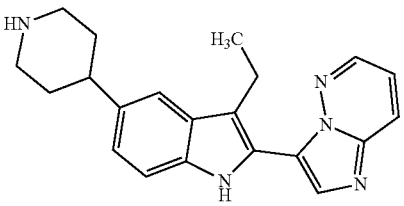 [SMILES: CCc1c(-c2cnc3cccnn23)[nH]c2ccc(C3CCNCC3)cc12] | 346.3 | 1.01 | E |
| 188 | 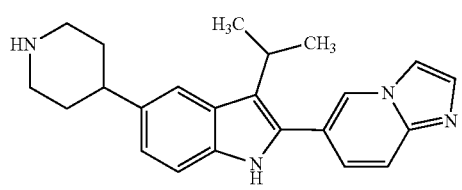 [SMILES: CC(C)c1c(-c2ccc3nccn3c2)[nH]c2ccc(C3CCNCC3)cc12] | 359.3 | 1.14 | E |
| 189 | 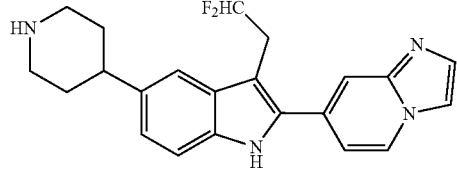 | 381.2 | 1.14 | E |
| 190 | 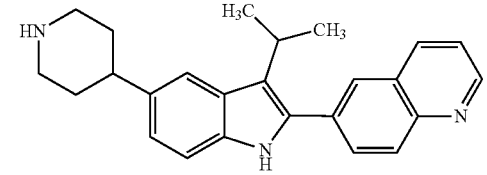 [SMILES: CC(C)c1c(-c2ccc3ncccc3c2)[nH]c2ccc(C3CCNCC3)cc12] | 370 | 1.4 | E |
| 191 | 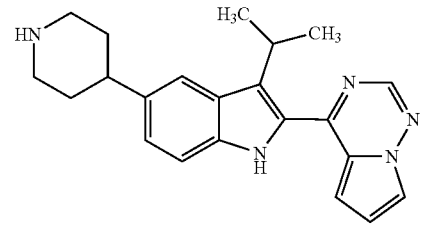 [SMILES: CC(C)c1c(-c2ncnn3cccc23)[nH]c2ccc(C3CCNCC3)cc12] | 360 | 1.5 | E |
| 192 | 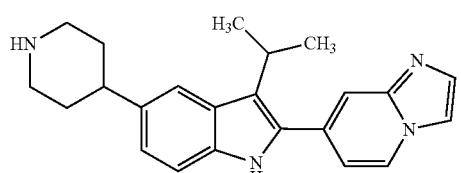 | 359.2 | 1.49 | E |
| 193 | 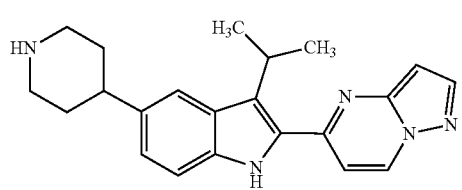 [SMILES: CC(C)c1c(-c2ccn3nccc3n2)[nH]c2ccc(C3CCNCC3)cc12] | 360 | 1.15 | E |

TABLE 4-continued

| Ex. No. | Structure | Obs. MS Ion | RT | HPLC Method |
|---|---|---|---|---|
| 194 | 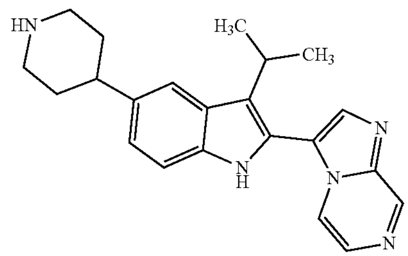 [SMILES: CC(C)c1c(-c2cnc3cnccn23)[nH]c2ccc(C3CCNCC3)cc12] | 360 | 1.12 | E |
| 195 | 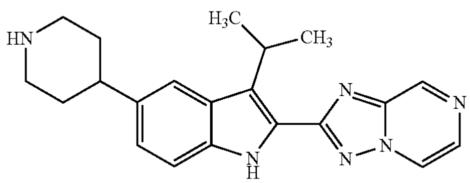 [SMILES: CC(C)c1c(-c2nc3cnccn3n2)[nH]c2ccc(C3CCNCC3)cc12] | 361.2 | 1.27 | E |
| 196 | 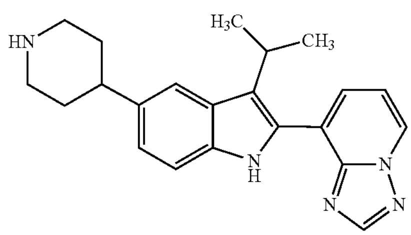 [SMILES: CC(C)c1c(-c2cccn3ncnc23)[nH]c2ccc(C3CCNCC3)cc12] | 360.2 | 1.221 | E |
| 197 | 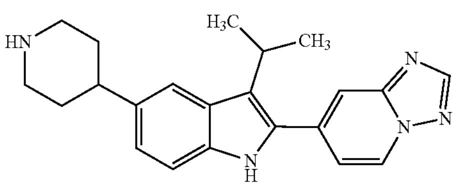 | 360 | 1.05 | E |
| 198 | 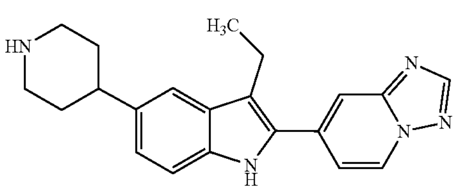 [SMILES: CCc1c(-c2ccn3ncnc3c2)[nH]c2ccc(C3CCNCC3)cc12] | 346.3 | 0.86 | E |
| 199 | 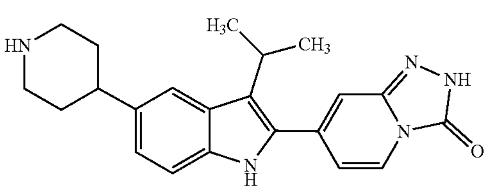 [SMILES: CC(C)c1c(-c2ccn3c(=O)[nH]nc3c2)[nH]c2ccc(C3CCNCC3)cc12] | 376 | 0.96 | E |
| 200 | 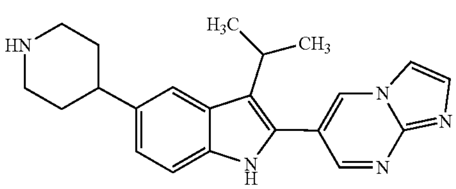 | 360.2 | 0.936 | E |

TABLE 4-continued

| Ex. No. | Structure | Obs. MS Ion | RT | HPLC Method |
|---|---|---|---|---|
| 201 | 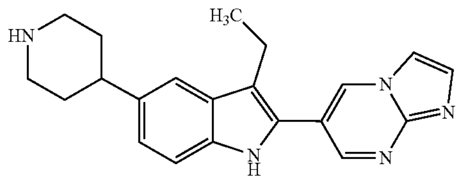 [SMILES: CCc1c(-c2cnc3nccn3c2)[nH]c2ccc(C3CCNCC3)cc12] | 346 | 1.38 | E |
| 202 | 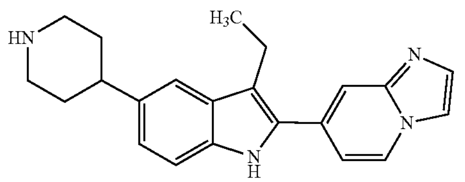 | 345 | 1.059 | E |
| 203 | 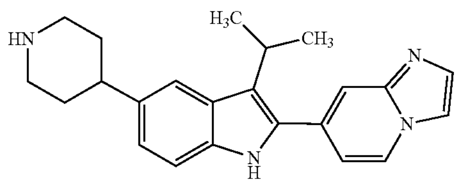 [SMILES: CC(C)c1c(-c2ccn3ccnc3c2)[nH]c2ccc(C3CCNCC3)cc12] | 359 | 1.15 | E |
| 204 | 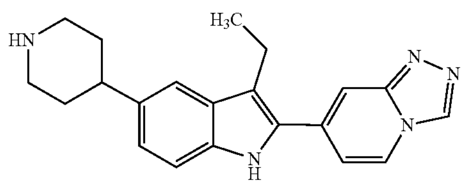 [SMILES: CCc1c(-c2ccn3cnnc3c2)[nH]c2ccc(C3CCNCC3)cc12] | 346 | 0.7 | E |
| 205 | 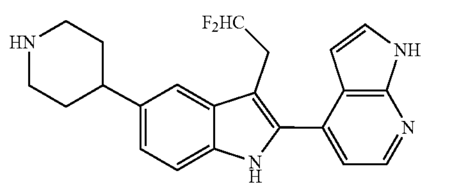 | 381 | 0.91 | E |
| 206 | 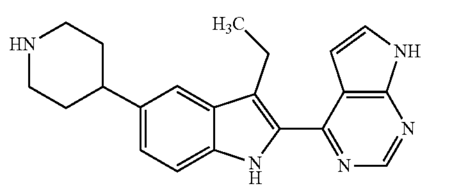 | 346.3 | 0.94 | E |
| 207 | 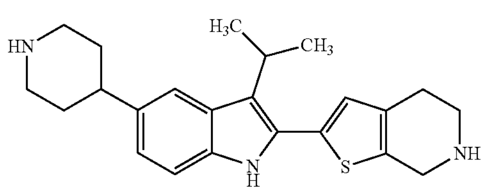 [SMILES: CC(C)c1c(-c2cc3c(s2)CNCC3)[nH]c2ccc(C3CCNCC3)cc12] | 380.2 | 1.16 | E |
| 208 | 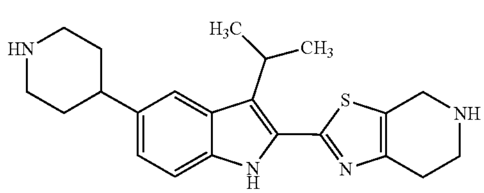 [SMILES: CC(C)c1c(-c2nc3c(s2)CNCC3)[nH]c2ccc(C3CCNCC3)cc12] | 381.2 | 1.13 | E |

TABLE 4-continued

| Ex. No. | Structure | Obs. MS Ion | RT | HPLC Method |
|---|---|---|---|---|
| 209 | 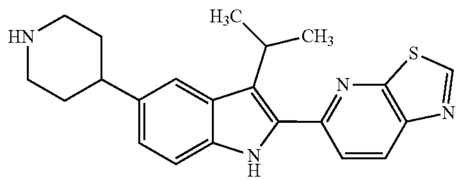 [SMILES: CC(C)c1c(-c2ccc3ncsc3n2)[nH]c2ccc(C3CCNCC3)cc12] | 377.1 | 1.443 | E |

Example 210

N-methyl-4-(3-methyl-5-(piperidin-4-yl)-1H-indol-2-yl)-1H-pyrrolo[2,3-b]pyridin-3-amine

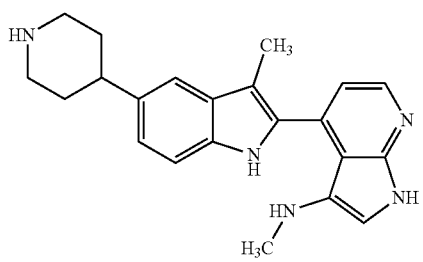

(210)

To a 2-dram vial were added tert-butyl 4-(3-methyl-2-(1H-pyrrolo[2,3-b]pyridin-4-yl)-1H-indol-5-yl)piperidine-1-carboxylate (0.025 g, 0.058 mmol), acetonitrile (1 mL) and Selectfluor (0.021 g, 0.058 mmol) in 0.5 mL of acetonitrile. The reaction mixture was stirred for 15 minutes at room temperature. The brown solution was treated with 2.0 M methylamine in THF (170 mg, 0.58 mmol) and heated at 60° C. for 1 hour. The reaction mixture was concentrated under a stream of nitrogen and to this residue were added DCM (0.5 mL) and 4 M HCl/dioxane (1.0 mL). The reaction mixture was capped and stirred for 30 minutes at room temperature, then concentrated under a stream of nitrogen. The residue was dissolved in DMF/MeOH (2.0 mL of a 1:1 solution) and filtered. The crude material was purified via preparative LC/MS. Fractions containing the desired product were combined and dried via centrifugal evaporation to afford N-methyl-4-(3-methyl-5-(piperidin-4-yl)-1H-indol-2-yl)-1H-pyrrolo[2,3-b]pyridin-3-amine (1.3 mg, 0.0034 mmol, 6.0% yield). MS ($M^{+1}$) m/z: 360.3 ($MH^+$). LC retention time 0.83 min [C1]. $^1$H NMR (500 MHz, DMSO-$d_6$) δ 12.12-11.90 (m, 1H), 7.34-7.21 (m, 2H), 7.16 (s, 2H), 7.05 (s, 2H), 3.47 (br d, J=18.4 Hz, 2H), 3.14-2.94 (m, 3H), 2.89 (s, 1H), 2.73 (s, 2H), 2.55 (s, 3H), 2.09-1.91 (m, 4H), 1.89-1.75 (m, 3H).

The following examples were prepared according to the general procedures for Examples 210.

TABLE 5

| Ex. No. | Structure | Obs. MS Ion | RT | HPLC Method |
|---|---|---|---|---|
| 211 | 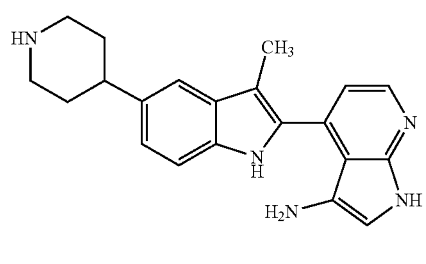 [SMILES: Cc1c(-c2ccnc3[nH]cc(N)c23)[nH]c2ccc(C3CCNCC3)cc12] | 346.2 | 0.67 | QC-ACN-AA-XB |
| 212 | 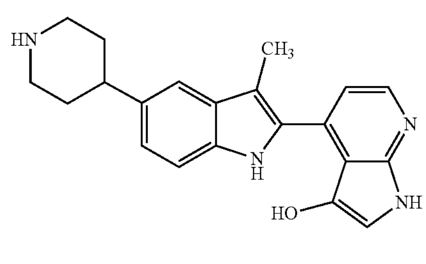 [SMILES: Cc1c(-c2ccnc3[nH]cc(O)c23)[nH]c2ccc(C3CCNCC3)cc12] | 347.3 | 0.68 | QC-ACN-TFA-XB |

TABLE 5-continued

| Ex. No. | Structure | Obs. MS Ion | RT | HPLC Method |
|---|---|---|---|---|
| 213 | 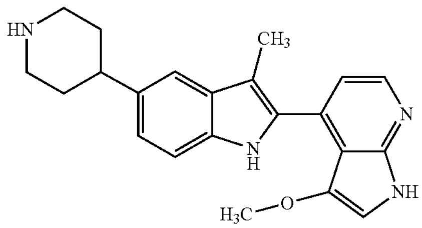 [SMILES: COc1c[nH]c2nccc(-c3[nH]c4ccc(C5CCNCC5)cc4c3C)c12] | 361.4 | 0.8 | QC-ACN-TFA-XB |
| 214 | 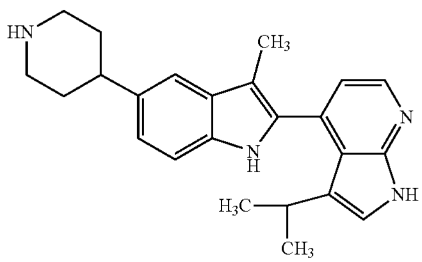 [SMILES: Cc1c(-c2ccnc3[nH]cc(C(C)C)c23)[nH]c2ccc(C3CCNCC3)cc12] | 373.1 | 0.79 | QC-ACN-TFA-XB |
| 215 | 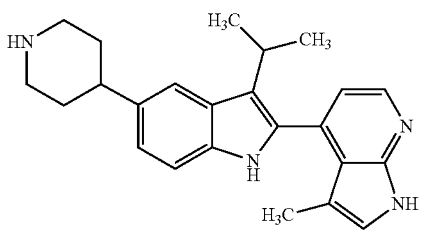 [SMILES: Cc1c[nH]c2nccc(-c3[nH]c4ccc(C5CCNCC5)cc4c3C(C)C)c12] | 373.1 | 1.2 | QC-ACN-AA-XB |
| 216 | 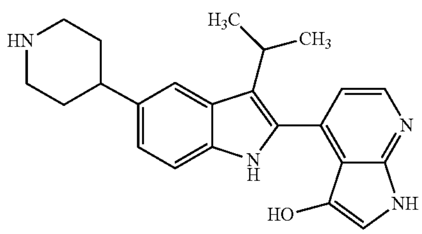 [SMILES: CC(C)c1c(-c2ccnc3[nH]cc(O)c23)[nH]c2ccc(C3CCNCC3)cc12] | 375.3 | 0.92 | QC-ACN-AA-XB |

Example 217

4-(3-ethyl-5-(piperidin-4-yl)-1H-indol-2-yl)-3-methyl-1H-pyrrolo[2,3-b]pyridine

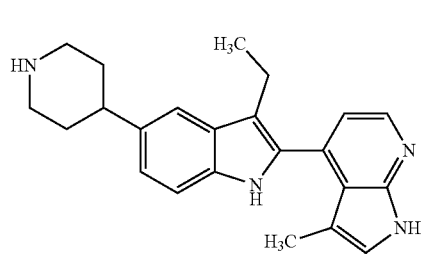

(217)

Intermediate 217A: tert-butyl 4-(2-(3-bromo-1H-pyrrolo[2,3-b]pyridin-4-yl)-3-ethyl-1H-indol-5-yl)piperidine-1-carboxylate

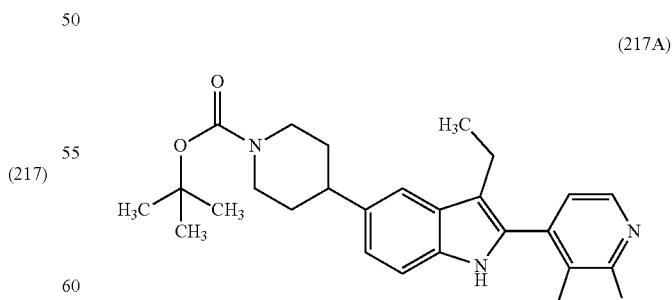

(217A)

In a 40 mL reaction vial were added tert-butyl 4-(2-bromo-3-ethyl-1H-indol-5-yl)piperidine-1-carboxylate (0.250 g, 0.614 mmol), THF (2 mL), 4-(4,4,5,5-tetramethyl-1,3,2-dioxaborolan-2-yl)-1H-pyrrolo[2,3-b]pyridine (0.180 g, 0.736 mmol), PdCl₂(dppf)-CH₂Cl₂ adduct (0.025 g, 0.031 mmol), and potassium phosphate solution (0.614 mL, 1.841 mmol). The mixture was capped and pump/purged with nitrogen gas 3 times. The reaction mixture was heated at 65° C. for 1 hour. The reaction mixture was acidified to pH=5 with 1 N HCl and extracted with ethyl acetate. The organics were washed with a saturated NaCl solution, dried over Na₂SO₄, filtered and concentrated to dryness. The residue was purified by silica gel chromatography using ethyl acetate/hexane as the eluent. Following concentration of the fractions, tert-butyl 4-(3-ethyl-2-(1H-pyrrolo[2,3-b] pyridin-4-yl)-1H-indol-5-yl)piperidine-1-carboxylate (0.127 g) was collected. LC-MS, $M^{+1}$=445.5, RT=1.08 min, Method F1.

tert-Butyl 4-(3-ethyl-2-(1H-pyrrolo[2,3-b]pyridin-4-yl)-1H-indol-5-yl)piperidine-1-carboxylate was combined with DCM (3.0 mL) and NBS (0.060 g, 0.310 mmol). The reaction mixture was stirred for 30 minutes at room temperature, followed by the addition of a 10% sodium sulfite solution (1.0 mL) and DCM. The mixture was washed with additional water and the layers were separated. The organics were washed with a saturated NaCl solution, dried over Na₂SO₄, filtered and concentrated to dryness. Tert-butyl 4-(2-(3-bromo-1H-pyrrolo[2,3-b]pyridin-4-yl)-3-ethyl-1H-indol-5-yl)piperidine-1-carboxylate (0.112 g, 0.214 mmol, 35% yield). MS ($M^{+1}$) m/z: 523.1 (MH⁺). LC retention time 1.14 min [A1]. ¹H NMR (400 MHz, CHLOROFORM-d) δ 9.11-9.02 (m, 1H), 8.44-8.39 (m, 1H), 8.24-8.18 (m, 1H), 7.59-7.53 (m, 1H), 7.44-7.38 (m, 2H), 7.27-7.24 (m, 1H), 7.18-7.14 (m, 1H), 6.71-6.67 (m, 1H), 4.42-4.23 (m, 2H), 4.19-4.09 (m, 1H), 3.05-2.94 (m, 2H), 2.94-2.77 (m, 3H), 2.00-1.91 (m, 2H), 1.84-1.72 (m, 2H), 1.55-1.52 (m, 9H), 1.40-1.34 (m, 3H).

Intermediate 217B: tert-butyl 3-bromo-4-(1-(tert-butoxycarbonyl)-5-(1-(tert-butoxycarbonyl) piperidin-4-yl)-3-ethyl-1H-indol-2-yl)-1H-pyrrolo[2,3-b]pyridine-1-carboxylate (217B)

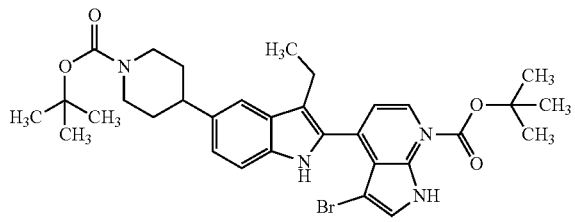

To a 40 mL reaction vial were added tert-butyl 4-(3-ethyl-2-(1H-pyrrolo[2,3-b]pyridin-4-yl)-1H-indol-5-yl)piperidine-1-carboxylate (0.293 g, 0.659 mmol), THF (10 mL), DMAP (0.805 mg, 6.59 µmol) and Boc-anhydride (0.383 mL, 1.648 mmol). The reaction mixture was stirred for 2 hours at room temperature. The reaction was quenched with water and a 10% 1N HCl solution. To this was added ethyl acetate and the layers were separated. The organics were washed with a saturated NaCl solution, dried over Na₂SO₄, filtered and concentrated to dryness to afford tert-butyl 3-bromo-4-(1-(tert-butoxycarbonyl)-5-(1-(tert-butoxycarbonyl)piperidin-4-yl)-3-ethyl-1H-indol-2-yl)-1H-pyrrolo[2,3-b]pyridine-1-carboxylate as a yellow solid (0.360 g, 0.497 mmol, 75% yield). MS (M+1) m/z: 725.7 (MH⁺). LC retention time 1.36 min [B1].

Example 217

To mixture of tert-butyl 3-bromo-4-(1-(tert-butoxycarbonyl)-5-(1-(tert-butoxycarbonyl)piperidin-4-yl)-3-ethyl-1H-indol-2-yl)-1H-pyrrolo[2,3-b]pyridine-1-carboxylate (100 mg, 0.138 mmol), Pd(dppf)Cl₂ (5.06 mg, 6.91 µmol) and K₂CO₃ (57.3 mg, 0.415 mmol) was added DMF (1.0 mL). The vial was fitted with a Teflon-lined septum and pump-purged with nitrogen gas three times. Next, dimethylzinc (1 M in heptane) (276 µl, 0.276 mmol) was added. The reaction mixture was heated at 95° C. for 4 hours. The reaction mixture was cooled to room temperature, diluted with ethyl acetate (10 mL), and washed with a saturated ammonium chloride solution (2×10 mL). The combined organics were then washed with a 10% LiCl solution (2×20 mL) and a saturated NaCl solution, dried over Na₂SO₄, and concentrated in vacuo. The crude material was dissolved in a small amount of DCM and purified by silica gel chromatography. The column was eluted with 0-75% ethyl acetate/hexane. Fractions were concentrated to afford tert-butyl 3-methyl-4-(1-(tert-butoxycarbonyl)-5-(1-(tert-butoxycarbonyl)piperidin-4-yl)-3-ethyl-1H-indol-2-yl)-1H-pyrrolo[2,3-b]pyridine-1-carboxylate as a tan oil. LC-MS, $M^{+1}$=559 (loss of one boc), RT=1.21 min, Method B1.

Tert-butyl 3-bromo-4-(1-(tert-butoxycarbonyl)-5-(1-(tert-butoxycarbonyl) piperidin-4-yl)-3-ethyl-1H-indol-2-yl)-1H-pyrrolo[2,3-b]pyridine-1-carboxylate (0.020 g) was taken up in 4 M HCL/dioxane (0.500 mL) and stirred for 30 minutes at room temperature. The reaction mixture was concentrated under a stream of nitrogen gas and diluted with DMSO (1.0 mL). The crude material was purified via preparative LC/MS. Fractions containing the desired product were combined and dried via centrifugal evaporation to afford 4-(3-ethyl-5-(piperidin-4-yl)-1H-indol-2-yl)-3-methyl-1H-pyrrolo[2,3-b]pyridine (0.0082 mg, 0.022 µmol, 0.016% yield). MS ($M^{+1}$) m/z: 359.3 (MH⁺). LC retention time 1.11 min [C1]. ¹H NMR (500 MHz, DMSO-d₆) δ 11.71-11.47 (m, 1H), 11.17 (s, 1H), 8.62 (br d, J=10.1 Hz, 1H), 8.35 (br d, J=9.1 Hz, 1H), 8.27 (d, J=4.7 Hz, 1H), 7.42 (s, 1H), 7.36-7.27 (m, 2H), 7.02 (br d, J=5.4 Hz, 2H), 3.51 (br d, J=11.4 Hz, 1H), 3.41 (br d, J=11.1 Hz, 1H), 3.05 (br d, J=12.1 Hz, 2H), 2.94 (br s, 1H), 2.65 (q, J=7.4 Hz, 2H), 2.08-1.97 (m, 2H), 1.95-1.86 (m, 2H), 1.83 (s, 3H), 1.11 (t, J=7.6 Hz, 3H).

The following example was prepared according to the general procedure for Example 217.

TABLE 6

| Ex. No. | Structure | Obs. MS Ion | RT | HPLC Method |
|---|---|---|---|---|
| 218 | HN-[structure with CH₃ groups, indole, pyrrolopyridine] | 346 | 0.92 | QC-ACN-TFA-XB |

Example 219

4-(3-methyl-5-(piperidin-4-yl)-1H-indol-2-yl)-3-ethyl-1H-pyrrolo[2,3-b]pyridine

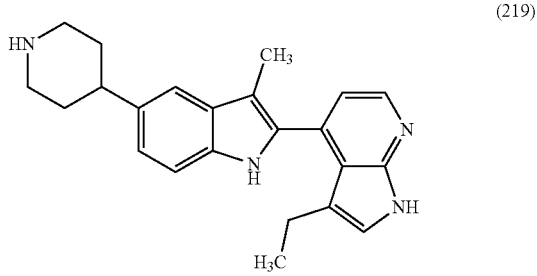 [SMILES: CCc1c[nH]c2nccc(-c3[nH]c4ccc(C5CCNCC5)cc4c3C)c12]

(219)

Intermediate 219A: tert-butyl 4-(1-(tert-butoxycarbonyl)-5-(1-(tert-butoxycarbonyl) piperidin-4-yl)-3-methyl-1H-indol-2-yl)-3-vinyl-1H-pyrrolo[2,3-b]pyridine-1-carboxylate

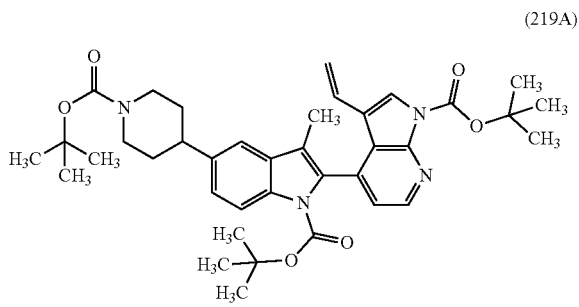 [SMILES: C=Cc1cn(C(=O)OC(C)(C)C)c2nccc(-c3c(C)c4cc(C5CCN(C(=O)OC(C)(C)C)CC5)ccc4n3C(=O)OC(C)(C)C)c12]

(219A)

To a 2-dram reaction vial were added tert-butyl 3-bromo-4-(1-(tert-butoxycarbonyl)-5-(1-(tert-butoxycarbonyl)piperidin-4-yl)-3-methyl-1H-indol-2-yl)-1H-pyrrolo[2,3-b]pyridine-1-carboxylate (0.100 g, 0.114 mmol), 4,4,5,5-tetramethyl-2-vinyl-1,3,2-dioxaborolane (0.033 g, 0.211 mmol), $PdCl_2$(dppf)-$CH_2Cl_2$ adduct (0.012 g, 0.014 mmol), THF (1.5 mL), and potassium phosphate solution (0.141 mL, 0.423 mmol). The vial was capped, pump/purged with nitrogen gas three times, and heated at 75° C. for 16 hours. The mixture was concentrated to give a brown residue. The residue was liquid loaded (DCM) onto an ISCO column and purified using 0-100% ethyl acetate/hexane as the eluent. Following concentration of the fractions, tert-butyl 4-(1-(tert-butoxycarbonyl)-5-(1-(tert-butoxycarbonyl)piperidin-4-yl)-3-methyl-1H-indol-2-yl)-3-vinyl-1H-pyrrolo[2,3-b]pyridine-1-carboxylate was obtained as a white solid. MS $(M^{+1})$ m/z: 657.3 $(MH^+)$. LC retention time 1.27 min [A1].

Example 219

To tert-butyl 4-(1-(tert-butoxycarbonyl)-5-(1-(tert-butoxycarbonyl)piperidin-4-yl)-3-methyl-1H-indol-2-yl)-3-vinyl-1H-pyrrolo[2,3-b]pyridine-1-carboxylate was added ethyl acetate (3 mL) and 10% w/w Pd/C (0.012 g, 0.014 mmol). The reaction mixture was pump/purged with nitrogen gas, evacuated and back-filled with hydrogen gas via balloon. The reaction mixture was stirred at room temperature for 1 hour, filtered through celite and the filtrate, and concentrated. To this solid was added DCM (0.5 mL) and TFA (0.5 mL). The reaction vessel was capped and the reaction mixture was stirred for 1 hour at room temperature, then concentrated under a stream of nitrogen gas and diluted with 2 mL of DMSO. The crude material was purified via preparative LC/MS. Fractions containing the desired product were combined and dried via centrifugal evaporation to afford 4-(3-methyl-5-(piperidin-4-yl)-1H-indol-2-yl)-3-ethyl-1H-pyrrolo[2,3-b]pyridine (0.0054 g, 0.0150 mmol, 11% yield). MS $(M^{+1})$ m/z: 359.3 $(MH^+)$. LC retention time 1.10 min [C1]. $^1$H NMR (500 MHz, DMSO-$d_6$) δ 11.51 (br d, J=6.3 Hz, 1H), 11.08 (br s, 1H), 8.24 (br s, 1H), 7.47-7.17 (m, 3H), 7.11-6.84 (m, 2H), 3.16 (br d, J=7.6 Hz, 1H), 2.87-2.67 (m, 3H), 2.33 (br d, J=5.7 Hz, 2H), 2.16 (br s, 3H), 1.91-1.62 (m, 6H), 0.82 (br s, 3H).

The following examples were prepared according to the general procedure for Example 219.

TABLE 7

| Ex. No. | Structure | Obs. MS Ion | HPLC RT | Method |
|---|---|---|---|---|
| 220 | 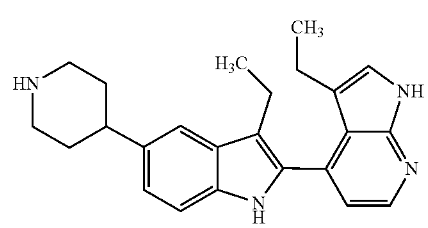 [SMILES: CCc1c(-c2ccnc3[nH]cc(CC)c23)[nH]c2ccc(C3CCNCC3)cc12] | 373.3 | 0.79 | QC-ACN-TFA-XB |

TABLE 7-continued

| Ex. No. | Structure | Obs. MS Ion | HPLC RT | Method |
|---|---|---|---|---|
| 221 | 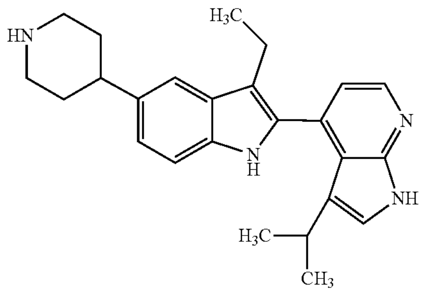 [SMILES: CCc1c(-c2ccnc3[nH]cc(C(C)C)c23)[nH]c2ccc(C3CCNCC3)cc12] | 387.4 | 0.85 | QC-ACN-TFA-XB |
| 222 | 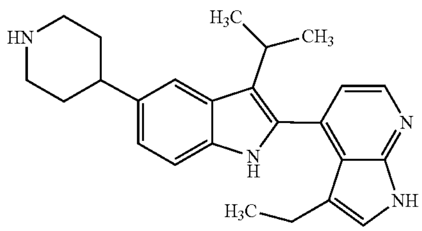 [SMILES: CCc1c[nH]c2nccc(-c3[nH]c4ccc(C5CCNCC5)cc4c3C(C)C)c12] | 387.1 | 1.23 | QC-ACN-AA-XB |
| 223 | 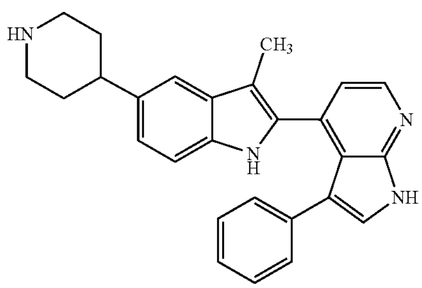 [SMILES: Cc1c(-c2ccnc3[nH]cc(-c4ccccc4)c23)[nH]c2ccc(C3CCNCC3)cc12] | 407.2 | 0.84 | QC-ACN-TFA-XB |
| 224 | 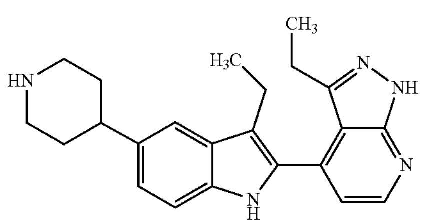 [SMILES: CCc1c(-c2ccnc3[nH]nc(CC)c23)[nH]c2ccc(C3CCNCC3)cc12] | 374.2 | 1.13 | QC-ACN-AA-XB |
| 225 | 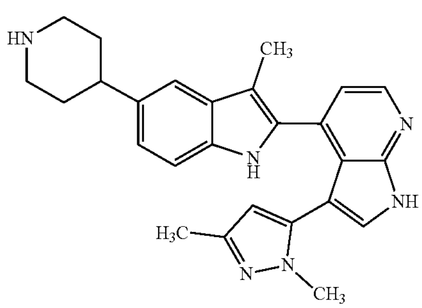 [SMILES: Cc1cc(-c2c[nH]c3nccc(-c4[nH]c5ccc(C6CCNCC6)cc5c4C)c23)n(C)n1] | 425.3 | 0.67 | QC-ACN-TFA-XB |

Example 226

4-(3-ethyl-5-(piperidin-4-yl)-1H-indol-2-yl)-3-methyl-1H-pyrazolo[3,4-b]pyridine

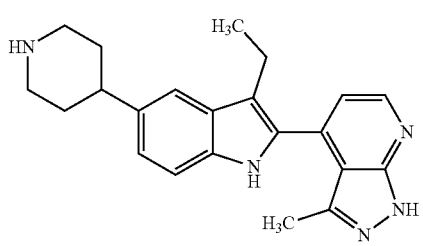
(226)

To a 2 dram reaction vial were added tert-butyl 4-(2-bromo-3-ethyl-1H-indol-5-yl) piperidine-1-carboxylate (0.035 g, 0.086 mmol), tert-butyl 3-methyl-4-(4,4,5,5-tetramethyl-1,3,2-dioxaborolan-2-yl)-1H-pyrazolo[3,4-b]pyridine-1-carboxylate (0.031 g, 0.086 mmol), PdCl$_2$(dppf)-CH$_2$Cl$_2$ adduct (3.51 mg, 4.30 μmol), 3 M potassium phosphate tribasic solution (0.086 mL, 0.258 mmol), and THF (3.0 mL). The vial was capped and pump/purged with nitrogen gas 3×, and heated at 65° C. for 2 hours. The reaction mixture was cooled to room temperature and the aqueous layer was pipetted off. Ethyl acetate was added to the remaining organics, followed by the addition of anhydrous sodium sulfate. The solids were filtered off and the organic filtrate was concentrated under a stream of nitrogen gas. The residue was redissolved in DCM (1.0 mL) and treated with 4 M hydrogen chloride/dioxane (1.074 mL, 4.30 mmol). The reaction mixture was stirred at room temperature for 2 hours. The volatiles were removed and the orange hued residue was dissolved in water/MeOH and filtered through a 0.45 μm syringe filter. The crude material was purified via preparative LC/MS. Fractions containing the product were combined and dried via centrifugal evaporation to afford 4-(3-ethyl-5-(piperidin-4-yl)-1H-indol-2-yl)-3-methyl-1H-pyrazolo[3,4-b]pyridine (0.0061 g, 0.016 mmol, 19% yield). MS (M$^{+1}$) m/z: 360.3 (MH$^+$). LC retention time 1.00 min [D1]. $^1$H NMR (500 MHz, DMSO-d$_6$) δ 11.17 (br s, 1H), 8.69 (br s, 1H), 8.31 (br s, 1H), 7.47-7.29 (m, 2H), 7.10-6.94 (m, 1H), 3.68-3.38 (m, 2H), 3.27 (br d, J=10.8 Hz, 2H), 2.97-2.78 (m, 6H), 1.99-1.71 (m, 6H), 1.28 (br d, J=6.7 Hz, 3H).

The following examples were prepared according to the general procedure for Example 226.

TABLE 8

| Ex. No. | Structure | Obs. MS Ion | RT | HPLC Method |
|---|---|---|---|---|
| 227 | 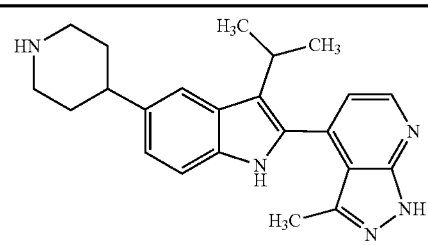 | 374.3 | 1.06 | QC-ACN-TFA-XB |
| 228 | 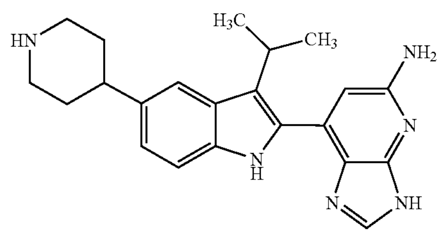 [SMILES: CC(C)c1c(-c2cc(N)nc3[nH]cnc23)[nH]c2ccc(C3CCNCC3)cc12] | 375.1 | 0.71 | QC-ACN-AA-XB |
| 229 | 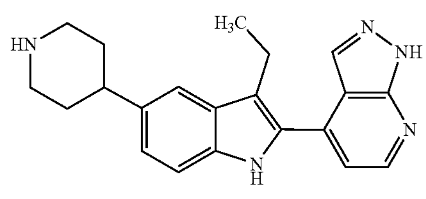 [SMILES: CCc1c(-c2ccnc3[nH]ncc23)[nH]c2ccc(C3CCNCC3)cc12] | 346 | 1.01 | QC-ACN-TFA-XB |
| 230 | 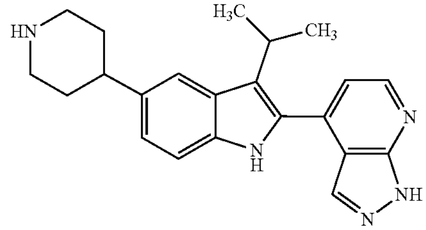 | 360.2 | 0.95 | QC-ACN-AA-XB |

TABLE 8-continued

| Ex. No. | Structure | Obs. MS Ion | RT | HPLC Method |
|---|---|---|---|---|
| 231 | 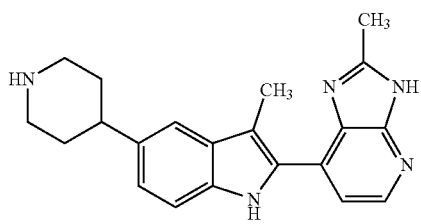 | 332.3 | 0.65 | QC-ACN-TFA-XB |

Example 232

2-methyl-7-(3-methyl-5-(piperidin-4-yl)-1H-indol-2-yl)-3H-imidazo[4,5-b]pyridine (232)

Intermediate 232A: 7-chloro-3-(4-methoxybenzyl)-3H-imidazo[4,5-b]pyridine

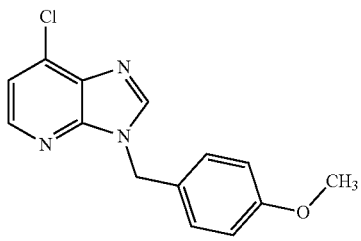

(232A)

To a 2-dram vial were added 7-chloro-1H-pyrazolo[4,3-b]pyridine (0.200 g, 1.302 mmol), potassium carbonate (0.540 g, 3.91 mmol), and DMF (2.5 mL). With stirring, 1-(chloromethyl)-4-methoxybenzene (0.245 g, 1.563 mmol) was added. The reaction mixture was stirred at room temperature for 2 hours. Water was added with ethyl acetate and the contents were transferred to a separatory funnel. The layers were separated and the organics were washed with brine, dried over anhydrous sodium sulfate, filtered and concentrated. The crude residue was purified by silica gel chromatography and following evaporation of the fractions, afforded 7-chloro-3-(4-methoxybenzyl)-3H-imidazo[4,5-b]pyridine. MS ($M^{+1}$) m/z: 274.0 ($MH^+$). LC retention time 1.21 min [A1].

Intermediate 232B: tert-butyl 5-(1-(tert-butoxycarbonyl)piperidin-4-yl)-2-(3-(4-methoxybenzyl)-2-methyl-3H-imidazo[4,5-b]pyridin-7-yl)-3-methyl-1H-indole-1-carboxylate

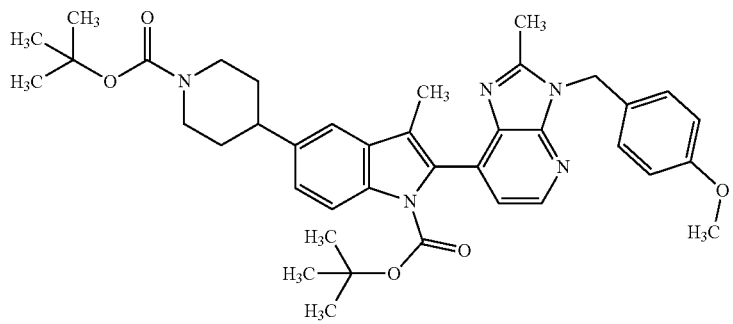

(232B)

To a 2-dram reaction vial were added tert-butyl 5-(1-(tert-butoxycarbonyl) piperidin-4-yl)-3-methyl-2-(4,4,5,5-tetramethyl-1,3,2-dioxaborolan-2-yl)-1H-indole-1-carboxylate (0.025 g, 0.046 mmol), 7-chloro-3-(4-methoxybenzyl)-2-methyl-3H-imidazo[4,5-b]pyridine (0.020 g, 0.069 mmol), $PdCl_2(dppf)$-$CH_2Cl_2$ adduct (3.10 mg, 4.36 μmol), 3 M potassium phosphate solution (0.046 mL, 0.139 mmol) and THF (3.0 mL). The mixture was capped and pump/purged with nitrogen gas three times and then heated at 75° C. for 12 hours. The mixture was cooled to room temperature and concentrated. The brown residue was diluted with ethyl acetate and poured into a separatory funnel. The organic phase was washed once with water followed by one wash with brine. The organics were collected, dried over anhydrous sodium sulfate, filtered and concentrated. The residue was purified by silica gel chromatography using 0-100% ethyl acetate/hexane as the eluent. Following concentration of the fractions, tert-butyl 5-(1-(tert-butoxycarbonyl)piperidin-4-yl)-2-(3-(4-methoxybenzyl)-2-methyl- 3H-imidazo[4,5-b]pyridin-7-yl)-3-methyl-1H-indole-1-carboxylate was obtained as a yellowish oil (0.018 g, 0.012 mmol, 58% yield). MS ($M^{+1}$) m/z: 666.7 ($MH^+$). LC retention time 1.09 min [B1].

Example 232

To a 2 dram vial containing tert-butyl 5-(1-(tert-butoxycarbonyl)piperidin-4-yl)-2-(3-(4-methoxybenzyl)-2-methyl-3H-imidazo[4,5-b]pyridin-7-yl)-3-methyl-1H-indole-1-carboxylate (0.018 g, 0.012 mmol) were added DCM (0.5 mL) and TFA (0.05 mL). The reaction mixture was stirred at room temperature for 30 minutes, concentrated under a stream of nitrogen gas and diluted with 2.0 mL of DMF. The crude material was purified via preparative LC/MS. Fractions containing the product were combined and dried via centrifugal evaporation to afford 2-methyl-7-(3-methyl-5-(piperidin-4-yl)-1H-indol-2-yl)-3H-imidazo[4,5-b]pyridine (0.0043, 0.012 mmol, 27% yield). MS ($M^{+1}$) m/z: 346.2 ($MH^+$). LC retention time 0.96 min [C1]. $^1$H NMR (500 MHz, DMSO-$d_6$) δ 8.37-8.25 (m, 1H), 7.59-7.38 (m, 3H), 7.08 (br d, J=8.5 Hz, 1H), 3.63-3.43 (m, 1H), 3.22 (br d, J=11.9 Hz, 2H), 2.89-2.74 (m, 3H), 2.61 (s, 3H), 2.55 (br s, 1H), 1.86 (s, 4H), 1.82-1.68 (m, 2H).

The following example was prepared according to the general procedure for Examples 226.

TABLE 9

| Ex. No. | Structure | Obs. MS Ion | RT | HPLC Method |
|---|---|---|---|---|
| 233 | 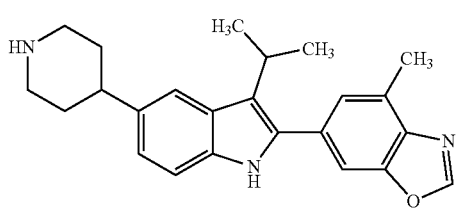 | 333.3 | 0.77 | QC-ACN-AA-XB |

Example 234

6-(3-isopropyl-5-(piperidin-4-yl)-1H-indol-2-yl)-4-methylbenzo[d]oxazole (234)

Intermediate 234:
1-(benzyloxy)-5-bromo-3-methyl-2-nitrobenzene

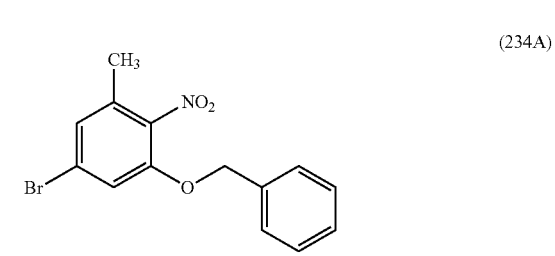 [SMILES: Cc1cc(Br)cc(OCc2ccccc2)c1[N+](=O)[O-]]
(234A)

To a 40 mL reaction vial were added 5-bromo-1-fluoro-3-methyl-2-nitrobenzene (0.250 g, 1.068 mmol), DMF (3.56 mL) and cesium carbonate (0.696 g, 2.137 mmol). With stirring, phenyl methanol (0.173 g, 1.602 mmol) was added. The reaction mixture was stirred at 50° C. for 1 hour. The mixture was diluted with water and ethyl acetate and added to a separatory funnel. The layers were separated and the organics were washed with water, then brine, and dried over anhydrous sodium sulfate. Following filtration, 1-(benzyloxy)-5-bromo-3-methyl-2-nitrobenzene was collected as a yellow solid (0.270 g, 0.838 mmol, 78% yield). MS ($M^{+1}$) m/z: 322.1 ($MH^+$). LC retention time 1.13 min [A1].

Intermediate 234B: tert-butyl 4-(2-(4-amino-3-hydroxy-5-methylphenyl)-3-isopropyl-1H-indol-5-yl)piperidine-1-carboxylate

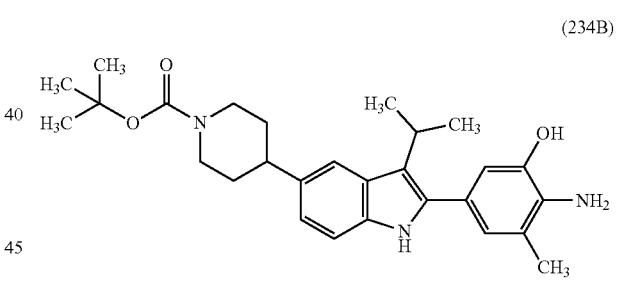
(234B)

Tert-butyl 4-(2-(3-(benzyloxy)-5-methyl-4-nitrophenyl)-3-isopropyl-1H-indol-5-yl) piperidine-1-carboxylate (0.100 g, 0.171 mmol) was dissolved in MeOH (3.0 mL). Under a stream of nitrogen gas, was added 10% Pd/C (0.010 g). The bottle was placed on the Parr shaker and pump/purged with nitrogen gas three times. The bottle was back-filled with hydrogen gas to a pressure of 50 psi and the contents were shaken for 1 hour. Following a pump/purge cycle (three times) with nitrogen gas, the vessel was diluted with MeOH and the solids were filtered through tightly packed celite. The filtrate was concentrated to give tert-butyl 4-(2-(4-amino-3-hydroxy-5-methylphenyl)-3-isopropyl-1H-indol-5-yl)piperidine-1-carboxylate (0.070 g, 0.151 mmol, 88% yield). MS ($M^{+1}$) m/z: 464.3 ($MH^+$). LC retention time 1.01 min [A1].

Intermediate 234C: tert-butyl 4-(3-isopropyl-2-(4-methylbenzo[d]oxazol-6-yl)-1H-indol-5-yl)piperidine-1-carboxylate

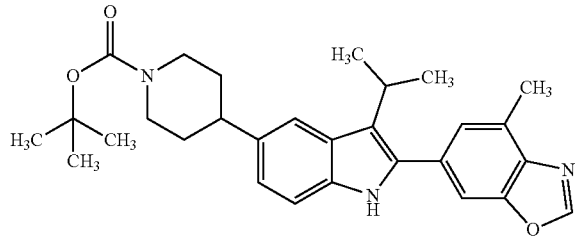

(234C)

To a 4 mL reaction vial were added tert-butyl 4-(2-(4-amino-3-hydroxy-5-methylphenyl)-3-isopropyl-1H-indol-5-yl)piperidine-1-carboxylate (0.153 g, 0.330 mmol), MeOH (1 mL) and triethyl orthoformate (0.055 mL, 0.330 mmol). The reaction mixture was capped and heated at 75° C. for 1 hour. Following cooling to room temperature, the volatiles were removed under a stream of nitrogen gas. The residue was purified by silica gel chromatography to afford tert-butyl 4-(3-isopropyl-2-(4-methylbenzo[d]oxazol-6-yl)-1H-indol-5-yl)piperidine-1-carboxylate (0.070 g, 0.148 mmol, 45% yield). $^1$H NMR (400 MHz, DMSO-$d_6$) δ 11.08-10.89 (m, 1H), 8.76 (s, 1H), 7.70-7.48 (m, 2H), 7.43-7.20 (m, 2H), 6.99 (dd, J=8.4, 1.6 Hz, 1H), 4.20-4.06 (m, 2H), 2.97-2.70 (m, 3H), 2.62 (s, 3H), 1.81 (br d, J=12.2 Hz, 2H), 1.68-1.51 (m, 2H), 1.50-1.35 (m, 16H).

Example 234

To tert-butyl 4-(3-isopropyl-2-(4-methylbenzo[d]oxazol-6-yl)-1H-indol-5-yl) piperidine-1-carboxylate (0.070 g, 0.148 mmol) was added 4 M HCl/dioxane (2.0 mL). The reaction mixture was stirred for 30 minutes at room temperature, then concentrated to dryness giving 0.08 g of crude product. The crude product (0.020 g) was purified via preparative LC/MS. Fractions containing the product were combined and dried via centrifugal evaporation to afford 6-(3-isopropyl-5-(piperidin-4-yl)-1H-indol-2-yl)-4-methylbenzo[d]oxazole (0.0067 g, 0.0180 mmol, 35% yield). MS (M$^{+1}$) m/z: 374.3 (MH$^+$). LC retention time 1.37 min [C1]. $^1$H NMR (500 MHz, DMSO-$d_6$) δ 11.04 (s, 1H), 8.69 (s, 1H), 7.65-7.49 (m, 2H), 7.41-7.26 (m, 2H), 6.99 (br d, J=8.6 Hz, 1H), 3.78 (br s, 2H), 3.46-3.24 (m, 2H), 3.01 (br s, 2H), 2.94-2.85 (m, 1H), 2.60 (s, 3H), 2.01-1.94 (m, 2H), 1.91-1.79 (m, 2H), 1.41 (br d, J=6.9 Hz, 6H).

Example 235

4-(3-isopropyl-5-(piperidin-4-yl)-1H-indol-2-yl)-1H-indazole-7-carbonitrile

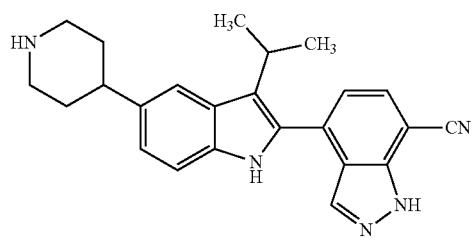

(235)

To a 2 dram vial with pressure relief septum were added tert-butyl 4-(1-(tert-butoxycarbonyl)-5-(1-(tert-butoxycarbonyl)piperidin-4-yl)-3-isopropyl-1H-indol-2-yl)-7-chloro-1H-indazole-1-carboxylate (0.026 g, 0.038 mmol), potassium ferrocyanide (6.91 mg, 0.019 mmol), 2nd generation XPhos precatalyst (0.207 mg, 0.263 µmol), Xphos (0.179 mg, 0.375 µmol), and dioxane (1.2 mL). The mixture was evacuated and flushed with nitrogen gas several times. Potassium acetate (0.460 mg, 4.69 µmol) and water (1.2 mL) were added. The vial was evacuated and flushed with nitrogen gas several times. The vial was heated at 100° C. for 4 hours, at which time the reaction mixture was cooled to room temperature. The mixture was partitioned between water (15 mL) and ethyl acetate (15 mL). The organic layer was separated and washed with brine (2×10 mL). The organics were dried over anhydrous sodium sulfate, filtered and concentrated under vacuum. The resulting oil was purified by silica chromatography. The like fractions were combined and dried under vacuum to give a white solid. The solid was dissolved in DCM (1.0 mL) and TFA (0.5 mL) was added to the mixture. The reaction mixture was stirred for 1 hour then concentrated, diluted with methanol. The crude material was purified via preparative LC/MS. Fractions containing the product were combined and dried via centrifugal evaporation to afford 4-(3-isopropyl-5-(piperidin-4-yl)-1H-indol-2-yl)-1H-indazole-7-carbonitrile (0.0018 g, 0.00446 µmol, 12% yield). MS (M$^{+1}$) m/z: 384.3 (MH$^+$). LC retention time 1.18 min [C1]. $^1$H NMR (500 MHz, DMSO-$d_6$) δ 11.17-11.01 (m, 1H), 8.08 (s, 1H), 7.88 (br d, J=7.4 Hz, 1H), 7.47 (s, 1H), 7.25 (br d, J=8.4 Hz, 1H), 7.14 (br d, J=7.5 Hz, 1H), 6.92 (br d, J=8.6 Hz, 1H), 3.24-2.99 (m, 4H), 2.87-2.65 (m, 4H), 1.76 (br s, 2H), 1.71-1.65 (m, 2H), 1.26 (br d, J=7.0 Hz, 6H).

The following example was prepared according to the general procedure for Examples 235.

TABLE 10

| Ex. No. | Structure | Obs. MS Ion | RT | HPLC Method |
|---|---|---|---|---|
| 236 | 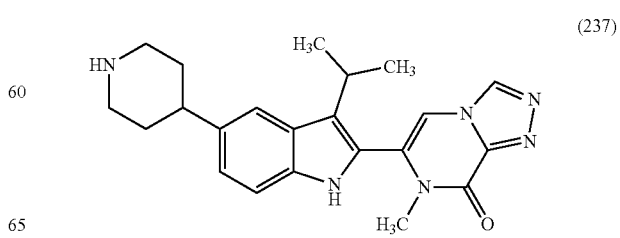 | 345.1 | 0.67 | QC-ACN-TFA-XB |

Example 237

6-(3-isopropyl-5-(piperidin-4-yl)-1H-indol-2-yl)-7-methyl-[1,2,4]triazolo[4,3-a]pyrazin-8(7H)-one (237)

Intermediate 237A: tert-butyl 4-(2-(8-chloro-[1,2,4]triazolo[4,3-a]pyrazin-6-yl)-3-isopropyl-1H-indol-5-yl)piperidine-1-carboxylate

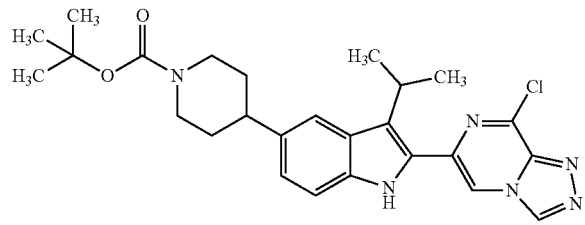

(237A)

To a solution of tert-butyl 4-(3-isopropyl-2-(4,4,5,5-tetramethyl-1,3,2-dioxaborolan-2-yl)-1H-indol-5-yl)piperidine-1-carboxylate (250 mg, 0.534 mmol), 6-bromo-8-chloro-[1,2,4]triazolo[4,3-a]pyrazine (150 mg, 0.640 mmol), and chloro(2-dicyclohexylphosphino-2',4',6'-triisopropyl-1,1'-biphenyl)[2-(2'-amino-1,1'-biphenyl)]palladium(II) (21.00 mg, 0.027 mmol) in THF (3558 µl) was added potassium phosphate tribasic (534 µl, 1.601 mmol). The biphasic mixture was degassed with nitrogen for 10 min. The vial was sealed. The reaction mixture was stirred at 65° C. After stirring for 15 hours, reaction mixture was taken down to room temperature and checked by LCMS. The product was observed (RT=1.03, $M^{+1}$=495). The reaction mixture was concentrated and taken up in DCM then purified by silica gel chromatography (24 g silica gel, Hexanes/EtOAc 0-100%) to afford tert-butyl 4-(2-(8-chloro-[1,2,4]triazolo[4,3-a]pyrazin-6-yl)-3-isopropyl-1H-indol-5-yl)piperidine-1-carboxylate (60 mg, 0.121 mmol, 22.71% yield). MS ($M^{+1}$) m/z: 495.3 ($MH^+$). LC retention time 1.07 min [A1].

Example 237

To a mixture of tert-butyl 4-(2-(8-chloro-[1,2,4]triazolo[4,3-a]pyrazin-6-yl)-3-isopropyl-1H-indol-5-yl)piperidine-1-carboxylate (42 mg, 0.085 mmol) in THF (1 mL) was added sodium hydroxide (0.170 mL, 0.170 mmol). The reaction mixture was stirred for 4 hours. LCMS shows conversion to the product by mass. The reaction mixture was diluted with dichloromethane and washed with water. The organic layer was dried with MgSO$_4$, filtered and concentrated.

To a mixture of tert-butyl 4-(2-(8-hydroxy-[1,2,4]triazolo[4,3-a]pyrazin-6-yl)-3-isopropyl-1H-indol-5-yl)piperidine-1-carboxylate (20 mg, 0.042 mmol) and potassium carbonate (11.60 mg, 0.084 mmol) in DMF (1 mL) was added iodomethane (3.15 µl, 0.050 mmol). The reaction mixture was stirred overnight. LCMS shows some conversion to the product mass (Rf=1.00, M+H=491). The reaction was quenched with water. The reaction mixture was diluted with ethyl acetate and washed with a saturated aqueous NaCl solution. The organic layer was dried with MgSO$_4$, filtered and concentrated. The crude residue was dissolved in DCM (1 mL) and then TFA (0.5 mL) was added. The mixture was stirred for 30 minutes. LCMS showed removal of the Boc group (R$_f$=0.55, M+H=391). The solvent was removed. The material was dissolved in DMF and the mixture containing the product was purified via preparative LC/MS. Fractions containing the desired product were combined and dried via centrifugal evaporation to afford 6-(3-isopropyl-5-(piperidin-4-yl)-1H-indol-2-yl)-7-methyl-[1,2,4]triazolo[4,3-a]pyrazin-8(7H)-one (0.9 mg, 2.213 µmol, 5.3% yield). MS ($M^{+1}$) m/z: 391.1 ($MH^+$). LC retention time 0.76 min [QC-ACN-AA-XB]. $^1$H NMR (500 MHz, DMSO-d$_6$) δ 9.53 (s, 1H), 7.57 (s, 1H), 7.25 (d, J=8.6 Hz, 1H), 7.12 (s, 1H), 6.99 (d, J=8.6 Hz, 1H), 3.65 (spt, J=7.0 Hz, 1H), 3.32 (s, 3H), 3.18 (dddd, J=12.9, 4.5, 3.9, 3.5 Hz, 1H), 3.18 (dddd, J=12.9, 4.5, 3.9, 3.5 Hz, 1H), 3.18 (ddd, J=12.9, 7.9, 4.5 Hz, 1H), 3.18 (ddd, J=12.9, 7.9, 4.5 Hz, 1H), 2.69 (tt, J=8.0, 4.5 Hz, 1H), 1.91 (tddd, J=4.5, 3.5, 2.7, −13.2 Hz, 1H), 1.91 (tddd, J=4.5, 3.5, 2.7, −13.2 Hz, 1H), 1.76 (dddd, J=8.0, 7.9, 4.5, −13.2 Hz, 1H), 1.76 (dddd, J=8.0, 7.9, 4.5, −13.2 Hz, 1H), 1.43 (d, J=7.0 Hz, 6H).

Example 238

7-(3-ethyl-5-(piperidin-4-yl)-1H-indol-2-yl)-1H-pyrazolo[4,3-b]pyridin-3-amine

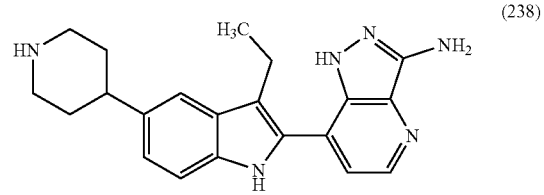 [SMILES: CCc1c(-c2ccnc3c(N)n[nH]c23)[nH]c2ccc(C3CCNCC3)cc12]

(238)

To a solution containing tert-butyl 4-(2-(2-cyano-3-fluoropyridin-4-yl)-3-ethyl-1H-indol-5-yl)piperidine-1-carboxylate (25 mg, 0.056 mmol), prepared according to the general Suzuki coupling procedure, in ethanol (0.5 mL) was added hydrazine (10 µl, 0.319 mmol). The vial was capped and heated at 65° C. for 4 h. The reaction mixture was concentrated to dryness and treated with TFA (1 mL) for 30 min and re-concentrated to dryness. The crude material was purified via preparative LC/MS. Fractions containing the product were combined and dried via centrifugal evaporation to afford 7-(3-ethyl-5-(piperidin-4-yl)-1H-indol-2-yl)-1H-pyrazolo[4,3-b]pyridin-3-amine, 2 TFA (9 mg, 0.015 mmol, 27.4% yield). MS ($M^{+1}$) m/z: 361.2 ($MH^+$). LC retention time 1.04 min [A1]. $^1$H NMR (500 MHz, DMSO-d$_6$) δ 11.28-11.17 (m, 1H), 8.75-8.61 (m, 1H), 8.48-8.35 (m, 2H), 7.51-7.44 (m, 1H), 7.42-7.35 (m, 2H), 7.12-7.01 (m, 2H), 3.68-3.55 (m, 1H), 3.43-3.38 (m, 1H), 3.11-3.00 (m, 2H), 2.98-2.91 (m, 1H), 2.90-2.87 (m, 1H), 2.87-2.80 (m, 2H), 2.76-2.71 (m, 1H), 2.06-1.95 (m, 2H), 1.93-1.86 (m, 2H), 1.24-1.11 (m, 3H).

The following examples were prepared according to the general procedure for Examples 235.

TABLE 11

| Ex. No. | Structure | Obs. MS Ion | RT | HPLC Method |
|---|---|---|---|---|
| 239 | 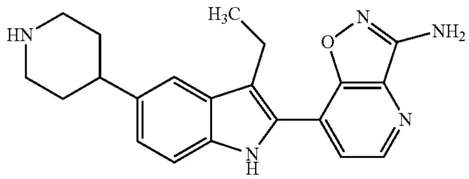 [SMILES: CCc1c(-c2ccnc3c(N)noc23)[nH]c2ccc(C3CCNCC3)cc12] | 362.2 | 0.89 | QC-ACN-TFA-XB |
| 240 | 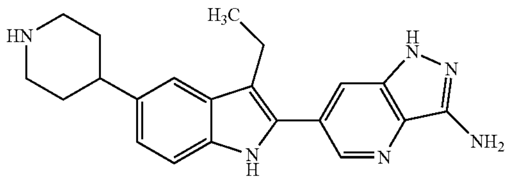 [SMILES: CCc1c(-c2cnc3c(N)n[nH]c3c2)[nH]c2ccc(C3CCNCC3)cc12] | 361.3 | 0.77 | QC-ACN-AA-XB |
| 241 | 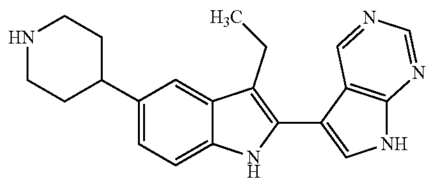 [SMILES: CCc1c(-c2c[nH]c3ncncc23)[nH]c2ccc(C3CCNCC3)cc12] | 346.1 | 0.77 | QC-ACN-AA-XB |
| 242 | 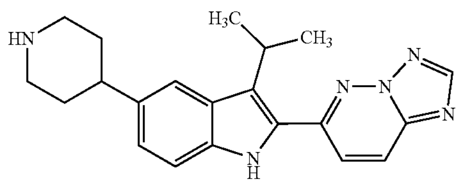 [SMILES: CC(C)c1c(-c2ccc3ncnn3n2)[nH]c2ccc(C3CCNCC3)cc12] | 361.4 | 0.72 | QC-ACN-AA-XB |
| 243 | 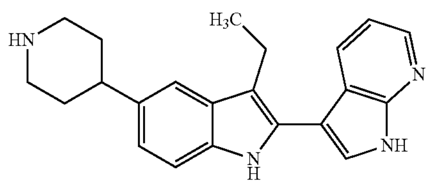 [SMILES: CCc1c(-c2c[nH]c3ncccc23)[nH]c2ccc(C3CCNCC3)cc12] | 345.1 | 0.95 | QC-ACN-AA-XB |
| 244 | 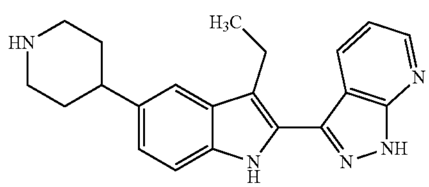 [SMILES: CCc1c(-c2n[nH]c3ncccc23)[nH]c2ccc(C3CCNCC3)cc12] | 346.4 | 0.95 | QC-ACN-AA-XB |
| 245 | 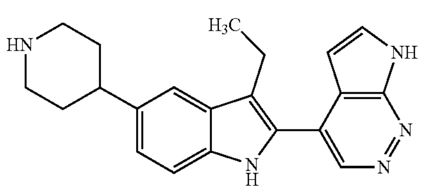 | 346.4 | 0.84 | QC-ACN-TFA-XB |

Example 246

4-(3-ethyl-5-(piperidin-4-yl)-1H-indol-2-yl)-5-methyl-1H-pyrrolo[2,3-b]pyridine

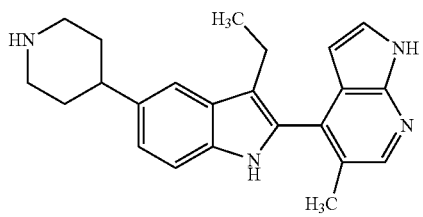
(246)

To a 2 mL microwave vial were added tert-butyl 5-(1-(tert-butoxycarbonyl) piperidin-4-yl)-3-ethyl-2-(6-methyl-4,8-dioxo-1,3,6,2-dioxazaborocan-2-yl)-1H-indole-1-carboxylate (22 mg, 0.038 mmol), 4-chloro-5-methyl-1-(triisopropylsilyl)-1H-pyrrolo[2,3-b]pyridine (18.27 mg, 0.057 mmol), THF (1450 µl), and 1,1'-bis(di-tert-butylphosphino) ferrocene palladium dichloride (1.229 mg, 1.885 µmol). The vial was evacuated and purged with N₂ several times. Sodium carbonate (106 µl, 0.264 mmol) was added and the reaction mixture was heated to 150° C. in a microwave until LCMS indicated the consumption of the starting materials. The reaction mixture was diluted with water (10 mL) and extracted with EtOAc (3×10 mL). The organic layer was combined, dried over magnesium sulfate, filtered and concentrated under vacuum. The resulting oil was purified by ISCO (4 g Silica, 100% Hexanes-25% EtOAc/Hexanes). Like fractions were combined and dried under vacuum to give a clear oil (24.7 mg, 0.035 mmol). tert-Butyl 5-(1-(tert-butoxycarbonyl)piperidin-4-yl)-3-ethyl-2-(5-methyl-1-(triisopropylsilyl)-1H-pyrrolo[2,3-b]pyridin-4-yl)-1H-indole-1-carboxylate (25 mg, 0.035 mmol) was dissolved in TFA (1 mL) and stirred at room temperature. After 1 hour, LCMS indicated the presence of product and the TIPS protected indole. Stirring was continued at room temperature. After 5 hours, the LCMS indicated that the reaction was incomplete. The TFA was concentrated under a stream of nitrogen. LCMS indicates 1:1 product to protected azaindole. The solution was dissolved in TFA (1 mL) and heated for 15 minutes at 40° C. LCMS indicated complete deprotection. The solution was concentrated under a stream of N₂ to give a brown oil. The crude material was purified via preparative LC/MS. Fractions containing the desired product were combined and dried via centrifugal evaporation to afford 4-(3-ethyl-5-(piperidin-4-yl)-1H-indol-2-yl)-5-methyl-1H-pyrrolo[2,3-b]pyridine, TFA (14.6 mg, 0.031 mmol, 89% yield). MS (M⁺¹) m/z: 359.3 (MH⁺). LC retention time 1.12 min [A1]. ¹H NMR (500 MHz, DMSO-d₆) δ 11.01-10.87 (m, 1H), 8.28-8.14 (m, 1H), 7.56-7.37 (m, 2H), 7.31-7.24 (m, 1H), 7.08-6.93 (m, 1H), 6.18-5.97 (m, 1H), 3.20-3.16 (m, 1H), 2.95-2.87 (m, 1H), 2.80-2.73 (m, 3H), 2.27-2.20 (m, 3H), 1.90-1.85 (m, 5H), 1.77-1.68 (m, 2H), 1.11-0.98 (m, 3H).

The following example was prepared according to the general procedure for Examples 246.

TABLE 12

| Ex. No | Structure | LCMS [M + H]⁺ | Rt (min) | Method |
|---|---|---|---|---|
| 247 | 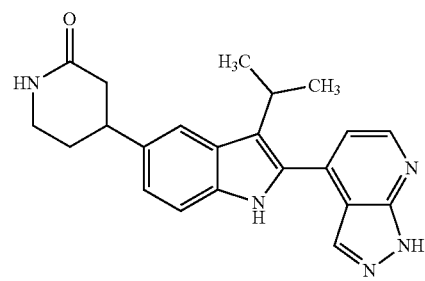 | 373.2 | 0.9 | QC-ACN-TFA-XB |

Example 248

4-(3-Isopropyl-2-(1H-pyrazolo[3,4-b]pyridin-4-yl)-1H-indol-5-yl)piperidin-2-one

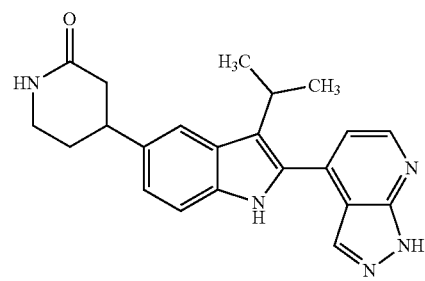
(248)

Intermediate 248A: Tert-butyl 2-oxo-4-(((trifluoromethyl)sulfonyl)oxy)-5,6-dihydropyridine-1(2H)-carboxylate

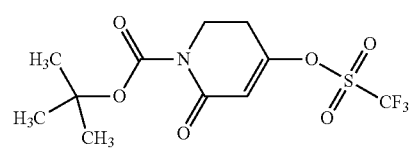
(248A)

To a stirred solution of tert-butyl 2,4-dioxopiperidine-1-carboxylate (3 g, 14.07 mmol) in DCM (60 mL) were added Et₃N (3.92 mL, 28.1 mmol) and N,N-bis(trifluoromethylsulfonyl)aniline (6.03 g, 16.88 mmol) respectively at 0° C. The reaction mixture was stirred for 1 h at 0° C., then warmed to room temperature, and stirred for 2 h. The reaction was quenched with 1 N HCl, extracted with DCM (2×100 mL), dried over sodium sulphate, and concentrated to afford crude material. The crude material was purified by ISCO using 40 g silica column. The compound was eluted in 40% in hexanes. The fraction was collected and concentrated to afford tert-butyl 2-oxo-4-(((trifluoromethyl) sulfonyl)oxy)-5,6-dihydropyridine-1(2H)-carboxylate (3.2 g, 9.27 mmol, 66% yield) as a white solid. $^1$H NMR (400 MHz, DMSO-$d_6$) δ ppm 6.2 (s, 1H), 4.26 (t, J=8.4 Hz, 2H), 2.86 (t, J=8.4 Hz, 2H), 1.44 (9H).

Intermediate 248B: 5-Bromo-3-isopropyl-1H-indole

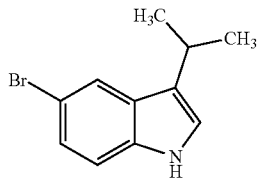

(248B)

A 250 mL round bottom flask was charged with triethylslilane (8.90 g, 77 mmol), trichloroacetic acid (6.25 g, 38.3 mmol) and toluene (50 mL). The solution was heated to 70° C., then a solution of 5-bromo-1H-indole (5.0 g, 25.5 mmol) and acetone (2.247 mL, 30.6 mmol) in toluene (30 mL) was added drop wise. The resulting brown solution was heated at 70° C. for 1.5 h. The solution was cooled to 10° C. The reaction was quenched with 10% sodium bicarbonate. The reaction mixture was diluted with diethyl ether. The organic layer was separated, dried and concentrated under vacuum to afford crude compound. The crude was purified using silica gel chromatography eluting with 5% ethyl acetate in hexanes to afford 5-bromo-3-isopropyl-1H-indole (5.5 g, 23.10 mmol 95% yield) as an oil. MS (M$^{+1}$) m/z: 238.3 (MH$^+$). LC retention time 1.55 min [L].

Intermediate 248C: 3-isopropyl-5-(4,4,5,5-tetramethyl-1,3,2-dioxaborolan-2-yl)-1H-indole

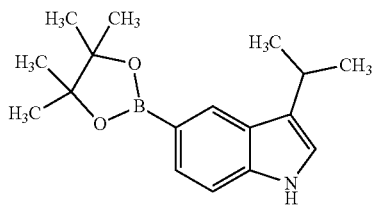

(248C)

To a stirred solution of 5-bromo-3-isopropyl-1H-indole (2 g, 8.40 mmol) and 4,4,4',4',5,5,5',5'-octamethyl-2,2'-bi(1,3,2-dioxaborolane) (3.84 g, 15.12 mmol) in dioxane (25 mL), was added potassium acetate (3.30 g, 33.6 mmol). The mixture was degassed for 10 min., followed by the addition of PdCl₂(dppf)-CH₂Cl₂ adduct (0.686 g, 0.840 mmol). The mixture was degassed again for 10 min and stirred at 90° C. for 16 h. The reaction mixture was brought to room temperature, filtered through a celite bed, washed with EtOAC, and concentrated to afford crude compound. The crude mass was purified by ISCO using 24 g silica column. The compound was eluted in 15% EA in hexanes. The fractions were collected and concentrated to afford 3-isopropyl-5-(4,4,5,5-tetramethyl-1,3,2-dioxaborolan-2-yl)-1H-indole (2 g, 7.01 mmol, 83% yield) as an off-white solid. MS (M$^{+1}$) m/z: 286.4 (MH$^+$). LC retention time 1.68 min [L].

Intermediate 248D: tert-Butyl 4-(3-isopropyl-1H-indol-5-yl)-6-oxo-3,6-dihydropyridine-1(2H)-carboxylate

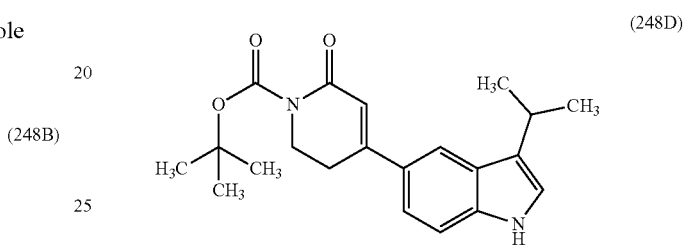

(248D)

To a stirred solution of 3-isopropyl-5-(4,4,5,5-tetramethyl-1,3,2-dioxaborolan-2-yl)-1H-indole (400 mg, 1.403 mmol), tert-butyl 2-oxo-4-(((trifluoromethyl)sulfonyl)oxy)-5,6-dihydropyridine-1(2H)-carboxylate (581 mg, 1.683 mmol) in THF (15 mL), and water (0.5 mL) was added potassium phosphate tribasic (893 mg, 4.21 mmol). The mixture was degassed with N₂ for 10 min, then PdCl₂(dppf)-CH₂Cl₂ adduct (57.3 mg, 0.07 mmol) was added. The mixture was degassed again for 10 min. The mixture was stirred at 75° C. for 16 h. The reaction mixture was brought to room temperature, extracted with EtOAc (2×30 mL), washed with water, brine, dried (Na₂SO₄), and concentrated to afford crude compound. The crude material was purified by ISCO using 24 g silica column. The compound was eluted in neat ethyl acetate, the fractions were collected and concentrated to afford tert-butyl 4-(3-isopropyl-1H-indol-5-yl)-2-oxo-5,6-dihydropyridine-1(2H)-carboxylate (400 mg, 1.129 mmol, 80% yield) as a brown solid. MS (M$^{+1}$) m/z: 299.4 (MH$^+$-tertbutyl). LC retention time 1.13 min [L].

Intermediate 248E: tert-Butyl 4-(3-isopropyl-1H-indol-5-yl)-2-oxopiperidine-1-carboxylate

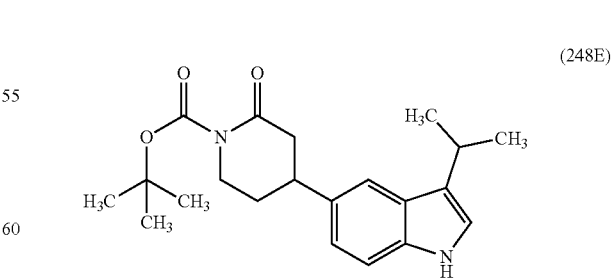

(248E)

To a stirred solution of tert-butyl 4-(3-isopropyl-1H-indol-5-yl)-2-oxo-5,6-dihydropyridine-1(2H)-carboxylate (400 mg, 1.129 mmol) in ethyl acetate (15 mL) was added Pd/C (120 mg, 1.129 mmol) at room temperature. The slurry was stirred at same temperature under H₂ bladder pressure for 16 h. The reaction mixture was filtered through celite bed washed with MeOH. The filtrates were collected and concentrated to afford tert-butyl 4-(3-isopropyl-1H-indol-5-yl)-2-oxopiperidine-1-carboxylate (200 mg, 0.561 mmol, 50% yield) as an off white solid. MS (M$^{+1}$) m/z: 301.4 (MH$^+$-tertbutyl). LC retention time 1.14 min [L].

Intermediate 248F: tert-Butyl 4-(2-bromo-3-isopropyl-1H-indol-5-yl)-2-oxopiperidine-1-carboxylate

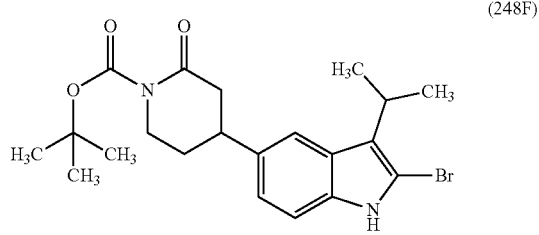 [SMILES: CC(C)c1c(Br)[nH]c2ccc(C3CCN(C(=O)OC(C)(C)C)C(=O)C3)cc12]

(248F)

To a stirred solution of tert-butyl 4-(3-isopropyl-1H-indol-5-yl)-2-oxopiperidine-1-carboxylate (200 mg, 0.561 mmol) in DCE (2 mL) was added NBS (80 mg, 0.449 mmol) dissolved in DCE (2 mL) at room temperature. The reaction mixture was stirred at same temperature for 20 min. The reaction mixture was diluted with water and extracted with DCM (2×20 mL). The combined organic extracts were dried (Na₂SO₄) and concentrated to afford crude compound. The crude material was purified by ISCO using 12 g silica column. The compound was eluted in 80% EA in hexanes, the fractions were collected and concentrated to afford tert-butyl 4-(2-bromo-3-isopropyl-1H-indol-5-yl)-2-oxopiperidine-1-carboxylate (100 mg, 0.230 mmol, 41% yield) as a brown solid. MS (M$^{+1}$) m/z: 379.2 (MH$^+$-tertbutyl). LC retention time 1.22 min [L].

Intermediate 248G: tert-Butyl 4-(3-isopropyl-2-(1-trityl-1H-pyrazolo[3,4-b]pyridin-4-yl)-1H-indol-5-yl)-2-oxo piperidine-1-carboxylate

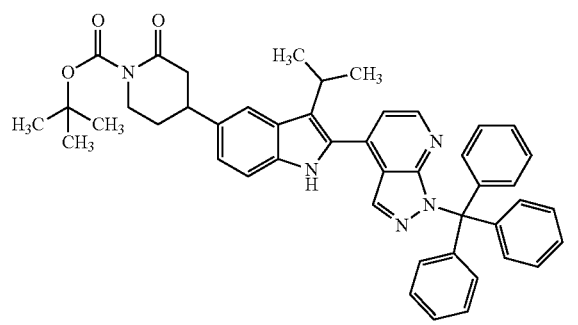

(248G)

To a stirred solution of tert-butyl 4-(2-bromo-3-isopropyl-1H-indol-5-yl)-2-oxopiperidine-1-carboxylate (50 mg, 0.115 mmol) and 4-(4,4,5,5-tetramethyl-1,3,2-dioxaborolan-2-yl)-1-trityl-1H-pyrazolo[3,4-b]pyridine (67.2 mg, 0.138 mmol) in a THF (5 mL) and water (0.2 mL) solvent mixture was added potassium phosphate tribasic (73.1 mg, 0.345 mmol). The mixture was degassed with N₂ for 10 min. Next, PdCl₂(dppf)-CH₂Cl₂ adduct (4.69 mg, 5.74 μmol) was added and the mixture was degassed again for 10 min. The reaction mixture was stirred at 80° C. for 16 h. The reaction mixture was brought to room temperature and filtered through celite bed washed with EtOAc. The filtrates were collected and concentrated to afford crude tert-butyl 4-(3-isopropyl-2-(1-trityl-1H-pyrazolo[3,4-b] pyridin-4-yl)-1H-indol-5-yl)-2-oxopiperidine-1-carboxylate (60 mg, 0.084 mmol, 73.0% yield) as a brown liquid. MS (M$^{+1}$) m/z: 716.5 (MH$^+$). LC retention time 1.46 min [L].

Example 248

To a stirred solution of tert-butyl 4-(3-isopropyl-2-(1-trityl-1H-pyrazolo[3,4-b]pyridin-4-yl)-1H-indol-5-yl)-2-oxopiperidine-1-carboxylate (60 mg, 0.084 mmol) in DCM (1 mL) was added 4 M HCl in 1,4-dioxane (0.2 mL) at room temperature. The mixture was stirred at room temperature for 16 h. The reaction mass was concentrated to afford the crude compound. The crude compound was purified by preparative LCMS purification. The fractions containing the desired product were combined and dried via centrifugal evaporation to afford 4-(3-isopropyl-2-(1H-pyrazolo[3,4-b]pyridin-4-yl)-1H-indol-5-yl)piperidin-2-one (3 mg, 7.79 μmol, 9.30% yield). MS (M$^{+1}$) m/z: 374.3 (MH$^+$). LC retention time 1.25 min [E]. $^1$H NMR (400 MHz, DMSO-d₆) δ ppm 13.79 (s, 1H), 11.25 (s, 2H), 8.60 (d, J=5.0 Hz, 1H), 8.18-8.14 (m, 1H), 7.67 (s, 1H), 7.56 (s, 1H), 7.39 (d, J=8.0 Hz, 1H), 7.20 (d, J=5.0 Hz, 1H), 7.11 (d, J=1.5 Hz, 1H), 3.25-3.17 (m, 4H), 2.40-2.32 (m, 3H), 2.02-1.91 (m, 2H), 1.44 (d, J=7.0 Hz, 6H).

Example 249

4-(3-isopropyl-5-(piperidin-4-yl)-6-(trifluoromethyl)-1H-indol-2-yl)-1H-pyrazolo[3,4-b]pyridine

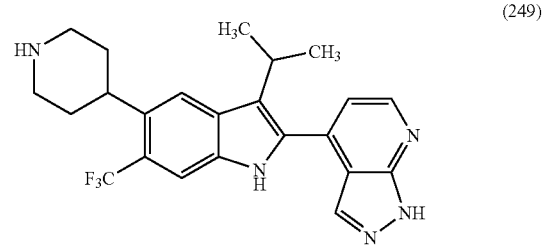 [SMILES: CC(C)c1c(-c2ccnc3[nH]ncc23)[nH]c2cc(C(F)(F)F)c(C3CCNCC3)cc12]

(249)

Intermediate 249A: 5-chloro-3-isopropyl-6-(trifluoromethyl)-1H-indole

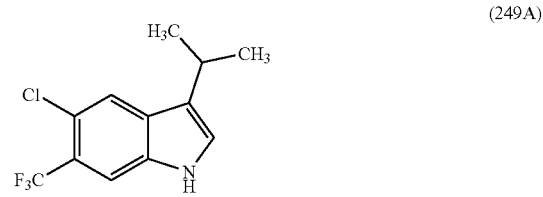 [SMILES: CC(C)c1c[nH]c2cc(C(F)(F)F)c(Cl)cc12]

(249A)

A 250 ml round bottom flask was charged with triethylsilane (2.18 ml, 13.66 mmol), trichloroacetic acid (1.12 g, 6.83 mmol) and toluene (10 mL). The solution was heated to 70° C. Next, a solution of 5-chloro-6-(trifluoromethyl)-1H-indole (1.000 g, 4.55 mmol) and acetone (0.401 mL, 5.46 mmol) in toluene (20 mL) was added drop-wise via an addition funnel. The resulting brown solution was heated at 90° C. for 2.5 hours. The solution was cooled to 10° C. The reaction was quenched with 2 M potassium phosphate solution. The mixture was diluted with diethyl ether. The organic layer was separated, dried and concentrated under vacuum to get crude compound. The crude was purified using silica gel chromatography (ISCO 40 g column) eluting with 0-40% ethyl acetate in hexanes over a run time of 15 minutes to afford 5-chloro-3-isopropyl-6-(trifluoromethyl)-1H-indole (1.063 g, 4.06 mmol, 89% yield) as an oil. LCMS retention time 3.16 min [Method F1].

Intermediate 249B: Tert-butyl 4-(3-isopropyl-6-(trifluoromethyl)-1H-indol-5-yl)-5,6-dihydropyridine-1(2H)-carboxylate

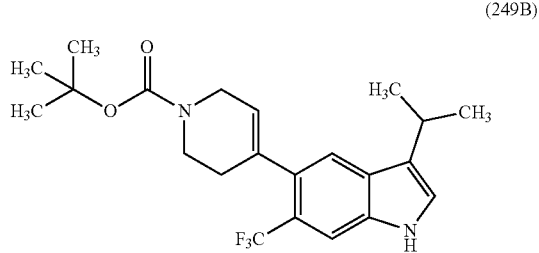

(249B)

To a mixture of 5-chloro-3-isopropyl-6-(trifluoromethyl)-1H-indole (0.500 g, 1.91 mmol, 2nd generation XPhos precatalyst (0.038 g, 0.048 mmol) and tert-butyl 4-(4,4,5,5-tetramethyl-1,3,2-dioxaborolan-2-yl)-5,6-dihydropyridine-1(2H)-carboxylate (0.620 g, 2.006 mmol) in a 40 ml reaction vial were added THF (5.0 mL), followed by a 3 M aqueous solution of tripotassium phosphate (1.91 mL, 5.73 mmol). The flask was fitted with a reflux condenser and septum. The system was evacuated under vacuum (via a needle from a nitrogen/vacuum manifold line) and back-filled with nitrogen gas. The procedure was repeated three times. The needle was removed and the reaction mixture was heated at 50° C. for 1 hour. The reaction mixture was diluted with ethyl acetate (100 mL), poured into a separatory funnel and washed with water (2×50 mL) and saturated aqueous sodium chloride solution (50 mL). The combined organics were dried over anhydrous sodium sulfate, filtered and the filtrate was concentrated in vacuo to give crude product. The crude was purified using silica gel chromatography (ISCO 40 g column) eluting with 0-50% ethyl acetate in hexanes over a run time of 12 minutes to afford tert-butyl 4-(3-isopropyl-6-(trifluoromethyl)-1H-indol-5-yl)-5,6-dihydropyridine-1(2H)-carboxylate (0.700 g, 1.72 mmol, 89% yield). LCMS retention time 1.21 min [Method B1]. MS (E⁻) m/z: 353.4 (M–H) (minus t-butyl of boc group).

Intermediate 249C: Tert-butyl 4-(3-isopropyl-6-(trifluoromethyl)-1H-indol-5-yl) piperidine-1-carboxylate

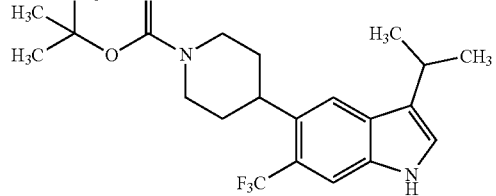

(249C)

To a 50 ml round bottom flask were added tert-butyl 4-(3-isopropyl-6-(trifluoromethyl)-1H-indol-5-yl)-5,6-dihydropyridine-1(2H)-carboxylate (0.700 g, 1.72 mmol) and ethyl acetate (10 ml). The flask was purged with nitrogen gas and 10% Pd/C (0.203 g, 0.191 mmol) was added. Following pump/purging with nitrogen gas three times, hydrogen gas was introduced via a balloon. The reaction mixture was stirred at room temperature overnight. The flask was evacuated and filled with nitrogen gas. The suspension was diluted with methanol (100 ml) and filtered through fluted filter paper and the filtrate was concentrated in vacuo to afford tert-butyl 4-(3-isopropyl-6-(trifluoromethyl)-1H-indol-5-yl) piperidine-1-carboxylate (0.550 g, 1.35 mmol, 70% yield) as an off-white solid. LC retention time 1.21 min [Method B1]. MS (E⁻) m/z: 355.4 (M–H) (minus t-butyl of boc group).

Intermediate 249D: Tert-butyl 4-(2-bromo-3-isopropyl-6-(trifluoromethyl)-1H-indol-5-yl)piperidine-1-carboxylate

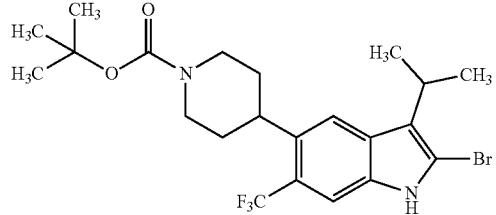

(249D)

To a solution of tert-butyl 4-(3-isopropyl-6-(trifluoromethyl)-1H-indol-5-yl) piperidine-1-carboxylate (0.590 g, 1.437 mmol) in DCM (20 mL) at 0° C., was added NBS (0.230 g, 1.365 mmol) in DCM (2.0 mL) drop-wise, via a pipet over 2 minutes. The resulting brown solution was stirred at room temperature for 15 minutes. The reaction was quenched with a 10% sodium sulfite solution (5 mL). The residue was diluted with DCM (50 mL) and water (20 ml) and the mixture was poured into a separatory funnel. The aqueous layer was separated. The organics were then washed with a saturated sodium chloride solution (20 ml), dried over anhydrous sodium sulfate, filtered and concentrated to give crude compound. The crude material was purified by ISCO using a 24 g silica column, eluting with 0-100% ethyl acetate in hexanes. The combined fractions were concentrated to give tert-butyl 4-(2-bromo-3-isopropyl-6-(trifluoromethyl)-1H-indol-5-yl)piperidine-1-carboxylate (0.460 g, 0.940 mmol, 65% yield) as a tan solid. LC retention time 1.26 min [Method B1]. MS (E⁻) m/z: 435.2 (M−H) (minus t-butyl of boc group).

Example 249

To a 2 dram reaction vial were added tert-butyl 4-(2-bromo-3-isopropyl-6-(trifluoromethyl)-1H-indol-5-yl)-5,6-dihydropyridine-1(2H)-carboxylate (0.060 g, 0.123 mmol), 4-(4,4,5,5-tetramethyl-1,3,2-dioxaborolan-2-yl)-1-trityl-1H-pyrazolo[3,4-b]pyridine (0.072 g, 0.148 mmol), PdCl₂(dppf)-CH₂Cl₂ adduct (0.005 g, 0.0061 mmol), THF (1.0 ml) and a 3 M tribasic potassium phosphate solution (0.123 mL, 0.369 mmol). The reaction mixture was degassed with nitrogen gas for 1 minutes and then heated at 65° C. for 1 hour. The reaction mixture was cooled to room temperature and diluted with ethyl acetate and water. The mixture was transferred to a separatory funnel and the layers were separated. The organics were then washed with a saturated sodium chloride solution, dried over anhydrous sodium sulfate, filtered and concentrated to dryness to afford tert-butyl 4-(3-isopropyl-6-(trifluoromethyl)-2-(1-trityl-1H-pyrazolo[3,4-b]pyridin-4-yl)-1H-indol-5-yl) piperidine-1-carboxylate. To the solid material were added DCM (0.5 ml) and 4 M HCl in dioxane (1.0 ml). The mixture was capped and stirred at room temperature for 1 hour, then concentrated to dryness under a stream of nitrogen gas. The residue was taken up in DMF (1 mL) and the solids were filtered through a 0.45 micron syringe filter. The crude material was purified via preparative LC/MS. Fractions containing the desired product were combined and dried via centrifugal evaporation to afford 4-(3-isopropyl-5-(piperidin-4-yl)-6-(trifluoromethyl)-1H-indol-2-yl)-1H-pyrazolo[3,4-b]pyridine (0.0038 g, 0.085 mmol, 7% yield). HPLC RT=1.103, M⁺¹=426.1, Method C1. HPLC RT=1.084, M⁺¹=426.2, Method D1. ¹H NMR (400 MHz, METHANOL-d₄) δ 8.84 (d, J=5.5 Hz, 1H), 8.64 (s, 1H), 8.04 (s, 1H), 7.91 (s, 1H), 7.59 (d, J=5.7 Hz, 1H), 4.86 (s, 3H), 3.66-3.49 (m, 4H), 3.31-3.18 (m, 2H), 2.24-2.11 (m, 4H), 1.60 (d, J=7.0 Hz, 6H).

Example 250

4-(3-isopropyl-6-methyl-5-(piperidin-4-yl)-1H-indol-2-yl)-1H-pyrazolo[3,4-b]pyridine (250)

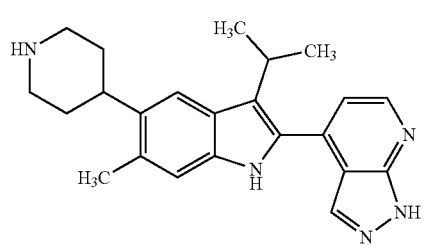

Intermediate 250A: Tert-butyl 5-chloro-3-isopropyl-6-methyl-1H-indole-1-carboxylate (250A)

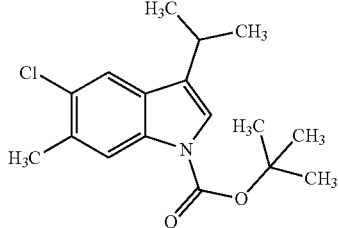

A 250 ml round bottom flask was charged with triethylsilane (29.4 ml, 184 mmol), trichloroacetic acid (15.0 g, 92.0 mmol) and toluene (75 mL). The solution was heated to 70° C., then a solution of 5-bromo-1H-indole (8.0 g, 61.0 mmol) and acetone (4.27 g, 73.6 mmol) in toluene (25 mL) was added drop-wise via an addition funnel. The resulting brown solution was heated at 90° C. for 4 h. The solution was cooled to 10° C. The reaction was quenched with 2 M potassium phosphate solution. The mixture was diluted with diethyl ether. The organic layer was separated, dried, and concentrated under vacuum to afford crude compound. The crude material was purified using silica gel chromatography (ISCO 80 g column) eluting with 0-15% ethyl acetate in hexanes over a run time of 12 minutes to afford 6-methyl-3-isopropyl-1H-indole (5.41 g, 31% yield) as a tan solid. LC retention time=1.37 min [Method A1]. MS (E⁻) m/z: 308.0 (M−H).

Intermediate 250B tert-butyl 5-(1-(tert-butoxycarbonyl)-1,2,3,6-tetrahydropyridin-4-yl)-3-isopropyl-6-methyl-1H-indole-1-carboxylate (250B)

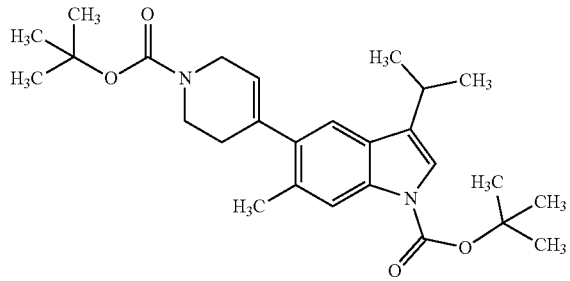

To a mixture of tert-butyl 5-chloro-3-isopropyl-6-methyl-1H-indole-1-carboxylate (0.600 g, 1.949 mmol), 2nd generation XPhos precatalyst (0.153 g, 0.195 mmol) and tert-butyl 4-(4,4,5,5-tetramethyl-1,3,2-dioxaborolan-2-yl)-5,6-dihydropyridine-1(2H)-carboxylate (0.633 g, 2.047 mmol) in a 40 ml reaction vial were added THF (10 mL) followed by an aqueous solution of tripotassium phosphate (1.949 mL, 5.85 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 75° C. for 18 hours. Upon cooling to room temperature, the reaction mixture was diluted with EtOAc (100 mL), poured into a separatory funnel, washed with water (2×50 mL) and a saturated aqueous NaCl solution (50 mL), dried over anhydrous sodium sulfate, and filtered. The filtrate was concentrated in vacuo to give crude product. The crude product was purified on silica gel and following concentration of the fractions, afforded tert-butyl 5-(1-(tert-butoxycarbonyl)-1,2,3,6-tetrahydropyridin-4-yl)-3-isopropyl-6-methyl-1H-indole-1-carboxylate (0.381 g, 0.750 mmol, 50% yield). LC retention time=1.37 min [Method F1]. MS (E⁻) m/z: 455.2 (M−H).

Intermediate 250C: tert-butyl 5-(1-(tert-butoxycarbonyl)piperidin-4-yl)-3-isopropyl-6-methyl-1H-indole-1-carboxylate

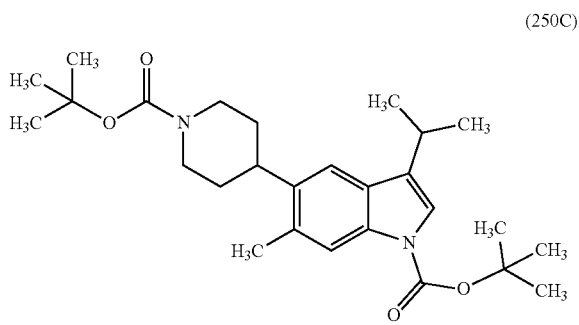 [SMILES: Cc1cc2c(cc1C1CCN(C(=O)OC(C)(C)C)CC1)c(C(C)C)cn2C(=O)OC(C)(C)C]

To a Parr bottle were added tert-butyl 5-(1-(tert-butoxycarbonyl)-1,2,3,6-tetrahydropyridin-4-yl)-3-isopropyl-6-methyl-1H-indole-1-carboxylate (0.381 g, 0.750 mmol), MeOH (7.0 ml), and under a stream of nitrogen gas, Pd(OH)$_2$ (0.137 g, 0.195 mmol). The vessel was pump/purged with nitrogen gas three times, then evacuated and back-filled with hydrogen gas to 55 psi. The reaction mixture was allowed to shake at room temperature overnight. The reaction mixture was filtered through fluted paper and concentrated to afford tert-butyl 5-(1-(tert-butoxycarbonyl)piperidin-4-yl)-3-isopropyl-6-methyl-1H-indole-1-carboxylate (0.333 g, 0.729 mmol, 37.4% yield).

Intermediate 250D: tert-butyl 2-bromo-5-(1-(tert-butoxycarbonyl)-1,2,3,6-tetrahydropyridin-4-yl)-3-isopropyl-6-methyl-1H-indole-1-carboxylate

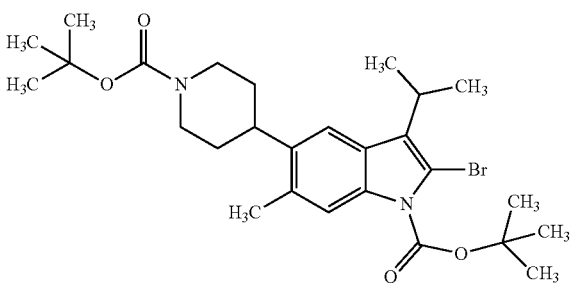

To a 100 ml round bottom flask were added tert-butyl 5-(4-(tert-butoxycarbonyl) piperazin-1-yl)-3-isopropyl-6-methyl-1H-indole-1-carboxylate (0.150 g, 0.329 mmol) and DCM (3.0 mL). NBS (0.058 g, 0.329 mmol) was dissolved in DCM (2.0 ml) and added drop-wise to the reaction mixture via a pipet over 1 minute. The reaction mixture was stirred for 15 minutes at room temperature. The reaction was quenched with the addition of a 10% sodium sulfite solution (2.0 ml). The mixture was diluted with DCM and the contents poured in a separatory funnel. Water was added and the layers were separated. The organics were washed with saturated sodium chloride solution, dried over anhydrous sodium sulfate, filtered and concentrated to afford tert-butyl 2-bromo-5-(1-(tert-butoxycarbonyl)-1,2,3,6-tetrahydropyridin-4-yl)-3-isopropyl-6-methyl-1H-indole-1-carboxylate (0.125 g, 0.233 mmol, 71% yield.

Example 250

To a 2 dram vial were added tert-butyl 2-bromo-5-(1-(tert-butoxycarbonyl)piperidin-4-yl)-3-isopropyl-6-methyl-1H-indole-1-carboxylate (0.040 g, 0.075 mmol), and tert-butyl 4-(4,4,5,5-tetramethyl-1,3,2-dioxaborolan-2-yl)-1H-pyrazolo[3,4-b] pyridine-1-carboxylate (0.031 g, 0.090 mmol), 2nd generation XPhos precatalyst (2.4 mg, 2.73 µmol) and THF (1.0 ml). To this mixture was added a 3 M potassium phosphate solution (0.075 mL, 0.224 mmol). The vial was capped and pump/purged with nitrogen three times. The reaction mixture was heated at 70° C. for 1 hour. The mixture was concentrated under a stream of nitrogen gas. The crude residue was diluted with DCM and the organics were washed with water and then brine. The combined extracts were dried over anhydrous sodium sulfate, filtered and concentrated in vacuo. The crude product was treated with TFA (0.100 ml) in DCM (1.0 ml) for 30 minutes at room temperature. The reaction mixture was concentrated. The residue was taken up in DMF (1 mL). The solids were filtered through a 0.45 micron syringe filter and the crude material was purified via preparative LC/MS. Fractions containing the desired product were combined and dried via centrifugal evaporation to afford tert-butyl 4-(4,4,5,5-tetramethyl-1,3,2-dioxaborolan-2-yl)-1H-pyrazolo[3,4-b] pyridine-1-carboxylate (0.0071 g, 0.018 mmol, 25% yield). HPLC RT=1.109, M⁺¹=374.1, Method C1. HPLC RT=0.820, M⁺¹=374.3, Method D1. ¹H NMR (500 MHz, DMSO-d$_6$) δ 11.19-11.01 (m, 1H), 8.59 (d, J=4.4 Hz, 1H), 8.12 (s, 1H), 7.57 (s, 1H), 7.31-7.10 (m, 2H), 3.68-3.49 (m, 1H), 3.33 (dt, J=13.8, 6.9 Hz, 1H), 3.24 (br d, J=11.4 Hz, 2H), 2.96 (br t, J=11.4 Hz, 1H), 2.92-2.80 (m, 2H), 2.55 (s, 3H), 2.41 (s, 3H), 1.79 (br s, 2H), 1.44 (br d, J=6.7 Hz, 6H).

Example 251

4-(3-ethyl-7-fluoro-5-(piperidin-4-yl)-1H-indol-2-yl)-1H-pyrazolo[3,4-b]pyridine

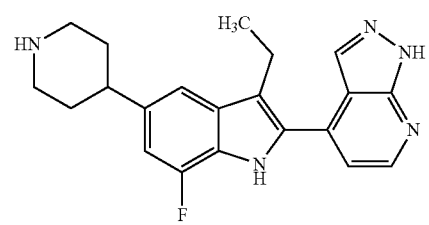

Intermediate 251A: 5-bromo-3-ethyl-7-fluoro-1H-indole

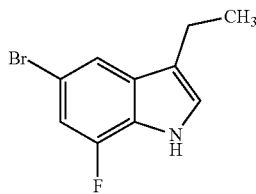
(251A)

To a tall reaction vial were added 5-bromo-7-fluoro-1H-indole (1.000 g, 4.67 mmol), Shvo's Catalyst (0.051 g, 0.047 mmol), potassium carbonate (0.032 g, 0.234 mmol), and diethylamine (0.683 g, 9.34 mmol). The reaction mixture was purged with nitrogen gas and heated to 155° C. for 12 hours. The reaction mixture was concentrated under a stream of nitrogen gas. The resulting residue was diluted with DCM and charged to 40G ISCO column, which was eluted with 0-100% ethyl acetate/hexane. The fractions were concentrated to afford 5-bromo-3-ethyl-7-fluoro-1H-indole as a brownish oil (0.650 g, 57%). LC retention time=1.42 min [Method A1]. MS (E⁻) m/z: 243 (M−H).

Intermediate 251B: tert-butyl 4-(3-ethyl-7-fluoro-1H-indol-5-yl)piperidine-1-carboxylate

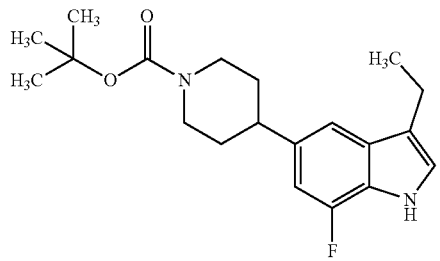
(251B)

To a mixture of 5-bromo-3-ethyl-7-fluoro-1H-indole (0.149 g, 0.615 mmol), PdCl₂(dppf)-CH₂Cl₂ adduct (0.013 g, 0.015 mmol), and tert-butyl 4-(4,4,5,5-tetramethyl-1,3,2-dioxaborolan-2-yl)-5,6-dihydropyridine-1(2H)-carboxylate (0.200 g, 0.646 mmol) in a 40 ml reaction vial were added THF (5 mL) followed by an aqueous 3 M solution of tripotassium phosphate (0.615 mL, 1.85 mmol). The vial was fitted with a Teflon-lined septum cap. The system was evacuated under vacuum (via a needle from a nitrogen/vacuum manifold line) and back-filled with nitrogen gas. The procedure was repeated three times. The needle was removed and the vial was heated at 75° C. for 18 hours. The reaction mixture was diluted with EtOAc (100 mL), poured into a separatory funnel and washed with water (2×50 mL) and saturated aqueous sodium chloride solution (50 mL). The organics were collected and dried over anhydrous sodium sulfate. The suspension was filtered and the filtrate concentrated in vacuo to give crude product. The crude product was purified using a 24G ISCO silica gel column, which was eluted with 0-50% ethyl acetate/hexane over a 20 minute period. The fractions were concentrated to afford tert-butyl 4-(3-ethyl-7-fluoro-1H-indol-5-yl)-5,6-dihydropyridine-1(2H)-carboxylate. LC retention time=1.52 min [Method A1]. MS (E⁻) m/z: 345 (M−H).

In a 100 ml round bottom flask were added tert-butyl 4-(3-ethyl-7-fluoro-1H-indol-5-yl)-5,6-dihydropyridine-1(2H)-carboxylate and ethyl acetate (5 ml). The flask was purged with nitrogen gas and 10% Pd/C (0.033 g, 0.031 mmol) was added. Following pump/purging with nitrogen gas three times, hydrogen gas was introduced via a balloon. The reaction mixture was stirred at room temperature overnight. The flask was evacuated and filled with nitrogen gas. The suspension was filtered through fluted filter paper and the filtrate was concentrated in vacuo to afford tert-butyl 4-(3-ethyl-7-fluoro-1H-indol-5-yl)piperidine-1-carboxylate (0.189 g, 89% yield). LC retention time=1.52 min [Method A1]. MS (E⁻) m/z: 347 (M−H).

Intermediate 251C: tert-butyl 4-(2-bromo-3-ethyl-7-fluoro-1H-indol-5-yl)piperidine-1-carboxylate

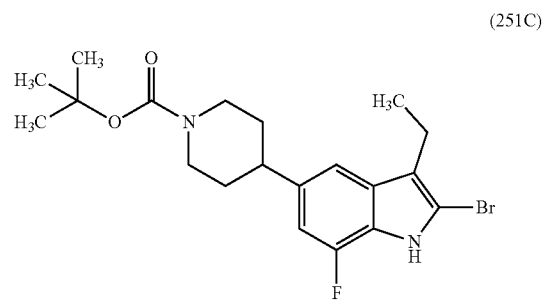 [SMILES: CCc1c(Br)[nH]c2c(F)cc(C3CCN(C(=O)OC(C)(C)C)CC3)cc12]
(251C)

To a 100 ml round bottom flask were added tert-butyl 4-(3-ethyl-7-fluoro-1H-indol-5-yl)piperidine-1-carboxylate (0.189 g, 0.546 mmol) and DCE (4 mL). NBS (0.092 g, 0.518 mmol) was dissolved in 1 ml of DCE and added drop-wise to the reaction mixture via a pipet over 2 minutes. The reaction was quenched with 2 ml of a 10% sodium sulfite solution. The volatiles were removed in vacuo. The residue was taken up in DCM (1 ml), filtered and loaded onto a 24G ISCO column, which was eluted using 0-50% ethyl acetate/heptane. Following concentration of fractions, tert-butyl 4-(2-bromo-3-ethyl-7-fluoro-1H-indol-5-yl)piperidine-1-carboxylate (0.210 g, 91% yield) was obtained as a white foam. LC retention time 1.61 min [Method A1]. MS (E⁻) m/z: 425/427 (M−H).

Example 251

To a 2 dram vial were added tert-butyl 4-(2-bromo-3-ethyl-7-fluoro-1H-indol-5-yl)piperidine-1-carboxylate (0.022 g, 0.052 mmol), (2-methylpyridin-4-yl)boronic acid (0.018 g, 0.129 mmol), 2nd generation XPhos precatalyst (2.035 mg, 2.59 µmol) and THF (1.0 ml). To the mixture was added a 3 M potassium phosphate solution (0.103 mL, 0.310 mmol). The vial was capped and pump/purged with nitrogen three times. The reaction mixture was heated at 65° C. for 1 hour. The mixture was concentrated under a stream of nitrogen gas. The crude residue was diluted with DCM and the organics were washed with water and then brine. The combined extracts were dried over anhydrous sodium sulfate, filtered and concentrated in vacuo. The crude product was treated with 4 M HCl/dioxane (2.0 ml) for 15 minutes. The reaction mixture was concentrated. The residue was taken up in DMF (1 mL) and the solids were filtered through a 0.45 micron syringe filter and the crude material was purified via preparative LC/MS. Fractions containing the product were combined and dried via centrifugal evaporation to afford 4-(3-ethyl-7-fluoro-5-(piperidin-4-yl)-1H-indol-2-yl)-1H-pyrazolo[3,4-b]pyridine (0.009 g, 0.024 mmol, 46% yield). HPLC RT=1.324, M+1=364.2, Method C1. HPLC RT=0.915, M+1=364.2, Method DL. $^1$H NMR (500 MHz, DMSO-$d_6$) δ 8.80-8.61 (m, 1H), 8.62 (d, J=4.7 Hz, 1H), 8.14 (s, 1H), 7.50-7.17 (m, 2H), 6.93 (d, J=12.5 Hz, 1H), 2.94-2.80 (m, 3H), 2.81-2.65 (m, 3H), 1.89-1.77 (m, 4H), 1.76-1.62 (m, 2H), 1.23 (t, J=7.4 Hz, 4H).

Example 252

4-(6-chloro-3-isopropyl-5-(piperidin-4-yl)-1H-indol-2-yl)-1H-pyrazolo[3,4-b]pyridine

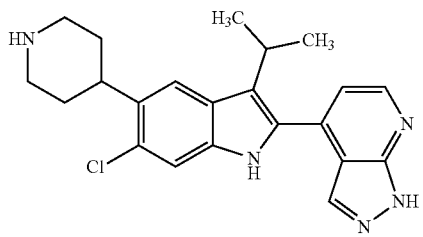

(252)

Intermediate 252A: 5-bromo-6-chloro-3-isopropyl-1H-indole

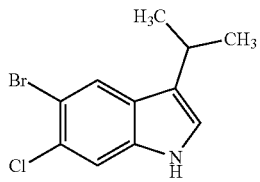

(252A)

In two separate 30 ml pressure tubes (500 mg each) were added 5-bromo-6-chloro-1H-indole (1.000 g, 4.34 mmol), Shvo's Catalyst (0.047 g, 0.043 mmol), potassium carbonate (0.030 g, 0.217 mmol), and propane-2-amine (1.02 g, 17.25 mmol). The reaction mixture was purged with nitrogen gas and heated to 165° C. for 96 hours. The reaction mixture was concentrated under a stream of nitrogen gas. The resulting residue was purified by silica gel chromatography. Following concentration of the fractions, 5-bromo-3-isopropyl-6-chloro-1H-indole was collected as a brownish oil (0.575 g, 0.211 mmol, 49% yield). LC retention time=1.14 min [Method F1]. MS (E⁻) m/z: 271.9/273.9/275.9 (M–H).

Intermediate 252B: tert-butyl 4-(6-chloro-3-isopropyl-1H-indol-5-yl)-5,6-dihydropyridine-1(2H)-carboxylate

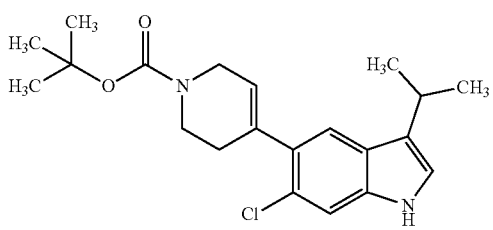

(252B)

To a mixture of 5-bromo-6-chloro-3-isopropyl-1H-indole (0.118 g, 0.433 mmol), PdCl$_2$(dppf)-CH$_2$Cl$_2$ adduct (0.018 g, 0.022 mmol), and tert-butyl 4-(4,4,5,5-tetramethyl-1,3,2-dioxaborolan-2-yl)-5,6-dihydropyridine-1(2H)-carboxylate (0.134 g, 0.433 mmol) in a screw cap vial were added THF (2.0 mL) followed by an aqueous solution of tripotassium phosphate (0.433 mL, 1.299 mmol). The vial was fitted with a Teflon lined septum cap. The system was evacuated under vacuum (via a needle from a nitrogen/vacuum manifold line) and back-filled with nitrogen gas. The procedure was repeated three times. The needle was removed and the vial was heated at 75° C. for 18 h. The reaction mixture was diluted with EtOAc (25 mL), poured into a separatory funnel, washed with water (2×15 mL) and saturated aqueous NaCl solution (5 mL), dried over anhydrous sodium sulfate, and filtered. The filtrate was concentrated in vacuo to afford crude product. The crude product was purified by silica gel chromatography. The fractions were collected to afford tert-butyl 4-(6-chloro-3-isopropyl-1H-indol-5-yl)-5,6-dihydropyridine-1(2H)-carboxylate (0.135 g, 0.360 mmol, 83% yield). LC retention time=1.02 min [Method B1]. MS (E⁻) m/z: 375.0 (M–H).

Intermediate 252C: tert-butyl 4-(6-chloro-3-isopropyl-1H-indol-5-yl)piperidine-1-carboxylate

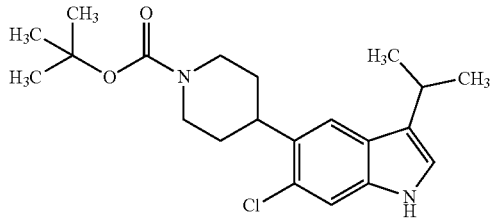

(252C)

To a 25 ml round bottom flask were added tert-butyl 4-(6-chloro-3-isopropyl-1H-indol-5-yl)-5,6-dihydropyridine-1(2H)-carboxylate (0.063 g, 0.168 mmol) and MeOH (5.0 mL). The flask was purged with nitrogen gas and platinum(iv) oxide (3.82 mg, 0.017 mmol) was added. Following pump/purging with nitrogen gas three times with vacuum, hydrogen gas was introduced, via a balloon. The reaction mixture was stirred at room temperature overnight. The flask was evacuated and back-filled with nitrogen gas. The suspension was filtered through fluted filter paper and the filtrate was concentrated to give tert-butyl 4-(6-chloro-3-isopropyl-1H-indol-5-yl)piperidine-1-carboxylate as a white solid carboxylate (0.060 g, 0.168 mmol, 98% yield). LC retention time=1.21 min [Method B1]. MS (E⁻) m/z: 377.0 (M–H).

Intermediate 252D: tert-butyl 4-(2-bromo-6-chloro-3-isopropyl-1H-indol-5-yl)piperidine-1-carboxylate

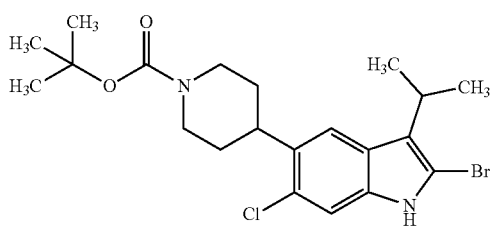

(252D)

To a solution of tert-butyl 4-(6-chloro-3-isopropyl-1H-indol-5-yl)piperidine-1-carboxylate as a white solid carboxylate (0.060 g, 0.168 mmol) and DCM (2.0 mL), NBS (0.030 g, 0.168 mmol) was dissolved in DCM (1.0 ml) and added drop-wise to the reaction mixture via an addition funnel over 1 minute. The resulting brown solution was stirred at room temperature for 15 minutes. The reaction mixture was quenched with a 10% sodium sulfite solution (1.0 mL). The residue was diluted with DCM (10 mL) and water (10 ml) and the mixture was poured into a separatory funnel. The aqueous layer was separated. The organics were then washed with a saturated sodium chloride solution (5.0 mL), dried over anhydrous sodium sulfate, filtered and concentrated to give tert-butyl 4-(2-bromo-6-chloro-3-isopropyl-1H-indol-5-yl)piperidine-1-carboxylate (0.065 g, 0.143 mmol, 85% yield). LC retention time 1.26 min [Method B1]. MS (E$^-$) m/z: 455.0 (M–H).

Intermediate 252E: Tert-butyl 4-(5-(1-(tert-butoxycarbonyl)piperidin-4-yl)-6-chloro-3-isopropyl-1H-indol-2-yl)-1H-pyrazolo[3,4-b]pyridine-1-carboxylate To a 2 dram reaction vial, tert-butyl 4-(2-bromo-3-isopropyl-6-chloro-1H-indol-5-yl) piperidine-1-carboxylate (0.050 g, 0.110 mmol) was taken in THF (2.0 mL), and tert-butyl 4-(4,4,5,5-tetramethyl-1,3,2-dioxaborolan-2-yl)-1H-pyrazolo[3,4-b]pyridine-1-carboxylate (0.038 g, 0.110 mmol), PdCl$_2$(dppf)-CH$_2$Cl$_2$ adduct (4.48 mg, 5.48 μmol), and a 3.0 M tripotassium phosphate solution (0.110 mL, 0.329 mmol) were added. The vial was capped and pump/purged with nitrogen gas three times. The reaction mixture was heated at 65° C. for 2 hours. The aqueous phase was pipetted off and the volatiles were removed under a stream of nitrogen gas. The residue was purified by silica gel chromatography and, following concentration of the fractions, tert-butyl 4-(5-(1-(tert-butoxycarbonyl)piperidin-4-yl)-6-chloro-3-isopropyl-1H-indol-2-yl)-1H-pyrazolo[3,4-b]pyridine-1-carboxylate was collected as a brownish residue (0.050 g, 0.110 mmol, 100% yield). LC retention time 1.14 min [Method B1]. MS (E$^-$) m/z: 494.1 (M–H) (massing as loss of boc group)

Example 252

Tert-butyl 4-(5-(1-(tert-butoxycarbonyl)piperidin-4-yl)-6-chloro-3-isopropyl-1H-indol-2-yl)-1H-pyrazolo[3,4-b]pyridine-1-carboxylate (0.050 g, 0.110 mmol) was treated with hydrogen chloride/dioxane (1.37 mL, 5.48 mmol). The reaction vessel was capped. The reaction mixture was stirred at room temperature for 2 hour, and then concentrated to dryness under a stream of nitrogen gas. The residue was taken up in DMF (1 mL) and the solids were filtered through a 0.45 micron syringe filter. The crude material was purified via preparative LC/MS. Fractions containing the desired product were combined and dried via centrifugal evaporation to afford 4-(6-chloro-3-isopropyl-5-(piperidin-4-yl)-1H-indol-2-yl)-1H-pyrazolo[3,4-b]pyridine (0.0018 g, 0.044 mmol, 4% yield). HPLC RT=1.271, M$^{+1}$=394.5, Method C1. HPLC RT=0.910, M$^{+1}$=394.1, Method D1. $^1$H NMR (500 MHz, DMSO-d$_6$) δ 11.60-11.23 (m, 1H), 8.62 (d, J=4.7 Hz, 1H), 8.15 (s, 1H), 7.69 (s, 1H), 7.48 (s, 1H), 7.23 (d, J=4.7 Hz, 1H), 3.40-3.28 (m, 1H), 3.14 (br d, J=11.8 Hz, 1H), 2.77-2.69 (m, 1H), 2.55 (s, 2H), 1.90-1.76 (m, 5H), 1.67 (br d, J=9.4 Hz, 2H), 1.44 (br d, J=7.1 Hz, 6H).

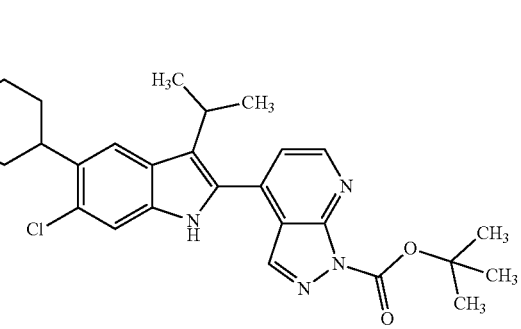

(252E)

Example 253

4-(6-fluoro-3-isopropyl-5-(piperidin-4-yl)-1H-indol-2-yl)-1H-pyrazolo[3,4-b]pyridine

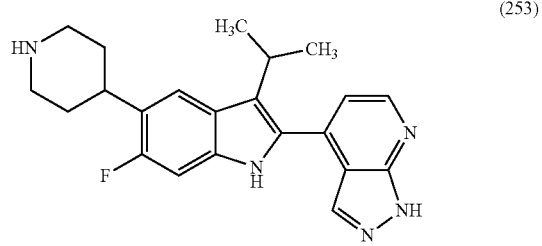 [SMILES: CC(C)c1c(-c2ccnc3[nH]ncc23)[nH]c2cc(F)c(C3CCNCC3)cc12]

(253)

Intermediate 253A:
5-chloro-6-fluoro-3-isopropyl-1H-indole

(253A)

A 250 ml round bottom flask was charged with triethylsilane (2.83 ml, 17.69 mmol), trichloroacetic acid (1.45 g, 8.85 mmol) and toluene (10 mL). The solution was heated to 70° C. and a solution of 5-chloro-6-fluoro-1H-indole (1.0 g, 5.90 mmol) and acetone (0.52 g, 7.08 mmol) in toluene (20 mL) was added drop-wise via an addition funnel. The resulting brown solution was heated at 90° C. for 2.5 hours. The solution was cooled to 10° C. The reaction mixture was quenched with 2 M potassium phosphate solution. The mixture was diluted with diethyl ether. The organic layer was separated, dried and concentrated under vacuum to get crude compound. The crude material was purified using silica gel chromatography (ISCO 24 g column) eluting with 0-40% ethyl acetate in hexanes over a run time of 10 minutes to afford 5-chloro-6-fluoro-3-isopropyl-1H-indole (1.1 g, 88% yield) as an oil. LCMS retention time 1.21 min [Method B1]. MS (E⁻) m/z: 212/214 (M–H).

Intermediate 253B: tert-butyl 4-(6-fluoro-3-isopropyl-2-(3,4-dimethoxyphenyl)-1H-indol-5-yl)-5,6-dihydropyridine-1(2H)-carboxylate

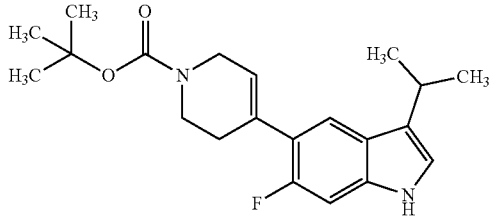
(253B)

To a mixture of 5-chloro-6-fluoro-3-isopropyl-1H-indole (1.790 g, 8.46 mmol), 2nd generation XPhos precatalyst (0.166 g, 0.211 mmol) and tert-butyl 4-(4,4,5,5-tetramethyl-1,3,2-dioxaborolan-2-yl)-5,6-dihydropyridine-1(2H)-carboxylate (2.75 g, 8.88 mmol) in a 250 ml round bottom flask were added THF (25 mL), followed by a 3 M aqueous solution of tripotassium phosphate (8.46 mL, 25.4 mmol). The flask was fitted with a reflux condenser and septum. The system was evacuated under vacuum (via a needle from a nitrogen/vacuum manifold line) and back-filled with nitrogen gas. The procedure was repeated three times. The needle was removed and the reaction mixture was heated at 50° C. for 1 hour. The reaction mixture was diluted with ethyl acetate (100 mL), poured into a separatory funnel and washed with water (2×50 mL) and saturated aqueous sodium chloride solution (50 mL). The combined organics were dried over anhydrous sodium sulfate, filtered and the filtrate was concentrated in vacuo to give crude product. The crude material was purified using silica gel chromatography (ISCO 40 g column) eluting with 0-50% ethyl acetate in hexanes over a run time of 12 minutes to afford tert-butyl 4-(6-fluoro-3-isopropyl-2-(3,4-dimethoxyphenyl)-1H-indol-5-yl)-5,6-dihydropyridine-1(2H)-carboxylate (1.4 g, 55% yield) as an oil. LCMS retention time 1.24 min [Method B1]. MS (E⁻) m/z: 359 (M–H).

Intermediate 253C: tert-butyl 4-(6-fluoro-3-isopropyl-1H-indol-5-yl)piperidine-1-carboxylate

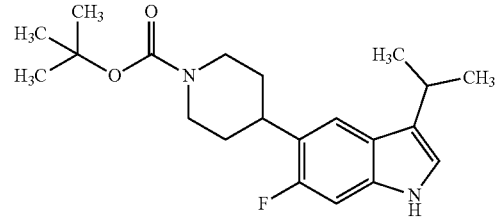
(253C)

To a 100 ml round bottom flask were added tert-butyl 4-(6-fluoro-3-isopropyl-2-(3,4-dimethoxyphenyl)-1H-indol-5-yl)-5,6-dihydropyridine-1(2H)-carboxylate (1.4 g, 3.91 mmol) and ethyl acetate (5 ml). The flask was purged with nitrogen gas and 10% Pd/C (0.325 g, 0.305 mmol) was added. Following pump/purging with nitrogen gas three times, hydrogen gas was introduced via a balloon. The reaction mixture was stirred at room temperature overnight. The flask was evacuated and filled with nitrogen gas. The suspension was diluted with methanol (100 ml) and filtered through fluted filter paper. The filtrate was concentrated in vacuo to afford tert-butyl 4-(6-fluoro-3-isopropyl-1H-indol-5-yl)piperidine-1-carboxylate (1.10 g, 88% yield) as an off-white solid. LC retention time 1.25 min [Method B1]. MS (E⁻) m/z: 361 (M–H).

Intermediate 253D: tert-butyl 4-(2-bromo-6-fluoro-3-isopropyl-1H-indol-5-yl)piperidine-1-carboxylate

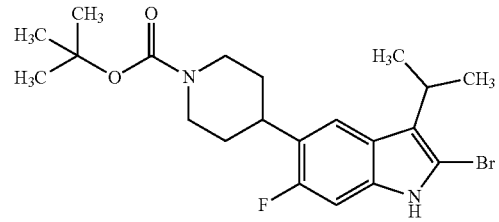
(253D)

To a solution of tert-butyl 4-(6-fluoro-3-isopropyl-1H-indol-5-yl)piperidine-1-carboxylate (1.00 g, 2.77 mmol) in DCM (20 mL) at 0° C., was added NBS (0.469 g, 2.64 mmol) in DCM (20 mL) drop-wise via an addition funnel over 10 minutes. The resulting brown solution was stirred at room temperature for 15 minutes. The reaction mixture was quenched with a 10% sodium sulfite solution (5 mL). The residue was diluted with DCM (50 mL) and water (20 ml) and the mixture was poured into a separatory funnel. The aqueous layer was separated. The organics were then washed with a saturated sodium chloride solution (20 ml), dried over anhydrous sodium sulfate, filtered and concentrated to give crude compound. The crude material was purified by ISCO using a 24 g silica column, eluting with 0-100% ethyl acetate in hexanes. The combined fractions were concentrated to give tert-butyl 4-(2-bromo-6-fluoro-3-isopropyl-1H-indol-5-yl) piperidine-1-carboxylate (0.4 g, 33% yield) as a tan solid. LC retention time 1.23 min [Method B1]. MS (E⁻) m/z: 439/441 (M−H).

Example 253

To a 2 dram reaction vial were added tert-butyl 4-(2-bromo-6-fluoro-3-isopropyl-1H-indol-5-yl)piperidine-1-carboxylate (0.150 g, 0.341 mmol), 4-(4,4,5,5-tetramethyl-1,3,2-dioxaborolan-2-yl)-1-trityl-1H-pyrazolo[3,4-b]pyridine (0.200 g, 0.410 mmol), PdCl$_2$(dppf)-CH$_2$Cl$_2$ adduct (0.014 g, 0.017 mmol), THF (1.0 ml) and a 3 M tribasic potassium phosphate solution (0.341 mL, 1.024 mmol). The reaction mixture was degassed with nitrogen gas for 5 minutes and then heated at 65° C. for 1 hour. The reaction mixture was cooled to room temperature and diluted with ethyl acetate and water. The mixture was transferred to a separatory funnel and the layers were separated. The organics were then washed with a saturated sodium chloride solution, dried over anhydrous sodium sulfate, filtered and concentrated to dryness. The residue was dissolved in DCM (1 ml) and loaded onto a 12 g ISCO column, which was eluted with 0-50% ethyl acetate/hexane with a run time of 10 minutes. The combined fractions were concentrated to give tert-butyl 4-(6-fluoro-3-isopropyl-2-(1-trityl-1H-pyrazolo[3,4-b]pyridin-4-yl)-1H-indol-5-yl)piperidine-1-carboxylate (0.175 g, 0.388 mmol, 92% yield). To this material (0.0250 g, 0.0554 mmol) were added DCM (0.5 ml) and 4 M HCl in dioxane (1.0 ml). The reaction mixture was capped and stirred at room temperature for 1 hour, then concentrated to dryness under a stream of nitrogen gas. The residue was taken up in DMF (1 mL) and the solids were filtered through a 0.45 micron syringe filter. The crude material was purified via preparative LC/MS. Fractions containing the desired product were combined and dried via centrifugal evaporation to afford 4-(6-fluoro-3-isopropyl-5-(piperidin-4-yl)-1H-indol-2-yl)-1H-pyrazolo[3,4-b]pyridine (0.010 g, 0.341 mmol, 40% yield). HPLC RT=1.567, M⁺¹=352.3, Method C1. HPLC RT=0.792, M⁺¹=352.3, Method DL. ¹H NMR (500 MHz, DMSO-d$_6$) δ 11.47-11.29 (m, 1H), 8.60 (d, J=4.5 Hz, 1H), 8.12 (s, 1H), 7.62 (br d, J=7.2 Hz, 1H), 7.28-7.12 (m, 2H), 3.40-3.20 (m, 3H), 2.95-2.80 (m, 2H), 1.87 (br s, 4H), 1.76 (s, 3H), 1.42 (br d, J=6.9 Hz, 6H).

Example 254

4-(3-ethyl-4-methyl-5-(piperidin-4-yl)-1H-indol-2-yl)-1H-pyrazolo[3,4-b]pyridine

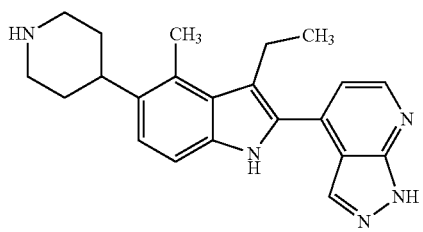

(254)

Intermediate 254A: 3-ethyl-4-methyl-1H-indole

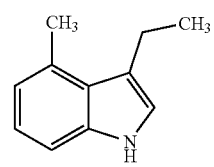

(254A)

In a steel bomb were added 4-methyl-1H-indole (3.00 g, 22.87 mmol), Shvo's catalyst (0.248 g, 0.229 mmol), potassium carbonate (0.158 g, 1.144 mmol) and diethylamine (3.35 g, 45.7 mmol). The reaction mixture was purged with nitrogen gas and heated to 155° C. for 12 hours. The reaction mixture was concentrated under a stream of nitrogen gas overnight. The resulting residue was purified by silica gel chromatography using ethyl acetate in hexane as the eluent. Like fractions were concentrated to afforded 3-ethyl-4-methyl-1H-indole (2.84 g, 17.84 mmol, 78% yield). LC retention time=1.03 min [Method A1]. MS (E⁻) m/z: 160.2 (M−H).

Intermediate 254B: Tert-butyl 4-(1-(tert-butoxycarbonyl)-3-ethyl-4-methyl-1H-indol-2-yl)-1H-pyrazolo[3,4-b]pyridine-1-carboxylate

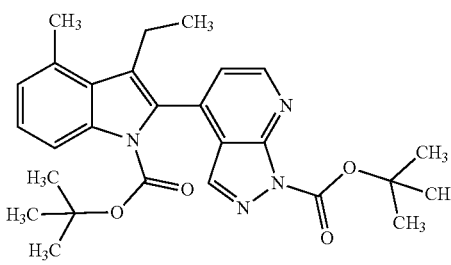

(254B)

To a solution of 3-ethyl-4-methyl-1H-indole (0.338 g, 2.123 mmol) and DCM (5.0 mL) was added drop-wise a solution of NBS (0.378 g, 2.123 mmol) dissolved in DCM (2.0 ml) via a pipet over 5 minute. The resulting solution was stirred at room temperature for 15 minutes. The reaction mixture was quenched with a 10% sodium sulfite solution (2.0 mL). The residue was diluted with DCM (10 mL) and water (10 ml) and the mixture was poured into a separatory funnel. The aqueous layer was separated. The organics were then washed with a saturated sodium chloride solution (5.0 mL), dried over anhydrous sodium sulfate, filtered and concentrated to give 2-bromo-3-ethyl-4-methyl-1H-indole.

To 2-bromo-3-ethyl-4-methyl-1H-indole were added boc-anhydride (0.986 mL, 4.25 mmol), catalytic DMAP (approximately 0.025 g) and THF (10 ml). The reaction mixture was stirred for 2 hours at room temperature, then diluted with dilute 1N HCl and extracted with ethyl acetate. The organics were washed with a saturated aqueous sodium chloride solution, dried over anhydrous sodium sulfate, filtered and concentrated. To this light oil was added tert-butyl 4-(4,4,5,5-tetramethyl-1,3,2-dioxaborolan-2-yl)-1H-pyrazolo[3,4-b]pyridine-1-carboxylate (0.806 g, 2.335 mmol), PdCl$_2$(dppf)-CH$_2$Cl$_2$ adduct (0.173 g, 0.212 mmol), THF (7.0 ml) and 3 M tribasic potassium phosphate solution (1.5 ml). The reaction mixture was purged with nitrogen gas for 2 minutes, then heated to 60° C. for 1.5 hours. The mixture was cooled and diluted with ethyl acetate and water and the mixture was poured into a separatory funnel. The aqueous layer was separated. The organics were then washed with a saturated aqueous sodium chloride solution, dried over anhydrous sodium sulfate, filtered and concentrated to give a brown residue. This crude material was purified by silica gel chromatography using ethyl acetate in hexane as the eluent. Like fractions were concentrated to afford tert-butyl 4-(1-(tert-butoxycarbonyl)-3-ethyl-4-methyl-1H-indol-2-yl)-1H-pyrazolo[3,4-b]pyridine-1-carboxylate (0.110 g, 0.231 mmol, 10% yield). LC retention time=1.22 min [Method F1]. MS (E⁻) m/z: 477.2 (M−H).

Intermediate 254C: Tert-butyl 4-(5-bromo-1-(tert-butoxycarbonyl)-3-ethyl-4-methyl-1H-indol-2-yl)-1H-pyrazolo[3,4-b]pyridine-1-carboxylate

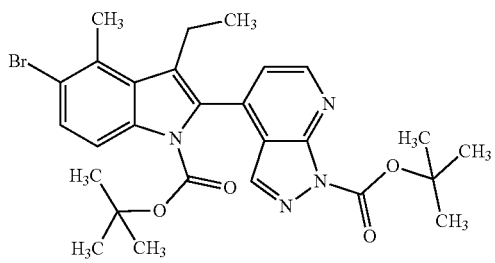

(254C)

To a solution of tert-butyl 4-(1-(tert-butoxycarbonyl)-3-ethyl-4-methyl-1H-indol-2-yl)-1H-pyrazolo[3,4-b]pyridine-1-carboxylate (0.110 g, 0.231 mmol) and DCM (2.0 mL) at −20° C., was added a solution of NBS (0.042 g, 0.231 mmol) dissolved in DCM (1.0 ml). The resulting solution was stirred at −20° C., and allowed to warm to room temperature for 5 hours. The reaction mixture was quenched with a 10% sodium sulfite solution (1.0 mL). The residue was diluted with DCM (10 mL) and water (10 ml) and the mixture was poured into a separatory funnel. The aqueous layer was separated. The organics were then washed with a saturated sodium chloride solution (5.0 mL), dried over anhydrous sodium sulfate, filtered and concentrated to afford tert-butyl 4-(5-bromo-1-(tert-butoxycarbonyl)-3-ethyl-4-methyl-1H-indol-2-yl)-1H-pyrazolo[3,4-b]pyridine-1-carboxylate. LC retention time=1.30 min [Method A1]. MS (E⁻) m/z: 555.5/557.5 (M−H).

Example 256

To tert-butyl 4-(5-bromo-1-(tert-butoxycarbonyl)-3-ethyl-4-methyl-1H-indol-2-yl)-1H-pyrazolo[3,4-b]pyridine-1-carboxylate was added tert-butyl 4-(4,4,5,5-tetramethyl-1,3,2-dioxaborolan-2-yl)-1H-pyrazolo[3,4-b]pyridine-1-carboxylate (0.082 g, 0.265 mmol), PdCl₂(dppf)-CH₂Cl₂ adduct (0.017 g, 0.021 mmol), THF (2.0 ml) and 3 M tribasic potassium phosphate solution (0.15 ml). The reaction mixture was purged with nitrogen gas for 2 minutes, then heated to 60° C. for 1.5 hours. The mixture was cooled and diluted with ethyl acetate and water and the mixture was poured into a separatory funnel. The aqueous layer was separated. The organics were then washed with a saturated aqueous sodium chloride solution, dried over anhydrous sodium sulfate, filtered and concentrated to give a brown residue. This crude material was purified by silica gel chromatography using ethyl acetate in hexane as the eluent. Following concentration of the like fractions, collected a tannish residue. To this was added MeOH (5.0 ml) and Pd(OH)₂ (0.034 g, 0.048 mmol). The vessel was placed on the Parr and pump/purged three times with nitrogen gas, then back-filled with hydrogen gas to a pressure of 50 psi. The reaction mixture was shaken for 16 hours at room temperature. The contents was diluted with MeOH, filtered through tightly packed celite and the filtrate was concentrated. This residue was diluted with DCM (0.5 ml) and then treated with TFA (1.0 mL). The reaction mixture was capped and stirred at room temperature for 2 hours, then concentrated to dryness under a stream of nitrogen gas. The residue was taken up in DMF (1 mL) and the solids were filtered through a 0.45 micron syringe filter. The crude material was purified via preparative LC/MS. Fractions containing the desired product were combined and dried via centrifugal evaporation to afford 4-(3-ethyl-4-methyl-5-(piperidin-4-yl)-1H-indol-2-yl)-1H-pyrazolo[3,4-b]pyridine (0.0005 g, 0.0015 mmol, 2% yield). HPLC RT=1.650, M⁺¹=359.3, Method C1. HPLC RT=1.440, M⁺¹=359.3, Method D1. ¹H NMR (500 MHz, DMSO-d₆) δ 8.02-7.94 (m, 1H), 7.48 (br d, J=8.8 Hz, 1H), 7.37-7.00 (m, 3H), 4.34 (br d, J=7.8 Hz, 1H), 4.05-3.96 (m, 2H), 3.97-3.78 (m, 2H), 3.46-3.32 (m, 2H), 3.12-2.87 (m, 3H), 2.65 (br s, 3H), 1.51 (br d, J=7.1 Hz, 2H), 1.10 (br t, J=7.1 Hz, 2H), 0.94 (br d, J=6.4 Hz, 3H).

Example 255

4-(3-isopropyl-6-methoxy-5-(piperidin-4-yl)-1H-indol-2-yl)-1H-pyrazolo[3,4-b]pyridine

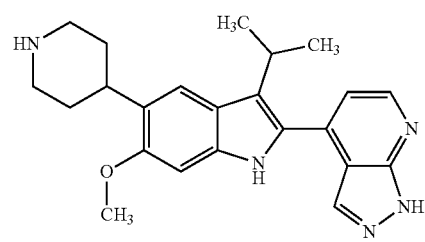

(255)

Intermediate 255A: 3-isopropyl-6-methoxy-1H-indole

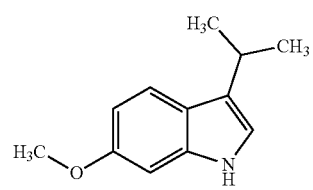

(255A)

In three separate 30 ml pressure tubes (730 mg each) were added 6-methoxy-1H-indole (2.2 g, 14.95 mmol), Shvo's Catalyst (0.162 g, 0.149 mmol), potassium carbonate (0.103 g, 0.747 mmol) and isopropylamine (3.50 g, 59.80 mmol). The reaction mixture was purged with nitrogen gas and heated to 155° C. for 12 hours. The reaction mixture was concentrated under a stream of nitrogen gas. The resulting residue was charged to an 80G ISCO column (solid loading on celite), which was eluted with 0-55% ethyl acetate/hexane. Following concentration of the fractions, 5-bromo-3-isopropyl-6-methoxy-1H-indole was collected as a brownish oil (1.36 g, 0.713 mmol, 48% yield). LC retention time=1.77 min [Method F1]. MS (E⁻) m/z: 190.1 (M–H).

Intermediate 255B:
5-bromo-2-chloro-3-isopropyl-6-methoxy-1H-indole

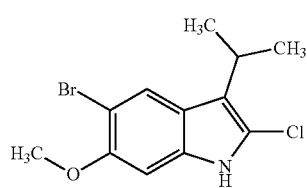

(255B)

In a 40 ml vial were added 3-isopropyl-6-methoxy-1H-indole (0.926 g, 4.89 mmol), acetonitrile (12 mL) and NCS (0.588 g, 4.400 mmol) suspended in acetonitrile (3.0 ml). The reaction mixture was stirred at room temperature for 30 minutes and was concentrated to dryness. This solid was diluted with CH₃CN (1.0 ml) and to this solution was added NBS (0.871 g, 4.89 mmol) in CH₃CN (3.0 ml). The reaction mixture was capped and heated at 80° C. for 40 minutes. The reaction mixture was quenched with a 10% sodium sulfite solution (5.0 mL). The residue was diluted with DCM (50 mL) and water (25 ml) and the mixture was poured into a separatory funnel. The aqueous layer was separated. The organics were then washed with a saturated sodium chloride solution (10 ml), dried over anhydrous sodium sulfate, filtered and concentrated to afford 5-bromo-2-chloro-3-isopropyl-6-methoxy-1H-indole (1.20 g, 4.80 mmol, 100% yield). LC retention time 1.15 min [Method B1]. MS (E⁻) m/z: 301.9/303.9 (M–H).

Intermediate 255C: tert-butyl 4-(2-chloro-3-isopropyl-6-methoxy-1H-indol-5-yl)-5,6-dihydropyridine-1(2H)-carboxylate

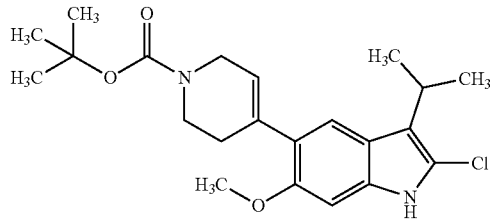

(255C)

To 5-bromo-2-chloro-3-isopropyl-6-methoxy-1H-indole (1.20 g, 4.80 mmol) were added tert-butyl 4-(4,4,5,5-tetramethyl-1,3,2-dioxaborolan-2-yl)-5,6-dihydropyridine-1(2H)-carboxylate (1.589 g, 5.14 mmol), PdCl₂(dppf)-CH₂Cl₂ adduct (0.200 g, 0.245 mmol), THF (20 ml) and potassium phosphate, tribasic (4.89 mL, 14.68 mmol). The reaction mixture was purged with nitrogen gas for 5 minutes, then heated to 60° C. for 1.5 hours. The reaction mixture was cooled and diluted with ethyl acetate and water. The mixture was poured into a separatory funnel and the layers were separated. The organics were collected, dried over anhydrous sodium sulfate, filtered and concentrated. The crude residue was purified on silica gel using 0-75% ethyl acetate/hexane. Like fractions were concentrated to afford tert-butyl 4-(2-chloro-3-isopropyl-6-methoxy-1H-indol-5-yl)-5,6-dihydropyridine-1(2H)-carboxylate (0.150 g, 0.370 mmol, 13% yield). LC retention time 1.23 min [Method B1]. MS (E⁻) m/z: 349.0/351.0 (M–H) (minus boc butyl group).

Intermediate 255D: Tert-butyl 4-(3-isopropyl-6-methoxy-1H-indol-5-yl)piperidine-1-carboxylate

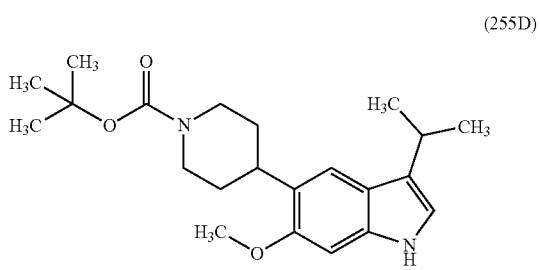 [SMILES: COc1cc2[nH]cc(C(C)C)c2cc1C1CCN(C(=O)OC(C)(C)C)CC1]

(255D)

To tert-butyl 4-(2-chloro-3-isopropyl-6-methoxy-1H-indol-5-yl)-5,6-dihydropyridine-1(2H)-carboxylate (0.150 g, 0.370 mmol) were added MeOH (5.0 ml) and Pd(OH)₂ (0.034 g, 0.048 mmol). The vessel was placed on the Parr and pump/purged three times with nitrogen gas, then backfilled with hydrogen gas to a pressure of 50 psi. The reaction mixture was shaken for 16 hours at room temperature. The contents was diluted with MeOH, filtered through tightly packed celite and the filtrate was concentrated to afford tert-butyl 4-(3-isopropyl-6-methoxy-1H-indol-5-yl)piperidine-1-carboxylate (0.140 g, 0.375 mmol, 100% yield). LC retention time 1.23 min [Method B1]. MS (E⁻) m/z: 317.1 (M–H) (minus boc butyl group).

Intermediate 254E: Tert-butyl 4-(2-bromo-3-isopropyl-6-methoxy-1H-indol-5-yl) piperidine-1-carboxylate

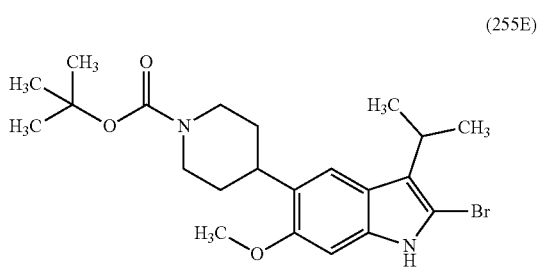 [SMILES: COc1cc2[nH]c(Br)c(C(C)C)c2cc1C1CCN(C(=O)OC(C)(C)C)CC1]

(255E)

A solution was prepared containing tert-butyl 4-(3-isopropyl-6-methoxy-1H-indol-5-yl)piperidine-1-carboxylate (0.052 g, 0.140 mmol) and DCM (2.0 mL). NBS (0.024 g, 0.133 mmol) was dissolved in DCM (1.0 ml) and added drop-wise to the solution via an addition funnel over 1 minute. The resulting brown solution was stirred at room temperature for 15 minutes. The reaction was quenched with a 10% sodium sulfite solution (1.0 mL). The residue was diluted with DCM (10 mL) and water (10 ml) and the mixture was poured into a separatory funnel. The aqueous layer was separated. The organics were then washed with a saturated sodium chloride solution (5.0 mL), dried over anhydrous sodium sulfate, filtered and concentrated to afford tert-butyl 4-(2-bromo-3-isopropyl-6-methoxy-1H-indol-5-yl)piperidine-1-carboxylate (0.055 g, 0.122 mmol, 87% yield). LC retention time 1.25 min [Method B1]. MS (E⁻) m/z: 395.0/397.0 (M–H) (minus boc butyl group).

Intermediate 255F: Tert-butyl 4-(5-(1-(tert-butoxycarbonyl)piperidin-4-yl)-3-isopropyl-6-methoxy-1H-indol-2-yl)-1H-pyrazolo[3,4-b]pyridine-1-carboxylate (255F)

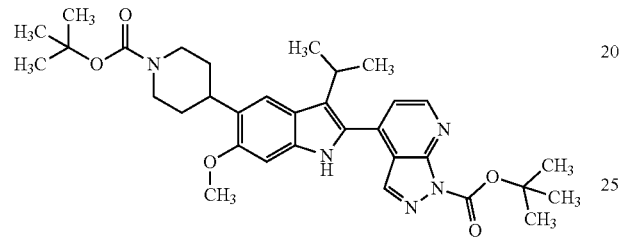

To a 2 dram reaction vial, a solution of tert-butyl 4-(2-bromo-3-isopropyl-6-methoxy-1H-indol-5-yl)piperidine-1-carboxylate (0.028 g, 0.062 mmol) in THF (3.0 mL), tert-butyl 4-(4,4,5,5-tetramethyl-1,3,2-dioxaborolan-2-yl)-1H-pyrazolo[3,4-b] pyridine-1-carboxylate (0.024 g, 0.069 mmol), 2nd generation XPhos precatalyst (2.71 mg, 3.44 μmol), and a 3.0 M tripotassium phosphate solution (0.069 mL, 0.206 mmol) were added. The vial was capped and pump/purged with nitrogen gas three times. The reaction mixture was heated at 65° C. for 2 hours. The aqueous layer was pipetted off and the volatiles were removed under a stream of nitrogen gas. The residue was diluted with 1 ml of DCM and loaded onto a 12G ISCO column, which was eluted with 0-100% ethyl acetate/hexane. Following concentration of the fractions, tert-butyl 4-(5-(1-(tert-butoxycarbonyl)piperidin-4-yl)-3-isopropyl-6-methoxy-1H-indol-2-yl)-1H-pyrazolo[3,4-b]pyridine-1-carboxylate was collected as a yellowish solid (0.033 g, 0.055 mmol, 90% yield).

Example 255

Tert-butyl 4-(5-(1-(tert-butoxycarbonyl)piperidin-4-yl)-3-isopropyl-6-methoxy-1H-indol-2-yl)-1H-pyrazolo[3,4-b] pyridine-1-carboxylate (0.033 g, 0.055 mmol) was treated with hydrogen chloride/dioxane (0.860 mL, 3.44 mmol). The reaction mixture was capped and stirred at room temperature for 2 hours, then concentrated to dryness under a stream of nitrogen gas. The residue was taken up in DMF (1 mL) and the solids were filtered through a 0.45 micron syringe filter. The crude material was purified via preparative LC/MS. Fractions containing the product were combined and dried via centrifugal evaporation to afford 4-(3-isopropyl-6-methoxy 5-(piperidin-4-yl)-1H-indol-2-yl)-1H-pyrazolo[3,4-b]pyridine (0.0076 g, 0.019 mmol, 27% yield). HPLC RT=1.030, M⁺¹=390.3, Method C1. HPLC RT=0.820, M⁺¹=390.3, Method D1. ¹H NMR (500 MHz, DMSO-d₆) δ 11.31-10.98 (m, 1H), 8.58 (d, J=4.7 Hz, 2H), 8.14 (s, 1H), 7.51 (s, 1H), 7.18 (d, J=4.7 Hz, 1H), 6.99 (s, 1H), 3.85 (s, 3H), 3.48-3.32 (m, 2H), 3.24 (br s, 1H), 3.07 (br d, J=11.4 Hz, 2H), 2.58-2.56 (m, 2H), 2.01-1.84 (m, 4H), 1.44 (d, J=6.7 Hz, 6H).

Example 256

4-(3,4-dimethyl-5-(piperidin-4-yl)-1H-indol-2-yl)-1H-pyrazolo[3,4-b]pyridine (258)

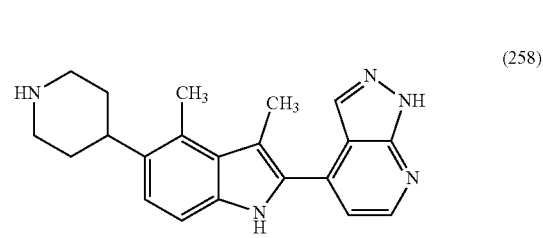 [SMILES: Cc1c(C2CCNCC2)ccc2[nH]c(-c3ccnc4[nH]ncc34)c(C)c12]

Intermediate 256A: 3,4-dimethyl-1H-indole (256A)

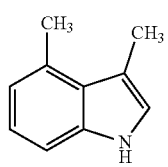

A solution of 4-methyl-1H-indole-3-carbaldehyde (2.200 g, 13.82 mmol) in THF (50 mL) was added to a refluxing mixture of lithium aluminum hydride (1.154 g, 30.4 mmol) in THF (50 mL) (reflux condenser fitted to a two neck flask) over 30 min. The reaction mixture was refluxed for 8 hours, cooled to room temperature and treated with diethyl ether (~50 mL). The reaction mixture was acidified to ~pH 3 with 1N HCl, while cooling in an ice bath. The reaction mixture was diluted with EtOAc (125 mL), poured into a separatory funnel and washed with water (2×50 mL), saturated aqueous NaCl solution (50 mL), then dried over anhydrous sodium sulfate, and filtered. The filtrate was concentrated in vacuo to afford 3,4-dimethyl-1H-indole (0.870 g, 5.99 mmol, 43% yield). LC retention time 1.15 min [Method F1]. MS (E⁻) m/z: 146.0 (M–H).

Intermediate 256B: 5-bromo-2-chloro-3,4-dimethyl-1H-indole (256B)

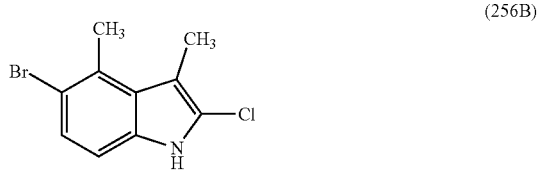

In a 40 ml vial were added 3,4-dimethyl-1H-indole (0.300 g, 2.066 mmol), acetonitrile (10 mL), and NCS (0.248 g, 1.860 mmol) suspended in acetonitrile (3.0 ml). The reaction mixture was stirred at room temperature for 30 minutes. To this solution was added NBS (0.368 g, 2.066 mmol) in CH₃CN (3.0 ml). The reaction mixture was capped and heated at 80° C. for 40 minutes. The reaction was quenched with a 10% sodium sulfite solution (5.0 mL). The residue was diluted with DCM (50 mL) and water (25 ml) and the mixture was poured into a separatory funnel. The aqueous layer was separated. The organics were then washed with a saturated sodium chloride solution (10 ml), dried over anhydrous sodium sulfate, filtered and concentrated to afford 5-bromo-2-chloro-3,4-dimethyl-1H-indole (0.550 g, 2.13 mmol, 100% yield). LC retention time 1.15 min [Method F1]. MS (E⁻) m/z: 259.1 (M–H).

Intermediate 256C: Tert-butyl 4-(2-chloro-3,4-dimethyl-1H-indol-5-yl)-5,6-dihydropyridine-1(2H)-carboxylate

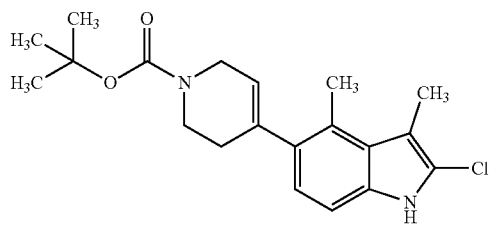
(256C)

To 3,4-dimethyl-1H-indole (0.550 g, 2.13 mmol) were added tert-butyl 4-(4,4,5,5-tetramethyl-1,3,2-dioxaborolan-2-yl)-5,6-dihydropyridine-1(2H)-carboxylate (0.958 g, 3.10 mmol), PdCl₂(dppf)-CH₂Cl₂ adduct (0.169 g, 0.207 mmol), THF (10 ml) and potassium phosphate, tribasic (2.5 mL, 7.30 mmol). The reaction mixture was purged with nitrogen gas for 5 minutes, then heated to 60° C. for 1.5 hours. The reaction mixture was cooled and diluted with ethyl acetate and water. The mixture was poured into a separatory funnel and the layers were separated. The organics were collected, dried over anhydrous sodium sulfate, filtered and concentrated. The crude residue was purified on silica gel using 0-75% ethyl acetate/hexane. Like fractions were concentrated to afford tert-butyl 4-(2-chloro-3,4-dimethyl-1H-indol-5-yl)-5,6-dihydropyridine-1(2H)-carboxylate (0.155 g, 0.430 mmol, 20% yield). LC retention time 1.36 min [Method F1]. MS (E⁻) m/z: 361.3 (M–H) (minus boc butyl group).

Intermediate 256D: Tert-butyl 4-(3,4-dimethyl-1H-indol-5-yl)piperidine-1-carboxylate

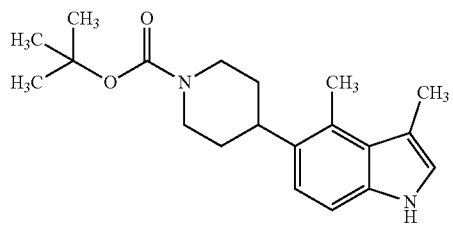
(256D)

To tert-butyl 4-(2-chloro-3,4-dimethyl-1H-indol-5-yl)-5,6-dihydropyridine-1(2H)-carboxylate (0.155 g, 0.430 mmol) in a pressure vessel were added MeOH (5.0 ml) and Pd(OH)₂ (0.034 g, 0.048 mmol). The pressure vessel was placed on a Parr hydrogenation apparatus and pump/purged three times with nitrogen gas, then back-filled with hydrogen gas to a pressure of 50 psi. The reaction mixture was shaken for 16 hours at room temperature. The contents was diluted with MeOH, filtered through tightly packed celite and the filtrate was concentrated to afford tert-butyl 4-(3,4-dimethyl-1H-indol-5-yl)piperidine-1-carboxylate (0.070 g, 0.212 mmol, 50% yield). LC retention time 1.23 min [Method F1]. MS (E⁻) m/z: 273.0 (M–H) (minus boc butyl group).

Intermediate 256E: Tert-butyl 4-(2-bromo-3,4-dimethyl-1H-indol-5-yl)piperidine-1-carboxylate

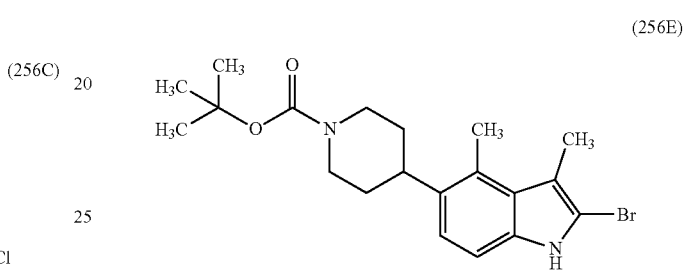
(256E)

To a solution of tert-butyl 4-(3,4-dimethyl-1H-indol-5-yl) piperidine-1-carboxylate (0.070 g, 0.212 mmol) and DCM (2.0 mL) was added NBS (0.036 g, 0.212 mmol) dissolved in DCM (0.5 ml) drop-wise via a pipet over 1 minute. The resulting solution was stirred at room temperature for 15 minutes. The reaction mixture was quenched with a 10% sodium sulfite solution (1.0 mL). The residue was diluted with DCM (10 mL) and water (10 ml) and the mixture was poured into a separatory funnel. The aqueous layer was separated. The organics were then washed with a saturated sodium chloride solution (5.0 mL), dried over anhydrous sodium sulfate, filtered and concentrated to afford tert-butyl 4-(2-bromo-3,4-dimethyl-1H-indol-5-yl)piperidine-1-carboxylate (0.060 g, 0.150 mmol, 71% yield). LC retention time 1.18 min [Method B1]. MS (E⁻) m/z: 351.0 (M–H) (minus boc butyl group).

Example 256

To a 2 dram reaction vial, a solution of tert-butyl 4-(2-bromo-3,4-dimethyl-1H-indol-5-yl) piperidine-1-carboxylate (0.035 g, 0.086 mmol) in THF (1.0 mL) and tert-butyl 4-(4,4,5,5-tetramethyl-1,3,2-dioxaborolan-2-yl)-1H-pyrazolo[3,4-b]pyridine-1-carboxylate (0.030 g, 0.086 mmol), PdCl₂(dppf)-CH₂Cl₂ adduct (3.51 mg, 4.30 µmol) and a 3.0 M tripotassium phosphate solution (0.086 mL, 0.258 mmol) were added. The vial was capped and pump/purged with nitrogen gas three times and heated at 65° C. for 2 hours. The mixture was cooled to room temperature and the aqueous layer was pipetted off and the volatiles were removed under a stream of nitrogen gas. This dry residue was diluted with DCM (0.5 ml) and then treated with 4 M hydrogen chloride/dioxane (0.860 mL, 3.44 mmol). The reaction mixture was capped and stirred at room temperature for 2 hour, then concentrated to dryness under a stream of nitrogen gas. The residue was taken up in DMF (1 mL) and the solids were filtered through a 0.45 micron syringe filter. The crude material was purified via preparative LC/MS. Fractions containing the desired product were combined and dried via centrifugal evaporation to afford 4-(3,4-dimethyl-5-(piperidin-4-yl)-1H-indol-2-yl)-1H-pyrazolo[3,4-b]pyridine (0.0019 g, 0.0045 mmol, 7% yield). HPLC RT=1.075, M⁺¹=346.1, Method C1. HPLC RT=0.750, M⁺¹=346.3, Method DL. ¹H NMR (500 MHz, DMSO-d₆) δ 11.23 (s, 1H), 8.59 (d, J=4.7 Hz, 1H), 8.13 (s, 1H), 7.33-7.18 (m, 2H), 7.05 (br d, J=8.4 Hz, 1H), 3.32-3.04 (m, 2H), 2.96-2.82 (m, 1H), 2.70 (s, 3H), 2.60 (s, 3H), 1.85-1.59 (m, 8H).

Example 257

6-(3-ethyl-4,6-difluoro-5-(piperidin-4-yl)-1H-indol-2-yl)imidazo[1,2-a]pyridine

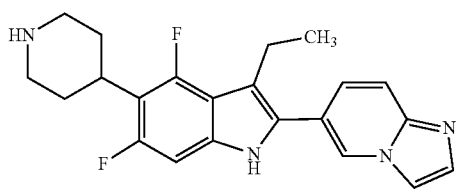

(257)

Intermediate 257A:
5-bromo-3-ethyl-4,6-difluoro-1H-indole

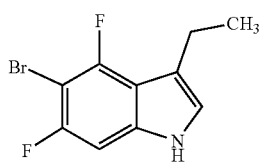

(257A)

To a tall tube were added 5-bromo-4,6-difluoro-1H-indole (0.500 g, 2.155 mmol), Shvo's catalyst (0.023 g, 0.022 mmol), potassium carbonate (0.015 g, 0.108 mmol) and diethylamine (0.315 g, 4.31 mmol). The reaction mixture was purged with nitrogen gas and heated to 155° C. for 12 hours. The reaction mixture was concentrated under a stream of nitrogen gas overnight. The resulting residue was purified by silica gel chromatography using ethyl acetate in hexane as the eluent. Like fractions were concentrated to afford 5-bromo-3-ethyl-4,6-difluoro-1H-indole (0.410 g, 1.57 mmol, 73% yield). LC retention time=1.12 min [Method A1]. MS (E⁻) m/z: 260.2 (M–H).

Intermediate 257B: Tert-butyl 4-(3-ethyl-4,6-difluoro-1H-indol-5-yl)-5,6-dihydropyridine-1(2H)-carboxylate

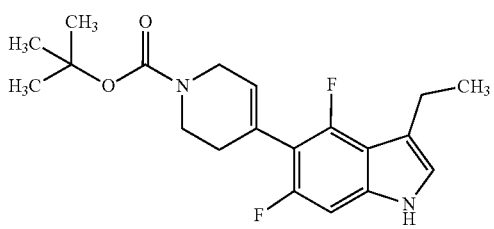

(257B)

To a mixture of 5-bromo-3-ethyl-4,6-difluoro-1H-indole (0.168 g, 0.646 mmol), 2nd generation XPhos precatalyst (0.013 g, 0.016 mmol) and tert-butyl 4-(4,4,5,5-tetramethyl-1,3,2-dioxaborolan-2-yl)-5,6-dihydropyridine-1(2H)-carboxylate (0.210 g, 0.678 mmol) in a 40 ml reaction vial were added THF (4.0 mL) followed by aqueous solution of tripotassium phosphate (0.646 mL, 1.938 mmol). The reaction mixture was purged with nitrogen gas for 5 minutes, then heated to 60° C. for 1.5 hours. The reaction mixture was cooled and diluted with ethyl acetate and water. The mixture was poured into a separatory funnel and the layers were separated. The organics were collected, dried over anhydrous sodium sulfate, filtered and concentrated. The crude residue was purified on silica gel using 0-75% ethyl acetate/hexane. Like fractions were concentrated to afford tert-butyl 4-(3-ethyl-4,6-difluoro-1H-indol-5-yl)-5,6-dihydropyridine-1(2H)-carboxylate (0.100 g, 0.275 mmol, 45% yield). LC retention time 1.14 min [Method B1]. MS (E⁻) m/z: 307.0 (M–H) (minus boc butyl group).

Intermediate 257C: Tert-butyl 4-(3-ethyl-4,6-difluoro-1H-indol-5-yl)piperidine-1-carboxylate

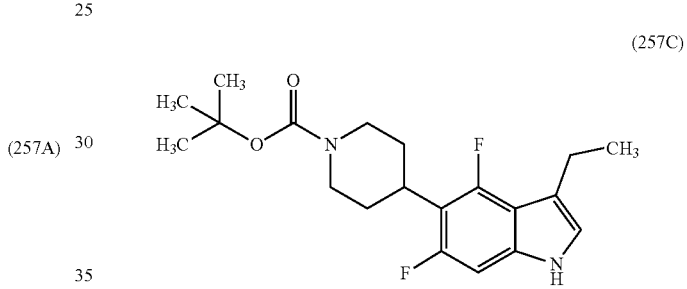

(257C)

To tert-butyl 4-(3-ethyl-4,6-difluoro-1H-indol-5-yl)-5,6-dihydropyridine-1(2H)-carboxylate (0.100 g, 0.275 mmol) were added MeOH (5.0 ml) and 10% Pd/C (0.069 g, 0.065 mmol). The vessel was placed was placed under a nitrogen atmosphere and pump/purged three times, then back-filled with hydrogen gas via a balloon. The reaction mixture was stirred for 16 hours at room temperature. The contents was diluted with MeOH, filtered through tightly packed celite and the filtrate was concentrated to afford tert-butyl 4-(3-ethyl-4,6-difluoro-1H-indol-5-yl)piperidine-1-carboxylate (0.085 g, 0.232 mmol, 100% yield). LC retention time 1.23 min [Method B1]. MS (E⁻) m/z: 309.1 (M–H) (minus boc butyl group).

Intermediate 257D: Tert-butyl 4-(2-bromo-3-ethyl-4,6-difluoro-1H-indol-5-yl)piperidine-1-carboxylate

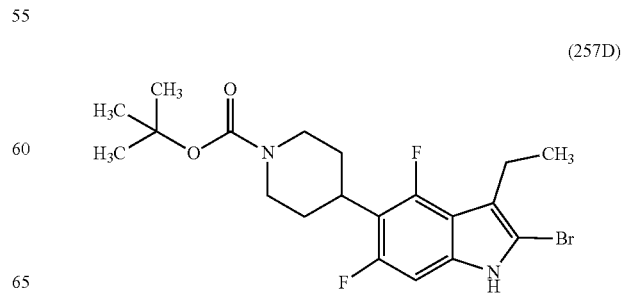

(257D)

To a solution of tert-butyl 4-(3-ethyl-4,6-difluoro-1H-indol-5-yl)piperidine-1-carboxylate (0.085 g, 0.232 mmol) and DCM (2.0 mL) was added NBS (0.036 g, 0.212 mmol) dissolved in DCM (0.5 ml) drop-wise via a pipet over 1 minute. The resulting solution was stirred at room temperature for 15 minutes. The reaction mixture was quenched with a 10% sodium sulfite solution (1.0 mL). The residue was diluted with DCM (10 mL) and water (10 ml) and the mixture was poured into a separatory funnel. The aqueous layer was separated. The organics were washed with a saturated sodium chloride solution (5.0 mL), dried over anhydrous sodium sulfate, filtered and concentrated to afford tert-butyl 4-(2-bromo-3-ethyl-4,6-difluoro-1H-indol-5-yl)piperidine-1-carboxylate (0.050 g, 0.113 mmol, 50% yield). LC retention time 1.25 min [Method B1]. MS (E⁻) m/z: 389.0 (M−H) (minus boc butyl group).

Example 257

To a 2 dram reaction vial, a solution of tert-butyl 4-(2-bromo-3-ethyl-4,6-difluoro-1H-indol-5-yl)piperidine-1-carboxylate (0.025 g, 0.056 mmol) in THF (1.0 mL) and imidazo[1,2-a]pyridin-6-ylboronic acid (9.0 mg, 0.056 mmol), 2nd generation XPhos precatalyst (2.218 mg, 2.82 µmol), and 3.0 M tripotassium phosphate solution (0.113 mL, 0.338 mmol) were added. The vial was capped and pump/purged with nitrogen gas three times and heated at 65° C. for 1 hour. The reaction mixture was cooled to room temperature. The aqueous layer was pipetted off and the volatiles were removed under a stream of nitrogen gas. The dry residue was diluted with DCM (0.5 ml) and then treated with 4 M hydrogen chloride/dioxane (1.0 mL, 4.00 mmol). The reaction mixture was capped and stirred at room temperature for 15 minutes, then concentrated to dryness under a stream of nitrogen gas. The residue was taken up in DMF (1 mL) and the solids were filtered through a 0.45 micron syringe filter. The crude material was purified via preparative LC/MS. Fractions containing the desired product were combined and dried via centrifugal evaporation to afford 6-(3-ethyl-4,6-difluoro-5-(piperidin-4-yl)-1H-indol-2-yl)imidazo[1,2-a]pyridine (0.0020 g, 0.0051 mmol, 9% yield). HPLC RT=1.062, M⁺¹=381.1, Method C1. HPLC RT=0.806, M⁺¹=381.1, Method D1. ¹H NMR (500 MHz, DMSO-d₆) δ 11.81 (s, 1H), 8.94 (s, 1H), 8.33 (s, 1H), 8.04 (s, 1H), 7.99 (br d, J=9.3 Hz, 1H), 7.84 (br d, J=9.3 Hz, 1H), 7.30 (s, 1H), 7.20 (s, 1H), 7.08 (br d, J=10.9 Hz, 1H), 3.51-3.29 (m, 1H), 3.08 (br d, J=11.5 Hz, 2H), 2.98-2.91 (m, 1H), 2.85 (br d, J=7.4 Hz, 1H), 2.25 (br d, J=12.1 Hz, 2H), 1.89 (br d, J=13.4 Hz, 2H), 1.30 (t, J=7.4 Hz, 3H), 1.23-1.11 (m, 1H).

Example 258

6-(4-fluoro-3-isopropyl-5-(piperidin-4-yl)-1H-indol-2-yl)imidazo[1,2-a]pyridine (258)

Intermediate 258A: Tert-butyl 4-(4-fluoro-3-isopropyl-1H-indol-5-yl)-5,6-dihydropyridine-1(2H)-carboxylate

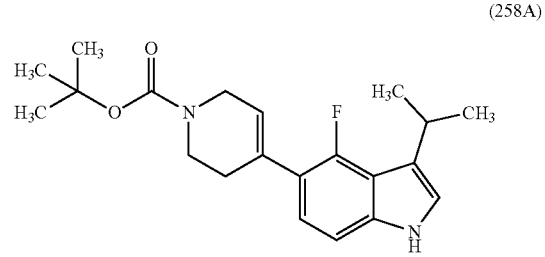 [SMILES: CC(C)c1c[nH]c2ccc(C3=CCN(C(=O)OC(C)(C)C)CC3)c(F)c12]

(258A)

To a 100 ml round bottom flask were added 2,2,2-trichloroacetic acid (0.246 g, 1.507 mmol), toluene (5 mL) and triethylsilane (0.481 mL, 3.01 mmol). With stirring, the solution was heated to 70° C. and a solution of 5-bromo-4-fluoro-1H-indole (0.215 g, 1.005 mmol) and acetone (0.089 mL, 1.205 mmol) in toluene (2.0 mL) was added drop-wise via a pipet. The resulting brown solution was heated at 90° C. for 2.5 hours. The solution was cooled to 10° C. The reaction mixture was quenched with 2 M potassium phosphate solution. The mixture was diluted with diethyl ether. The organic layer was separated, dried and concentrated under vacuum to get crude compound.

To a mixture of crude 5-bromo-4-fluoro-3-isopropyl-1H-indole (0.310 g, 1.210 mmol), 2nd generation XPhos precatalyst (0.024 g, 0.030 mmol) and tert-butyl 4-(4,4,5,5-tetramethyl-1,3,2-dioxaborolan-2-yl)-5,6-dihydropyridine-1(2H)-carboxylate (0.393 g, 1.271 mmol) were added THF (6.0 mL) followed by an aqueous solution of tripotassium phosphate (1.210 mL, 3.63 mmol). The flask was fitted with a reflux condenser and septum. The system was evacuated under vacuum (via a needle from a nitrogen/vacuum manifold line) and backfilled with nitrogen gas. The procedure was repeated three times. The needle was removed and the reaction mixture was heated at 50° C. for 1 hour. The reaction mixture was diluted with EtOAc (100 mL), poured into a separatory funnel and washed with water (2×50 mL) and saturated aqueous sodium chloride solution (15 mL) dried over anhydrous sodium sulfate, filtered and the filtrate concentrated in vacuo to give crude product. The material was purified by silica gel chromatography and following concentration of the like fractions, afforded tert-butyl 4-(4-fluoro-3-isopropyl-1H-indol-5-yl)-5,6-dihydropyridine-1(2H)-carboxylate (0.280 g, 0.780 mmol, 50% yield). LCMS retention time 1.18 min [Method B1]. MS (E⁻) m/z: 303.3 (M−H) (minus boc butyl group).

Intermediate 258B: Tert-butyl 4-(4-fluoro-3-isopropyl-1H-indol-5-yl)piperidine-1-carboxylate

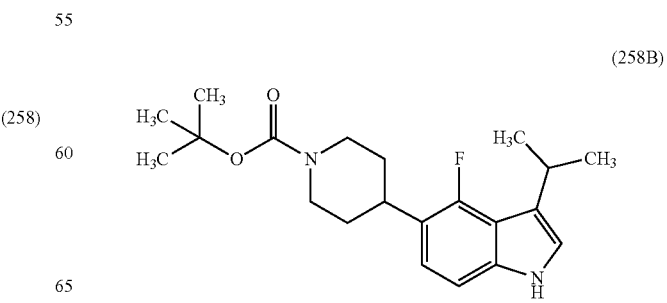

(258B)

To a 100 ml round bottom flask were added tert-butyl 4-(4-fluoro-3-isopropyl-1H-indol-5-yl)-5,6-dihydropyridine-1(2H)-carboxylate (0.280 g, 0.780 mmol) and ethyl acetate (5 ml). The flask was purged with nitrogen gas and Pd/C (0.325 g, 0.305 mmol) was added. Following pump/purging with nitrogen gas three times, hydrogen gas was introduced via a balloon. The reaction mixture was stirred at room temperature for 4 hours. The flask was evacuated and filled with nitrogen gas. The suspension was diluted with methanol (100 ml) and filtered through fluted filter paper. The filtrate was concentrated in vacuo to afford tert-butyl 4-(4-fluoro-3-isopropyl-1H-indol-5-yl) piperidine-1-carboxylate (0.255 g, 0.707 mmol, 89% yield) as an off-white solid. LC retention time 1.19 min [Method B1]. MS (E⁻) m/z: 305.3 (M–H) (minus boc butyl group).

Intermediate 258C: Tert-butyl 4-(2-bromo-4-fluoro-3-isopropyl-1H-indol-5-yl) piperidine-1-carboxylate

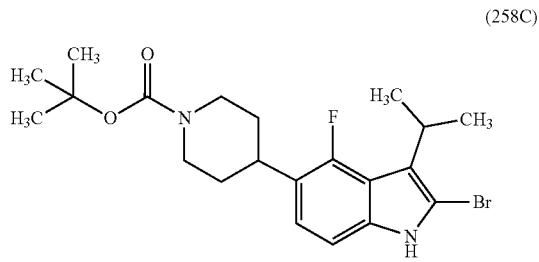 [SMILES: CC(C)c1c(Br)[nH]c2ccc(C3CCN(C(=O)OC(C)(C)C)CC3)c(F)c12]

(258C)

To a solution of tert-butyl 4-(6-fluoro-3-isopropyl-1H-indol-5-yl)piperidine-1-carboxylate (0.215 g, 0.596 mmol) in DCM 10 mL at 0° C., was added NBS (0.100 g, 0.567 mmol) in DCM (2.0 mL) drop-wise via a pipet. The resulting solution was stirred at room temperature for 15 minutes. The reaction mixture was quenched with a 10% sodium sulfite solution (1.0 mL). The residue was diluted with DCM (50 mL) and water (20 ml) and the mixture was poured into a separatory funnel. The aqueous layer was separated. The organics were then washed with a saturated sodium chloride solution (20 ml), dried over anhydrous sodium sulfate, filtered and concentrated to afford tert-butyl 4-(2-bromo-4-fluoro-3-isopropyl-1H-indol-5-yl)piperidine-1-carboxylate (0.230 g, 0.523 mmol, 88% yield). LC retention time 1.26 min [Method B1]. MS (E⁻) m/z: 383.1/383.5 (M–H) (minus boc butyl group).

Example 258

To a 2 dram reaction vial were added tert-butyl 4-(2-chloro-4-fluoro-3-isopropyl-1H-indol-5-yl)piperidine-1-carboxylate (0.025 g, 0.063 mmol), 2nd generation XPhos precatalyst (2.490 mg, 3.17 μmol), imidazo[1,2-a]pyridin-6-ylboronic acid (10.2 mg, 0.063 mmol), THF (1.0 ml) and 3.0 M potassium phosphate tribasic solution (0.127 mL, 0.380 mmol). The reaction mixture was degassed with nitrogen gas for 5 minutes and then heated at 65° C. for 1 hour. The reaction mixture was cooled to room temperature and diluted with ethyl acetate and water. The mixture was transferred to a separatory funnel and the layers were separated. The organics were then washed with a saturated sodium chloride solution, dried over anhydrous sodium sulfate, filtered and concentrated to dryness. The residue was dissolved in DCM (0.5 ml) and 4 M HCl in dioxane (1.0 ml) was added. The reaction mixture was capped and stirred at room temperature for 15 minutes, then concentrated to dryness under a stream of nitrogen gas. The residue was taken up in DMF (1 mL) and the solids were filtered through a 0.45 micron syringe filter. The crude material was purified via preparative LC/MS. Fractions containing the desired product were combined and dried via centrifugal evaporation to afford 6-(4-fluoro-3-isopropyl-5-(piperidin-4-yl)-1H-indol-2-yl)imidazo[1,2-a]pyridine (0.0028 g, 0.0714 mmol, 11% yield). HPLC RT=1.604, M⁺¹=377.3, Method C1. HPLC RT=0.862, M⁺¹=377.2, Method DL. H NMR (500 MHz, DMSO-d₆) δ 11.46-11.32 (m, 1H), 8.69 (s, 1H), 8.08 (s, 1H), 7.78-7.59 (m, 2H), 7.34 (br d, J=9.1 Hz, 1H), 7.17 (d, J=8.3 Hz, 1H), 7.04 (br t, J=7.4 Hz, 1H), 3.26 (br s, 1H), 3.23-3.07 (m, 1H), 2.88-2.72 (m, 2H), 1.86 (s, 3H), 1.76 (br s, 4H), 1.34 (br d, J=6.9 Hz, 6H).

The following example was prepared according to the general procedure for Examples 260.

TABLE 13

| Ex. No. | Structure | Obs. MS Ion | RT | HPLC Method |
|---|---|---|---|---|
| 259 | 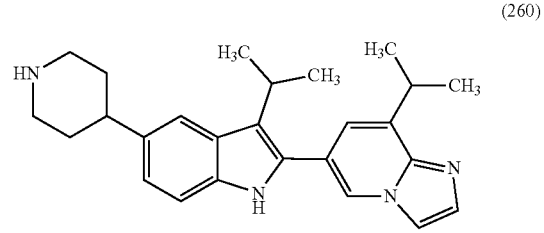 [SMILES: CC(C)c1c(-c2cc(C(C)C)c3nccn3c2)[nH]c2ccc(C3CCNCC3)cc12] | 378.3 | 0.65 | B1 |

Example 260

8-Isopropyl-6-(3-isopropyl-5-(piperidin-4-yl)-1H-indol-2-yl)imidazo[1,2-a]pyridine (260)

Intermediate 260A: Methyl 2-aminonicotinate

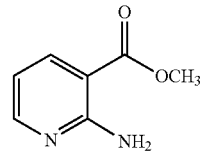

(260A)

To a solution of 2-aminonicotinic acid (5 g, 36.2 mmol) in methanol (20 mL) was added thionyl chloride (7.93 mL, 109 mmol) at 0° C. The mixture was brought to room temperature and stirred at 80° C. for 3 h. The reaction mixture was concentrated to remove methanol, diluted with DCM (100 mL) and washed with water (2×20 mL) and sodium bicarbonate (2×20 mL). The layer was dried over sodium sulphate and concentrated under vacuum to afford methyl 2-aminonicotinate (5.2 g, 31.0 mmol, 86% yield) as a white solid. MS (M$^{+1}$) m/z: 153.1 (MH$^+$). LC retention time 0.71 min [L].

Intermediate 260B: Methyl 2-amino-5-bromonicotinate

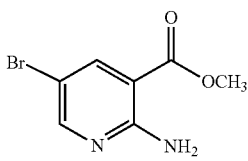

(260B)

To a solution of methyl 2-aminonicotinate (1 g, 6.57 mmol) in acetonitrile (20 mL) was added NBS (1.287 g, 7.23 mmol) at 0° C. The mixture was warmed to room temperature and then stirred at room temperature for 2 h. The reaction mixture was diluted with DCM (20 mL) and washed with water (2×10 mL). The organic layer was dried over sodium sulfate, concentrated under reduced pressure to afford methyl 2-amino-5-bromonicotinate (1.26 g, 5.08 mmol, 77% yield) as an off-white solid. MS (M$^{+1}$) m/z: 232.9 (MH$^+$). LC retention time 1.09 min [L].

Intermediate 260C: 2-(2-Amino-5-bromopyridin-3-yl)propan-2-ol

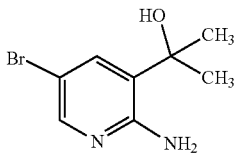

(260C)

To a solution of methyl 2-amino-5-bromonicotinate (100 mg, 0.433 mmol) in THF (5 mL) was added methylmagnesium chloride (0.361 mL, 1.082 mmol) at 0° C. The reaction mixture was stirred at same temperature for 1 h. The reaction mixture was quenched with cold water (2 mL), extracted with DCM (2×10 mL), the organic layer was dried over sodium sulphate and concentrated to get crude product. The crude product was purified by ISCO using 12 g silica column. The compound was eluted in 32% of ethyl acetate in hexane, the fractions was collected and concentrated to afford 2-(2-amino-5-bromopyridin-3-yl)propan-2-ol (64 mg, 0.161 mmol, 37.1% yield) as a yellow oil. MS (M$^{+1}$) m/z: 233.0 (MH$^+$). LC retention time 0.88 min [L].

Intermediate 260D: 5-bromo-3-(prop-1-en-2-yl)pyridin-2-amine

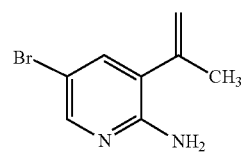

(260D)

To a solution of 2-(2-amino-5-bromopyridin-3-yl)propan-2-ol (100 mg, 0.433 mol) in acetic acid (10 mL) was added H$_2$SO$_4$ (1 mL, 18.76 mmol) at room temperature. The reaction mixture was stirred at 100° C. for 16 h. The reaction mixture was concentrated to evaporate acetic acid, basified with 10% aqueous NaOH (2 mL), extracted with DCM (2×20 mL), the combined organic extracts was dried (Na$_2$SO$_4$) and concentrated to afford 5-bromo-3-(prop-1-en-2-yl)pyridin-2-amine (84 mg, 0.313 mmol, 72.3% yield) as an oil. MS (M$^{+1}$) m/z: 233.0 (MH$^+$). LC retention time 0.87 min [L].

Intermediate 260E: 6-Bromo-8-(prop-1-en-2-yl)imidazo[1,2-a]pyridine

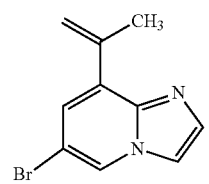

(260E)

To a solution of 5-bromo-3-(prop-1-en-2-yl)pyridin-2-amine (100 mg, 0.469 mmol) in ethanol, was added chloroacetaldehyde (0.124 mL, 1.408 mmol) at room temperature. The mixture was stirred at 90° C. for 16 h. The reaction mass was concentrated, triturated with ethyl acetate, then dried under vacuum to afford 6-bromo-8-(prop-1-en-2-yl)imidazo[1,2-a]pyridine (100 mg, 0.422 mmol, 90% yield) as a yellow solid. MS (M$^{+1}$) m/z: 238.9 (MH$^+$). LC retention time 0.96 min [L].

Intermediate 260F: Tert-butyl 4-(3-isopropyl-2-(8-(prop-1-en-2-yl)imidazo[1,2-a]pyridin-6-yl)-1H-indol-5-yl)piperidine-1-carboxylate

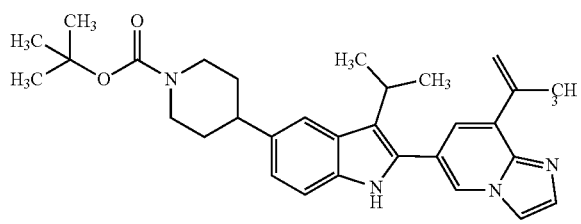

(260F)

Tert-butyl 4-(3-isopropyl-2-(8-(prop-1-en-2-yl)imidazo[1,2-a]pyridin-6-yl)-1H-indol-5-yl)piperidine-1-carboxylate (80 mg, 13% yield) was prepared according to the general procedure described in Example 237 using tert-butyl 4-(3-isopropyl-2-(4,4,5,5-tetramethyl-1,3,2-dioxaborolan-2-yl)-1H-indol-5-yl)piperidine-1-carboxylate as the starting intermediate. MS (M$^{+1}$) m/z: 499.5 (MH$^{+}$). LC retention time 1.76 min [L].

Intermediate 260G: 6-(3-Isopropyl-5-(piperidin-4-yl)-1H-indol-2-yl)-8-(prop-1-en-2-yl) imidazo[1,2-a]pyridine (260G)

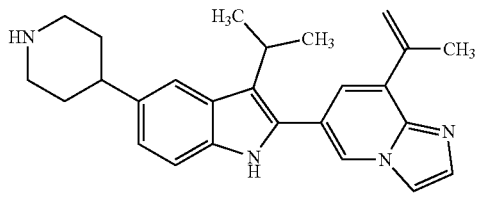

6-(3-Isopropyl-5-(piperidin-4-yl)-1H-indol-2-yl)-8-(prop-1-en-2-yl)imidazo[1,2-a]pyridine (30 mg, 47% yield) was prepared according to the general procedure described in Intermediate 3B using tert-butyl 4-(3-isopropyl-2-(8-(prop-1-en-2-yl) imidazo[1,2-a]pyridin-6-yl)-1H-indol-5-yl)piperidine-1-carboxylate as the starting intermediate. MS (M$^{+1}$) m/z: 399.4 (MH$^{+}$). LC retention time 1.10 min [L].

Example 260

To a solution of 6-(3-isopropyl-5-(piperidin-4-yl)-1H-indol-2-yl)-8-(prop-1-en-2-yl)imidazo[1,2-a]pyridine (50 mg, 0.125 mmol) in methanol (2 mL) was added palladium on Carbon (163 mg, 0.125 mmol) at room temperature. The mixture was stirred at room temperature under hydrogen bladder for 2 h. The reaction mixture was filtered through celite and concentrated under vacuum to get crude compound. The crude material was purified by Preparative LCMS purification. Fractions containing the desired product were combined and dried via centrifugal evaporation to afford 8-isopropyl-6-(3-isopropyl-5-(piperidin-4-yl)-1H-indol-2-yl)imidazo[1,2-a]pyridine (2 mg, 4.99 μmol, 4% yield). MS (M$^{+1}$) m/z: 401.2 (MH$^{+}$). LC retention time 1.58 min [E]. $^{1}$H NMR (400 MHz, METHANOL-d$_{4}$) δ ppm 1.43 (d, J=6.85 Hz, 6H) 1.50 (d, J=7.09 Hz, 6H) 1.93-2.07 (m, 5H) 2.13 (br. s., 3H) 3.11-3.22 (m, 4H) 3.35 (s, 2H) 3.52 (d, J=11.74 Hz, 3H) 3.65 (d, J=6.60 Hz, 2H) 4.56 (s, 12H) 7.06 (d, J=8.31 Hz, 1H) 7.26-7.37 (m, 3H) 7.62 (d, J=9.29 Hz, 2H) 7.92 (s, 1H) 8.40 (s, 1H).

Example 261

6-(3-isopropyl-5-(piperidin-4-yl)-1H-indol-2-yl)-8-methylimidazo[1,2-a]pyridine-3-carboxamide (261)

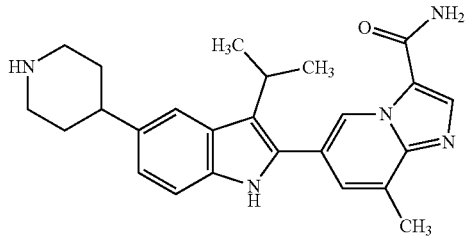

Intermediate 261A: 6-Bromo-8-methylimidazo[1,2-a]pyridine-3-carbonitrile (261A)

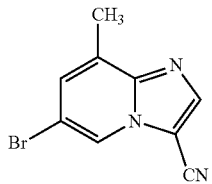

To a stirred solution of 5-bromo-3-methylpyridin-2-amine (1.5 g, 8.02 mmol) in methanol (10 mL) was added DMF-DMA (2.0 mL, 14.94 mmol) at room temperature. The mixture was stirred at 70° C. for 16 h, cooled to room temperature, and concentrated under reduced pressure to afford (E)-N'-(5-bromo-3-methylpyridin-2-yl)-N,N-dimethylformimidamide as a brown oil. To a stirred solution of (E)-N'-(5-bromo-3-methylpyridin-2-yl)-N,N-dimethylformimidamide in acetonitrile (10 mL) was added bromoacetonitrile (1.676 mL, 24.0 mmol) at room temperature. The mixture was stirred at 70° C. for 12 h. The reaction mixture was cooled to room temperature and concentrated under reduced pressure. The residue was dissolved in acetonitrile (10 mL), and DIPEA (8.40 mL, 48.1 mmol) was added at room temperature. The reaction mixture was stirred at room temperature for 4 h. The reaction mass was partitioned between water (50 mL) and ethyl acetate (100 mL). The aqueous layer was further extracted with ethyl acetate (3×50 mL), the combined organic extracts were washed with water (50 mL), dried over Na$_{2}$SO$_{4}$, concentrated and dried under vacuum to afford 6-bromo-8-methylimidazo[1,2-a]pyridine-3-carbonitrile (1.6 g, 6.78 mmol, 85% yield) as a brown solid. MS (M$^{+1}$) m/z: 238.0 (MH$^{+}$). LC retention time 1.56 min [M].

Intermediate 261B: Tert-butyl 4-(2-(3-cyano-8-methylimidazo[1,2-a]pyridin-6-yl)-3-isopropyl-1H-indol-5-yl)piperidine-1-carboxylate (261B)

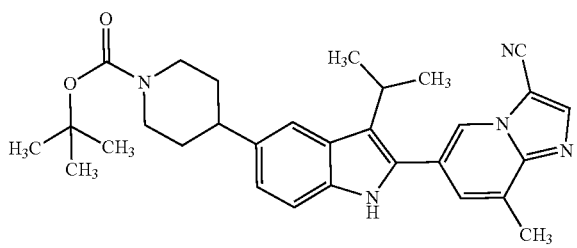

To a solution of tert-butyl 4-(3-isopropyl-2-(4,4,5,5-tetramethyl-1,3,2-dioxaborolan-2-yl)-1H-indol-5-yl)piperidine-1-carboxylate (0.4 g, 0.854 mmol) and 6-bromo-8-methylimidazo[1,2-a]pyridine-3-carbonitrile (0.222 g, 0.939 mmol) in dioxane (10 mL) and water (1 mL) solvent mixture was added potassium phosphate, tribasic (0.446 g, 2.56 mmol) at room temperature. The mixture was degassed for 10 minutes with nitrogen. Next, PdCl$_{2}$(dppf)-CH$_{2}$Cl$_{2}$ adduct (0.035 g, 0.043 mmol) was added and the reaction mixture was degassed again for 5 min. The reaction mixture was stirred at 90° C. for 12 h. The reaction mixture was diluted with ethyl acetate (100 mL), washed with water (2×50 mL), brine (20 mL), dried over sodium sulphate, and concentrated to get crude product. The crude material was purified by ISCO using 12 g silica column. The compound was eluted with 28% ethyl acetate in hexane, the fractions were collected and concentrated to afford tert-butyl 4-(2-(3-cyano-8-methylimidazo[1,2-a]pyridin-6-yl)-3-isopropyl-1H-indol-5-yl)piperidine-1-carboxylate (0.3 g, 0.603 mmol, 70% yield) as a yellow solid. MS (M$^{+1}$) m/z: 498.2 (MH$^+$). LC retention time 3.997 min [M].

Example 261

To a solution of tert-butyl 4-(2-(3-cyano-8-methylimidazo[1,2-a]pyridin-6-yl)-3-isopropyl-1H-indol-5-yl)piperidine-1-carboxylate (0.04 g, 0.080 mmol) in DCM (2 mL) was added 4 M HCl in dioxane (0.201 mL, 0.804 mmol) at room temperature. The mixture was stirred at same temperature for 1 h. The reaction mixture was concentrated to afford crude product. The crude material was purified by Prep LCMS. The fractions containing the product were combined and dried via centrifugal evaporation to afford 6-(3-isopropyl-5-(piperidin-4-yl)-1H-indol-2-yl)-8-methylimidazo[1,2-a]pyridine-3-carboxamide (4.4 mg, 13% yield) as a pale solid. MS (M$^{+1}$) m/z: 416.3 (MH$^+$). LC retention time 0.73 min [L]. $^1$H NMR (400 MHz, DMSO-d$_6$) δ ppm 11.14 (s, 1H), 9.57 (s, 1H), 8.39 (s, 1H), 7.55 (s, 1H), 7.43 (s, 1H), 7.32 (d, J=8.3 Hz, 1H), 7.01 (d, J=8.6 Hz, 1H), 3.33-3.12 (m, 1H), 3.19-3.17 (d, J=6.3 Hz, 3H), 2.87-2.74 (m, 2H), 2.62 (s, 3H), 2.61, 1.84 (br. s., 2H), 1.44 (d, J=6.8 Hz, 6H).

Example 262

N-cyclopropyl-6-(3-isopropyl-5-(piperidin-4-yl)-1H-indol-2-yl)-8-methylimidazo[1,2-a]pyridine-2-carboxamide (262)

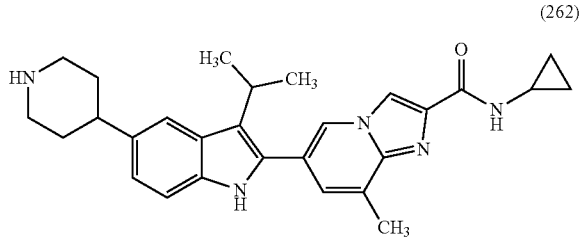 [SMILES: Cc1cc(-c2[nH]c3ccc(C4CCNCC4)cc3c2C(C)C)cn2cc(C(=O)NC3CC3)nc12]

Intermediate 262A: Ethyl 6-bromo-8-methylimidazo[1,2-a]pyridine-2-carboxylate (262A)

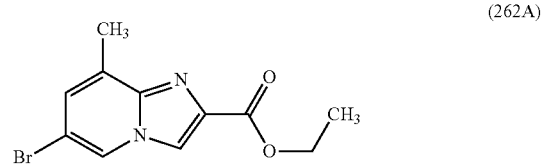 [SMILES: CCOC(=O)c1cn2cc(Br)cc(C)c2n1]

To a solution of 5-bromo-3-methylpyridin-2-amine (1.1 g, 5.88 mmol) in ethanol (10 mL) was added ethyl 3-bromo-2-oxopropanoate (1.37 g, 7.06 mmol). The reaction mixture was stirred at 90° C. for 16 h. The reaction mixture was concentrated, then triturated with ethyl acetate (2 mL) to get ethyl 6-bromo-8-methylimidazo[1,2-a]pyridine-2-carboxylate (1.42 g, 4.32 mmol, 73.5% yield) as pale yellow solid. MS (M$^{+1}$) m/z: 285 (MH$^+$). LC retention time 1.08 min [L].

Intermediate 262B: Ethyl 6-(5-(1-(tert-butoxycarbonyl)piperidin-4-yl)-3-isopropyl-1H-indol-2-yl)-8-methylimidazo[1,2-a]pyridine-2-carboxylate (262B)

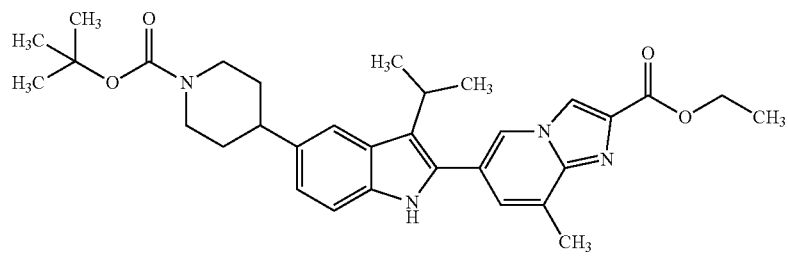

To a solution of tert-butyl 4-(3-isopropyl-2-(4,4,5,5-tetramethyl-1,3,2-dioxaborolan-2-yl)-1H-indol-5-yl)piperidine-1-carboxylate (600 mg, 1.281 mmol) and ethyl 6-bromo-8-methylimidazo[1,2-a]pyridine-2-carboxylate (435 mg, 1.537 mmol) in a mixture of dioxane (15 mL) and water (5.00 mL) solvent mixture was added potassium phosphate tribasic (816 mg, 3.84 mmol). The reaction mixture was degassed for 15 min with nitrogen, then [1,1'-bis(diphenylphosphino)ferrocene]dichloropalladium(II) (94 mg, 0.128 mmol) was added and the mixture was degassed for 2 min. The mixture was stirred at 90° C. for 16 h. The reaction mass was diluted with water (5 mL) and extracted with DCM (2×20 mL), the combined organic layers, dried over sodium sulphate and concentrated to afford crude compound. The crude material was purified by ISCO using 12 g silica column. The compound was eluted in neat EA, the fractions was collected and concentrated to afford ethyl 6-(5-(1-(tert-butoxycarbonyl)piperidin-4-yl)-3-isopropyl-1H-indol-2-yl)-8-methylimidazo[1,2-a]pyridine-2-carboxylate (600 mg, 1.1 mmol, 95% yield) as a brown solid. MS (M$^{+1}$) m/z: 545.2 (MH$^+$). LC retention time 3.97 min [M].

Intermediate 262C: 6-(5-(1-(Tert-butoxycarbonyl)piperidin-4-yl)-3-isopropyl-1H-indol-2-yl)-8-methylimidazo[1,2-a]pyridine-2-carboxylic acid

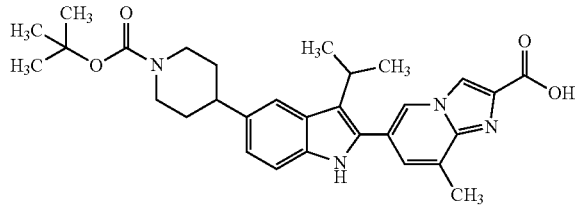

(262C)

To a solution of ethyl 6-(5-(1-(tert-butoxycarbonyl)piperidin-4-yl)-3-isopropyl-1H-indol-2-yl)-8-methylimidazo[1,2-a]pyridine-2-carboxylate (600 mg, 1.102 mmol) in a MeOH (5 mL), THF (5 mL), and water (5 mL) solvent mixture was added LiOH (79 mg, 3.30 mmol) at room temperature. The mixture was stirred at room temperature for 16 h. The reaction mixture was acidified with 10% citric acid, extracted with DCM (2×50 mL), the combined organic extracts was concentrated and dried under vacuum to afford 6-(5-(1-(tert-butoxycarbonyl)piperidin-4-yl)-3-isopropyl-1H-indol-2-yl)-8-methylimidazo[1,2-a]pyridine-2-carboxylic acid (750 mg, 0.809 mmol, 73.4% yield, purity 56%) as a brown solid. LCMS retention time 1.11 min [D]. MS (E⁻) m/z: 517.4 (M+H). MS (M⁺¹) m/z: 517.4 (MH⁺). LC retention time 1.11 min [L].

Intermediate 262D: Tert-butyl 4-(2-(2-(cyclopropylcarbamoyl)-8-methylimidazo[1,2-a]pyridin-6-yl)-3-isopropyl-1H-indol-5-yl)piperidine-1-carboxylate

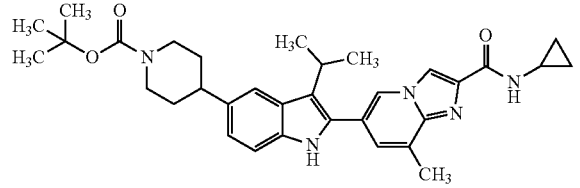

(262D)

To a solution of 6-(5-(1-(tert-butoxycarbonyl)piperidin-4-yl)-3-isopropyl-1H-indol-2-yl)-8-methylimidazo[1,2-a]pyridine-2-carboxylic acid (50 mg, 0.097 mmol) in DMF (2 mL) were added TEA (0.027 mL, 0.194 mmol), cyclopropanamine (11 mg, 0.197 mmol) and HATU (44.2 mg, 0.116 mmol) at room temperature. The reaction mixture was stirred at same temperature for 16 h. The reaction was quenched with water and extracted with DCM (2×10 mL), the combined organic extracts was concentrated to afford crude tert-butyl 4-(2-(2-(cyclopropylcarbamoyl)-8-methylimidazo[1,2-a]pyridin-6-yl)-3-isopropyl-1H-indol-5-yl)piperidine-1-carboxylate (64 mg, 0.071 mmol, 73.8% yield) as an off-white solid. MS (M⁺¹) m/z: 556.5 (MH⁺). LC retention time 1.66 min [L].

Example 262

To a solution of tert-butyl 4-(2-(2-(cyclopropylcarbamoyl)-8-methylimidazo[1,2-a]pyridin-6-yl)-3-isopropyl-1H-indol-5-yl)piperidine-1-carboxylate (50 mg, 0.090 mmol) in dioxane (2 mL) was added 4 M hydrochloric acid in dioxane (0.5 mL, 2.000 mmol) at room temperature. The mixture was stirred at room temperature for 2 h. The reaction mixture was concentrated to get crude compound. The crude material was purified by Preparative LCMS. The fractions containing the desired product were combined and dried via centrifugal evaporation to afford N-cyclopropyl-6-(3-isopropyl-5-(piperidin-4-yl)-1H-indol-2-yl)-8-methylimidazo[1,2-a]pyridine-2-carboxamide (4.7 mg, 10.32 µmol, 11.47% yield). MS (M⁺¹) m/z: 456.3 (MH⁺). LC retention time 1.52 min [E]. ¹H NMR (400 MHz, METHANOL-d₄) δ ppm 0.67-0.73 (m, 2H) 0.82-0.89 (m, 2H) 1.44-1.51 (m, 6H) 1.88-2.17 (m, 6H) 2.63 (s, 3H) 2.86-3.02 (m, 2H) 3.11-3.20 (m, 2H) 3.35 (s, 1H) 3.51 (d, J=12.47 Hz, 2H) 7.06 (d, J=8.31 Hz, 1H) 7.29-7.36 (m, 2H) 7.63 (s, 1H) 8.34-8.42 (m, 2H).

Example 263

6-(3-isopropyl-5-(piperidin-4-yl)-1H-indol-2-yl)-8-methoxy-N,N-dimethylimidazo[1,2-a]pyridine-2-carboxamide

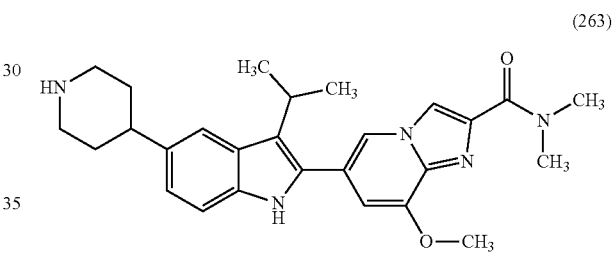

(263)

Intermediate 263A: Ethyl 6-bromo-8-methoxyimidazo[1,2-a]pyridine-2-carboxylate

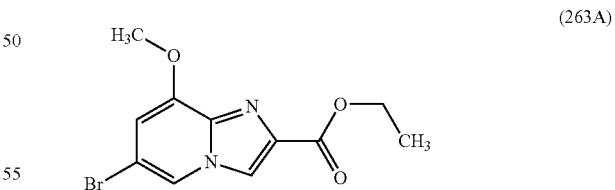

(263A)

To a solution of 5-bromo-3-methoxypyridin-2-amine (0.5 g, 2.463 mmol) in ethanol (4 mL) was added ethyl 3-bromo-2-oxopropanoate (0.480 g, 2.463 mmol) at room temperature. The resulting solution was refluxed for 12 h. The reaction mass was concentrated under high vacuum to afford a solid. The solid was washed with ethyl acetate (2×5 mL), dried under vacuum to afford ethyl 6-bromo-8-methoxyimidazo[1,2-a]pyridine-2-carboxylate (0.45 g, 1.504 mmol, 61% yield) as a pale yellow solid. MS (M⁺¹) m/z: 301.0 (MH⁺). LC retention time 1.40 min [M].

Intermediate 263B: Ethyl 6-(5-(1-(tert-butoxycarbonyl)piperidin-4-yl)-3-isopropyl-1H-indol-2-yl)-8-methoxy imidazo[1,2-a]pyridine-2-carboxylate (263B)

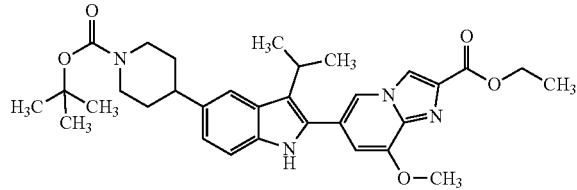

To a solution of tert-butyl 4-(3-isopropyl-2-(4,4,5,5-tetramethyl-1,3,2-dioxaborolan-2-yl)-1H-indol-5-yl)piperidine-1-carboxylate (0.5 g, 1.067 mmol) and ethyl 6-bromo-8-methoxyimidazo[1,2-a]pyridine-2-carboxylate (0.351 g, 1.174 mmol) in a mixture of dioxane (15 mL) and water (1 mL) was added potassium phosphate tribasic (0.558 g, 3.20 mmol). The reaction mixture was degassed for 10 min, $PdCl_2(dppf)\text{-}CH_2Cl_2$ adduct (0.044 g, 0.053 mmol) was added, and the reaction mixture was degassed again for 5 min. The reaction mixture was stirred at 90° C. for 3 h. The reaction mixture was diluted with ethyl acetate (100 mL), washed with water (2×50 mL), brine (50 mL), dried over sodium sulphate, and concentrated to afford crude compound. The crude material was triturated diethyl ether (3×5 mL), and dried under high vacuum to afford ethyl 6-(5-(1-(tert-butoxycarbonyl)piperidin-4-yl)-3-isopropyl-1H-indol-2-yl)-8-methoxyimidazo[1,2-a]pyridine-2-carboxylate (0.35 g, 0.624 mmol, 58.5% yield) as a pale yellow solid. MS $(M^{+1})$ m/z: 561.4 $(MH^+)$. LC retention time 2.86 min [M].

Intermediate 263C: 6-(5-(1-(tert-butoxycarbonyl)piperidin-4-yl)-3-isopropyl-1H-indol-2-yl)-8-methoxyimidazo[1,2-a]pyridine-2-carboxylic acid (263C)

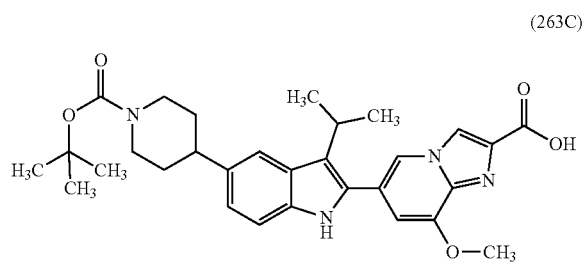 [SMILES: COc1cc(-c2[nH]c3ccc(C4CCN(C(=O)OC(C)(C)C)CC4)cc3c2C(C)C)cn2cc(C(=O)O)nc12]

To a solution of ethyl 6-(5-(1-(tert-butoxycarbonyl)piperidin-4-yl)-3-isopropyl-1H-indol-2-yl)-8-methoxyimidazo[1,2-a]pyridine-2-carboxylate (0.35 g, 0.624 mmol) in THF (3 mL), methanol (3 mL) and water (1 mL) was added lithium hydroxide (0.075 g, 3.12 mmol) at room temperature. The reaction mixture was stirred at room temperature for 5 h. The reaction mass was concentrated under vacuum, the residue was diluted with water (3 mL), and acidified with 1.5N HCl. The precipitated out solid was filtered, washed with diethyl ether and dried under vacuum to afford 6-(5-(1-(tert-butoxycarbonyl) piperidin-4-yl)-3-isopropyl-1H-indol-2-yl)-8-methoxyimidazo[1,2-a]pyridine-2-carboxylic acid (0.32 g, 0.601 mmol, 96% yield). MS $(M^{+1})$ m/z: 533.2 $(MH^+)$. LC retention time 1.85 min [M].

Intermediate 263D: Tert-butyl 4-(2-(2-(dimethylcarbamoyl)-8-methoxyimidazo[1,2-a]pyridin-6-yl)-3-isopropyl-1H-indol-5-yl)piperidine-1-carboxylate (263D)

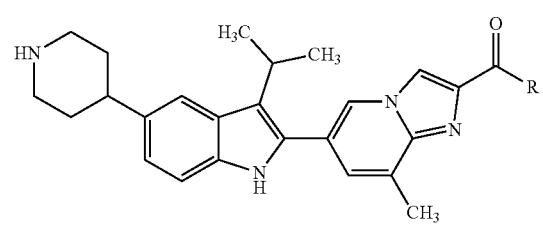

To a solution of 6-(5-(1-(tert-butoxycarbonyl)piperidin-4-yl)-3-isopropyl-1H-indol-2-yl)-8-methoxyimidazo[1,2-a]pyridine-2-carboxylic acid (0.06 g, 0.113 mmol) and dimethylamine in THF (5.08 mg, 0.113 mmol) and DMF (2 mL) were added TEA (0.031 mL, 0.225 mmol) and HATU (0.047 g, 0.124 mmol) at room temperature. The reaction mixture was stirred at same temperature for 3 h. The reaction mass was diluted with DCM (10 mL), washed with water (10 mL), dried over sodium sulphate, and concentrated to afford tert-butyl 4-(2-(2-(dimethylcarbamoyl)-8-methoxyimidazo[1,2-a] pyridin-6-yl)-3-isopropyl-1H-indol-5-yl)piperidine-1-carboxylate (0.065 g, 0.033 mmol, 28.9% yield) as a brown solid. MS $(M^{+1})$ m/z: 560.2 $(MH^+)$. LC retention time 2.80 min [M].

Example 263

To a solution of tert-butyl 4-(2-(2-(dimethylcarbamoyl)-8-methoxyimidazo[1,2-a]pyridin-6-yl)-3-isopropyl-1H-indol-5-yl)piperidine-1-carboxylate (0.065 g, 0.116 mmol) in DCM (2 mL) was added 4 M hydrochloric acid in dioxane (0.290 mL, 1.161 mmol) at room temperature. The mixture was stirred at same temperature for 1 h. The reaction mass was concentrated to afford crude product. The crude sample was purified by prep LCMS. The fractions containing the desired product were combined and dried via centrifugal evaporation to afford 6-(3-isopropyl-5-(piperidin-4-yl)-1H-indol-2-yl)-8-methoxy-N,N-dimethylimidazo[1,2-a]pyridine-2-carboxamide (1.6 mg, 3.48 μmol, 3% yield) as a pale yellow solid. MS $(M^{+1})$ m/z: 460.2 $(MH^+)$. LC retention time 1.27 min [E]. $^1H$ NMR (400 MHz, DMSO-$d_6$) δ ppm 11.09 (s, 1H), 8.42 (s, 1H), 8.29 (s, 1H), 7.56 (s, 1H), 7.33 (d, J=8.3 Hz, 1H), 7.01 (d, J=8.8 Hz, 1H), 6.80 (s, 1H), 4.03 (s, 3H), 3.10 (br. s., 3H), 3.02 (br. s., 4H), 2.97-2.82 (m, 4H), 1.96-1.89 (m, 3H), 1.80 (d, J=9.8 Hz, 2H), 1.45 (d, J=7.1 Hz, 6H).

The following examples were according to the general procedure described in Example 262.

TABLE 14

| Ex. No | R | LCMS [M + H]+ | Rt (min) | Method |
|---|---|---|---|---|
| 264 | -NH(CH₃) | 430.1 | 1.33 | E |
| 265 | -N(CH₃)₂ | 444.1 | 1.33 | E |
| 266 | -N(CH₃)(CH₂CH₃) | 458.3 | 1.53 | E |
| 267 | -NH(CH₂CH₂OH) | 460.2 | 1.24 | E |
| 268 | -N(CH₃)(CH₂CH₂OH) | 473.62 | 1.1 | E |
| 269 | -NH(CH₂CH₂OCH₃) | 474.3 | 1.46 | E |
| 270 | -NH(CH₂C(CH₃)₂OH) | 488.3 | 1.33 | E |

Example 271

6-(3-isopropyl-5-(piperidin-4-yl)-1H-indol-2-yl)-7,8-dimethylimidazo[1,2-a]pyridine

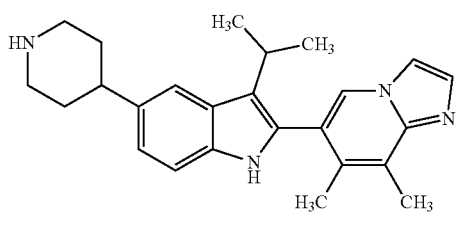

(271)

Intermediate 271A:
5-bromo-3-chloro-4-methylpyridin-2-amine

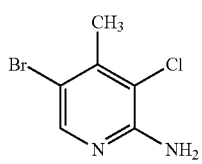

(271A)

To a stirred solution of 5-bromo-4-methylpyridin-2-amine (1.0 g, 5.35 mmol) in DMF (25.0 mL) at 0° C. was added portion wise NCS (1.428 g, 10.69 mmol). The mixture was stirred at room temperature for 5 h. The reaction was quenched with cold water. The reaction mixture was diluted with ethyl acetate and the layers were separated. The aqueous layer was extracted with ethyl acetate (2×50 mL), the combined organic layers was washed with water (50 mL), brine (10 mL), dried over sodium sulphate and concentrated to get crude material. The crude material was purified by ISCO using silica column 40 g silica column. The compound was eluted in 25% ethyl acetate in hexanes, the fractions was collected and concentrated to afford 5-bromo-3-chloro-4-methylpyridin-2-amine (0.700 g, 3.16 mmol, 59% yield) as a light brown solid. MS (M⁺¹) m/z: 222.9 (MH⁺). LC retention time 1.14 min [L].

Intermediate 271B:
6-bromo-8-chloro-7-methylimidazo[1,2-a] pyridine

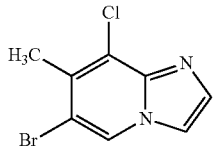

(271B)

To a solution of 5-bromo-3-chloro-4-methylpyridin-2-amine (0.5 g, 2.258 mmol) in ethanol (20 mL) was added 2-chloroacetaldehyde (1.772 g, 11.29 mmol) at 0° C. The mixture was stirred at 70° C. for 16 h and cooled to room temperature. Volatiles were evaporated to get crude material. The residue was diluted with aqueous NaHCO₃, extracted with ethyl acetate (3×200 mL), combined organic extracts was dried over sodium sulphate and concentrated to get crude material. The crude material was purified by ISCO using 40 g silica column. The compound was eluted in 55% ethyl acetate in hexane, the fractions was collected and concentrated to afford 6-bromo-8-chloro-7-methylimidazo [1,2-a]pyridine (0.5 g, 2.037 mmol, 90% yield) as a light yellow color solid. MS (M⁺¹) m/z: 246.9 (MH⁺). LC retention time 1.01 min [L].

Intermediate 271C: Tert-butyl 4-(2-(8-chloro-7-methylimidazo[1,2-a]pyridin-6-yl)-3-isopropyl-1H-indol-5-yl)piperidine-1-carboxylate

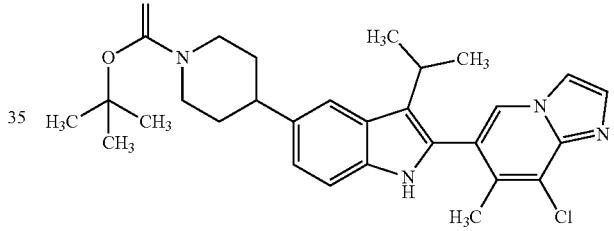

(271C)

Tert-butyl 4-(2-(8-chloro-7-methylimidazo[1,2-a]pyridin-6-yl)-3-isopropyl-1H-indol-5-yl) piperidine-1-carboxylate (0.7 g, 1.38 mmol, 81% yield) was prepared according to the general procedure described in Intermediate 3A using tert-butyl 4-(3-isopropyl-2-(4,4,5,5-tetramethyl-1,3,2-dioxaborolan-2-yl)-1H-indol-5-yl)piperidine-1-carboxylate as the starting intermediate. MS (M*l) m/z: 507.5 (MH⁺). LC retention time 1.63 min [L].

Intermediate 271D: Tert-butyl 4-(2-(7,8-dimethylimidazo[1,2-a]pyridin-6-yl)-3-isopropyl-1H-indol-5-yl)piperidine-1-carboxylate

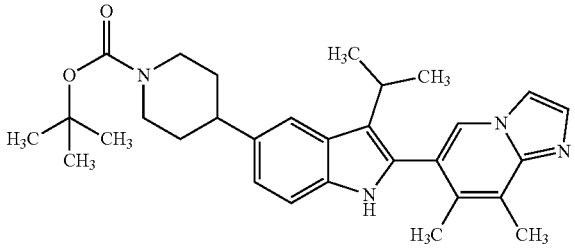

(271D)

A solution of tert-butyl 4-(2-(8-chloro-7-methylimidazo[1,2-a]pyridin-6-yl)-3-isopropyl-1H-indol-5-yl)piperidine-1-carboxylate (0.2 g, 0.394 mmol), methylboronic acid (0.118 g, 1.972 mmol) in dioxane (10.0 mL) and water (3.0 mL) was degassed for 5 min. Next, 2-dicyclohexylphosphino-2',4',6'-triisopropylbiphenyl (0.038 g, 0.079 mmol), palladium(II) acetate (0.018 g, 0.079 mmol) and tripotassium phosphate (0.251 g, 1.183 mmol) were added. The reaction mixture was stirred at 95° C. for 14 h in a sealed tube. The reaction mixture was cooled to room temperature, diluted with ethyl acetate, filtered the solids, the filtrates was washed with water, brine, dried over sodium sulphate and concentrate to afford crude compound. The crude compound was purified by ISCO using 24 g silica column, the compound was eluted in 80% ethyl acetate in hexanes, the fractions was collected and concentrated to afford tert-butyl 4-(2-(7,8-dimethylimidazo[1,2-a]pyridin-6-yl)-3-isopropyl-1H-indol-5-yl)piperidine-1-carboxylate (0.11 g, 0.226 mmol, 57% yield) as a pale yellow solid. MS ($M^{+1}$) m/z: 487.6 (MH$^+$). LC retention time 1.63 min [L].

Example 271

6-(3-isopropyl-5-(piperidin-4-yl)-1H-indol-2-yl)-7,8-dimethylimidazo[1,2-a]pyridine (20 mg, 50 μmol, 24.4% yield) was prepared according to the general procedure described in Example 3 using tert-butyl 4-(2-(7,8-dimethylimidazo[1,2-a]pyridin-6-yl)-3-isopropyl-1H-indol-5-yl)piperidine-1-carboxylate as the starting intermediate. MS ($M^{+1}$) m/z: 387.2 (MH$^+$). LC retention time 1.38 min [E]. $^1$H NMR (400 MHz, METHANOL-d$_4$) δ ppm 8.31 (s, 1H) 7.81 (d, J=1.47 Hz, 1H) 7.63 (s, 1H) 7.57 (d, J=1.47 Hz, 1H) 7.34 (d, J=8.56 Hz, 1H) 7.08 (dd, J=8.44, 1.59 Hz, 1H) 3.80 (s, 1H) 3.54 (d, J=12.47 Hz, 4H) 3.37 (s, 1H) 3.19 (td, J=12.90, 3.06 Hz, 2H) 2.93-3.07 (m, 2H) 2.60 (s, 3H) 2.11-2.25 (m, 5H) 1.87-2.09 (m, 4H) 1.32-1.48 (m, 6H).

The following example was prepared according to the general procedure described in Example 271.

TABLE 15

| Ex. No. | Structure | LCMS [M + H]$^+$ | Rt (min) | Method |
|---|---|---|---|---|
| 272 | 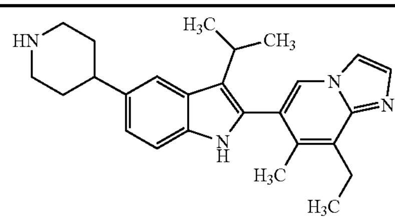 | 401.2 | 1.47 | E |

Intermediate 273A: Tert-butyl 4-(3-isopropyl-2-(7-methyl-8-(prop-1-en-2-yl) imidazo[1,2-a] pyridin-6-yl)-1H-indol-5-yl) piperidine-1-carboxylate

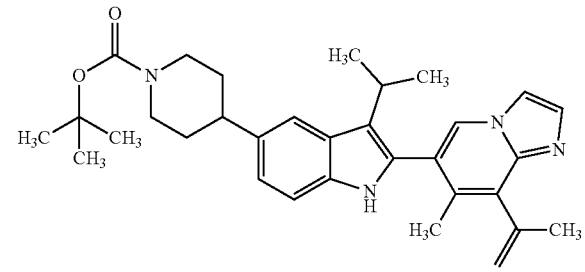

(273A)

Tert-butyl 4-(3-isopropyl-2-(7-methyl-8-(prop-1-en-2-yl) imidazo[1,2-a] pyridin-6-yl)-1H-indol-5-yl) piperidine-1-carboxylate (0.45 g, 0.088 mmol, 29.7% yield) was prepared according to the general procedure described in Ex-219A using tert-butyl 4-(2-(8-chloro-7-methylimidazo[1,2-a]pyridin-6-yl)-3-isopropyl-1H-indol-5-yl)piperidine-1-carboxylate (0.150 g, 0.296 mmol) as the starting intermediate. MS ($M^{+1}$) m/z: 513.5 (MH$^+$). LC retention time 1.71 min [L].

Example 273

8-isopropyl-6-(3-isopropyl-5-(piperidin-4-yl)-1H-indol-2-yl)-7-methylimidazo[1,2-a]pyridine (273)

Intermediate 273B: Tert-butyl 4-(3-isopropyl-2-(8-isopropyl-7-methylimidazo[1,2-a]pyridin-6-yl)-1H-indol-5-yl)piperidine-1-carboxylate (273B)

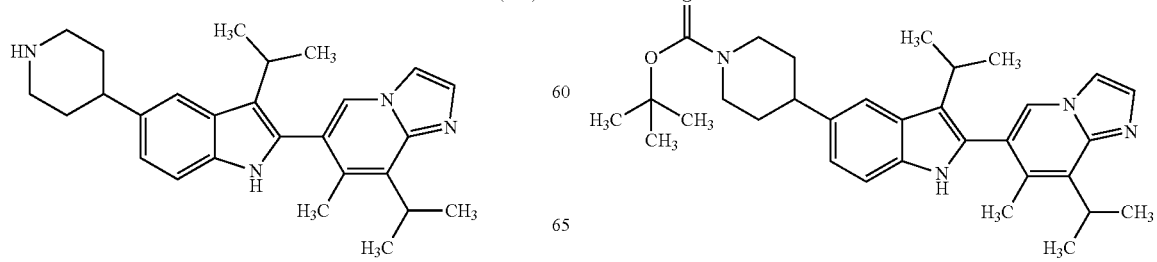

To a solution of tert-butyl 4-(3-isopropyl-2-(7-methyl-8-(prop-1-en-2-yl)imidazo [1,2-a]pyridin-6-yl)-1H-indol-5-yl)piperidine-1-carboxylate (0.048 g, 0.094 mmol) in ethyl acetate (5.0 mL) and MeOH (5.0 mL) solvent mixture was added Pd/C (0.020 g, 0.187 mmol). The resulting slurry was stirred at room temperature for 6 h under a hydrogen bladder. The reaction mixture was diluted with ethyl acetate, filtered through celite, and washed with excess methanol. The filtrate was collected and concentrated to afford tert-butyl 4-(3-isopropyl-2-(8-isopropyl-7-methylimidazo[1,2-a]pyridin-6-yl)-1H-indol-5-yl)piperidine-1-carboxylate (0.03 g, 0.058 mmol, 62.3% yield) as a light brown solid. MS $(M^{+1})$ m/z: 515.6 $(MH^+)$. LC retention time 1.85 min [L].

Example 273

To a solution of tert-butyl 4-(3-isopropyl-2-(8-isopropyl-7-methylimidazo[1,2-a]pyridin-6-yl)-1H-indol-5-yl)piperidine-1-carboxylate (0.028 g, 0.054 mmol) in dioxane (1.0 mL) was added 4 M HCl in dioxane (0.340 mL, 1.360 mmol) at room temperature. The mixture was stirred at room temperature for 2 h. The volatiles was evaporated to afford the crude compound. The crude material was purified by preparative LC/MS. The fractions containing desired product were combined and dried via centrifugal evaporation to afford 8-isopropyl-6-(3-isopropyl-5-(piperidin-4-yl)-1H-indol-2-yl)-7-methylimidazo[1,2-a]pyridine as a pale solid (0.010 g, 0.024 mmol, 43.5% yield). MS $(M^{+1})$ m/z: 415.3 $(MH^+)$. LC retention time 1.66 min [E]. $^1$H NMR (400 MHz, METHANOL-$d_4$) δ ppm 8.30 (s, 1H) 7.80 (d, J=1.47 Hz, 1H) 7.63 (s, 1H) 7.56 (d, J=1.22 Hz, 1H) 7.34 (d, J=8.31 Hz, 1H) 7.08 (d, J=8.31 Hz, 1H) 3.72-3.89 (m, 1H) 3.53 (d, J=12.47 Hz, 2H) 3.38 (s, 1H) 3.13-3.25 (m, 24H) 2.91-3.09 (m, 2H) 2.12-2.27 (m, 4H) 1.91-2.10 (m, 4H) 1.50-1.68 (m, 6H) 1.27-1.44 (m, 6H).

Example 274

5-(3-isopropyl-5-(piperidin-4-yl)-1H-indol-2-yl)-N,7-dimethylpyrazolo[1,5-a]pyridine-3-carboxamide

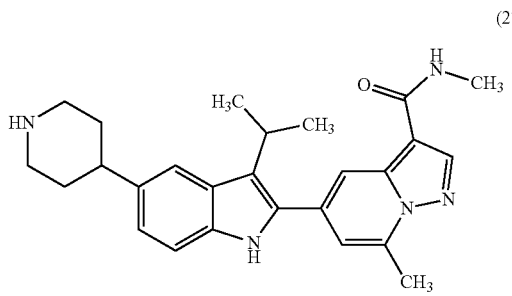

(274)

Intermediate 274A: Tert-butyl (2-methylpyridin-4-yl) carbamate

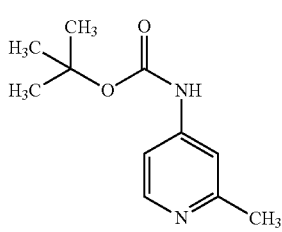

(274A)

To a stirred solution of 2-methylpyridin-4-amine (8.0 g, 74.0 mmol) in dichloromethane (300 mL) were added TEA (30.9 mL, 222 mmol), DMAP (4.52 g, 37.0 mmol) and BOC$_2$O (17.18 mL, 74.0 mmol) at 0° C. The mixture was stirred at room temperature for 16 h. The reaction mixture was quenched with cold water and diluted with chloroform (300 mL). The layers were separated. The organic layer was washed with water, brine, dried over sodium sulphate and concentrated to get crude compound. The crude was purified by ISCO using 120 g silica column, compound was eluted in 55% ethyl acetate in hexanes, the fractions was collected and concentrated to afford tert-butyl (2-methylpyridin-4-yl) carbamate (10.0 g, 48.0 mmol, 64.9% yield) as a brown solid. MS (M+1) m/z: 209.1 $(MH^+)$. LC retention time 0.95 min [L].

Intermediate 274B: 1-amino-4-((tert-butoxycarbonyl) amino)-2-methylpyridin-1-ium

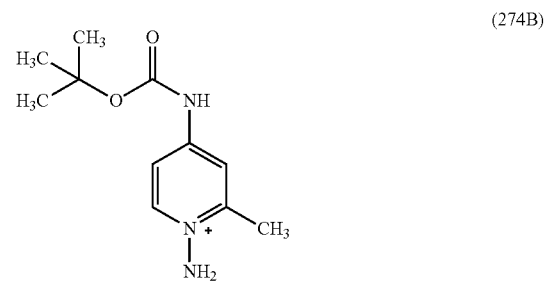 [SMILES: Cc1cc(NC(=O)OC(C)(C)C)cc[n+]1N]

(274B)

To a solution of tert-butyl (2-methylpyridin-4-yl)carbamate (6.0 g, 28.8 mmol) in acetonitrile (300.0 mL) was added O-(2,4-dinitrophenyl)hydroxylamine (5.74 g, 28.8 mmol) at room temperature. The mixture was stirred at 50° C. for 48 h. The reaction mixture was cooled to room temperature, concentrated and dried under vacuum to afford 1-amino-4-(tert-butoxycarbonyl)amino)-2-methylpyridin-1-ium (10.5 g, 46.8 mmol, 162% yield) as a yellow color solid. MS $(M^{+1})$ m/z: 224.1 $(MH^+)$. LC retention time 0.67 min [L].

Intermediate 274C: Ethyl 5-((tert-butoxycarbonyl) amino)-7-methylpyrazolo[1,5-a]pyridine-3-carboxylate

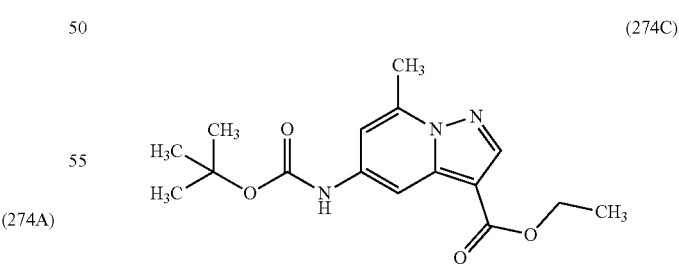

(274C)

To a stirred solution of 1-amino-4-((tert-butoxycarbonyl) amino)-2-methylpyridin-1-ium (10.5 g, 46.8 mmol) and ethyl propiolate (4.59 g, 46.8 mmol) in DMF (80.0 mL) was added K$_2$CO$_3$ (19.41 g, 140 mmol) at 0° C. The mixture was stirred at room temperature for 16 hr., cool to room temperature, and concentrated. The residue was dissolved in cold water and extracted with chloroform (2×100 mL). The combined organic extracts was washed with brine, dried over sodium sulfate and concentrated to get crude material. The crude material was purified by ISCO using 40 g silica column, compound was eluted with 65-90% ethyl acetate in hexanes, the fractions was collected and concentrated to afford ethyl 5-((tert-butoxycarbonyl)amino)-7-methylpyrazolo[1,5-a]pyridine-3-carboxylate (6.0 g, 18.79 mmol, 40% yield) as a light yellow solid. MS (M$^{+1}$) m/z: 320.1 (MH$^+$). LC retention time 1.3 min [L].

Intermediate 274D: Ethyl 5-amino-7-methylpyrazolo[1,5-a]pyridine-3-carboxylate

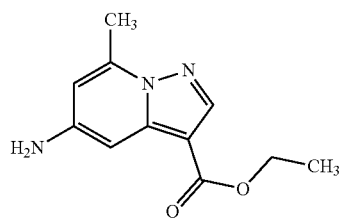

(274D)

To a solution of ethyl 5-((tert-butoxycarbonyl)amino)-7-methylpyrazolo[1,5-a]pyridine-3-carboxylate (6.0 g, 18.79 mmol) in dichloromethane (100 mL) was added TFA (28.9 mL, 376 mmol) at 0° C. The mixture was stirred at room temperature for 16 h. The reaction mass was concentrated, the residue was diluted with water (100 mL), brought to basic pH with 10% aqueous NaHCO$_3$, stirred for 30 min, and extracted with ethyl acetate (2×250 mL). The combined organic extracts was washed with water, brine, dried over sodium sulphate and concentrated to get crude compound. The crude compound was purified by ISCO using 40 g silica column, the compound was eluted with 55% ethyl acetate in hexanes, the fractions were collected and concentrated afford ethyl 5-amino-7-methylpyrazolo[1,5-a]pyridine-3-carboxylate (4.1 g, 18.70 mmol, 100% yield) as a brown solid. MS (M$^{+1}$) m/z: 220.1 (MH$^+$). LC retention time 0.83 min [L].

Intermediate 274E: Ethyl 5-bromo-7-methylpyrazolo[1,5-a]pyridine-3-carboxylate

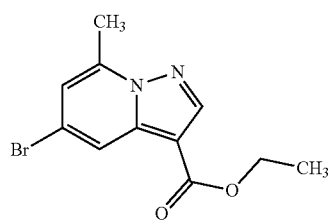

(274E)

To a solution of ethyl 5-amino-7-methylpyrazolo[1,5-a]pyridine-3-carboxylate (4.0 g, 18.24 mmol) in aqueous HBr (55.0 mL, 639 mmol, 50%) was added a solution of sodium nitrite (3.78 g, 54.7 mmol) in water (15.0 mL) at 0° C. The mixture was stirred for 30 min) at 0° C. Next, copper(I) bromide (6.54 g, 45.6 mmol) in aqueous HBr (19.82 mL, 365 mmol, 50%) was added. The reaction mixture was stirred at 50° C. for 30 min. The reaction was quenched with cold water. The reaction mixture was neutralized with 10% NaOH solution and extracted with chloroform (2×300 mL). The organic extracts were combined and washed with water, brine, dried over sodium sulphate and concentrated to get crude compound. The crude compound was purified by ISCO using 40 g silica column, compound was eluted with 55% ethyl acetate/n-hexanes, the fractions was collected and concentrated to afford ethyl 5-bromo-7-methylpyrazolo[1,5-a]pyridine-3-carboxylate (1.3 g, 4.59 mmol, 25.2% yield) as an off-white solid. MS (M*l) m/z: 283.0 (MH$^+$). LC retention time 1.37 min [L].

Intermediate 274F: Ethyl 5-(5-(1-(tert-butoxycarbonyl) piperidin-4-yl)-3-isopropyl-1H-indol-2-yl)-7-methylpyrazolo[1,5-a]pyridine-3-carboxylate

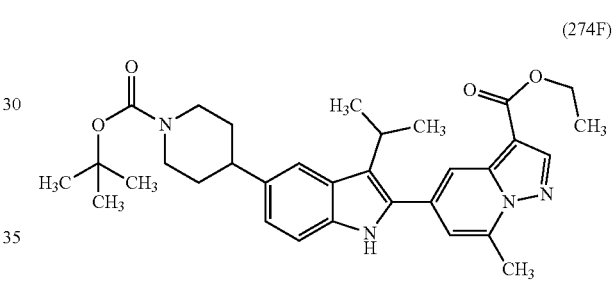

(274F)

To a stirred solution of—tert-butyl 4-(3-isopropyl-2-(4,4,5,5-tetramethyl-1,3,2-dioxaborolan-2-yl)-1H-indol-5-yl)piperidine-1-carboxylate (0.500 g, 1.067 mmol) and ethyl-5-bromo-7-methylpyrazolo[1,5-a]pyridine-3-carboxylate (0.363 g, 1.281 mmol) in dioxane (20.0 mL)/water (3.0 mL) was degassed for 5 min. Next, PdCl$_2$(dppf)-CH$_2$Cl$_2$ adduct (0.087 g, 0.107 mmol) and tri potassium phosphate (0.680 g, 3.20 mmol) were added. The reaction mixture was stirred at 95° C. for 3 h in a sealed tube. The reaction mixture was diluted with ethyl acetate, filtered and washed with excess ethyl acetate. The filtrate was washed with water, brine, dried over sodium sulphate and concentrated to get crude compound. The crude compound was purified by ISCO using 40 g silica column, compound was eluted with 35% ethyl acetate in hexanes, the fractions were collected and concentrated to afford ethyl 5-(5-(1-(tert-butoxycarbonyl) piperidin-4-yl)-3-isopropyl-1H-indol-2-yl)-7-methylpyrazolo[1,5-a]pyridine-3-carboxylate (0.380 g, 0.698 mmol, 65% yield) as a light yellow solid. MS (M$^{+1}$) m/z: 545.4 (MH$^+$). LC retention time 1.89 min [L].

Intermediate 274G: 5-(5-(1-(tert-butoxycarbonyl)piperidin-4-yl)-3-isopropyl-1H-indol-2-yl)-7-methylpyrazolo[1,5-a]pyridine-3-carboxylic acid

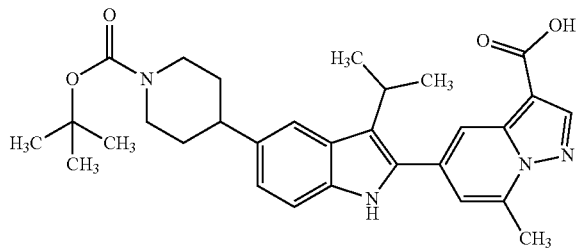

(274G)

To a solution of ethyl 5-(5-(1-(tert-butoxycarbonyl)piperidin-4-yl)-3-isopropyl-1H-indol-2-yl)-7-methylpyrazolo[1,5-a]pyridine-3-carboxylate (0.350 g, 0.643 mmol) in THF (5 mL) and ethanol (5 mL) solvent mixture was added lithium hydroxide (0.154 g, 6.43 mmol) in water (5 mL) at room temperature. The mixture was stirred at 50° C. for 16 h. The reaction mixture was cooled to room temperature, concentrated, diluted with water (10 mL), and pH was brought to acidic with 5% aqueous HCl solution. The mixture was extracted with ethyl acetate (2×200 mL), combined organic extracts were washed with brine dried over sodium sulphate, concentrated and dried under vacuum to afford (5-(1-(tert-butoxycarbonyl) piperidin-4-yl)-3-isopropyl-1H-indol-2-yl)-7-methylpyrazolo[1,5-a]pyridine-3-carboxylic acid (0.250 g, 0.484 mmol, 75% yield) as a brown solid. MS ($M^{+1}$) m/z: 517.3 ($MH^+$). LC retention time 1.25 min [L].

Intermediate 274H: Tert-butyl 4-(3-isopropyl-2-(7-methyl-3-(methylcarbamoyl) pyrazolo [1,5-a]pyridin-5-yl)-1H-indol-5-yl)piperidine-1-carboxylate

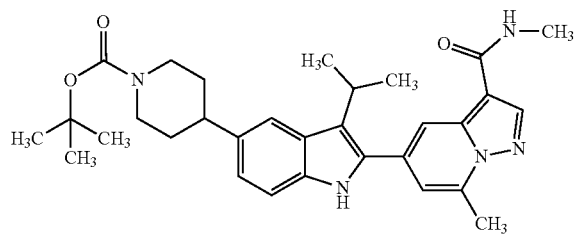

(274H)

To a solution of 5-(5-(1-(tert-butoxycarbonyl)piperidin-4-yl)-3-isopropyl-1H-indol-2-yl)-7-methylpyrazolo[1,5-a]pyridine-3-carboxylic acid (0.1 g, 0.194 mmol) and methanamine hydrochloride (0.039 g, 0.581 mmol) in DMF (5.0 mL) were added TEA (0.081 mL, 0.581 mmol) and HATU (0.074 g, 0.194 mmol) at 0° C. The mixture was stirred at room temperature for 14 h. The reaction mixture was diluted with ethyl acetate, washed with water, brine, dried over $Na_2SO_4$ and evaporated to afford crude tert-butyl 4-(3-isopropyl-2-(7-methyl-3-(methylcarbamoyl)pyrazolo[1,5-a]pyridin-5-yl)-1H-indol-5-yl)piperidine-1-carboxylate (0.140 g, 0.264 mmol, 137% yield). MS ($M^{-1}$) m/z: 528.7 ($MH^-$). LC retention time 1.52 min [L].

Example 274

To a solution of tert-butyl 4-(3-isopropyl-2-(7-methyl-3-(methylcarbamoyl) pyrazolo[1,5-a]pyridin-5-yl)-1H-indol-5-yl)piperidine-1-carboxylate (0.09 g, 0.170 mmol) in 1,4-dioxane (5.0 mL) was added 4 M HCl in dioxane (1.062 mL, 4.25 mmol) at room temperature. The mixture was stirred room temperature for 2h. The reaction mass was concentrated to get crude compound. The crude compound was purified using preparative LC/MS. The fractions containing the desired product were combined and dried via centrifugal evaporation to afford 5-(3-isopropyl-5-(piperidin-4-yl)-1H-indol-2-yl)-N,7-dimethylpyrazolo[1,5-a]pyridine-3-carboxamide (5 mg, 0.012 mmol, 6.85% yield) as an off-white solid. MS ($M^{+1}$) m/z: 430.1 ($MH^+$). LC retention time 1.35 min [E]. $^1H$ NMR (400 MHz, METHANOL-$d_4$) δ ppm 8.36 (s, 1H) 8.21 (s, 1H) 7.56 (s, 1H) 7.27 (d, J=8.53 Hz, 1H) 6.97-7.01 (m, 2H) 3.42-3.37 (m, 3H) 3.25 (s, 2H) 3.06-3.00 (m, 2H) 2.84 (s, 4H) 2.72 (s, 3H) 2.04-2.00 (m, 2H) 1.86-1.93 (m, 3H) 1.800 (s, 3H) 1.43 (d, J=7.53 Hz, 6H).

The following example was prepared according to the general procedure described in Example 274.

| Ex. No | Structure | LCMS [M + H]+ | Rt (min) | Method |
|---|---|---|---|---|
| 275 | 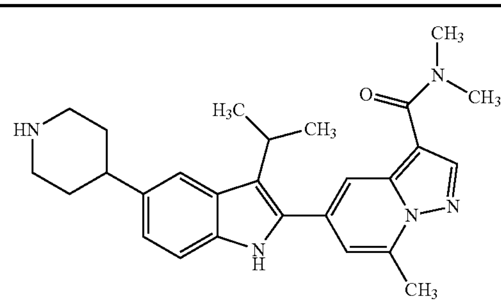 | 444.1 | 1.453 | E |

Example 276

2-(4-(3-isopropyl-2-(1H-pyrazolo[3,4-b]pyridin-4-yl)-1H-indol-5-yl)piperidin-1-yl)-N-methylacetamide

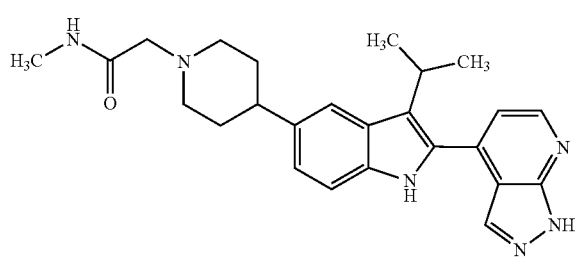

(276)

To a stirred solution of 4-(3-isopropyl-5-(piperidin-4-yl)-1H-indol-2-yl)-1H-pyrazolo[3,4-b]pyridine (20 mg, 0.056 mmol) in DCM (2 mL) was added 2-chloro-n-methylacetamide (7.18 mg, 0.067 mmol). The solution was cooled to 0° C. Next, TEA (0.023 mL, 0.167 mmol) was added and the reaction mixture was stirred room temperature for 16 hours. The reaction mixture was concentrated, dissolved in DMSO and purified by preparative HPLC. The fractions containing the product were combined and dried via centrifugal evaporation to afford 2-(4-(3-isopropyl-2-(1H-pyrazolo[3,4-b]pyridin-4-yl)-1H-indol-5-yl)piperidin-1-yl)-N-methylacetamide (2.0 mg, 0.0044 mmol, 12% yield). MS ($M^{+1}$) m/z: 431.3 ($MH^+$). LC retention time 0.97 min [E]. $^1H$ NMR (400 MHz, DMSO-$d_6$) δ 13.86-13.75 (m, 1H), 11.25-11.15 (m, 1H), 8.65-8.50 (m, 1H), 8.17-8.02 (m, 1H), 7.64-7.57 (m, 1H), 7.41-7.32 (m, 1H), 7.24-7.17 (m, 1H), 7.12-7.05 (m, 1H), 2.97-2.87 (m, 4H), 2.54-2.51 (m, 2H), 2.47-2.37 (m, 2H), 2.22-2.12 (m, 2H), 1.87-1.74 (m, 3H), 1.46-1.47 (m, 6H), 1.28-1.17 (m, 2H).

TABLE 16

| Ex. No. | Structure | Obs. MS Ion | RT | HPLC Method |
|---|---|---|---|---|
| 277 | 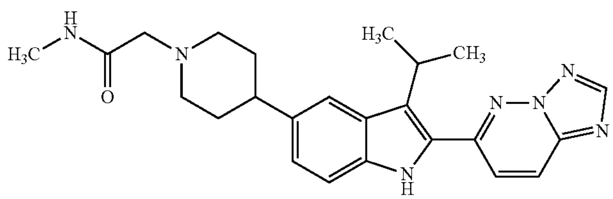 [SMILES: CNC(=O)CN1CCC(c2ccc3[nH]c(-c4ccc5ncnn5n4)c(C(C)C)c3c2)CC1] | 432.0 | 0.62 | A1 |
| 278 | 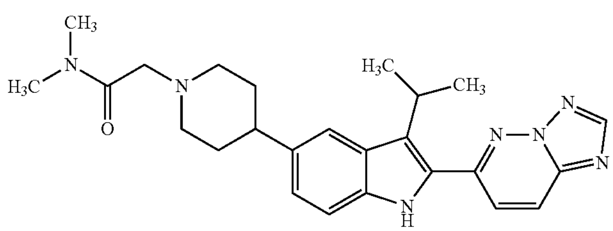 [SMILES: CC(C)c1c(-c2ccc3ncnn3n2)[nH]c2ccc(C3CCN(CC(=O)N(C)C)CC3)cc12] | 446.0 | 0.63 | A1 |
| 279 | 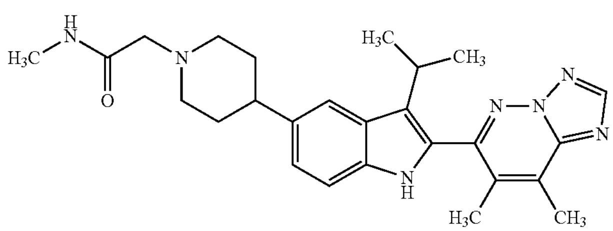 [SMILES: CNC(=O)CN1CCC(c2ccc3[nH]c(-c4nn5ncnc5c(C)c4C)c(C(C)C)c3c2)CC1] | 460.1 | 0.65 | A1 |
| 280 | 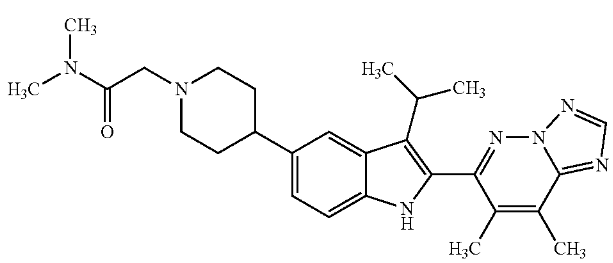 [SMILES: Cc1c(-c2[nH]c3ccc(C4CCN(CC(=O)N(C)C)CC4)cc3c2C(C)C)nn2ncnc2c1C] | 474.1 | 0.67 | A1 |

TABLE 16-continued
| Ex. No. | Structure | Obs. MS Ion | RT | HPLC Method |
|---|---|---|---|---|
| 281 | 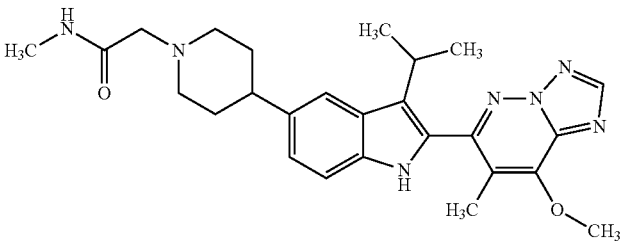 [SMILES: CNC(=O)CN1CCC(c2ccc3[nH]c(-c4nn5ncnc5c(OC)c4C)c(C(C)C)c3c2)CC1] | 476.3 | 0.70 | B1 |
| 282 | 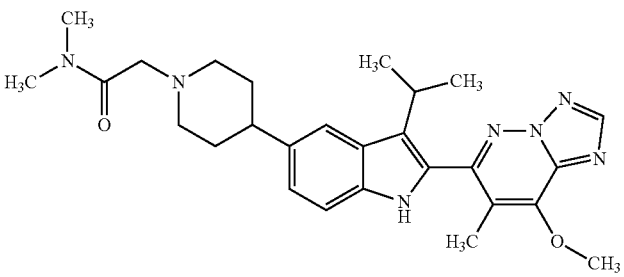 [SMILES: COc1c(C)c(-c2[nH]c3ccc(C4CCN(CC(=O)N(C)C)CC4)cc3c2C(C)C)nn2ncnc12] | 490.3 | 0.72 | B1 |
| 283 | 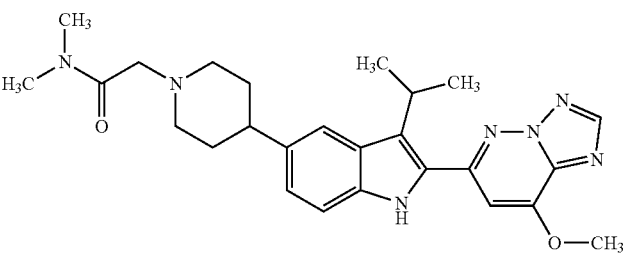 [SMILES: COc1cc(-c2[nH]c3ccc(C4CCN(CC(=O)N(C)C)CC4)cc3c2C(C)C)nn2ncnc12] | 476.3 | 1.17 | QC-ACN-AA-XB |
| 284 | 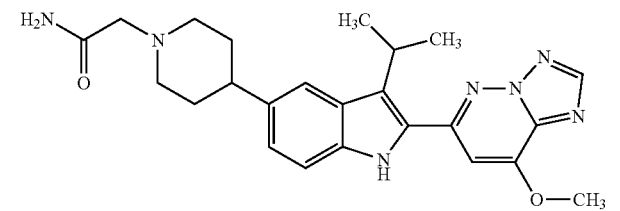 [SMILES: COc1cc(-c2[nH]c3ccc(C4CCN(CC(N)=O)CC4)cc3c2C(C)C)nn2ncnc12] | 448.1 | 1.07 | QC-ACN-TFA-XB |
| 285 | 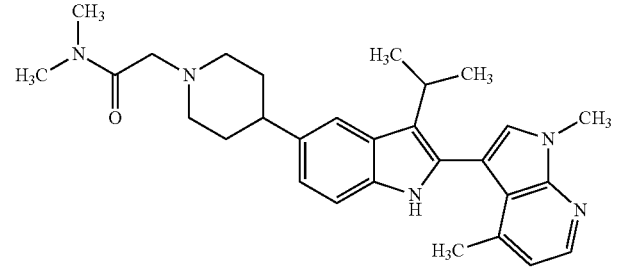 | 472.4 | 1.11 | QC-ACN-TFA-XB |
| 286 | 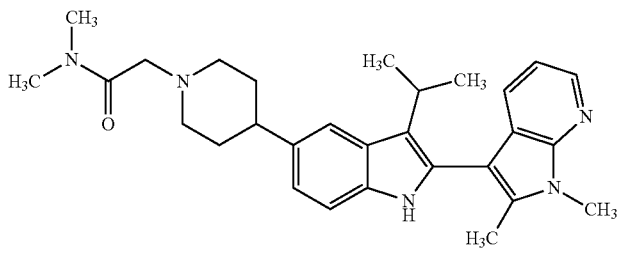 | 472.1 | 1.7 | QC-ACN-AA-XB |

TABLE 16-continued

| Ex. No. | Structure | Obs. MS Ion | RT | HPLC Method |
|---|---|---|---|---|
| 287 | 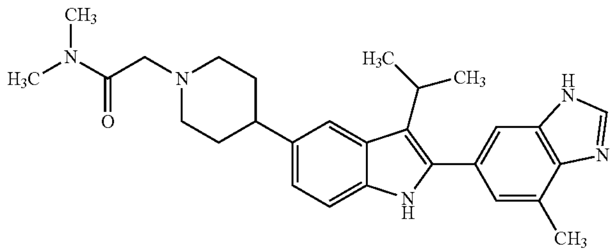 [SMILES: Cc1cc(-c2[nH]c3ccc(C4CCN(CC(=O)N(C)C)CC4)cc3c2C(C)C)cc2[nH]cnc12] | 458.2 | 0.93 | QC-ACN-TFA-XB |
| 288 | 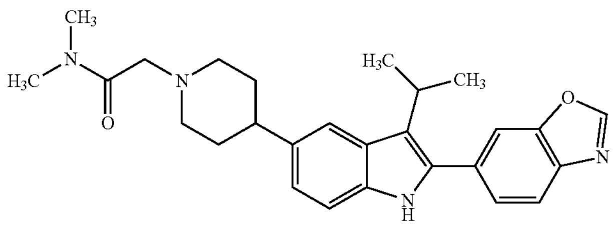 [SMILES: CC(C)c1c(-c2ccc3ncoc3c2)[nH]c2ccc(C3CCN(CC(=O)N(C)C)CC3)cc12] | 444.9 | 1.34 | QC-ACN-TFA-XB |
| 289 | 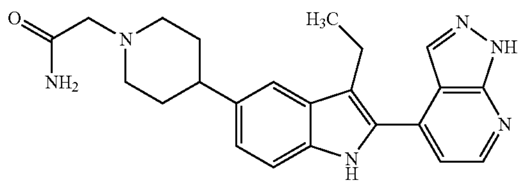 [SMILES: CCc1c(-c2ccnc3[nH]ncc23)[nH]c2ccc(C3CCN(CC(N)=O)CC3)cc12] | 403.3 | 1.2 | QC-ACN-AA-XB |
| 290 | 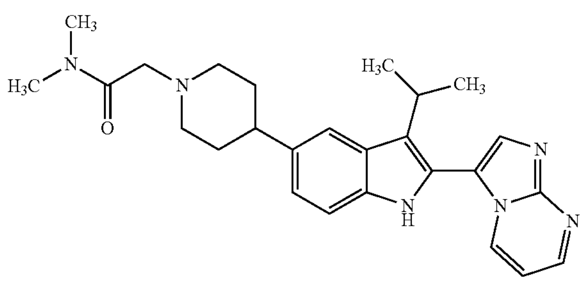 [SMILES: CC(C)c1c(-c2cnc3ncccn23)[nH]c2ccc(C3CCN(CC(=O)N(C)C)CC3)cc12] | 445 | 1.12 | QC-ACN-AA-XB |
| 291 | 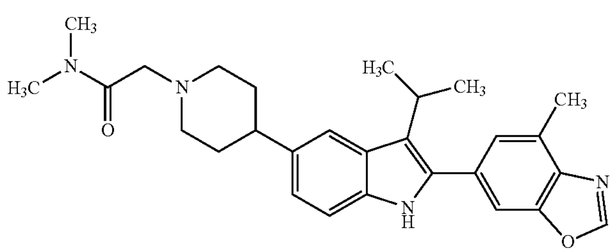 [SMILES: Cc1cc(-c2[nH]c3ccc(C4CCN(CC(=O)N(C)C)CC4)cc3c2C(C)C)cc2ocnc12] | 459 | 1.84 | QC-ACN-AA-XB |
| 292 | 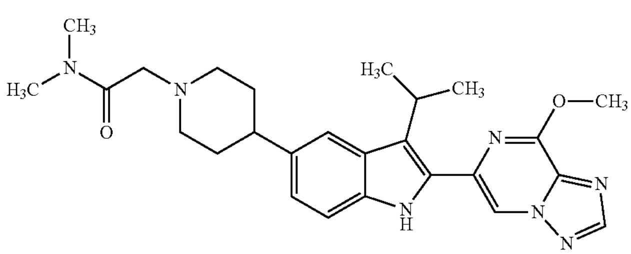 [SMILES: COc1nc(-c2[nH]c3ccc(C4CCN(CC(=O)N(C)C)CC4)cc3c2C(C)C)cn2ncnc12] | 476.1 | 1.47 | QC-ACN-AA-XB |

TABLE 16-continued

| Ex. No. | Structure | Obs. MS Ion | RT | HPLC Method |
|---|---|---|---|---|
| 293 | 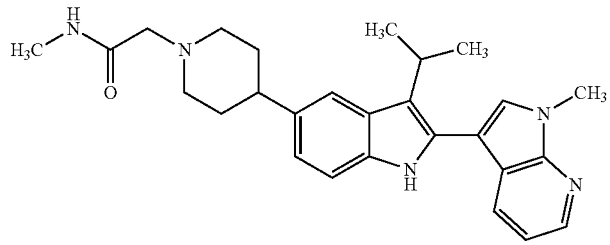 | 444.4 | 1.76 | QC-ACN-AA-XB |
| 294 | 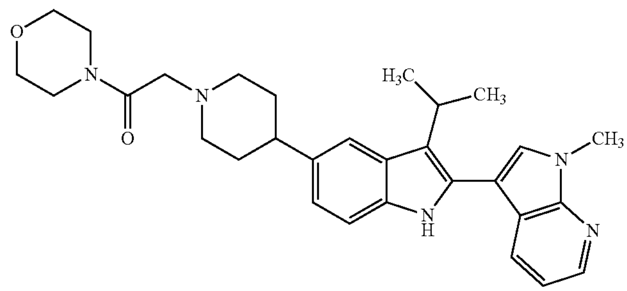 [SMILES: CC(C)c1c(-c2cn(C)c3ncccc23)[nH]c2ccc(C3CCN(CC(=O)N4CCOCC4)CC3)cc12] | 500.4 | 1.43 | QC-ACN-TFA-XB |
| 295 | 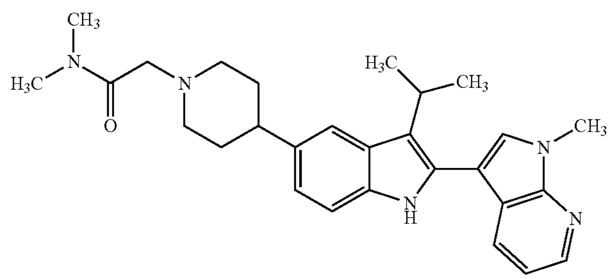 | 458.1 | 1.14 | QC-ACN-TFA-XB |
| 296 | 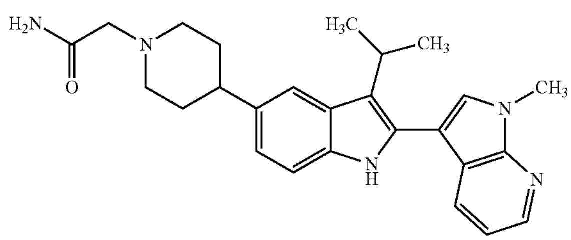 [SMILES: CC(C)c1c(-c2cn(C)c3ncccc23)[nH]c2ccc(C3CCN(CC(N)=O)CC3)cc12] | 430.3 | 1.05 | QC-ACN-TFA-XB |
| 297 | 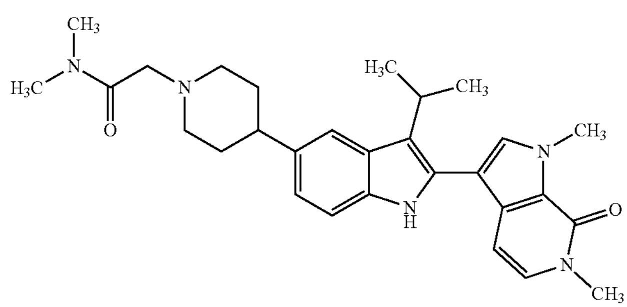 [SMILES: CC(C)c1c(-c2cn(C)c3c(=O)n(C)ccc23)[nH]c2ccc(C3CCN(CC(=O)N(C)C)CC3)cc12] | 488.1 | 1.52 | QC-ACN-AA-XB |
| 298 | 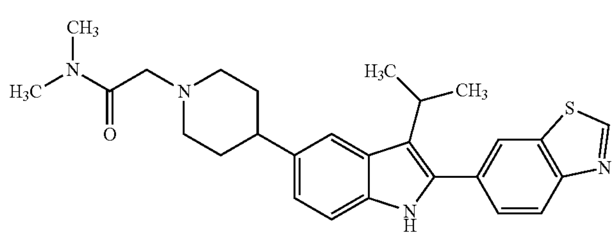 [SMILES: CC(C)c1c(-c2ccc3ncsc3c2)[nH]c2ccc(C3CCN(CC(=O)N(C)C)CC3)cc12] | 460.9 | 1.4 | QC-ACN-TFA-XB |

TABLE 16-continued

| Ex. No. | Structure | Obs. MS Ion | RT | HPLC Method |
|---|---|---|---|---|
| 299 | 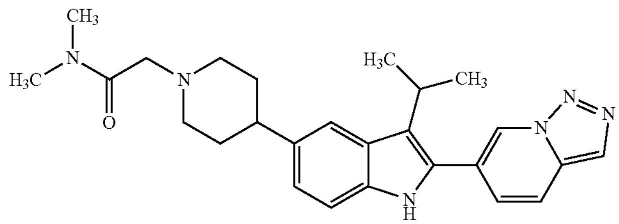 | 444.9 | 1.45 | QC-ACN-AA-XB |
| 300 | 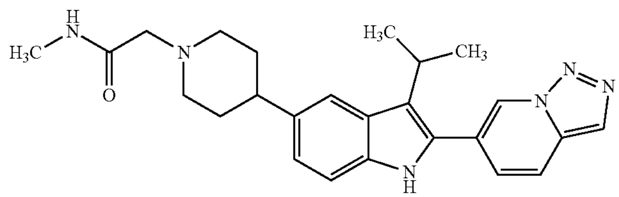 [SMILES: CNC(=O)CN1CCC(c2ccc3[nH]c(-c4ccc5cnnn5c4)c(C(C)C)c3c2)CC1] | 430.9 | 1.29 | QC-ACN-TFA-XB |
| 301 | 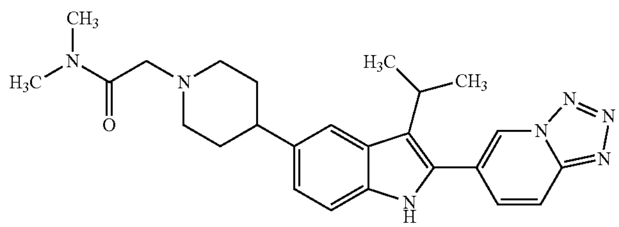 [SMILES: CC(C)c1c(-c2ccc3nnnn3c2)[nH]c2ccc(C3CCN(CC(=O)N(C)C)CC3)cc12] | 446.4 | 1.34 | QC-ACN-AA-XB |
| 302 | 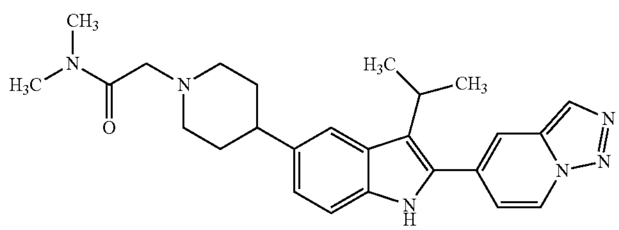 [SMILES: CC(C)c1c(-c2ccn3nncc3c2)[nH]c2ccc(C3CCN(CC(=O)N(C)C)CC3)cc12] | 445.4 | 1.34 | QC-ACN-AA-XB |
| 303 | 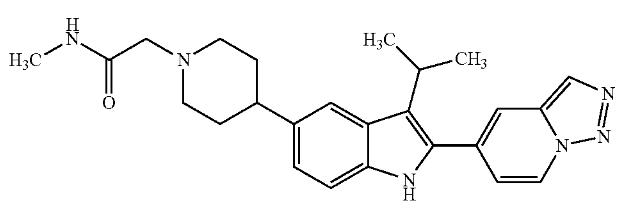 [SMILES: CNC(=O)CN1CCC(c2ccc3[nH]c(-c4ccn5nncc5c4)c(C(C)C)c3c2)CC1] | 431.1 | 1.46 | QC-ACN-AA-XB |
| 304 | 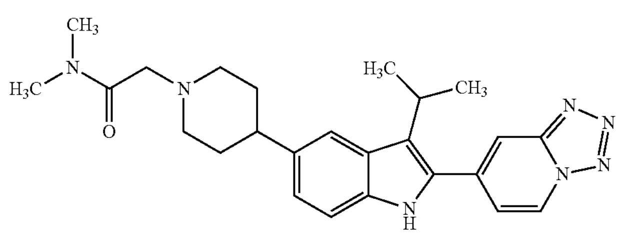 | 446 | 1.1 | QC-ACN-TFA-XB |
| 305 | 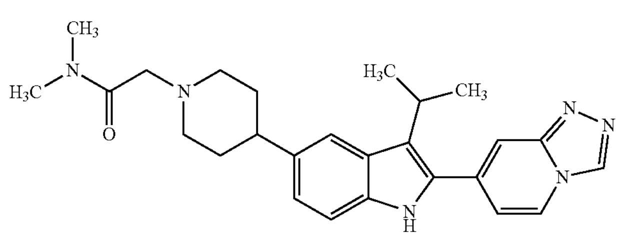 [SMILES: CC(C)c1c(-c2ccn3nnnc3c2)[nH]c2ccc(C3CCN(CC(=O)N(C)C)CC3)cc12] | 445 | 1.08 | QC-ACN-AA-XB |

TABLE 16-continued

| Ex. No. | Structure | Obs. MS Ion | RT | HPLC Method |
|---|---|---|---|---|
| 306 | 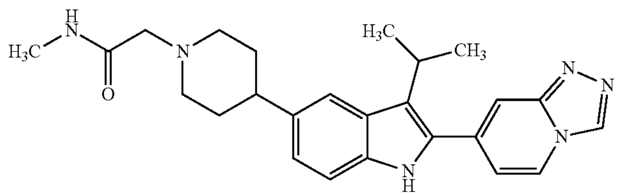 [SMILES: CNC(=O)CN1CCC(c2ccc3[nH]c(-c4ccn5cnnc5c4)c(C(C)C)c3c2)CC1] | 431.1 | 1.21 | QC-ACN-AA-XB |
| 307 | 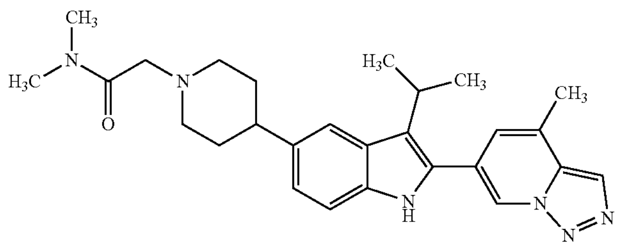 [SMILES: Cc1cc(-c2[nH]c3ccc(C4CCN(CC(=O)N(C)C)CC4)cc3c2C(C)C)cn2nncc12] | 459.3 | 1.71 | QC-ACN-AA-XB |
| 308 | 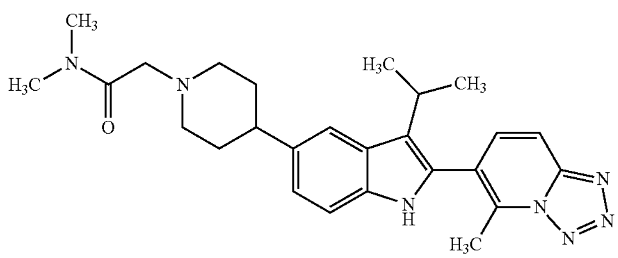 [SMILES: Cc1c(-c2[nH]c3ccc(C4CCN(CC(=O)N(C)C)CC4)cc3c2C(C)C)ccc2nnnn12] | 460.2 | 1.43 | QC-ACN-AA-XB |
| 309 | 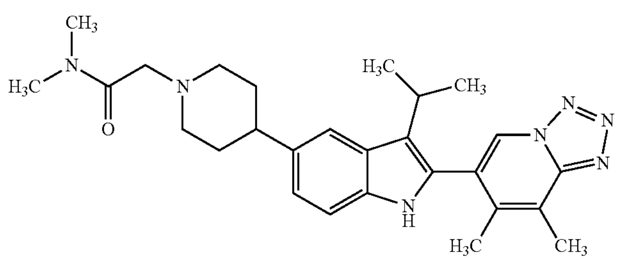 [SMILES: Cc1c(-c2[nH]c3ccc(C4CCN(CC(=O)N(C)C)CC4)cc3c2C(C)C)cn2nnnc2c1C] | 473.9 | 1.59 | QC-ACN-AA-XB |
| 310 | 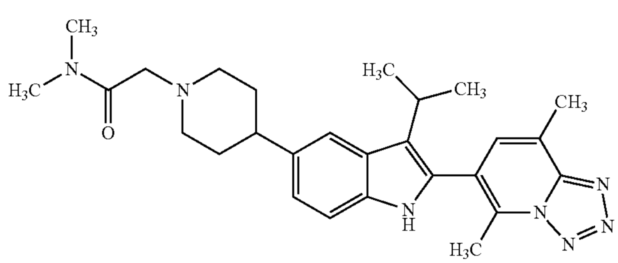 [SMILES: Cc1cc(-c2[nH]c3ccc(C4CCN(CC(=O)N(C)C)CC4)cc3c2C(C)C)c(C)n2nnnc12] | 474.2 | 1.61 | QC-ACN-AA-XB |
| 311 | 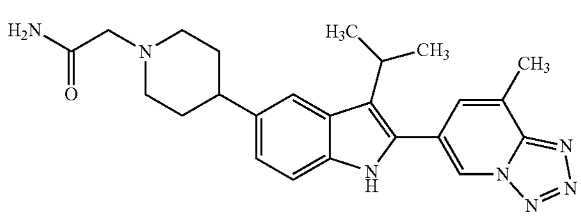 [SMILES: Cc1cc(-c2[nH]c3ccc(C4CCN(CC(N)=O)CC4)cc3c2C(C)C)cn2nnnc12] | 432.2 | 1.55 | QC-ACN-AA-XB |

TABLE 16-continued

| Ex. No. | Structure | Obs. MS Ion | RT | HPLC Method |
|---|---|---|---|---|
| 312 | 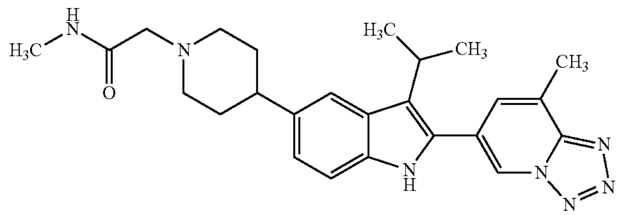 [SMILES: CNC(=O)CN1CCC(c2ccc3[nH]c(-c4cc(C)c5nnnn5c4)c(C(C)C)c3c2)CC1] | 446 | 1.66 | QC-ACN-AA-XB |
| 313 | 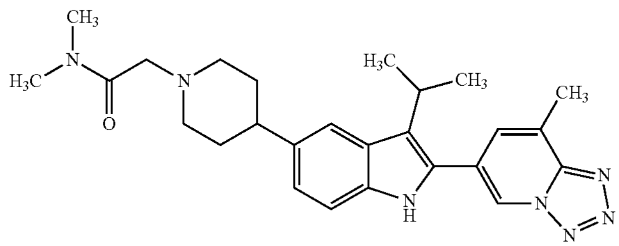 [SMILES: Cc1cc(-c2[nH]c3ccc(C4CCN(CC(=O)N(C)C)CC4)cc3c2C(C)C)cn2nnnc12] | 460 | 1.5 | QC-ACN-AA-XB |
| 314 | 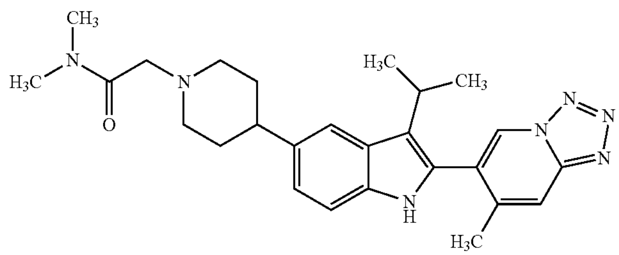 [SMILES: Cc1cc2nnnn2cc1-c1[nH]c2ccc(C3CCN(CC(=O)N(C)C)CC3)cc2c1C(C)C] | 460.4 | 1.26 | QC-ACN-AA-XB |
| 315 | 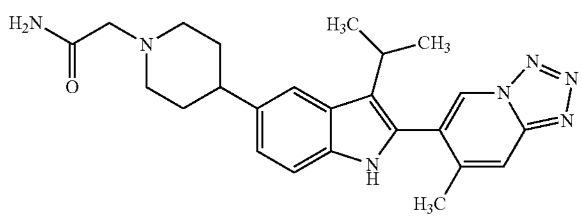 [SMILES: Cc1cc2nnnn2cc1-c1[nH]c2ccc(C3CCN(CC(N)=O)CC3)cc2c1C(C)C] | 432.3 | 1.46 | QC-ACN-AA-XB |
| 316 | 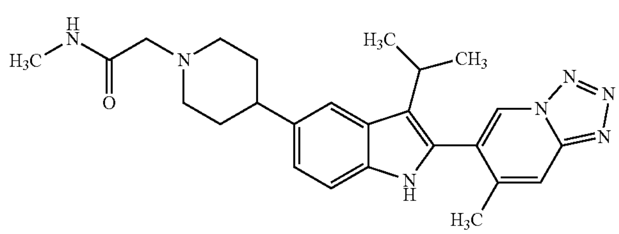 [SMILES: CNC(=O)CN1CCC(c2ccc3[nH]c(-c4cn5nnnc5cc4C)c(C(C)C)c3c2)CC1] | 446 | 1.58 | QC-ACN-AA-XB |
| 317 | 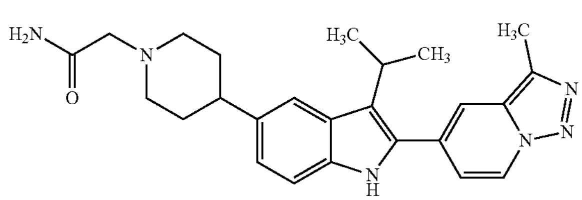 [SMILES: Cc1nnn2ccc(-c3[nH]c4ccc(C5CCN(CC(N)=O)CC5)cc4c3C(C)C)cc12] | 431.4 | 1.49 | QC-ACN-AA-XB |

TABLE 16-continued

| Ex. No. | Structure | Obs. MS Ion | RT | HPLC Method |
|---|---|---|---|---|
| 318 | 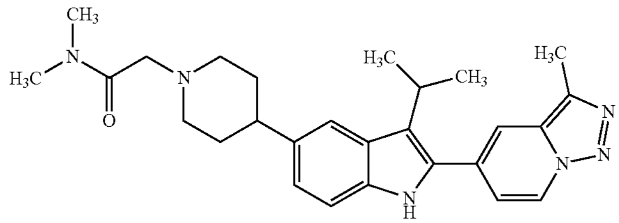 [SMILES: Cc1nnn2ccc(-c3[nH]c4ccc(C5CCN(CC(=O)N(C)C)CC5)cc4c3C(C)C)cc12] | 459.4 | 1.42 | QC-ACN-AA-XB |
| 319 | 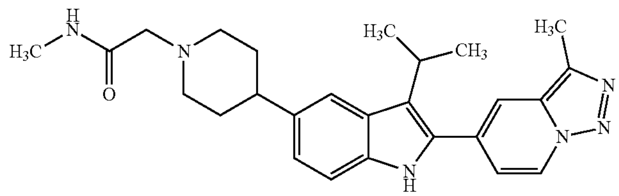 [SMILES: CNC(=O)CN1CCC(c2ccc3[nH]c(-c4ccn5nnc(C)c5c4)c(C(C)C)c3c2)CC1] | 445.4 | 1.6 | QC-ACN-AA-XB |
| 320 | 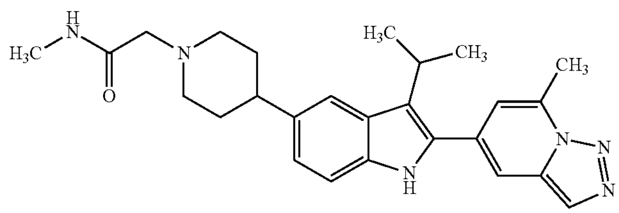 [SMILES: CNC(=O)CN1CCC(c2ccc3[nH]c(-c4cc(C)n5nncc5c4)c(C(C)C)c3c2)CC1] | 445.2 | 1.19 | QC-ACN-TFA-XB |
| 321 | 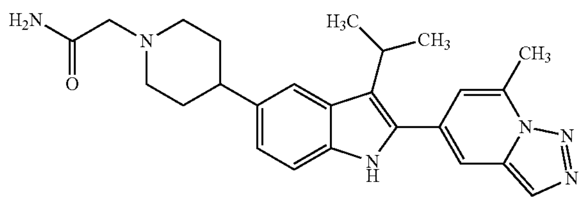 [SMILES: Cc1cc(-c2[nH]c3ccc(C4CCN(CC(N)=O)CC4)cc3c2C(C)C)cc2cnnn12] | 430.9 | 1.42 | QC-ACN-AA-XB |
| 322 | 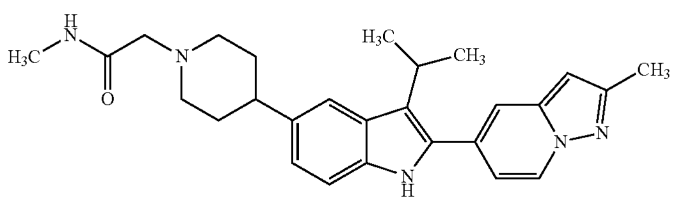 | 444.3 | 2.21 | F |
| 323 | 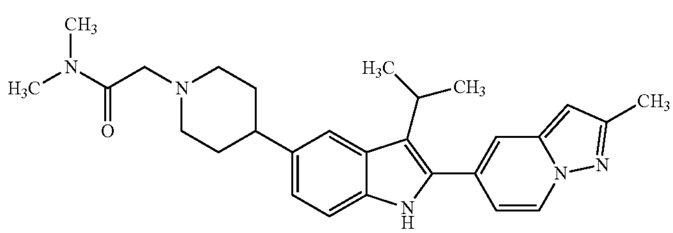 | 458.3 | 1.64 | F |
| 324 | 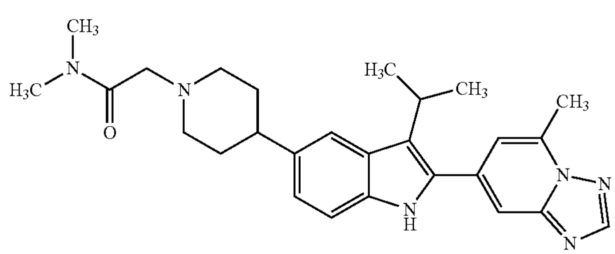 [SMILES: Cc1cc(-c2[nH]c3ccc(C4CCN(CC(=O)N(C)C)CC4)cc3c2C(C)C)cc2ncnn12] | 459.3 | 1.60 | E |

TABLE 16-continued

| Ex. No. | Structure | Obs. MS Ion | RT | HPLC Method |
|---|---|---|---|---|
| 325 | 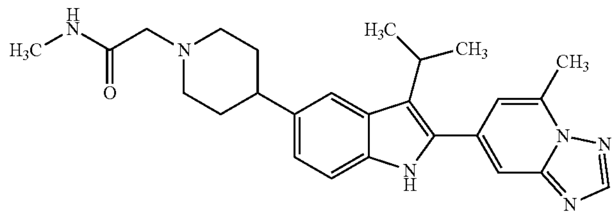 [SMILES: CNC(=O)CN1CCC(c2ccc3[nH]c(-c4cc(C)n5ncnc5c4)c(C(C)C)c3c2)CC1] | 445.3 | 1.31 | F |
| 326 | 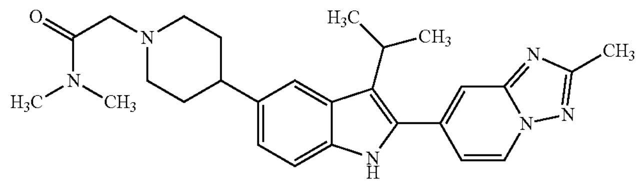 [SMILES: Cc1nc2cc(-c3[nH]c4ccc(C5CCN(CC(=O)N(C)C)CC5)cc4c3C(C)C)ccn2n1] | 459.3 | 1.23 | F |
| 327 | 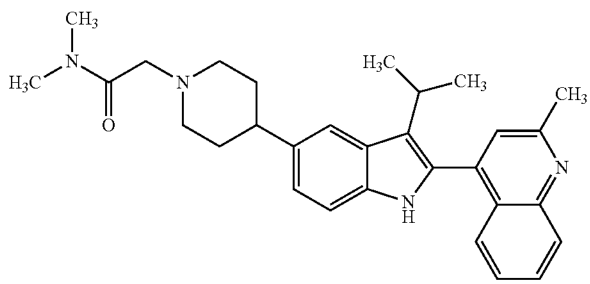 [SMILES: Cc1cc(-c2[nH]c3ccc(C4CCN(CC(=O)N(C)C)CC4)cc3c2C(C)C)c2ccccc2n1] | 469.3 | 1.92 | E |
| 328 | 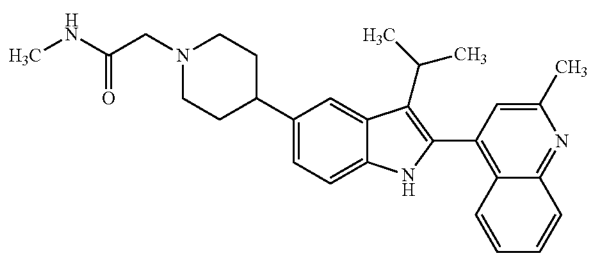 [SMILES: CNC(=O)CN1CCC(c2ccc3[nH]c(-c4cc(C)nc5ccccc45)c(C(C)C)c3c2)CC1] | 455.3 | 2.13 | E |
| 329 | 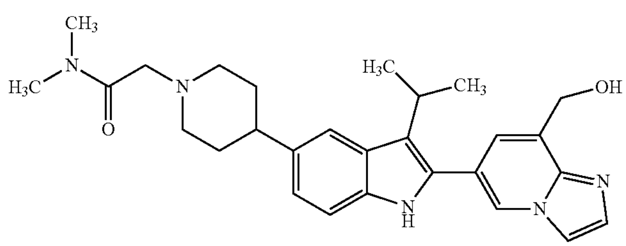 [SMILES: CC(C)c1c(-c2cc(CO)c3nccn3c2)[nH]c2ccc(C3CCN(CC(=O)N(C)C)CC3)cc12] | 474.3 | 1.43 | E |
| 330 | 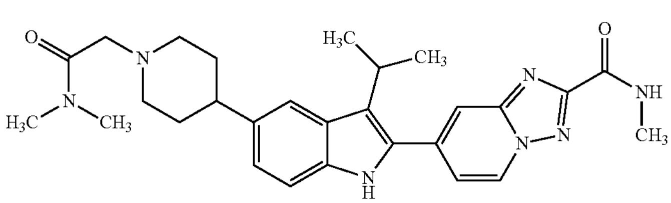 [SMILES: CNC(=O)c1nc2cc(-c3[nH]c4ccc(C5CCN(CC(=O)N(C)C)CC5)cc4c3C(C)C)ccn2n1] | 501.3 | 1.81 | E |
| 331 | 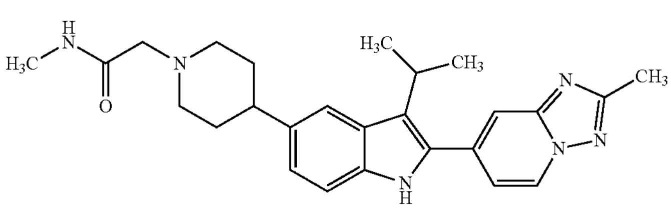 | 445.3 | 1.19 | F |

TABLE 16-continued
| Ex. No. | Structure | Obs. MS Ion | RT | HPLC Method |
|---|---|---|---|---|
| 332 | 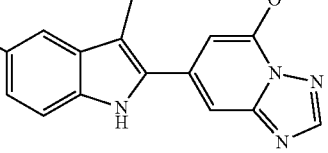 | 461.2 | 1.21 | F |
| 333 | 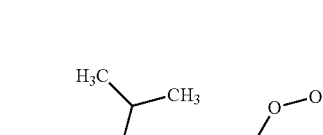 | 475.3 | 1.26 | E |
| 334 | 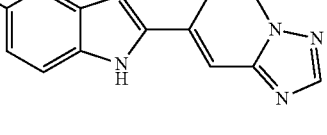 | 488.1 | 1.80 | E |
| 335 | 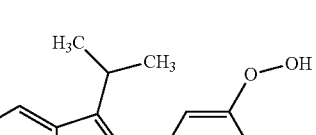 | 474.1 | 1.15 | F |
| 336 | 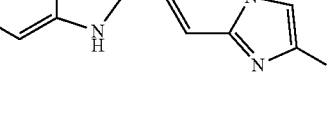 | 475.2 | 2.16 | E |
| 337 | 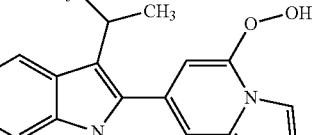 | 461.2 | 1.96 | E |

TABLE 16-continued

| Ex. No. | Structure | Obs. MS Ion | RT | HPLC Method |
|---|---|---|---|---|
| 338 | 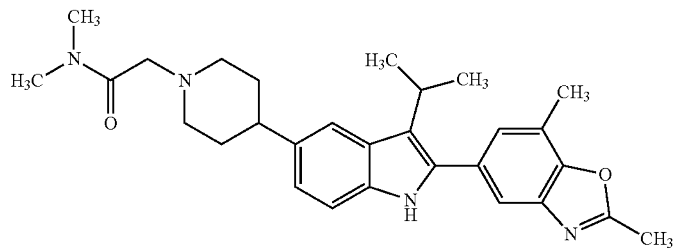 | 473.3 | 1.75 | F |
| 339 | 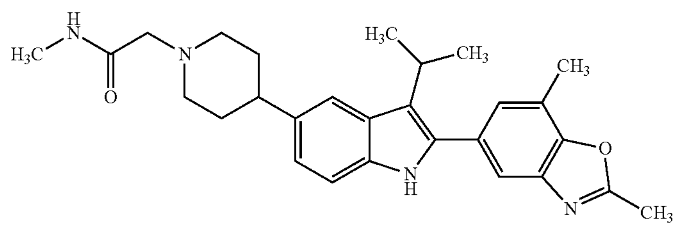 | 459.3 | 1.68 | F |
| 340 | 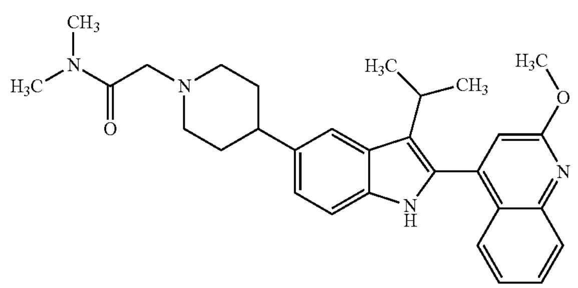 [SMILES: COc1cc(-c2[nH]c3ccc(C4CCN(CC(=O)N(C)C)CC4)cc3c2C(C)C)c2ccccc2n1] | 485.3 | 1.80 | F |
| 341 | 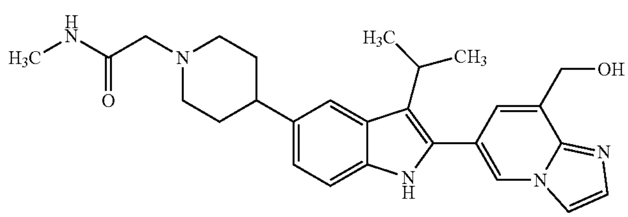 [SMILES: CNC(=O)CN1CCC(c2ccc3[nH]c(-c4cc(CO)c5nccn5c4)c(C(C)C)c3c2)CC1] | 460.2 | 1.57 | E |
| 342 | 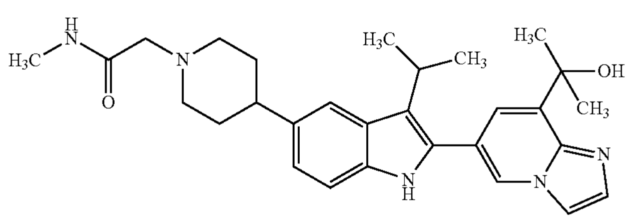 [SMILES: CNC(=O)CN1CCC(c2ccc3[nH]c(-c4cc(C(C)(C)O)c5nccn5c4)c(C(C)C)c3c2)CC1] | 488.3 | 1.88 | E |
| 343 | 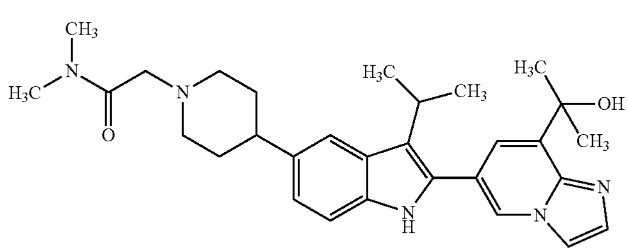 [SMILES: CC(C)c1c(-c2cc(C(C)(C)O)c3nccn3c2)[nH]c2ccc(C3CCN(CC(=O)N(C)C)CC3)cc12] | 502.3 | 1.12 | F |

TABLE 16-continued

| Ex. No. | Structure | Obs. MS Ion | RT | HPLC Method |
|---|---|---|---|---|
| 344 | 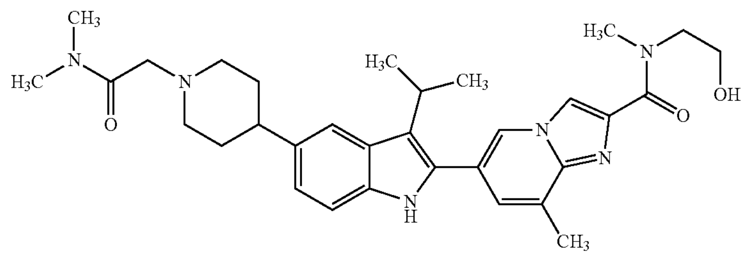 [SMILES: Cc1cc(-c2[nH]c3ccc(C4CCN(CC(=O)N(C)C)CC4)cc3c2C(C)C)cn2cc(C(=O)N(C)CCO)nc12] | 559.3 | 1.52 | E |
| 345 | 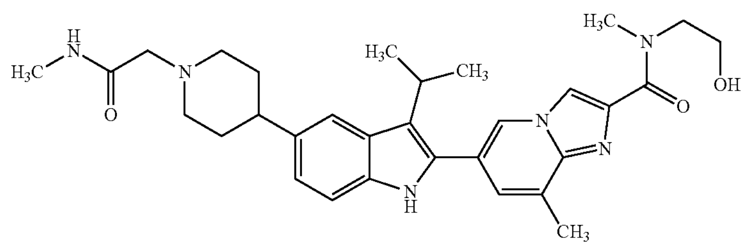 [SMILES: CNC(=O)CN1CCC(c2ccc3[nH]c(-c4cc(C)c5nc(C(=O)N(C)CCO)cn5c4)c(C(C)C)c3c2)CC1] | 545.3 | 1.04 | F |
| 346 | 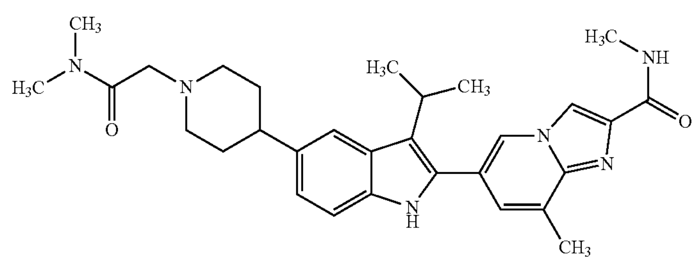 [SMILES: CNC(=O)c1cn2cc(-c3[nH]c4ccc(C5CCN(CC(=O)N(C)C)CC5)cc4c3C(C)C)cc(C)c2n1] | 515.3 | 1.65 | E |
| 347 | 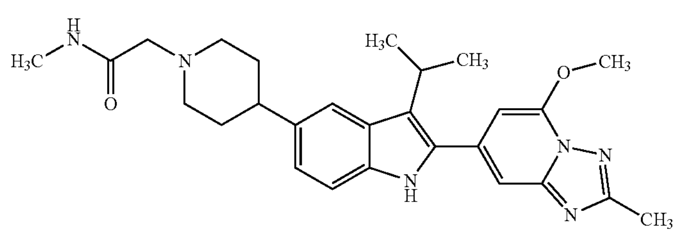 | 475.2 | 1.18 | E |
| 348 | 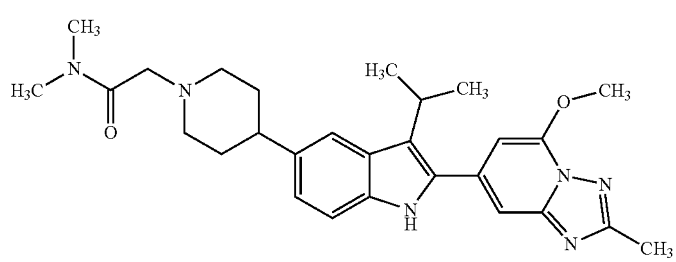 | 489.2 | 1.52 | E |
| 349 | 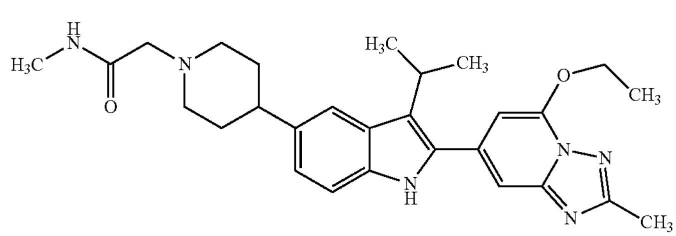 | 489.3 | 1.03 | F |

TABLE 16-continued

| Ex. No. | Structure | Obs. MS Ion | RT | HPLC Method |
|---|---|---|---|---|
| 350 | 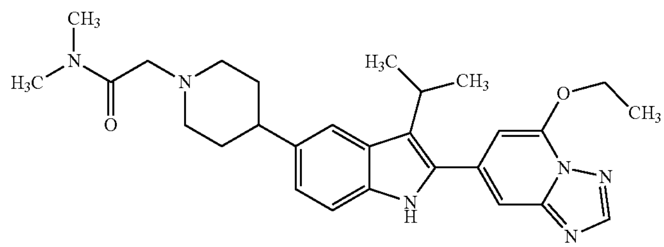 [SMILES: CCOc1cc(-c2[nH]c3ccc(C4CCN(CC(=O)N(C)C)CC4)cc3c2C(C)C)cc2ncnn12] | 489.2 | 1.35 | F |
| 351 | 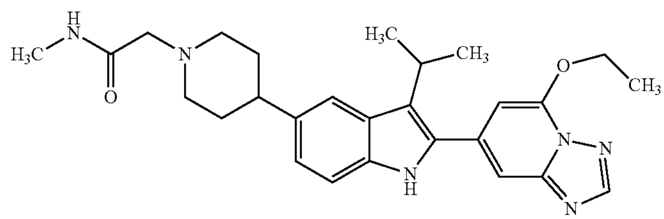 [SMILES: CCOc1cc(-c2[nH]c3ccc(C4CCN(CC(=O)NC)CC4)cc3c2C(C)C)cc2ncnn12] | 475.2 | 1.30 | F |
| 352 | 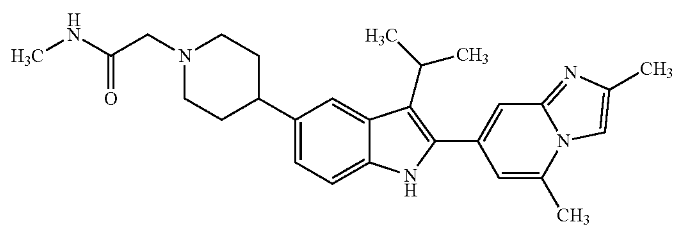 | 458.2 | 1.12 | F |
| 353 | 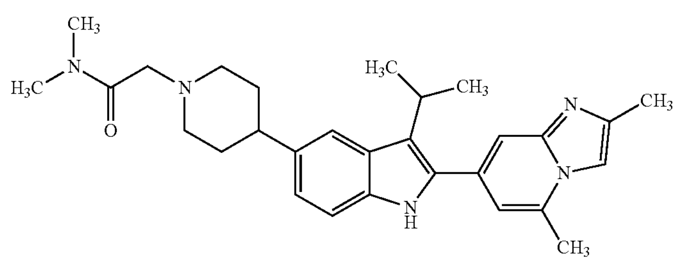 | 472.2 | 1.75 | E |
| 354 | 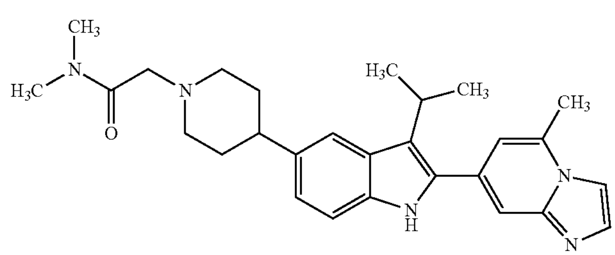 | 458.2 | 1.12 | F |
| 355 | 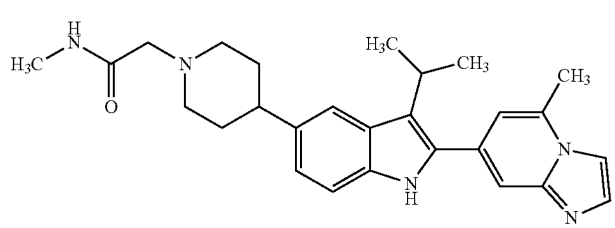 | 444.1 | 1.09 | F |

TABLE 16-continued

| Ex. No. | Structure | Obs. MS Ion | RT | HPLC Method |
|---|---|---|---|---|
| 356 | 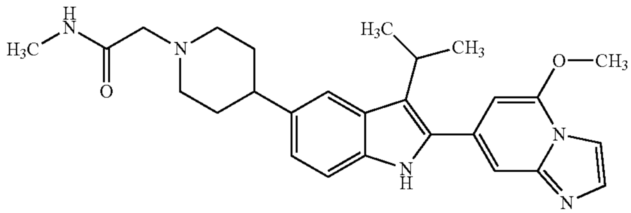 [SMILES: CNC(=O)CN1CCC(c2ccc3[nH]c(-c4cc(OC)n5ccnc5c4)c(C(C)C)c3c2)CC1] | 460.1 | 1.09 | F |
| 357 | 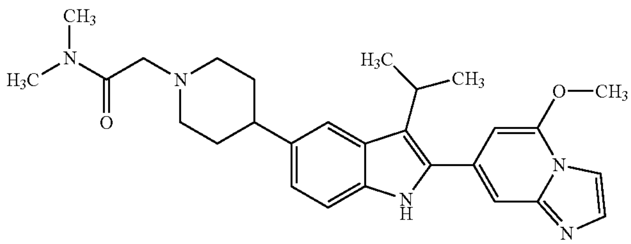 [SMILES: COc1cc(-c2[nH]c3ccc(C4CCN(CC(=O)N(C)C)CC4)cc3c2C(C)C)cc2nccn12] | 474.1 | 1.68 | E |
| 359 | 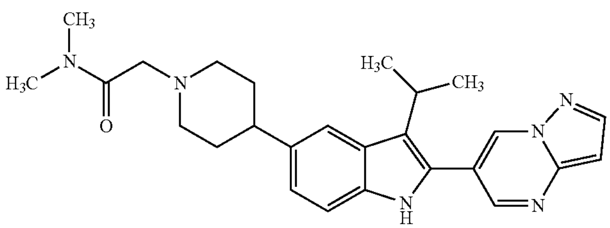 | 445.0 | 1.39 | F |
| 360 | 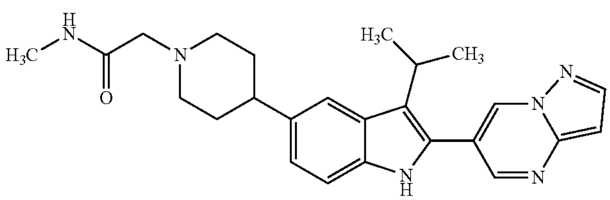 | 431.0 | 1.82 | E |
| 361 | 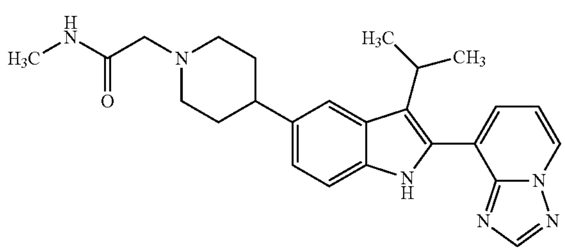 [SMILES: CNC(=O)CN1CCC(c2ccc3[nH]c(-c4cccn5ncnc45)c(C(C)C)c3c2)CC1] | 431.3 | 1.71 | E |
| 362 | 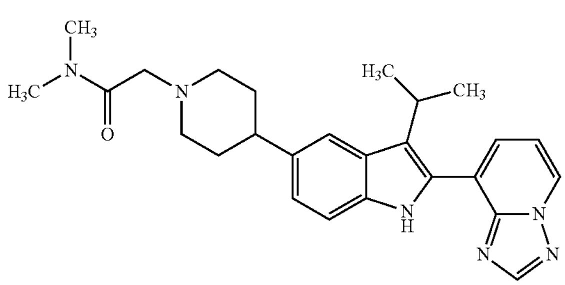 [SMILES: CC(C)c1c(-c2cccn3ncnc23)[nH]c2ccc(C3CCN(CC(=O)N(C)C)CC3)cc12] | 445.3 | 1.64 | E |

TABLE 16-continued

| Ex. No. | Structure | Obs. MS Ion | RT | HPLC Method |
|---|---|---|---|---|
| 363 | 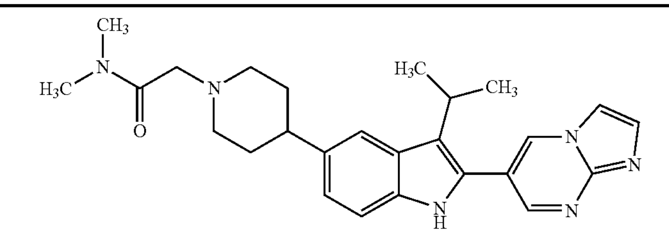 | 445.3 | 1.31 | E |
| 364 | 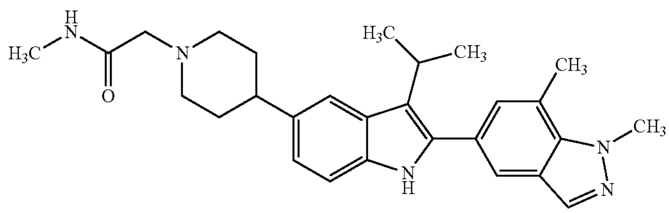 | 458.3 | 2.19 | E |
| 365 | 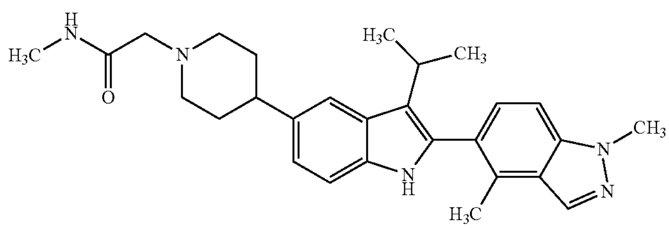 | 458.3 | 2.11 | E |
| 366 | 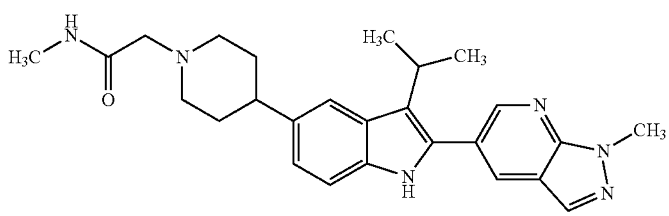 | 445.2 | 1.88 | E |
| 367 | 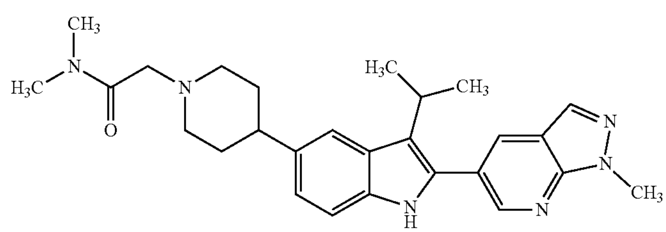 | 459.3 | 1.73 | E |
| 368 | 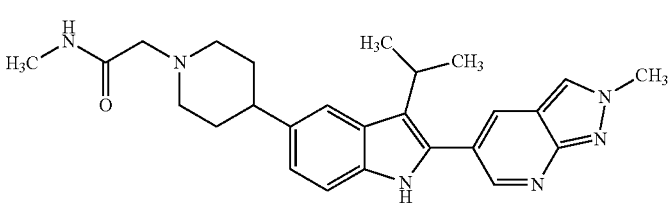 | 445.3 | 1.40 | E |
| 369 | 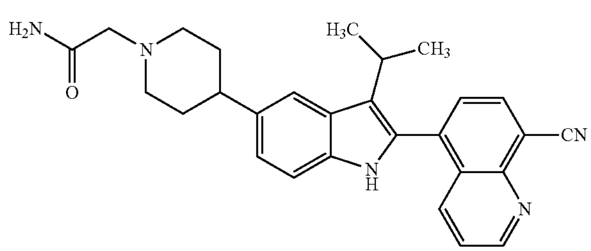 [SMILES: CC(C)c1c(-c2ccc(C#N)c3ncccc23)[nH]c2ccc(C3CCN(CC(N)=O)CC3)cc12] | 452.3 | 1.27 | F |

TABLE 16-continued

| Ex. No. | Structure | Obs. MS Ion | RT | HPLC Method |
|---|---|---|---|---|
| 370 | 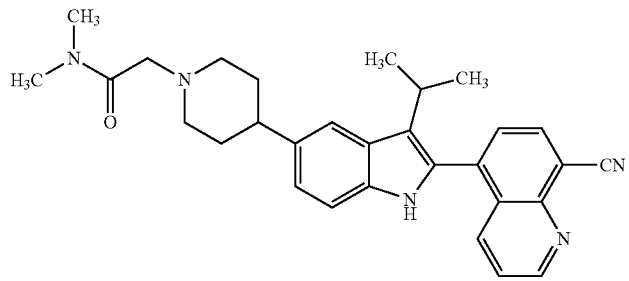 [SMILES: CC(C)c1c(-c2ccc(C#N)c3ncccc23)[nH]c2ccc(C3CCN(CC(=O)N(C)C)CC3)cc12] | 480.3 | 1.61 | E |
| 371 | 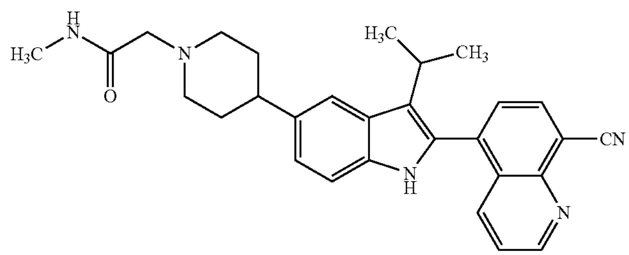 [SMILES: CNC(=O)CN1CCC(c2ccc3[nH]c(-c4ccc(C#N)c5ncccc45)c(C(C)C)c3c2)CC1] | 466.3 | 1.76 | E |
| 372 | 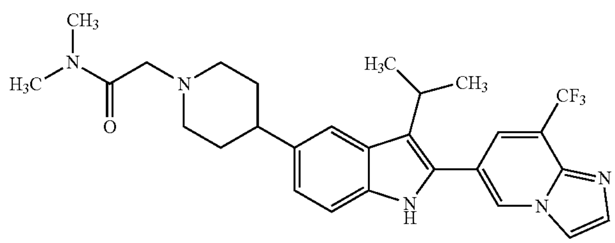 | 512.0 | 1.78 | E |
| 373 | 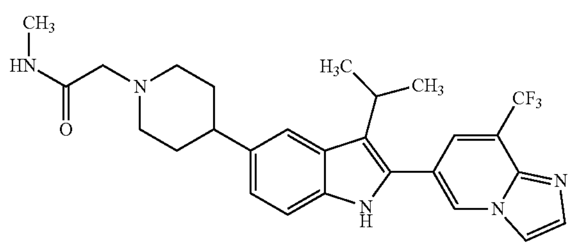 [SMILES: CNC(=O)CN1CCC(c2ccc3[nH]c(-c4cc(C(F)(F)F)c5nccn5c4)c(C(C)C)c3c2)CC1] | 498.0 | 1.96 | E |
| 374 | 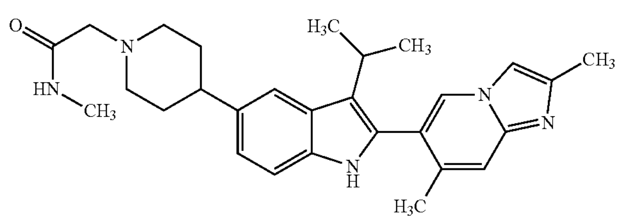 [SMILES: CNC(=O)CN1CCC(c2ccc3[nH]c(-c4cn5cc(C)nc5cc4C)c(C(C)C)c3c2)CC1] | 458.3 | 1.82 | E |
| 375 | 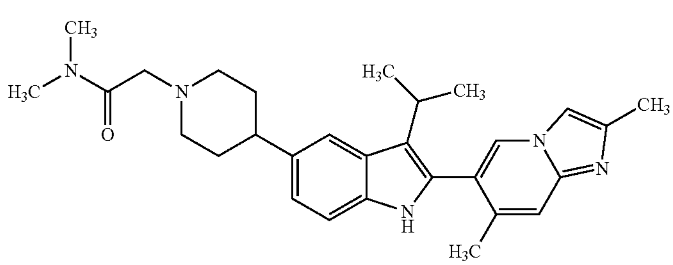 | 472.3 | 1.66 | E |

TABLE 16-continued

| Ex. No. | Structure | Obs. MS Ion | RT | HPLC Method |
|---|---|---|---|---|
| 376 | 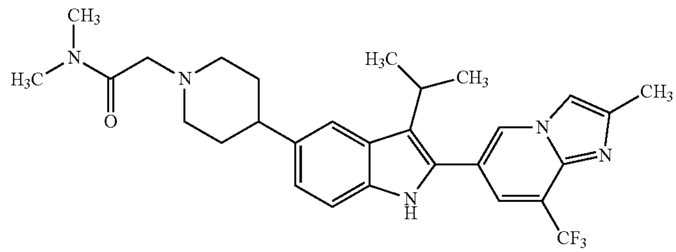 | 526.0 | 1.88 | E |
| 377 | 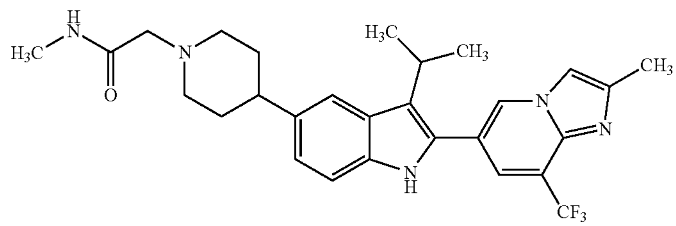 | 512.0 | 2.05 | E |
| 378 | 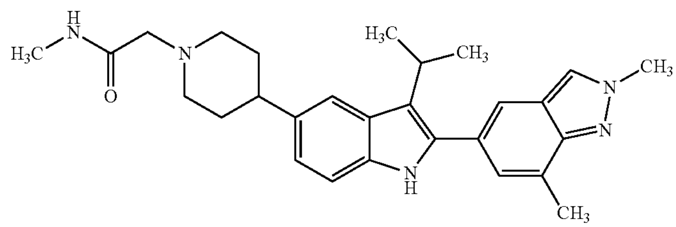 | 458.3 | 1.99 | E |
| 379 | 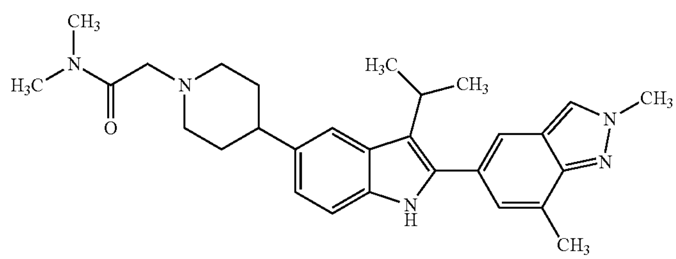 | 472.3 | 1.81 | E |
| 380 | 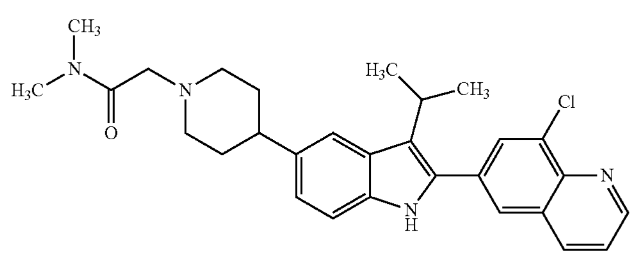 [SMILES: CC(C)c1c(-c2cc(Cl)c3ncccc3c2)[nH]c2ccc(C3CCN(CC(=O)N(C)C)CC3)cc12] | 490.0 | 1.98 | E |
| 381 | 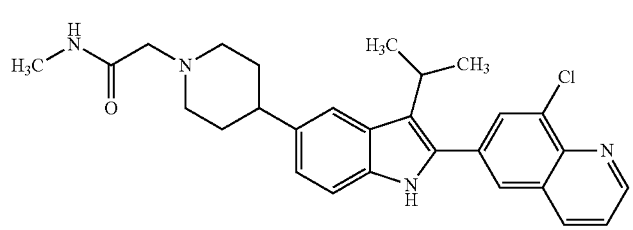 [SMILES: CNC(=O)CN1CCC(c2ccc3[nH]c(-c4cc(Cl)c5ncccc5c4)c(C(C)C)c3c2)CC1] | 475.1 | 2.14 | E |

TABLE 16-continued

| Ex. No. | Structure | Obs. MS Ion | RT | HPLC Method |
|---|---|---|---|---|
| 382 | 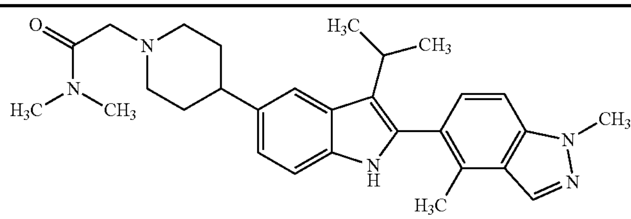 | 472.3 | 1.90 | E |
| 383 | 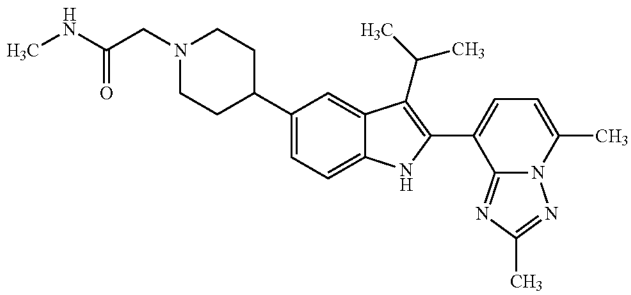 | 459.3 | 1.80 | E |
| 384 | 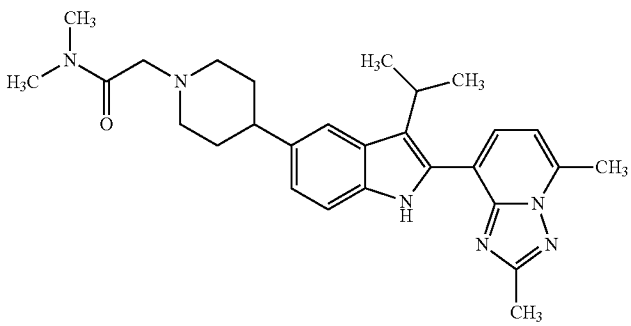 | 473.3 | 1.64 | E |
| 385 | 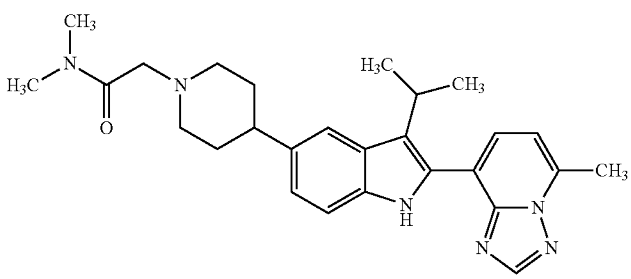 | 459.3 | 1.71 | E |
| 386 | 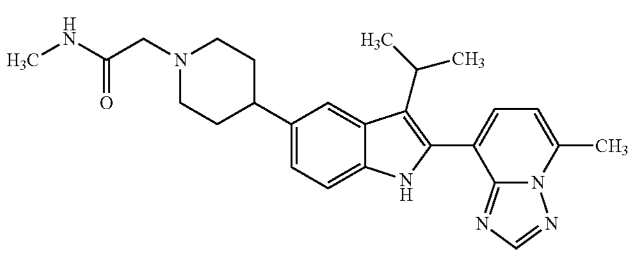 | 445.3 | 1.74 | E |
| 387 | 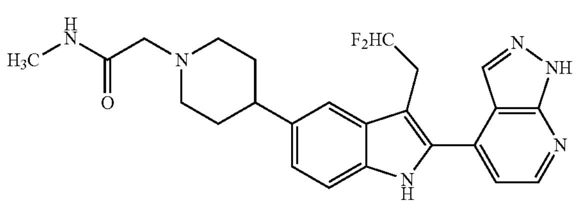 [SMILES: CNC(=O)CN1CCC(c2ccc3[nH]c(-c4ccnc5[nH]ncc45)c(CC(F)F)c3c2)CC1] | 453.0 | 0.92 | E |

TABLE 16-continued

| Ex. No. | Structure | Obs. MS Ion | RT | HPLC Method |
|---|---|---|---|---|
| 388 | 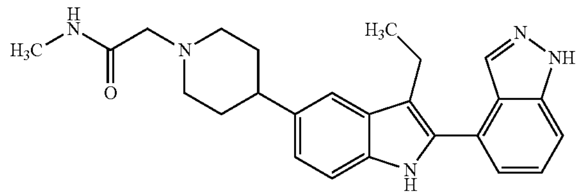 [SMILES: CCc1c(-c2cccc3[nH]ncc23)[nH]c2ccc(C3CCN(CC(=O)NC)CC3)cc12] | 416.0 | 1.57 | E |
| 389 | 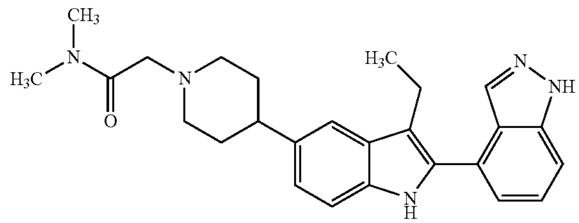 [SMILES: CCc1c(-c2cccc3[nH]ncc23)[nH]c2ccc(C3CCN(CC(=O)N(C)C)CC3)cc12] | 430.0 | 1.44 | E |
| 390 | 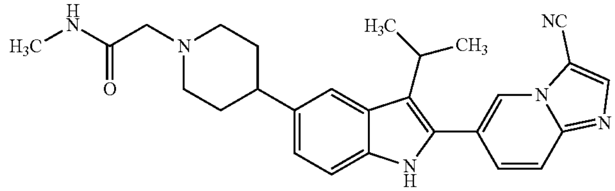 [SMILES: CNC(=O)CN1CCC(c2ccc3[nH]c(-c4ccc5ncc(C#N)n5c4)c(C(C)C)c3c2)CC1] | 455.3 | 1.12 | F |
| 391 | 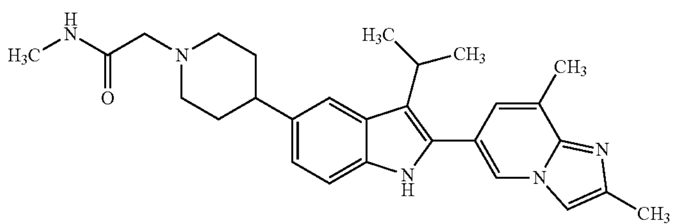 | 458.3 | 2.52 | H |
| 392 | 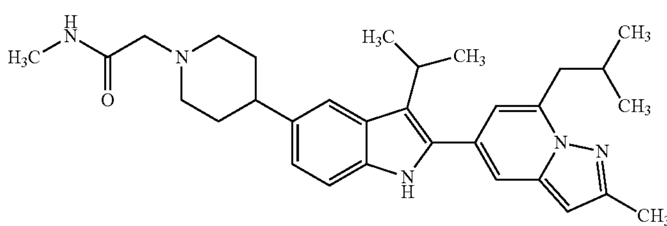 | 501.4 | 2.36 | E |
| 393 | 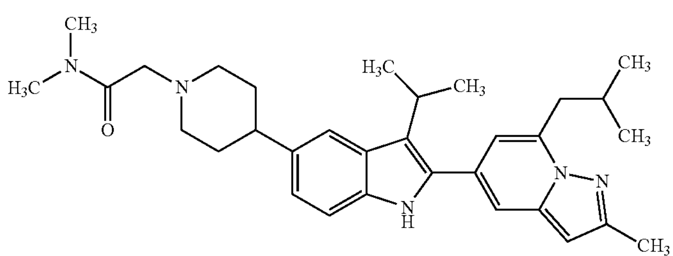 | 515.4 | 2.17 | E |
| 394 | 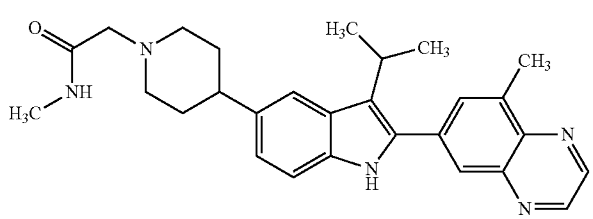 [SMILES: CNC(=O)CN1CCC(c2ccc3[nH]c(-c4cc(C)c5nccnc5c4)c(C(C)C)c3c2)CC1] | 456.2 | 2.14 | E |

TABLE 16-continued

| Ex. No. | Structure | Obs. MS Ion | RT | HPLC Method |
|---|---|---|---|---|
| 395 | 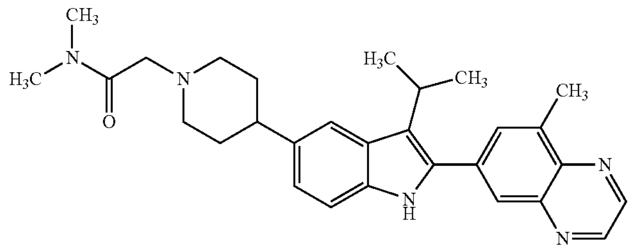 [SMILES: Cc1cc(-c2[nH]c3ccc(C4CCN(CC(=O)N(C)C)CC4)cc3c2C(C)C)cc2nccnc12] | 470.1 | 1.62 | F |
| 396 | 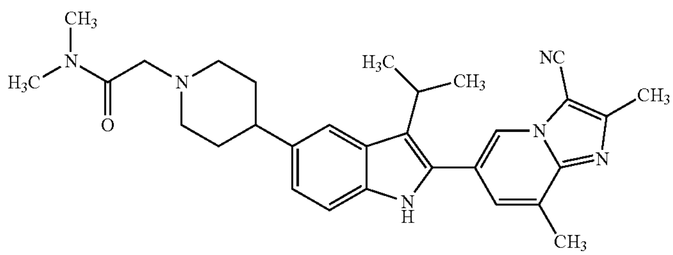 | 486.2 | 1.80 | E |
| 397 | 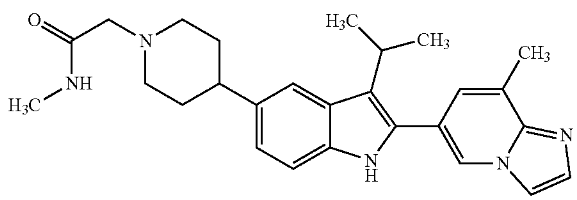 [SMILES: CNC(=O)CN1CCC(c2ccc3[nH]c(-c4cc(C)c5nccn5c4)c(C(C)C)c3c2)CC1] | 444.0 | 0.83 | F |
| 398 | 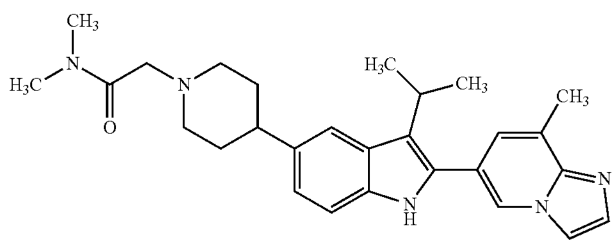 | 458.0 | 0.87 | F |
| 399 | 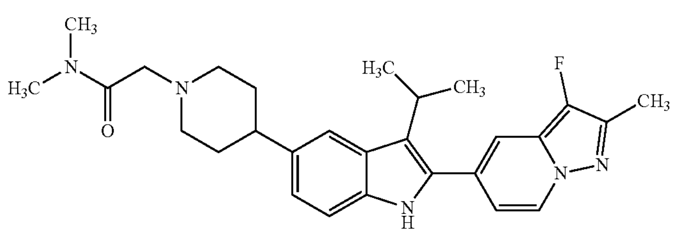 | 476.0 | 2.00 | E |
| 400 | 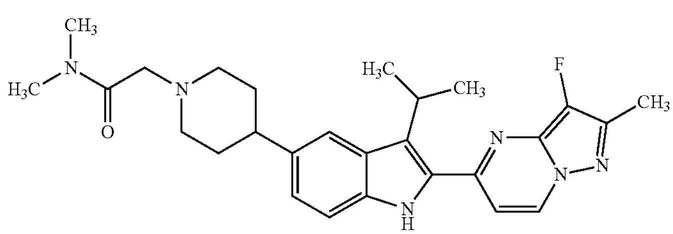 | 477.0 | 1.92 | E |

TABLE 16-continued

| Ex. No. | Structure | Obs. MS Ion | RT | HPLC Method |
|---|---|---|---|---|
| 401 | 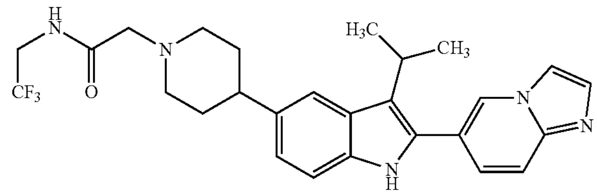 [SMILES: CC(C)c1c(-c2ccc3nccn3c2)[nH]c2ccc(C3CCN(CC(=O)NCC(F)(F)F)CC3)cc12] | 498.2 | 2.10 | F |
| 402 | 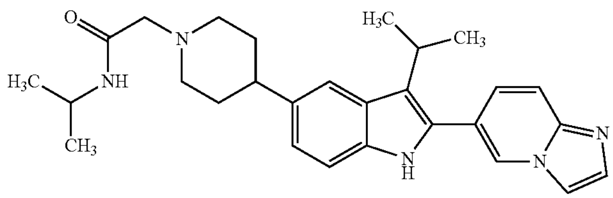 [SMILES: CC(C)NC(=O)CN1CCC(c2ccc3[nH]c(-c4ccc5nccn5c4)c(C(C)C)c3c2)CC1] | 458.2 | 1.95 | E |
| 403 | 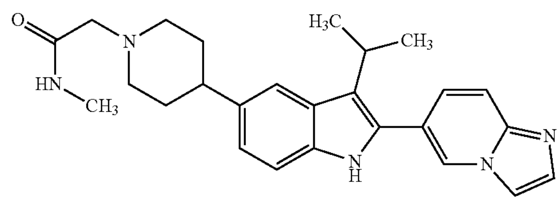 [SMILES: CNC(=O)CN1CCC(c2ccc3[nH]c(-c4ccc5nccn5c4)c(C(C)C)c3c2)CC1] | 430.3 | 1.72 | E |
| 404 | 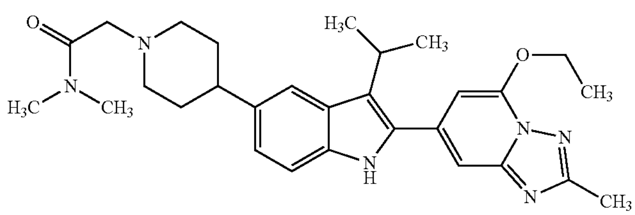 [SMILES: CCOc1cc(-c2[nH]c3ccc(C4CCN(CC(=O)N(C)C)CC4)cc3c2C(C)C)cc2nc(C)nn12] | 503.2 | 1.31 | F |
| 405 | 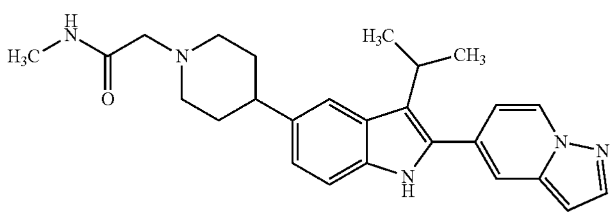 [SMILES: CNC(=O)CN1CCC(c2ccc3[nH]c(-c4ccn5nccc5c4)c(C(C)C)c3c2)CC1] | 430.2 | 2.03 | E |
| 406 | 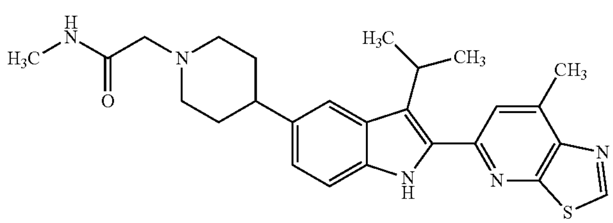 [SMILES: CNC(=O)CN1CCC(c2ccc3[nH]c(-c4cc(C)c5ncsc5n4)c(C(C)C)c3c2)CC1] | 462.1 | 2.14 | E |
| 407 | 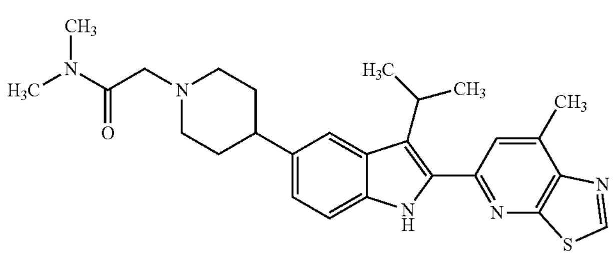 [SMILES: Cc1cc(-c2[nH]c3ccc(C4CCN(CC(=O)N(C)C)CC4)cc3c2C(C)C)nc2scnc12] | 476.1 | 1.92 | E |

TABLE 16-continued

| Ex. No. | Structure | Obs. MS Ion | RT | HPLC Method |
|---|---|---|---|---|
| 408 | 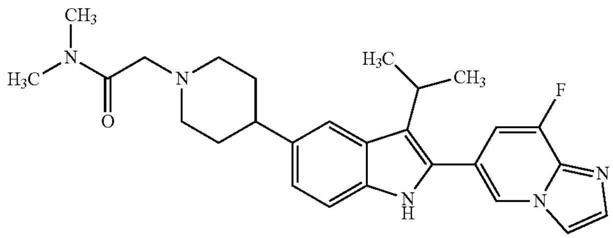 [SMILES: CC(C)c1c(-c2cc(F)c3nccn3c2)[nH]c2ccc(C3CCN(CC(=O)N(C)C)CC3)cc12] | 462.3 | 1.60 | E |
| 409 | 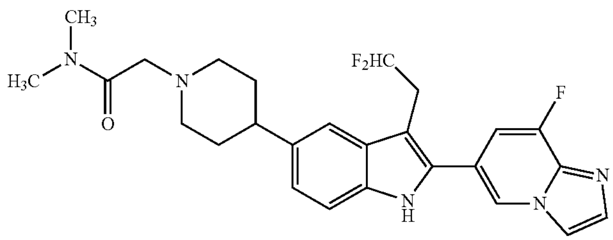 [SMILES: CN(C)C(=O)CN1CCC(c2ccc3[nH]c(-c4cc(F)c5nccn5c4)c(CC(F)F)c3c2)CC1] | 484.2 | 1.57 | E |
| 410 | 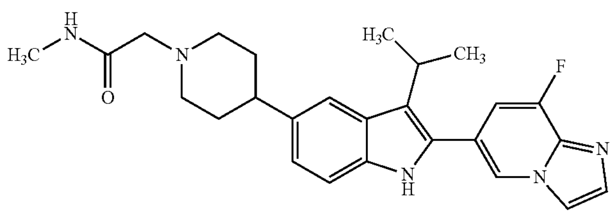 [SMILES: CNC(=O)CN1CCC(c2ccc3[nH]c(-c4cc(F)c5nccn5c4)c(C(C)C)c3c2)CC1] | 448.2 | 1.75 | E |
| 411 | 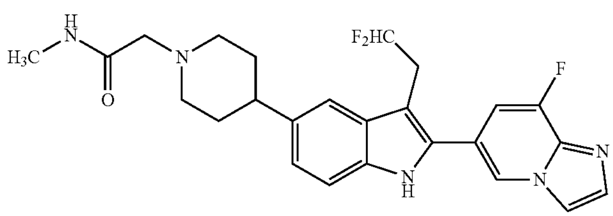 [SMILES: CNC(=O)CN1CCC(c2ccc3[nH]c(-c4cc(F)c5nccn5c4)c(CC(F)F)c3c2)CC1] | 470.2 | 1.73 | E |
| 412 | 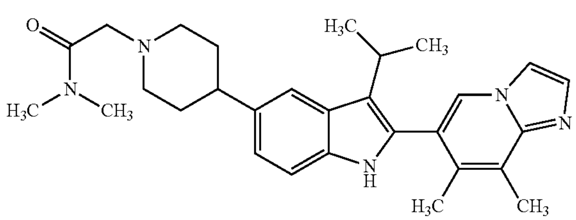 [SMILES: Cc1c(-c2[nH]c3ccc(C4CCN(CC(=O)N(C)C)CC4)cc3c2C(C)C)cn2ccnc2c1C] | 472.3 | 1.65 | E |
| 413 | 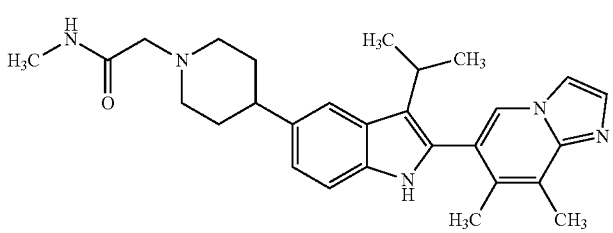 [SMILES: CNC(=O)CN1CCC(c2ccc3[nH]c(-c4cn5ccnc5c(C)c4C)c(C(C)C)c3c2)CC1] | 458.3 | 1.87 | E |

TABLE 16-continued

| Ex. No. | Structure | Obs. MS Ion | RT | HPLC Method |
|---|---|---|---|---|
| 414 | 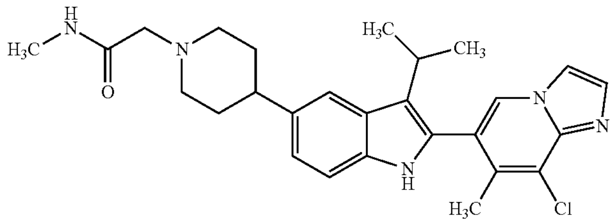 [SMILES: CNC(=O)CN1CCC(c2ccc3[nH]c(-c4cn5ccnc5c(Cl)c4C)c(C(C)C)c3c2)CC1] | 478.2 | 1.90 | E |
| 415 | 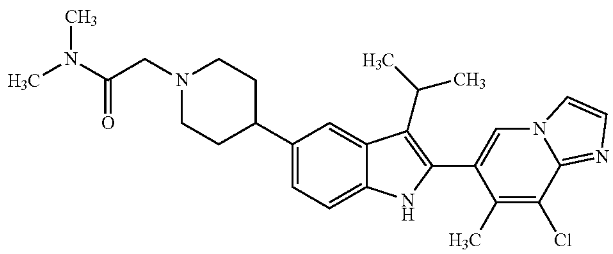 [SMILES: Cc1c(-c2[nH]c3ccc(C4CCN(CC(=O)N(C)C)CC4)cc3c2C(C)C)cn2ccnc2c1Cl] | 492.2 | 1.74 | E |
| 416 | 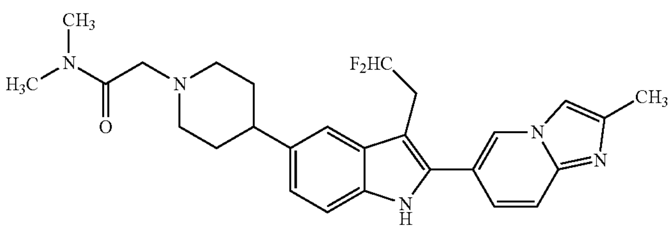 | 480.3 | 1.36 | E |
| 417 | 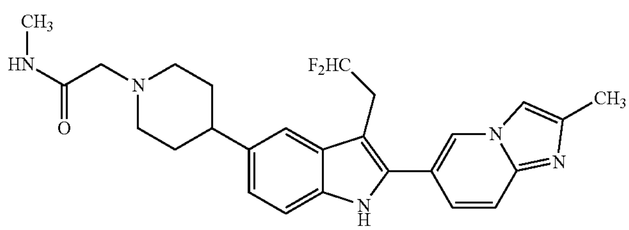 [SMILES: CNC(=O)CN1CCC(c2ccc3[nH]c(-c4ccc5nc(C)cn5c4)c(CC(F)F)c3c2)CC1] | 466.3 | 1.51 | E |
| 418 | 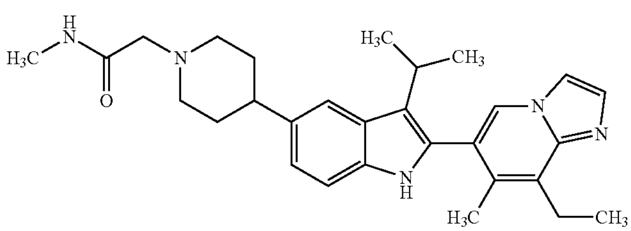 [SMILES: CCc1c(C)c(-c2[nH]c3ccc(C4CCN(CC(=O)NC)CC4)cc3c2C(C)C)cn2ccnc12] | 472.3 | 1.98 | E |
| 419 | 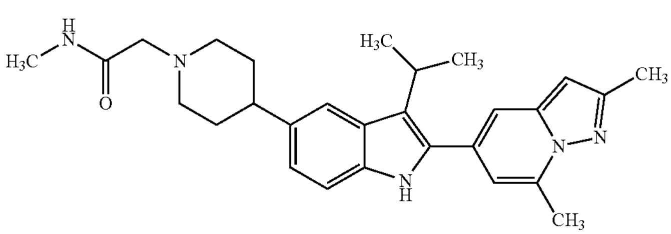 | 458.3 | 2.30 | E |

TABLE 16-continued

| Ex. No. | Structure | Obs. MS Ion | RT | HPLC Method |
|---|---|---|---|---|
| 420 | 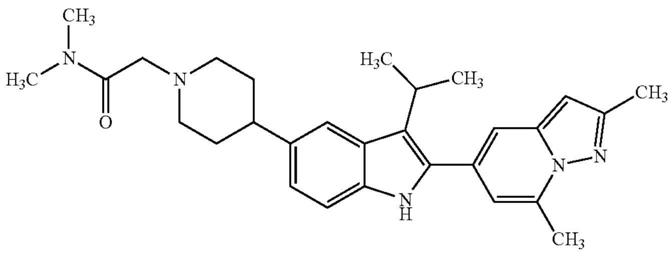 | 472.3 | 2.12 | E |
| 421 | 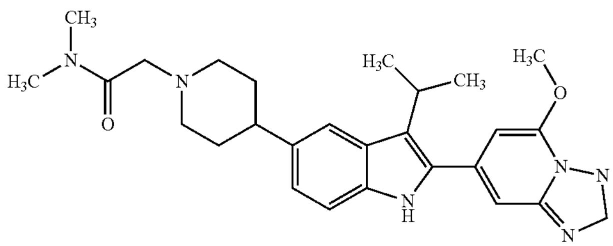 [SMILES: COC1=CC(c2[nH]c3ccc(C4CCN(CC(=O)N(C)C)CC4)cc3c2C(C)C)=CC2=NCNN12] | 475.1 | 1.51 | E |
| 422 | 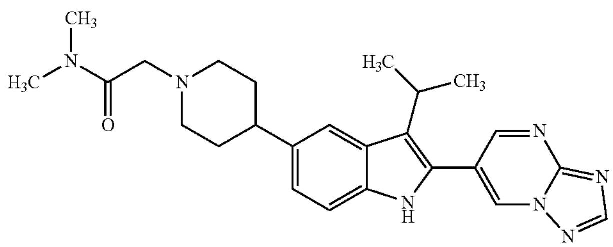 [SMILES: CC(C)c1c(-c2cnc3ncnn3c2)[nH]c2ccc(C3CCN(CC(=O)N(C)C)CC3)cc12] | 446.0 | 1.38 | E |
| 423 | 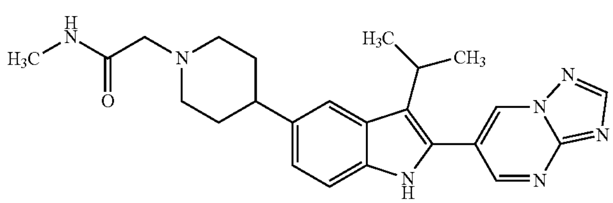 [SMILES: CNC(=O)CN1CCC(c2ccc3[nH]c(-c4cnc5ncnn5c4)c(C(C)C)c3c2)CC1] | 432.0 | 1.52 | E |
| 424 | 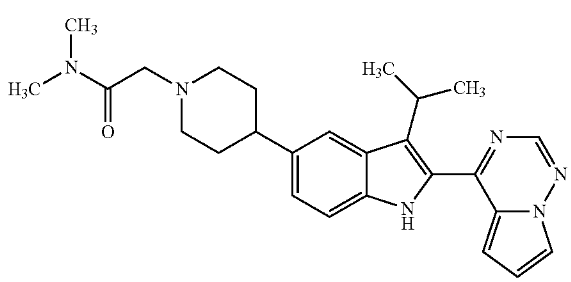 [SMILES: CC(C)c1c(-c2ncnn3cccc23)[nH]c2ccc(C3CCN(CC(=O)N(C)C)CC3)cc12] | 445.0 | 1.93 | E |
| 425 | 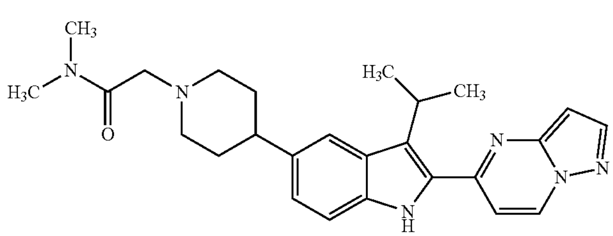 [SMILES: CC(C)c1c(-c2ccn3nccc3n2)[nH]c2ccc(C3CCN(CC(=O)N(C)C)CC3)cc12] | 445.0 | 1.74 | E |

TABLE 16-continued
| Ex. No. | Structure | Obs. MS Ion | RT | HPLC Method |
|---|---|---|---|---|
| 426 | 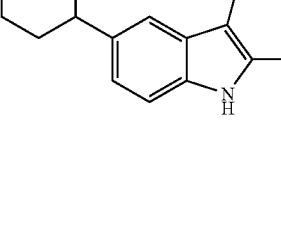 | 445.0 | 1.46 | E |
| 427 | 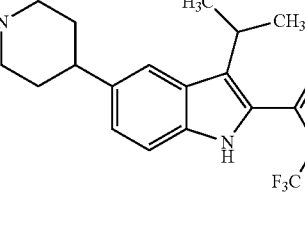 | 512.1 | 1.75 | E |
| 428 | 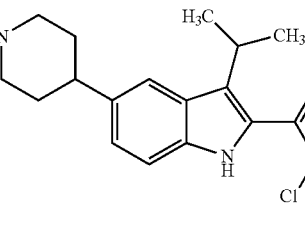 | 478.1 | 1.66 | E |
| 429 | 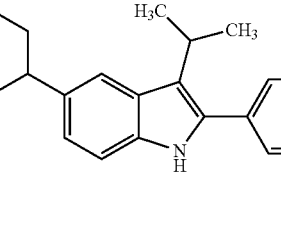 | 472.1 | 1.95 | E |
| 430 | 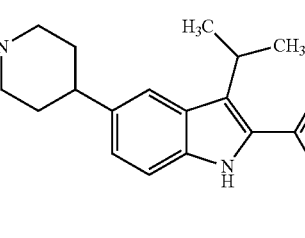 | 483.1 | 1.51 | F |
| 431 | 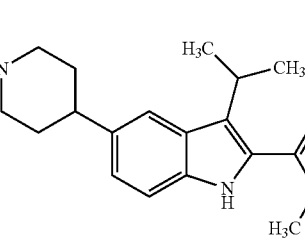 | 458.1 | 1.57 | E |

TABLE 16-continued
| Ex. No. | Structure | Obs. MS Ion | RT | HPLC Method |
|---|---|---|---|---|
| 432 | 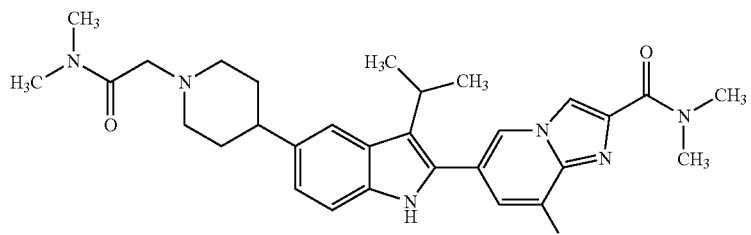 | 545.3 | 1.58 | E |
| 433 | 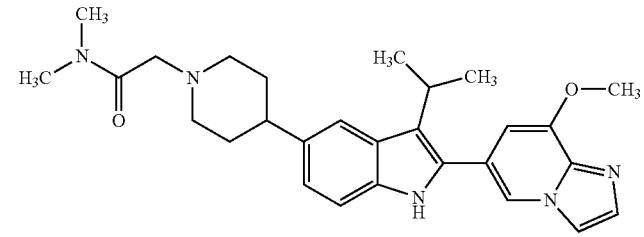 [SMILES: COc1cc(-c2[nH]c3ccc(C4CCN(CC(=O)N(C)C)CC4)cc3c2C(C)C)cn2ccnc12] | 474.0 | 1.55 | E |
| 434 | 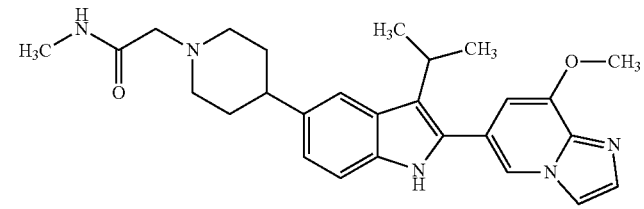 [SMILES: CNC(=O)CN1CCC(c2ccc3[nH]c(-c4cc(OC)c5nccn5c4)c(C(C)C)c3c2)CC1] | 460.0 | 1.71 | E |
| 435 | 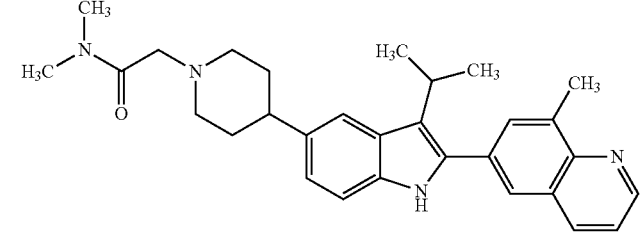 [SMILES: Cc1cc(-c2[nH]c3ccc(C4CCN(CC(=O)N(C)C)CC4)cc3c2C(C)C)cc2cccnc12] | 469.0 | 1.98 | E |
| 436 | 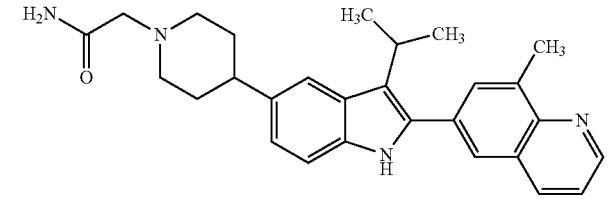 [SMILES: Cc1cc(-c2[nH]c3ccc(C4CCN(CC(N)=O)CC4)cc3c2C(C)C)cc2cccnc12] | 441.1 | 2.12 | E |
| 437 | 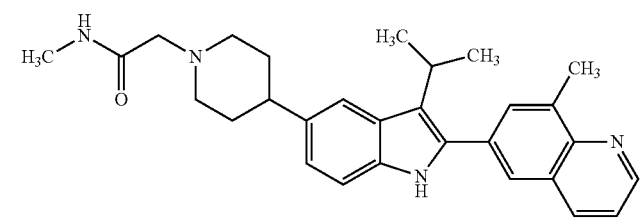 [SMILES: CNC(=O)CN1CCC(c2ccc3[nH]c(-c4cc(C)c5ncccc5c4)c(C(C)C)c3c2)CC1] | 455.0 | 2.19 | E |

TABLE 16-continued

| Ex. No. | Structure | Obs. MS Ion | RT | HPLC Method |
|---|---|---|---|---|
| 438 | 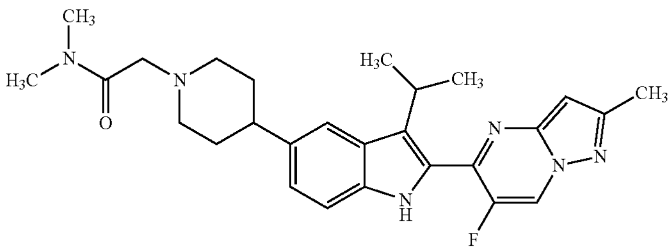 | 477.0 | 1.84 | E |
| 439 | 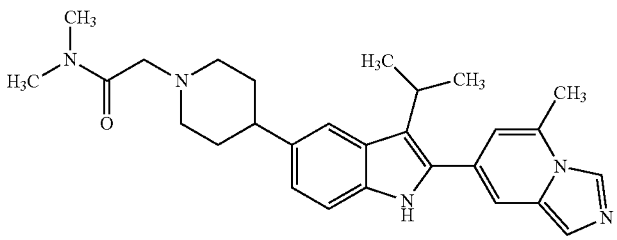 [SMILES: Cc1cc(-c2[nH]c3ccc(C4CCN(CC(=O)N(C)C)CC4)cc3c2C(C)C)cc2cncn12] | 458.3 | 1.12 | F |
| 440 | 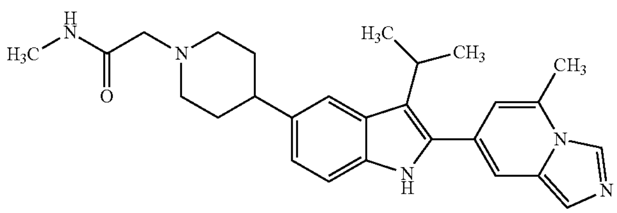 | 444.2 | 1.85 | E |
| 441 | 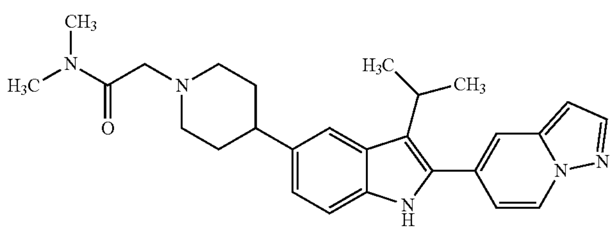 | 444.3 | 1.85 | E |
| 442 | 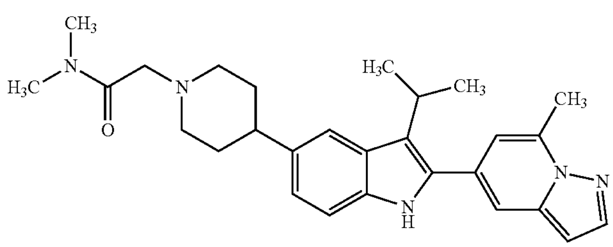 [SMILES: Cc1cc(-c2[nH]c3ccc(C4CCN(CC(=O)N(C)C)CC4)cc3c2C(C)C)cc2ccnn12] | 458.4 | 1.70 | E |
| 443 | 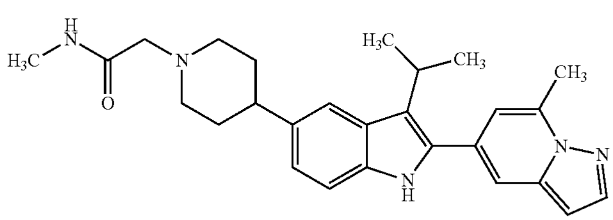 [SMILES: CNC(=O)CN1CCC(c2ccc3[nH]c(-c4cc(C)n5nccc5c4)c(C(C)C)c3c2)CC1] | 444.3 | 2.09 | E |

TABLE 16-continued

| Ex. No. | Structure | Obs. MS Ion | RT | HPLC Method |
|---|---|---|---|---|
| 444 | 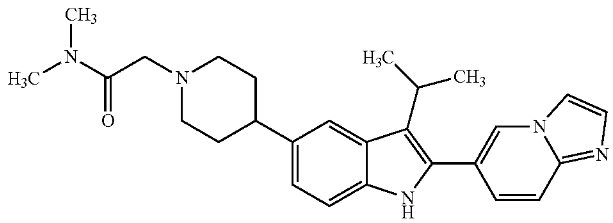 [SMILES: CC(C)c1c(-c2ccc3nccn3c2)[nH]c2ccc(C3CCN(CC(=O)N(C)C)CC3)cc12] | 444.2 | 1.53 | E |
| 445 | 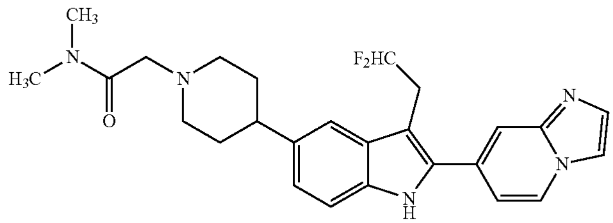 [SMILES: CN(C)C(=O)CN1CCC(c2ccc3[nH]c(-c4ccn5ccnc5c4)c(CC(F)F)c3c2)CC1] | 466.2 | 1.33 | E |
| 446 | 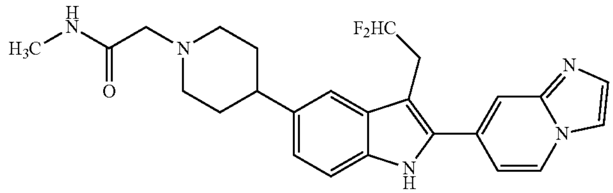 [SMILES: CNC(=O)CN1CCC(c2ccc3[nH]c(-c4ccn5ccnc5c4)c(CC(F)F)c3c2)CC1] | 452.2 | 1.42 | E |
| 447 | 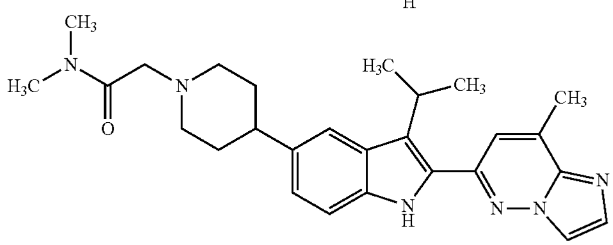 | 459.3 | 1.75 | E |
| 448 | 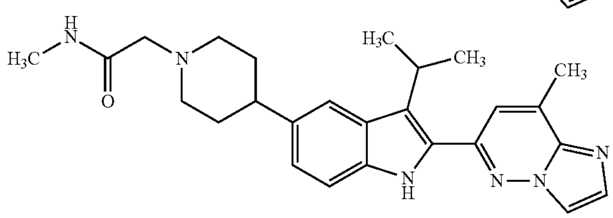 | 445.2 | 1.91 | E |

Example 449

2-(dimethylamino)-1-(4-(3-isopropyl-2-(1H-pyrazolo[3,4-b]pyridin-4-yl)-1H-indol-5-yl)piperidin-1-yl)ethanone

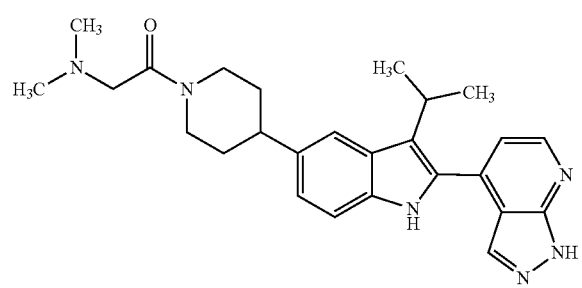

(449)

To a stirred solution of 2-chloro-1-(4-(3-isopropyl-2-(1H-pyrazolo[3,4-b]pyridin-4-yl)-1H-indol-5-yl)piperidin-1-yl)ethanone (0.025 g, 0.057 mmol) in THF (1 mL) was added DIPEA (0.015 mL, 0.086 mmol), followed by dimethylamine (0.034 mL, 0.069 mmol). The resulting mixture was stirred at 25° C. for 12 hours. The reaction mixture was concentrated under a stream of nitrogen gas. The crude was purified via preparative LC/MS. The fractions containing the desired product were combined and dried via centrifugal evaporation to give 2-(dimethylamino)-1-(4-(3-isopropyl-2-(1H-pyrazolo[3,4-b]pyridin-4-yl)-1H-indol-5-yl)piperidin-1-yl)ethanone (15.0 mg, 0.0340 mmol, 59% yield). MS $(M^{+1})$ m/z: 445.3 $(MH^+)$. LC retention time 1.42 min [E]. $^1$H NMR (400 MHz, DMSO-$d_6$) δ ppm 13.79 (br. s., 1H) 11.22 (s, 1H) 8.60 (d, J=4.71 Hz, 1H) 8.13 (s, 1H) 7.62 (s, 1H) 7.37 (d, J=8.41 Hz, 1H) 7.20 (d, J=4.77 Hz, 1H) 7.06 (dd, J=8.50, 1.47 Hz, 1H) 4.54 (d, J=12.67 Hz, 1H) 4.20 (d, J=13.05 Hz, 1H) 3.07-3.18 (m, 3H) 2.84-2.91 (m, 1H) 2.61-2.70 (m, 1H)

2.21 (s, 6H) 1.88-1.93 (m, 1H) 1.85 (d, J=12.05 Hz, 2H) 1.63-1.74 (m, 1H) 1.48-1.56 (m, 1H) 1.44 (d, J=7.03 Hz, 6H) 0.97 (d, J=12.06 Hz, 1H).

Example 450

2-(dimethylamino)-1-(4-(3-isopropyl-2-(1-(methylsulfonyl)-1H-pyrrolo[2,3-b]pyridin-4-yl)-1H-indol-5-yl)piperidin-1-yl)ethanone

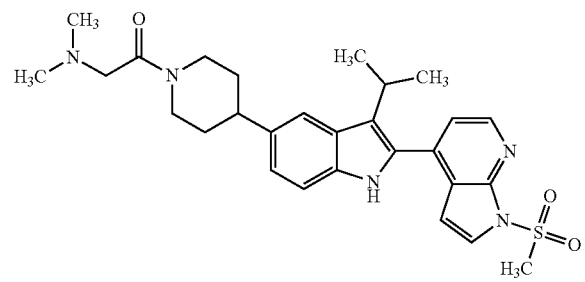

(450)

To a stirred solution of 4-(3-isopropyl-5-(piperidin-4-yl)-1H-indol-2-yl)-1-(methylsulfonyl)-1H-pyrrolo[2,3-b]pyridine (0.02 g, 0.046 mmol), TEA (0.019 mL, 0.137 mmol) and HATU (0.035 g, 0.092 mmol) in DMF (1 mL) was added N,N-dimethylglycine (4.72 mg, 0.046 mmol). The resulting reaction mixture was stirred at 25° C. for 12 hrs. The reaction mixture was diluted with DCM and washed with water. The aqueous layer was extracted (2×50 mL) with additional DCM. The combined organics were dried over anhydrous sodium sulfate and concentrated. The crude was purified via preparative LC/MS. The fractions containing the desired product were combined and dried via centrifugal evaporation to afford 2-(dimethylamino)-1-(4-(3-isopropyl-2-(1-(methylsulfonyl)-1H-pyrrolo[2,3-b]pyridin-4-yl)-1H-indol-5-yl)piperidin-1-yl)ethanone (1.0 mg, 0.0019 mmol, 4.1% yield). MS (M$^{+1}$) m/z: 522.3 (MH$^+$). LC retention time 1.42 min [E]. $^1$H NMR (400 MHz, DMSO-d$_6$) δ=11.17 (s, 1H), 8.53 (d, J=5.0 Hz, 1H), 7.82 (d, J=4.0 Hz, 1H), 7.60 (s, 1H), 7.42-7.32 (m, 2H), 7.05 (dd, J=8.5, 1.5 Hz, 1H), 6.75 (d, J=4.0 Hz, 1H), 4.54 (d, J=13.1 Hz, 1H), 4.20 (d, J=13.1 Hz, 1H), 3.80 (s, 3H), 3.21 (dt, J=14.1, 7.0 Hz, 2H), 3.15-3.05 (m, 3H), 2.87 (t, J=12.3 Hz, 1H), 2.71-2.62 (m, 1H), 2.21 (s, 6H), 1.89-1.81 (m, 3H), 1.72-1.64 (m, 1H), 1.55-1.47 (m, 1H), 1.41 (d, J=7.0 Hz, 6H).

The following examples were prepared according to the general procedures for Example 276.

TABLE 17

| Ex. No. | Structure | Obs. MS Ion | RT | HPLC Method |
|---|---|---|---|---|
| 451 | 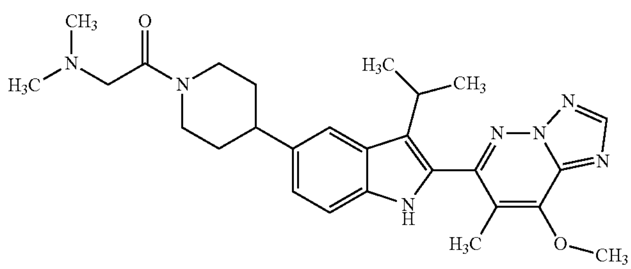 [SMILES: COc1c(C)c(-c2[nH]c3ccc(C4CCN(C(=O)CN(C)C)CC4)cc3c2C(C)C)nn2ncnc12] | 490.1 | 1.61 | QC-ACN-AA-XB |
| 452 | 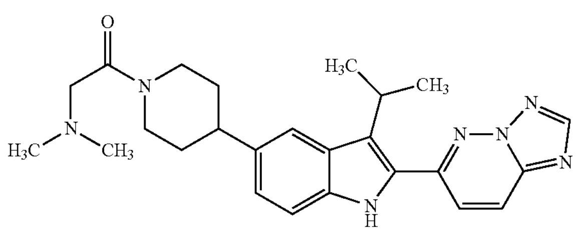 [SMILES: CC(C)c1c(-c2ccc3ncnn3n2)[nH]c2ccc(C3CCN(C(=O)CN(C)C)CC3)cc12] | 446.3 | 0.66 | K |
| 453 | 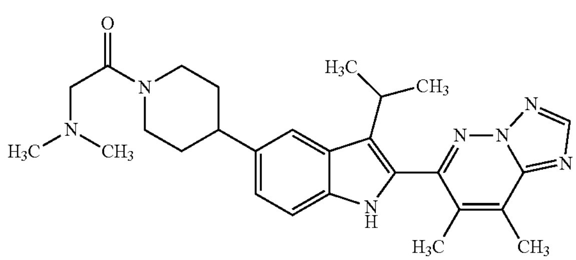 | 474.2 | 0.69 | K |

TABLE 17-continued

| Ex. No. | Structure | Obs. MS Ion | RT | HPLC Method |
|---|---|---|---|---|
| 454 | 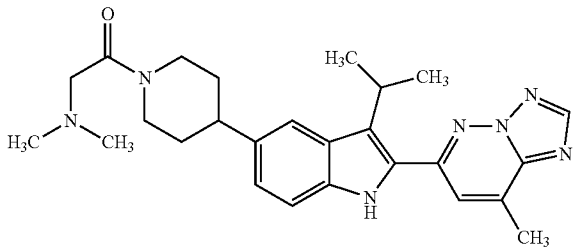 [SMILES: Cc1cc(-c2[nH]c3ccc(C4CCN(C(=O)CN(C)C)CC4)cc3c2C(C)C)nn2ncnc12] | 460.2 | 0.67 | K |
| 455 | 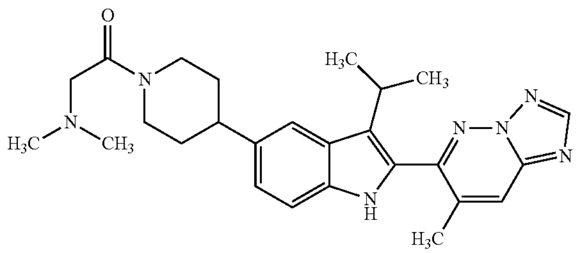 [SMILES: Cc1cc2ncnn2nc1-c1[nH]c2ccc(C3CCN(C(=O)CN(C)C)CC3)cc2c1C(C)C] | 460.2 | 0.67 | B2 |
| 456 | 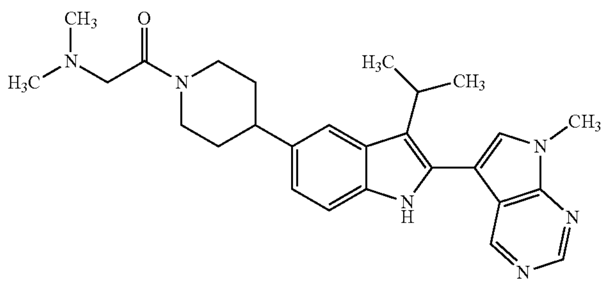 | 459.1 | 1.34 | QC-ACN-AA-XB |
| 457 | 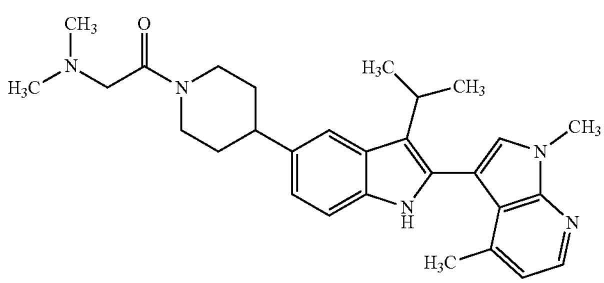 | 472.4 | 1.61 | QC-ACN-AA-XB |
| 458 | 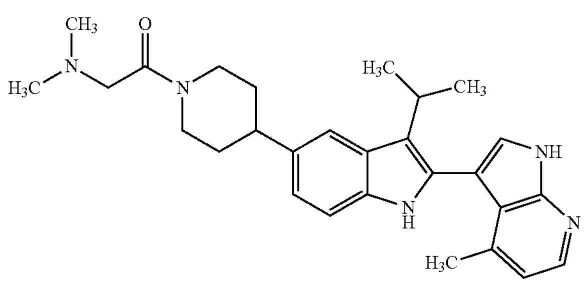 [SMILES: Cc1ccnc2[nH]cc(-c3[nH]c4ccc(C5CCN(C(=O)CN(C)C)CC5)cc4c3C(C)C)c12] | 458.3 | 1.44 | QC-ACN-AA-XB |

TABLE 17-continued

| Ex. No. | Structure | Obs. MS Ion | RT | HPLC Method |
|---|---|---|---|---|
| 459 | 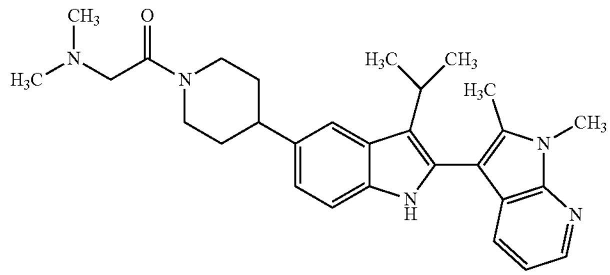 | 472.1 | 1.43 | QC-ACN-TFA-XB |
| 460 | 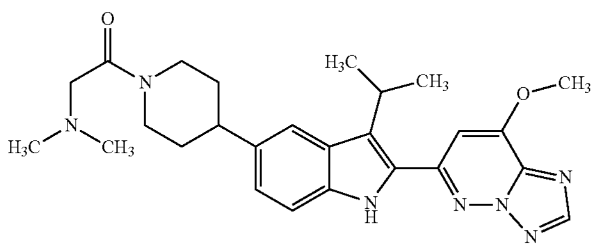 [SMILES: COc1cc(-c2[nH]c3ccc(C4CCN(C(=O)CN(C)C)CC4)cc3c2C(C)C)nn2ncnc12] | 476.2 | 0.68 | A1 |
| 461 | 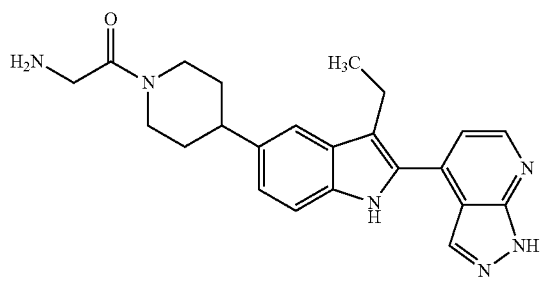 [SMILES: CCc1c(-c2ccnc3[nH]ncc23)[nH]c2ccc(C3CCN(C(=O)CN)CC3)cc12] | 403.4 | 0.93 | QC-ACN-TFA-XB |
| 462 | 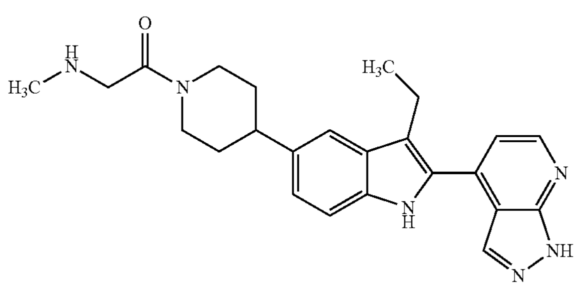 [SMILES: CCc1c(-c2ccnc3[nH]ncc23)[nH]c2ccc(C3CCN(C(=O)CNC)CC3)cc12] | 417.3 | 1.03 | QC-ACN-AA-XB |
| 463 | 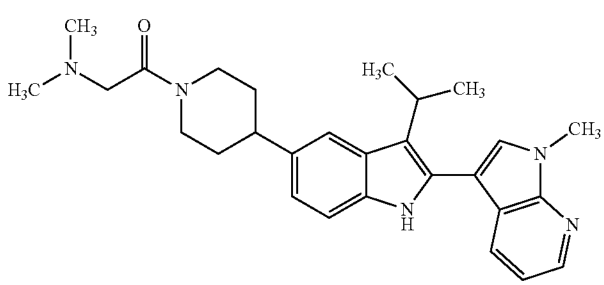 | 458 | 1.41 | QC-ACN-TFA-XB |

TABLE 17-continued
| Ex. No. | Structure | Obs. MS Ion | RT | HPLC Method |
|---|---|---|---|---|
| 464 | 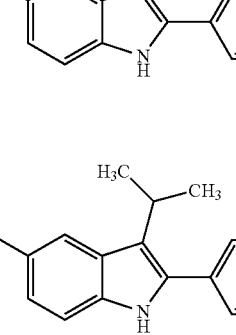 | 445 | 1.45 | QC-ACN-TFA-XB |
| 465 | 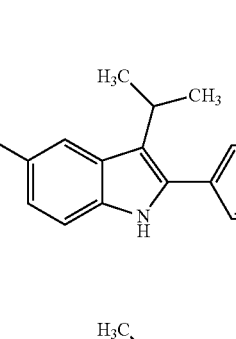 | 445.4 | 1.33 | QC-ACN-AA-XB |
| 466 | 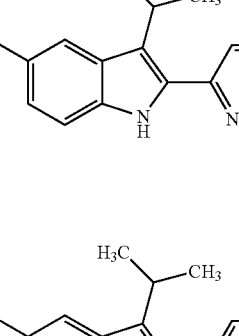 | 445.4 | 1.09 | QC-ACN-AA-XB |
| 467 | 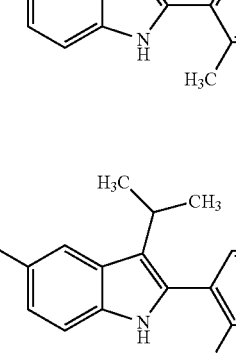 | 459 | 1.55 | QC-ACN-AA-XB |
| 468 | 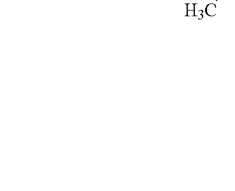 | 474.2 | 1.47 | QC-ACN-AA-XB |
| 469 | 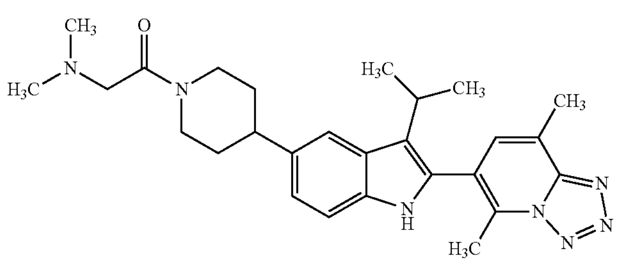 [SMILES: Cc1cc(-c2[nH]c3ccc(C4CCN(C(=O)CN(C)C)CC4)cc3c2C(C)C)c(C)n2nnnc12] | 474.1 | 1.5 | QC-ACN-TFA-XB |

TABLE 17-continued

| Ex. No. | Structure | Obs. MS Ion | RT | HPLC Method |
|---|---|---|---|---|
| 470 | 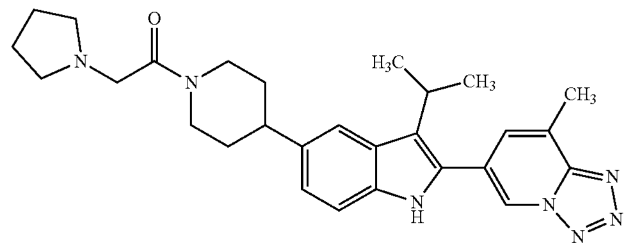 [SMILES: Cc1cc(-c2[nH]c3ccc(C4CCN(C(=O)CN5CCCC5)CC4)cc3c2C(C)C)cn2nnnc12] | 486 | 1.53 | QC-ACN-TFA-XB |
| 471 | 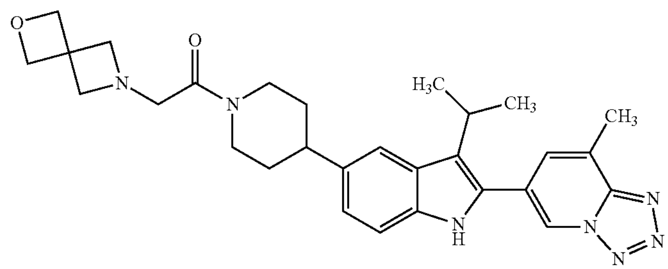 [SMILES: Cc1cc(-c2[nH]c3ccc(C4CCN(C(=O)CN5CC6(COC6)C5)CC4)cc3c2C(C)C)cn2nnnc12] | 514.4 | 1.49 | QC-ACN-AA-XB |
| 472 | 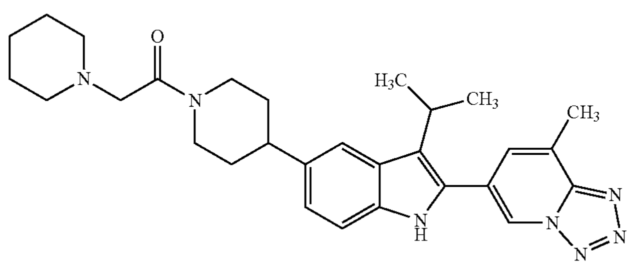 [SMILES: Cc1cc(-c2[nH]c3ccc(C4CCN(C(=O)CN5CCCCC5)CC4)cc3c2C(C)C)cn2nnnc12] | 500 | 1.53 | QC-ACN-TFA-XB |
| 473 | 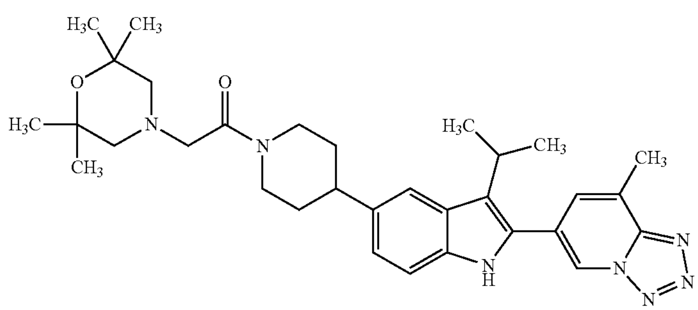 [SMILES: Cc1cc(-c2[nH]c3ccc(C4CCN(C(=O)CN5CC(C)(C)OC(C)(C)C5)CC4)cc3c2C(C)C)cn2nnnc12] | 558.5 | 1.67 | QC-ACN-TFA-XB |
| 474 | 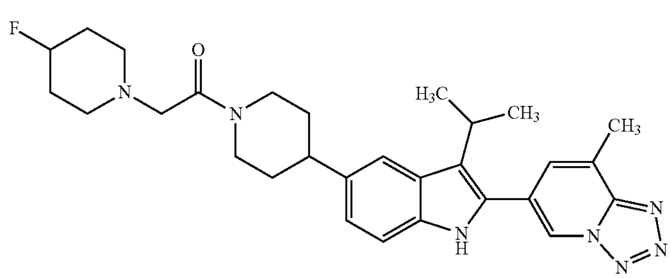 [SMILES: Cc1cc(-c2[nH]c3ccc(C4CCN(C(=O)CN5CCC(F)CC5)CC4)cc3c2C(C)C)cn2nnnc12] | 518 | 1.55 | QC-ACN-TFA-XB |

TABLE 17-continued

| Ex. No. | Structure | Obs. MS Ion | RT | HPLC Method |
|---|---|---|---|---|
| 475 | 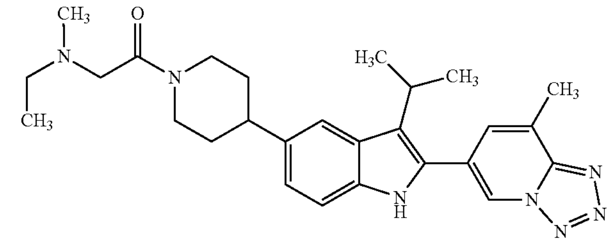 [SMILES: CCN(C)CC(=O)N1CCC(c2ccc3[nH]c(-c4cc(C)c5nnnn5c4)c(C(C)C)c3c2)CC1] | 474 | 1.45 | QC-ACN-AA-XB |
| 476 | 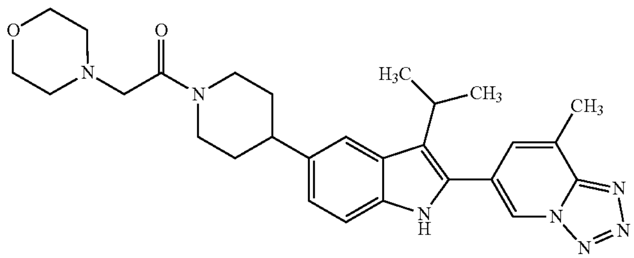 [SMILES: Cc1cc(-c2[nH]c3ccc(C4CCN(C(=O)CN5CCOCC5)CC4)cc3c2C(C)C)cn2nnnc12] | 502.4 | 1.69 | QC-ACN-AA-XB |
| 477 | 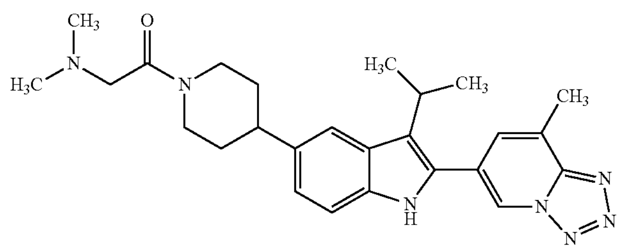 [SMILES: Cc1cc(-c2[nH]c3ccc(C4CCN(C(=O)CN(C)C)CC4)cc3c2C(C)C)cn2nnnc12] | 460 | 1.46 | QC-ACN-AA-XB |
| 478 | 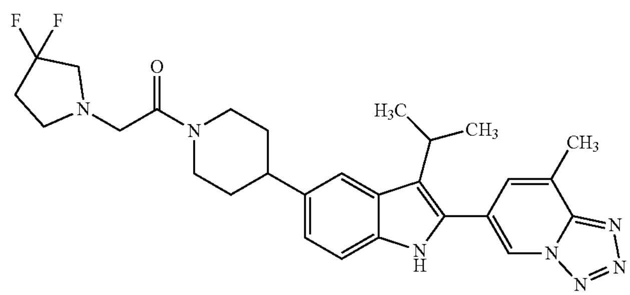 [SMILES: Cc1cc(-c2[nH]c3ccc(C4CCN(C(=O)CN5CCC(F)(F)C5)CC4)cc3c2C(C)C)cn2nnnc12] | 522.4 | 1.96 | QC-ACN-AA-XB |
| 479 | 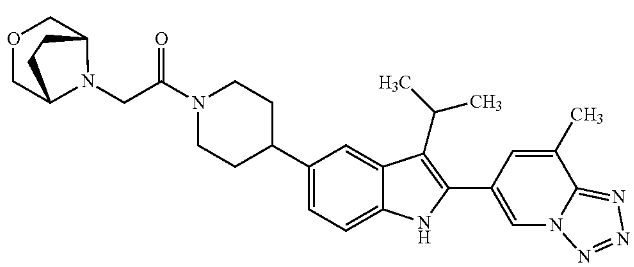 [SMILES: Cc1cc(-c2[nH]c3ccc(C4CCN(C(=O)CN5[C@@H]6CC[C@H]5COC6)CC4)cc3c2C(C)C)cn2nnnc12] | 528.5 | 1.46 | QC-ACN-TFA-XB |
| 480 | 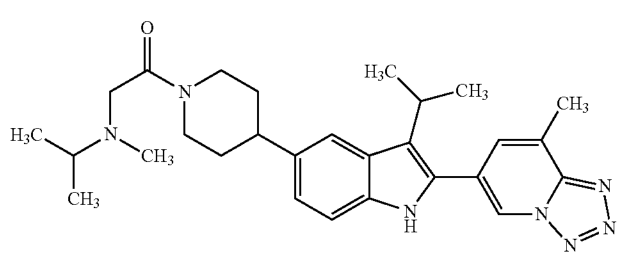 [SMILES: Cc1cc(-c2[nH]c3ccc(C4CCN(C(=O)CN(C)C(C)C)CC4)cc3c2C(C)C)cn2nnnc12] | 488 | 1.63 | QC-ACN-TFA-XB |

TABLE 17-continued
| Ex. No. | Structure | Obs. MS Ion | RT | HPLC Method |
|---|---|---|---|---|
| 481 | 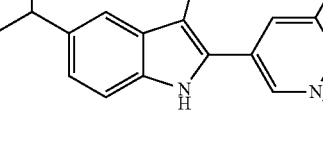 | 502.1 | 1.68 | QC-ACN-TFA-XB |
| 482 | 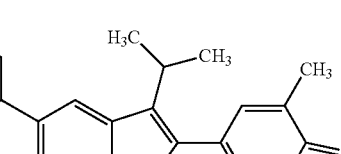 | 536.5 | 2.09 | QC-ACN-AA-XB |
| 483 | 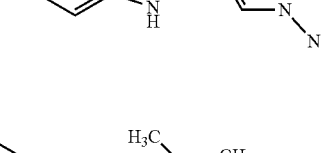 | 486 | 2.12 | QC-ACN-AA-XB |
| 484 | 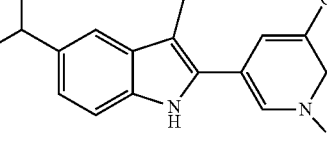 | 528.2 | 1.92 | QC-ACN-AA-XB |
| 485 | 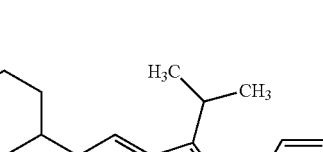 | 550.4 | 1.71 | QC-ACN-AA-XB |
| 486 | 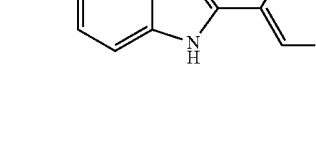 | 460.2 | 1.28 | QC-ACN-TFA-XB |

TABLE 17-continued
| Ex. No. | Structure | Obs. MS Ion | RT | HPLC Method |
|---|---|---|---|---|
| 487 | 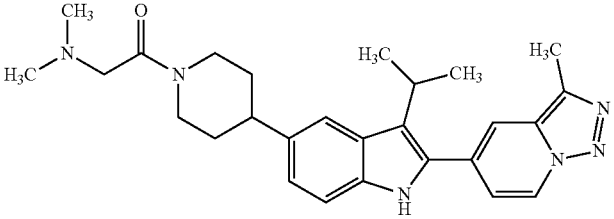 [SMILES: Cc1nnn2ccc(-c3[nH]c4ccc(C5CCN(C(=O)CN(C)C)CC5)cc4c3C(C)C)cc12] | 459.1 | 1.42 | QC-ACN-TFA-XB |
| 488 | 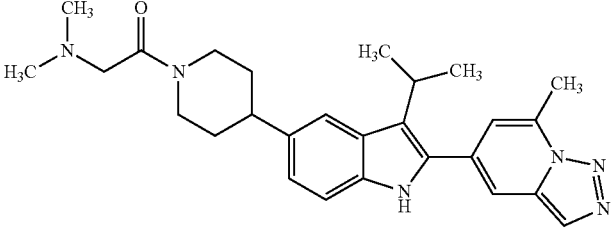 [SMILES: Cc1cc(-c2[nH]c3ccc(C4CCN(C(=O)CN(C)C)CC4)cc3c2C(C)C)cc2cnnn12] | 459.4 | 1.39 | QC-ACN-AA-XB |
| 489 | 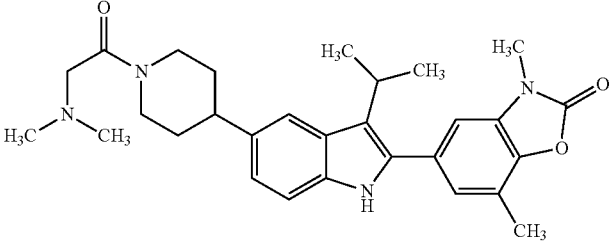 [SMILES: Cc1cc(-c2[nH]c3ccc(C4CCN(C(=O)CN(C)C)CC4)cc3c2C(C)C)cc2c1oc(=O)n2C] | 489.3 | 1.89 | E |
| 490 | 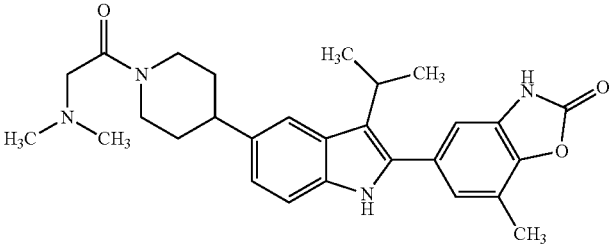 [SMILES: Cc1cc(-c2[nH]c3ccc(C4CCN(C(=O)CN(C)C)CC4)cc3c2C(C)C)cc2[nH]c(=O)oc12] | 475.2 | 1.76 | E |
| 491 | 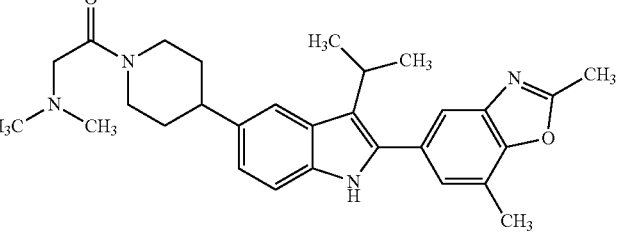 | 473.3 | 2.01 | E |
| 492 | 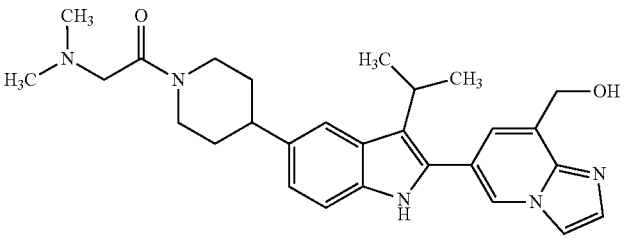 [SMILES: CC(C)c1c(-c2cc(CO)c3nccn3c2)[nH]c2ccc(C3CCN(C(=O)CN(C)C)CC3)cc12] | 474.3 | 1.39 | E |

TABLE 17-continued

| Ex. No. | Structure | Obs. MS Ion | RT | HPLC Method |
|---|---|---|---|---|
| 493 | 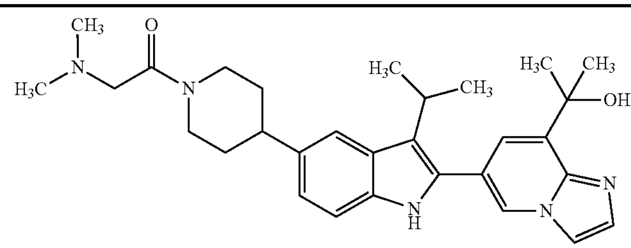 | 502.3 | 1.65 | E |
| 494 | 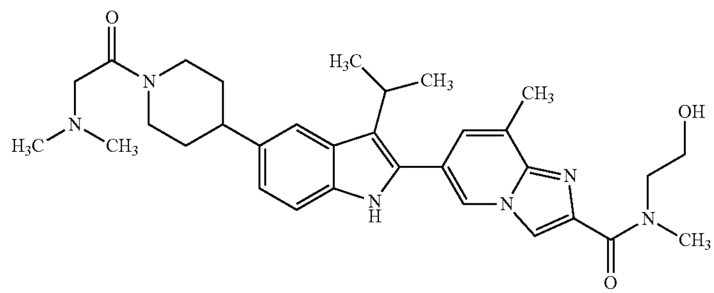 [SMILES: Cc1cc(-c2[nH]c3ccc(C4CCN(C(=O)CN(C)C)CC4)cc3c2C(C)C)cn2cc(C(=O)N(C)CCO)nc12] | 559.3 | 1.16 | F |
| 495 | 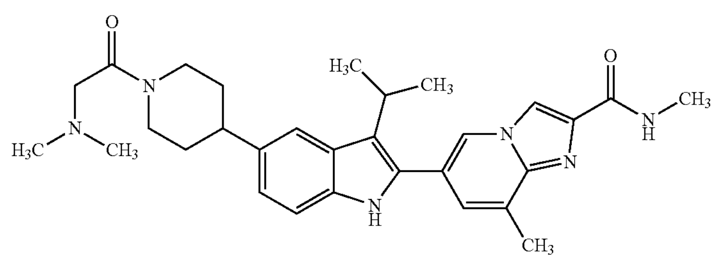 | 515.3 | 1.30 | F |
| 496 | 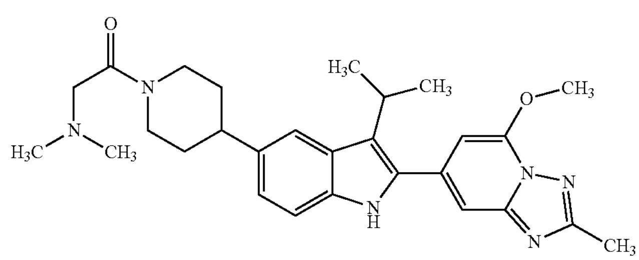 | 489.2 | 1.47 | F |
| 497 | 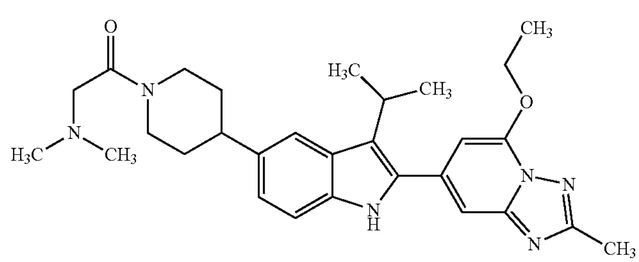 | 503.3 | 1.13 | F |
| 498 | 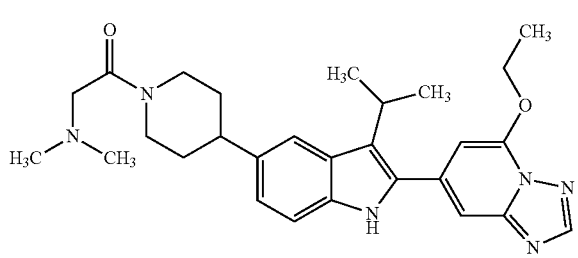 [SMILES: CCOc1cc(-c2[nH]c3ccc(C4CCN(C(=O)CN(C)C)CC4)cc3c2C(C)C)cc2ncnn12] | 489.2 | 1.54 | E |

TABLE 17-continued

| Ex. No. | Structure | Obs. MS Ion | RT | HPLC Method |
|---|---|---|---|---|
| 499 | 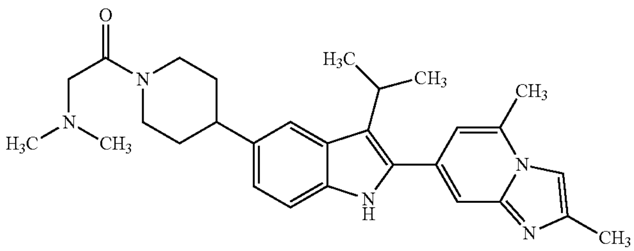 | 472.2 | 1.70 | E |
| 500 | 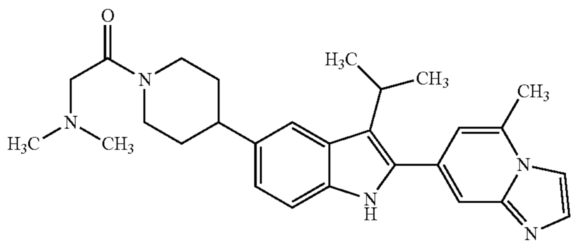 [SMILES: Cc1cc(-c2[nH]c3ccc(C4CCN(C(=O)CN(C)C)CC4)cc3c2C(C)C)cc2nccn12] | 458.1 | 1.59 | E |
| 501 | 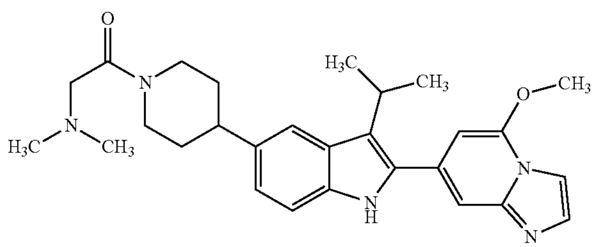 [SMILES: COc1cc(-c2[nH]c3ccc(C4CCN(C(=O)CN(C)C)CC4)cc3c2C(C)C)cc2nccn12] | 474.1 | 1.62 | E |
| 502 | 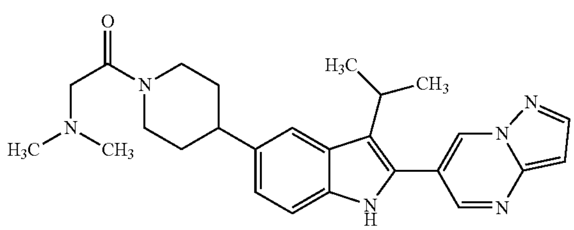 [SMILES: CC(C)c1c(-c2cnc3ccnn3c2)[nH]c2ccc(C3CCN(C(=O)CN(C)C)CC3)cc12] | 445 | 1.57 | E |
| 503 | 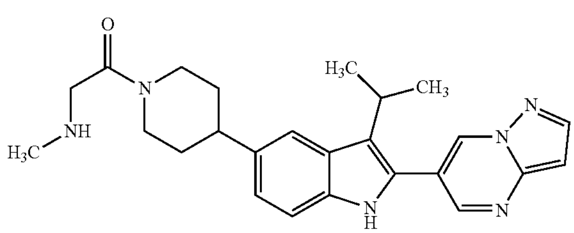 [SMILES: CNCC(=O)N1CCC(c2ccc3[nH]c(-c4cnc5ccnn5c4)c(C(C)C)c3c2)CC1] | 431 | 1.48 | E |
| 504 | 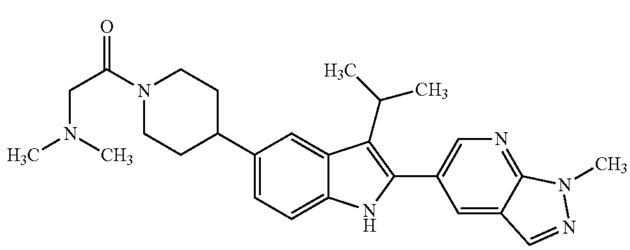 | 459.3 | 1.64 | E |

TABLE 17-continued
| Ex. No. | Structure | Obs. MS Ion | RT | HPLC Method |
|---|---|---|---|---|
| 505 | 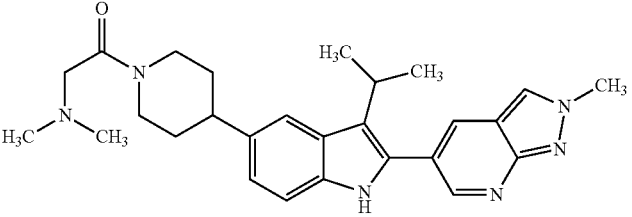 | 459.3 | 1.40 | E |
| 506 | 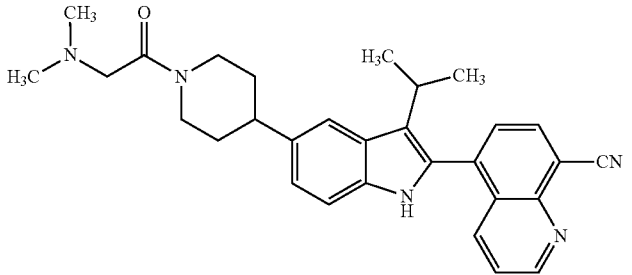 [SMILES: CC(C)c1c(-c2ccc(C#N)c3ncccc23)[nH]c2ccc(C3CCN(C(=O)CN(C)C)CC3)cc12] | 480.3 | 1.55 | E |
| 507 | 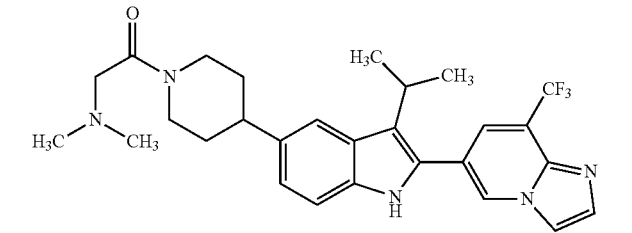 [SMILES: CC(C)c1c(-c2cc(C(F)(F)F)c3nccn3c2)[nH]c2ccc(C3CCN(C(=O)CN(C)C)CC3)cc12] | 512 | 1.70 | E |
| 508 | 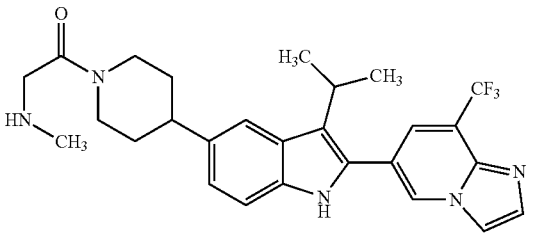 | 498.3 | 1.55 | E |
| 509 | 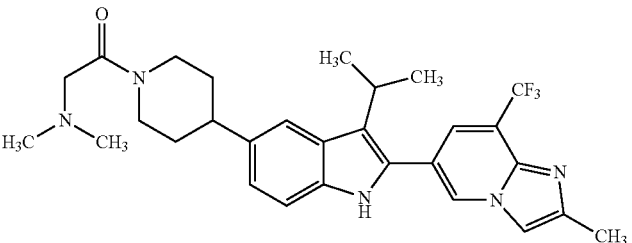 | 472.3 | 1.60 | E |
| 510 | 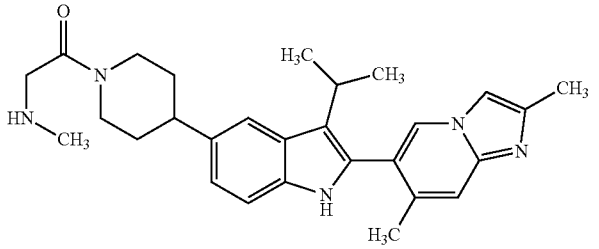 [SMILES: CNCC(=O)N1CCC(c2ccc3[nH]c(-c4cn5cc(C)nc5cc4C)c(C(C)C)c3c2)CC1] | 458.3 | 1.57 | E |

TABLE 17-continued

| Ex. No. | Structure | Obs. MS Ion | RT | HPLC Method |
|---|---|---|---|---|
| 511 | 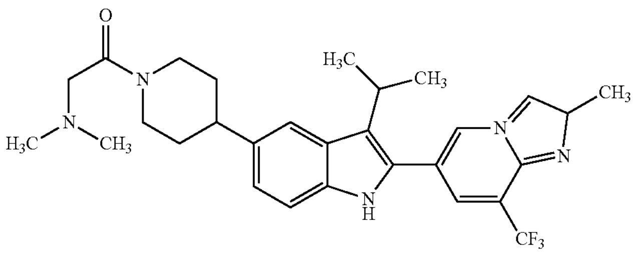 | 526 | 1.80 | E |
| 512 | 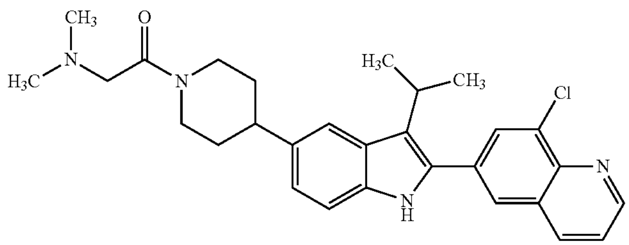 [SMILES: CC(C)c1c(-c2cc(Cl)c3ncccc3c2)[nH]c2ccc(C3CCN(C(=O)CN(C)C)CC3)cc12] | 490 | 1.89 | E |
| 513 | 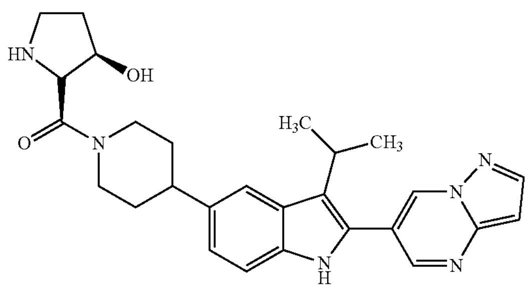 | 473 | 1.29 | E |
| 514 | 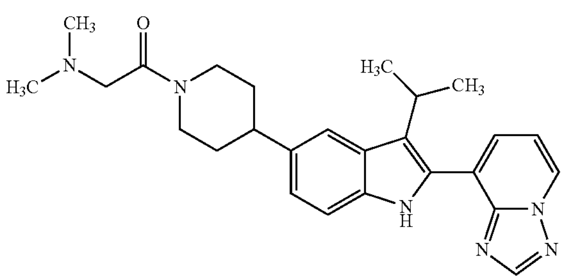 [SMILES: CC(C)c1c(-c2cccn3ncnc23)[nH]c2ccc(C3CCN(C(=O)CN(C)C)CC3)cc12] | 445 | 1.47 | E |
| 515 | 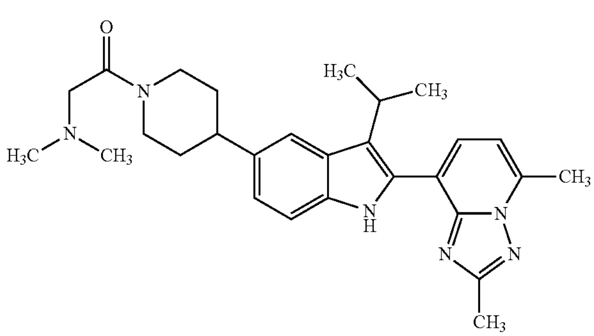 | 473 | 1.58 | E |

TABLE 17-continued

| Ex. No. | Structure | Obs. MS Ion | RT | HPLC Method |
|---|---|---|---|---|
| 516 | 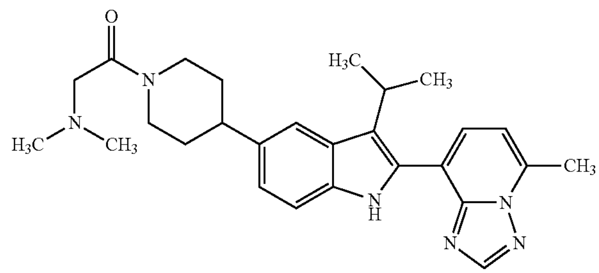 | 459 | 1.65 | E |
| 517 | 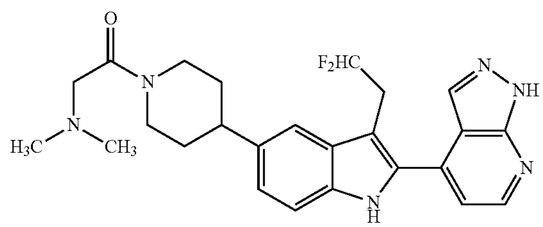 [SMILES: CN(C)CC(=O)N1CCC(c2ccc3[nH]c(-c4ccnc5[nH]ncc45)c(CC(F)F)c3c2)CC1] | 467 | 0.99 | E |
| 518 | 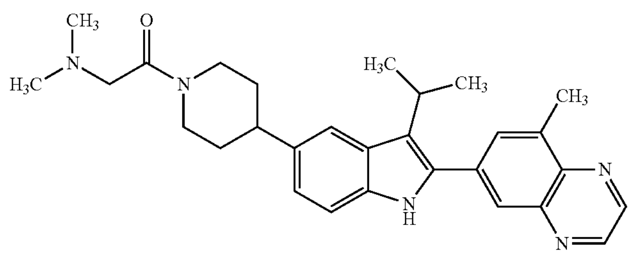 [SMILES: Cc1cc(-c2[nH]c3ccc(C4CCN(C(=O)CN(C)C)CC4)cc3c2C(C)C)cc2nccnc12] | 470.1 | 1.84 | E |
| 519 | 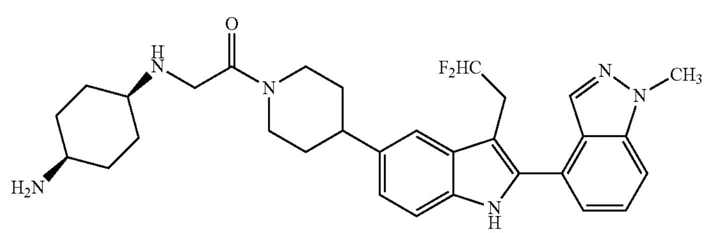 [SMILES: Cn1ncc2c(-c3[nH]c4ccc(C5CCN(C(=O)CN[C@H]6CC[C@@H](N)CC6)CC5)cc4c3CC(F)F)cccc21] | 513 | 2.05 | E |
| 520 | 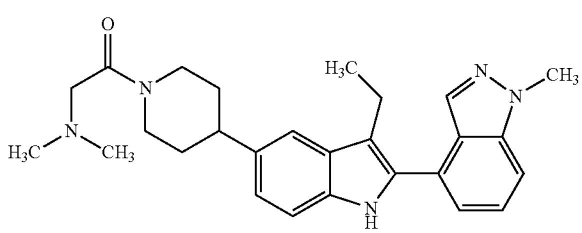 | 444 | 2.38 | E |
| 521 | 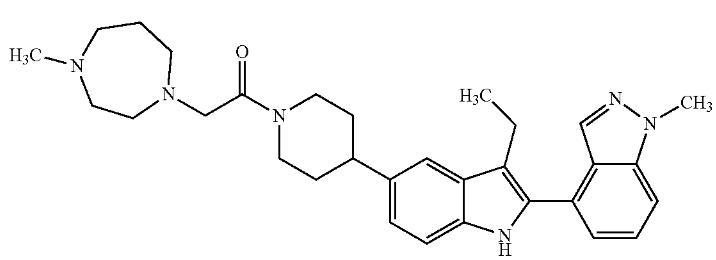 | 513 | 1.15 | E |

TABLE 17-continued

| Ex. No. | Structure | Obs. MS Ion | RT | HPLC Method |
|---|---|---|---|---|
| 522 | 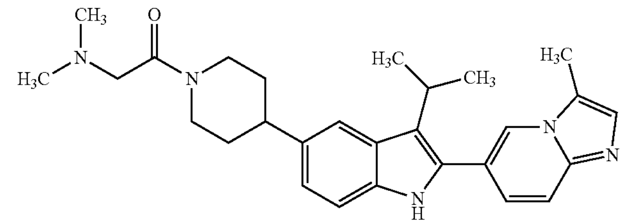 [SMILES: Cc1cnc2ccc(-c3[nH]c4ccc(C5CCN(C(=O)CN(C)C)CC5)cc4c3C(C)C)cn12] | 458.3 | 1.55 | E |
| 523 | 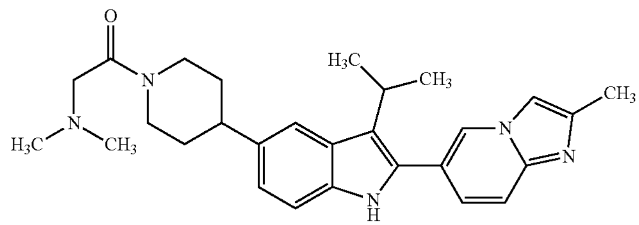 | 458.3 | 1.58 | F |
| 524 | 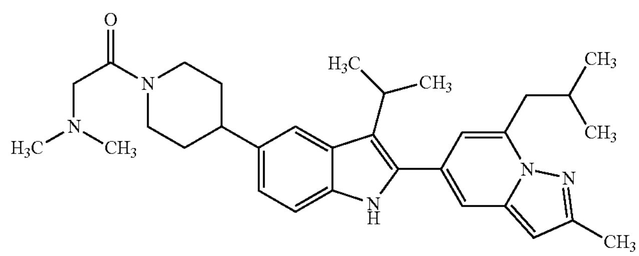 | 515.4 | 2.08 | F |
| 526 | 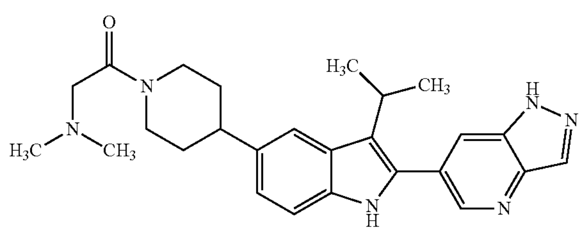 [SMILES: CC(C)c1c(-c2cnc3cn[nH]c3c2)[nH]c2ccc(C3CCN(C(=O)CN(C)C)CC3)cc12] | 445.2 | 0.96 | F |
| 527 | 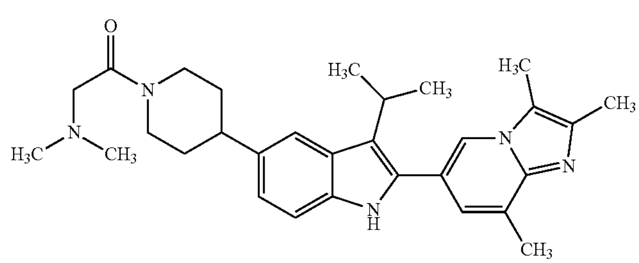 | 486.2 | 1.74 | E |
| 528 | 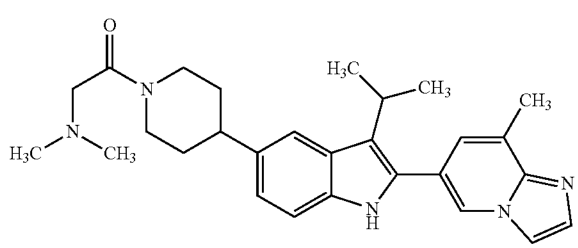 | 458 | 1.55 | E |

TABLE 17-continued

| Ex. No. | Structure | Obs. MS Ion | RT | HPLC Method |
|---|---|---|---|---|
| 529 | 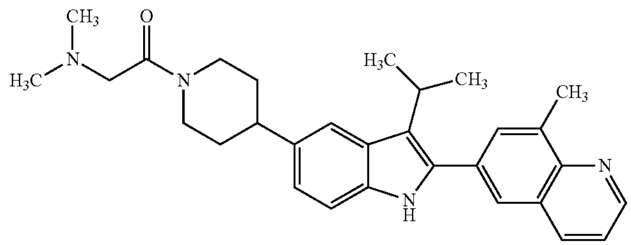 [SMILES: Cc1cc(-c2[nH]c3ccc(C4CCN(C(=O)CN(C)C)CC4)cc3c2C(C)C)cc2cccnc12] | 469.2 | 1.95 | E |
| 530 | 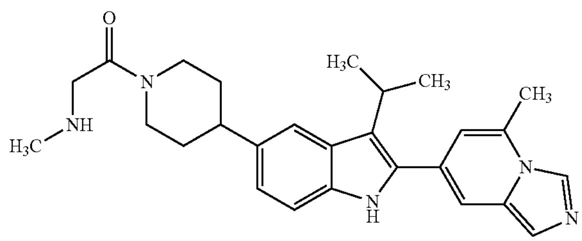 [SMILES: CNCC(=O)N1CCC(c2ccc3[nH]c(-c4cc(C)n5cncc5c4)c(C(C)C)c3c2)CC1] | 444.3 | 1.53 | E |
| 531 | 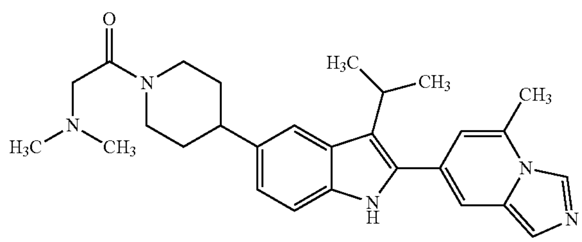 [SMILES: Cc1cc(-c2[nH]c3ccc(C4CCN(C(=O)CN(C)C)CC4)cc3c2C(C)C)cc2cncn12] | 458.3 | 1.64 | E |
| 532 | 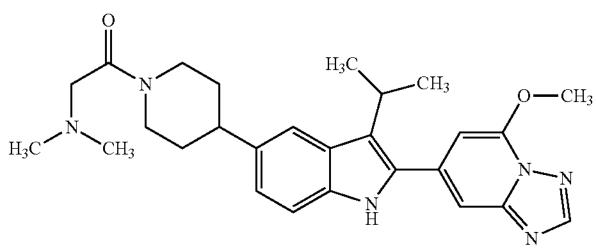 [SMILES: COc1cc(-c2[nH]c3ccc(C4CCN(C(=O)CN(C)C)CC4)cc3c2C(C)C)cc2ncnn12] | 475.2 | 1.44 | E |
| 533 | 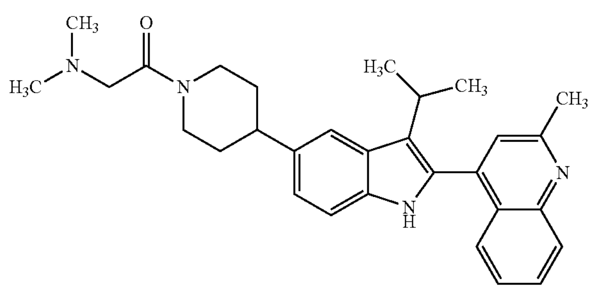 | 469.3 | 1.83 | E |
| 534 | 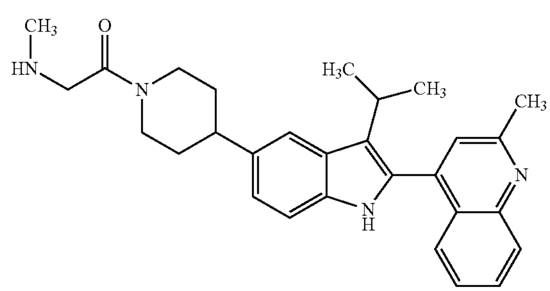 [SMILES: CNCC(=O)N1CCC(c2ccc3[nH]c(-c4cc(C)nc5ccccc45)c(C(C)C)c3c2)CC1] | 455.2 | 1.66 | E |

TABLE 17-continued

| Ex. No. | Structure | Obs. MS Ion | RT | HPLC Method |
|---|---|---|---|---|
| 535 | 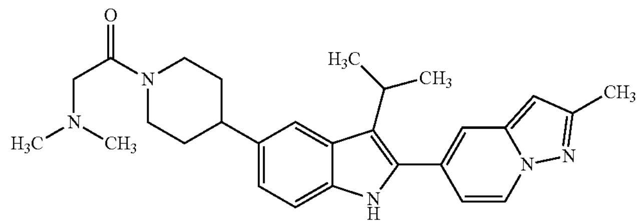 | 458.3 | 1.96 | E |
| 536 | 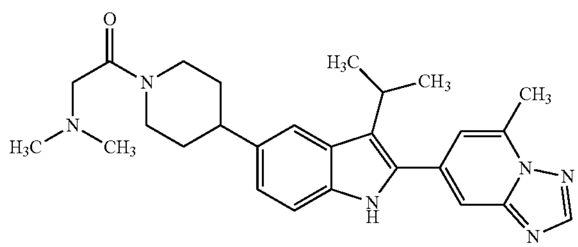 [SMILES: Cc1cc(-c2[nH]c3ccc(C4CCN(C(=O)CN(C)C)CC4)cc3c2C(C)C)cc2ncnn12] | 459.3 | 1.58 | E |
| 537 | 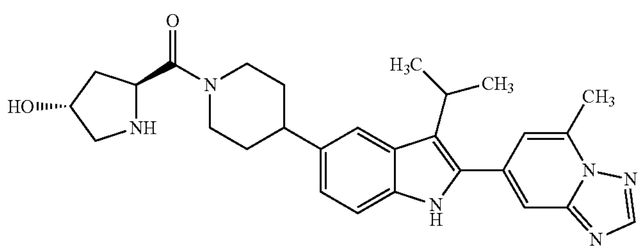 [SMILES: Cc1cc(-c2[nH]c3ccc(C4CCN(C(=O)[C@@H]5C[C@@H](O)CN5)CC4)cc3c2C(C)C)cc2ncnn12] | 487.3 | 1.43 | E |
| 538 | 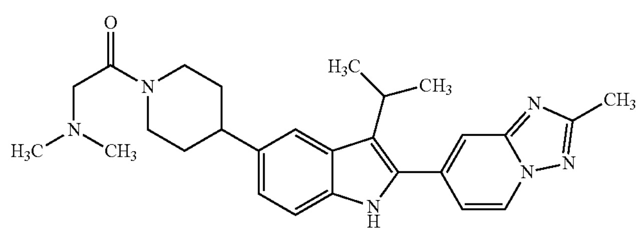 | 459.3 | 1.55 | E |
| 539 | 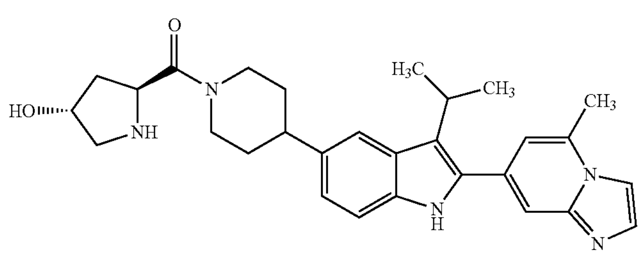 | 486.1 | 1.46 | E |
| 540 | 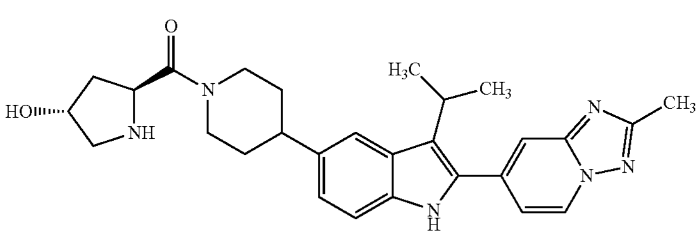 [SMILES: Cc1nc2cc(-c3[nH]c4ccc(C5CCN(C(=O)[C@@H]6C[C@@H](O)CN6)CC5)cc4c3C(C)C)ccn2n1] | 487.3 | 1.28 | E |

TABLE 17-continued

| Ex. No. | Structure | Obs. MS Ion | RT | HPLC Method |
|---|---|---|---|---|
| 541 | 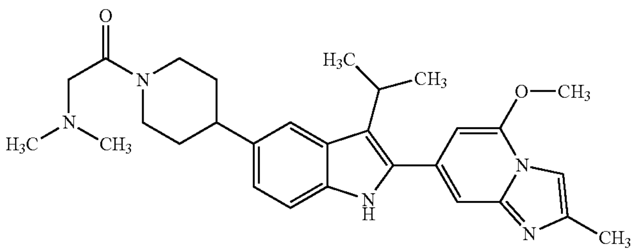 | 488.2 | 1.24 | F |
| 542 | 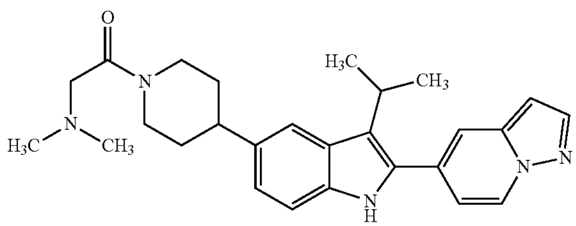 [SMILES: CC(C)c1c(-c2ccn3nccc3c2)[nH]c2ccc(C3CCN(C(=O)CN(C)C)CC3)cc12] | 444.2 | 1.80 | E |
| 543 | 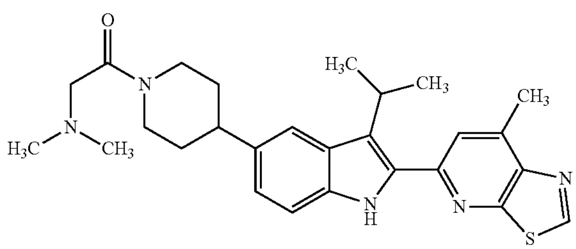 [SMILES: Cc1cc(-c2[nH]c3ccc(C4CCN(C(=O)CN(C)C)CC4)cc3c2C(C)C)nc2scnc12] | 476.1 | 1.87 | E |
| 544 | 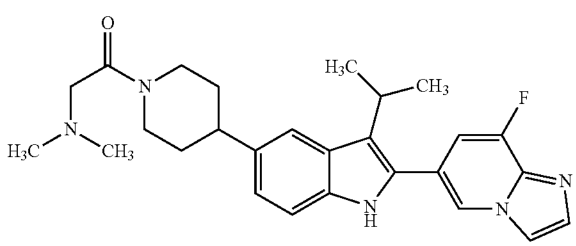 [SMILES: CC(C)c1c(-c2cc(F)c3nccn3c2)[nH]c2ccc(C3CCN(C(=O)CN(C)C)CC3)cc12] | 462.3 | 1.42 | E |
| 545 | 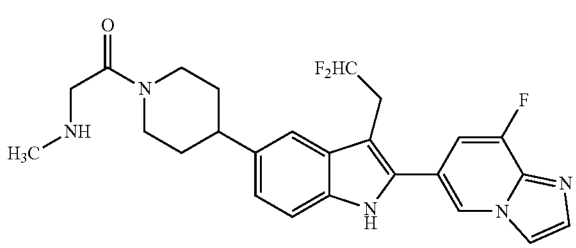 [SMILES: CNCC(=O)N1CCC(c2ccc3[nH]c(-c4cc(F)c5nccn5c4)c(CC(F)F)c3c2)CC1] | 470.2 | 1.25 | E |
| 546 | 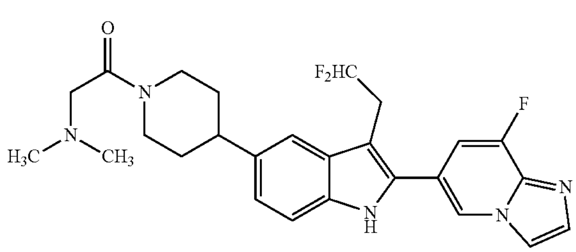 [SMILES: CN(C)CC(=O)N1CCC(c2ccc3[nH]c(-c4cc(F)c5nccn5c4)c(CC(F)F)c3c2)CC1] | 484.2 | 1.37 | E |

TABLE 17-continued

| Ex. No. | Structure | Obs. MS Ion | RT | HPLC Method |
|---|---|---|---|---|
| 547 | 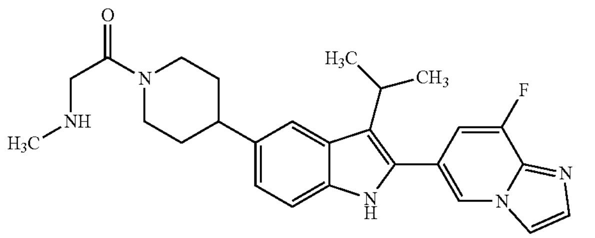 [SMILES: CNCC(=O)N1CCC(c2ccc3[nH]c(-c4cc(F)c5nccn5c4)c(C(C)C)c3c2)CC1] | 448.2 | 1.09 | E |
| 548 | 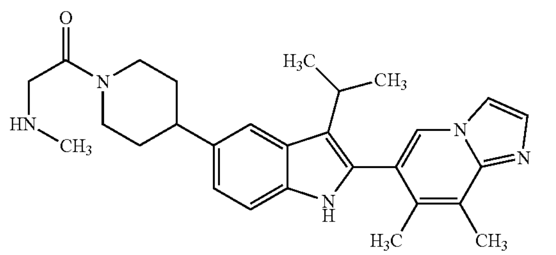 [SMILES: CNCC(=O)N1CCC(c2ccc3[nH]c(-c4cn5ccnc5c(C)c4C)c(C(C)C)c3c2)CC1] | 458.3 | 1.44 | E |
| 549 | 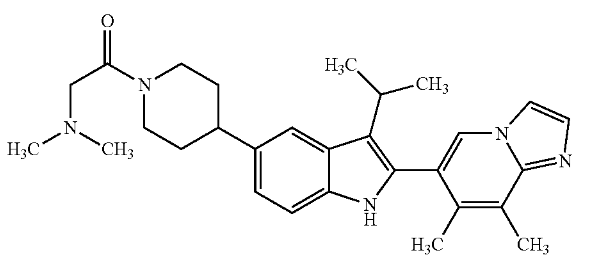 [SMILES: Cc1c(-c2[nH]c3ccc(C4CCN(C(=O)CN(C)C)CC4)cc3c2C(C)C)cn2ccnc2c1C] | 472.3 | 1.18 | F |
| 550 | 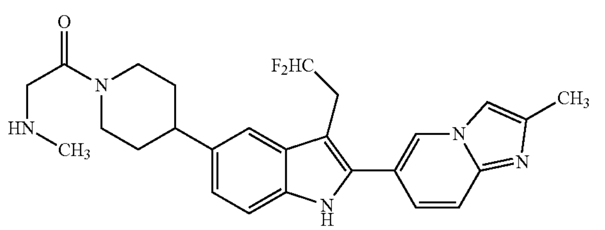 [SMILES: CNCC(=O)N1CCC(c2ccc3[nH]c(-c4ccc5nc(C)cn5c4)c(CC(F)F)c3c2)CC1] | 466.2 | 1.14 | E |
| 551 | 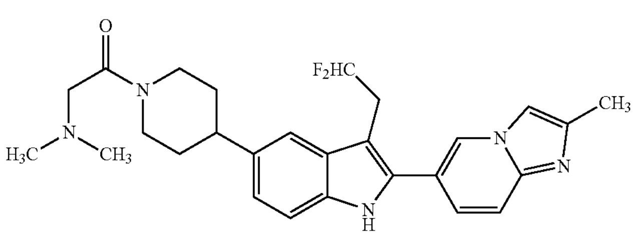 | 480.3 | 1.30 | E |
| 552 | 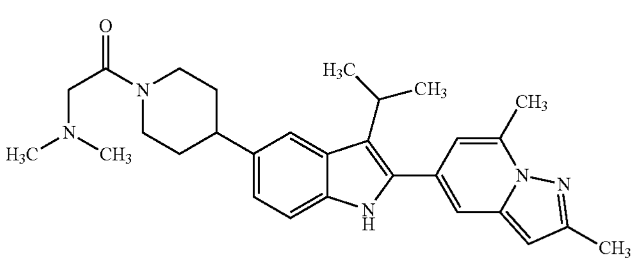 | 472.3 | 2.05 | E |

TABLE 17-continued
| Ex. No. | Structure | Obs. MS Ion | RT | HPLC Method |
|---|---|---|---|---|
| 553 | 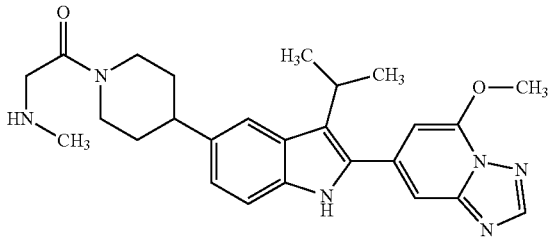 [SMILES: CNCC(=O)N1CCC(c2ccc3[nH]c(-c4cc(OC)n5ncnc5c4)c(C(C)C)c3c2)CC1] | 461.1 | 1.33 | E |
| 554 | 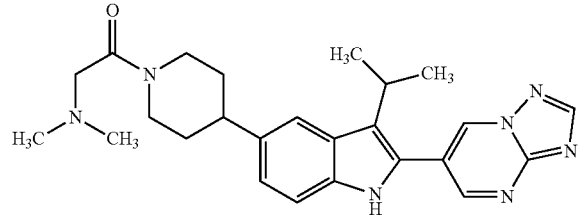 [SMILES: CC(C)c1c(-c2cnc3ncnn3c2)[nH]c2ccc(C3CCN(C(=O)CN(C)C)CC3)cc12] | 446 | 1.24 | F |
| 555 | 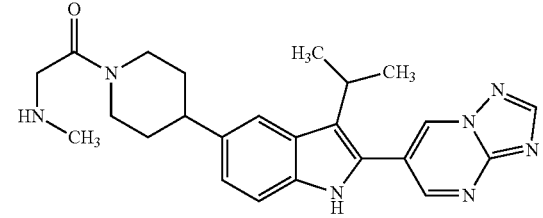 [SMILES: CNCC(=O)N1CCC(c2ccc3[nH]c(-c4cnc5ncnn5c4)c(C(C)C)c3c2)CC1] | 432 | 1.2 | E |
| 556 | 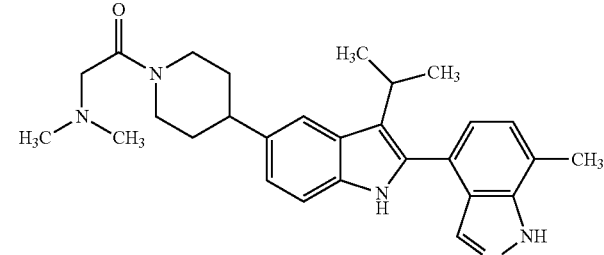 | 478 | 1.51 | E |
| 557 | 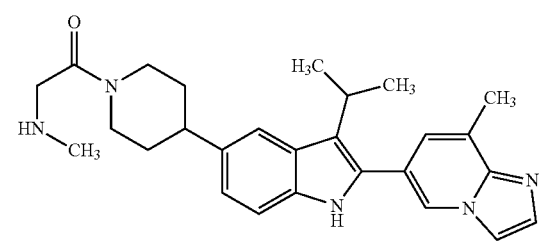 [SMILES: CNCC(=O)N1CCC(c2ccc3[nH]c(-c4cc(C)c5nccn5c4)c(C(C)C)c3c2)CC1] | 444.2 | 1.41 | E |
| 558 | 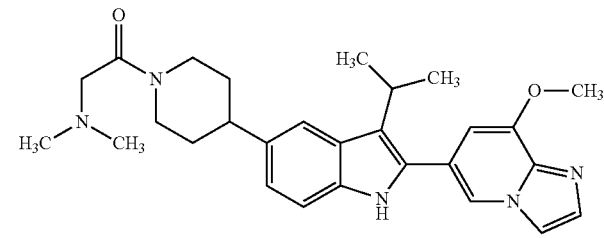 [SMILES: COc1cc(-c2[nH]c3ccc(C4CCN(C(=O)CN(C)C)CC4)cc3c2C(C)C)cn2ccnc12] | 474.3 | 1.36 | E |

TABLE 17-continued

| Ex. No. | Structure | Obs. MS Ion | RT | HPLC Method |
|---|---|---|---|---|
| 559 | 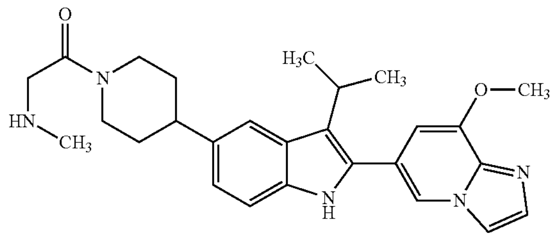 [SMILES: CNCC(=O)N1CCC(c2ccc3[nH]c(-c4cc(OC)c5nccn5c4)c(C(C)C)c3c2)CC1] | 460.3 | 1.2 | E |
| 560 | 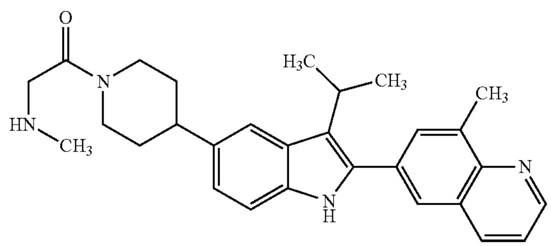 [SMILES: CNCC(=O)N1CCC(c2ccc3[nH]c(-c4cc(C)c5ncccc5c4)c(C(C)C)c3c2)CC1] | 456.4 | 1.5 | E |
| 562 | 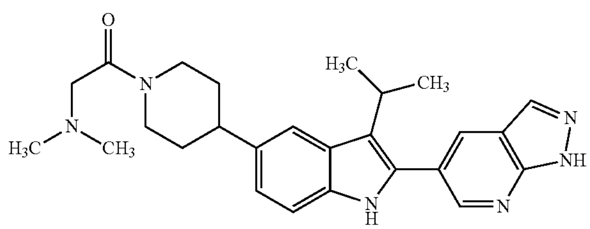 [SMILES: CC(C)c1c(-c2cnc3[nH]ncc3c2)[nH]c2ccc(C3CCN(C(=O)CN(C)C)CC3)cc12] | 445.2 | 1.88 | H |
| 563 | 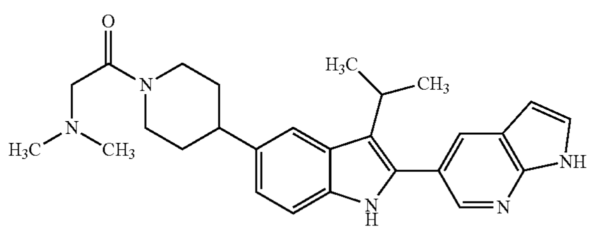 [SMILES: CC(C)c1c(-c2cnc3[nH]ccc3c2)[nH]c2ccc(C3CCN(C(=O)CN(C)C)CC3)cc12] | 444.4 | 1.73 | H |
| 564 | 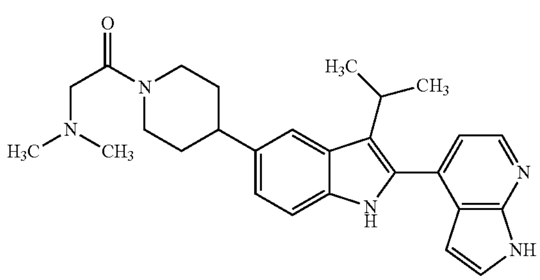 [SMILES: CC(C)c1c(-c2ccnc3[nH]ccc23)[nH]c2ccc(C3CCN(C(=O)CN(C)C)CC3)cc12] | 444.4 | 2.14 | H |
| 565 | 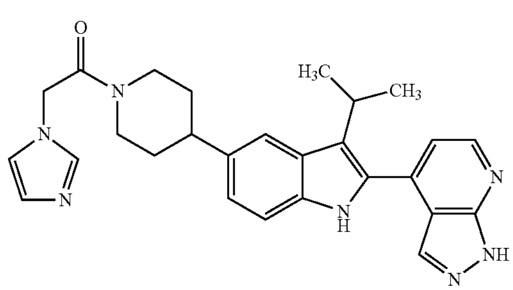 [SMILES: CC(C)c1c(-c2ccnc3[nH]ncc23)[nH]c2ccc(C3CCN(C(=O)Cn4ccnc4)CC3)cc12] | 468.3 | 1.09 | F |

TABLE 17-continued

| Ex. No. | Structure | Obs. MS Ion | RT | HPLC Method |
|---|---|---|---|---|
| 566 | 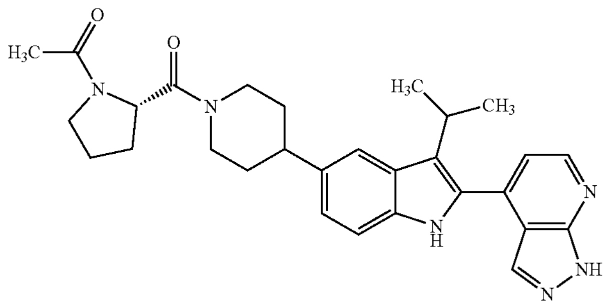 [SMILES: CC(=O)N1CCC[C@H]1C(=O)N1CCC(c2ccc3[nH]c(-c4ccnc5[nH]ncc45)c(C(C)C)c3c2)CC1] | 499.4 | 1.32 | F |
| 567 | 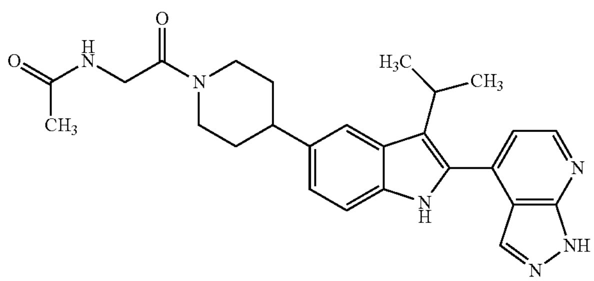 [SMILES: CC(=O)NCC(=O)N1CCC(c2ccc3[nH]c(-c4ccnc5[nH]ncc45)c(C(C)C)c3c2)CC1] | 459.3 | 1.23 | F |
| 568 | 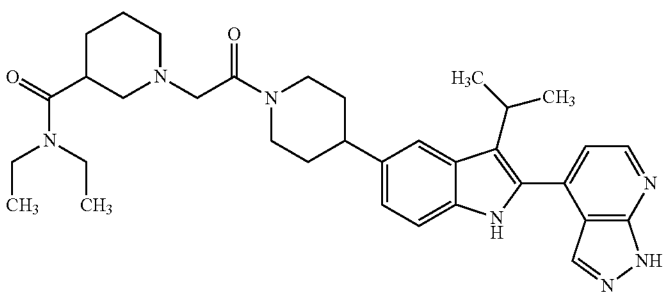 [SMILES: CCN(CC)C(=O)C1CCCN(CC(=O)N2CCC(c3ccc4[nH]c(-c5ccnc6[nH]ncc56)c(C(C)C)c4c3)CC2)C1] | 583.4 | 1.89 | H |
| 569 | 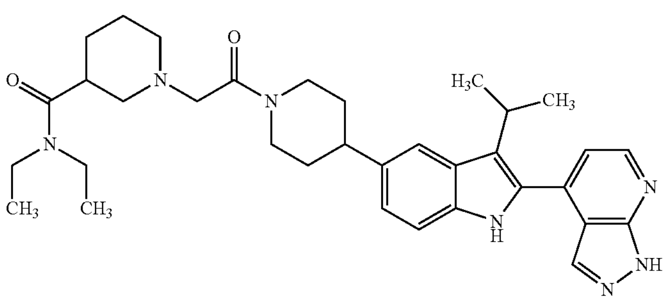 [SMILES: CCN(CC)C(=O)C1CCCN(CC(=O)N2CCC(c3ccc4[nH]c(-c5ccnc6[nH]ncc56)c(C(C)C)c4c3)CC2)C1] | 583.4 | 1.89 | H |
| 570 | 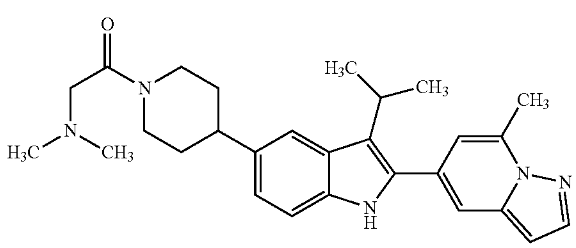 [SMILES: Cc1cc(-c2[nH]c3ccc(C4CCN(C(=O)CN(C)C)CC4)cc3c2C(C)C)cc2ccnn12] | 458.3 | 1.82 | E |

TABLE 17-continued

| Ex. No. | Structure | Obs. MS Ion | RT | HPLC Method |
|---|---|---|---|---|
| 571 | 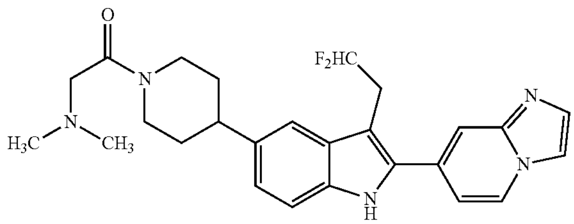 [SMILES: CN(C)CC(=O)N1CCC(c2ccc3[nH]c(-c4ccn5ccnc5c4)c(CC(F)F)c3c2)CC1] | 466.2 | 1.33 | E |
| 572 | 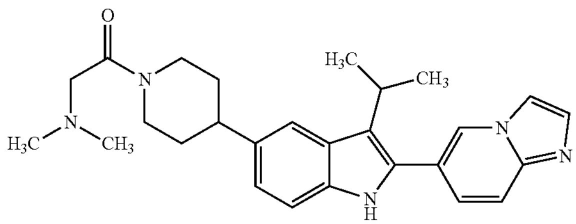 [SMILES: CC(C)c1c(-c2ccc3nccn3c2)[nH]c2ccc(C3CCN(C(=O)CN(C)C)CC3)cc12] | 444.2 | 1.5 | E |
| 573 | 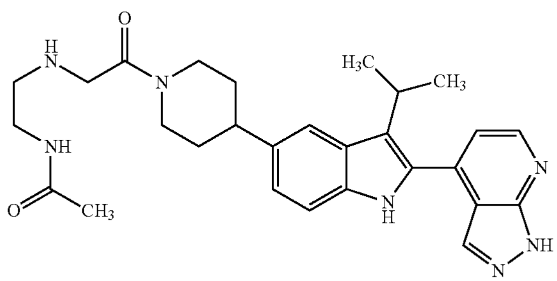 [SMILES: CC(=O)NCCNCC(=O)N1CCC(c2ccc3[nH]c(-c4ccnc5[nH]ncc45)c(C(C)C)c3c2)CC1] | 502.4 | 1.50 | E |
| 574 | 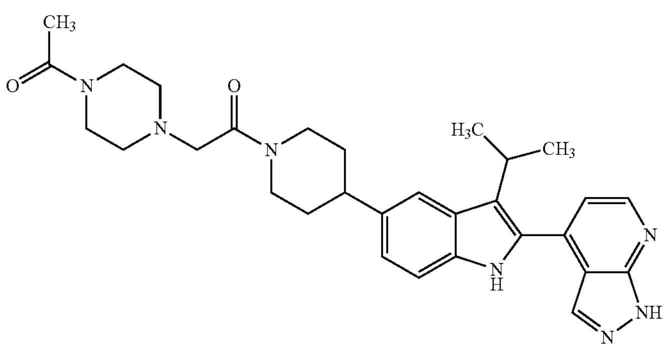 [SMILES: CC(=O)N1CCN(CC(=O)N2CCC(c3ccc4[nH]c(-c5ccnc6[nH]ncc56)c(C(C)C)c4c3)CC2)CC1] | 528.4 | 0.94 | F |
| 575 | 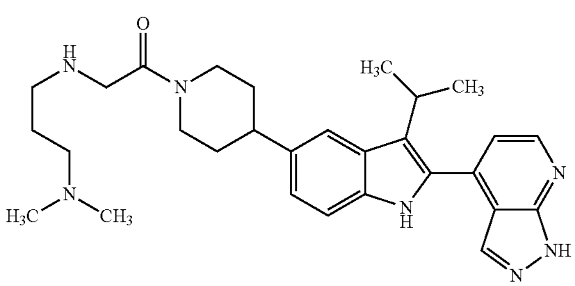 [SMILES: CC(C)c1c(-c2ccnc3[nH]ncc23)[nH]c2ccc(C3CCN(C(=O)CNCCCN(C)C)CC3)cc12] | 502.4 | 1.14 | E |

TABLE 17-continued

| Ex. No. | Structure | Obs. MS Ion | RT | HPLC Method |
|---|---|---|---|---|
| 576 | 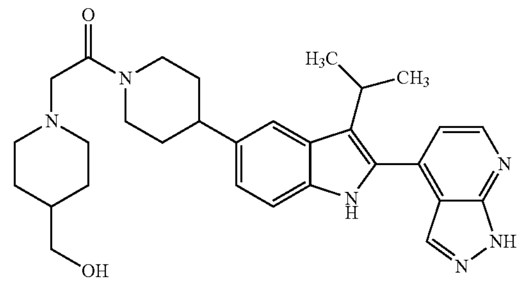 [SMILES: CC(C)c1c(-c2ccnc3[nH]ncc23)[nH]c2ccc(C3CCN(C(=O)CN4CCC(CO)CC4)CC3)cc12] | 515.4 | 1.15 | E |
| 577 | 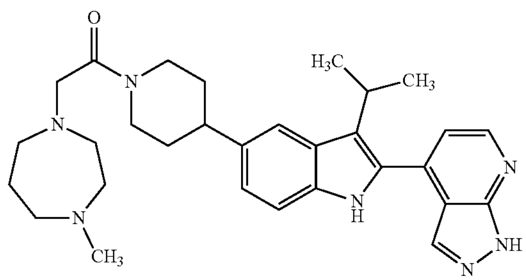 [SMILES: CC(C)c1c(-c2ccnc3[nH]ncc23)[nH]c2ccc(C3CCN(C(=O)CN4CCCN(C)CC4)CC3)cc12] | 514.4 | 1.09 | E |
| 578 | 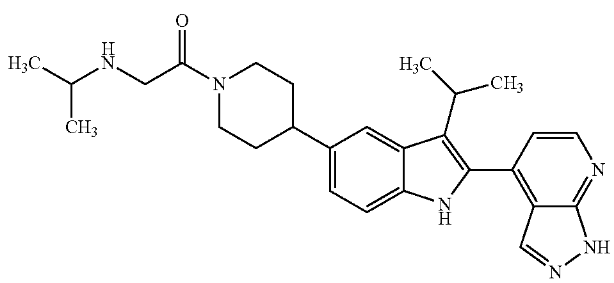 [SMILES: CC(C)NCC(=O)N1CCC(c2ccc3[nH]c(-c4ccnc5[nH]ncc45)c(C(C)C)c3c2)CC1] | 459.4 | 1.23 | E |
| 579 | 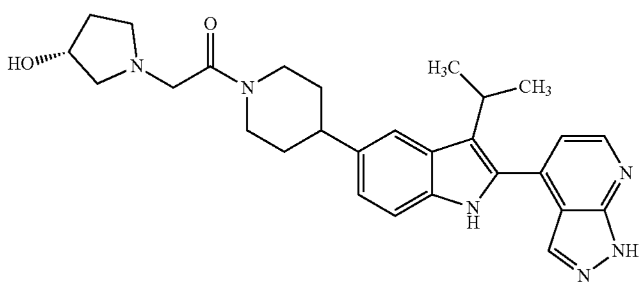 [SMILES: CC(C)c1c(-c2ccnc3[nH]ncc23)[nH]c2ccc(C3CCN(C(=O)CN4CC[C@@H](O)C4)CC3)cc12] | 487.4 | 1.19 | E |
| 580 | 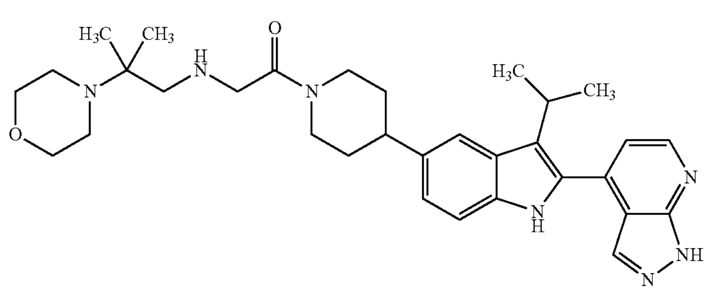 [SMILES: CC(C)c1c(-c2ccnc3[nH]ncc23)[nH]c2ccc(C3CCN(C(=O)CNCC(C)(C)N4CCOCC4)CC3)cc12] | 558.5 | 0.88 | F |

TABLE 17-continued

| Ex. No. | Structure | Obs. MS Ion | RT | HPLC Method |
|---|---|---|---|---|
| 581 | 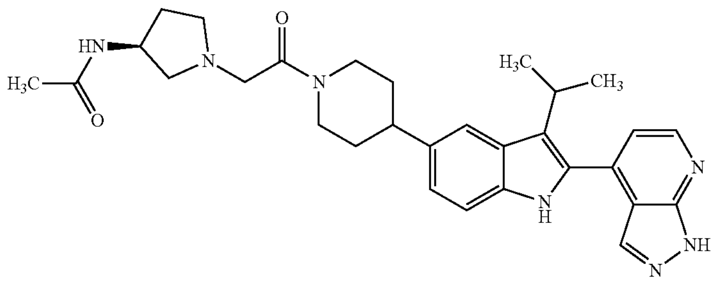 [SMILES: CC(=O)N[C@H]1CCN(CC(=O)N2CCC(c3ccc4[nH]c(-c5ccnc6[nH]ncc56)c(C(C)C)c4c3)CC2)C1] | 528.4 | 1.31 | E |
| 582 | 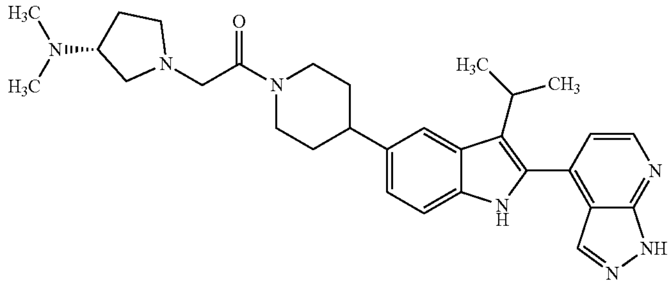 [SMILES: CC(C)c1c(-c2ccnc3[nH]ncc23)[nH]c2ccc(C3CCN(C(=O)CN4CC[C@@H](N(C)C)C4)CC3)cc12] | 514.4 | 0.91 | F |
| 583 | 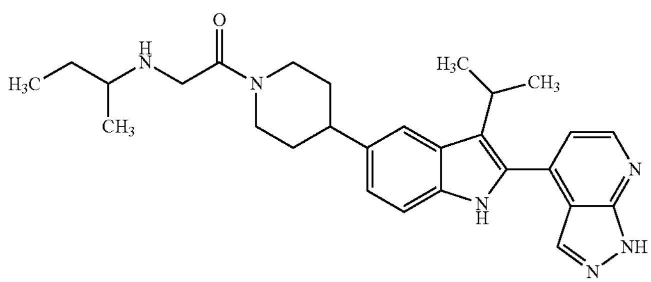 [SMILES: CCC(C)NCC(=O)N1CCC(c2ccc3[nH]c(-c4ccnc5[nH]ncc45)c(C(C)C)c3c2)CC1] | 473.4 | 1.16 | E |
| 584 | 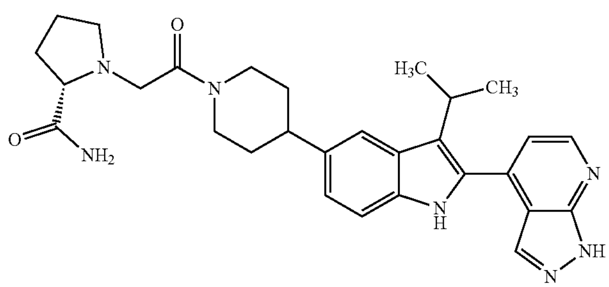 [SMILES: CC(C)c1c(-c2ccnc3[nH]ncc23)[nH]c2ccc(C3CCN(C(=O)CN4CCC[C@H]4C(N)=O)CC3)cc12] | 514.4 | 1.31 | E |
| 585 | 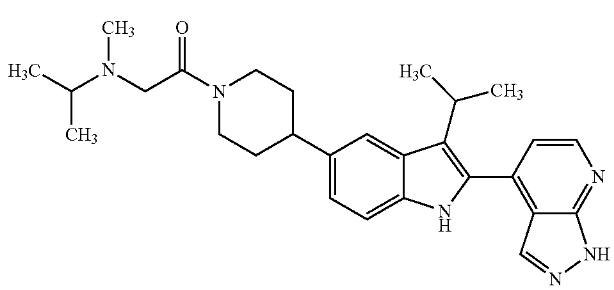 [SMILES: CC(C)c1c(-c2ccnc3[nH]ncc23)[nH]c2ccc(C3CCN(C(=O)CN(C)C(C)C)CC3)cc12] | 473.4 | 0.85 | F |

TABLE 17-continued
| Ex. No. | Structure | Obs. MS Ion | RT | HPLC Method |
|---|---|---|---|---|
| 586 | 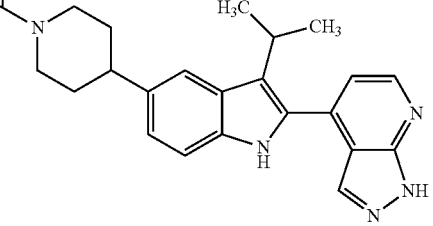 | 542.4 | 1.16 | E |
| 587 | 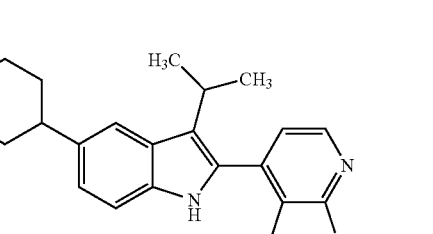 | 500.4 | 1.28 | E |
| 588 | 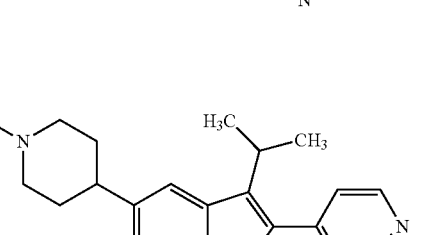 | 584.5 | 1.54 | E |
| 589 | 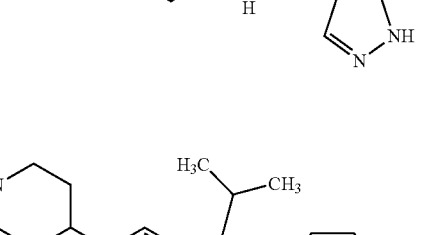 | 502.4 | 0.93 | F |
| 590 | 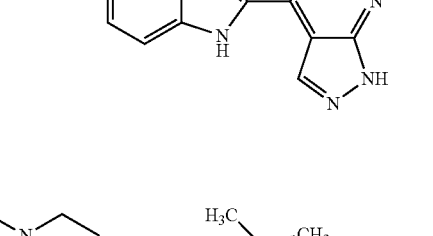 | 514.4 | 1.13 | E |

TABLE 17-continued

| Ex. No. | Structure | Obs. MS Ion | RT | HPLC Method |
|---|---|---|---|---|
| 591 | 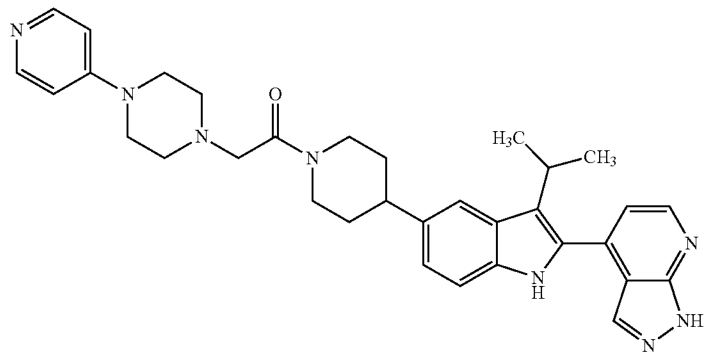 [SMILES: CC(C)c1c(-c2ccnc3[nH]ncc23)[nH]c2ccc(C3CCN(C(=O)CN4CCN(c5ccncc5)CC4)CC3)cc12] | 563.4 | 1.30 | E |

TABLE 18

| Ex. No. | Structure | Obs. MS Ion | RT | HPLC Method |
|---|---|---|---|---|
| 592 | 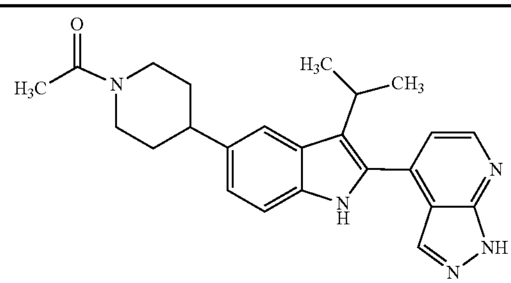 | 402.3 | 1.54 | QC-ACN-AA-XB |
| 593 | 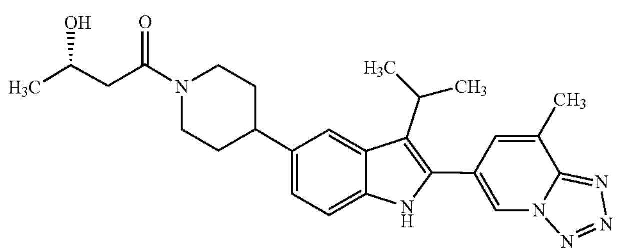 [SMILES: Cc1cc(-c2[nH]c3ccc(C4CCN(C(=O)C[C@H](C)O)CC4)cc3c2C(C)C)cn2nnnc12] | 461 | 2.22 | QC-ACN-AA-XB |
| 594 | 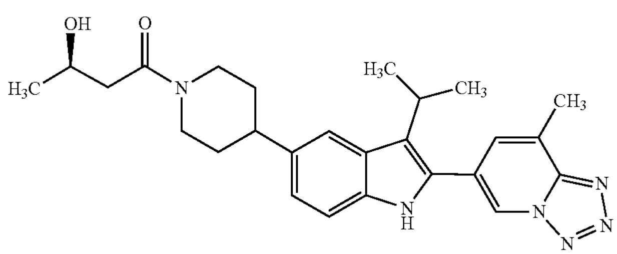 | 461 | 2.23 | QC-ACN-AA-XB |
| 595 | 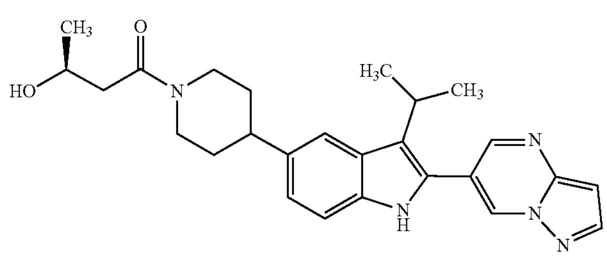 [SMILES: CC(C)c1c(-c2cnc3ccnn3c2)[nH]c2ccc(C3CCN(C(=O)C[C@H](C)O)CC3)cc12] | 446.0 | 1.83 | E |

TABLE 18-continued

| Ex. No. | Structure | Obs. MS Ion | RT | HPLC Method |
|---|---|---|---|---|
| 596 | 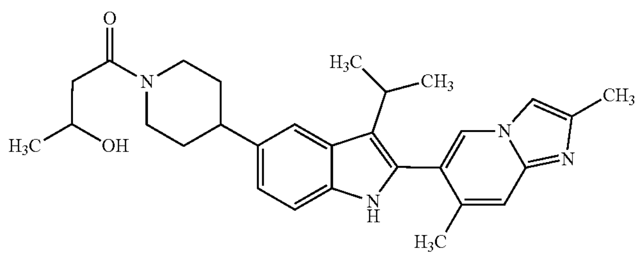 [SMILES: Cc1cn2cc(-c3[nH]c4ccc(C5CCN(C(=O)CC(C)O)CC5)cc4c3C(C)C)c(C)cc2n1] | 473.3 | 1.79 | E |
| 597 | 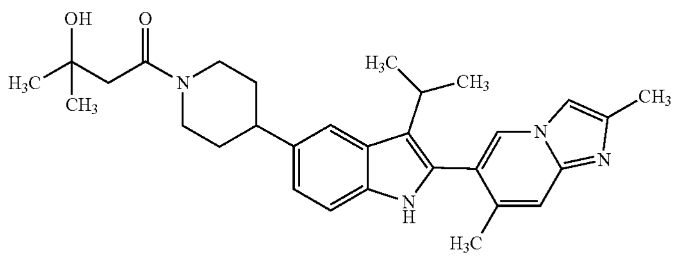 [SMILES: Cc1cn2cc(-c3[nH]c4ccc(C5CCN(C(=O)CC(C)(C)O)CC5)cc4c3C(C)C)c(C)cc2n1] | 487.3 | 1.94 | E |
| 598 | 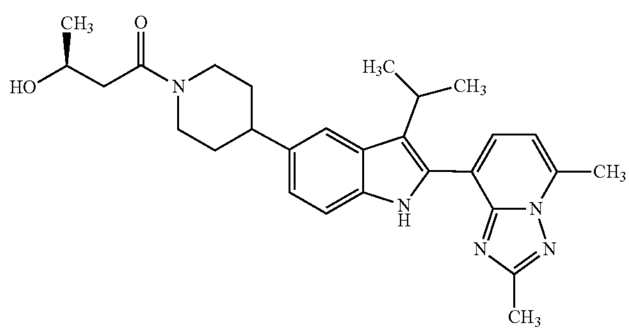 [SMILES: Cc1nc2c(-c3[nH]c4ccc(C5CCN(C(=O)C[C@H](C)O)CC5)cc4c3C(C)C)ccc(C)n2n1] | 474.3 | 1.78 | E |
| 599 | 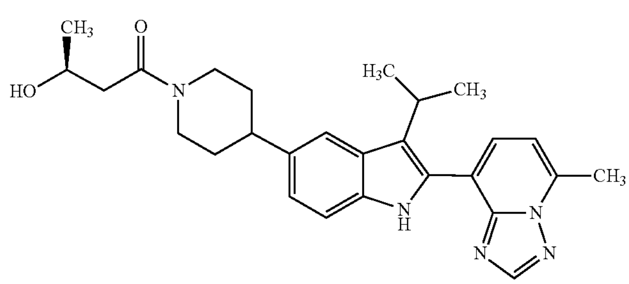 [SMILES: Cc1ccc(-c2[nH]c3ccc(C4CCN(C(=O)C[C@H](C)O)CC4)cc3c2C(C)C)c2ncnn12] | 460.3 | 1.84 | E |
| 600 | 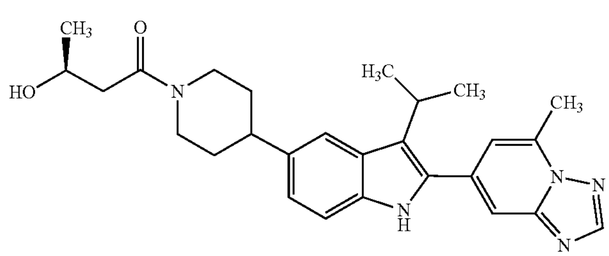 [SMILES: Cc1cc(-c2[nH]c3ccc(C4CCN(C(=O)C[C@H](C)O)CC4)cc3c2C(C)C)cc2ncnn12] | 460.3 | 1.74 | E |

TABLE 18-continued

| Ex. No. | Structure | Obs. MS Ion | RT | HPLC Method |
|---|---|---|---|---|
| 601 | 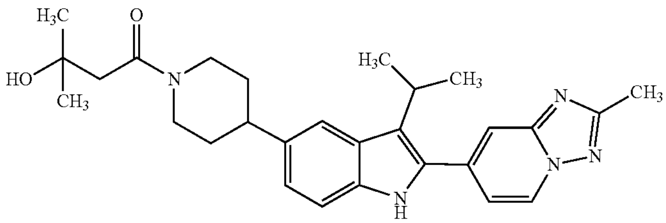 [SMILES: Cc1nc2cc(-c3[nH]c4ccc(C5CCN(C(=O)CC(C)(C)O)CC5)cc4c3C(C)C)ccn2n1] | 474.3 | 1.72 | F |
| 602 | 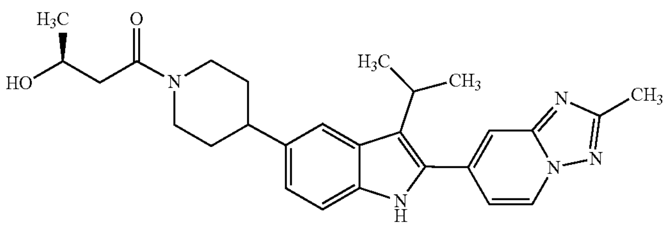 [SMILES: Cc1nc2cc(-c3[nH]c4ccc(C5CCN(C(=O)C[C@H](C)O)CC5)cc4c3C(C)C)ccn2n1] | 460.3 | 1.75 | E |
| 603 | 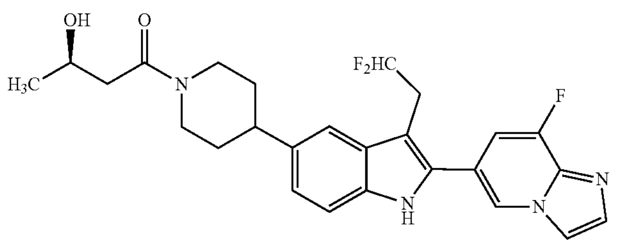 [SMILES: C[C@@H](O)CC(=O)N1CCC(c2ccc3[nH]c(-c4cc(F)c5nccn5c4)c(CC(F)F)c3c2)CC1] | 485.2 | 1.74 | E |
| 604 | 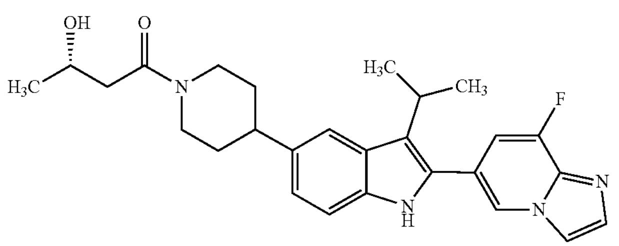 [SMILES: CC(C)c1c(-c2cc(F)c3nccn3c2)[nH]c2ccc(C3CCN(C(=O)C[C@H](C)O)CC3)cc12] | 463.2 | 1.73 | E |
| 605 | 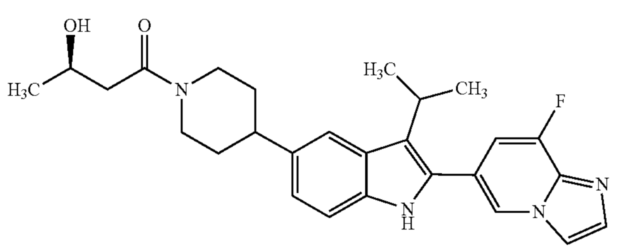 [SMILES: CC(C)c1c(-c2cc(F)c3nccn3c2)[nH]c2ccc(C3CCN(C(=O)C[C@@H](C)O)CC3)cc12] | 463.3 | 1.73 | E |
| 606 | 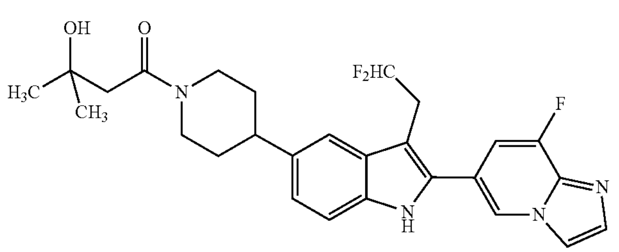 [SMILES: CC(C)(O)CC(=O)N1CCC(c2ccc3[nH]c(-c4cc(F)c5nccn5c4)c(CC(F)F)c3c2)CC1] | 499.3 | 1.89 | E |

TABLE 18-continued
| Ex. No. | Structure | Obs. MS Ion | RT | HPLC Method |
|---|---|---|---|---|
| 607 | 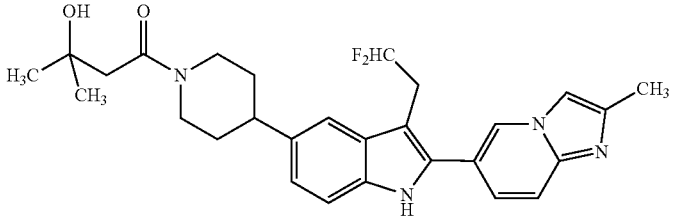 [SMILES: Cc1cn2cc(-c3[nH]c4ccc(C5CCN(C(=O)CC(C)(C)O)CC5)cc4c3CC(F)F)ccc2n1] | 495.3 | 1.66 | E |
| 608 | 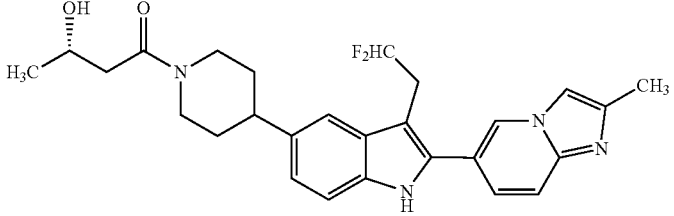 [SMILES: Cc1cn2cc(-c3[nH]c4ccc(C5CCN(C(=O)C[C@H](C)O)CC5)cc4c3CC(F)F)ccc2n1] | 481.3 | 1.51 | E |
| 609 | 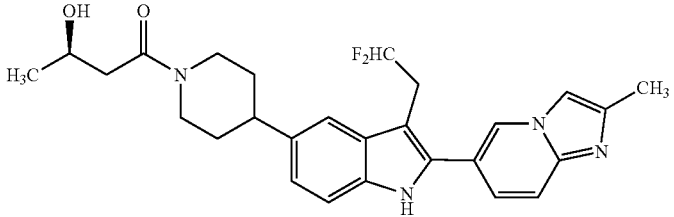 [SMILES: Cc1cn2cc(-c3[nH]c4ccc(C5CCN(C(=O)C[C@@H](C)O)CC5)cc4c3CC(F)F)ccc2n1] | 481.3 | 1.50 | E |
| 610 | 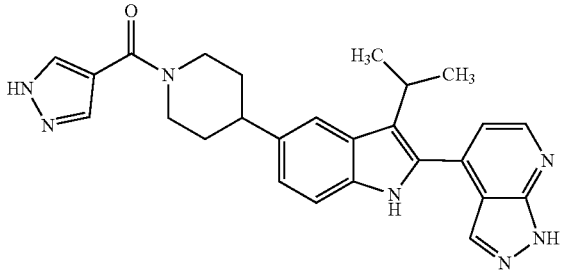 [SMILES: CC(C)c1c(-c2ccnc3[nH]ncc23)[nH]c2ccc(C3CCN(C(=O)c4cn[nH]c4)CC3)cc12] | 454.3 | 1.26 | F |
| 611 | 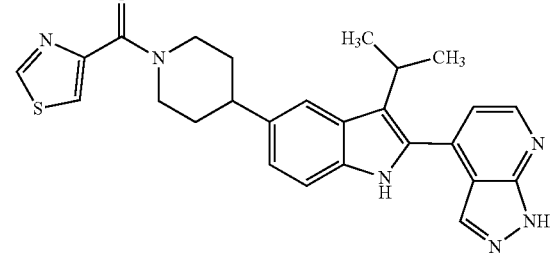 | 471.3 | 1.46 | F |
| 612 | 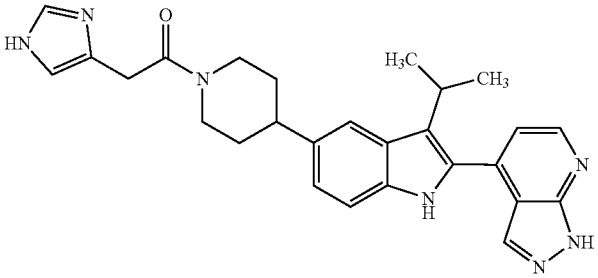 [SMILES: CC(C)c1c(-c2ccnc3[nH]ncc23)[nH]c2ccc(C3CCN(C(=O)Cc4c[nH]cn4)CC3)cc12] | 468.3 | 1.07 | F |

TABLE 18-continued

| Ex. No. | Structure | Obs. MS Ion | RT | HPLC Method |
|---|---|---|---|---|
| 613 | 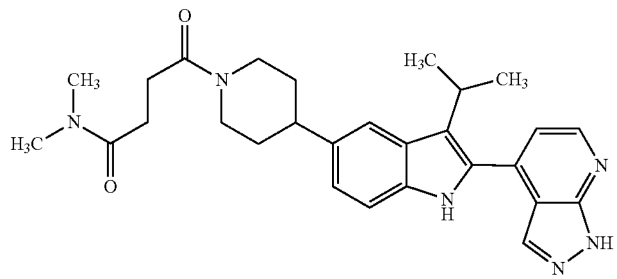 [SMILES: CC(C)c1c(-c2ccnc3[nH]ncc23)[nH]c2ccc(C3CCN(C(=O)CCC(=O)N(C)C)CC3)cc12] | 487.4 | 1.41 | E |
| 614 | 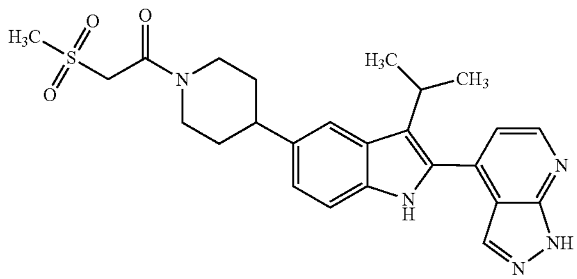 [SMILES: CC(C)c1c(-c2ccnc3[nH]ncc23)[nH]c2ccc(C3CCN(C(=O)CS(C)(=O)=O)CC3)cc12] | 480.3 | 1.38 | E |
| 615 | 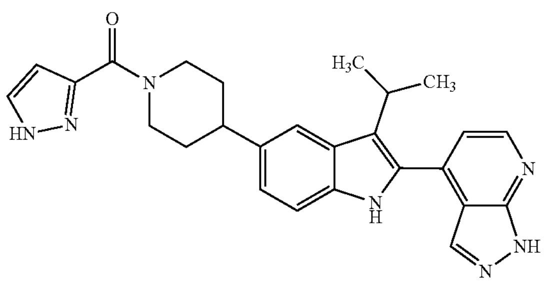 [SMILES: CC(C)c1c(-c2ccnc3[nH]ncc23)[nH]c2ccc(C3CCN(C(=O)c4cc[nH]n4)CC3)cc12] | 454.3 | 1.38 | E |
| 616 | 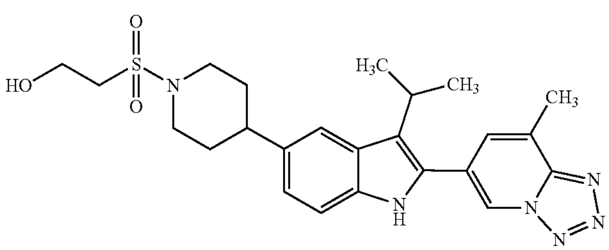 [SMILES: Cc1cc(-c2[nH]c3ccc(C4CCN(S(=O)(=O)CCO)CC4)cc3c2C(C)C)cn2nnnc12] | 483 | 1.25 | QC-ACN-AA-XB |
| 617 | 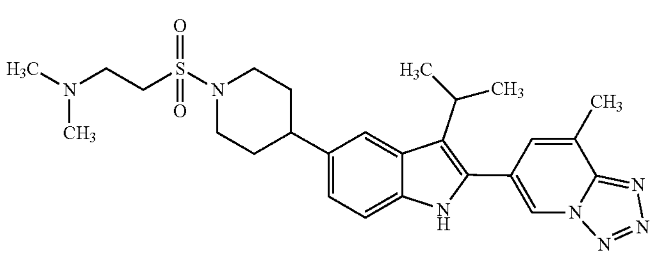 [SMILES: Cc1cc(-c2[nH]c3ccc(C4CCN(S(=O)(=O)CCN(C)C)CC4)cc3c2C(C)C)cn2nnnc12] | 510.3 | 1.94 | QC-ACN-AA-XB |

Example 618

1-(4-(3-isopropyl-2-(8-methyltetrazolo[1,5-a]pyridin-6-yl)-1H-indol-5-yl)piperidin-1-yl)-3-(pyrrolidin-1-yl)propan-1-one (618)

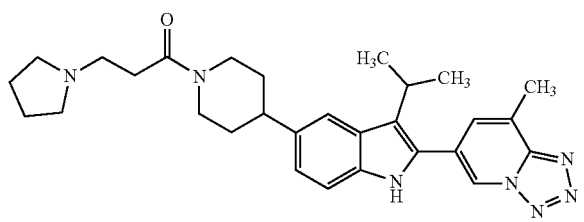

1-(4-(3-isopropyl-2-(8-methyltetrazolo[1,5-a]pyridin-6-yl)-1H-indol-5-yl)piperidin-1-yl)prop-2-en-1-one (21.43 mg, 0.050 mmol) was dissolved in DMF (1 mL). TEA (0.035 mL, 0.250 mmol) and pyrrolidine (3.56 mg, 0.050 mmol) were added sequentially, and the reaction mixture was stirred at 80° C. for 90 minutes. The reaction mixture was cooled to room temperature and diluted with a few drops of water and DMF. The crude product was purified via preparative HPLC. The fractions containing the desired product were combined and dried via centrifugal evaporation to give 1-(4-(3-isopropyl-2-(8-methyltetrazolo[1,5-a]pyridin-6-yl)-1H-indol-5-yl)piperidin-1-yl)-3-(pyrrolidin-1-yl)propan-1-one (7.7 mg, 0.015 mmol, 30.8% yield). HPLC Ret. Time 1.445 min. MS (M+1) m/z: 500.0, Method C1. $^1$H NMR (500 MHz, DMSO-$d_6$) δ 11.22 (s, 1H), 9.13 (s, 1H), 7.76 (s, 1H), 7.58 (s, 1H), 7.33 (d, J=8.2 Hz, 1H), 7.10-6.92 (m, 1H), 4.65-4.50 (m, 1H), 4.10-3.96 (m, 1H), 3.56-3.31 (m, 4H), 2.89 (s, 2H), 2.78-2.60 (m, 8H), 1.95-1.78 (m, 3H), 1.69 (br s, 5H), 1.44 (br d, J=7.0 Hz, 7H).

TABLE 19

| Ex. No. | Structure | Obs. MS Ion | RT | HPLC Method |
|---|---|---|---|---|
| 619 | 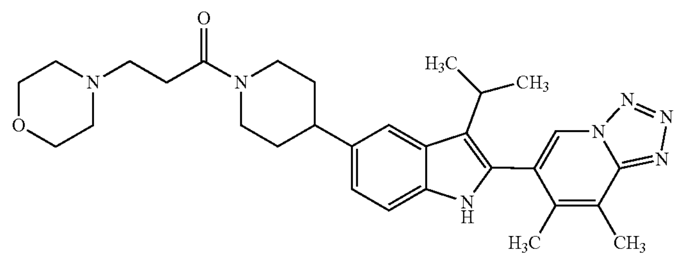 [SMILES: Cc1c(-c2[nH]c3ccc(C4CCN(C(=O)CCN5CCOCC5)CC4)cc3c2C(C)C)cn2nnnc2c1C] | 530.4 | 1.4 | QC-ACN-TFA-XB |
| 620 | 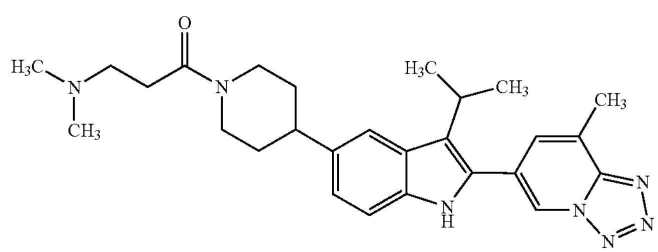 [SMILES: Cc1cc(-c2[nH]c3ccc(C4CCN(C(=O)CCN(C)C)CC4)cc3c2C(C)C)cn2nnnc12] | 474.4 | 1.5 | QC-ACN-TFA-XB |
| 621 | 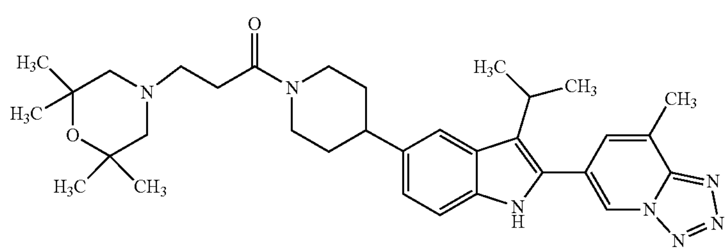 [SMILES: Cc1cc(-c2[nH]c3ccc(C4CCN(C(=O)CCN5CC(C)(C)OC(C)(C)C5)CC4)cc3c2C(C)C)cn2nnnc12] | 572.0 | 1.82 | QC-ACN-TFA-XB |
| 622 | 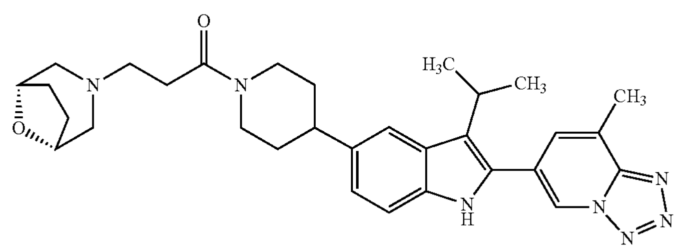 [SMILES: Cc1cc(-c2[nH]c3ccc(C4CCN(C(=O)CCN5C[C@H]6CC[C@@H](C5)O6)CC4)cc3c2C(C)C)cn2nnnc12] | 542.4 | 1.85 | QC-ACN-AA-XB |

TABLE 19-continued

| Ex. No. | Structure | Obs. MS Ion | RT | HPLC Method |
|---|---|---|---|---|
| 623 | 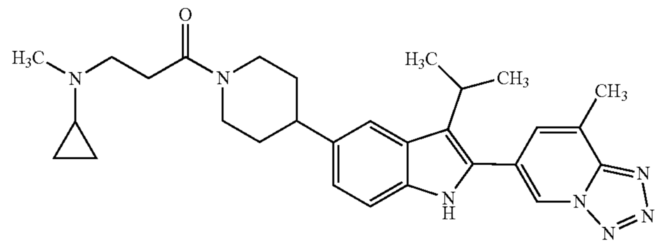 [SMILES: Cc1cc(-c2[nH]c3ccc(C4CCN(C(=O)CCN(C)C5CC5)CC4)cc3c2C(C)C)cn2nnnc12] | 500.1 | 1.45 | QC-ACN-TFA-XB |
| 624 | 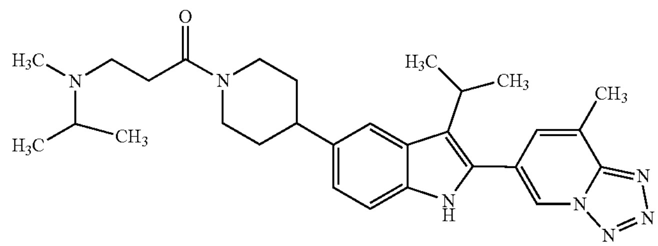 [SMILES: Cc1cc(-c2[nH]c3ccc(C4CCN(C(=O)CCN(C)C(C)C)CC4)cc3c2C(C)C)cn2nnnc12] | 502.3 | 1.53 | QC-ACN-AA-XB |
| 625 | 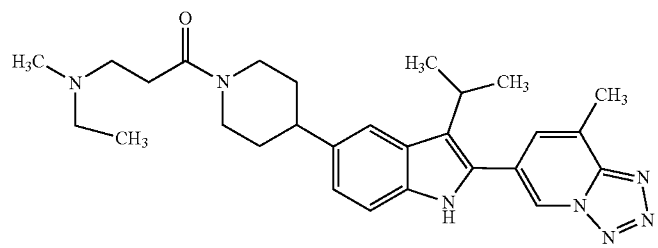 [SMILES: CCN(C)CCC(=O)N1CCC(c2ccc3[nH]c(-c4cc(C)c5nnnn5c4)c(C(C)C)c3c2)CC1] | 488.5 | 1.47 | QC-ACN-AA-XB |
| 626 | 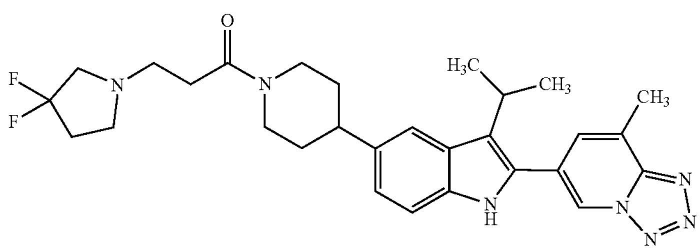 [SMILES: Cc1cc(-c2[nH]c3ccc(C4CCN(C(=O)CCN5CCC(F)(F)C5)CC4)cc3c2C(C)C)cn2nnnc12] | 536.2 | 1.93 | QC-ACN-AA-XB |
| 627 | 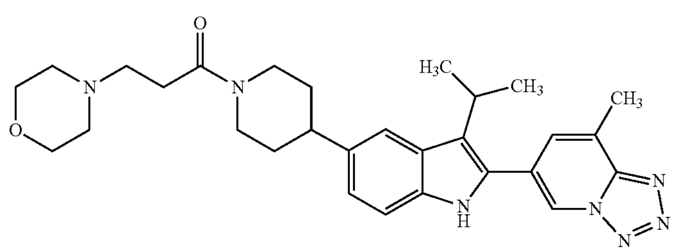 [SMILES: Cc1cc(-c2[nH]c3ccc(C4CCN(C(=O)CCN5CCOCC5)CC4)cc3c2C(C)C)cn2nnnc12] | 516.5 | 1.69 | QC-ACN-AA-XB |
| 628 | 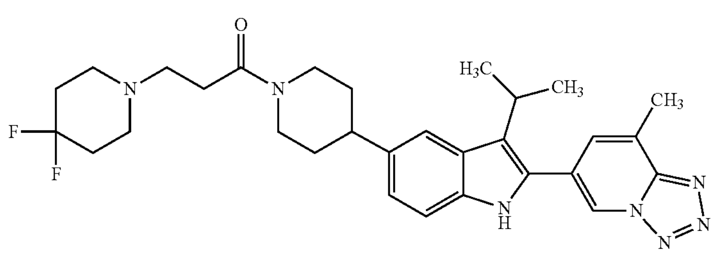 [SMILES: Cc1cc(-c2[nH]c3ccc(C4CCN(C(=O)CCN5CCC(F)(F)CC5)CC4)cc3c2C(C)C)cn2nnnc12] | 550.2 | 1.95 | QC-ACN-AA-XB |

TABLE 19-continued
| Ex. No. | Structure | Obs. MS Ion | RT | HPLC Method |
|---|---|---|---|---|
| 629 | 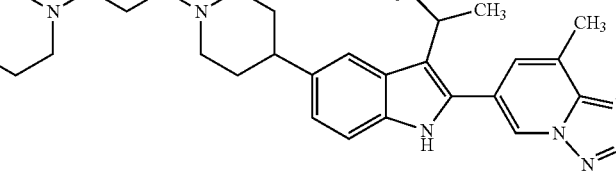 | 514 | 1.72 | QC-ACN-AA-XB |
| 631 | 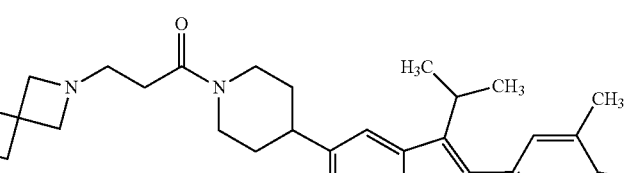 | 528.4 | 1.48 | QC-ACN-AA-XB |
| 632 | 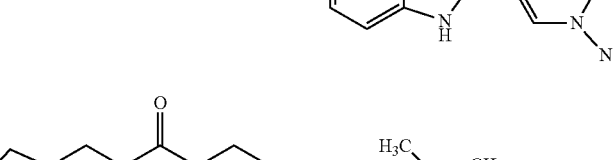 | 512.4 | 1.48 | QC-ACN-AA-XB |
| 633 | 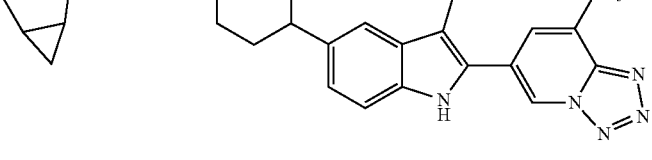 | 532.4 | 1.57 | QC-ACN-TFA-XB |
| 634 | 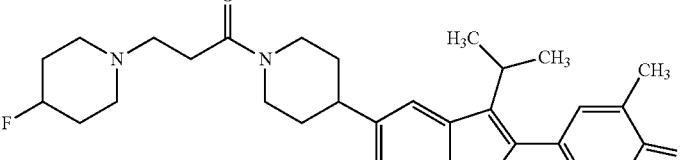 | 564 | 1.58 | QC-ACN-AA-XB |
| 635 | 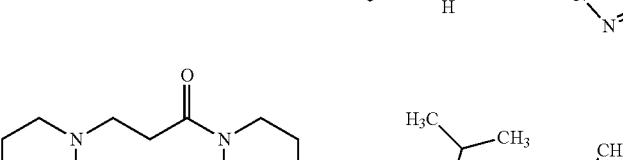 | 542.2 | 1.51 | QC-ACN-TFA-XB |

TABLE 19-continued

| Ex. No. | Structure | Obs. MS Ion | RT | HPLC Method |
|---|---|---|---|---|
| 636 | 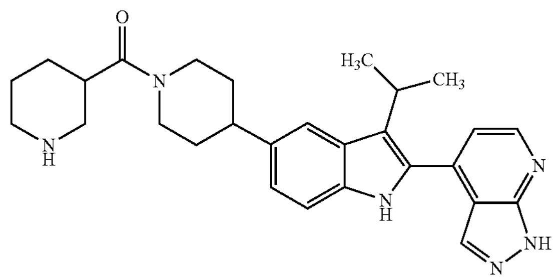 [SMILES: CC(C)c1c(-c2ccnc3[nH]ncc23)[nH]c2ccc(C3CCN(C(=O)C4CCCNC4)CC3)cc12] | 471.4 | 1.11 | QC-ACN-AA-XB |
| 637 | 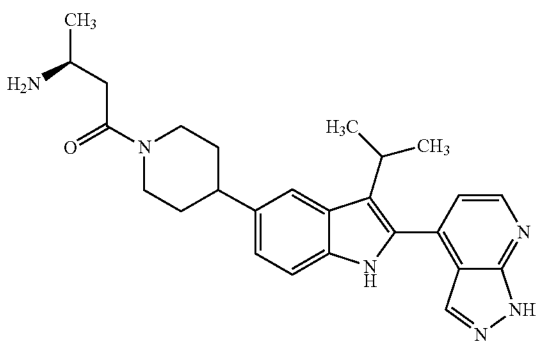 [SMILES: CC(C)c1c(-c2ccnc3[nH]ncc23)[nH]c2ccc(C3CCN(C(=O)C[C@H](C)N)CC3)cc12] | 445.0 | 1.10 | E |
| 638 | 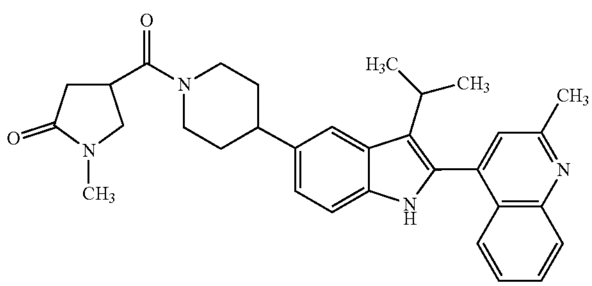 [SMILES: Cc1cc(-c2[nH]c3ccc(C4CCN(C(=O)C5CC(=O)N(C)C5)CC4)cc3c2C(C)C)c2ccccc2n1] | 509.3 | 1.96 | E |
| 639 | 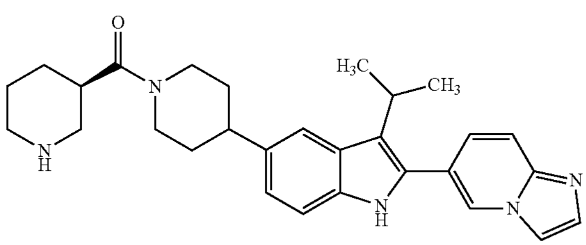 [SMILES: CC(C)c1c(-c2ccc3nccn3c2)[nH]c2ccc(C3CCN(C(=O)[C@@H]4CCCNC4)CC3)cc12] | 470.3 | 1.51 | E |
| 640 | 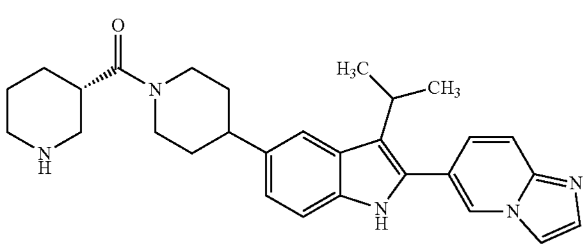 [SMILES: CC(C)c1c(-c2ccc3nccn3c2)[nH]c2ccc(C3CCN(C(=O)[C@H]4CCCNC4)CC3)cc12] | 470.3 | 1.41 | F |

TABLE 19-continued

| Ex. No. | Structure | Obs. MS Ion | RT | HPLC Method |
|---|---|---|---|---|
| 641 | 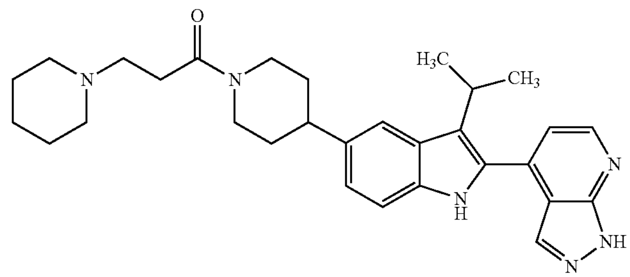 [SMILES: CC(C)c1c(-c2ccnc3[nH]ncc23)[nH]c2ccc(C3CCN(C(=O)CCN4CCCCC4)CC3)cc12] | 499.4 | 1.19 | F |
| 642 | 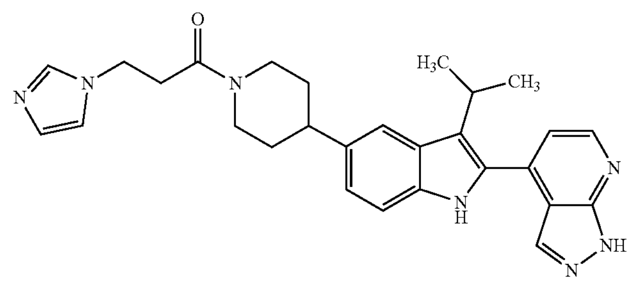 [SMILES: CC(C)c1c(-c2ccnc3[nH]ncc23)[nH]c2ccc(C3CCN(C(=O)CCn4ccnc4)CC3)cc12] | 482.4 | 1.37 | E |
| 643 | 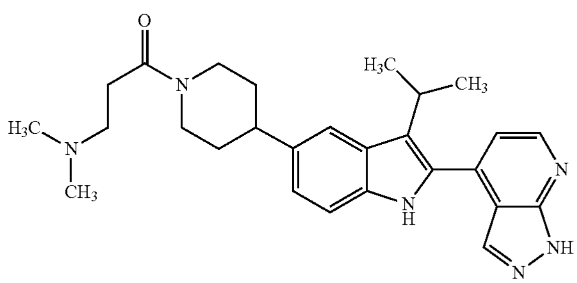 [SMILES: CC(C)c1c(-c2ccnc3[nH]ncc23)[nH]c2ccc(C3CCN(C(=O)CCN(C)C)CC3)cc12] | 459.4 | 1.16 | E |
| 644 | 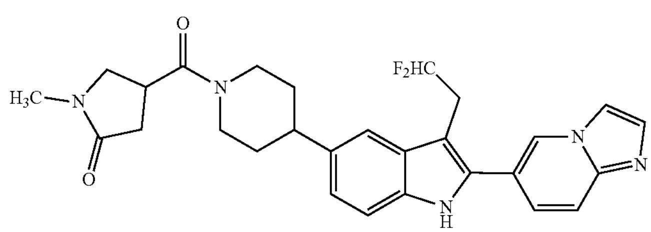 [SMILES: CN1CC(C(=O)N2CCC(c3ccc4[nH]c(-c5ccc6nccn6c5)c(CC(F)F)c4c3)CC2)CC1=O] | 506.2 | 1.53 | E |
| 645 | 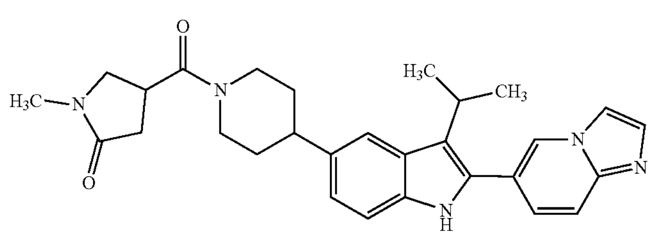 [SMILES: CC(C)c1c(-c2ccc3nccn3c2)[nH]c2ccc(C3CCN(C(=O)C4CC(=O)N(C)C4)CC3)cc12] | 484.3 | 1.66 | E |

TABLE 19-continued

| Ex. No. | Structure | Obs. MS Ion | RT | HPLC Method |
|---|---|---|---|---|
| 646 | 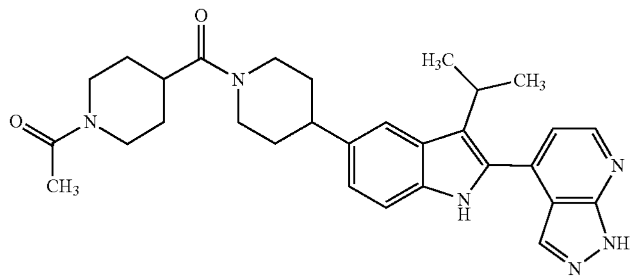 [SMILES: CC(=O)N1CCC(C(=O)N2CCC(c3ccc4[nH]c(-c5ccnc6[nH]ncc56)c(C(C)C)c4c3)CC2)CC1] | 513.4 | 1.43 | E |
| 647 | 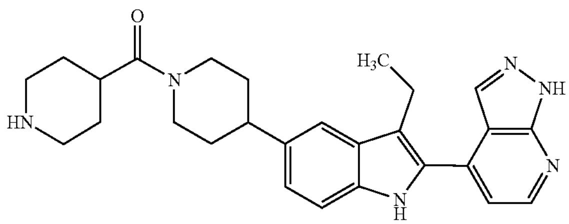 [SMILES: CCc1c(-c2ccnc3[nH]ncc23)[nH]c2ccc(C3CCN(C(=O)C4CCNCC4)CC3)cc12] | 457.2 | 0.96 | QC-ACN-TFA-XB |
| 648 | 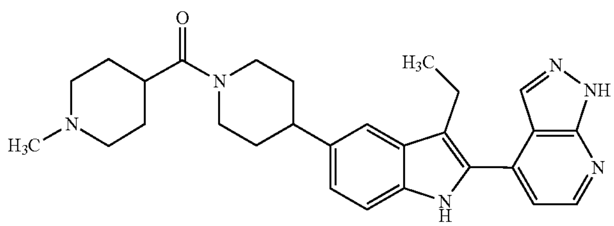 [SMILES: CCc1c(-c2ccnc3[nH]ncc23)[nH]c2ccc(C3CCN(C(=O)C4CCN(C)CC4)CC3)cc12] | 471.4 | 1.07 | QC-ACN-AA-XB |
| 649 | 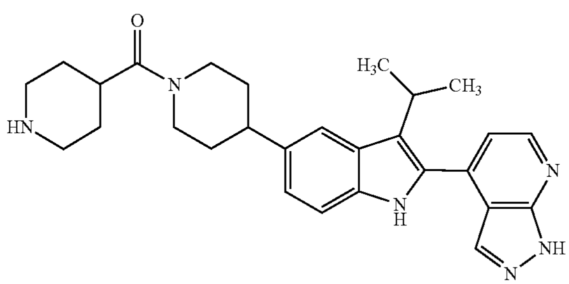 [SMILES: CC(C)c1c(-c2ccnc3[nH]ncc23)[nH]c2ccc(C3CCN(C(=O)C4CCNCC4)CC3)cc12] | 471.3 | 1.09 | QC-ACN-AA-XB |

Example 650

2-(4-(3-isopropyl-2-(1H-pyrazolo[3,4-b]pyridin-4-yl)-1H-indol-5-yl)piperidin-1-yl)-N-methyl-ethanamine dihydrochloride (650)

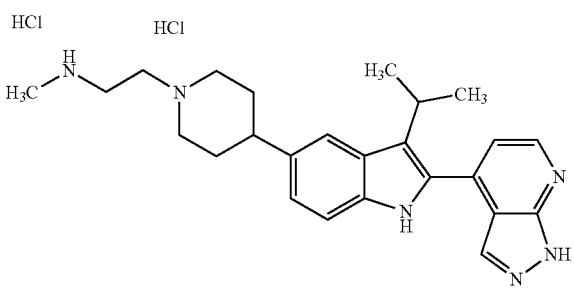

In a 2 dram vial was added 4-(3-isopropyl-5-(piperidin-4-yl)-1H-indol-2-yl)-1H-pyrazolo[3,4-b]pyridine hydrochloride (0.150 g, 0.379 mmol), DCM (1 mL), TEA (0.528 mL, 3.79 mmol), tert-butyl methyl(2-oxoethyl)carbamate (0.098 g, 0.568 mmol) and 1 drop of acetic acid. After 5 minutes, sodium triacetoxyborohydride (0.321 g, 1.515 mmol) was added and the reaction mixture was stirred at room temperature for 1 hour. To this was added water and DCM. The mixture was poured into a separatory funnel and the layers were separated. The organics were washed with saturated NaCl solution, dried over anhydrous sodium sulfate, filtered and concentrated. The material was purified by silica gel chromatography, eluting with 0-20% MeOH/DCM-1% TEA. Following concentrations of the fractions, the protected intermediate was collected as a tan oil. This was diluted with 0.5 mL of DCM and treated with 4 M HCl/dioxane. The reaction mixture was capped and stirred for 1 hour at room temperature. The volatiles were removed and the residue was triturated with diethylether, filtered and washed with diethylether to give 2-(4-(3-isopropyl-2-(1H- pyrazolo[3,4-b]pyridin-4-yl)-1H-indol-5-yl)piperidin-1-yl)-N-methylethanamine dihydrochloride (85.0 mg, 0.192 mmol, 45% yield). MS (M+1) m/z: 417.3 (MH+). LC retention time 0.620 min [B1]. $^1$H NMR (400 MHz, DMSO-d$_6$) δ 10.32-10.21 (m, 1H), 9.52-9.28 (m, 2H), 8.61 (d, J=4.6 Hz, 1H), 8.14 (s, 1H), 7.67 (s, 1H), 7.43 (d, J=8.4 Hz, 1H), 7.22 (d, J=4.8 Hz, 1H), 7.08 (dd, J=8.4, 1.3 Hz, 1H), 3.72 (br s, 2H), 3.48 (br s, 4H), 3.44-3.33 (m, 2H), 3.26-3.14 (m, 3H), 2.65 (s, 4H), 2.29-2.16 (m, 2H), 2.15-2.00 (m, 2H), 1.45 (d, J=7.0 Hz, 6H).

TABLE 20

| Ex. No. | Structure | Obs. MS Ion | RT | HPLC Method |
|---|---|---|---|---|
| 651 | 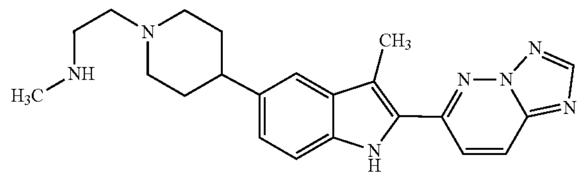 [SMILES: CNCCN1CCC(c2ccc3[nH]c(-c4ccc5ncnn5n4)c(C)c3c2)CC1] | 390.3 | 0.73 | QC-ACN-TFA-XB |
| 652 | 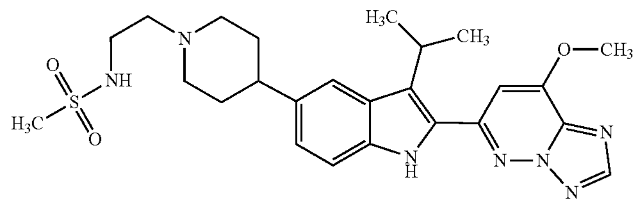 [SMILES: COc1cc(-c2[nH]c3ccc(C4CCN(CCNS(C)(=O)=O)CC4)cc3c2C(C)C)nn2ncnc12] | 512.1 | 1.31 | QC-ACN-AA-XB |
| 653 | 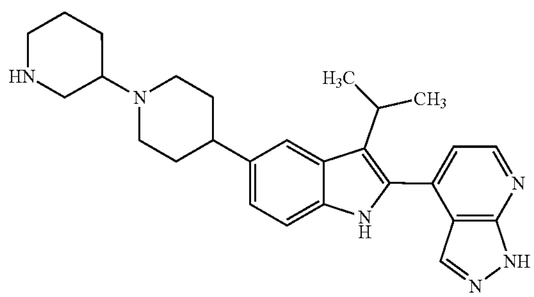 [SMILES: CC(C)c1c(-c2ccnc3[nH]ncc23)[nH]c2ccc(C3CCN(C4CCCNC4)CC3)cc12] | 443.3 | 1.03 | QC-ACN-TFA-XB |
| 654 | 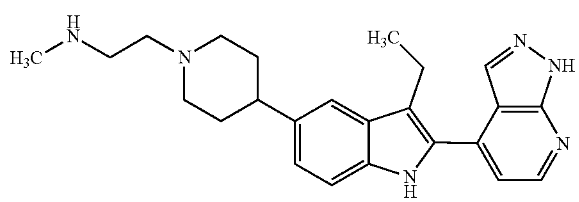 [SMILES: CCc1c(-c2ccnc3[nH]ncc23)[nH]c2ccc(C3CCN(CCNC)CC3)cc12] | 403.3 | 1.32 | QC-ACN-AA-XB |
| 655 | 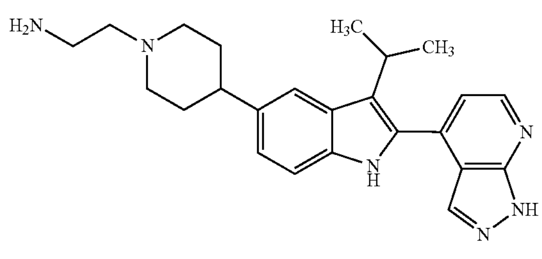 [SMILES: CC(C)c1c(-c2ccnc3[nH]ncc23)[nH]c2ccc(C3CCN(CCN)CC3)cc12] | 403.2 | 0.68 | QC-ACN-TFA-XB |
| 656 | 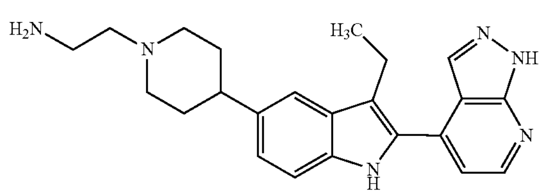 [SMILES: CCc1c(-c2ccnc3[nH]ncc23)[nH]c2ccc(C3CCN(CCN)CC3)cc12] | 389.2 | 0.85 | QC-ACN-AA-XB |

TABLE 20-continued

| Ex. No. | Structure | Obs. MS Ion | RT | HPLC Method |
|---|---|---|---|---|
| 657 | 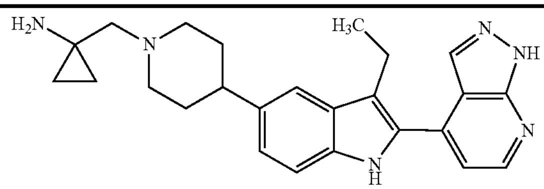 | 415.2 | 1.25 | QC-ACN-AA-XB |
| 658 | 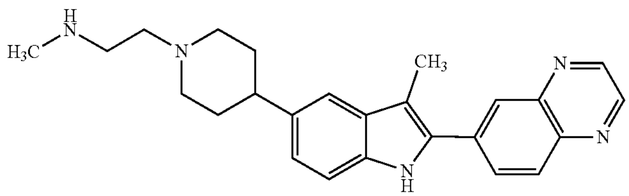 [SMILES: CNCCN1CCC(c2ccc3[nH]c(-c4ccc5nccnc5c4)c(C)c3c2)CC1] | 400.3 | 1.28 | QC-ACN-AA-XB |
| 659 | 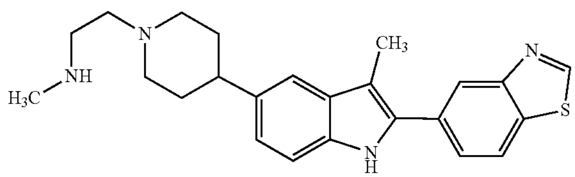 [SMILES: CNCCN1CCC(c2ccc3[nH]c(-c4ccc5scnc5c4)c(C)c3c2)CC1] | 405.1 | 1.18 | QC-ACN-TFA-XB |
| 660 | 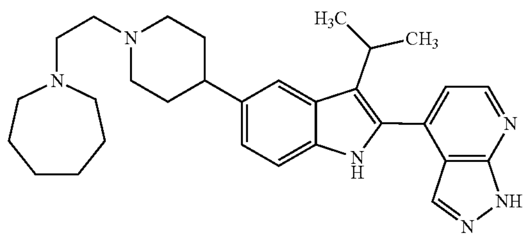 [SMILES: CC(C)c1c(-c2ccnc3[nH]ncc23)[nH]c2ccc(C3CCN(CCN4CCCCCC4)CC3)cc12] | 485.3 | 1.55 | QC-ACN-AA-XB |
| 661 | 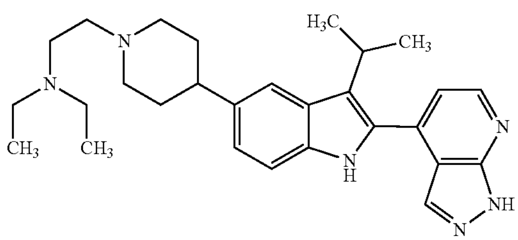 [SMILES: CCN(CC)CCN1CCC(c2ccc3[nH]c(-c4ccnc5[nH]ncc45)c(C(C)C)c3c2)CC1] | 459.3 | 1.4 | QC-ACN-AA-XB |
| 662 | 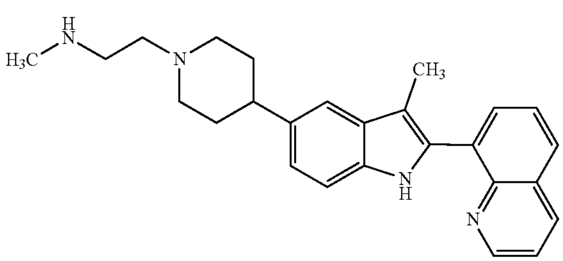 [SMILES: CNCCN1CCC(c2ccc3[nH]c(-c4cccc5cccnc45)c(C)c3c2)CC1] | 399.4 | 0.84 | QC-ACN-TFA-XB |
| 663 | 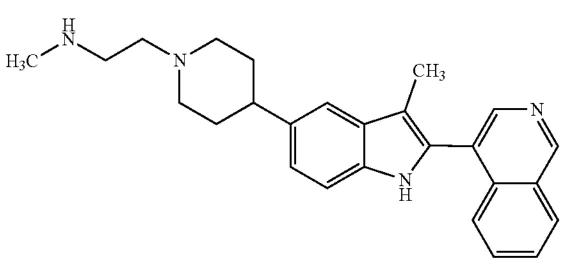 [SMILES: CNCCN1CCC(c2ccc3[nH]c(-c4cncc5ccccc45)c(C)c3c2)CC1] | 399.4 | 0.65 | QC-ACN-TFA-XB |

TABLE 20-continued
| Ex. No. | Structure | Obs. MS Ion | RT | HPLC Method |
|---|---|---|---|---|
| 664 | 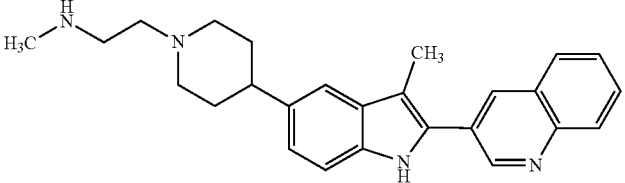 [SMILES: CNCCN1CCC(c2ccc3[nH]c(-c4cnc5ccccc5c4)c(C)c3c2)CC1] | 399.3 | 1.45 | QC-ACN-AA-XB |
| 665 | 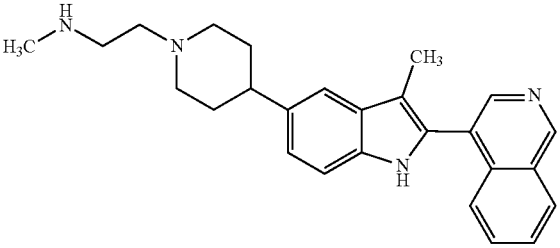 [SMILES: CNCCN1CCC(c2ccc3[nH]c(-c4cncc5ccccc45)c(C)c3c2)CC1] | 399.3 | 0.68 | QC-ACN-TFA-XB |
| 666 | 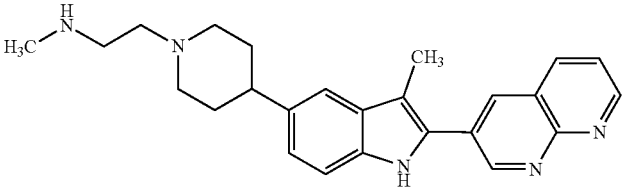 [SMILES: CNCCN1CCC(c2ccc3[nH]c(-c4cnc5ncccc5c4)c(C)c3c2)CC1] | 399.3 | 1.36 | QC-ACN-AA-XB |
| 667 | 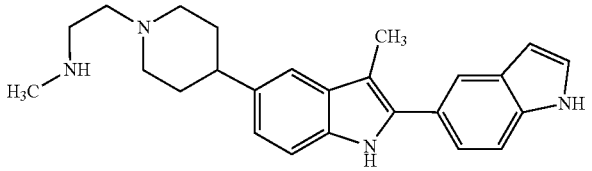 [SMILES: CNCCN1CCC(c2ccc3[nH]c(-c4ccc5[nH]ccc5c4)c(C)c3c2)CC1] | 387.4 | 1.39 | FC-ACN-AA-XB |
| 668 | 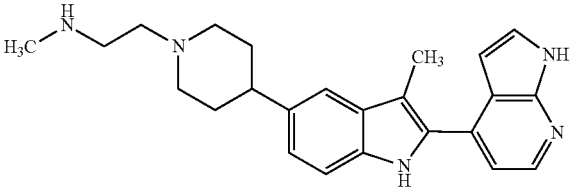 [SMILES: CNCCN1CCC(c2ccc3[nH]c(-c4ccnc5[nH]ccc45)c(C)c3c2)CC1] | 388.3 | 1.1 | QC-ACN-AA-XB |
| 669 | 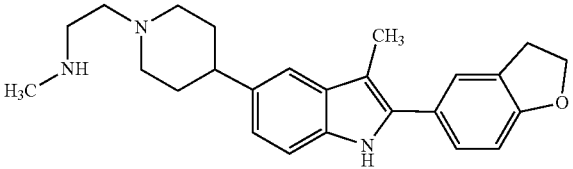 [SMILES: CNCCN1CCC(c2ccc3[nH]c(-c4ccc5c(c4)CCO5)c(C)c3c2)CC1] | 390.4 | 1.56 | QC-ACN-AA-XB |
| 670 | 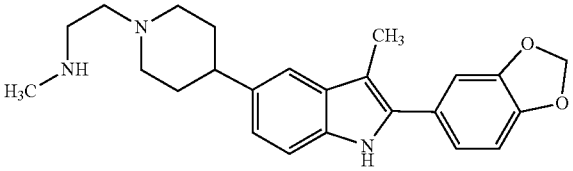 [SMILES: CNCCN1CCC(c2ccc3[nH]c(-c4ccc5c(c4)OCO5)c(C)c3c2)CC1] | 392.2 | 1.24 | QC-ACN-TFA-XB |

TABLE 20-continued
| Ex. No. | Structure | Obs. MS Ion | RT | HPLC Method |
|---|---|---|---|---|
| 671 | 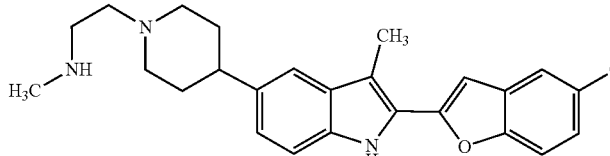 | 418.2 | 1.78 | QC-ACN-AA-XB |
| 672 | 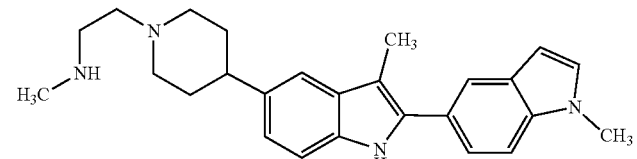 | 401.4 | 1.63 | QC-ACN-AA-XB |
| 673 | 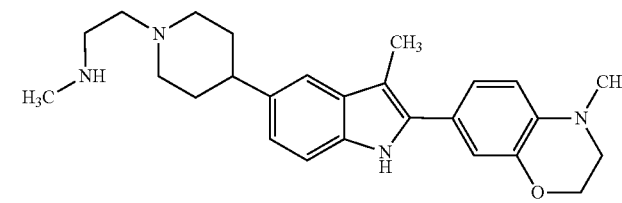 | 419.4 | 1.14 | QC-ACN-TFA-XB |
| 674 | 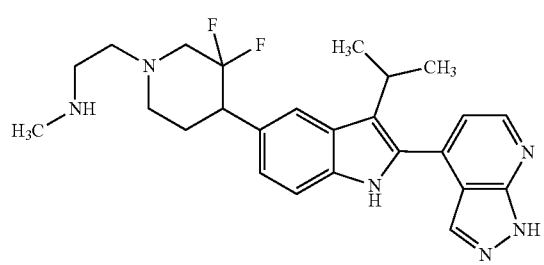 [SMILES: CNCCN1CCC(c2ccc3[nH]c(-c4ccnc5[nH]ncc45)c(C(C)C)c3c2)C(F)(F)C1] | 453.2 | 1.39 | E |
| 675 | 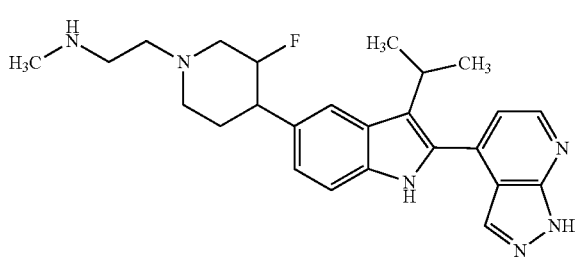 [SMILES: CNCCN1CCC(c2ccc3[nH]c(-c4ccnc5[nH]ncc45)c(C(C)C)c3c2)C(F)C1] | 435.2 | 1.72 | H |
| 676 | 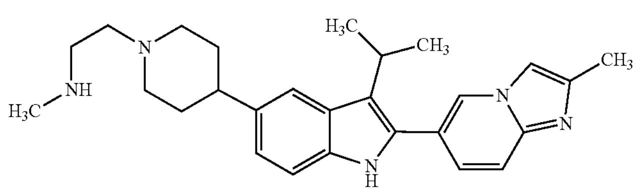 | 430.3 | 1.57 | E |
| 677 | 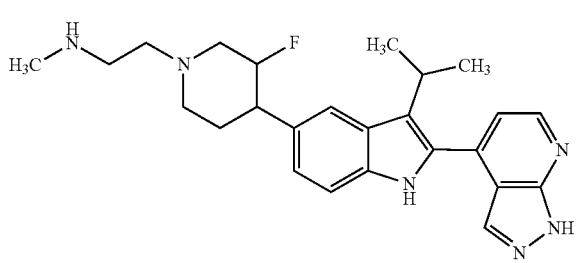 [SMILES: CNCCN1CCC(c2ccc3[nH]c(-c4ccnc5[nH]ncc45)c(C(C)C)c3c2)C(F)C1] | 435.4 | 1.87 | H |

TABLE 20-continued

| Ex. No. | Structure | Obs. MS Ion | RT | HPLC Method |
|---|---|---|---|---|
| 678 | 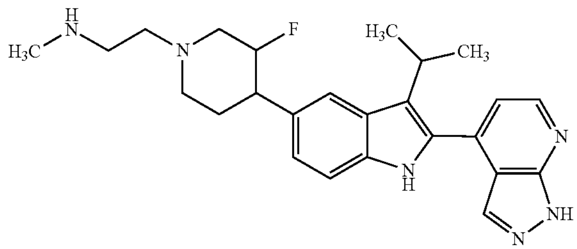 [SMILES: CNCCN1CCC(c2ccc3[nH]c(-c4ccnc5[nH]ncc45)c(C(C)C)c3c2)C(F)C1] | 435.4 | 1.72 | H |
| 679 | 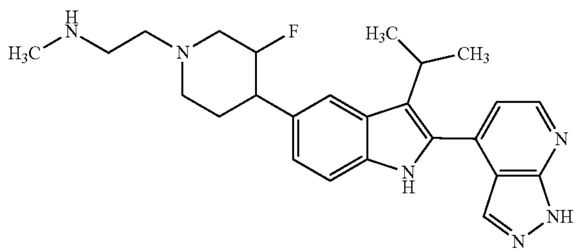 [SMILES: CNCCN1CCC(c2ccc3[nH]c(-c4ccnc5[nH]ncc45)c(C(C)C)c3c2)C(F)C1] | 435.4 | 1.72 | H |
| 680 | 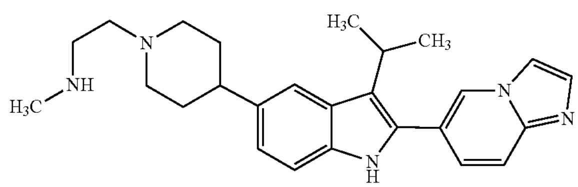 [SMILES: CNCCN1CCC(c2ccc3[nH]c(-c4ccc5nccn5c4)c(C(C)C)c3c2)CC1] | 416.2 | 1.56 | E |
| 681 | 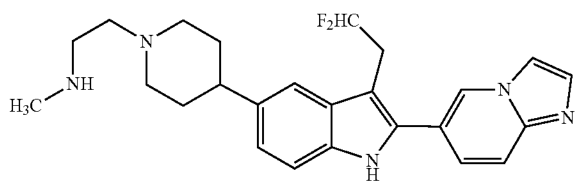 [SMILES: CNCCN1CCC(c2ccc3[nH]c(-c4ccc5nccn5c4)c(CC(F)F)c3c2)CC1] | 438.2 | 1.40 | E |

Example 682

4-(3-isopropyl-5-(1-(tetrahydro-2H-pyran-4-yl)piperidin-4-yl)-1H-indol-2-yl)-1H-pyrazolo[3,4-b]pyridine

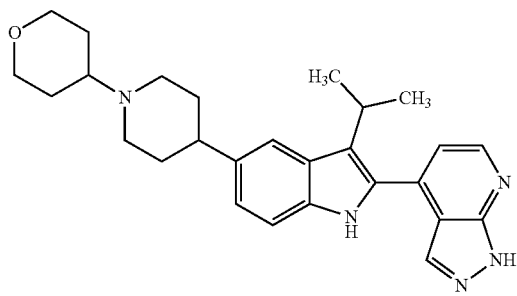

(682)

In a 2 dram vial was added 4-(3-isopropyl-5-(piperidin-4-yl)-1H-indol-2-yl)-1H-pyrazolo[3,4-b]pyridine hydrochloride (0.020 g, 0.051 mmol), DCM (1 mL), dihydro-2H-pyran-4(3H)-one (5.06 mg, 0.051 mmol) and 1 drop of acetic acid. After 5 minutes, sodium triacetoxyborohydride (0.043 g, 0.202 mmol) was added and the reaction mixture was stirred at room temperature for 16 hours. The reaction mixture was concentrated under a stream of nitrogen gas, then diluted with MeOH/ACN/Water and filtered through a 0.45 micron filter. The crude was purified via preparative LC/MS. The fractions containing the desired product were combined and dried via centrifugal evaporation to afford 4-(3-isopropyl-5-(1-(tetrahydro-2H-pyran-4-yl)piperidin-4-yl)-1H-indol-2-yl)-1H-pyrazolo[3,4-b]pyridine (2.8 mg, 0.0061 mmol, 12% yield). HPLC Ret. Time 1.496 min. MS (M+1) m/z: 444.3, Method C1. HPLC Ret. Time 1.062 min. MS (M$^{+1}$) m/z: 444.3, Method D1. $^1$H NMR (500 MHz, DMSO-d$_6$) δ 11.22 (s, 1H), 8.66-8.54 (m, 1H), 8.14 (s, 1H), 7.62 (s, 1H), 7.37 (d, J=8.4 Hz, 1H), 7.20 (d, J=4.6 Hz, 1H), 7.08 (br d, J=8.2 Hz, 1H), 3.91 (br d, J=7.0 Hz, 2H), 3.30 (br t, J=11.9 Hz, 2H), 3.03 (br d, J=10.4 Hz, 2H), 2.25 (br t, J=11.0 Hz, 2H), 1.91-1.78 (m, 6H), 1.73 (br d, J=12.4 Hz, 4H), 1.53-1.39 (m, 7H).

| Ex. No. | Structure | Obs. MS Ion | RT | HPLC Method |
|---|---|---|---|---|
| 683 | 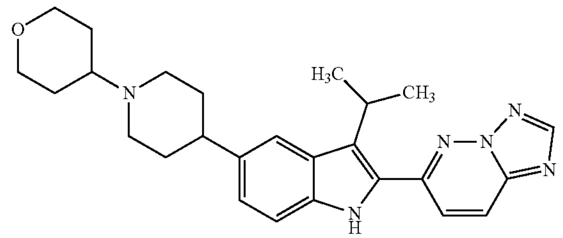 [SMILES: CC(C)c1c(-c2ccc3ncnn3n2)[nH]c2ccc(C3CCN(C4CCOCC4)CC3)cc12] | 445.2 | 0.65 | B1 |
| 684 | 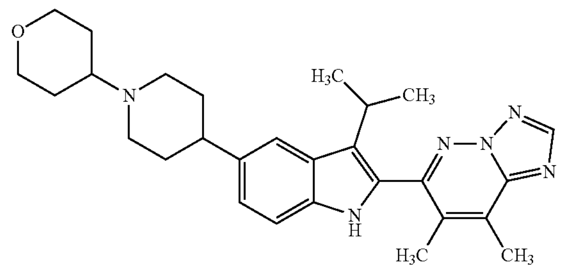 [SMILES: Cc1c(-c2[nH]c3ccc(C4CCN(C5CCOCC5)CC4)cc3c2C(C)C)nn2ncnc2c1C] | 473.1 | 0.67 | A1 |
| 685 | 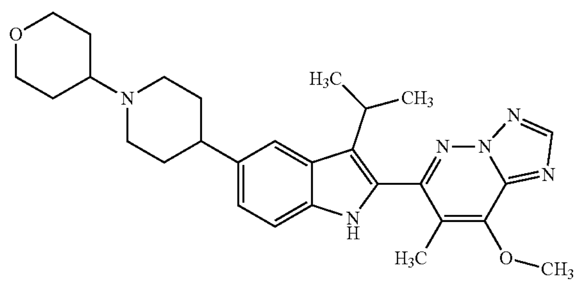 [SMILES: COc1c(C)c(-c2[nH]c3ccc(C4CCN(C5CCOCC5)CC4)cc3c2C(C)C)nn2ncnc12] | 489.0 | 0.73 | A1 |
| 686 | 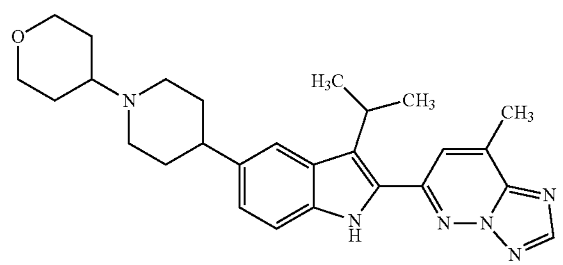 [SMILES: Cc1cc(-c2[nH]c3ccc(C4CCN(C5CCOCC5)CC4)cc3c2C(C)C)nn2ncnc12] | 459.1 | 0.65 | A1 |
| 687 | 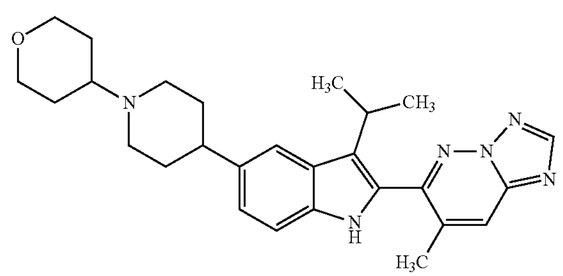 [SMILES: Cc1cc2ncnn2nc1-c1[nH]c2ccc(C3CCN(C4CCOCC4)CC3)cc2c1C(C)C] | 459.1 | 0.65 | A1 |

| Ex. No. | Structure | Obs. MS Ion | RT | HPLC Method |
|---|---|---|---|---|
| 688 | 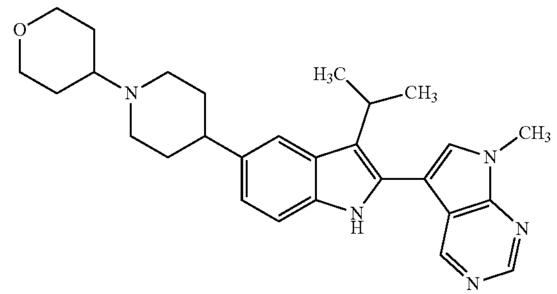 [SMILES: CC(C)c1c(-c2cn(C)c3ncncc23)[nH]c2ccc(C3CCN(C4CCOCC4)CC3)cc12] | 458.1 | 1.12 | QC-ACN-TFA-XB |
| 689 | 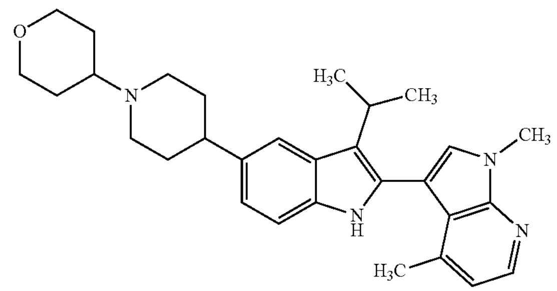 [SMILES: Cc1ccnc2c1c(-c1[nH]c3ccc(C4CCN(C5CCOCC5)CC4)cc3c1C(C)C)cn2C] | 471.4 | 1.6 | QC-ACN-AA-XB |
| 690 | 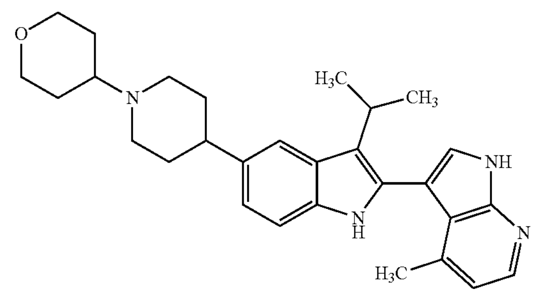 [SMILES: Cc1ccnc2[nH]cc(-c3[nH]c4ccc(C5CCN(C6CCOCC6)CC5)cc4c3C(C)C)c12] | 457.4 | 1.43 | QC-ACN-AA-XB |
| 691 | 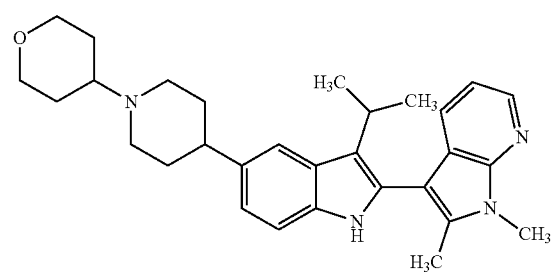 [SMILES: Cc1c(-c2[nH]c3ccc(C4CCN(C5CCOCC5)CC4)cc3c2C(C)C)c2cccnc2n1C] | 471.1 | 1.23 | QC-ACN-TFA-XB |
| 692 | 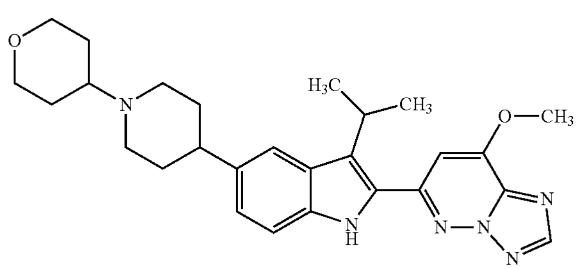 [SMILES: COc1cc(-c2[nH]c3ccc(C4CCN(C5CCOCC5)CC4)cc3c2C(C)C)nn2ncnc12] | 475.2 | 0.67 | A1 |

| Ex. No. | Structure | Obs. MS Ion | RT | HPLC Method |
|---|---|---|---|---|
| 693 | 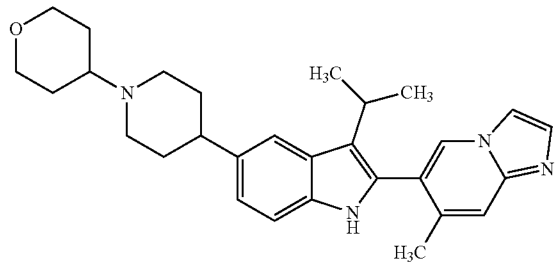 [SMILES: Cc1cc2nccn2cc1-c1[nH]c2ccc(C3CCN(C4CCOCC4)CC3)cc2c1C(C)C] | 457.3 | 0.94 | QC-ACN-TFA-XB |
| 694 | 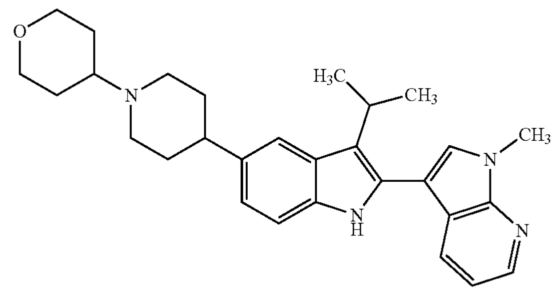 [SMILES: CC(C)c1c(-c2cn(C)c3ncccc23)[nH]c2ccc(C3CCN(C4CCOCC4)CC3)cc12] | 457 | 1.72 | QC-ACN-AA-XB |
| 695 | 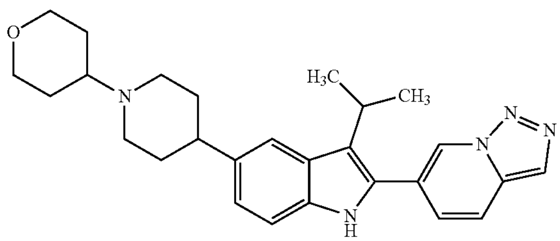 [SMILES: CC(C)c1c(-c2ccc3cnnn3c2)[nH]c2ccc(C3CCN(C4CCOCC4)CC3)cc12] | 443.9 | 1.42 | QC-ACN-AA-XB |
| 696 | 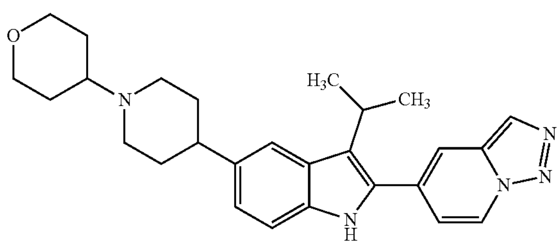 [SMILES: CC(C)c1c(-c2ccn3nncc3c2)[nH]c2ccc(C3CCN(C4CCOCC4)CC3)cc12] | 443.9 | 1.33 | QC-ACN-TFA-XB |
| 697 | 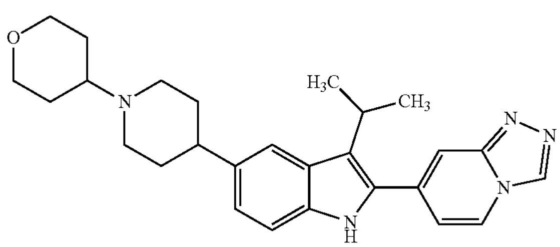 [SMILES: CC(C)c1c(-c2ccn3cnnc3c2)[nH]c2ccc(C3CCN(C4CCOCC4)CC3)cc12] | 444.2 | 1.07 | QC-ACN-AA-XB |
| 698 | 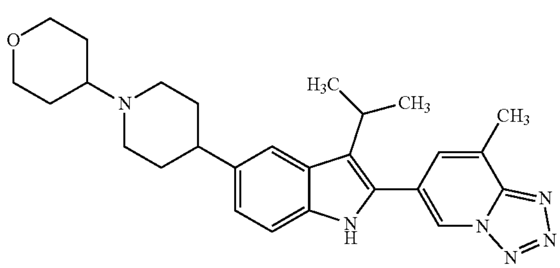 [SMILES: Cc1cc(-c2[nH]c3ccc(C4CCN(C5CCOCC5)CC4)cc3c2C(C)C)cn2nnnc12] | 459.2 | 1.46 | QC-ACN-AA-XB |

| Ex. No. | Structure | Obs. MS Ion | RT | HPLC Method |
|---|---|---|---|---|
| 699 | 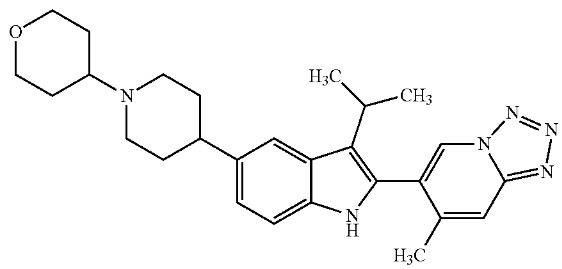 [SMILES: Cc1cc2nnnn2cc1-c1[nH]c2ccc(C3CCN(C4CCOCC4)CC3)cc2c1C(C)C] | 459 | 1.37 | QC-ACN-AA-XB |
| 700 | 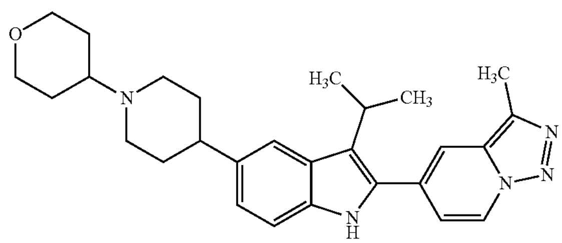 [SMILES: Cc1nnn2ccc(-c3[nH]c4ccc(C5CCN(C6CCOCC6)CC5)cc4c3C(C)C)cc12] | 458.4 | 1.4 | QC-ACN-AA-XB |
| 701 | 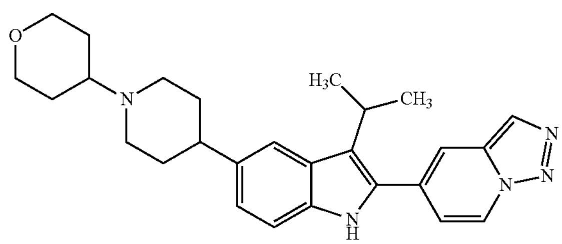 [SMILES: CC(C)c1c(-c2ccn3nncc3c2)[nH]c2ccc(C3CCN(C4CCOCC4)CC3)cc12] | 458 | 1.26 | QC-ACN-TFA-XB |
| 702 | 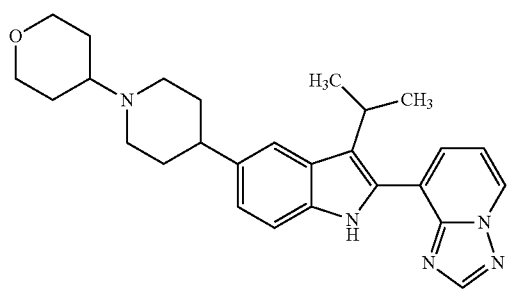 [SMILES: CC(C)c1c(-c2cccn3ncnc23)[nH]c2ccc(C3CCN(C4CCOCC4)CC3)cc12] | 444.3 | 1.39 | E |
| 703 | 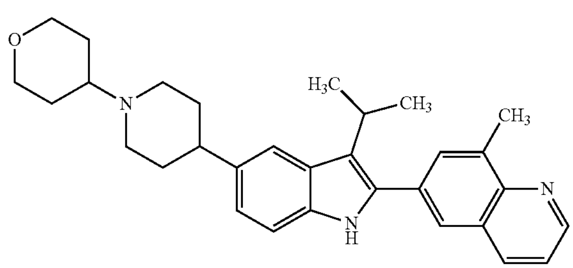 [SMILES: Cc1cc(-c2[nH]c3ccc(C4CCN(C5CCOCC5)CC4)cc3c2C(C)C)cc2cccnc12] | 445.3 | 1.72 | H |

| Ex. No. | Structure | Obs. MS Ion | RT | HPLC Method |
|---|---|---|---|---|
| 704 | 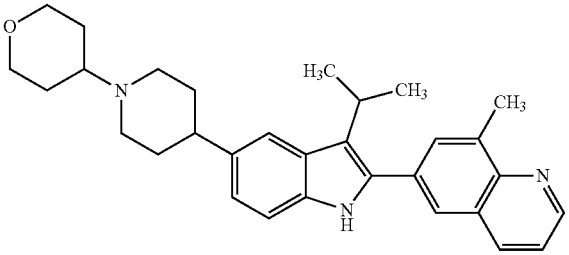 [SMILES: Cc1cc(-c2[nH]c3ccc(C4CCN(C5CCOCC5)CC4)cc3c2C(C)C)cc2cccnc12] | 468.2 | 1.57 | E |
| 705 | 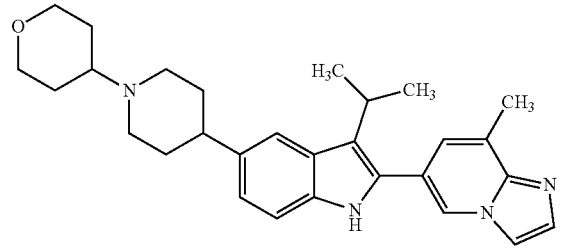 [SMILES: Cc1cc(-c2[nH]c3ccc(C4CCN(C5CCOCC5)CC4)cc3c2C(C)C)cn2ccnc12] | 457.3 | 1.87 | H |
| 706 | 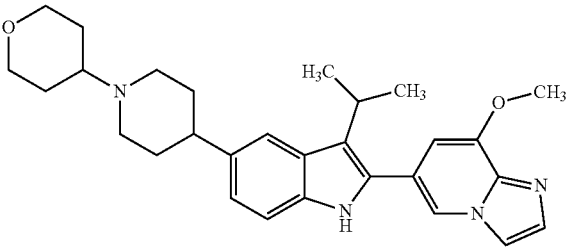 [SMILES: COc1cc(-c2[nH]c3ccc(C4CCN(C5CCOCC5)CC4)cc3c2C(C)C)cn2ccnc12] | 473.3 | 1.72 | H |
| 707 | 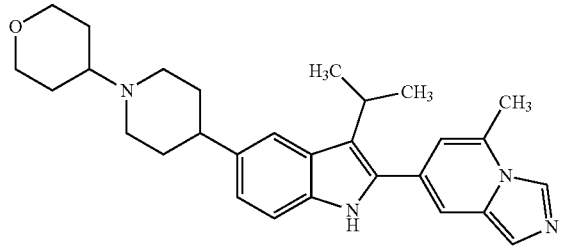 [SMILES: Cc1cc(-c2[nH]c3ccc(C4CCN(C5CCOCC5)CC4)cc3c2C(C)C)cc2cncn12] | 457.3 | 1.72 | H |
| 708 | 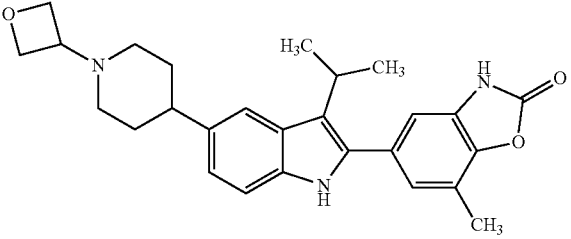 [SMILES: Cc1cc(-c2[nH]c3ccc(C4CCN(C5COC5)CC4)cc3c2C(C)C)cc2[nH]c(=O)oc12] | 446.2 | 1.56 | E |
| 709 | 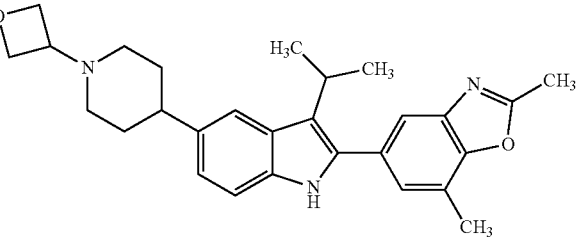 | 444.2 | 1.40 | E |

US 11,739,098 B2
371                                                                                                                                  372
-continued
| Ex. No. | Structure | Obs. MS Ion | RT | HPLC Method |
|---|---|---|---|---|
| 710 | 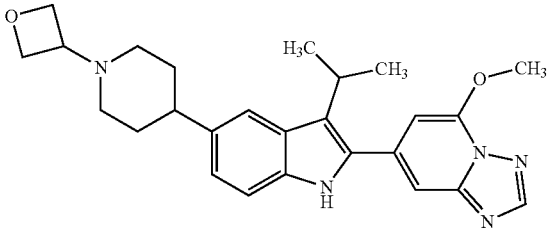 [SMILES: COc1cc(-c2[nH]c3ccc(C4CCN(C5COC5)CC4)cc3c2C(C)C)cc2ncnn12] | 446.1 | 1.75 | E |
| 711 | 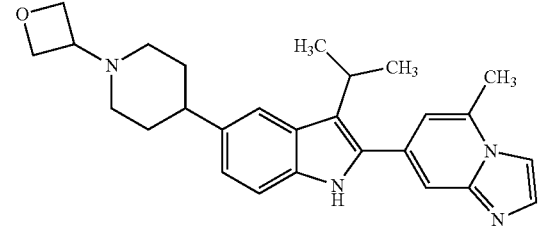 [SMILES: Cc1cc(-c2[nH]c3ccc(C4CCN(C5COC5)CC4)cc3c2C(C)C)cc2nccn12] | 429.1 | 1.98 | E |
| 712 | 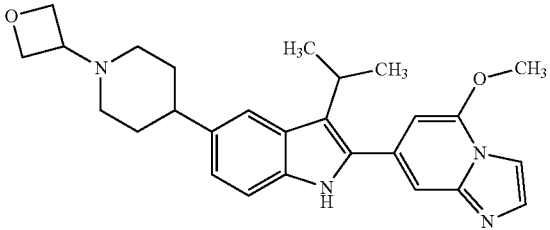 [SMILES: COc1cc(-c2[nH]c3ccc(C4CCN(C5COC5)CC4)cc3c2C(C)C)cc2nccn12] | 445.1 | 1.96 | E |
| 713 | 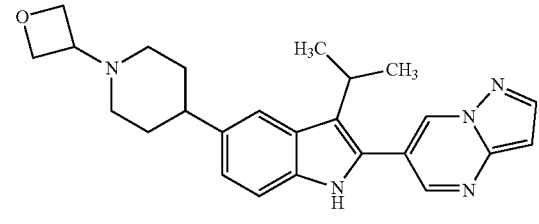 [SMILES: CC(C)c1c(-c2cnc3ccnn3c2)[nH]c2ccc(C3CCN(C4COC4)CC3)cc12] | 416.2 | 1.97 | E |
| 714 | 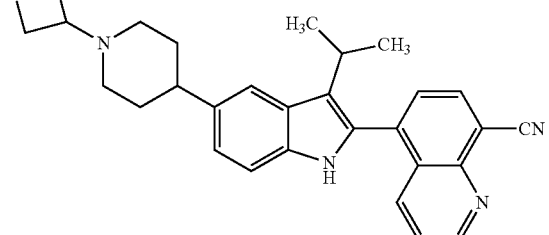 | 451.3 | 1.91 | E |
| 715 | 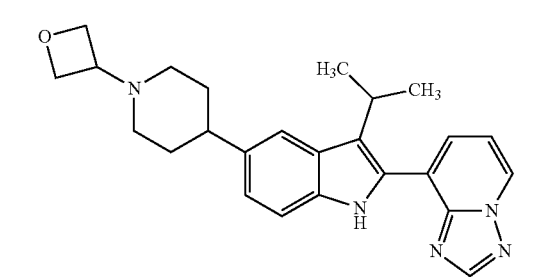 [SMILES: CC(C)c1c(-c2cccn3ncnc23)[nH]c2ccc(C3CCN(C4COC4)CC3)cc12] | 416.2 | 2.00 | E |

| Ex. No. | Structure | Obs. MS Ion | RT | HPLC Method |
|---|---|---|---|---|
| 716 | 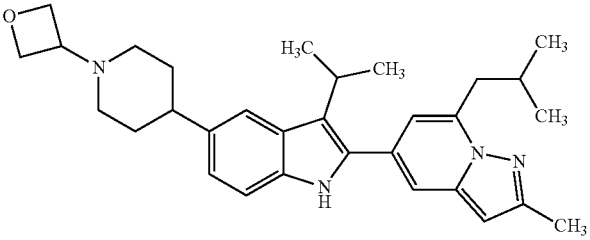 [SMILES: Cc1cc2cc(-c3[nH]c4ccc(C5CCN(C6COC6)CC5)cc4c3C(C)C)cc(CC(C)C)n2n1] | 486.4 | 2.50 | E |
| 717 | 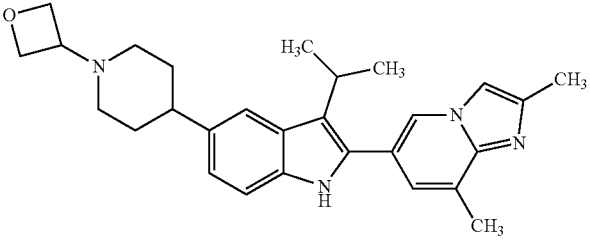 [SMILES: Cc1cn2cc(-c3[nH]c4ccc(C5CCN(C6COC6)CC5)cc4c3C(C)C)cc(C)c2n1] | 443.3 | 0.87 | F |
| 718 | 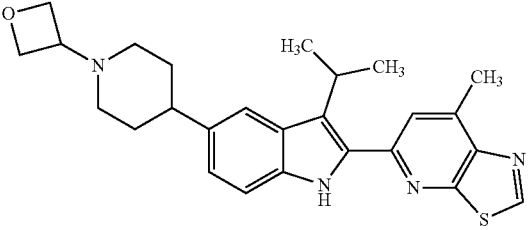 [SMILES: Cc1cc(-c2[nH]c3ccc(C4CCN(C5COC5)CC4)cc3c2C(C)C)nc2scnc12] | 447.1 | 2.27 | E |
| 719 | 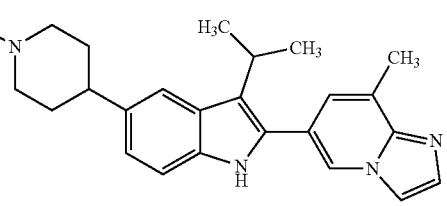 | 429.2 | 1.87 | E |
| 720 | 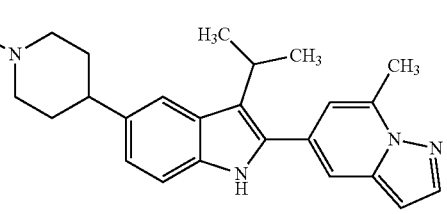 | 429.2 | 2.23 | E |
| 721 | 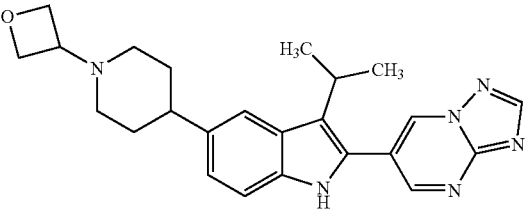 [SMILES: CC(C)c1c(-c2cnc3ncnn3c2)[nH]c2ccc(C3CCN(C4COC4)CC3)cc12] | 417.2 | 1.70 | E |

-continued

| Ex. No. | Structure | Obs. MS Ion | RT | HPLC Method |
|---|---|---|---|---|
| 722 | 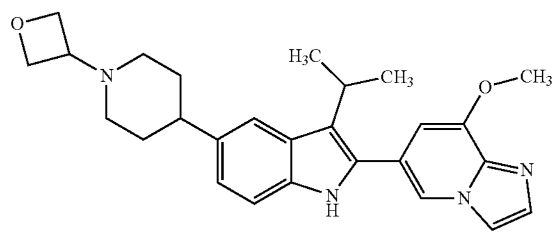 [SMILES: COc1cc(-c2[nH]c3ccc(C4CCN(C5COC5)CC4)cc3c2C(C)C)cn2ccnc12] | 445.3 | 1.69 | E |
| 723 | 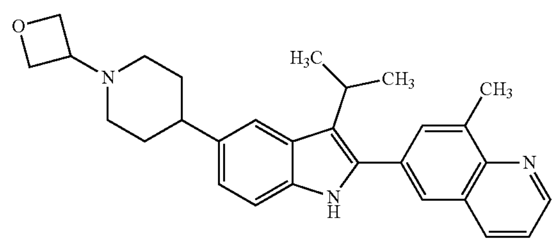 [SMILES: Cc1cc(-c2[nH]c3ccc(C4CCN(C5COC5)CC4)cc3c2C(C)C)cc2cccnc12] | 440.1 | 2.41 | E |
| 724 | 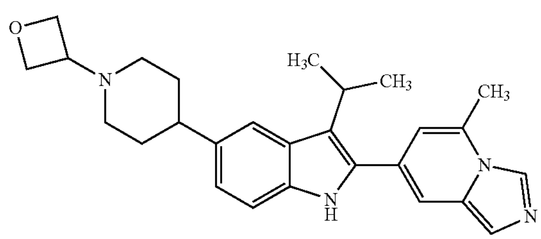 [SMILES: Cc1cc(-c2[nH]c3ccc(C4CCN(C5COC5)CC4)cc3c2C(C)C)cc2cncn12] | 429.2 | 1.98 | E |
| 725 | 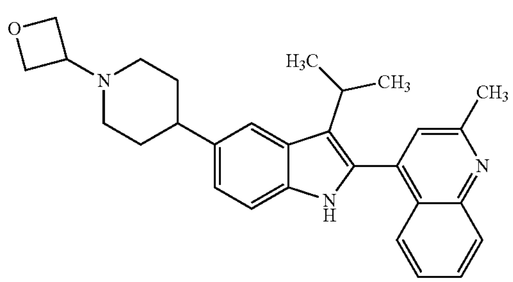 [SMILES: Cc1cc(-c2[nH]c3ccc(C4CCN(C5COC5)CC4)cc3c2C(C)C)c2ccccc2n1] | 440.2 | 2.25 | E |
| 726 | 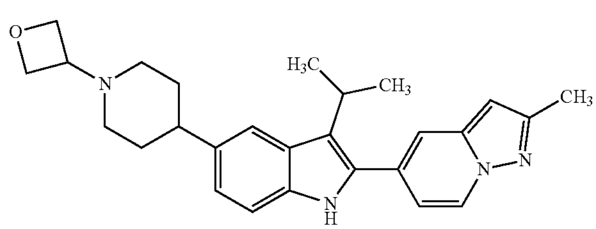 [SMILES: Cc1cc2cc(-c3[nH]c4ccc(C5CCN(C6COC6)CC5)cc4c3C(C)C)ccn2n1] | 429.3 | 2.21 | E |
| 727 | 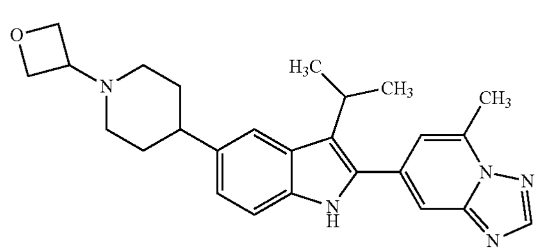 [SMILES: Cc1cc(-c2[nH]c3ccc(C4CCN(C5COC5)CC4)cc3c2C(C)C)cc2ncnn12] | 430.3 | 1.29 | E |

-continued

| Ex. No. | Structure | Obs. MS Ion | RT | HPLC Method |
|---|---|---|---|---|
| 728 | 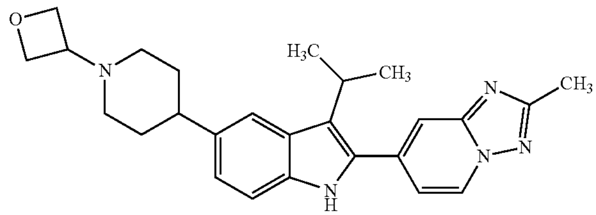 [SMILES: Cc1nc2cc(-c3[nH]c4ccc(C5CCN(C6COC6)CC5)cc4c3C(C)C)ccn2n1] | 430.3 | 1.91 | E |
| 729 | 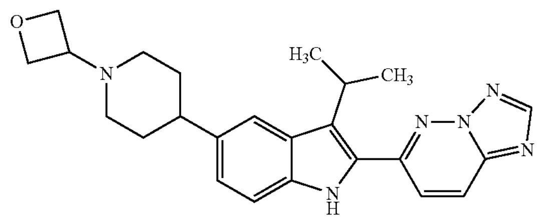 [SMILES: CC(C)c1c(-c2ccc3ncnn3n2)[nH]c2ccc(C3CCN(C4COC4)CC3)cc12] | 432 | 0.62 | B1 |
| 730 | 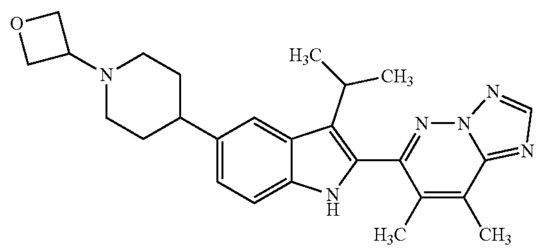 [SMILES: Cc1c(-c2[nH]c3ccc(C4CCN(C5COC5)CC4)cc3c2C(C)C)nn2ncnc2c1C] | 445.2 | 0.65 | B1 |
| 731 | 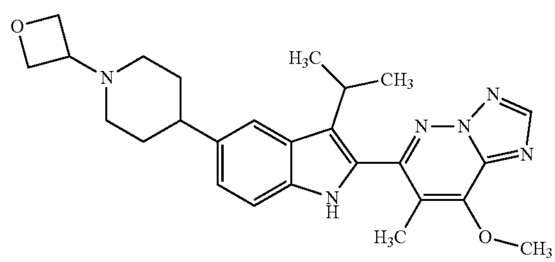 [SMILES: COc1c(C)c(-c2[nH]c3ccc(C4CCN(C5COC5)CC4)cc3c2C(C)C)nn2ncnc12] | 461.1 | 0.70 | A1 |
| 732 | 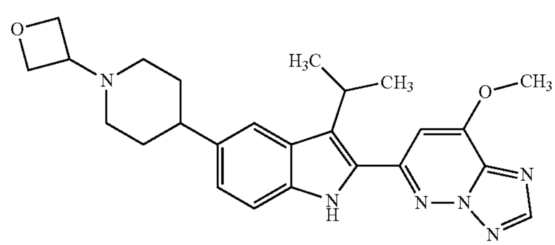 [SMILES: COc1cc(-c2[nH]c3ccc(C4CCN(C5COC5)CC4)cc3c2C(C)C)nn2ncnc12] | 447.2 | 0.64 | A1 |
| 733 | 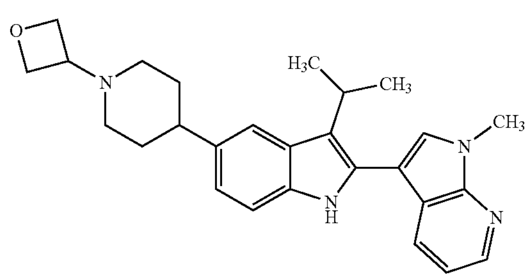 [SMILES: CC(C)c1c(-c2cn(C)c3ncccc23)[nH]c2ccc(C3CCN(C4COC4)CC3)cc12] | 429 | 2.03 | QC-ACN-AA-XB |

| Ex. No. | Structure | Obs. MS Ion | RT | HPLC Method |
|---|---|---|---|---|
| 734 | 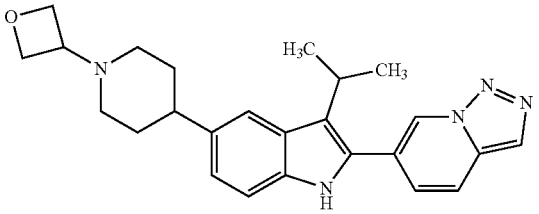 [SMILES: CC(C)c1c(-c2ccc3cnnn3c2)[nH]c2ccc(C3CCN(C4COC4)CC3)cc12] | 416.2 | 1.6 | QC-ACN-AA-XB |
| 735 | 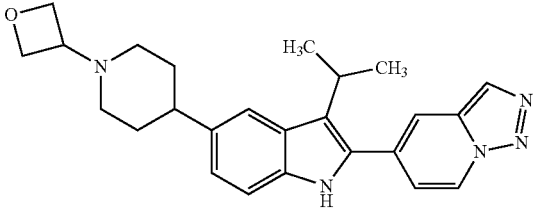 [SMILES: CC(C)c1c(-c2ccn3nncc3c2)[nH]c2ccc(C3CCN(C4COC4)CC3)cc12] | 416.3 | 1.66 | QC-ACN-AA-XB |
| 736 | 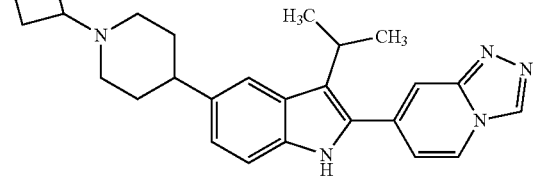 | 416.3 | 0.8 | QC-ACN-TFA-XB |
| 737 | 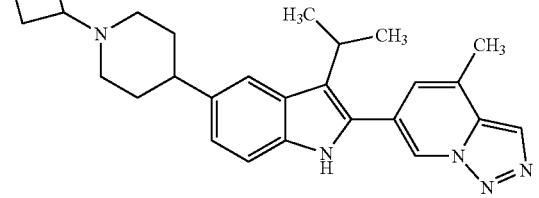 | 430.3 | 1.81 | QC-ACN-AA-XB |
| 738 | 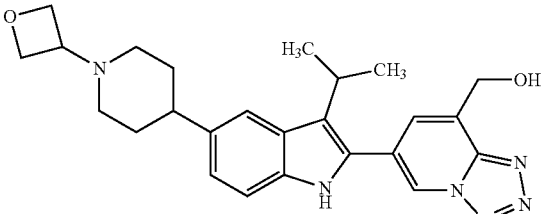 | 447.2 | 1 | QC-ACN-TFA-XB |
| 739 | 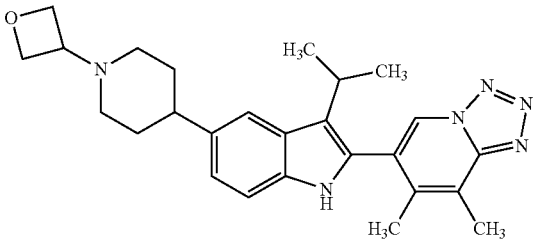 [SMILES: Cc1c(-c2[nH]c3ccc(C4CCN(C5COC5)CC4)cc3c2C(C)C)cn2nnnc2c1C] | 445.2 | 1.9 | QC-ACN-AA-XB |

-continued
| Ex. No. | Structure | Obs. MS Ion | RT | HPLC Method |
|---|---|---|---|---|
| 740 | 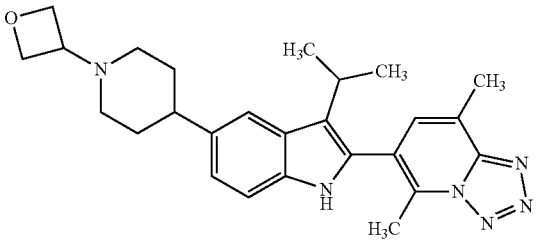 [SMILES: Cc1cc(-c2[nH]c3ccc(C4CCN(C5COC5)CC4)cc3c2C(C)C)c(C)n2nnnc12] | 445.1 | 1.92 | QC-ACN-AA-XB |
| 741 | 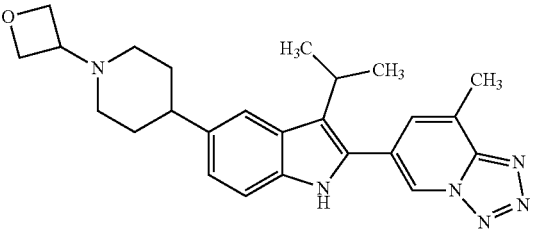 [SMILES: Cc1cc(-c2[nH]c3ccc(C4CCN(C5COC5)CC4)cc3c2C(C)C)cn2nnnc12] | 431 | 1.2 | QC-ACN-TFA-XB |
| 742 | 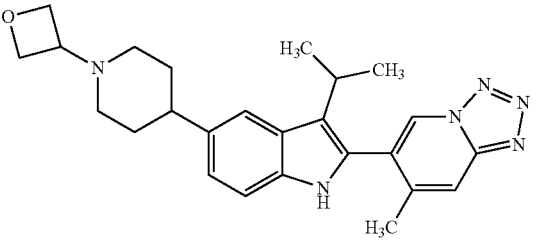 [SMILES: Cc1cc2nnnn2cc1-c1[nH]c2ccc(C3CCN(C4COC4)CC3)cc2c1C(C)C] | 431.1 | 1.72 | QC-ACN-AA-XB |
| 743 | 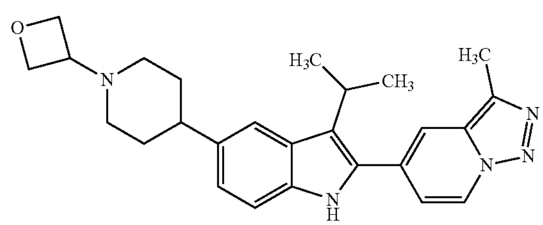 [SMILES: Cc1nnn2ccc(-c3[nH]c4ccc(C5CCN(C6COC6)CC5)cc4c3C(C)C)cc12] | 430.1 | 1.3 | QC-ACN-TFA-XB |
| 744 | 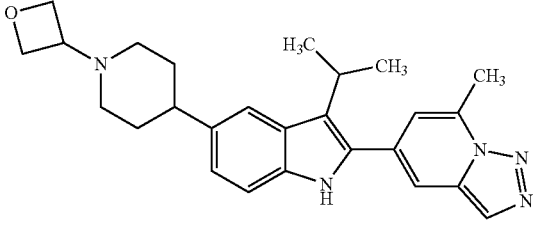 [SMILES: Cc1cc(-c2[nH]c3ccc(C4CCN(C5COC5)CC4)cc3c2C(C)C)cc2cnnn12] | 429.9 | 1.18 | QC-ACN-TFA-XB |

Example 745

1-(4-(3-isopropyl-2-(8-methyltetrazolo[1,5-a]pyridin-6-yl)-1H-indol-5-yl)piperidin-1-yl)-2-methylpropan-2-ol, TFA

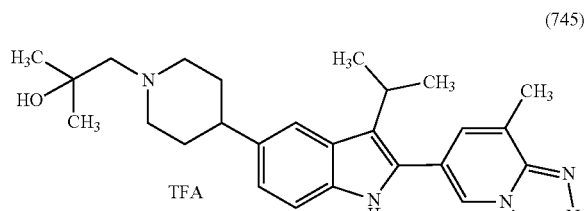
(745)

6-(3-isopropyl-5-(piperidin-4-yl)-1H-indol-2-yl)-8-methyltetrazolo[1,5-a]pyridine, HCl (21.57 mg, 0.0525 mmol) was dissolved in MeOH (1 mL). Potassium carbonate (43.5 μmg, 0.315 mmol) and 2,2-dimethyloxirane (0.014 mL, 0.158 mmol) were added, sequentially and the reaction mixture was stirred for 3 hours at room temperature. The reaction mixture was diluted with DMF and a drop of water. The crude product was purified via preparative HPLC. The fractions containing the desired product were combined and dried via centrifugal evaporation to give 1-(4-(3-isopropyl-2-(8-methyltetrazolo[1,5-a]pyridin-6-yl)-1H-indol-5-yl)piperidin-1-yl)-2-methylpropan-2-ol, TFA (10.3 mg, 0.018 mmol, 35.0% yield). HPLC Ret. Time 1.564 min. MS (M$^{+1}$) m/z: 447.3, Method C1. $^1$H NMR (500 MHz, DMSO-d$_6$) δ 11.29 (s, 1H), 9.20-9.06 (m, 1H), 7.76 (s, 1H), 7.67-7.55 (m, 1H), 7.37 (br d, J=8.4 Hz, 1H), 7.07 (br d, J=8.3 Hz, 1H), 3.61-3.49 (m, 4H), 3.40-3.24 (m, 2H), 3.22-3.07 (m, 2H), 2.89 (br d, J=3.5 Hz, 1H), 2.74 (s, 3H), 2.29-2.03 (m, 2H), 1.95 (br d, J=12.8 Hz, 2H), 1.45 (br d, J=6.9 Hz, 6H), 1.29 (s, 6H).

| Ex. No. | Structure | Obs. MS Ion | HPLC RT | HPLC Method |
|---|---|---|---|---|
| 746 | 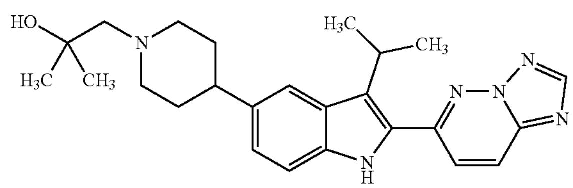 [SMILES: CC(C)c1c(-c2ccc3ncnn3n2)[nH]c2ccc(C3CCN(CC(C)(C)O)CC3)cc12] | 433.0 | 0.66 | A1 |
| 747 | 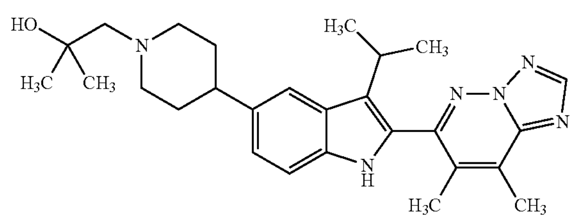 | 461.4 | 0.68 | B1 |
| 748 | 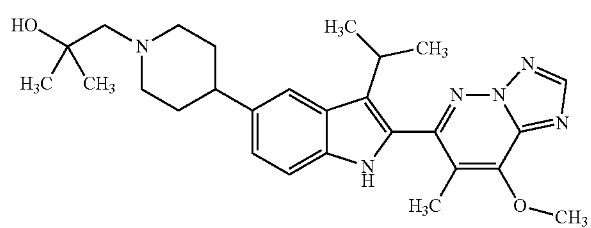 [SMILES: COc1c(C)c(-c2[nH]c3ccc(C4CCN(CC(C)(C)O)CC4)cc3c2C(C)C)nn2ncnc12] | 477.3 | 0.71 | K |
| 749 | 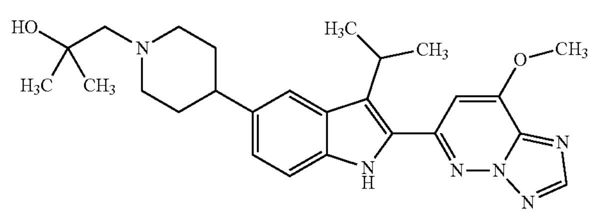 [SMILES: COc1cc(-c2[nH]c3ccc(C4CCN(CC(C)(C)O)CC4)cc3c2C(C)C)nn2ncnc12] | 463.1 | 1.21 | QC-ACN-AA-XB |

385 386
-continued

| Ex. No. | Structure | Obs. MS Ion | RT | HPLC Method |
|---|---|---|---|---|
| 750 | 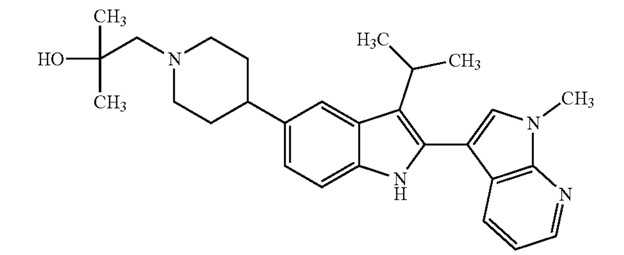 [SMILES: CC(C)c1c(-c2cn(C)c3ncccc23)[nH]c2ccc(C3CCN(CC(C)(C)O)CC3)cc12] | 445 | 1.8 | QC-ACN-AA-XB |
| 752 | 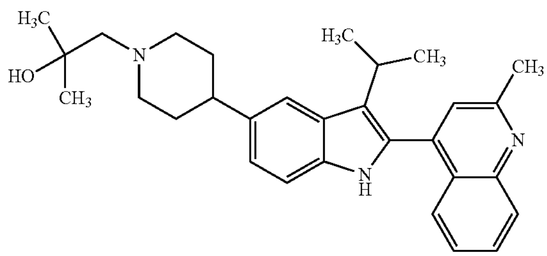 [SMILES: Cc1cc(-c2[nH]c3ccc(C4CCN(CC(C)(C)O)CC4)cc3c2C(C)C)c2ccccc2n1] | 456.3 | 1.95 | E |
| 753 | 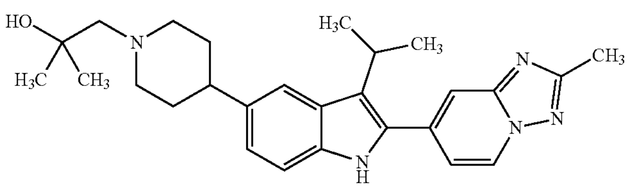 [SMILES: Cc1nc2cc(-c3[nH]c4ccc(C5CCN(CC(C)(C)O)CC5)cc4c3C(C)C)ccn2n1] | 446.3 | 1.66 | E |
| 754 | 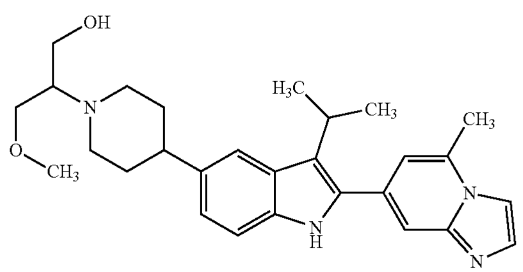 [SMILES: COCC(CO)N1CCC(c2ccc3[nH]c(-c4cc(C)n5ccnc5c4)c(C(C)C)c3c2)CC1] | 461.2 | 1.64 | E |
| 755 | 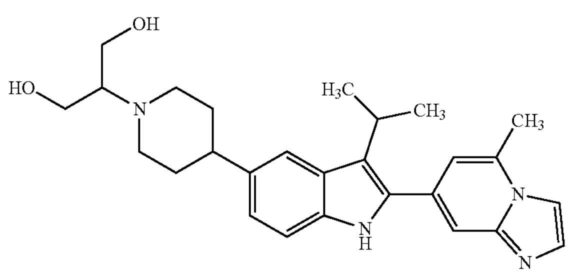 [SMILES: Cc1cc(-c2[nH]c3ccc(C4CCN(C(CO)CO)CC4)cc3c2C(C)C)cc2nccn12] | 447.1 | 1.43 | E |
| 756 | 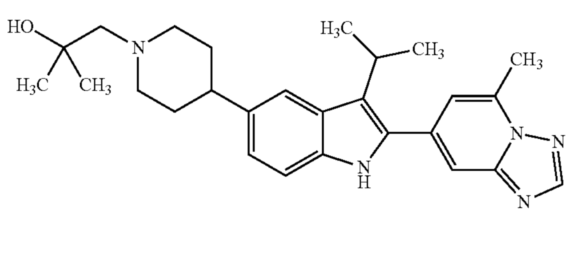 [SMILES: Cc1cc(-c2[nH]c3ccc(C4CCN(CC(C)(C)O)CC4)cc3c2C(C)C)cc2ncnn12] | 446.3 | 1.79 | E |

-continued

| Ex. No. | Structure | Obs. MS Ion | RT | HPLC Method |
|---|---|---|---|---|
| 757 | 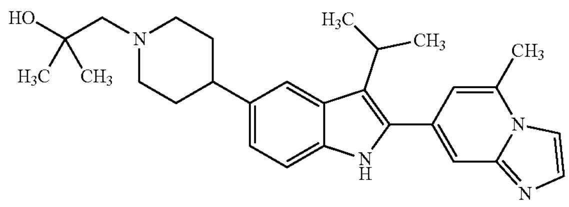 [SMILES: Cc1cc(-c2[nH]c3ccc(C4CCN(CC(C)(C)O)CC4)cc3c2C(C)C)cc2nccn12] | 445.1 | 1.73 | E |
| 758 | 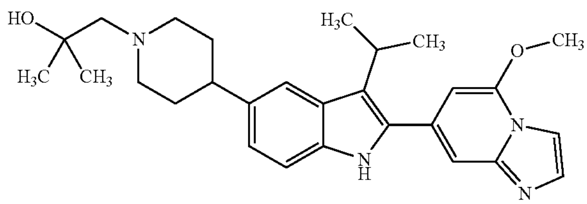 [SMILES: COc1cc(-c2[nH]c3ccc(C4CCN(CC(C)(C)O)CC4)cc3c2C(C)C)cc2nccn12] | 461.1 | 1.73 | E |
| 759 | 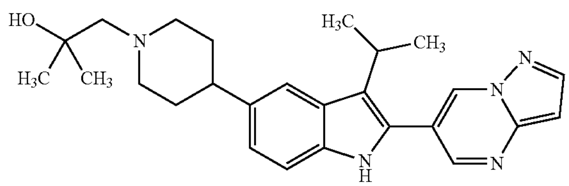 [SMILES: CC(C)c1c(-c2cnc3ccnn3c2)[nH]c2ccc(C3CCN(CC(C)(C)O)CC3)cc12] | 432.2 | 1.72 | E |
| 760 | 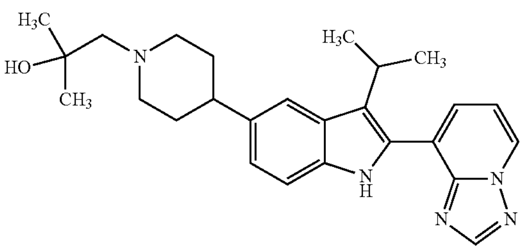 [SMILES: CC(C)c1c(-c2cccn3ncnc23)[nH]c2ccc(C3CCN(CC(C)(C)O)CC3)cc12] | 432.2 | 1.69 | E |
| 761 | 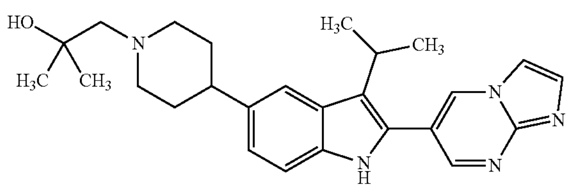 [SMILES: CC(C)c1c(-c2cnc3nccn3c2)[nH]c2ccc(C3CCN(CC(C)(C)O)CC3)cc12] | 432.3 | 1.36 | E |
| 762 | 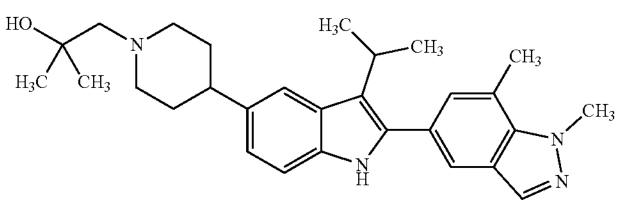 [SMILES: Cc1cc(-c2[nH]c3ccc(C4CCN(CC(C)(C)O)CC4)cc3c2C(C)C)cc2cnn(C)c12] | 459.3 | 2.11 | E |
| 763 | 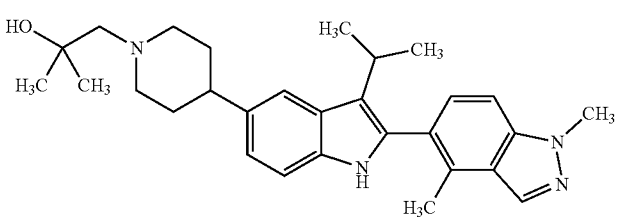 [SMILES: Cc1c(-c2[nH]c3ccc(C4CCN(CC(C)(C)O)CC4)cc3c2C(C)C)ccc2c1cnn2C] | 459.3 | 1.78 | E |

-continued

| Ex. No. | Structure | Obs. MS Ion | RT | HPLC Method |
|---|---|---|---|---|
| 764 | 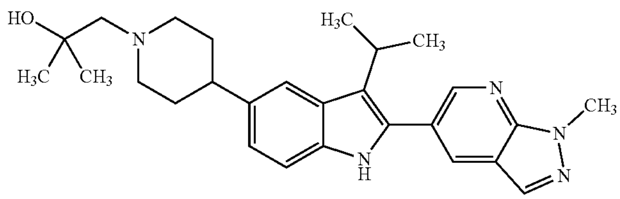 [SMILES: CC(C)c1c(-c2cnc3c(cnn3C)c2)[nH]c2ccc(C3CCN(CC(C)(C)O)CC3)cc12] | 446.2 | 1.78 | E |
| 765 | 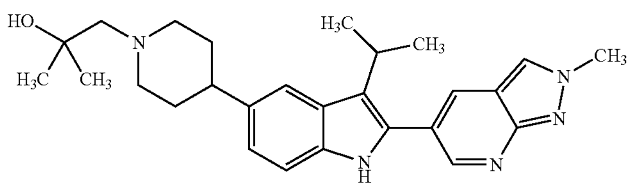 [SMILES: CC(C)c1c(-c2cnc3nn(C)cc3c2)[nH]c2ccc(C3CCN(CC(C)(C)O)CC3)cc12] | 446.3 | 1.49 | E |
| 766 | 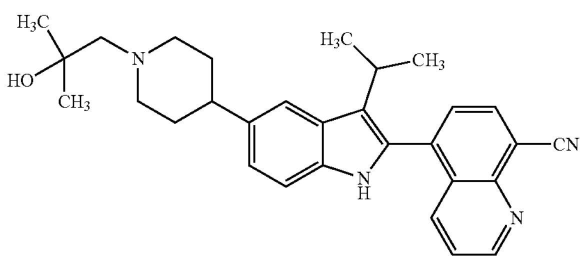 [SMILES: CC(C)c1c(-c2ccc(C#N)c3ncccc23)[nH]c2ccc(C3CCN(CC(C)(C)O)CC3)cc12] | 467.3 | 1.68 | E |
| 767 | 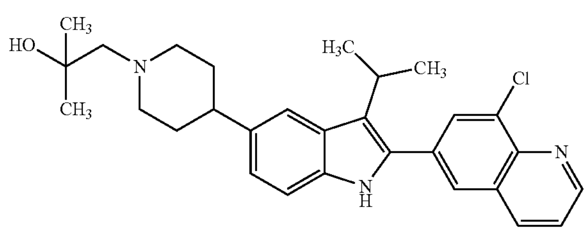 [SMILES: CC(C)c1c(-c2cc(Cl)c3ncccc3c2)[nH]c2ccc(C3CCN(CC(C)(C)O)CC3)cc12] | 477.0 | 2.06 | E |
| 768 | 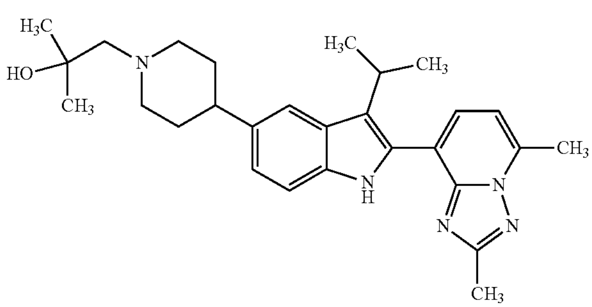 [SMILES: Cc1nc2c(-c3[nH]c4ccc(C5CCN(CC(C)(C)O)CC5)cc4c3C(C)C)ccc(C)n2n1] | 460.3 | 1.71 | E |
| 769 | 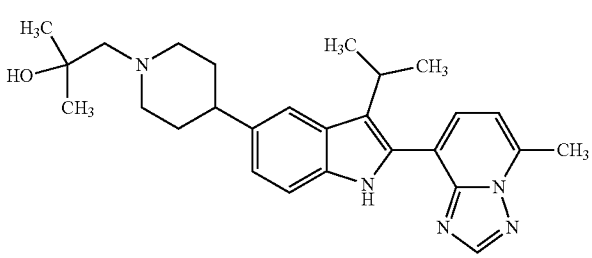 [SMILES: Cc1ccc(-c2[nH]c3ccc(C4CCN(CC(C)(C)O)CC4)cc3c2C(C)C)c2ncnn12] | 446.0 | 1.65 | E |

-continued
| Ex. No. | Structure | Obs. MS Ion | RT | HPLC Method |
|---|---|---|---|---|
| 770 | 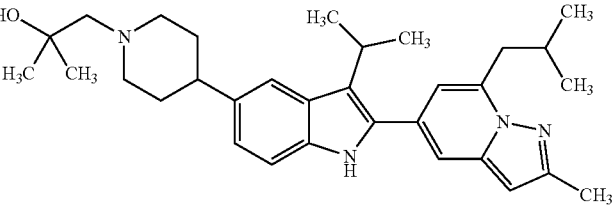 | 502.4 | 2.31 | E |
| 771 | 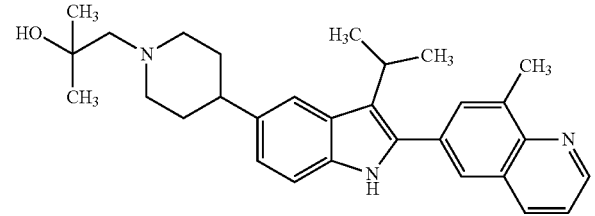 [SMILES: Cc1cc(-c2[nH]c3ccc(C4CCN(CC(C)(C)O)CC4)cc3c2C(C)C)cc2cccnc12] | 456.2 | 1.26 | F |
| 772 | 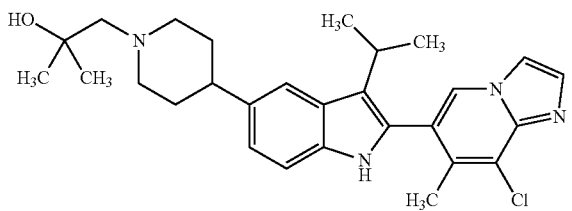 [SMILES: Cc1c(-c2[nH]c3ccc(C4CCN(CC(C)(C)O)CC4)cc3c2C(C)C)cn2ccnc2c1Cl] | 479.2 | 1.81 | E |
| 773 | 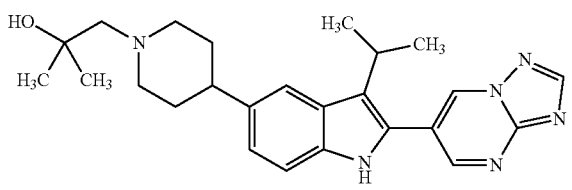 | 433.0 | 1.41 | E |
| 774 | 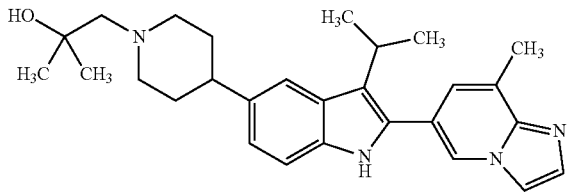 [SMILES: Cc1cc(-c2[nH]c3ccc(C4CCN(CC(C)(C)O)CC4)cc3c2C(C)C)cn2ccnc12] | 445.0 | 1.68 | E |
| 775 | 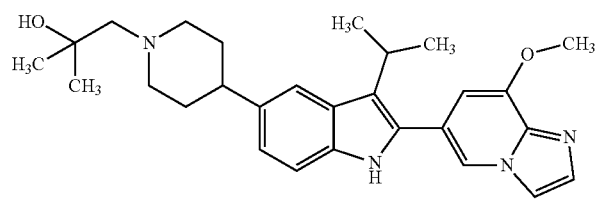 [SMILES: COc1cc(-c2[nH]c3ccc(C4CCN(CC(C)(C)O)CC4)cc3c2C(C)C)cn2ccnc12] | 461.3 | 1.49 | E |
| 776 | 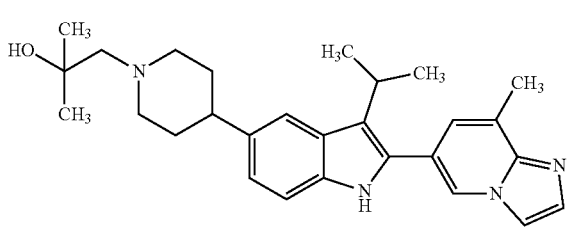 [SMILES: Cc1cc(-c2[nH]c3ccc(C4CCN(CC(C)(C)O)CC4)cc3c2C(C)C)cn2ccnc12] | 445.3 | 1.74 | E |

-continued

| Ex. No. | Structure | Obs. MS Ion | RT | HPLC Method |
|---|---|---|---|---|
| 777 | 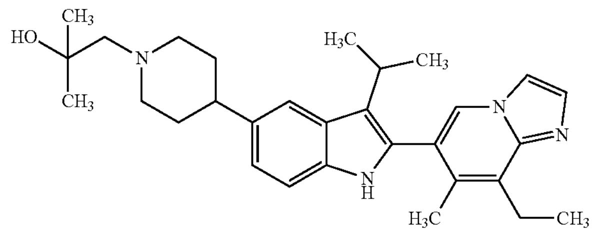 [SMILES: CCc1c(C)c(-c2[nH]c3ccc(C4CCN(CC(C)(C)O)CC4)cc3c2C(C)C)cn2ccnc12] | 473.3 | 1.90 | E |
| 778 | 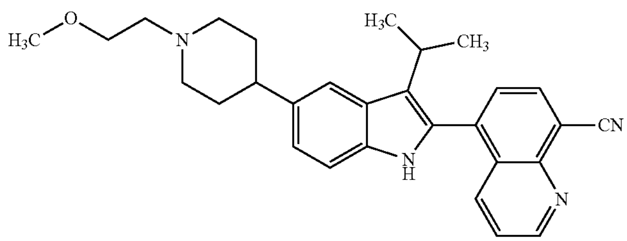 [SMILES: COCCN1CCC(c2ccc3[nH]c(-c4ccc(C#N)c5ncccc45)c(C(C)C)c3c2)CC1] | 453.0 | 1.63 | E |
| 779 | 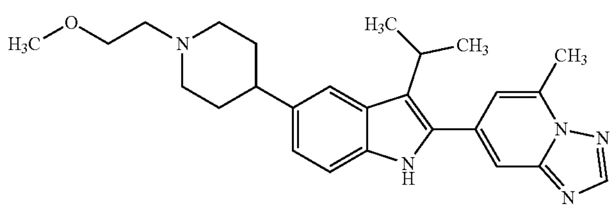 [SMILES: COCCN1CCC(c2ccc3[nH]c(-c4cc(C)n5ncnc5c4)c(C(C)C)c3c2)CC1] | 432.1 | 1.95 | E |
| 780 | 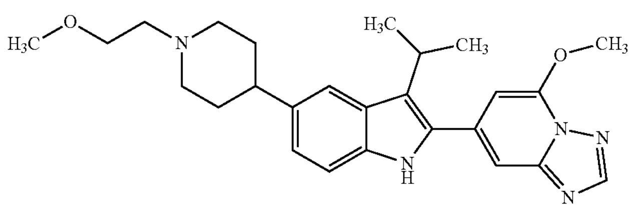 [SMILES: COCCN1CCC(c2ccc3[nH]c(-c4cc(OC)n5ncnc5c4)c(C(C)C)c3c2)CC1] | 448.2 | 1.48 | E |
| 781 | 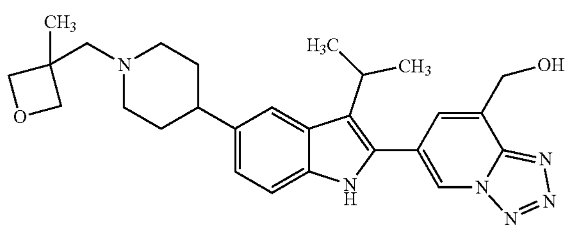 [SMILES: CC(C)c1c(-c2cc(CO)c3nnnn3c2)[nH]c2ccc(C3CCN(CC4(C)COC4)CC3)cc12] | 475.1 | 1.33 | QC-ACN-AA-XB |

TABLE 21

| Ex. No. | Structure | Obs. MS Ion | RT | HPLC Method |
|---|---|---|---|---|
| 782 | 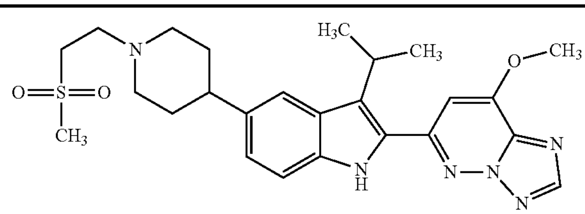 | 497 | 1.64 | QC-ACN-AA-XB |

TABLE 21-continued
| Ex. No. | Structure | Obs. MS Ion | RT | HPLC Method |
|---|---|---|---|---|
| 783 | 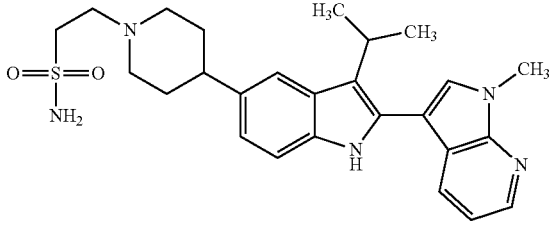 [SMILES: CC(C)c1c(-c2cn(C)c3ncccc23)[nH]c2ccc(C3CCN(CCS(N)(=O)=O)CC3)cc12] | 480 | 1.83 | QC-ACN-AA-XB |
| 784 | 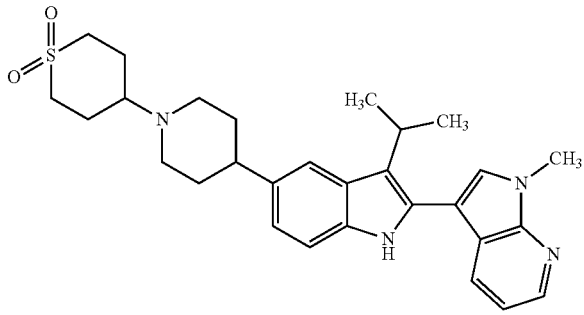 [SMILES: CC(C)c1c(-c2cn(C)c3ncccc23)[nH]c2ccc(C3CCN(C4CCS(=O)(=O)CC4)CC3)cc12] | 505 | 1.91 | QC-ACN-AA-XB |
| 785 | 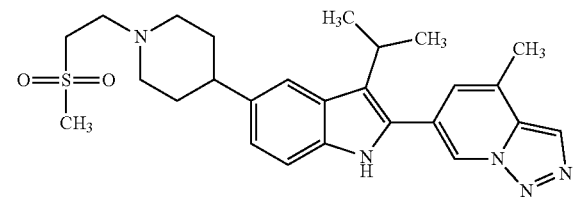 [SMILES: Cc1cc(-c2[nH]c3ccc(C4CCN(CCS(C)(=O)=O)CC4)cc3c2C(C)C)cn2nncc12] | 480.3 | 1.8 | QC-ACN-AA-XB |
| 786 | 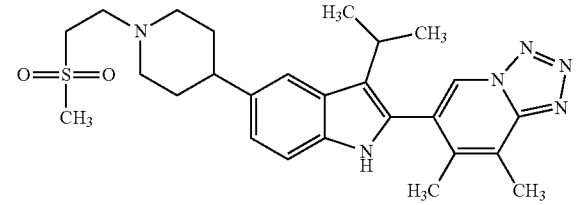 [SMILES: Cc1c(-c2[nH]c3ccc(C4CCN(CCS(C)(=O)=O)CC4)cc3c2C(C)C)cn2nnnc2c1C] | 495.2 | 1.79 | QC-ACN-AA-XB |
| 787 | 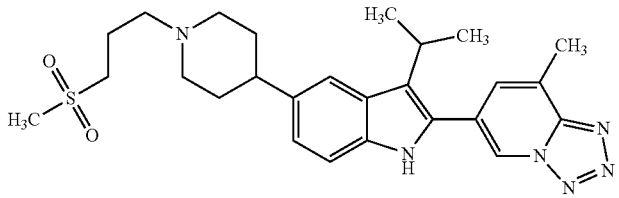 [SMILES: Cc1cc(-c2[nH]c3ccc(C4CCN(CCCS(C)(=O)=O)CC4)cc3c2C(C)C)cn2nnnc12] | 495.4 | 1.4 | QC-ACN-AA-XB |
| 788 | 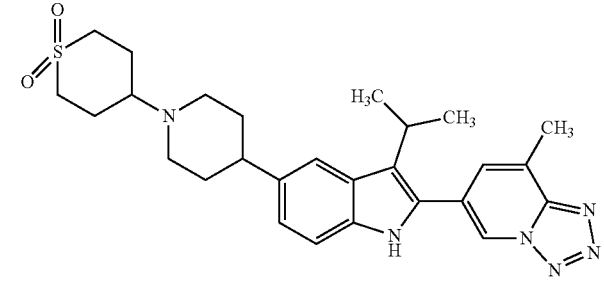 [SMILES: Cc1cc(-c2[nH]c3ccc(C4CCN(C5CCS(=O)(=O)CC5)CC4)cc3c2C(C)C)cn2nnnc12] | 507.3 | 1.61 | QC-ACN-AA-XB |

TABLE 21-continued

| Ex. No. | Structure | Obs. MS Ion | RT | HPLC Method |
|---|---|---|---|---|
| 789 | 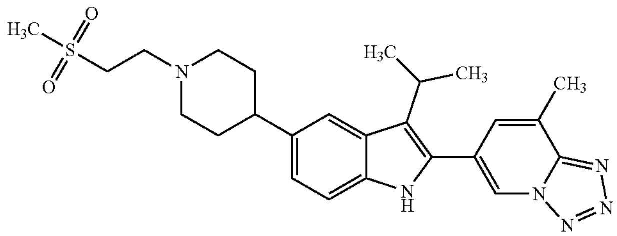 [SMILES: Cc1cc(-c2[nH]c3ccc(C4CCN(CCS(C)(=O)=O)CC4)cc3c2C(C)C)cn2nnnc12] | 481.4 | 1.73 | QC-ACN-AA-XB |
| 790 | 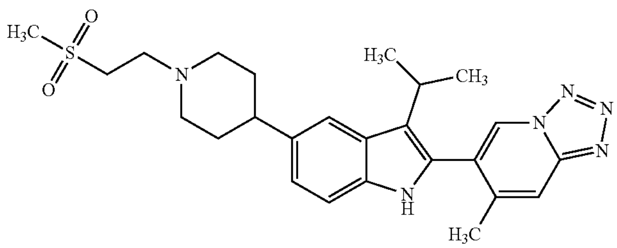 [SMILES: Cc1cc2nnnn2cc1-c1[nH]c2ccc(C3CCN(CCS(C)(=O)=O)CC3)cc2c1C(C)C] | 481 | 1.15 | QC-ACN-TFA-XB |
| 791 | 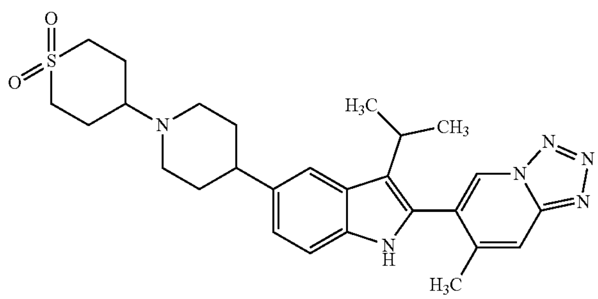 [SMILES: Cc1cc2nnnn2cc1-c1[nH]c2ccc(C3CCN(C4CCS(=O)(=O)CC4)CC3)cc2c1C(C)C] | 507.1 | 1.54 | QC-ACN-AA-XB |
| 792 | 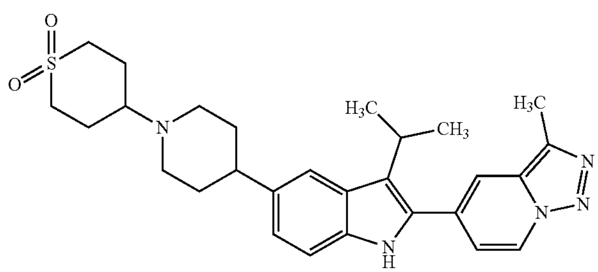 [SMILES: Cc1nnn2ccc(-c3[nH]c4ccc(C5CCN(C6CCS(=O)(=O)CC6)CC5)cc4c3C(C)C)cc12] | 506.2 | 1.58 | QC-ACN-AA-XB |
| 793 | 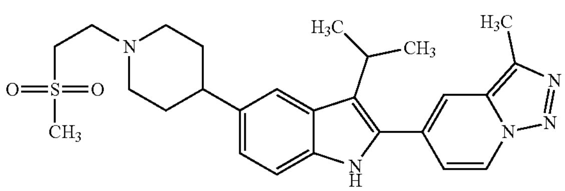 [SMILES: Cc1nnn2ccc(-c3[nH]c4ccc(C5CCN(CCS(C)(=O)=O)CC5)cc4c3C(C)C)cc12] | 480.3 | 1.69 | QC-ACN-AA-XB |
| 794 | 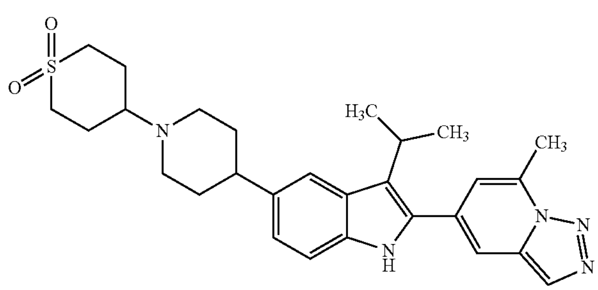 [SMILES: Cc1cc(-c2[nH]c3ccc(C4CCN(C5CCS(=O)(=O)CC5)CC4)cc3c2C(C)C)cc2cnnn12] | 506.4 | 1.58 | QC-ACN-AA-XB |

TABLE 21-continued
| Ex. No. | Structure | Obs. MS Ion | RT | HPLC Method |
|---|---|---|---|---|
| 795 | 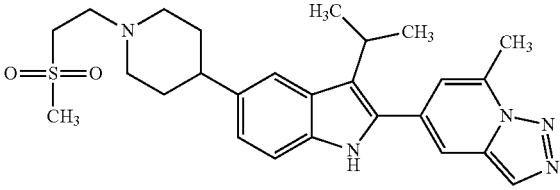 [SMILES: Cc1cc(-c2[nH]c3ccc(C4CCN(CCS(C)(=O)=O)CC4)cc3c2C(C)C)cc2cnnn12] | 480.1 | 1.64 | QC-ACN-AA-XB |
| 796 | 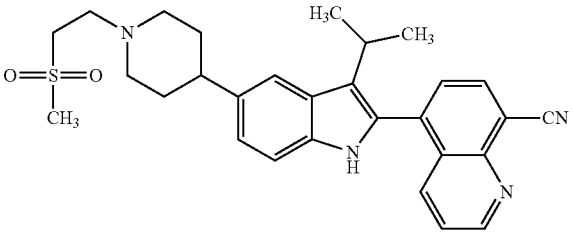 [SMILES: CC(C)c1c(-c2ccc(C#N)c3ncccc23)[nH]c2ccc(C3CCN(CCS(C)(=O)=O)CC3)cc12] | 501.3 | 1.83 | E |
| 797 | 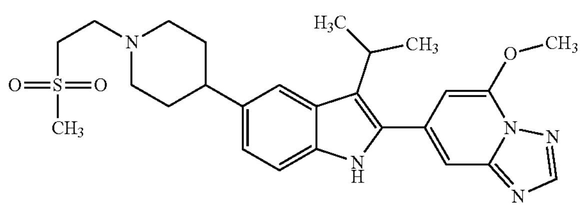 [SMILES: COc1cc(-c2[nH]c3ccc(C4CCN(CCS(C)(=O)=O)CC4)cc3c2C(C)C)cc2ncnn12] | 496.1 | 1.72 | E |
| 798 | 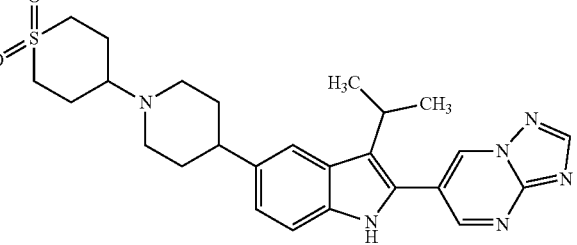 | 493.0 | 1.53 | E |
| 799 | 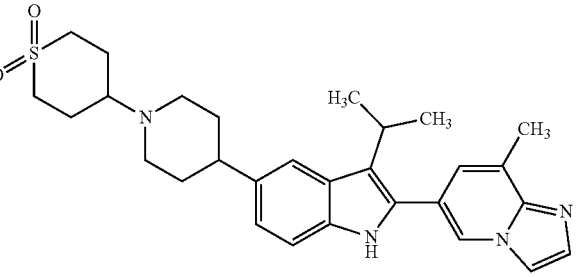 | 505.0 | 1.79 | E |
| 800 | 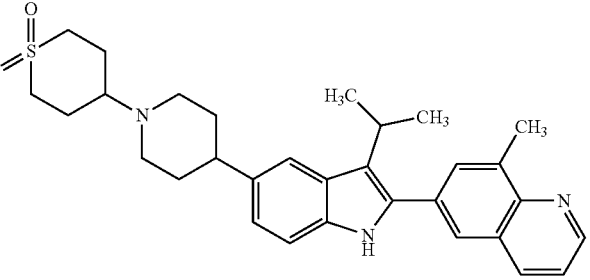 | 516.4 | 1.01 | F |

TABLE 21-continued

| Ex. No. | Structure | Obs. MS Ion | RT | HPLC Method |
|---|---|---|---|---|
| 801 | 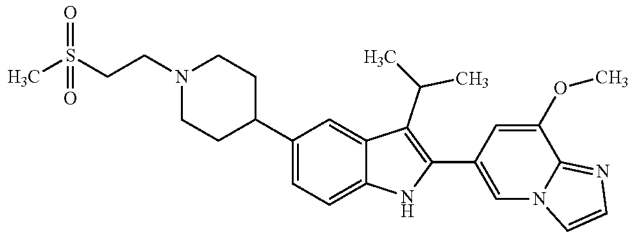 [SMILES: COc1cc(-c2[nH]c3ccc(C4CCN(CCS(C)(=O)=O)CC4)cc3c2C(C)C)cn2ccnc12] | 495.2 | 1.81 | E |

TABLE 22

| Ex. No. | Structure | Obs. MS Ion | RT | HPLC Method |
|---|---|---|---|---|
| 802 | 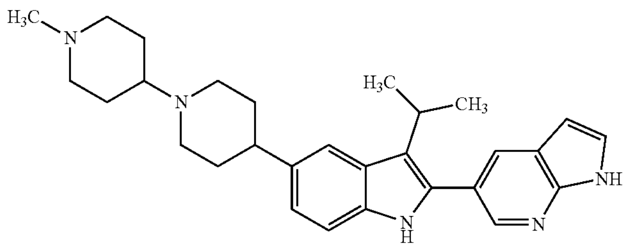 [SMILES: CC(C)c1c(-c2cnc3[nH]ccc3c2)[nH]c2ccc(C3CCN(C4CCN(C)CC4)CC3)cc12] | 456.2 | 1.99 | H |
| 803 | 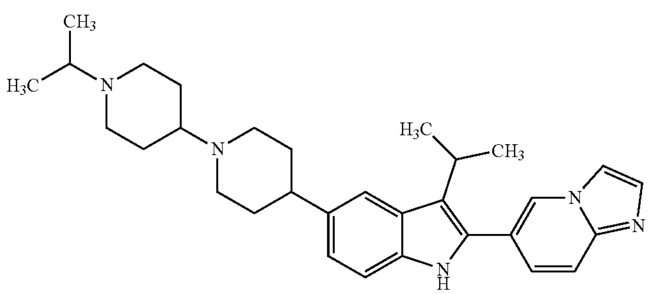 [SMILES: CC(C)c1c(-c2ccc3nccn3c2)[nH]c2ccc(C3CCN(C4CCN(C(C)C)CC4)CC3)cc12] | 484.3 | 1.49 | E |
| 804 | 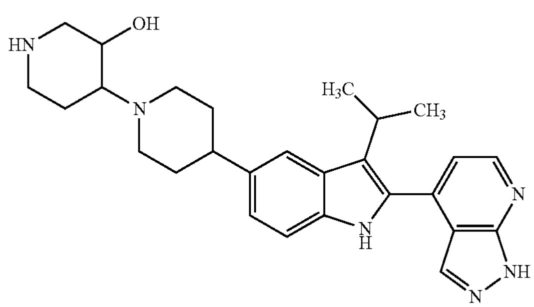 [SMILES: CC(C)c1c(-c2ccnc3[nH]ncc23)[nH]c2ccc(C3CCN(C4CCNCC4O)CC3)cc12] | 459.1 | 0.71 | QC-ACN-TFA-XB |
| 805 | 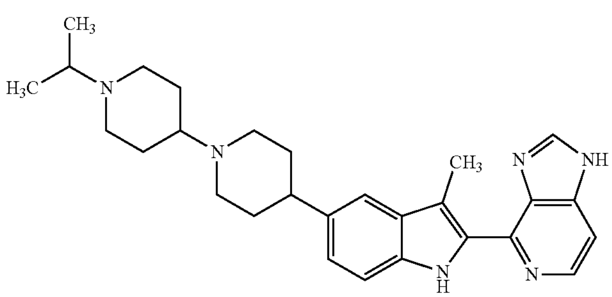 [SMILES: Cc1c(-c2nccc3[nH]cnc23)[nH]c2ccc(C3CCN(C4CCN(C(C)C)CC4)CC3)cc12] | 457.3 | 0.83 | QC-ACN-AA-XB |

TABLE 22-continued

| Ex. No. | Structure | Obs. MS Ion | RT | HPLC Method |
|---|---|---|---|---|
| 806 | 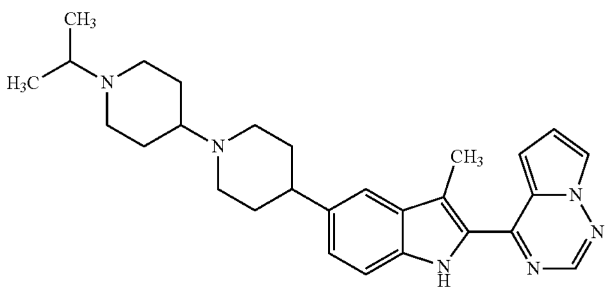 [SMILES: Cc1c(-c2ncnn3cccc23)[nH]c2ccc(C3CCN(C4CCN(C(C)C)CC4)CC3)cc12] | 457.3 | 0.9 | QC-ACN-TFA-XB |
| 807 | 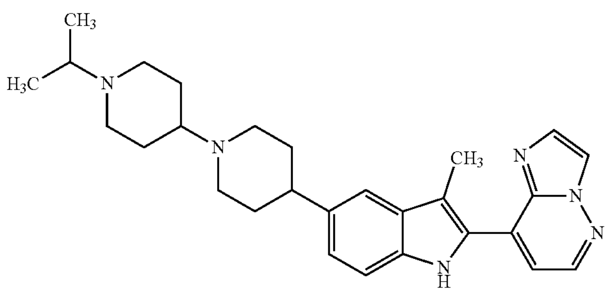 [SMILES: Cc1c(-c2ccnn3ccnc23)[nH]c2ccc(C3CCN(C4CCN(C(C)C)CC4)CC3)cc12] | 457.3 | 0.84 | QC-ACN-TFA-XB |
| 808 | 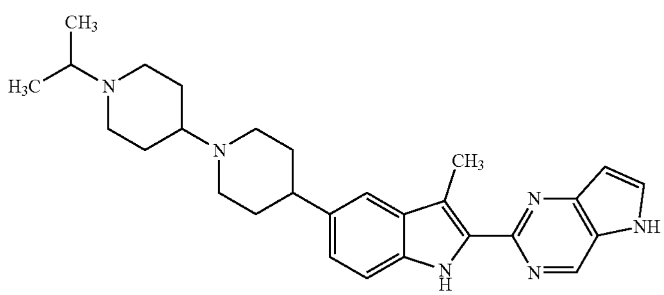 [SMILES: Cc1c(-c2ncc3[nH]ccc3n2)[nH]c2ccc(C3CCN(C4CCN(C(C)C)CC4)CC3)cc12] | 457.2 | 0.63 | QC-ACN-TFA-XB |
| 809 | 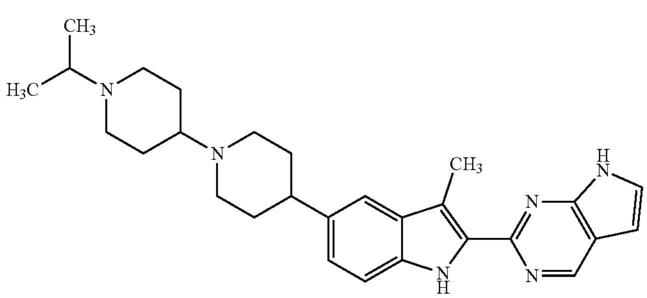 [SMILES: Cc1c(-c2ncc3cc[nH]c3n2)[nH]c2ccc(C3CCN(C4CCN(C(C)C)CC4)CC3)cc12] | 457.3 | 1.25 | QC-ACN-AA-XB |
| 810 | 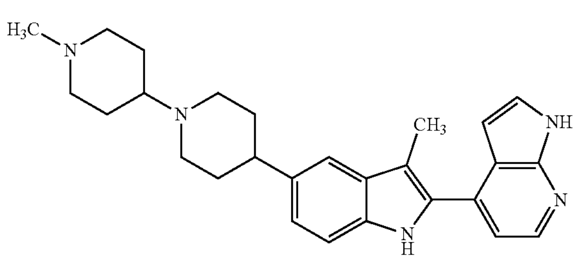 [SMILES: Cc1c(-c2ccnc3[nH]ccc23)[nH]c2ccc(C3CCN(C4CCN(C)CC4)CC3)cc12] | 428.3 | 0.99 | QC-ACN-AA-XB |

TABLE 22-continued

| Ex. No. | Structure | Obs. MS Ion | RT | HPLC Method |
|---|---|---|---|---|
| 811 | 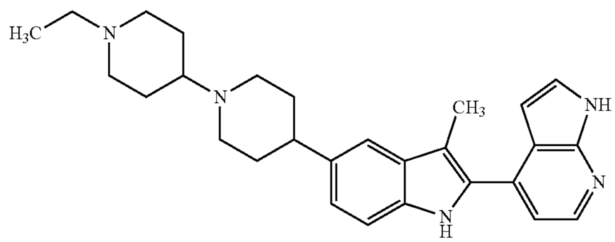 [SMILES: CCN1CCC(N2CCC(c3ccc4[nH]c(-c5ccnc6[nH]ccc56)c(C)c4c3)CC2)CC1] | 442.4 | 0.66 | QC-ACN-TFA-XB |
| 812 | 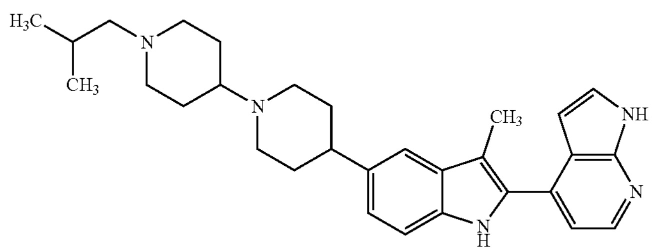 [SMILES: Cc1c(-c2ccnc3[nH]ccc23)[nH]c2ccc(C3CCN(C4CCN(CC(C)C)CC4)CC3)cc12] | 470.4 | 1.34 | QC-ACN-AA-XB |
| 813 | 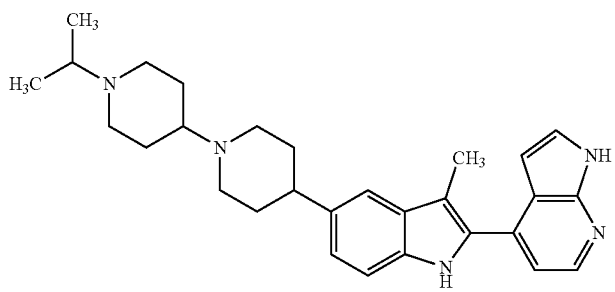 [SMILES: Cc1c(-c2ccnc3[nH]ccc23)[nH]c2ccc(C3CCN(C4CCN(C(C)C)CC4)CC3)cc12] | 456.4 | 0.63 | QC-ACN-TFA-XB |
| 814 | 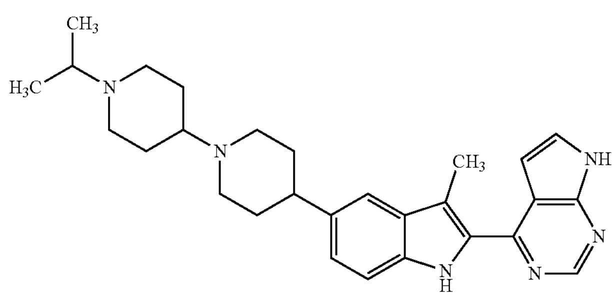 | 457.3 | 1.01 | QC-ACN-AA-XB |
| 815 | 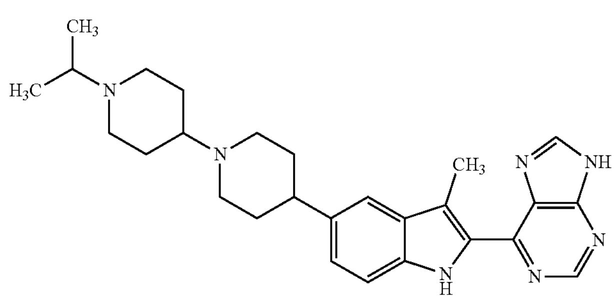 | 458.3 | 0.67 | QC-ACN-TFA-XB |

TABLE 22-continued
| Ex. No. | Structure | Obs. MS Ion | RT | HPLC Method |
|---|---|---|---|---|
| 816 | 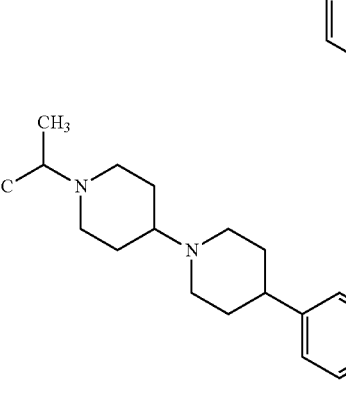 | 458.3 | 0.98 | QC-ACN-AA-XB |
| 817 | 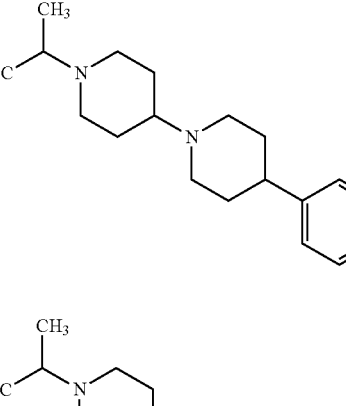 | 472.4 | 1.29 | BCQC-ACN-AA-XB |
| 818 | 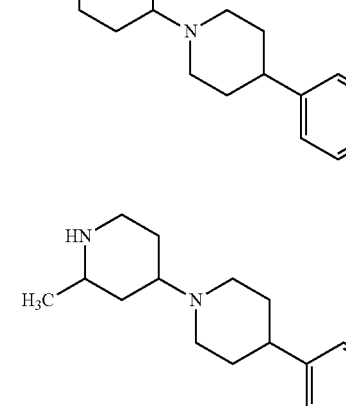 | 472.3 | 1.15 | QC-ACN-AA-XB |
| 819 | 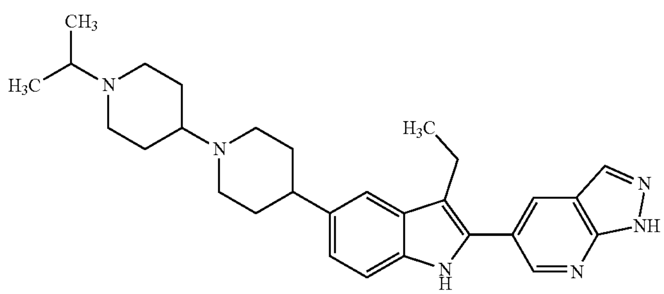 [SMILES: CCc1c(-c2cnc3[nH]ncc3c2)[nH]c2ccc(C3CCN(C4CCN(C(C)C)CC4)CC3)cc12] | 471.3 | 0.86 | QC-ACN-TFA-XB |
| 820 | 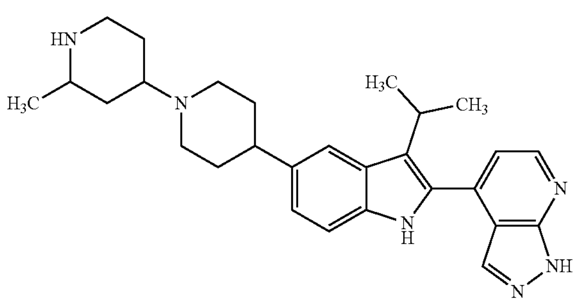 [SMILES: CC1CC(N2CCC(c3ccc4[nH]c(-c5ccnc6[nH]ncc56)c(C(C)C)c4c3)CC2)CCN1] | 457.3 | 0.82 | QC-ACN-TFA-XB |

TABLE 22-continued

| Ex. No. | Structure | Obs. MS Ion | RT | HPLC Method |
|---|---|---|---|---|
| 821 | 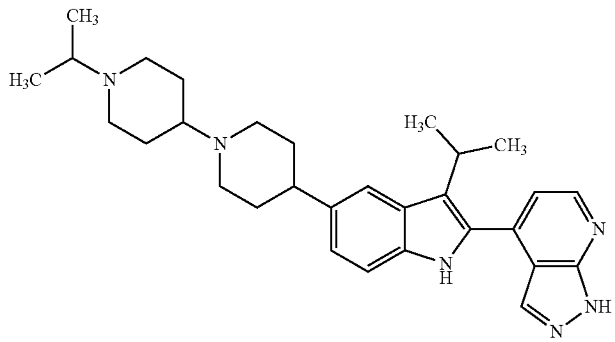 [SMILES: CC(C)c1c(-c2ccnc3[nH]ncc23)[nH]c2ccc(C3CCN(C4CCN(C(C)C)CC4)CC3)cc12] | 485.4 | 1.21 | QC-ACN-AA-XB |
| 822 | 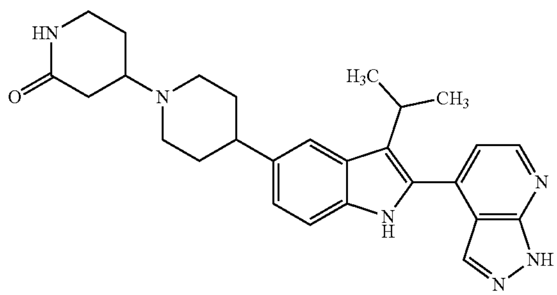 [SMILES: CC(C)c1c(-c2ccnc3[nH]ncc23)[nH]c2ccc(C3CCN(C4CCNC(=O)C4)CC3)cc12] | 457.3 | 1.29 | QC-ACN-TFA-XB |
| 823 | 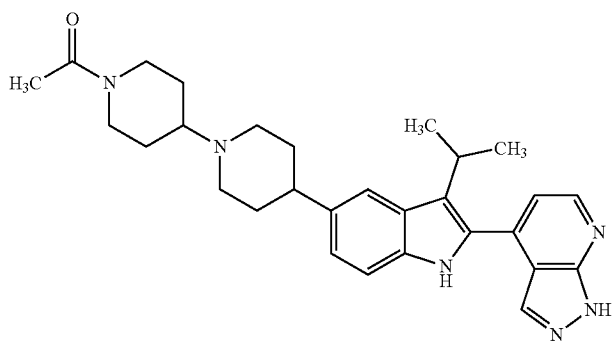 [SMILES: CC(=O)N1CCC(N2CCC(c3ccc4[nH]c(-c5ccnc6[nH]ncc56)c(C(C)C)c4c3)CC2)CC1] | 485.3 | 0.96 | QC-ACN-TFA-XB |
| 824 | 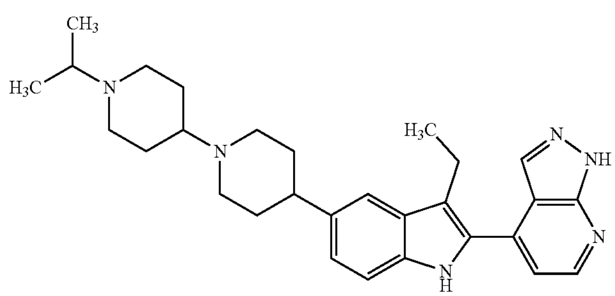 [SMILES: CCc1c(-c2ccnc3[nH]ncc23)[nH]c2ccc(C3CCN(C4CCN(C(C)C)CC4)CC3)cc12] | 471.3 | 1.13 | QC-ACN-AA-XB |
| 825 | 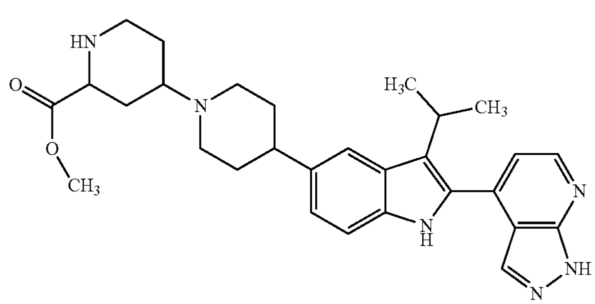 [SMILES: COC(=O)C1CC(N2CCC(c3ccc4[nH]c(-c5ccnc6[nH]ncc56)c(C(C)C)c4c3)CC2)CCN1] | 501.1 | 1.14 | QC-ACN-AA-XB |

TABLE 22-continued

| Ex. No. | Structure | Obs. MS Ion | HPLC RT | Method |
|---|---|---|---|---|
| 826 | 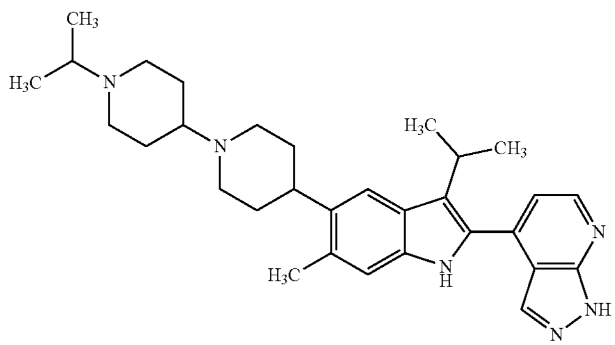 [SMILES: Cc1cc2[nH]c(-c3ccnc4[nH]ncc34)c(C(C)C)c2cc1C1CCN(C2CCN(C(C)C)CC2)CC1] | 499.3 | 0.79 | QC-ACN-TFA-XB |
| 827 | 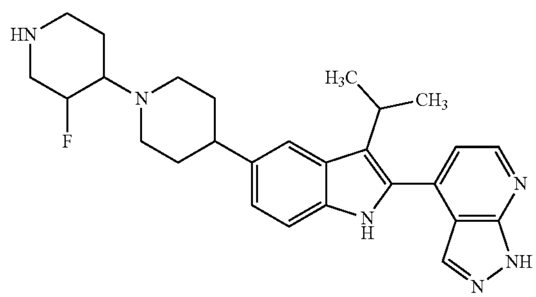 [SMILES: CC(C)c1c(-c2ccnc3[nH]ncc23)[nH]c2ccc(C3CCN(C4CCNCC4F)CC3)cc12] | 461.3 | 1.18 | QC-ACN-AA-XB |
| 828 | 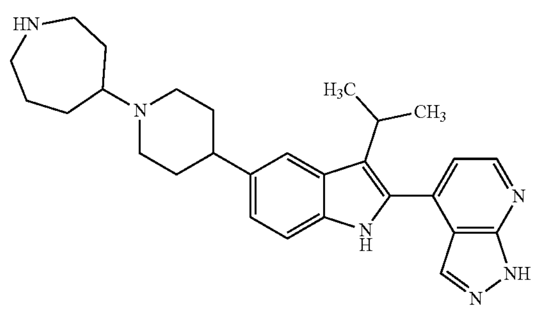 [SMILES: CC(C)c1c(-c2ccnc3[nH]ncc23)[nH]c2ccc(C3CCN(C4CCCNCC4)CC3)cc12] | 457.4 | 0.85 | QC-ACN-TFA-XB |
| 829 | 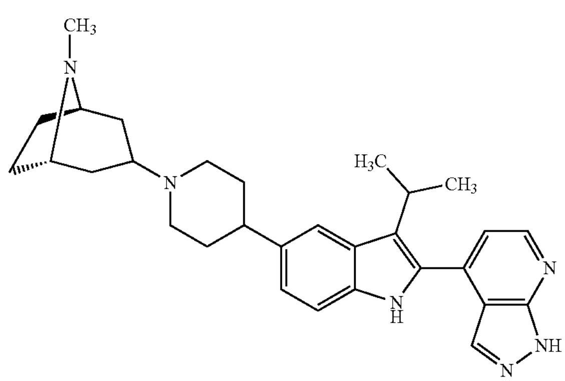 [SMILES: CC(C)c1c(-c2ccnc3[nH]ncc23)[nH]c2ccc(C3CCN(C4C[C@H]5CC[C@@H](C4)N5C)CC3)cc12] | 483.4 | 1.15 | QC-ACN-AA-XB |

TABLE 22-continued

| Ex. No. | Structure | Obs. MS Ion | RT | HPLC Method |
|---|---|---|---|---|
| 830 | 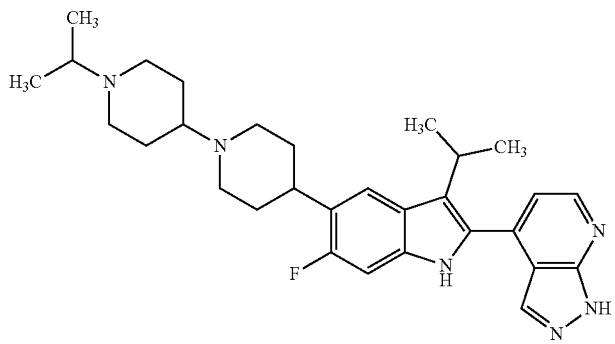 [SMILES: CC(C)c1c(-c2ccnc3[nH]ncc23)[nH]c2cc(F)c(C3CCN(C4CCN(C(C)C)CC4)CC3)cc12] | 503.4 | 1.82 | QC-ACN-AA-XB |
| 831 | 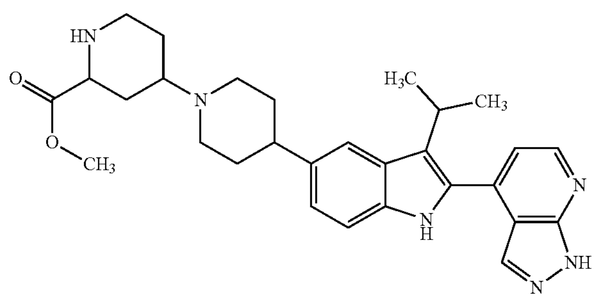 [SMILES: COC(=O)C1CC(N2CCC(c3ccc4[nH]c(-c5ccnc6[nH]ncc56)c(C(C)C)c4c3)CC2)CCN1] | 501 | 0.85 | QC-ACN-TFA-XB |
| 832 | 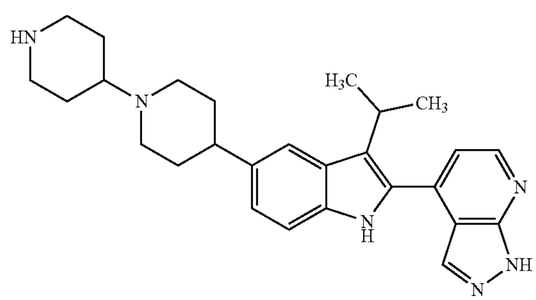 [SMILES: CC(C)c1c(-c2ccnc3[nH]ncc23)[nH]c2ccc(C3CCN(C4CCNCC4)CC3)cc12] | 443.4 | 0.85 | QC-ACN-TFA-XB |
| 833 | 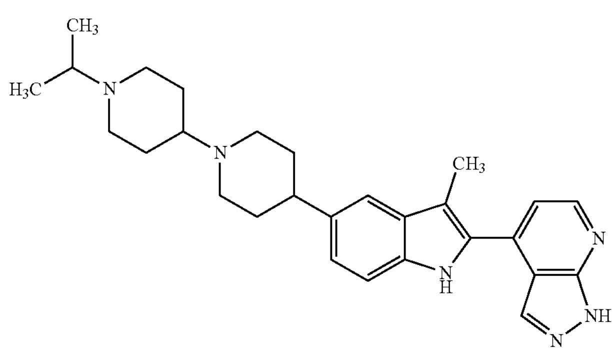 [SMILES: Cc1c(-c2ccnc3[nH]ncc23)[nH]c2ccc(C3CCN(C4CCN(C(C)C)CC4)CC3)cc12] | 457.3 | 0.94 | QC-ACN-AA-XB |

TABLE 22-continued

| Ex. No. | Structure | Obs. MS Ion | RT | HPLC Method |
|---|---|---|---|---|
| 834 | 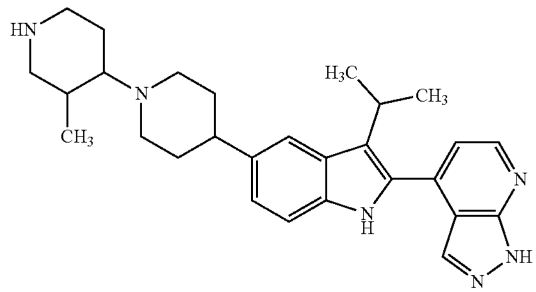 [SMILES: CC(C)c1c(-c2ccnc3[nH]ncc23)[nH]c2ccc(C3CCN(C4CCNCC4C)CC3)cc12] | 457.4 | 1.69 | QC-ACN-AA-XB |
| 835 | 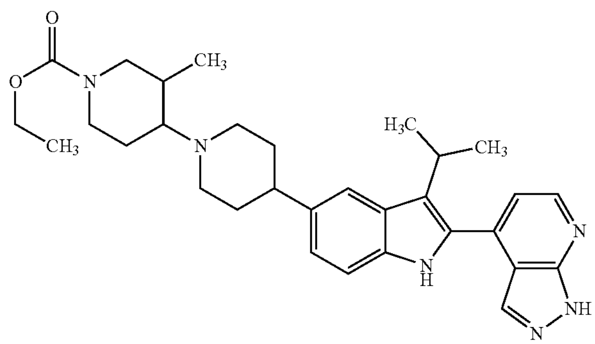 [SMILES: CCOC(=O)N1CCC(N2CCC(c3ccc4[nH]c(-c5ccnc6[nH]ncc56)c(C(C)C)c4c3)CC2)C(C)C1] | 529.2 | 1.49 | QC-ACN-AA-XB |
| 836 | 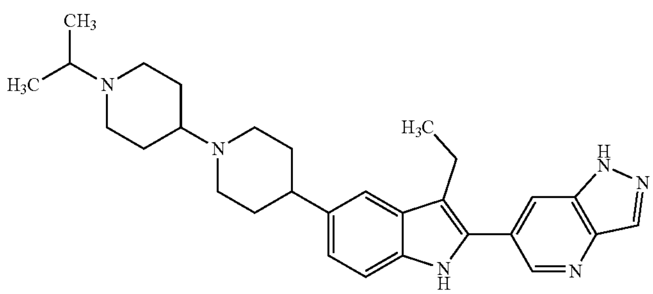 [SMILES: CCc1c(-c2cnc3cn[nH]c3c2)[nH]c2ccc(C3CCN(C4CCN(C(C)C)CC4)CC3)cc12] | 471.4 | 1.1 | QC-ACN-AA-XB |
| 837 | 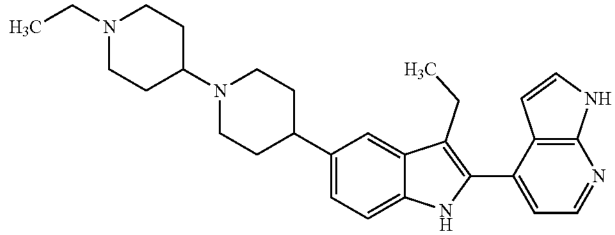 [SMILES: CCc1c(-c2ccnc3[nH]ccc23)[nH]c2ccc(C3CCN(C4CCN(CC)CC4)CC3)cc12] | 456.3 | 1.01 | QC-ACN-AA-XB |
| 838 | 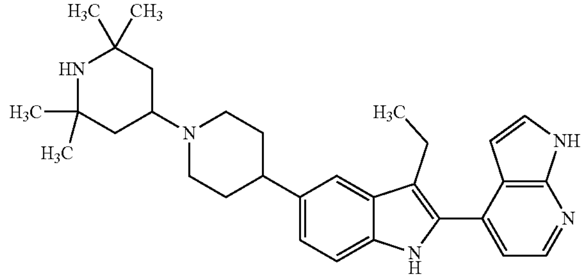 [SMILES: CCc1c(-c2ccnc3[nH]ccc23)[nH]c2ccc(C3CCN(C4CC(C)(C)NC(C)(C)C4)CC3)cc12] | 484.3 | 1.2 | QC-ACN-AA-XB |

TABLE 22-continued

| Ex. No. | Structure | Obs. MS Ion | RT | HPLC Method |
|---|---|---|---|---|
| 839 | 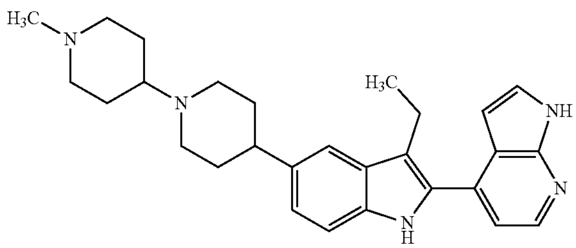 [SMILES: CCc1c(-c2ccnc3[nH]ccc23)[nH]c2ccc(C3CCN(C4CCN(C)CC4)CC3)cc12] | 442.3 | 1.08 | QC-ACN-AA-XB |
| 840 | 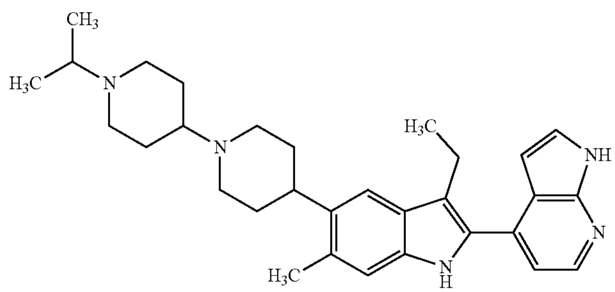 [SMILES: CCc1c(-c2ccnc3[nH]ccc23)[nH]c2cc(C)c(C3CCN(C4CCN(C(C)C)CC4)CC3)cc12] | 484.2 | 0.75 | QC-ACN-TFA-XB |
| 841 | 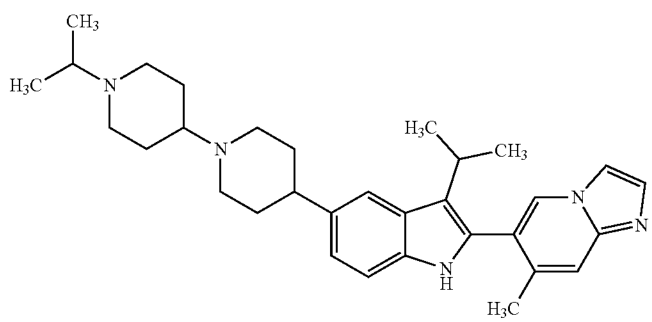 [SMILES: Cc1cc2nccn2cc1-c1[nH]c2ccc(C3CCN(C4CCN(C(C)C)CC4)CC3)cc2c1C(C)C] | 498.2 | 0.77 | QC-ACN-TFA-XB |
| 842 | 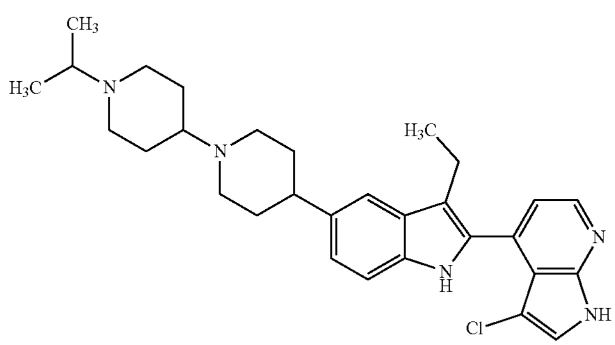 [SMILES: CCc1c(-c2ccnc3[nH]cc(Cl)c23)[nH]c2ccc(C3CCN(C4CCN(C(C)C)CC4)CC3)cc12] | 504.3 | 1.37 | QC-ACN-AA-XB |
| 843 | 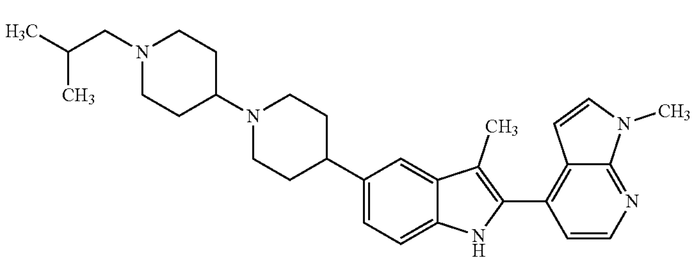 [SMILES: Cc1c(-c2ccnc3c2ccn3C)[nH]c2ccc(C3CCN(C4CCN(CC(C)C)CC4)CC3)cc12] | 484.2 | 0.74 | QC-ACN-TFA-XB |

TABLE 22-continued

| Ex. No. | Structure | Obs. MS Ion | RT | HPLC Method |
|---|---|---|---|---|
| 844 | 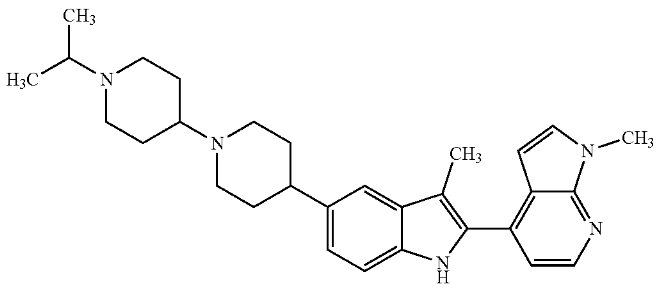 [SMILES: Cc1c(-c2ccnc3c2ccn3C)[nH]c2ccc(C3CCN(C4CCN(C(C)C)CC4)CC3)cc12] | 470.3 | 0.69 | QC-ACN-TFA-XB |
| 845 | 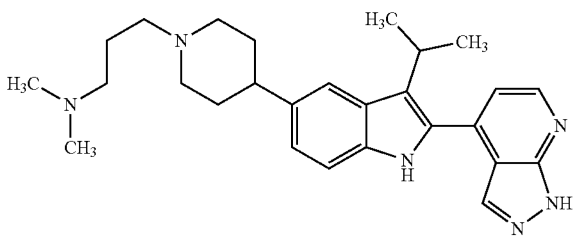 [SMILES: CC(C)c1c(-c2ccnc3[nH]ncc23)[nH]c2ccc(C3CCN(CCCN(C)C)CC3)cc12] | 445.4 | 0.88 | QC-ACN-AA-XB |
| 846 | 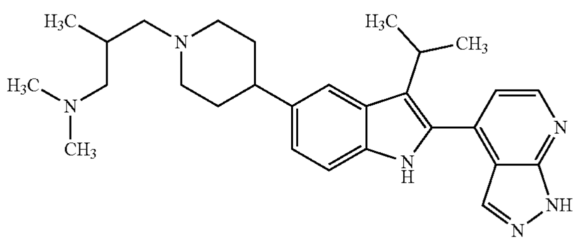 [SMILES: CC(CN(C)C)CN1CCC(c2ccc3[nH]c(-c4ccnc5[nH]ncc45)c(C(C)C)c3c2)CC1] | 459.3 | 1.02 | QC-ACN-AA-XB |
| 847 | 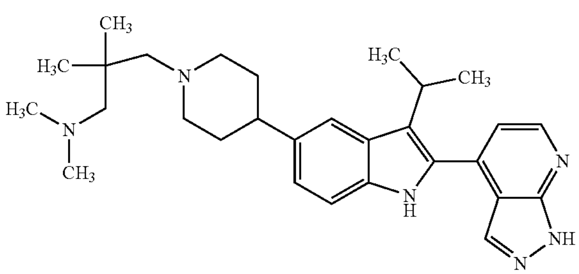 [SMILES: CC(C)c1c(-c2ccnc3[nH]ncc23)[nH]c2ccc(C3CCN(CC(C)(C)CN(C)C)CC3)cc12] | 473.3 | 0.76 | QC-ACN-TFA-XB |
| 848 | 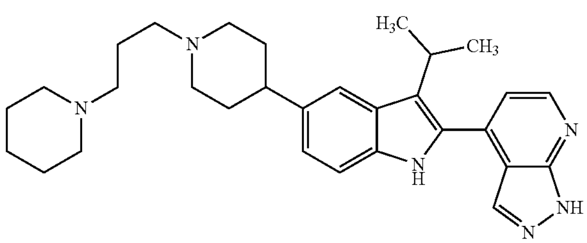 [SMILES: CC(C)c1c(-c2ccnc3[nH]ncc23)[nH]c2ccc(C3CCN(CCCN4CCCCC4)CC3)cc12] | 485.4 | 0.86 | QC-ACN-TFA-XB |
| 849 | 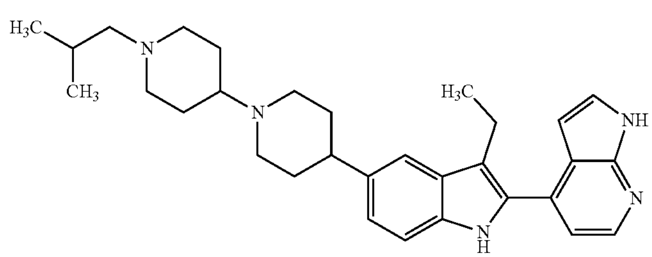 [SMILES: CCc1c(-c2ccnc3[nH]ccc23)[nH]c2ccc(C3CCN(C4CCN(CC(C)C)CC4)CC3)cc12] | 484.4 | 0.79 | QC-ACN-TFA-XB |

TABLE 22-continued

| Ex. No. | Structure | Obs. MS Ion | RT | HPLC Method |
|---|---|---|---|---|
| 850 | 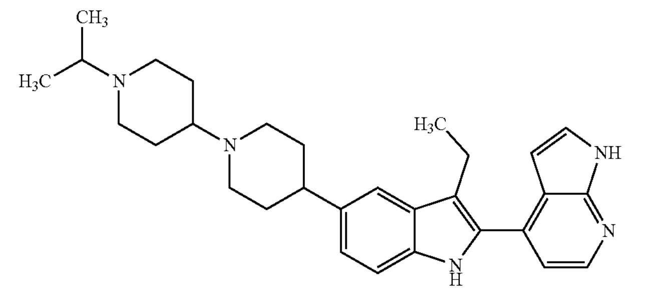 [SMILES: CCc1c(-c2ccnc3[nH]ccc23)[nH]c2ccc(C3CCN(C4CCN(C(C)C)CC4)CC3)cc12] | 470.4 | 1.26 | QC-ACN-AA-XB |
| 851 | 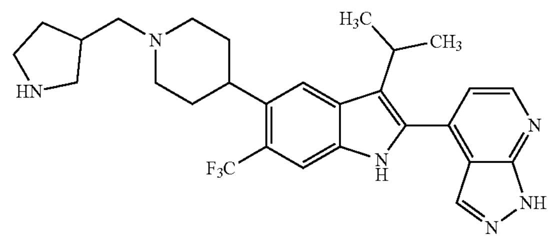 [SMILES: CC(C)c1c(-c2ccnc3[nH]ncc23)[nH]c2cc(C(F)(F)F)c(C3CCN(CC4CCNC4)CC3)cc12] | 511.3 | 1 | QC-ACN-TFA-XB |
| 852 | 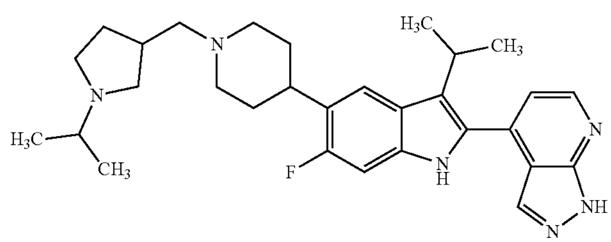 [SMILES: CC(C)c1c(-c2ccnc3[nH]ncc23)[nH]c2cc(F)c(C3CCN(CC4CCN(C(C)C)C4)CC3)cc12] | 503.4 | 0.93 | QC-ACN-TFA-XB |
| 853 | 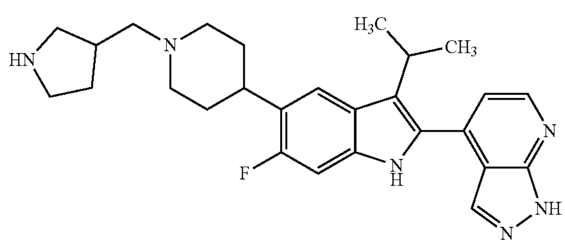 [SMILES: CC(C)c1c(-c2ccnc3[nH]ncc23)[nH]c2cc(F)c(C3CCN(CC4CCNC4)CC3)cc12] | 461.4 | 1.91 | QC-ACN-AA-XB |
| 854 | 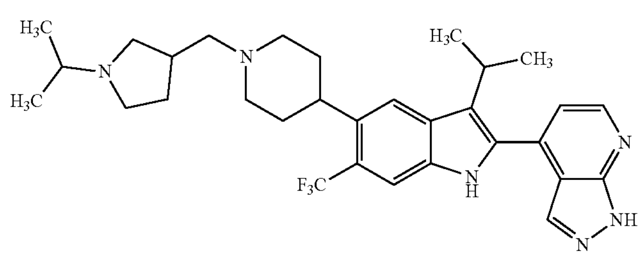 [SMILES: CC(C)c1c(-c2ccnc3[nH]ncc23)[nH]c2cc(C(F)(F)F)c(C3CCN(CC4CCN(C(C)C)C4)CC3)cc12] | 553.1 | 1.4 | QC-ACN-AA-XB |
| 855 | 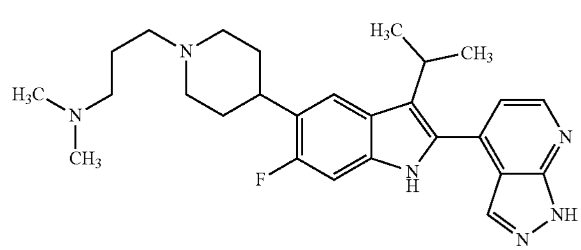 [SMILES: CC(C)c1c(-c2ccnc3[nH]ncc23)[nH]c2cc(F)c(C3CCN(CCCN(C)C)CC3)cc12] | 463.4 | 0.87 | QC-ACN-TFA-XB |

TABLE 22-continued
| Ex. No. | Structure | Obs. MS Ion | RT | HPLC Method |
|---|---|---|---|---|
| 856 | 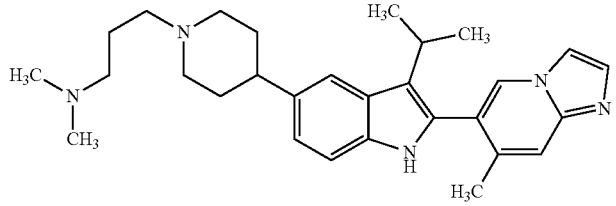 [SMILES: Cc1cc2nccn2cc1-c1[nH]c2ccc(C3CCN(CCCN(C)C)CC3)cc2c1C(C)C] | 458.3 | 0.73 | QC-ACN-TFA-XB |
| 857 | 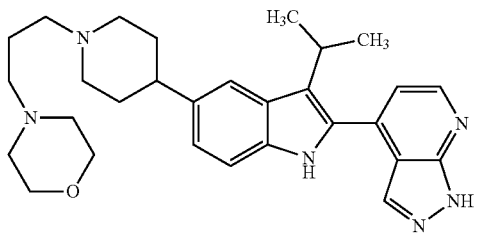 [SMILES: CC(C)c1c(-c2ccnc3[nH]ncc23)[nH]c2ccc(C3CCN(CCCN4CCOCC4)CC3)cc12] | 487.3 | 1.2 | QC-ACN-AA-XB |
| 858 | 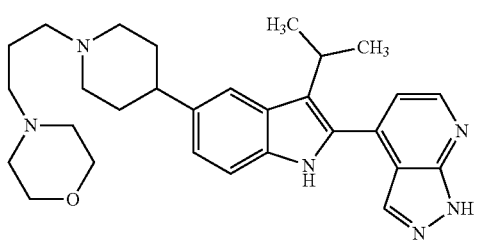 [SMILES: CC(C)c1c(-c2ccnc3[nH]ncc23)[nH]c2ccc(C3CCN(CCCN4CCOCC4)CC3)cc12] | 487.2 | 0.75 | QC-ACN-TFA-XB |
TABLE 23
| Ex. No. | Structure | Obs. MS Ion | RT | HPLC Method |
|---|---|---|---|---|
| 859 | 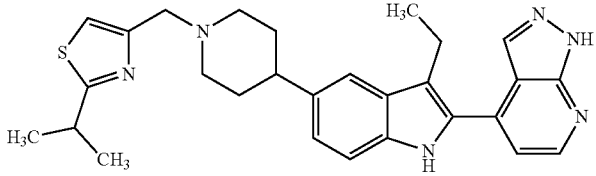 [SMILES: CCc1c(-c2ccnc3[nH]ncc23)[nH]c2ccc(C3CCN(Cc4csc(C(C)C)n4)CC3)cc12] | 485.3 | 1.19 | QC-ACN-TFA-XB |
| 860 | 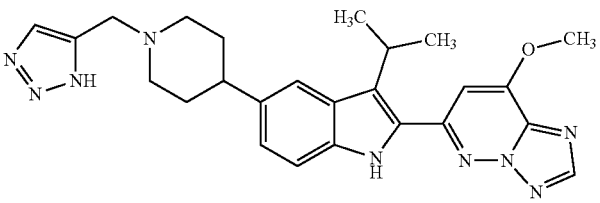 [SMILES: COc1cc(-c2[nH]c3ccc(C4CCN(Cc5cnn[nH]5)CC4)cc3c2C(C)C)nn2ncnc12] | 472.3 | 1.41 | QC-ACN-AA-XB |
| 861 | 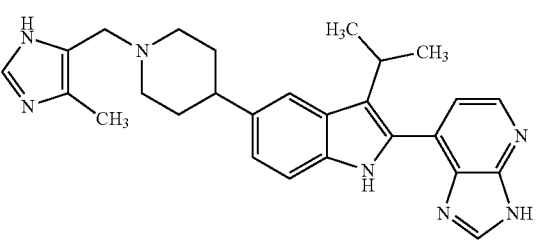 [SMILES: Cc1nc[nH]c1CN1CCC(c2ccc3[nH]c(-c4ccnc5[nH]cnc45)c(C(C)C)c3c2)CC1] | 454.4 | 0.95 | QC-ACN-AA-XB |

TABLE 23-continued

| Ex. No. | Structure | Obs. MS Ion | RT | HPLC Method |
|---|---|---|---|---|
| 862 | 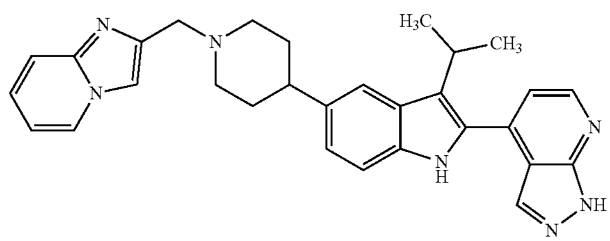 [SMILES: CC(C)c1c(-c2ccnc3[nH]ncc23)[nH]c2ccc(C3CCN(Cc4cn5ccccc5n4)CC3)cc12] | 490.2 | 1.19 | QC-ACN-AA-XB |
| 863 | 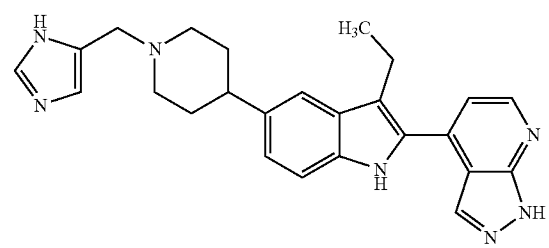 [SMILES: CCc1c(-c2ccnc3[nH]ncc23)[nH]c2ccc(C3CCN(Cc4cnc[nH]4)CC3)cc12] | 426.2 | 0.63 | QC-ACN-TFA-XB |
| 864 | 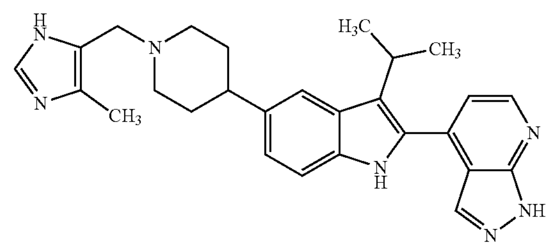 [SMILES: Cc1nc[nH]c1CN1CCC(c2ccc3[nH]c(-c4ccnc5[nH]ncc45)c(C(C)C)c3c2)CC1] | 454.4 | 0.77 | QC-ACN-TFA-XB |
| 865 | 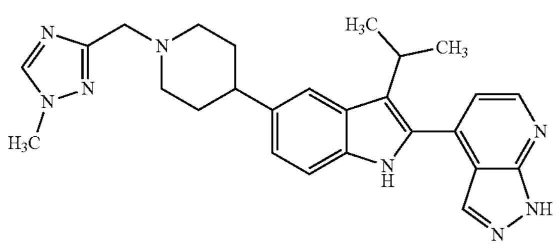 [SMILES: CC(C)c1c(-c2ccnc3[nH]ncc23)[nH]c2ccc(C3CCN(Cc4ncn(C)n4)CC3)cc12] | 455.2 | 0.9 | QC-ACN-TFA-XB |
| 866 | 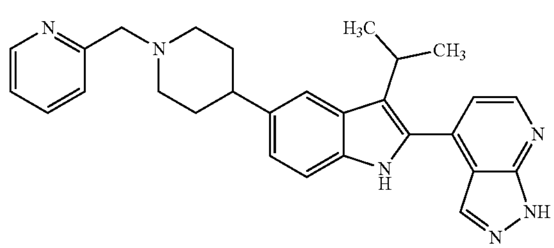 [SMILES: CC(C)c1c(-c2ccnc3[nH]ncc23)[nH]c2ccc(C3CCN(Cc4ccccn4)CC3)cc12] | 451.3 | 1.38 | QC-ACN-AA-XB |
| 867 | 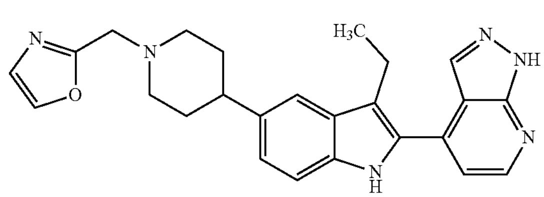 [SMILES: CCc1c(-c2ccnc3[nH]ncc23)[nH]c2ccc(C3CCN(Cc4ncco4)CC3)cc12] | 427.2 | 0.81 | QC-ACN-TFA-XB |

TABLE 23-continued

| Ex. No. | Structure | Obs. MS Ion | RT | HPLC Method |
|---|---|---|---|---|
| 868 | 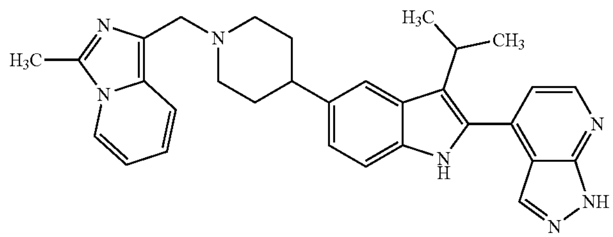 [SMILES: Cc1nc(CN2CCC(c3ccc4[nH]c(-c5ccnc6[nH]ncc56)c(C(C)C)c4c3)CC2)c2ccccn12] | 504.4 | 1.0 | QC-ACN-TFA-XB |
| 869 | 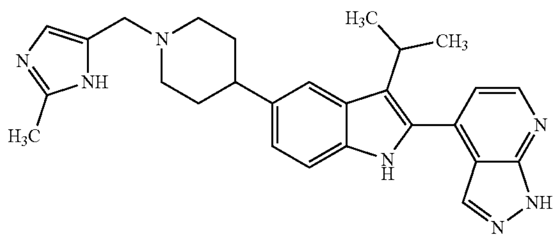 [SMILES: Cc1ncc(CN2CCC(c3ccc4[nH]c(-c5ccnc6[nH]ncc56)c(C(C)C)c4c3)CC2)[nH]1] | 454.4 | 0.75 | QC-ACN-TFA-XB |
| 870 | 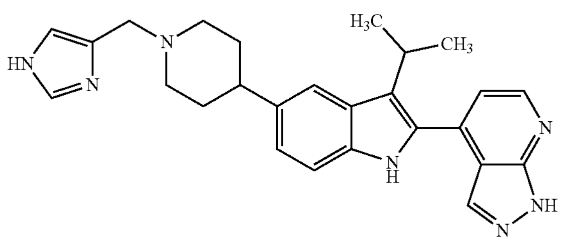 [SMILES: CC(C)c1c(-c2ccnc3[nH]ncc23)[nH]c2ccc(C3CCN(Cc4c[nH]cn4)CC3)cc12] | 440.2 | 0.73 | QC-ACN-TFA-XB |
| 871 | 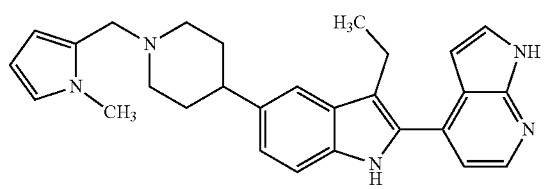 [SMILES: CCc1c(-c2ccnc3[nH]ccc23)[nH]c2ccc(C3CCN(Cc4cccn4C)CC3)cc12] | 438.3 | 1.64 | QC-ACN-AA-XB |
| 872 | 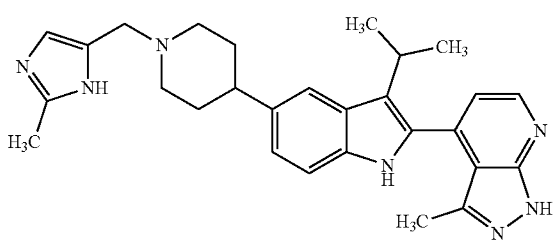 [SMILES: Cc1ncc(CN2CCC(c3ccc4[nH]c(-c5ccnc6[nH]nc(C)c56)c(C(C)C)c4c3)CC2)[nH]1] | 468.3 | 0.77 | QC-ACN-TFA-XB |
| 873 | 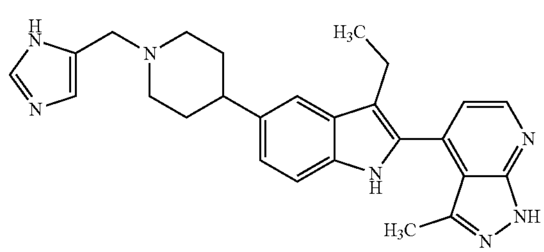 [SMILES: CCc1c(-c2ccnc3[nH]nc(C)c23)[nH]c2ccc(C3CCN(Cc4cnc[nH]4)CC3)cc12] | 440.3 | 1.04 | QC-ACN-AA-XB |

TABLE 23-continued

| Ex. No. | Structure | Obs. MS Ion | RT | HPLC Method |
|---|---|---|---|---|
| 874 | 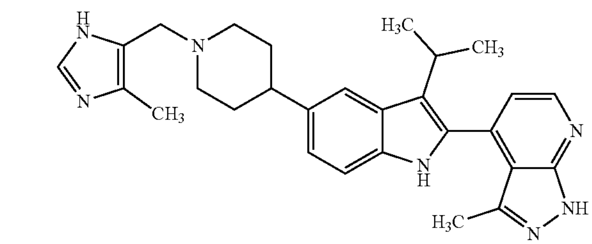 [SMILES: Cc1nc[nH]c1CN1CCC(c2ccc3[nH]c(-c4ccnc5[nH]nc(C)c45)c(C(C)C)c3c2)CC1] | 468.3 | 0.89 | QC-ACN-TFA-XB |
| 875 | 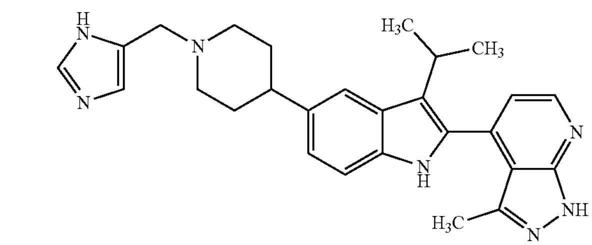 [SMILES: Cc1n[nH]c2nccc(-c3[nH]c4ccc(C5CCN(Cc6cnc[nH]6)CC5)cc4c3C(C)C)c12] | 454.3 | 0.94 | QC-ACN-TFA-XB |
| 876 | 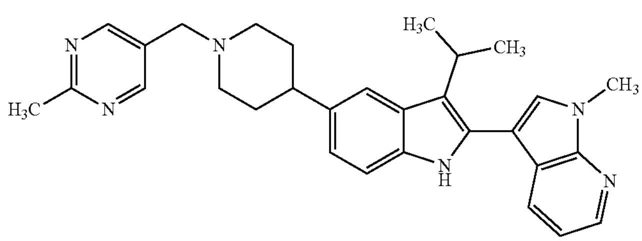 | 479 | 1.34 | QC-ACN-TFA-XB |
| 877 | 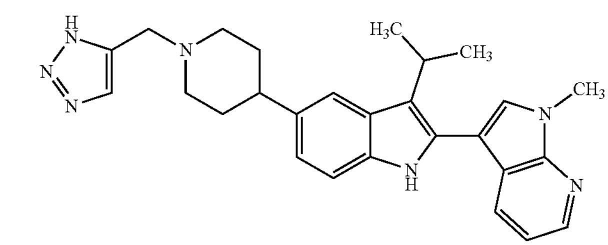 [SMILES: CC(C)c1c(-c2cn(C)c3ncccc23)[nH]c2ccc(C3CCN(Cc4cnn[nH]4)CC3)cc12] | 454.1 | 1.5 | QC-ACN-AA-XB |
| 878 | 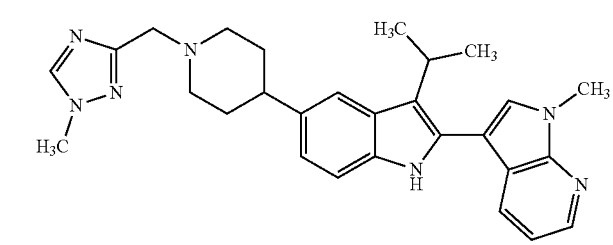 [SMILES: CC(C)c1c(-c2cn(C)c3ncccc23)[nH]c2ccc(C3CCN(Cc4ncn(C)n4)CC3)cc12] | 468.2 | 1.59 | QC-ACN-AA-XB |
| 879 | 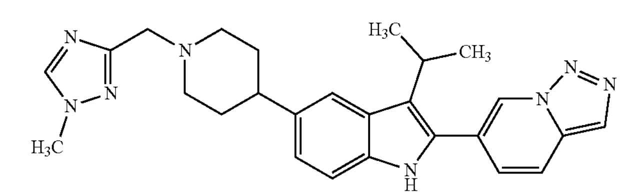 [SMILES: CC(C)c1c(-c2ccc3cnnn3c2)[nH]c2ccc(C3CCN(Cc4ncn(C)n4)CC3)cc12] | 455 | 1.55 | QC-ACN-AA-XB |

TABLE 23-continued

| Ex. No. | Structure | Obs. MS Ion | RT | HPLC Method |
|---|---|---|---|---|
| 880 | 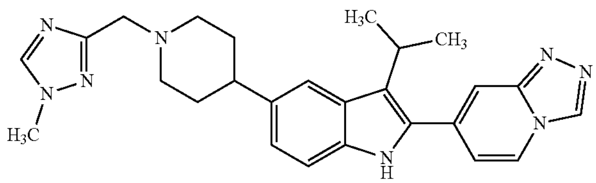 [SMILES: CC(C)c1c(-c2ccn3cnnc3c2)[nH]c2ccc(C3CCN(Cc4ncn(C)n4)CC3)cc12] | 455.2 | 1.33 | QC-ACN-AA-XB |
| 881 | 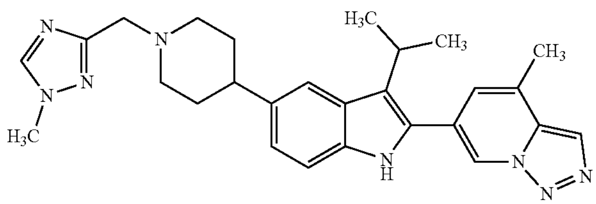 [SMILES: Cc1cc(-c2[nH]c3ccc(C4CCN(Cc5ncn(C)n5)CC4)cc3c2C(C)C)cn2nncc12] | 469.4 | 1.5 | QC-ACN-AA-XB |
| 882 | 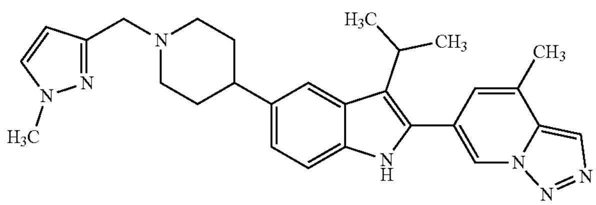 [SMILES: Cc1cc(-c2[nH]c3ccc(C4CCN(Cc5ccn(C)n5)CC4)cc3c2C(C)C)cn2nncc12] | 468 | 1.48 | QC-ACN-TFA-XB |
| 883 | 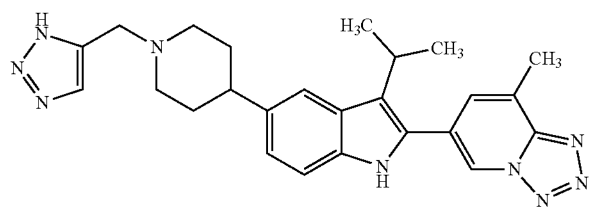 [SMILES: Cc1cc(-c2[nH]c3ccc(C4CCN(Cc5cnn[nH]5)CC4)cc3c2C(C)C)cn2nnnc12] | 455.9 | 1.53 | QC-ACN-AA-XB |
| 884 | 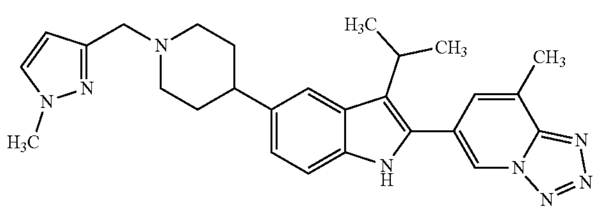 [SMILES: Cc1cc(-c2[nH]c3ccc(C4CCN(Cc5ccn(C)n5)CC4)cc3c2C(C)C)cn2nnnc12] | 469 | 1.44 | QC-ACN-AA-XB |
| 885 | 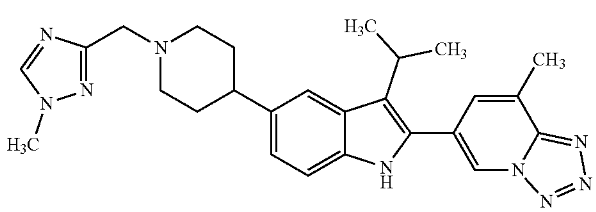 [SMILES: Cc1cc(-c2[nH]c3ccc(C4CCN(Cc5ncn(C)n5)CC4)cc3c2C(C)C)cn2nnnc12] | 470 | 1.53 | QC-ACN-AA-XB |
| 886 | 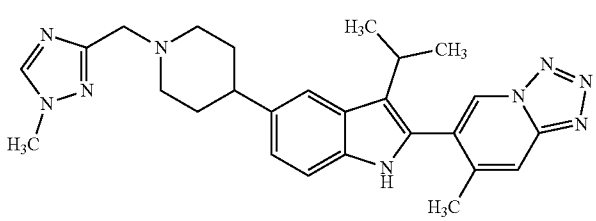 [SMILES: Cc1cc2nnnn2cc1-c1[nH]c2ccc(C3CCN(Cc4ncn(C)n4)CC3)cc2c1C(C)C] | 470 | 1.17 | QC-ACN-TFA-XB |

TABLE 23-continued

| Ex. No. | Structure | Obs. MS Ion | RT | HPLC Method |
|---|---|---|---|---|
| 887 | 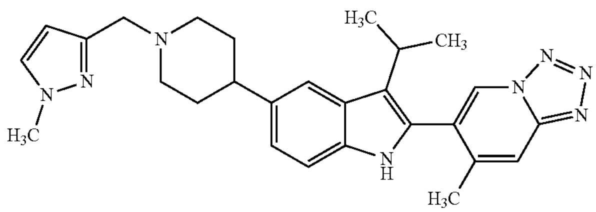 [SMILES: Cc1cc2nnnn2cc1-c1[nH]c2ccc(C3CCN(Cc4ccn(C)n4)CC3)cc2c1C(C)C] | 469.4 | 1.43 | QC-ACN-AA-XB |
| 888 | 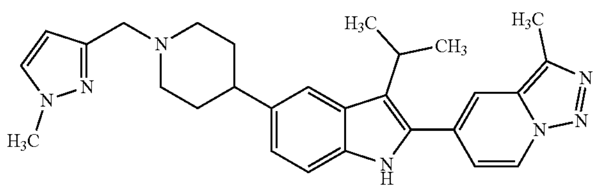 [SMILES: Cc1nnn2ccc(-c3[nH]c4ccc(C5CCN(Cc6ccn(C)n6)CC5)cc4c3C(C)C)cc12] | 468 | 1.42 | QC-ACN-AA-XB |
| 889 | 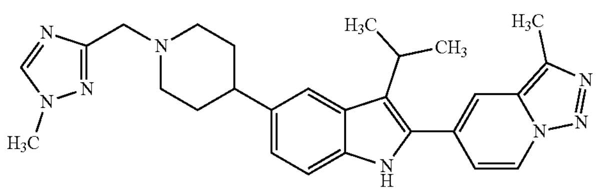 [SMILES: Cc1nnn2ccc(-c3[nH]c4ccc(C5CCN(Cc6ncn(C)n6)CC5)cc4c3C(C)C)cc12] | 469.4 | 1.38 | QC-ACN-AA-XB |
| 890 | 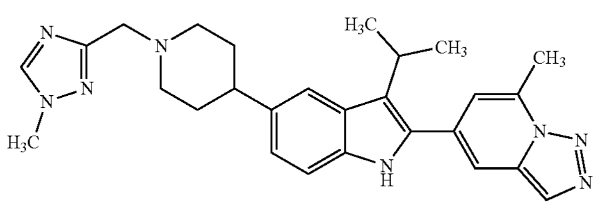 [SMILES: Cc1cc(-c2[nH]c3ccc(C4CCN(Cc5ncn(C)n5)CC4)cc3c2C(C)C)cc2cnnn12] | 469.4 | 1.25 | QC-ACN-TFA-XB |
| 891 | 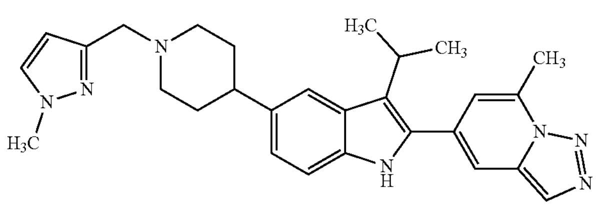 [SMILES: Cc1cc(-c2[nH]c3ccc(C4CCN(Cc5ccn(C)n5)CC4)cc3c2C(C)C)cc2cnnn12] | 468 | 1.4 | QC-ACN-AA-XB |
| 892 | 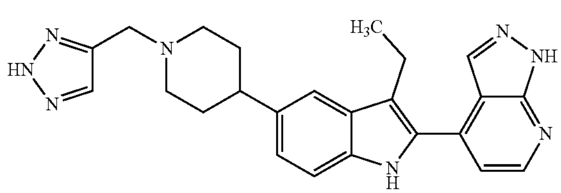 [SMILES: CCc1c(-c2ccnc3[nH]ncc23)[nH]c2ccc(C3CCN(Cc4cn[nH]n4)CC3)cc12] | 427.3 | 0.74 | QC-ACN-TFA-XB |
| 893 | 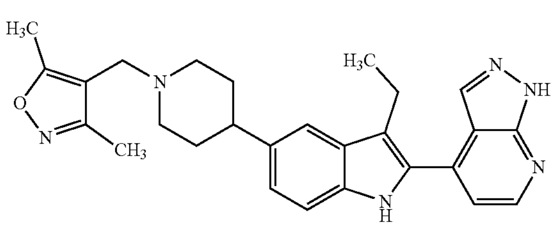 [SMILES: CCc1c(-c2ccnc3[nH]ncc23)[nH]c2ccc(C3CCN(Cc4c(C)noc4C)CC3)cc12] | 455.2 | 0.92 | QC-ACN-TFA-XB |

TABLE 23-continued

| Ex. No. | Structure | Obs. MS Ion | RT | HPLC Method |
|---|---|---|---|---|
| 894 | 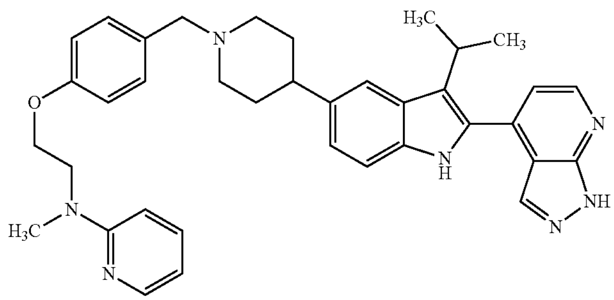 [SMILES: CC(C)c1c(-c2ccnc3[nH]ncc23)[nH]c2ccc(C3CCN(Cc4ccc(OCCN(C)c5ccccn5)cc4)CC3)cc12] | 600.5 | 1.98 | QC-ACN-AA-XB |
| 895 | 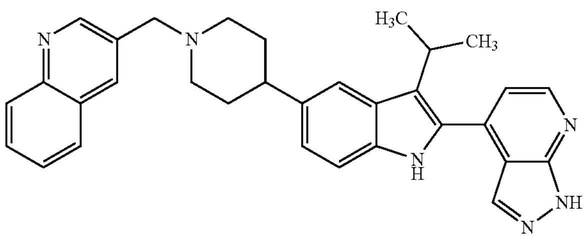 [SMILES: CC(C)c1c(-c2ccnc3[nH]ncc23)[nH]c2ccc(C3CCN(Cc4cnc5ccccc5c4)CC3)cc12] | 501.2 | 1.95 | QC-ACN-AA-XB |
| 896 | 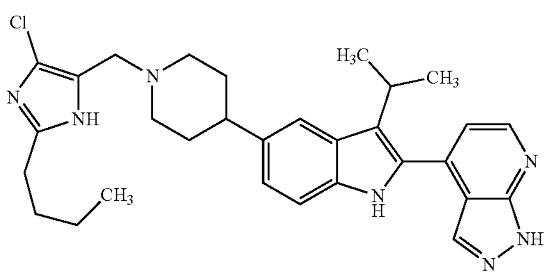 [SMILES: CCCCc1nc(Cl)c(CN2CCC(c3ccc4[nH]c(-c5ccnc6[nH]ncc56)c(C(C)C)c4c3)CC2)[nH]1] | 530.1 | 1.28 | QC-ACN-TFA-XB |
| 897 | 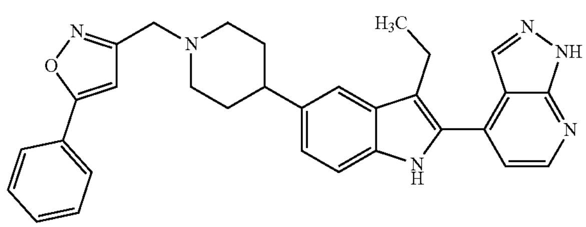 [SMILES: CCc1c(-c2ccnc3[nH]ncc23)[nH]c2ccc(C3CCN(Cc4cc(-c5ccccc5)on4)CC3)cc12] | 503.3 | 1.26 | QC-ACN-TFA-XB |
| 898 | 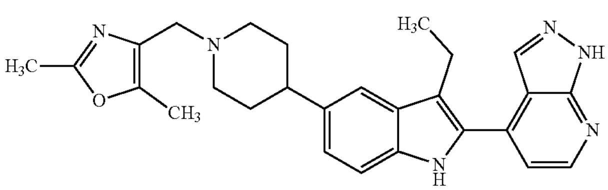 [SMILES: CCc1c(-c2ccnc3[nH]ncc23)[nH]c2ccc(C3CCN(Cc4nc(C)oc4C)CC3)cc12] | 455.3 | 0.96 | QC-ACN-TFA-XB |
| 899 | 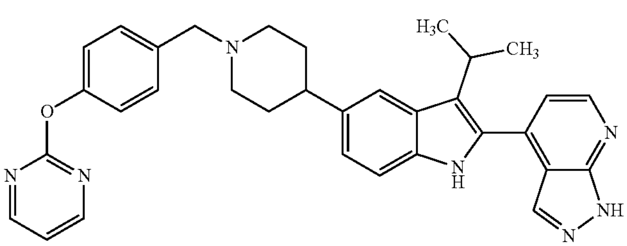 [SMILES: CC(C)c1c(-c2ccnc3[nH]ncc23)[nH]c2ccc(C3CCN(Cc4ccc(Oc5ncccn5)cc4)CC3)cc12] | 544.4 | 1.61 | QC-ACN-AA-XB |

TABLE 23-continued

| Ex. No. | Structure | Obs. MS Ion | RT | HPLC Method |
|---|---|---|---|---|
| 900 | 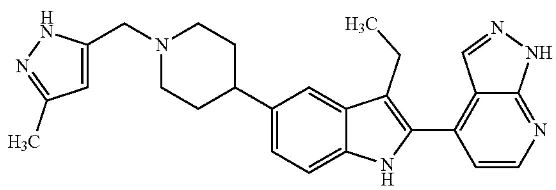 [SMILES: CCc1c(-c2ccnc3[nH]ncc23)[nH]c2ccc(C3CCN(Cc4cc(C)n[nH]4)CC3)cc12] | 440.3 | 0.88 | QC-ACN-TFA-XB |
| 901 | 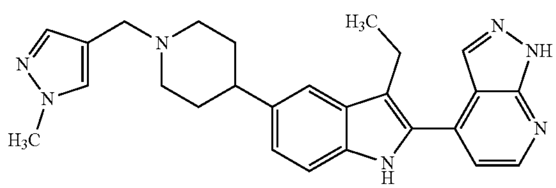 [SMILES: CCc1c(-c2ccnc3[nH]ncc23)[nH]c2ccc(C3CCN(Cc4cnn(C)c4)CC3)cc12] | 440.2 | 0.95 | QC-ACN-TFA-XB |
| 902 | 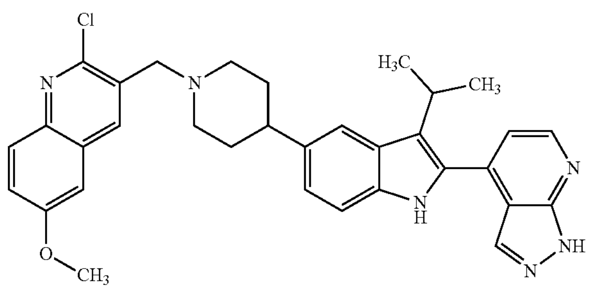 [SMILES: COc1ccc2nc(Cl)c(CN3CCC(c4ccc5[nH]c(-c6ccnc7[nH]ncc67)c(C(C)C)c5c4)CC3)cc2c1] | 565.4 | 2.44 | QC-ACN-AA-XB |
| 903 | 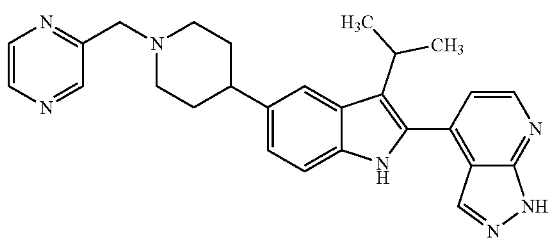 [SMILES: CC(C)c1c(-c2ccnc3[nH]ncc23)[nH]c2ccc(C3CCN(Cc4cnccn4)CC3)cc12] | 452.4 | 0.9 | QC-ACN-TFA-XB |
| 904 | 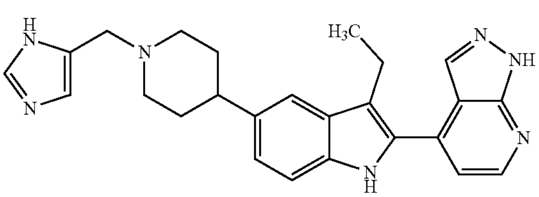 [SMILES: CCc1c(-c2ccnc3[nH]ncc23)[nH]c2ccc(C3CCN(Cc4cnc[nH]4)CC3)cc12] | 426.1 | 1.0 | QC-ACN-AA-XB |
| 905 | 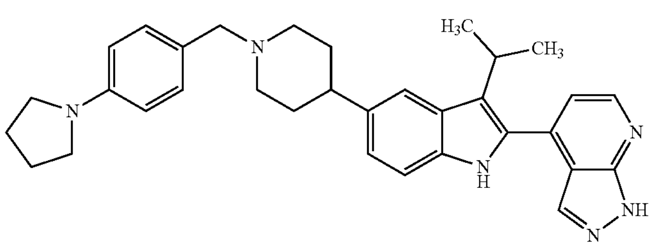 [SMILES: CC(C)c1c(-c2ccnc3[nH]ncc23)[nH]c2ccc(C3CCN(Cc4ccc(N5CCCC5)cc4)CC3)cc12] | 519.4 | 1.88 | QC-ACN-AA-XB |

TABLE 23-continued
| Ex. No. | Structure | Obs. MS Ion | RT | HPLC Method |
|---|---|---|---|---|
| 906 | 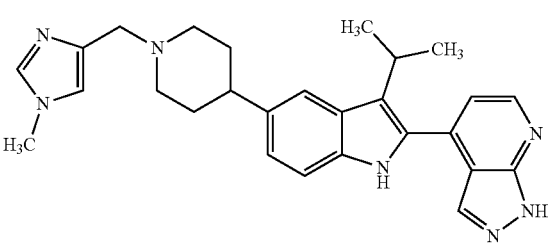 [SMILES: CC(C)c1c(-c2ccnc3[nH]ncc23)[nH]c2ccc(C3CCN(Cc4cn(C)cn4)CC3)cc12] | 454.4 | 1.12 | QC-ACN-AA-XB |
| 907 | 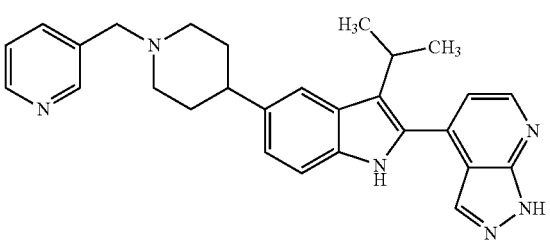 [SMILES: CC(C)c1c(-c2ccnc3[nH]ncc23)[nH]c2ccc(C3CCN(Cc4cccnc4)CC3)cc12] | 451.4 | 1.66 | QC-ACN-AA-XB |
| 908 | 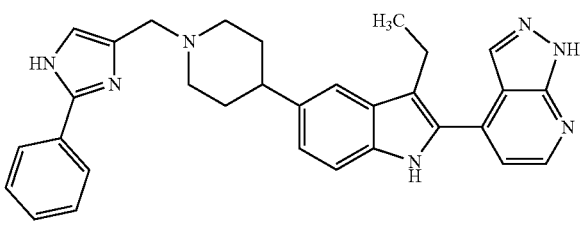 [SMILES: CCc1c(-c2ccnc3[nH]ncc23)[nH]c2ccc(C3CCN(Cc4c[nH]c(-c5ccccc5)n4)CC3)cc12] | 502.3 | 1.37 | QC-ACN-AA-XB |
| 909 | 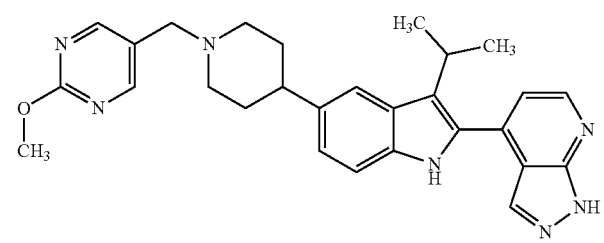 [SMILES: COc1ncc(CN2CCC(c3ccc4[nH]c(-c5ccnc6[nH]ncc56)c(C(C)C)c4c3)CC2)cn1] | 482.4 | 0.94 | QC-ACN-TFA-XB |
| 910 | 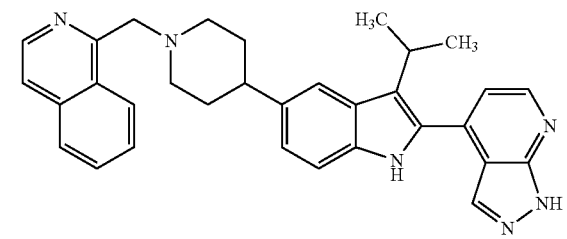 [SMILES: CC(C)c1c(-c2ccnc3[nH]ncc23)[nH]c2ccc(C3CCN(Cc4nccc5ccccc45)CC3)cc12] | 501.3 | 1.75 | QC-ACN-AA-XB |
| 911 | 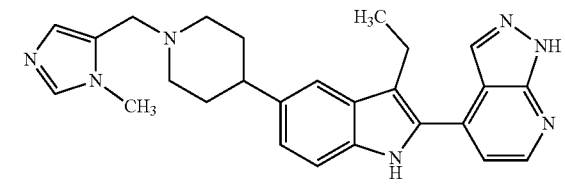 [SMILES: CCc1c(-c2ccnc3[nH]ncc23)[nH]c2ccc(C3CCN(Cc4cncn4C)CC3)cc12] | 440.3 | 0.64 | QC-ACN-TFA-XB |

TABLE 23-continued

| Ex. No. | Structure | Obs. MS Ion | RT | HPLC Method |
|---|---|---|---|---|
| 912 | 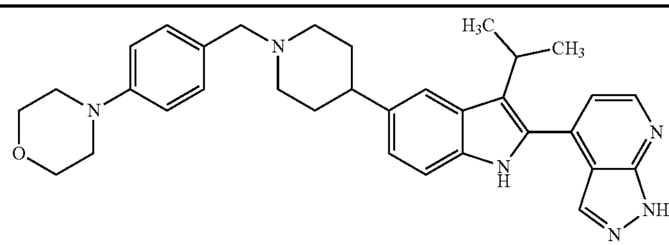 | 535.3 | 1.13 | QC-ACN-TFA-XB |
| 913 | 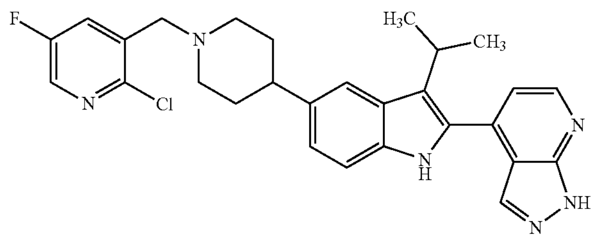 [SMILES: CC(C)c1c(-c2ccnc3[nH]ncc23)[nH]c2ccc(C3CCN(Cc4cc(F)cnc4Cl)CC3)cc12] | 503.3 | 1.08 | QC-ACN-TFA-XB |
| 914 | 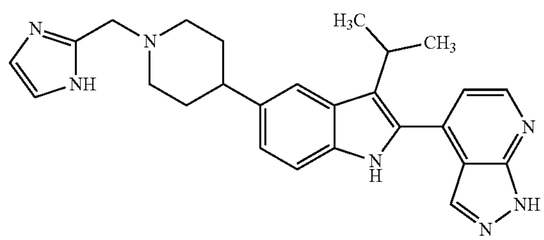 [SMILES: CC(C)c1c(-c2ccnc3[nH]ncc23)[nH]c2ccc(C3CCN(Cc4ncc[nH]4)CC3)cc12] | 440.4 | 1.25 | QC-ACN-AA-XB |
| 915 | 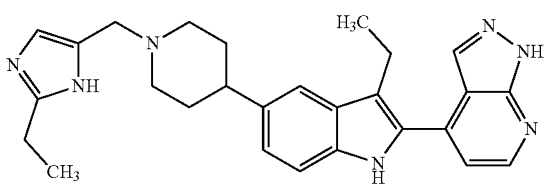 [SMILES: CCc1ncc(CN2CCC(c3ccc4[nH]c(-c5ccnc6[nH]ncc56)c(CC)c4c3)CC2)[nH]1] | 454.2 | 0.8 | QC-ACN-TFA-XB |
| 916 | 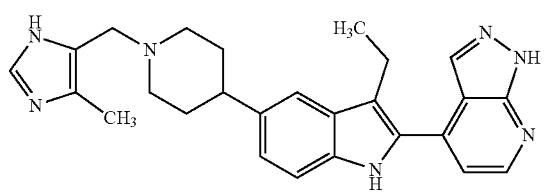 [SMILES: CCc1c(-c2ccnc3[nH]ncc23)[nH]c2ccc(C3CCN(Cc4[nH]cnc4C)CC3)cc12] | 440.2 | 1.07 | QC-ACN-AA-XB |
| 917 | 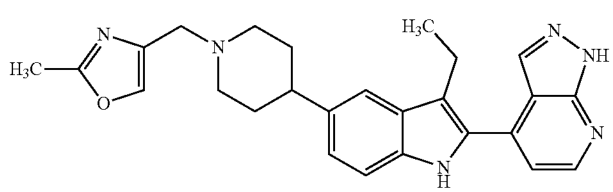 [SMILES: CCc1c(-c2ccnc3[nH]ncc23)[nH]c2ccc(C3CCN(Cc4coc(C)n4)CC3)cc12] | 441.3 | 1.36 | QC-ACN-AA-XB |
| 918 | 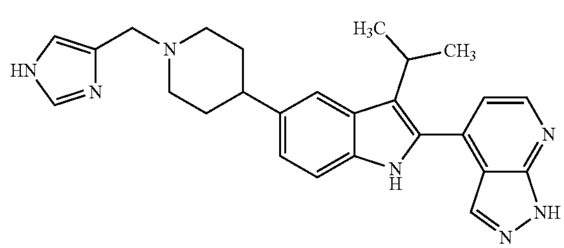 [SMILES: CC(C)c1c(-c2ccnc3[nH]ncc23)[nH]c2ccc(C3CCN(Cc4c[nH]cn4)CC3)cc12] | 440.4 | 0.7 | QC-ACN-TFA-XB |

TABLE 23-continued

| Ex. No. | Structure | Obs. MS Ion | RT | HPLC Method |
|---|---|---|---|---|
| 919 | 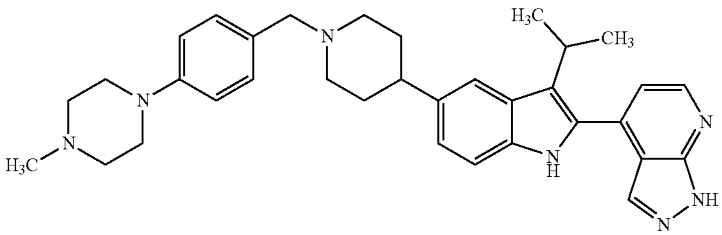 [SMILES: CC(C)c1c(-c2ccnc3[nH]ncc23)[nH]c2ccc(C3CCN(Cc4ccc(N5CCN(C)CC5)cc4)CC3)cc12] | 548.4 | 0.85 | QC-ACN-TFA-XB |
| 920 | 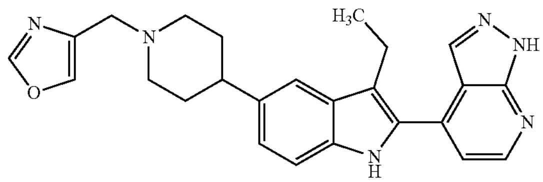 [SMILES: CCc1c(-c2ccnc3[nH]ncc23)[nH]c2ccc(C3CCN(Cc4cocn4)CC3)cc12] | 427.2 | 1.31 | QC-ACN-AA-XB |
| 921 | 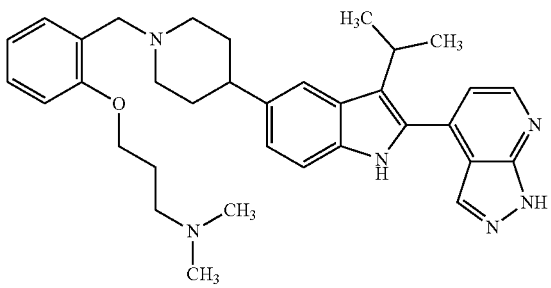 [SMILES: CC(C)c1c(-c2ccnc3[nH]ncc23)[nH]c2ccc(C3CCN(Cc4ccccc4OCCCN(C)C)CC3)cc12] | 551.4 | 1.39 | QC-ACN-AA-XB |
| 922 | 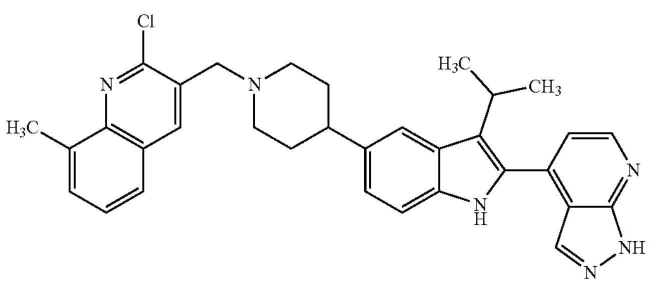 [SMILES: Cc1cccc2cc(CN3CCC(c4ccc5[nH]c(-c6ccnc7[nH]ncc67)c(C(C)C)c5c4)CC3)c(Cl)nc12] | 549 | 1.61 | QC-ACN-TFA-XB |
| 923 | 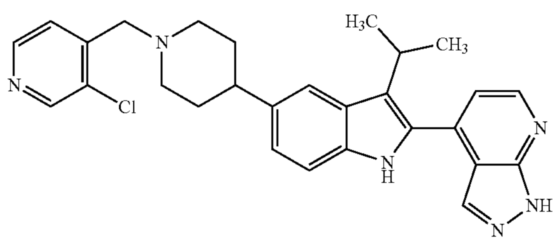 [SMILES: CC(C)c1c(-c2ccnc3[nH]ncc23)[nH]c2ccc(C3CCN(Cc4ccncc4Cl)CC3)cc12] | 485.3 | 1.02 | QC-ACN-TFA-XB |
| 924 | 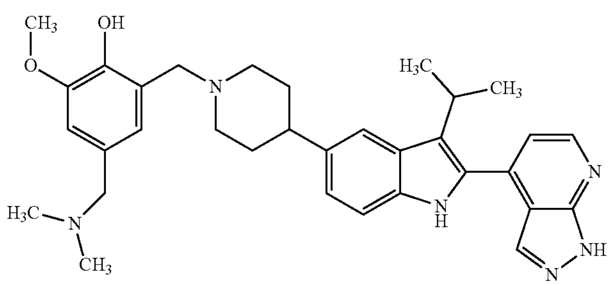 [SMILES: COc1cc(CN(C)C)cc(CN2CCC(c3ccc4[nH]c(-c5ccnc6[nH]ncc56)c(C(C)C)c4c3)CC2)c1O] | 553.4 | 0.92 | QC-ACN-AA-XB |

TABLE 23-continued

| Ex. No. | Structure | Obs. MS Ion | RT | HPLC Method |
|---|---|---|---|---|
| 925 | 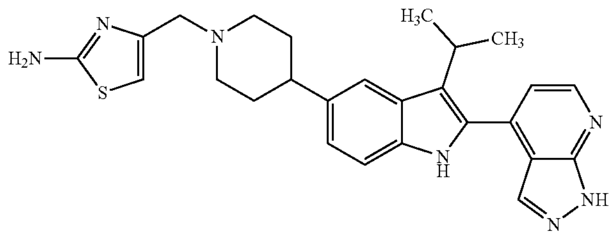 [SMILES: CC(C)c1c(-c2ccnc3[nH]ncc23)[nH]c2ccc(C3CCN(Cc4csc(N)n4)CC3)cc12] | 472.3 | 0.79 | QC-ACN-TFA-XB |
| 926 | 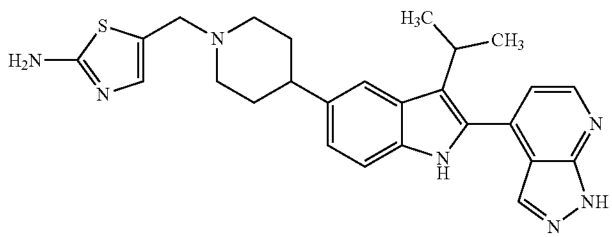 [SMILES: CC(C)c1c(-c2ccnc3[nH]ncc23)[nH]c2ccc(C3CCN(Cc4cnc(N)s4)CC3)cc12] | 472.2 | 1.18 | QC-ACN-AA-XB |
| 927 | 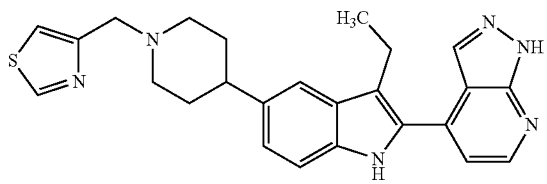 [SMILES: CCc1c(-c2ccnc3[nH]ncc23)[nH]c2ccc(C3CCN(Cc4cscn4)CC3)cc12] | 443.3 | 0.88 | QC-ACN-TFA-XB |
| 928 | 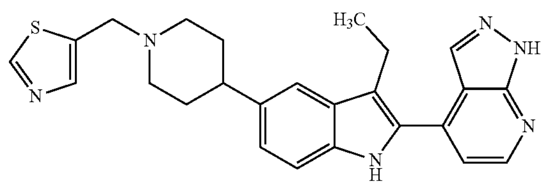 [SMILES: CCc1c(-c2ccnc3[nH]ncc23)[nH]c2ccc(C3CCN(Cc4cncs4)CC3)cc12] | 443.2 | 1.66 | QC-ACN-AA-XB |
| 929 | 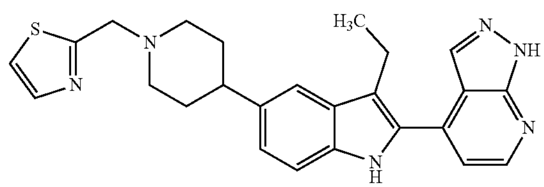 [SMILES: CCc1c(-c2ccnc3[nH]ncc23)[nH]c2ccc(C3CCN(Cc4nccs4)CC3)cc12] | 443.2 | 0.87 | QC-ACN-TFA-XB |
| 930 | 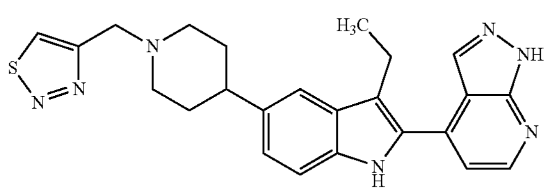 [SMILES: CCc1c(-c2ccnc3[nH]ncc23)[nH]c2ccc(C3CCN(Cc4csnn4)CC3)cc12] | 444.2 | 1.61 | QC-ACN-AA-XB |
| 931 | 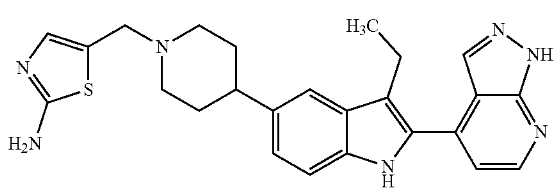 [SMILES: CCc1c(-c2ccnc3[nH]ncc23)[nH]c2ccc(C3CCN(Cc4cnc(N)s4)CC3)cc12] | 458.2 | 1.31 | QC-ACN-AA-XB |

TABLE 23-continued
| Ex. No. | Structure | Obs. MS Ion | RT | HPLC Method |
|---|---|---|---|---|
| 932 | 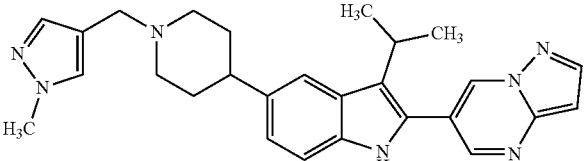 | 454.3 | 1.46 | E |
| 933 | 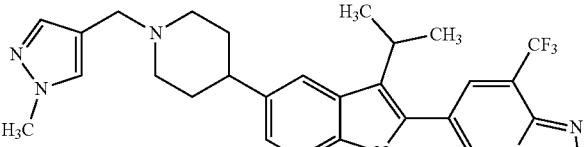 | 521.0 | 1.65 | E |
| 934 | 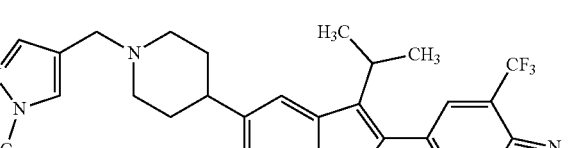 | 535.3 | 1.81 | E |
| 935 | 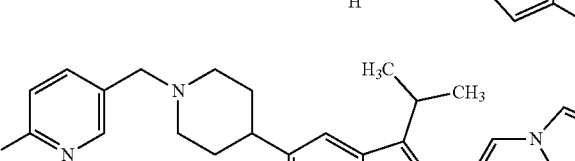 | 480.3 | 2.14 | E |
| 936 | 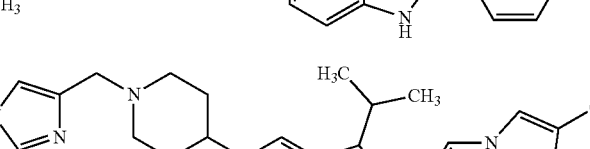 | 453.3 | 1.38 | E |
| 937 | 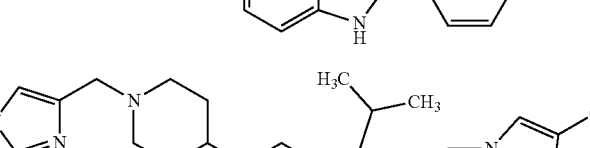 | 467.3 | 0.96 | F |
| 938 | 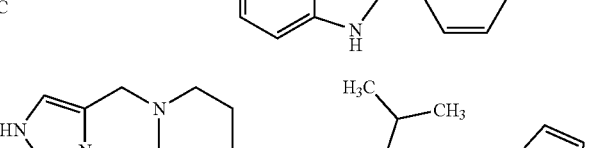 | 453.3 | 1.32 | E |
| 939 | 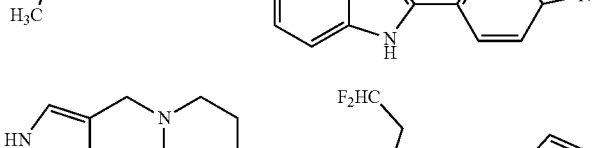 | 475.2 | 1.23 | E |

TABLE 23-continued
| Ex. No. | Structure | Obs. MS Ion | RT | HPLC Method |
|---|---|---|---|---|
| 940 | 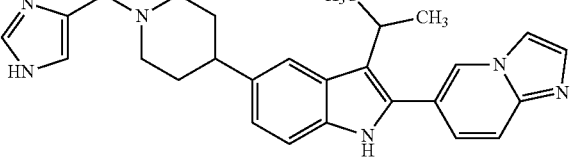 | 439.3 | 1.30 | E |
| 941 | 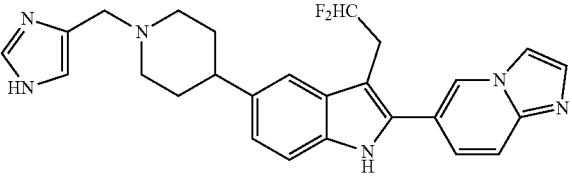 [SMILES: FC(F)Cc1c(-c2ccc3nccn3c2)[nH]c2ccc(C3CCN(Cc4c[nH]cn4)CC3)cc12] | 461.2 | 1.20 | E |
| 942 | 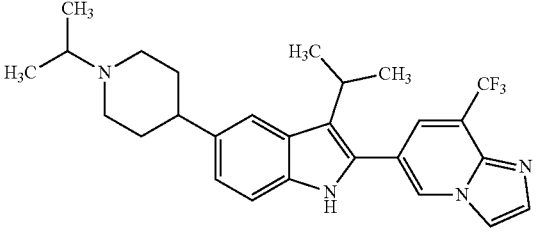 [SMILES: CC(C)c1c(-c2cc(C(F)(F)F)c3nccn3c2)[nH]c2ccc(C3CCN(C(C)C)CC3)cc12] | 469.0 | 1.60 | E |
| 943 | 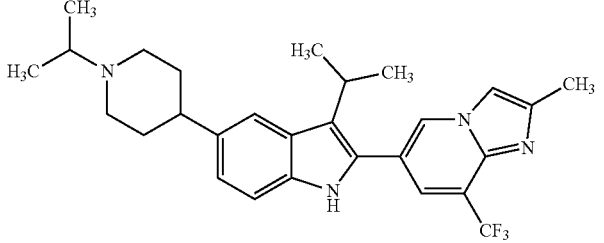 [SMILES: Cc1cn2cc(-c3[nH]c4ccc(C5CCN(C(C)C)CC5)cc4c3C(C)C)cc(C(F)(F)F)c2n1] | 483.0 | 1.81 | E |
| 944 | 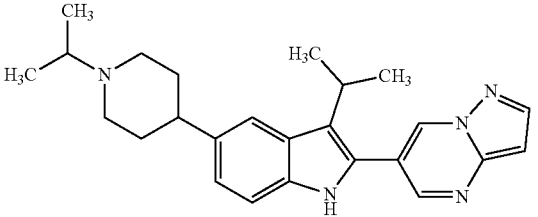 [SMILES: CC(C)c1c(-c2cnc3ccnn3c2)[nH]c2ccc(C3CCN(C(C)C)CC3)cc12] | 402.3 | 1.43 | E |
| 945 | 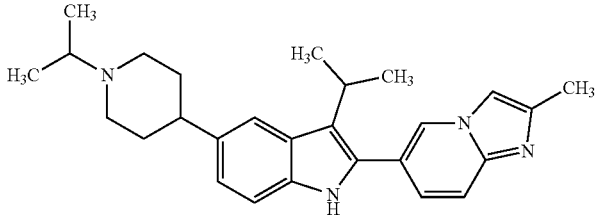 [SMILES: Cc1cn2cc(-c3[nH]c4ccc(C5CCN(C(C)C)CC5)cc4c3C(C)C)ccc2n1] | 415.2 | 1.51 | F |
| 946 | 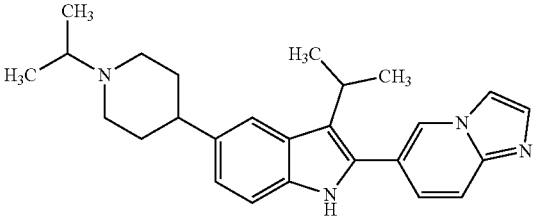 [SMILES: CC(C)c1c(-c2ccc3nccn3c2)[nH]c2ccc(C3CCN(C(C)C)CC3)cc12] | 401.3 | 1.43 | E |

TABLE 23-continued

| Ex. No. | Structure | Obs. MS Ion | RT | HPLC Method |
|---|---|---|---|---|
| 947 | 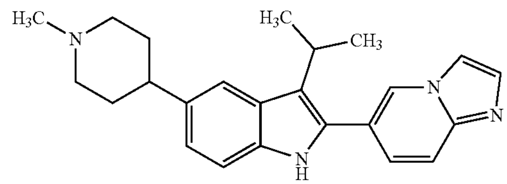 [SMILES: CC(C)c1c(-c2ccc3nccn3c2)[nH]c2ccc(C3CCN(C)CC3)cc12] | 373.2 | 1.33 | E |
| 948 | 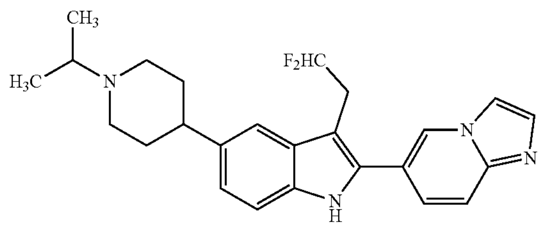 [SMILES: CC(C)N1CCC(c2ccc3[nH]c(-c4ccc5nccn5c4)c(CC(F)F)c3c2)CC1] | 423.2 | 1.32 | E |
| 949 | 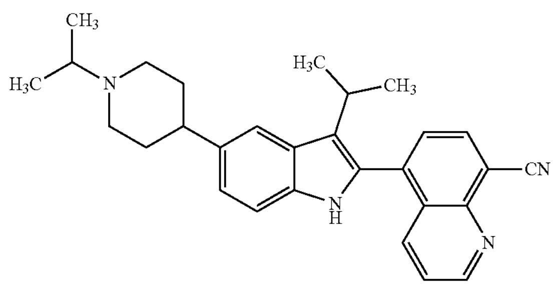 [SMILES: CC(C)c1c(-c2ccc(C#N)c3ncccc23)[nH]c2ccc(C3CCN(C(C)C)CC3)cc12] | 437.3 | 1.47 | F |
| 950 | 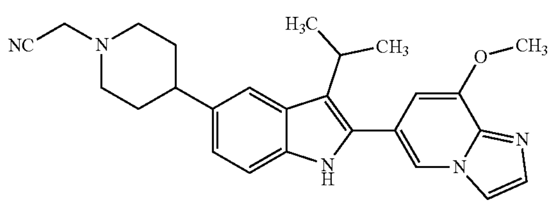 [SMILES: COc1cc(-c2[nH]c3ccc(C4CCN(CC#N)CC4)cc3c2C(C)C)cn2ccnc12] | 428.2 | 1.93 | E |
| 951 | 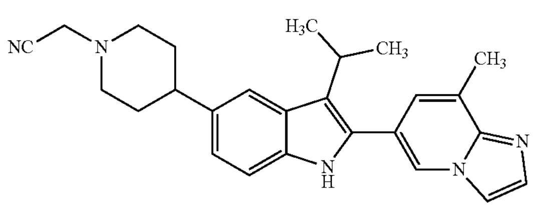 [SMILES: Cc1cc(-c2[nH]c3ccc(C4CCN(CC#N)CC4)cc3c2C(C)C)cn2ccnc12] | 412.2 | 2.07 | E |
| 952 | 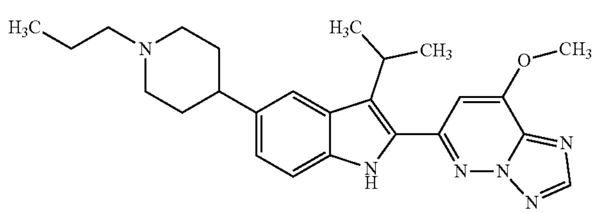 [SMILES: CCCN1CCC(c2ccc3[nH]c(-c4cc(OC)c5ncnn5n4)c(C(C)C)c3c2)CC1] | 433 | 1.47 | QC-ACN-AA-XB |
| 953 | 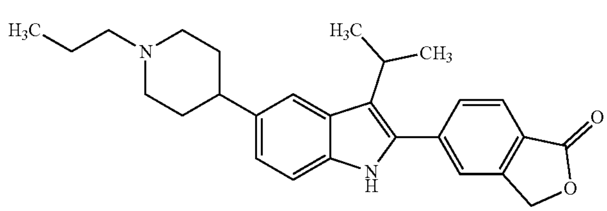 [SMILES: CCCN1CCC(c2ccc3[nH]c(-c4ccc5c(c4)COC5=O)c(C(C)C)c3c2)CC1] | 417 | 1.61 | QC-ACN-AA-XB |

TABLE 23-continued

| Ex. No. | Structure | Obs. MS Ion | RT | HPLC Method |
|---|---|---|---|---|
| 954 | 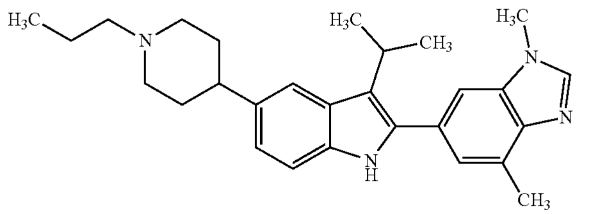 [SMILES: CCCN1CCC(c2ccc3[nH]c(-c4cc(C)c5ncn(C)c5c4)c(C(C)C)c3c2)CC1] | 429.3 | 1.02 | QC-ACN-TFA-XB |
| 955 | 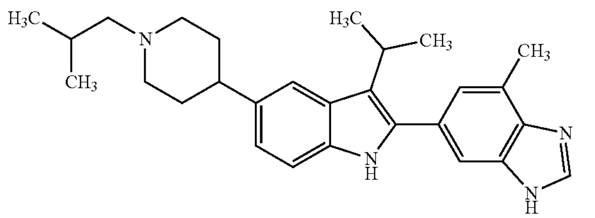 [SMILES: Cc1cc(-c2[nH]c3ccc(C4CCN(CC(C)C)CC4)cc3c2C(C)C)cc2[nH]cnc12] | 429 | 1.44 | QC-ACN-AA-XB |
| 956 | 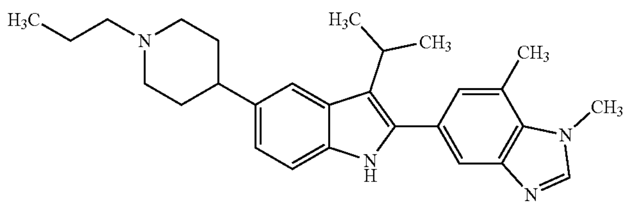 [SMILES: CCCN1CCC(c2ccc3[nH]c(-c4cc(C)c5c(c4)ncn5C)c(C(C)C)c3c2)CC1] | 429.2 | 1.58 | QC-ACN-AA-XB |
| 957 | 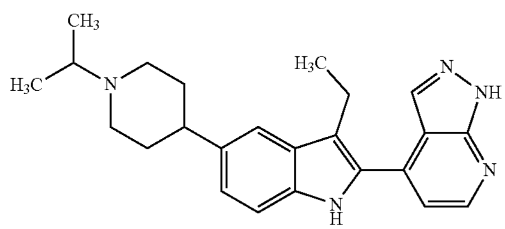 [SMILES: CCc1c(-c2ccnc3[nH]ncc23)[nH]c2ccc(C3CCN(C(C)C)CC3)cc12] | 388.3 | 1.09 | QC-ACN-AA-XB |
| 958 | 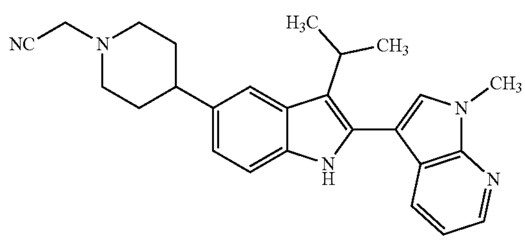 [SMILES: CC(C)c1c(-c2cn(C)c3ncccc23)[nH]c2ccc(C3CCN(CC#N)CC3)cc12] | 412.3 | 1.41 | QC-ACN-TFA-XB |
| 959 | 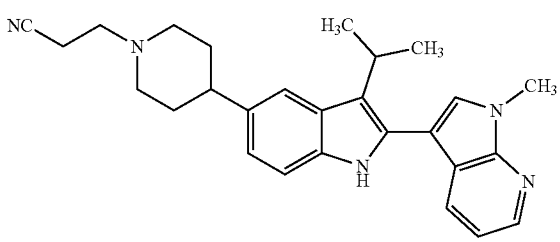 [SMILES: CC(C)c1c(-c2cn(C)c3ncccc23)[nH]c2ccc(C3CCN(CCC#N)CC3)cc12] | 426 | 1.36 | QC-ACN-TFA-XB |
| 960 | 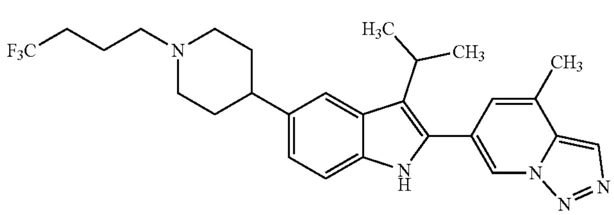 [SMILES: Cc1cc(-c2[nH]c3ccc(C4CCN(CCCC(F)(F)F)CC4)cc3c2C(C)C)cn2nncc12] | 484 | 2.05 | QC-ACN-AA-XB |

TABLE 23-continued

| Ex. No. | Structure | Obs. MS Ion | RT | HPLC Method |
|---|---|---|---|---|
| 961 | 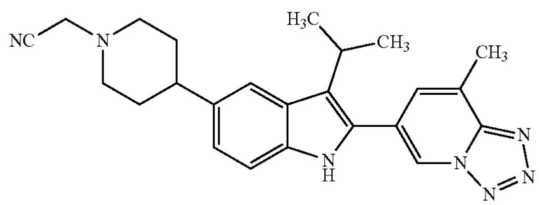 [SMILES: Cc1cc(-c2[nH]c3ccc(C4CCN(CC#N)CC4)cc3c2C(C)C)cn2nnnc12] | 414.1 | 1.3 | QC-ACN-TFA-XB |
| 962 | 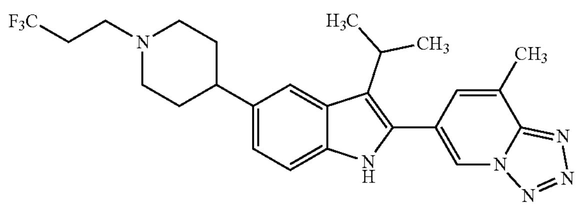 [SMILES: Cc1cc(-c2[nH]c3ccc(C4CCN(CCC(F)(F)F)CC4)cc3c2C(C)C)cn2nnnc12] | 471.1 | 1.45 | QC-ACN-TFA-XB |
| 963 | 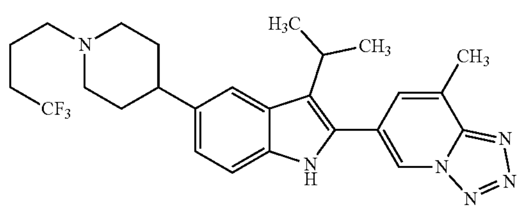 [SMILES: Cc1cc(-c2[nH]c3ccc(C4CCN(CCCC(F)(F)F)CC4)cc3c2C(C)C)cn2nnnc12] | 485.1 | 1.53 | QC-CN-TFA-XB |
| 964 | 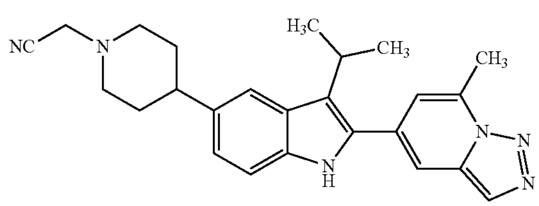 [SMILES: Cc1cc(-c2[nH]c3ccc(C4CCN(CC#N)CC4)cc3c2C(C)C)cc2cnnn12] | 413.2 | 1.3 | QC-ACN-TFA-XB |
| 965 | 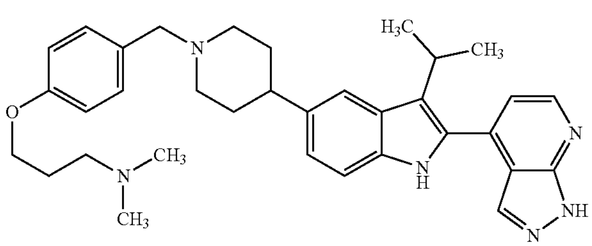 [SMILES: CC(C)c1c(-c2ccnc3[nH]ncc23)[nH]c2ccc(C3CCN(Cc4ccc(OCCCN(C)C)cc4)CC3)cc12] | 551.3 | 1.34 | QC-ACN-AA-XB |
| 966 | 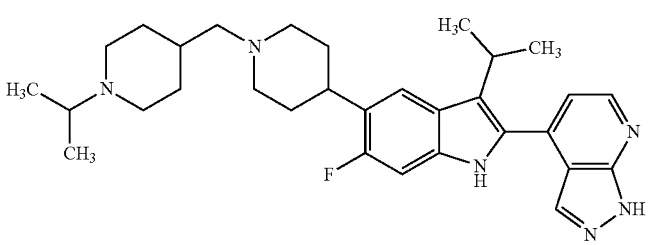 [SMILES: CC(C)c1c(-c2ccnc3[nH]ncc23)[nH]c2cc(F)c(C3CCN(CC4CCN(C(C)C)CC4)CC3)cc12] | 517.1 | 0.92 | QC-ACN-TFA-XB |

TABLE 23-continued

| Ex. No. | Structure | Obs. MS Ion | RT | HPLC Method |
|---|---|---|---|---|
| 967 | 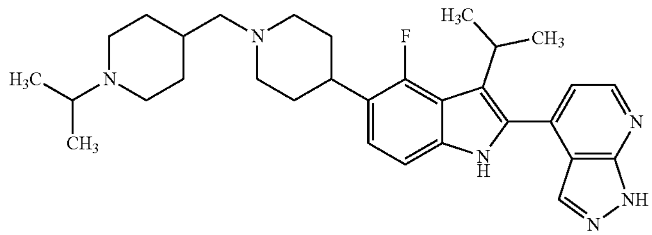 [SMILES: CC(C)c1c(-c2ccnc3[nH]ncc23)[nH]c2ccc(C3CCN(CC4CCN(C(C)C)CC4)CC3)c(F)c12] | 517.1 | 1.23 | QC-ACN-AA-XB |

BIOLOGICAL ASSAYS

The pharmacological properties of the compounds of this invention may be confirmed by a number of biological assays. The exemplified biological assays, which follow, have been carried out with compounds of the invention.

TLR7/8/9 Inhibition Reporter Assays

HEK-Blue™-cells (Invivogen) overexpressing human TLR7, TLR8 or TLR9 receptors were used for screening inhibitors of these receptors using an inducible SEAP (secreted embryonic alkaline phosphatase) reporter gene under the control of the IFN-β minimal promoter fused to five NF-κB and AP-1-binding sites. Briefly, cells are seeded into Greiner 384 well plates (15000 cells per well for TLR7, 20,000 for TLR8 and 25,000 for TLR9) and then treated with test compounds in DMSO to yield a final dose response concentration range of 0.05 nM-50 μM. After a 30 minute compound pre-treatment at room temperature, the cells are then stimulated with a TLR7 ligand (gardiquimod at a final concentration of 7.5 μM), TLR8 ligand (R848 at a final concentration of 15.9 μM) or TLR9 ligand (ODN2006 at a final concentration of 5 nM) to activate NF-κB and AP-1 which induce the production of SLAP After a 22 hour incubation at 37 TC, 50 $CO_2$, SLAP levels are determined with the addition of HLK-Blue™ Detection reagent (Invivogen), a cell culture medium that allows for detection of SLAP, according to manufacturer's specifications. The percent inhibition is determined as the 00 reduction in the HEK-Blue signal present in wells treated with agonist plus DMSO alone compared to wells treated with a known inhibitor.

TABLE 24

TLR7/8/9 Reporter Assay Data

| Ex. No. | TLR7 $IC_{50}$ | TLR8 $IC_{50}$ | TLR9 $IC_{50}$ |
|---|---|---|---|
| 1 | A | A | C |
| 2 | A | A | C |
| 3 | B | A | B |
| 4 | B | B | B |
| 5 | B | C | C |
| 6 | A | B | C |
| 7 | A | A | B |
| 8 | B | NA-1 | C |
| 9 | A | A | C |
| 10 | A | A | B |
| 11 | A | B | B |
| 12 | B | C | B |
| 13 | A | A | B |
| 14 | NA-1 | NA-1 | B |
| 15 | B | C | B |
| 16 | B | NA-1 | C |
| 17 | A | A | B |
| 18 | A | A | C |
| 19 | B | C | B |
| 20 | NA-1 | NA-1 | C |
| 21 | C | B | C |
| 22 | B | A | C |
| 23 | A | A | B |
| 24 | C | C | C |
| 25 | C | C | B |
| 26 | B | B | B |
| 27 | A | A | C |
| 28 | C | C | B |
| 29 | B | A | B |
| 30 | A | A | C |
| 31 | A | A | C |
| 32 | A | A | C |
| 33 | A | A | B |
| 34 | C | NA-1 | C |
| 35 | A | A | C |
| 36 | A | A | B |
| 37 | A | A | C |
| 38 | A | A | B |
| 39 | B | B | C |
| 40 | C | C | B |
| 41 | B | B | C |
| 42 | C | B | C |
| 43 | B | A | C |
| 44 | C | C | C |
| 45 | B | B | C |
| 46 | A | A | C |
| 47 | B | NA-1 | C |
| 48 | A | A | C |
| 49 | A | A | C |
| 50 | B | C | C |
| 51 | A | A | B |
| 52 | C | C | B |
| 53 | B | A | C |
| 54 | A | A | B |
| 55 | B | C | C |
| 56 | C | C | C |
| 57 | B | C | C |
| 58 | C | C | C |
| 59 | A | A | B |
| 60 | A | B | B |
| 61 | A | A | B |
| 62 | B | B | B |
| 63 | A | A | B |
| 64 | A | A | B |
| 65 | C | C | C |
| 66 | C | C | C |
| 67 | B | B | C |
| 68 | C | C | C |
| 69 | B | A | B |
| 70 | B | B | C |

TABLE 24-continued

TLR7/8/9 Reporter Assay Data

| Ex. No. | TLR7 IC$_{50}$ | TLR8 IC$_{50}$ | TLR9 IC$_{50}$ |
|---|---|---|---|
| 71 | A | B | C |
| 72 | B | A | C |
| 73 | A | A | C |
| 74 | A | A | C |
| 75 | A | A | B |
| 76 | A | A | C |
| 77 | A | A | B |
| 78 | A | A | C |
| 79 | A | B | B |
| 80 | A | B | C |
| 81 | A | B | C |
| 82 | A | B | C |
| 83 | A | B | B |
| 84 | B | B | B |
| 86 | B | B | B |
| 87 | A | A | B |
| 88 | A | B | C |
| 89 | B | A | B |
| 90 | A | B | C |
| 91 | B | B | B |
| 92 | A | B | C |
| 93 | A | A | B |
| 94 | A | A | C |
| 95 | C | B | C |
| 96 | A | A | B |
| 97 | C | B | C |
| 98 | C | B | C |
| 99 | B | B | C |
| 100 | C | NA-2 | C |
| 101 | A | A | C |
| 102 | C | C | C |
| 103 | C | B | C |
| 104 | A | A | C |
| 105 | A | B | C |
| 106 | B | B | C |
| 107 | C | NA-1 | C |
| 108 | NA-2 | C | C |
| 109 | A | A | B |
| 110 | A | A | B |
| 111 | A | B | NT |
| 112 | A | A | B |
| 113 | A | A | B |
| 114 | A | B | B |
| 115 | A | B | B |
| 116 | B | B | C |
| 117 | A | A | B |
| 118 | A | A | B |
| 119 | B | B | C |
| 120 | A | A | B |
| 121 | A | C | C |
| 122 | A | B | B |
| 123 | A | B | B |
| 124 | A | A | B |
| 125 | A | A | B |
| 126 | A | B | B |
| 127 | A | A | B |
| 128 | A | A | C |
| 129 | A | NT | B |
| 130 | B | A | C |
| 131 | A | B | B |
| 132 | A | B | B |
| 133 | A | A | C |
| 134 | A | B | B |
| 135 | B | A | C |
| 136 | A | A | B |
| 137 | A | B | B |
| 138 | A | A | C |
| 139 | A | A | C |
| 140 | A | B | C |
| 141 | A | A | C |
| 142 | A | A | C |
| 143 | A | A | C |
| 144 | NA-1 | NA-1 | C |
| 145 | A | C | C |
| 146 | A | B | NA-2 |
| 147 | A | A | C |
| 148 | A | B | C |
| 149 | B | C | C |
| 150 | C | C | C |
| 151 | B | B | B |
| 152 | A | A | C |
| 153 | A | A | C |
| 154 | A | A | C |
| 155 | A | A | C |
| 156 | A | B | B |
| 157 | A | A | B |
| 158 | A | A | C |
| 159 | A | C | B |
| 160 | B | B | B |
| 161 | B | A | B |
| 162 | A | B | B |
| 163 | B | B | B |
| 164 | A | A | B |
| 165 | A | B | C |
| 166 | C | B | C |
| 167 | B | B | B |
| 168 | B | B | B |
| 169 | B | C | C |
| 170 | A | A | B |
| 171 | A | A | C |
| 172 | A | A | C |
| 173 | B | A | C |
| 174 | NA-2 | C | C |
| 175 | B | B | C |
| 176 | C | C | C |
| 177 | A | A | C |
| 178 | B | B | C |
| 179 | A | A | C |
| 180 | C | C | C |
| 181 | C | NA-1 | C |
| 182 | C | C | C |
| 183 | B | B | C |
| 184 | B | B | B |
| 185 | B | B | C |
| 186 | C | C | C |
| 187 | C | C | C |
| 188 | A | B | B |
| 189 | A | B | A |
| 190 | A | C | C |
| 191 | B | B | B |
| 192 | A | A | C |
| 193 | B | B | C |
| 194 | C | C | B |
| 195 | C | A | C |
| 196 | A | A | C |
| 197 | A | A | C |
| 198 | A | B | C |
| 199 | A | A | B |
| 200 | B | B | B |
| 201 | C | B | C |
| 202 | C | C | B |
| 203 | A | A | B |
| 204 | B | B | B |
| 205 | A | A | B |
| 206 | B | A | C |
| 207 | B | C | A |
| 208 | C | C | A |
| 209 | A | A | C |
| 210 | C | C | C |
| 211 | C | C | C |
| 212 | C | C | C |
| 213 | C | B | C |
| 214 | C | C | B |
| 215 | B | B | C |
| 216 | C | B | C |
| 217 | B | B | B |
| 218 | A | A | B |
| 219 | B | B | B |
| 220 | B | B | C |
| 221 | B | C | B |

TABLE 24-continued

TLR7/8/9 Reporter Assay Data

| Ex. No. | TLR7 IC$_{50}$ | TLR8 IC$_{50}$ | TLR9 IC$_{50}$ |
|---|---|---|---|
| 222 | B | A | C |
| 223 | C | C | B |
| 224 | B | A | B |
| 225 | B | B | B |
| 226 | A | A | B |
| 227 | A | A | B |
| 228 | A | A | B |
| 229 | A | A | B |
| 230 | A | A | B |
| 231 | B | B | C |
| 232 | C | C | B |
| 233 | C | C | NT |
| 234 | A | A | C |
| 235 | C | C | C |
| 236 | A | A | B |
| 237 | NA-1 | NA-1 | C |
| 238 | A | B | C |
| 239 | C | B | B |
| 240 | C | C | C |
| 241 | A | A | C |
| 242 | A | A | C |
| 243 | A | A | B |
| 244 | B | B | C |
| 245 | B | B | C |
| 246 | A | A | B |
| 247 | A | A | C |
| 248 | B | A | NA-2 |
| 249 | A | B | C |
| 250 | A | A | B |
| 251 | A | B | B |
| 252 | A | A | B |
| 253 | A | A | B |
| 254 | C | C | NA-2 |
| 255 | A | B | C |
| 256 | A | A | C |
| 257 | A | A | A |
| 258 | A | A | B |
| 259 | A | A | B |
| 260 | A | B | C |
| 261 | A | B | C |
| 262 | A | A | B |
| 263 | NT | A | C |
| 264 | A | A | B |
| 265 | A | A | C |
| 266 | A | A | C |
| 267 | A | A | C |
| 268 | A | A | C |
| 269 | A | A | B |
| 270 | B | B | C |
| 271 | A | A | B |
| 272 | A | A | B |
| 273 | A | B | B |
| 274 | B | NA-1 | C |
| 275 | B | NA-1 | C |
| 276 | A | A | C |
| 277 | A | A | C |
| 278 | A | A | C |
| 279 | A | A | C |
| 280 | A | A | C |
| 281 | A | A | C |
| 282 | A | A | C |
| 283 | A | B | C |
| 284 | A | A | C |
| 285 | A | A | C |
| 286 | A | A | C |
| 287 | C | B | C |
| 288 | A | A | C |
| 289 | A | A | C |
| 290 | B | A | C |
| 291 | A | A | C |
| 292 | A | A | C |
| 293 | A | A | C |
| 294 | A | A | C |
| 295 | A | A | C |
| 296 | A | A | C |

TABLE 24-continued

TLR7/8/9 Reporter Assay Data

| Ex. No. | TLR7 IC$_{50}$ | TLR8 IC$_{50}$ | TLR9 IC$_{50}$ |
|---|---|---|---|
| 297 | A | A | C |
| 298 | A | A | C |
| 299 | B | B | B |
| 300 | B | B | C |
| 301 | A | B | C |
| 302 | A | B | C |
| 303 | A | B | C |
| 304 | A | B | C |
| 305 | B | B | C |
| 306 | B | B | C |
| 307 | B | B | C |
| 308 | B | A | C |
| 309 | A | A | C |
| 310 | A | A | C |
| 311 | A | A | C |
| 312 | A | A | C |
| 313 | A | A | C |
| 314 | A | A | C |
| 315 | A | A | C |
| 316 | A | B | C |
| 317 | A | A | C |
| 318 | A | A | C |
| 319 | A | A | C |
| 320 | A | A | C |
| 321 | A | A | C |
| 322 | B | C | C |
| 323 | B | C | C |
| 324 | A | A | C |
| 325 | A | A | C |
| 326 | A | B | C |
| 327 | A | A | C |
| 328 | A | A | C |
| 329 | A | A | B |
| 330 | A | A | C |
| 331 | A | C | C |
| 332 | A | A | B |
| 333 | A | A | C |
| 334 | B | B | B |
| 335 | B | C | C |
| 336 | A | B | C |
| 337 | B | B | C |
| 338 | A | B | C |
| 339 | A | B | C |
| 340 | A | B | C |
| 341 | A | A | B |
| 342 | A | B | B |
| 343 | A | B | B |
| 344 | A | A | C |
| 345 | A | B | C |
| 346 | A | A | C |
| 347 | A | A | C |
| 348 | A | A | C |
| 349 | A | A | C |
| 350 | A | A | C |
| 351 | A | A | C |
| 352 | B | B | B |
| 353 | B | C | B |
| 354 | B | B | B |
| 355 | B | B | B |
| 356 | B | B | B |
| 357 | B | B | B |
| 359 | C | NA-1 | C |
| 360 | C | NA-1 | C |
| 361 | B | B | C |
| 362 | B | B | C |
| 363 | B | B | B |
| 364 | B | NA-1 | C |
| 365 | A | B | NA-2 |
| 366 | A | A | C |
| 367 | A | A | C |
| 368 | C | NA-1 | C |
| 369 | A | A | C |
| 370 | A | A | C |
| 371 | A | A | C |
| 372 | A | A | C |

TABLE 24-continued

TLR7/8/9 Reporter Assay Data

| Ex. No. | TLR7 IC$_{50}$ | TLR8 IC$_{50}$ | TLR9 IC$_{50}$ |
|---|---|---|---|
| 373 | A | A | C |
| 374 | A | B | B |
| 375 | A | B | A |
| 376 | A | B | B |
| 377 | A | B | C |
| 378 | A | B | C |
| 379 | A | A | C |
| 380 | A | A | C |
| 381 | A | B | C |
| 382 | A | A | C |
| 383 | C | B | C |
| 384 | C | B | C |
| 385 | A | A | C |
| 386 | A | B | C |
| 387 | B | A | C |
| 388 | C | C | NA-2 |
| 389 | C | C | C |
| 390 | B | B | NA-2 |
| 391 | A | A | B |
| 392 | NA-1 | NA-1 | C |
| 393 | NA-1 | NA-1 | C |
| 394 | A | B | C |
| 395 | A | A | C |
| 396 | A | B | B |
| 397 | A | A | B |
| 398 | A | A | B |
| 399 | A | C | C |
| 400 | NA-1 | C | C |
| 401 | B | B | C |
| 402 | A | B | C |
| 403 | A | A | C |
| 404 | A | A | C |
| 405 | A | A | C |
| 406 | A | A | C |
| 407 | A | A | C |
| 408 | A | B | C |
| 409 | A | B | C |
| 410 | A | B | C |
| 411 | A | B | C |
| 412 | A | A | B |
| 413 | A | A | B |
| 414 | A | A | C |
| 415 | A | A | C |
| 416 | A | NA-1 | A |
| 417 | A | NT | B |
| 418 | A | B | C |
| 419 | A | B | C |
| 420 | A | A | C |
| 421 | A | A | C |
| 422 | A | B | C |
| 423 | A | A | C |
| 424 | B | B | B |
| 425 | B | B | C |
| 426 | NA-1 | C | C |
| 427 | B | A | C |
| 428 | A | A | C |
| 429 | A | B | B |
| 430 | B | A | C |
| 431 | A | B | C |
| 432 | A | A | C |
| 433 | A | A | B |
| 434 | A | A | B |
| 435 | A | A | C |
| 436 | A | A | C |
| 437 | A | A | C |
| 438 | B | B | C |
| 439 | A | A | C |
| 440 | A | A | B |
| 441 | A | A | C |
| 442 | A | A | C |
| 443 | A | A | C |
| 444 | A | A | B |
| 445 | A | B | C |
| 446 | A | B | B |
| 447 | A | A | C |
| 448 | A | A | C |
| 449 | A | A | C |
| 450 | C | A | B |
| 451 | A | A | C |
| 452 | A | A | C |
| 453 | A | A | C |
| 454 | A | A | C |
| 455 | A | A | C |
| 456 | A | A | C |
| 457 | A | A | C |
| 458 | A | B | C |
| 459 | A | A | C |
| 460 | A | A | C |
| 461 | B | A | C |
| 462 | A | A | C |
| 463 | A | A | C |
| 464 | B | B | B |
| 465 | A | B | C |
| 466 | A | B | B |
| 467 | B | C | C |
| 468 | A | A | C |
| 469 | A | A | C |
| 470 | A | A | C |
| 471 | A | A | C |
| 472 | A | A | C |
| 473 | A | B | NA-2 |
| 474 | A | A | C |
| 475 | A | A | C |
| 476 | A | A | C |
| 477 | A | A | C |
| 478 | A | B | NA-2 |
| 479 | A | A | C |
| 480 | A | A | C |
| 481 | A | A | C |
| 482 | A | B | NA-2 |
| 483 | A | A | C |
| 484 | A | A | C |
| 485 | A | A | NA-2 |
| 486 | A | B | C |
| 487 | A | A | C |
| 488 | A | A | C |
| 489 | A | B | C |
| 490 | B | B | C |
| 491 | B | C | C |
| 492 | A | A | B |
| 493 | A | C | B |
| 494 | A | A | C |
| 495 | A | A | B |
| 496 | A | A | C |
| 497 | A | A | C |
| 498 | A | A | B |
| 499 | B | C | B |
| 500 | B | B | B |
| 501 | B | B | B |
| 502 | C | NA-1 | B |
| 503 | B | NA-1 | B |
| 504 | A | B | C |
| 505 | B | NA-1 | C |
| 506 | A | A | C |
| 507 | A | A | B |
| 508 | A | B | B |
| 509 | A | A | B |
| 510 | A | C | B |
| 511 | A | B | B |
| 512 | A | A | C |
| 513 | C | NA-1 | C |
| 514 | B | B | C |
| 515 | C | B | C |
| 516 | A | A | C |
| 517 | B | A | B |
| 518 | A | A | C |
| 519 | NA-2 | NA-2 | C |
| 520 | NA-2 | NA-2 | C |
| 521 | NT | NA-2 | C |
| 522 | B | B | B |

TABLE 24-continued

TLR7/8/9 Reporter Assay Data

| Ex. No. | TLR7 IC$_{50}$ | TLR8 IC$_{50}$ | TLR9 IC$_{50}$ |
|---|---|---|---|
| 523 | A | B | B |
| 524 | NA-1 | NA-1 | C |
| 526 | A | A | C |
| 527 | A | B | B |
| 528 | A | A | B |
| 529 | A | A | C |
| 530 | A | A | B |
| 531 | A | A | B |
| 532 | A | A | C |
| 533 | A | A | B |
| 534 | A | A | C |
| 535 | B | C | C |
| 536 | A | A | C |
| 537 | A | A | C |
| 538 | A | B | C |
| 539 | C | C | C |
| 540 | A | C | C |
| 541 | B | B | B |
| 542 | A | B | C |
| 543 | A | A | C |
| 544 | A | A | C |
| 545 | A | C | B |
| 546 | A | B | B |
| 547 | A | B | B |
| 548 | A | B | B |
| 549 | A | A | B |
| 550 | A | NT | B |
| 551 | A | NA-1 | B |
| 552 | A | A | B |
| 553 | A | A | B |
| 554 | A | B | C |
| 555 | A | B | C |
| 556 | B | B | C |
| 557 | A | A | B |
| 558 | A | A | B |
| 559 | A | A | B |
| 560 | A | A | C |
| 562 | A | A | C |
| 563 | B | C | C |
| 564 | A | A | C |
| 565 | A | A | C |
| 566 | B | B | NA-2 |
| 567 | A | B | NA-2 |
| 568 | A | A | C |
| 569 | A | A | B |
| 570 | A | A | C |
| 571 | A | B | A |
| 572 | A | B | C |
| 573 | A | A | C |
| 574 | A | A | NA-2 |
| 575 | A | A | B |
| 576 | A | A | C |
| 577 | A | A | B |
| 578 | A | A | C |
| 579 | A | A | B |
| 580 | A | A | C |
| 581 | A | A | C |
| 582 | A | A | B |
| 583 | A | A | C |
| 584 | A | A | C |
| 585 | A | A | C |
| 586 | A | A | C |
| 587 | B | B | NA-2 |
| 588 | A | A | B |
| 589 | A | A | C |
| 590 | A | A | B |
| 591 | A | A | B |
| 592 | B | B | NA-2 |
| 593 | A | A | NT |
| 594 | A | A | C |
| 595 | NA-1 | NA-1 | NA-2 |
| 596 | A | NA-1 | C |
| 597 | B | NA-1 | C |
| 598 | NA-1 | C | NA-2 |
| 599 | B | B | C |
| 600 | A | B | C |
| 601 | A | NA-1 | C |
| 602 | A | NA-1 | NA-2 |
| 603 | B | NA-1 | NA-2 |
| 604 | A | C | NA-2 |
| 605 | A | C | NA-2 |
| 606 | B | NA-1 | C |
| 607 | B | C | NA-2 |
| 608 | B | NA-1 | C |
| 609 | B | NA-1 | C |
| 610 | B | B | C |
| 611 | A | B | C |
| 612 | A | A | C |
| 613 | B | B | NA-2 |
| 614 | A | A | NA-2 |
| 615 | B | B | C |
| 616 | A | B | NA-2 |
| 617 | A | A | C |
| 618 | A | A | B |
| 619 | A | A | C |
| 620 | A | A | C |
| 621 | A | A | C |
| 622 | A | A | C |
| 623 | A | A | C |
| 624 | A | A | B |
| 625 | A | A | C |
| 626 | A | B | NA-2 |
| 627 | A | A | C |
| 628 | A | A | C |
| 629 | A | A | C |
| 631 | A | A | B |
| 632 | A | A | C |
| 633 | A | A | C |
| 634 | A | B | NA-2 |
| 635 | A | A | C |
| 636 | A | A | B |
| 637 | A | A | C |
| 638 | A | B | NA-2 |
| 639 | A | B | B |
| 640 | A | B | C |
| 641 | A | A | C |
| 642 | A | A | C |
| 643 | A | A | B |
| 644 | B | C | NA-2 |
| 645 | A | B | NA-2 |
| 646 | B | A | C |
| 647 | B | B | C |
| 648 | A | A | C |
| 649 | B | B | C |
| 650 | A | A | B |
| 651 | A | A | A |
| 652 | A | A | C |
| 653 | A | A | B |
| 654 | A | A | B |
| 655 | A | A | B |
| 656 | A | A | B |
| 657 | B | A | B |
| 658 | C | C | B |
| 659 | C | NA-1 | B |
| 660 | A | A | B |
| 661 | A | A | B |
| 662 | C | NA-1 | C |
| 663 | C | NA-1 | B |
| 664 | NT | NA-1 | B |
| 665 | NA-2 | NA-1 | B |
| 666 | C | NA-1 | B |
| 667 | C | C | B |
| 668 | B | A | B |
| 669 | C | B | C |
| 670 | B | B | C |
| 671 | NA-2 | NA-1 | C |
| 672 | NA-2 | NA-1 | B |
| 673 | NA-2 | NA-1 | C |
| 674 | A | A | B |
| 675 | A | A | B |

TABLE 24-continued

TLR7/8/9 Reporter Assay Data

| Ex. No. | TLR7 IC$_{50}$ | TLR8 IC$_{50}$ | TLR9 IC$_{50}$ |
|---|---|---|---|
| 676 | A | B | B |
| 677 | A | A | B |
| 678 | B | A | C |
| 679 | A | A | B |
| 680 | A | A | B |
| 681 | A | A | A |
| 682 | A | A | C |
| 683 | A | A | C |
| 684 | A | A | C |
| 685 | A | A | C |
| 686 | A | A | C |
| 687 | A | A | C |
| 688 | A | A | C |
| 689 | A | A | C |
| 690 | A | A | C |
| 691 | A | A | C |
| 692 | A | A | C |
| 693 | A | A | B |
| 694 | A | A | C |
| 695 | B | A | B |
| 696 | A | B | C |
| 697 | B | B | B |
| 698 | A | A | C |
| 699 | A | A | C |
| 700 | A | A | B |
| 701 | A | A | B |
| 703 | A | A | C |
| 704 | A | B | C |
| 705 | A | A | B |
| 706 | A | A | B |
| 707 | A | A | B |
| 708 | B | B | C |
| 709 | B | C | C |
| 710 | A | A | C |
| 711 | B | B | C |
| 712 | B | B | B |
| 713 | NA-1 | NA-1 | C |
| 714 | A | A | NA-2 |
| 716 | NA-1 | NA-1 | C |
| 717 | A | B | B |
| 718 | A | A | C |
| 719 | A | A | B |
| 720 | A | A | C |
| 721 | A | B | C |
| 722 | A | A | C |
| 723 | A | B | C |
| 724 | B | B | C |
| 725 | A | B | C |
| 726 | B | NA-1 | NA-2 |
| 727 | A | A | C |
| 728 | A | C | C |
| 729 | A | B | C |
| 730 | A | A | C |
| 731 | A | A | C |
| 732 | A | A | C |
| 733 | A | A | C |
| 734 | B | B | C |
| 735 | A | B | C |
| 736 | A | B | C |
| 737 | C | C | C |
| 738 | A | A | C |
| 739 | A | A | C |
| 740 | B | A | C |
| 741 | A | A | C |
| 742 | A | B | C |
| 743 | A | A | C |
| 744 | A | A | C |
| 745 | A | A | C |
| 746 | A | A | C |
| 747 | A | A | C |
| 748 | A | A | C |
| 749 | A | A | C |
| 750 | A | A | C |
| 752 | A | A | C |
| 753 | A | B | B |
| 754 | C | B | B |
| 755 | B | B | A |
| 756 | A | A | C |
| 757 | C | B | B |
| 758 | B | A | B |
| 759 | B | C | C |
| 760 | B | A | C |
| 761 | A | B | B |
| 762 | B | B | C |
| 763 | A | A | C |
| 764 | A | A | C |
| 765 | B | C | C |
| 766 | A | A | C |
| 767 | A | A | C |
| 768 | NA-1 | C | C |
| 769 | A | A | C |
| 770 | NA-1 | NA-1 | C |
| 771 | A | A | C |
| 772 | A | A | C |
| 773 | B | A | C |
| 774 | A | A | B |
| 775 | A | A | B |
| 776 | A | A | B |
| 777 | A | A | B |
| 778 | A | A | C |
| 779 | A | A | C |
| 780 | A | A | C |
| 781 | A | A | C |
| 782 | A | A | C |
| 783 | A | A | C |
| 784 | A | A | C |
| 785 | C | B | C |
| 786 | A | A | C |
| 787 | A | A | C |
| 788 | A | A | C |
| 789 | A | A | C |
| 790 | A | A | C |
| 791 | A | A | C |
| 792 | A | A | C |
| 793 | A | A | C |
| 794 | A | A | C |
| 795 | A | A | C |
| 796 | A | A | C |
| 797 | A | A | C |
| 798 | A | A | C |
| 799 | A | A | B |
| 800 | A | B | C |
| 801 | NT | A | C |
| 802 | B | B | B |
| 803 | A | A | B |
| 804 | A | A | B |
| 805 | C | C | A |
| 806 | C | A | A |
| 807 | C | C | B |
| 808 | C | C | A |
| 809 | C | C | B |
| 810 | A | A | B |
| 811 | A | A | A |
| 812 | A | A | A |
| 813 | A | A | A |
| 814 | B | A | A |
| 815 | C | A | A |
| 816 | B | A | A |
| 818 | NT | NA-1 | B |
| 819 | B | A | B |
| 820 | A | A | A |
| 821 | A | A | A |
| 823 | A | A | C |
| 824 | A | A | A |
| 825 | NT | A | B |
| 826 | A | A | B |
| 827 | A | A | B |
| 828 | C | A | B |
| 829 | A | A | B |
| 830 | A | A | A |

TABLE 24-continued

TLR7/8/9 Reporter Assay Data

| Ex. No. | TLR7 IC$_{50}$ | TLR8 IC$_{50}$ | TLR9 IC$_{50}$ |
|---|---|---|---|
| 831 | A | A | B |
| 832 | A | A | B |
| 833 | A | A | A |
| 834 | A | A | B |
| 835 | B | B | C |
| 836 | A | A | A |
| 837 | A | A | B |
| 838 | A | A | B |
| 839 | A | A | A |
| 840 | C | C | B |
| 841 | A | A | A |
| 842 | B | A | B |
| 843 | C | A | A |
| 844 | C | A | A |
| 845 | B | B | B |
| 846 | A | A | B |
| 847 | A | A | B |
| 848 | B | B | B |
| 849 | B | A | B |
| 850 | A | A | B |
| 851 | A | B | B |
| 852 | A | A | B |
| 853 | A | A | A |
| 854 | A | B | B |
| 856 | A | A | B |
| 857 | C | C | B |
| 858 | C | C | B |
| 859 | B | B | C |
| 860 | A | A | C |
| 861 | A | A | B |
| 862 | A | A | C |
| 863 | B | A | B |
| 864 | A | A | B |
| 865 | A | A | C |
| 866 | A | A | C |
| 867 | B | B | C |
| 868 | A | A | B |
| 869 | A | A | B |
| 870 | A | A | B |
| 871 | B | A | C |
| 872 | C | A | B |
| 873 | A | A | B |
| 874 | A | A | B |
| 875 | B | A | B |
| 876 | A | A | C |
| 877 | A | A | C |
| 878 | A | A | C |
| 879 | B | B | C |
| 880 | B | B | C |
| 881 | C | B | C |
| 882 | C | B | C |
| 883 | A | A | C |
| 884 | A | A | C |
| 885 | A | A | C |
| 886 | A | A | C |
| 887 | A | A | C |
| 888 | A | A | C |
| 889 | A | A | C |
| 890 | A | A | C |
| 891 | A | A | B |
| 892 | A | A | C |
| 893 | B | A | C |
| 894 | B | A | B |
| 895 | B | A | C |
| 896 | B | A | C |
| 897 | C | B | C |
| 898 | B | A | C |
| 899 | A | A | B |
| 900 | B | A | C |
| 901 | B | A | C |
| 902 | B | B | NA-2 |
| 903 | A | A | C |
| 904 | B | A | B |
| 905 | B | A | C |
| 906 | A | A | B |
| 907 | A | A | C |
| 908 | B | B | C |
| 909 | A | A | C |
| 910 | B | B | C |
| 911 | B | A | C |
| 912 | A | A | B |
| 913 | B | B | NA-2 |
| 914 | A | A | C |
| 915 | B | A | B |
| 916 | B | B | B |
| 917 | B | A | C |
| 918 | A | A | B |
| 919 | A | A | B |
| 920 | B | A | C |
| 921 | B | A | B |
| 922 | C | C | C |
| 923 | B | B | NT |
| 924 | A | A | B |
| 925 | A | A | C |
| 926 | A | A | C |
| 927 | A | A | C |
| 928 | B | A | C |
| 929 | B | A | C |
| 930 | B | A | C |
| 931 | NA-2 | NA-2 | NA-2 |
| 932 | B | C | B |
| 933 | A | A | B |
| 934 | A | B | C |
| 935 | A | A | B |
| 936 | A | B | A |
| 937 | A | B | A |
| 938 | A | A | B |
| 939 | B | B | B |
| 940 | A | A | A |
| 941 | B | B | B |
| 942 | A | B | C |
| 943 | A | B | B |
| 944 | C | NA-1 | C |
| 945 | A | B | B |
| 946 | A | A | B |
| 947 | A | A | B |
| 948 | A | B | B |
| 950 | A | A | B |
| 951 | A | A | B |
| 952 | A | A | C |
| 953 | A | A | C |
| 954 | A | A | B |
| 955 | A | A | B |
| 956 | A | B | B |
| 957 | B | A | C |
| 958 | A | A | C |
| 959 | A | A | NA-2 |
| 960 | B | B | C |
| 961 | A | A | B |
| 962 | A | A | NA-2 |
| 963 | A | A | C |
| 964 | A | A | B |
| 965 | A | A | B |
| 966 | A | A | A |
| 967 | B | B | C |

Ranges: A = <100 nM;
B = 100 to 1000 nM;
C = >1000 to 50000 nM;
NA-1 = >3125 nM;
NA-2 = >50000 nM;
NT = not tested.

What is claimed is:
1. A compound of Formula (I)

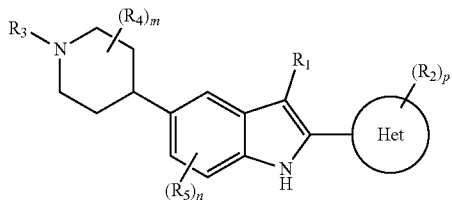

or a salt thereof, wherein:
Ring Het is a 10-membered heterocyclic ring selected from:

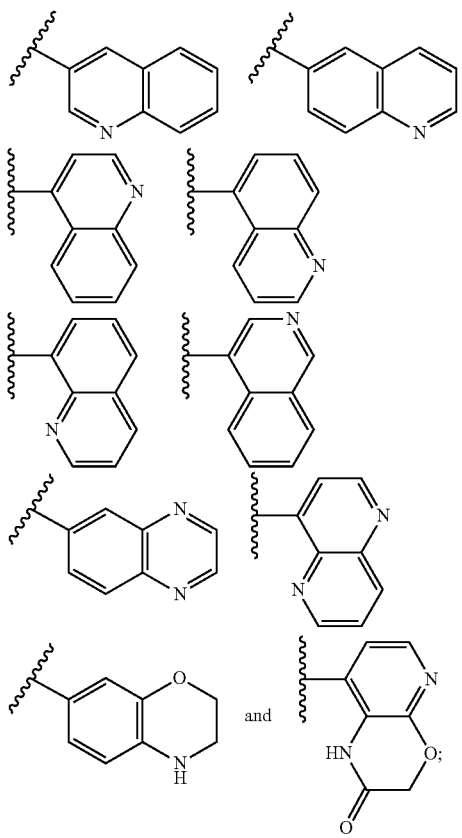

$R_1$ is H, Cl, —CN, $C_{1-4}$ alkyl, $C_{1-3}$ fluoroalkyl, $C_{1-3}$ hydroxyalkyl, $C_{1-3}$ hydroxy-fluoroalkyl, $C_{3-6}$ cycloalkyl, —CH$_2$($C_{3-6}$ cycloalkyl), —C(O)O($C_{1-3}$ alkyl), or tetrahydropyranyl;

each $R_2$ is independently halo, —CN, —OH, —NO$_2$, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, —O(CH$_2$)$_{1-2}$OH, —(CH$_2$)$_{0-4}$O($C_{1-4}$ alkyl), $C_{1-3}$ fluoroalkoxy, —(CH$_2$)$_{1-4}$O($C_{1-3}$ alkyl), —O(CH$_2$)$_{1-2}$OC(O)($C_{1-3}$ alkyl), —O(CH$_2$)$_{1-2}$NR$_x$R$_x$, —C(O)O($C_{1-3}$ alkyl), —C(O)NR$_y$R$_y$, —C(O)NR$_x$($C_{1-5}$ hydroxyalkyl), —C(O)NR$_x$($C_{2-6}$ alkoxyalkyl), —C(O)NR$_x$($C_{3-6}$ cycloalkyl), —NR$_y$R$_y$, —NR$_y$($C_{1-3}$ fluoroalkyl), —NR$_y$($C_{1-4}$ hydroxyalkyl), —NR$_x$CH$_2$(phenyl), —NR$_x$S(O)$_2$($C_{3-6}$ cycloalkyl), —NR$_x$C(O)($C_{1-3}$ alkyl), —NR$_x$(CH$_2$-cyclopropyl), —S(O)$_2$($C_{1-3}$ alkyl), $C_{3-6}$ cycloalkyl, phenyl, morpholinyl, dioxothiomorpholinyl, dimethyl pyrazolyl, methylpiperidinyl, methylpiperazinyl, amino-oxadiazolyl, imidazolyl, triazolyl, or —C(O)(thiazolyl);

$R_3$ is:
(a) -L$_1$-A; or
(b) H, $C_{1-6}$ alkyl, $C_{1-3}$ fluoroalkyl, $C_{1-3}$ cyanoalkyl, $C_{1-6}$ hydroxyalkyl, $C_{1-3}$ hydroxy-fluoroalkyl, —CR$_x$R$_x$CR$_x$(OH)CR$_x$=CR$_x$R$_x$, —C=N(NR$_x$R$_x$), —(CR$_x$R$_x$)$_{1-4}$O($C_{1-3}$ alkyl), —(CR$_x$R$_x$)$_{1-4}$O(CR$_x$R$_x$)$_{1-3}$O($C_{1-3}$ alkyl), —CH$_2$CH(OH)CH$_2$O($C_{1-3}$ alkyl), —(CR$_x$R$_x$)$_{1-3}$S($C_{1-3}$ alkyl), —(CH$_2$)$_{1-3}$C(O)OC(CH$_3$)$_3$, —(CR$_x$R$_x$)$_{0-3}$NR$_y$R$_y$, —(CR$_x$R$_x$)$_{0-3}$NR$_x$($C_{1-4}$ hydroxyalkyl), —CH$_2$CH(OH)CH$_2$NR$_x$R$_y$, —C(O)H, —C(O)($C_{1-6}$ alkyl), —C(O)($C_{1-4}$ hydroxyalkyl), —C(O)($C_{1-3}$ fluoroalkyl), —C(O)($C_{1-3}$ chloroalkyl), —C(O)($C_{1-3}$ cyanoalkyl), —(CR$_x$R$_x$)$_{0-3}$C(O)OH, —C(O)(CH$_2$)$_{0-2}$O($C_{1-4}$ alkyl), —C(O)(CR$_x$R$_x$)$_{0-2}$O(CR$_x$R$_x$)$_{1-2}$O($C_{1-3}$ alkyl), —C(O)(CR$_x$R$_x$)$_{0-2}$O(CR$_x$R$_x$)$_{1-2}$NR$_y$R$_y$, —C(O)CR$_x$R$_x$S(O)$_2$($C_{1-3}$ alkyl), —C(O)CR$_x$R$_x$NR$_x$S(O)$_2$($C_{1-3}$ alkyl), —C(O)CR$_x$R$_x$OC(O)($C_{1-3}$ alkyl), —C(O)(CR$_x$R$_x$)$_{0-3}$NR$_y$R$_y$, —C(O)(CR$_x$R$_x$)$_{0-1}$NR$_x$($C_{1-3}$ cyanoalkyl), —C(O)(CR$_x$R$_x$)$_{0-2}$NR$_y$($C_{1-6}$ hydroxyalkyl), —C(O)(CR$_x$R$_x$)$_{0-2}$NR$_x$($C_{1-3}$ fluoroalkyl), —C(O)(CR$_x$R$_x$)$_{0-1}$NR$_x$($C_{1-5}$ hydroxy-fluoroalkyl), —C(O)(CR$_x$R$_x$)$_{0-1}$NR$_x$(CH$_2$)$_{1-2}$O($C_{1-3}$ hydroxyalkyl), —C(O)(CR$_x$R$_x$)$_{0-2}$NR$_x$(CH$_2$)$_{1-2}$NR$_x$C(O)($C_{1-2}$ alkyl), —C(O)(CR$_x$R$_x$)$_{0-2}$NR$_x$((CR$_x$R$_x$)$_{1-2}$O($C_{1-2}$ alkyl)), —C(O)(CR$_x$R$_x$)$_{0-2}$N((CR$_x$R$_x$)$_{1-2}$O($C_{1-2}$ alkyl))$_2$, —C(O)(CR$_x$R$_x$)$_{0-2}$NR$_x$(CR$_x$R$_x$)$_{1-3}$NR$_x$R$_x$, —C(O)CR$_x$(NH$_2$)(CR$_x$R$_x$)$_{1-4}$NR$_x$R$_x$, —C(O)CR$_x$(NH$_2$)(CR$_x$R$_x$)$_{1-4}$NR$_x$C(O)NR$_x$R$_x$, —C(O)(CR$_x$R$_x$)$_{0-3}$NR$_x$(CH$_2$)$_{0-1}$C(O)($C_{1-3}$ alkyl), —C(O)(CR$_x$R$_x$)$_{0-3}$N((CH$_2$)$_{0-1}$C(O)($C_{1-3}$ alkyl))$_2$, —C(O)(CR$_x$R$_x$)$_{0-1}$NR$_x$(CH$_2$)$_{0-1}$C(O)($C_{1-3}$ cyanoalkyl), —C(O)(CR$_x$R$_x$)$_{0-2}$NR$_x$(CH$_2$)$_{1-2}$C(O)NR$_y$R$_y$, —C(O)(CR$_x$R$_x$)$_{1-3}$C(O)NR$_y$R$_y$, —C(O)(CR$_x$R$_x$)$_{1-3}$S(O)$_2$NR$_y$R$_y$, —C(O)(CR$_x$R$_x$)$_{0-2}$NR$_x$(CHR$_y$(CH$_2$OH)), —(CR$_x$R$_x$)$_{1-2}$C(O)NR$_y$R$_y$, —CH(CN)C(O)NR$_y$R$_y$, —(CR$_x$R$_x$)$_{1-2}$C(O)NR$_y$($C_{1-3}$ fluoroalkyl), —(CR$_x$R$_x$)$_{1-2}$C(O)NR$_y$($C_{1-4}$ hydroxyalkyl), —(CR$_x$R$_x$)$_{1-2}$C(O)NR$_y$($C_{1-3}$ cyanoalkyl), —(CR$_x$R$_x$)$_{1-2}$C(O)NR$_x$(CH$_2$)$_{1-2}$O($C_{1-3}$ alkyl), —(CR$_x$R$_x$)$_{1-2}$C(O)NR$_x$CH($C_{1-4}$ alkyl)($C_{1-3}$ hydroxyalkyl), —(CR$_x$R$_x$)$_{1-2}$C(O)NR$_x$CH($C_{1-3}$ hydroxyalkyl)($C_{3-6}$ cycloalkyl), —(CH$_2$)$_{1-2}$C(O)NR$_x$(CH$_2$)$_{1-2}$C(O)NR$_x$R$_x$, —(CH$_2$)$_{1-2}$C(O)NR$_x$(CH$_2$)$_{1-2}$S($C_{1-3}$ alkyl), —(CH$_2$)$_{1-2}$C(O)NR$_x$(CH$_2$)$_{1-2}$S(O)$_2$OH, —(CH$_2$)$_{1-2}$C(O)NR$_x$(CH$_2$)$_{1-2}$NR$_x$C(O)($C_{1-3}$ alkyl), —(CH$_2$)$_{1-2}$C(O)NR$_x$(CH$_2$)$_{1-3}$NR$_x$R$_x$, —(CH$_2$)$_{1-2}$C(O)N(CH$_2$CH$_3$)(CH$_2$)$_{1-3}$NR$_x$R$_x$, —(CR$_x$R$_x$)$_{0-3}$S(O)$_2$($C_{1-4}$ alkyl), —(CH$_2$)$_{0-2}$S(O)$_2$($C_{1-3}$ fluoroalkyl), —(CR$_x$R$_x$)$_{0-2}$S(O)$_2$NR$_y$R$_y$, —(CR$_x$R$_x$)$_{0-2}$NR$_x$S(O)$_2$($C_{1-3}$ alkyl), —C(O)C(O)OH, —C(O)C(O)NR$_y$R$_y$, or —C(O)C(O)NR$_y$(CR$_x$R$_x$)$_{1-2}$NR$_y$R$_y$;

L$_1$ is a bond, —(CR$_x$R$_x$)$_{1-2}$—, —(CR$_x$R$_x$)$_{1-2}$CR$_x$(OH)—, —(CR$_x$R$_x$)$_{1-2}$O—, —CR$_x$R$_x$C(O)—, —(CR$_x$R$_x$)$_2$NR$_x$(CR$_x$R$_x$)$_{0-1}$—, —CR$_x$R$_x$C(O)NR$_x$(CR$_x$R$_x$)$_{0-4}$—, —C(O)(CR$_x$R$_x$)$_{0-3}$—, —C(O)(CR$_x$R$_x$)$_{0-2}$NR$_x$(CR$_x$R$_x$)$_{0-2}$—, —C(O)(CR$_x$R$_x$)$_{0-2}$N($C_{1-2}$ hydroxyalkyl)(CR$_x$R$_x$)$_{0-2}$—, —C(O)(CR$_x$R$_x$)$_{0-2}$NR$_x$(CR$_x$R$_x$)$_{1-2}$CR$_x$(OH)—, —C(O)(CR$_x$R$_x$)$_{1-2}$C(O)NR$_x$—, —(CR$_x$R$_x$)$_{0-2}$C(O)NR$_x$(CR$_x$R$_x$)$_{1-2}$CR$_x$(OH)—, —(CR$_x$R$_x$)$_{0-2}$C(O)N($C_{1-2}$ hydroxyalkyl)(CR$_x$R$_x$)$_{1-2}$—, —C(O)(CR$_x$R$_x$)$_{0-1}$O—, —C(O)(CR$_x$R$_x$)$_{1-2}$NHS(O)$_2$—, —C(O)CR$_x$(NH$_2$)CR$_x$R$_x$—, —C(O)C(O)(CR$_x$R$_x$)$_{0-2}$—, —C(O)NR$_x$(CR$_x$R$_x$)$_{1-2}$—, or —S(O)$_2$—;

A is 3-oxa-8-azabicyclo[3.2.1]octanyl, 8-oxa-3-azabicyclo[3.2.1]octanyl, 1,1-dioxidothiomorpholinyl, 1,2-dioxotetrahydro-2H-thiopyranyl, 1,4-diazepanyl, 2-azabicyclo[3.1.0]hexanyl, azabicyclo[3.2.1]octanyl, 2-oxa-6-azaspiro[3.3]heptanyl, azepanyl, $C_{3-7}$ cycloalkyl, imidazo[1,2-a]pyridinyl, imidazo[1,5-a]pyridinyl, imidazolyl, isoxazolyl, morpholinyl, oxadiazolyl, oxazolyl, oxetanyl, phenyl, piperazinonyl, piperazinyl, piperidinonyl, piperidinyl, pyrazinyl, pyrazolyl, pyridazinyl, pyridinyl, pyrimidinyl, pyrrolidinonyl, pyrrolidinyl, pyrrolyl, quinolinyl, tetrahydrofuranyl, tetrahydropyranyl, tetrahydrothiopyranyl, tetrazolyl, thiadiazolyl, thiazolyl, or triazolyl, each substituted with zero to 4 substituents independently selected from F, Cl, —OH, —CN, $C_{1-6}$ alkyl, $C_{1-3}$ fluoroalkyl, $C_{1-5}$ hydroxyalkyl, —$CH_2NR_xR_x$, $C_{1-3}$ alkoxy, —$O(CH_2)_{1-3}NR_xR_x$, —$O(CH_2)_{1-3}NR_x$(pyridinyl), —$C(O)(C_{1-3}$ alkyl), —$C(O)O(C_{1-3}$ alkyl), —$C(O)NR_yR_y$, —$NR_xR_x$, —$NR_xC(O)(C_{1-3}$ alkyl), —O(pyrimidinyl), $C_{3-6}$ cycloalkyl, morpholinyl, phenyl, methyl piperazinyl, pyridinyl, and pyrrolidinyl;

each $R_x$ is independently H or —$CH_3$;
each $R_y$ is independently H or $C_{1-6}$ alkyl;
each $R_4$ is independently F, —OH, $C_{1-2}$ alkyl, or —$OCH_3$; or two $R_4$ attached to the same carbon atom form =O; or wherein when m is at least 2, two $R_4$, each attached to a different carbon atom adjacent to the nitrogen atom in the piperidinyl ring, can form a —$CH_2CH_2$— bridge;
each $R_5$ is independently F, Cl, —CN, $C_{1-2}$ alkyl, $C_{1-2}$ fluoroalkyl, or —$OCH_3$;
m is zero, 1, 2, 3, or 4;
n is zero, 1, or 2; and
p is zero, 1, 2, 3, or 4.

2. The compound according to claim 1 or a salt thereof, wherein:
$R_1$ is H, Cl, —CN, $C_{1-4}$ alkyl, $C_{1-2}$ fluoroalkyl, $C_{1-2}$ hydroxyalkyl, or —$C(O)O(C_{1-2}$ alkyl);
each $R_2$ is independently F, Cl, —CN, —OH, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, $C_{1-4}$ alkoxy, —$NR_yR_y$, —$C(O)NR_yR_y$, —$C(O)NR_x(C_{1-4}$ hydroxyalkyl), —$C(O)NR_x(C_{2-4}$ alkoxyalkyl), —$C(O)NR_x(C_{3-6}$ cycloalkyl), —$S(O)_2(C_{1-3}$ alkyl), $C_{3-6}$ cycloalkyl, morpholinyl, phenyl, or dimethyl pyrazolyl;
$R_3$ is:
(a) -$L_1$-A; or
(b) H, $C_{1-6}$ alkyl, $C_{1-3}$ fluoroalkyl, $C_{1-3}$ cyanoalkyl, $C_{1-5}$ hydroxyalkyl, —$(CR_xR_x)_{1-2}O(C_{1-2}$ alkyl), —$(CR_xR_x)_{1-4}O(CR_xR_x)_{1-3}O(C_{1-3}$ alkyl), —$CH_2CH(OH)CH_2O(C_{1-3}$ alkyl), —$(CR_xR_x)_{1-3}S(C_{1-3}$ alkyl), —$(CH_2)_{1-3}C(O)OC(CH_3)_3$, —$(CR_xR_x)_{0-3}NR_yR_y$, —$(CR_xR_x)_{0-3}NR_x(C_{1-4}$ hydroxyalkyl), —$CH_2CH(OH)CH_2NR_xR_y$, —$C(O)(C_{1-6}$ alkyl), —$C(O)(C_{1-4}$ hydroxyalkyl), —$C(O)(C_{1-3}$ fluoroalkyl), —$C(O)(C_{1-3}$ chloroalkyl), —$C(O)(C_{1-3}$ cyanoalkyl), —$(CR_xR_x)_{0-3}C(O)OH$, —$C(O)(CH_2)_{0-2}O(C_{1-4}$ alkyl), —$C(O)(CR_xR_x)_{0-2}O(CR_xR_x)_{1-2}O(C_{1-3}$ alkyl), —$C(O)(CH_2)_{0-2}O(CH_2)_{1-2}NR_yR_y$, —$C(O)CR_xR_xS(O)_2(C_{1-2}$ alkyl), —$C(O)CR_xR_xNR_xS(O)_2(C_{1-2}$ alkyl), —$C(O)CR_xR_xOC(O)(C_{1-3}$ alkyl), —$C(O)(CR_xR_x)_{0-2}NR_yR_y$, —$C(O)(CR_xR_x)_{0-2}NR_x(C_{1-2}$ cyanoalkyl), —$C(O)(CR_xR_x)_{0-2}NR_y(C_{1-6}$ hydroxyalkyl), —$C(O)(CR_xR_x)_{0-2}NR_x(C_{1-3}$ fluoroalkyl), —$C(O)(CR_xR_x)_{0-1}NR_x(C_{1-5}$ hydroxy-fluoroalkyl), —$C(O)(CR_xR_x)_{0-1}NR_x((CR_xR_x)_{1-2}O(C_{1-2}$ alkyl)), —$C(O)(CR_xR_x)_{0-1}NR_x(CH_2)_{1-2}O(C_{1-3}$ hydroxyalkyl), —$C(O)(CR_xR_x)_{0-1}NR_x(CH_2)_{1-2}NR_xC(O)(C_{1-2}$ alkyl), —$C(O)(CR_xR_x)_{0-2}NR_x((CR_xR_x)_{1-2}O(C_{1-2}$ alkyl)), —$C(O)(CR_xR_x)_{0-1}NR_x(CR_xR_x)_{1-3}NR_xR_x$, —$C(O)CR_x(NH_2)$ $(CR_xR_x)_{1-4}NR_xR_x$, —$C(O)CR_x(NH_2)(CR_xR_x)_{1-4}NR_xC(O)NR_xR_x$, —$C(O)(CR_xR_x)_{0-3}NR_x(CH_2)_{0-1}C(O)(C_{1-3}$ alkyl), —$C(O)(CR_xR_x)_{0-1}NR_x(CH_2)_{0-1}C(O)(C_{1-3}$ cyanoalkyl), —$C(O)(CR_xR_x)_{0-2}NR_x(CH_2)_{1-2}C(O)NR_yR_y$, —$C(O)(CR_xR_x)_{0-2}NR_x(CHR_y(CH_2OH))$, —$(CR_xR_x)_{1-2}C(O)NR_yR_y$, —$(CR_xR_x)_{1-2}C(O)NR_y(C_{1-3}$ fluoroalkyl), —$(CR_xR_x)_{1-2}C(O)NR_x(C_{1-4}$ hydroxyalkyl), —$(CR_xR_x)_{1-2}C(O)NR_x(C_{1-3}$ cyanoalkyl), —$CH(CN)C(O)NR_yR_y$, —$(CR_xR_x)_{1-2}C(O)NR_x(CH_2)_{1-2}O(C_{1-3}$ alkyl), —$(CR_xR_x)_{1-2}C(O)NR_xCH(C_{1-4}$ alkyl) $(C_{1-3}$ hydroxyalkyl), —$(CH_2)_{1-2}C(O)NR_x(CH_2)_{1-2}C(O)NR_xR_x$, —$(CH_2)_{1-2}S(O)_2NR_x(CH_2)_{1-2}S(C_{1-2}$ alkyl), —$(CH_2)_{1-2}C(O)NR_x(CH_2)_{1-2}S(O)_2OH$, —$(CH_2)_{1-2}C(O)NR_x(CH_2)_{1-2}NR_xC(O)(C_{1-3}$ alkyl), —$(CH_2)_{1-2}C(O)NR_x(CH_2)_{1-3}NR_xR_x$, —$(CH_2)_{1-2}C(O)N(CH_2CH_3)(CH_2)_{1-3}NR_xR_x$, —$(CR_xR_x)_{1-3}S(O)_2(C_{1-4}$ alkyl), —$(CH_2)_{0-2}S(O)_2(C_{1-3}$ fluoroalkyl), —$(CH_2)_{1-2}S(O)_2NR_yR_y$, —$C(O)C(O)OH$, —$C(O)C(O)NR_yR_y$, or —$C(O)C(O)NR_x(CR_xR_x)_{1-2}NR_yR_y$;

$L_1$ is a bond, —$(CR_xR_x)_{1-2}$—, —$(CR_xR_x)_{1-2}CR_x(OH)$—, —$(CR_xR_x)_{1-2}O$—, —$CR_xR_xC(O)$—, —$(CR_xR_x)_2NR_x(CR_xR_x)_{0-1}$—, —$CR_xR_xC(O)NR_x(CR_xR_x)_{0-4}$—, —$C(O)(CR_xR_x)_{0-3}$—, —$C(O)(CR_xR_x)_{0-2}NR_x(CR_xR_x)_{0-2}$—, —$C(O)(CR_xR_x)_{0-2}N(C_{1-2}$ hydroxyalkyl)$(CR_xR_x)_{0-2}$—, —$C(O)(CR_xR_x)_{0-2}NR_x(CR_xR_x)_{1-2}CR_x(OH)$—, —$C(O)(CR_xR_x)_{1-2}C(O)NR_x$—, —$(CR_xR_x)_{0-2}C(O)NR_x(CR_xR_x)_{1-2}CR_x(OH)$—, —$(CR_xR_x)_{0-2}C(O)N(C_{1-2}$ hydroxyalkyl)$(CR_xR_x)_{1-2}$—, —$C(O)(CR_xR_x)_{0-1}O$—, —$C(O)(CR_xR_x)_{1-2}NHS(O)_2$—, —$C(O)CR_x(NH_2)CR_xR_x$—, —$C(O)C(O)(CR_xR_x)_{0-2}$—, —$C(O)NR_x(CR_xR_x)_{1-2}$—, or —$S(O)_2$—;

each $R_5$ is independently F, Cl, —CN, $C_{1-2}$ alkyl, or —$OCH_3$;
m is zero, 1, or 2;
n is zero or 1; and
p is zero, 1, or 2.

3. The compound according to claim 1 or a salt thereof, wherein:
$R_1$ is —$CH_3$, —$CH_2CH_3$, —$CH(CH_3)_2$, —$CH_2OH$, —$CH_2CHF_2$, or —$C(O)OCH_3$;
each $R_2$ is independently F, Cl, —CN, —OH, —$CH_3$, —$CH_2CH_3$, —$CH(CH_3)_2$, —$CH_2CH(CH_3)_2$, —$CF_3$, —$CH_2OH$, —$C(CH_3)_2OH$, —$OCH_3$, —$OCH_2CH_3$, —$NH_2$, —$NH(CH_3)$, —$C(O)NH_2$, —$C(O)NH(CH_3)$, —$C(O)N(CH_3)_2$, —$C(O)NH(CH_2CH_2OH)$, —$C(O)NH(CH_2CH_2OCH_3)$, —$C(O)NH(CH_2C(CH_3)_2OH)$, —$C(O)NH(cyclopropyl)$, —$C(O)N(CH_3)(CH_2CH_3)$, —$C(O)N(CH_3)(CH_2CH_2OH)$, —$S(O)_2CH_3$, phenyl, or dimethyl pyrazolyl;
$R_3$ is:
(a) -$L_1$-A; or
(b) H, —$CH_3$, —$CH(CH_3)_2$, —$CH_2CH_2CH_3$, —$CH_2CH(CH_3)_2$, —$CH_2CH_2CF_3$, —$CH_2CH_2CH_2CF_3$, —$CH_2CN$, —$CH_2CH_2CN$, —$CH_2C(CH_3)_2OH$, —$CH(CH_2OH)_2$, —$CH_2CH_2OCH_3$, —$CH(CH_2OH)(CH_2OCH_3)$, —$CH_2CH_2NH_2$, —$CH_2CH_2NH(CH_3)$, —$CH_2CH_2N(CH_2CH_3)_2$, —$CH_2CH_2CH_2N(CH_3)_2$, —$CH_2CH(CH_3)CH_2N(CH_3)_2$, —$CH_2C(CH_3)_2CH_2N(CH_3)_2$, —$CH_2CH_2NH(S(O)_2)CH_3$, —$CH_2CH_2S(O)_2CH_3$, —$CH_2CH_2CH_2S(O)_2CH_3$, —$CH_2CH_2S(O)_2NH_2$, —$CH_2C(O)NH_2$, —$CH_2C(O)NH(CH_3)$, —$CH_2C(O)N(CH_3)_2$, —$CH_2C(O)NH(CF_3)$, —$C(O)CH_2CH(CH_3)OH$, —$C(O)CH_2C(CH_3)_2OH$, —$C(O)CH_2NH_2$, —$C(O)CH_2NH(CH_3)$, —$C(O)CH_2NH(CH(CH_3)_2)$, —$C(O)CH_2N(CH_3)_2$, —$C(O)CH_2N(CH_3)(CH(CH_3)_2)$, —$C(O)CH_2NH(CH_2C(CH_3)_3)$, —$C(O)$ CH₂NH(CH(CH₃)CH₂CH₃), —C(O)CH₂NH(CH₂CH₂CH₂N(CH₃)₂), —C(O)CH₂N(CH₃)(CH₂CH(CH₃)₂), —C(O)CH₂CH₂N(CH₃)₂, —C(O)CH₂CH₂N(CH₃)(CH₂CH₃), —C(O)CH₂CH₂N(CH₃)(CH(CH₃)₂), —C(O)CH₂CH(CH₃)NH₂, —C(O)CH₂NHC(O)CH₃, —C(O)CH₂CH₂C(O)N(CH₃)₂, —C(O)CH₂NH(CH₂CH₂NHC(O)CH₃), —C(O)CH₂S(O)₂CH₃, —S(O)₂CH₂CH₂OH, or —S(O)₂CH₂CH₂N(CH₃)₂;

$L_1$ is a bond, —CH₂—, —CH₂CH₂—, —CH₂CH₂CH₂—, —CH₂C(O)—, —C(O)—, —C(O)CH₂—, —C(O)CH₂CH₂—, —C(O)CH₂NH—, —C(O)CH₂N(CH₃)—, —C(O)CH₂CH₂N(CH₃)—, or —C(O)CH₂NHCH₂C(CH₃)₂—;

A is (1R,5S)-3-oxa-8-azabicyclo[3.2.1]octanyl, (1R,5S)-8-oxa-3-azabicyclo[3.2.1]octanyl, 1,1-dioxidothiomorpholinyl, 1,2-dioxotetrahydro-2H-thiopyranyl, 1,4-diazepanyl, 2-azabicyclo[3.1.0]hexanyl, azabicyclo[3.2.1]octanyl, 2-oxa-6-azaspiro[3.3]heptanyl, azepanyl, cyclohexyl, cyclopropyl, imidazo[1,2-a]pyridinyl, imidazo[1,5-a]pyridinyl, imidazolyl, isoxazolyl, morpholinyl, oxadiazolyl, oxazolyl, oxetanyl, phenyl, piperazinonyl, piperazinyl, piperidinonyl, piperidinyl, pyrazolyl, pyridinyl, pyrimidinyl, pyrrolidinonyl, pyrrolidinyl, quinolinyl, tetrahydropyranyl, thiadiazolyl, thiazolyl, or triazolyl, each substituted with zero to 4 substituents independently selected from F, Cl, —OH, —CH₃, —CH₂H₃, —CH(CH₃)₂, —CH₂CH₂CH₃, —CH₂CH(CH₃)₂, —CH₂OH, —CH₂N(CH₃)₂, —OCH₃, —OCH₂CH₂CH₂N(CH₃)₂, —OCH₂CH₂N(CH₃)(pyridinyl), —C(O)CH₃, —C(O)OCH₃, —C(O)OCH₂CH₃, —C(O)NH₂, —C(O)N(CH₂CH₃)₂, —NH₂, —N(CH₃)₂, —NHC(O)CH₃, —O(pyrimidinyl), morpholinyl, phenyl, methyl piperazinyl, pyridinyl, and pyrrolidinyl;

each $R_4$ is independently F or —OH, or two $R_4$ attached to the same carbon atom form =O;

each $R_5$ is independently F, Cl, —CH₃, —CF₃, or —OCH₃;

m is zero, 1, or 2;

n is zero, 1, or 2; and p is zero, 1, 2, or 3.

4. The compound according to claim 1 or a salt thereof, wherein:

$R_3$ is -$L_1$-A; and $L_1$ is a bond, —(CR$_x$R$_x$)$_{1-2}$—, —(CR$_x$R$_x$)$_{1-2}$CR$_x$(OH)—, —(CR$_x$R$_x$)$_{1-2}$O—, —CR$_x$R$_x$C(O)—, —(CR$_x$R$_x$)$_2$NR$_x$(CR$_x$R$_x$)$_{0-1}$—, —CR$_x$R$_x$C(O)NR$_x$(CR$_x$R$_x$)$_{0-4}$—, —C(O)(CR$_x$R$_x$)$_{0-3}$—, —C(O)(CR$_x$R$_x$)$_{0-2}$NR$_x$(CR$_x$R$_x$)$_{0-2}$—, —C(O)(CR$_x$R$_x$)$_{0-2}$N(C$_{1-2}$ hydroxyalkyl)(CR$_x$R$_x$)$_{0-2}$—, —C(O)(CR$_x$R$_x$)$_{0-2}$NR$_x$(CR$_x$R$_x$)$_{1-2}$CR$_x$(OH)—, —C(O)(CR$_x$R$_x$)$_{1-2}$C(O)NR$_x$—, —(CR$_x$R$_x$)$_{0-2}$C(O)NR$_x$(CR$_x$R$_x$)$_{1-2}$CR$_x$(OH)—, —(CR$_x$R$_x$)$_{0-2}$C(O)N(C$_{1-2}$ hydroxyalkyl)(CR$_x$R$_x$)$_{1-2}$—, —C(O)(CR$_x$R$_x$)$_{0-1}$O—, —C(O)(CR$_x$R$_x$)$_{1-2}$NHS(O)$_2$—, —C(O)CR$_x$(NH$_2$)CR$_x$R$_x$—, —C(O)C(O)(CR$_x$R$_x$)$_{0-2}$—, —C(O)NR$_x$(CR$_x$R$_x$)$_{1-2}$—, or —S(O)$_2$—.

5. The compound according to claim 1 or a salt thereof, wherein A is azepanyl, cyclohexyl, cyclopropyl, imidazo[1,2-a]pyridinyl, imidazo[1,5-a]pyridinyl, imidazolyl, isoxazolyl, morpholinyl, oxadiazolyl, oxazolyl, oxetanyl, phenyl, piperazinonyl, piperazinyl, piperidinonyl, piperidinyl, pyrazolyl, pyridinyl, pyrimidinyl, pyrrolidinonyl, pyrrolidinyl, quinolinyl, tetrahydropyranyl, thiadiazolyl, thiazolyl, or triazolyl, each substituted with zero to 4 substituents independently selected from F, Cl, —OH, —CH₃, —CH₂H₃, —CH(CH₃)₂, —CH₂CH₂CH₃, —CH₂CH(CH₃)₂, —CH₂OH, —CH₂N(CH₃)₂, —OCH₃, —OCH₂CH₂CH₂N(CH₃)₂, —OCH₂CH₂N(CH₃)(pyridinyl), —C(O)CH₃, —C(O)OCH₃, —C(O)OCH₂CH₃, —C(O)NH₂, —C(O)N(CH₂CH₃)₂, —NH₂, —N(CH₃)₂, —NHC(O)CH₃, —O(pyrimidinyl), morpholinyl, phenyl, methyl piperazinyl, pyridinyl, and pyrrolidinyl.

6. The compound according to claim 1 or a salt thereof, wherein $R_3$ is H, $C_{1-6}$ alkyl, $C_{1-3}$ fluoroalkyl, $C_{1-3}$ cyanoalkyl, $C_{1-5}$ hydroxyalkyl, —(CR$_x$R$_x$)$_{1-2}$O(C$_{1-2}$ alkyl), —(CR$_x$R$_x$)$_{1-4}$O(CR$_x$R$_x$)$_{1-3}$O(C$_{1-3}$ alkyl), —CH₂CH(OH)CH₂O(C$_{1-3}$ alkyl), —(CR$_x$R$_x$)$_{1-3}$S(C$_{1-3}$ alkyl), —(CH$_2$)$_{1-3}$C(O)OC(CH$_3$)$_3$, —(CR$_x$R$_x$)$_{0-3}$NR$_x$R$_y$, —(CR$_x$R$_x$)$_{0-3}$NR$_x$(C$_{1-4}$ hydroxyalkyl), —CH₂CH(OH)CH₂NR$_x$R$_y$, —C(O)(C$_{1-6}$ alkyl), —C(O)(C$_{1-4}$ hydroxyalkyl), —C(O)(C$_{1-3}$ fluoroalkyl), —C(O)(C$_{1-3}$ chloroalkyl), —C(O)(C$_{1-3}$ cyanoalkyl), —(CR$_x$R$_x$)$_{0-3}$C(O)OH, —C(O)(CH$_2$)$_{0-2}$O(C$_{1-4}$ alkyl), —C(O)(CR$_x$R$_x$)$_{0-2}$O(CR$_x$R$_x$)$_{1-2}$O(C$_{1-3}$ alkyl), —C(O)(CH$_2$)$_{0-2}$O(CH$_2$)$_{1-2}$NR$_x$R$_y$, —C(O)CR$_x$R$_x$S(O)$_2$(C$_{1-2}$ alkyl), —C(O)CR$_x$R$_x$NR$_x$S(O)$_2$(C$_{1-2}$ alkyl), —C(O)CR$_x$R$_x$OC(O)(C$_{1-3}$ alkyl), —C(O)(CR$_x$R$_x$)$_{0-2}$NR$_x$R$_y$, —C(O)(CR$_x$R$_x$)$_{0-2}$NR$_x$(C$_{1-2}$ cyanoalkyl), —C(O)(CR$_x$R$_x$)$_{0-2}$NR$_x$(C$_{1-6}$ hydroxyalkyl), —C(O)(CR$_x$R$_x$)$_{0-2}$NR$_x$(C$_{1-3}$ fluoroalkyl), —C(O)(CR$_x$R$_x$)$_{0-1}$NR$_x$(C$_{1-5}$ hydroxyfluoroalkyl), —C(O)(CR$_x$R$_x$)$_{0-1}$NR$_x$((CR$_x$R$_x$)$_{1-2}$O(C$_{1-2}$ alkyl)), —C(O)(CR$_x$R$_x$)$_{0-1}$NR$_x$(CH$_2$)$_{1-2}$O(C$_{1-3}$ hydroxyalkyl), —C(O)(CR$_x$R$_x$)$_{0-1}$NR$_x$(CH$_2$)$_{1-2}$NR$_x$C(O)(C$_{1-2}$ alkyl), —C(O)(CR$_x$R$_x$)$_{0-2}$NR$_x$((CR$_x$R$_x$)$_{1-2}$O(C$_{1-2}$ alkyl)), —C(O)(CR$_x$R$_x$)$_{0-1}$NR$_x$(CR$_x$R$_x$)$_{1-3}$NR$_x$R$_x$, —C(O)CR$_x$(NH$_2$)(CR$_x$R$_x$)$_{1-4}$NR$_x$R$_x$, —C(O)CR$_x$(NH$_2$)(CR$_x$R$_x$)$_{1-4}$NR$_x$C(O)NR$_x$R$_x$, —C(O)(CR$_x$R$_x$)$_{0-3}$NR$_x$(CH$_2$)$_{0-1}$C(O)(C$_{1-3}$ alkyl), —C(O)(CR$_x$R$_x$)$_{0-1}$NR$_x$(CH$_2$)$_{0-1}$C(O)(C$_{1-3}$ cyanoalkyl), —C(O)(CR$_x$R$_x$)$_{0-2}$NR$_x$(CH$_2$)$_{1-2}$C(O)NR$_y$R$_y$, —C(O)(CR$_x$R$_x$)$_{0-2}$NR$_x$(CHR$_y$(CH$_2$OH)), —(CR$_x$R$_x$)$_{1-2}$C(O)NR$_y$R$_y$, —(CR$_x$R$_x$)$_{1-2}$C(O)NR$_y$(C$_{1-3}$ fluoroalkyl), —(CR$_x$R$_x$)$_{1-2}$C(O)NR$_y$(C$_{1-4}$ hydroxyalkyl), —(CR$_x$R$_x$)$_{1-2}$C(O)NR$_x$(C$_{1-3}$ cyanoalkyl), —CH(CN)C(O)NR$_y$R$_y$, —(CR$_x$R$_x$)$_{1-2}$C(O)NR$_x$(CH$_2$)$_{1-2}$O(C$_{1-3}$ alkyl), —(CR$_x$R$_x$)$_{1-2}$C(O)NR$_x$CH(C$_{1-4}$ alkyl)(C$_{1-3}$ hydroxyalkyl), —(CH$_2$)$_{1-2}$C(O)NR$_x$(CH$_2$)$_{1-2}$C(O)NR$_x$R$_x$, —(CH$_2$)$_{1-2}$S(O)$_2$NR$_x$(CH$_2$)$_{1-2}$S(C$_{1-2}$ alkyl), —(CH$_2$)$_{1-2}$C(O)NR$_x$(CH$_2$)$_{1-2}$S(O)$_2$OH, —(CH$_2$)$_{1-2}$C(O)NR$_x$(CH$_2$)$_{1-2}$NR$_x$C(O)(C$_{1-3}$ alkyl), —(CH$_2$)$_{1-2}$C(O)NR$_x$(CH$_2$)$_{1-3}$NR$_x$R$_x$, —(CH$_2$)$_{1-2}$C(O)N(CH$_2$CH$_3$)(CH$_2$)$_{1-3}$NR$_x$R$_x$, —(CR$_x$R$_x$)$_{1-3}$S(O)$_2$(C$_{1-4}$ alkyl), —(CH$_2$)$_{0-2}$S(O)$_2$(C$_{1-3}$ fluoroalkyl), —(CH$_2$)$_{1-2}$S(O)$_2$NR$_y$R$_y$, —C(O)C(O)OH, —C(O)C(O)NR$_y$R$_y$, or —C(O)C(O)NR$_y$(CR$_x$R$_x$)$_{1-2}$NR$_y$R$_y$.

7. The compound according to claim 1 or a salt thereof, wherein said Ring Het is selected from:

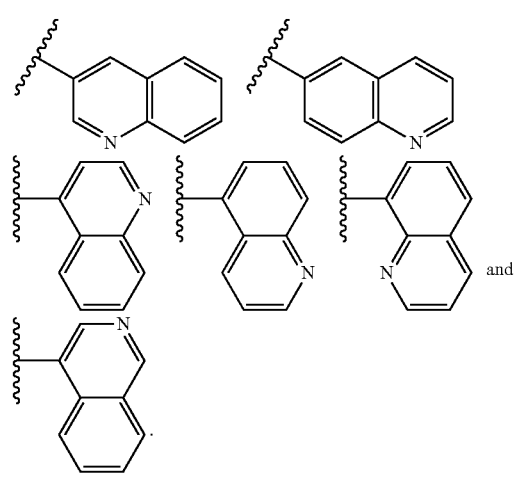

8. The compound according to claim 1 or a salt thereof, wherein said Ring Het is selected from:

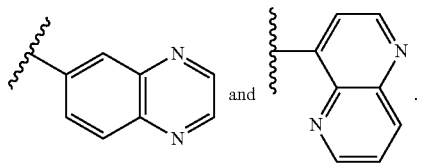 [SMILES: *c1ccc2nccnc2c1 ; *c1ccnc2cccnc12]

9. The compound according to claim 1 or a salt thereof, wherein said Ring Het is selected from

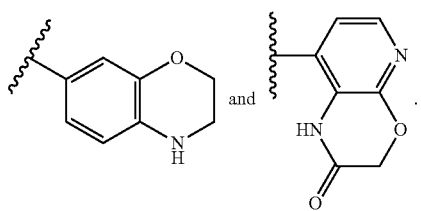 [SMILES: *c1ccc2c(c1)OCCN2 ; *c1ccnc2c1NC(=O)CO2]

10. The compound according to claim 1 or a salt thereof, wherein said compound is selected from:
- 4-(3-isopropyl-5-(piperidin-4-yl)-1H-indol-2-yl)-1,5-naphthyridine (22);
- 8-(3-isopropyl-5-(piperidin-4-yl)-1H-indol-2-yl)-1H-pyrido[2,3-b][1,4]oxazin-2(3H)-one (68);
- 6-(3-isopropyl-5-(piperidin-4-yl)-1H-indol-2-yl)-8-methylquinoxalin-2-ol (87);
- 7-(3-isopropyl-5-(piperidin-4-yl)-1H-indol-2-yl)-5-methylquinoxaline (88);
- 4-(3-isopropyl-5-(piperidin-4-yl)-1H-indol-2-yl)-2-methylquinoline (104);
- 4-(3-isopropyl-5-(piperidin-4-yl)-1H-indol-2-yl)-2-methoxyquinoline (105);
- 4-hydroxy-6-(3-isopropyl-5-(piperidin-4-yl)-1H-indol-2-yl)-8-methylquinoline-3-carbonitrile (107);
- 5-(3-isopropyl-5-(piperidin-4-yl)-1H-indol-2-yl)quinoline-8-carbonitrile (109);
- 8-chloro-6-(3-isopropyl-5-(piperidin-4-yl)-1H-indol-2-yl)quinoline (139);
- 6-(3-isopropyl-5-(piperidin-4-yl)-1H-indol-2-yl)-7-methylquinoline (140);
- 6-(3-isopropyl-5-(piperidin-4-yl)-1H-indol-2-yl)-8-methylquinoline (141);
- 6-(3-isopropyl-5-(piperidin-4-yl)-1H-indol-2-yl)quinoxaline (165);
- 6-(3-isopropyl-5-(piperidin-4-yl)-1H-indol-2-yl)quinoline (190);
- 2-(4-(3-isopropyl-2-(2-methylquinolin-4-yl)-1H-indol-5-yl) piperidin-1-yl)-N,N-dimethylacetamide (327);
- 2-(4-(3-isopropyl-2-(2-methylquinolin-4-yl)-1H-indol-5-yl)piperidin-1-yl)-N-methylacetamide (328);
- 2-(4-(3-isopropyl-2-(2-methoxyquinolin-4-yl)-1H-indol-5-yl) piperidin-1-yl)-N,N-dimethylacetamide (340);
- 2-(4-(2-(8-cyanoquinolin-5-yl)-3-isopropyl-1H-indol-5-yl)piperidin-1-yl)acetamide (369);
- 2-(4-(2-(8-cyanoquinolin-5-yl)-3-isopropyl-1H-indol-5-yl)piperidin-1-yl)-N,N-dimethylacetamide (370);
- 2-(4-(2-(8-cyanoquinolin-5-yl)-3-isopropyl-1H-indol-5-yl)piperidin-1-yl)-N-methylacetamide (371);
- 2-(4-(2-(8-chloroquinolin-6-yl)-3-isopropyl-1H-indol-5-yl)piperidin-1-yl)-N,N-dimethylacetamide (380);
- 2-(4-(2-(8-chloroquinolin-6-yl)-3-isopropyl-1H-indol-5-yl)piperidin-1-yl)-N-methylacetamide (381);
- 2-(4-(3-isopropyl-2-(8-methylquinoxalin-6-yl)-1H-indol-5-yl) piperidin-1-yl)-N-methylacetamide (394);
- 2-(4-(3-isopropyl-2-(8-methylquinoxalin-6-yl)-1H-indol-5-yl)piperidin-1-yl)-N,N-dimethylacetamide (395);
- 2-(4-(3-isopropyl-2-(8-methylquinolin-6-yl)-1H-indol-5-yl)piperidin-1-yl)-N,N-dimethylacetamide (435);
- 2-(4-(3-isopropyl-2-(8-methylquinolin-6-yl)-1H-indol-5-yl)piperidin-1-yl)acetamide (436);
- 2-(4-(3-isopropyl-2-(8-methylquinolin-6-yl)-1H-indol-5-yl)piperidin-1-yl)-N-methylacetamide (437);
- 5-(5-(1-(dimethylglycyl)piperidin-4-yl)-3-isopropyl-1H-indol-2-yl)quinoline-8-carbonitrile (506);
- 1-(4-(2-(8-chloroquinolin-6-yl)-3-isopropyl-1H-indol-5-yl)piperidin-1-yl)-2-(dimethylamino)ethan-1-one (512);
- 2-(dimethylamino)-1-(4-(3-isopropyl-2-(8-methylquinoxalin-6-yl)-1H-indol-5-yl) piperidin-1-yl)ethan-1-one (518);
- 2-(dimethylamino)-1-(4-(3-isopropyl-2-(8-methylquinolin-6-yl)-1H-indol-5-yl) piperidin-1-yl)ethan-1-one (529);
- 2-(dimethylamino)-1-(4-(3-isopropyl-2-(2-methylquinolin-4-yl)-1H-indol-5-yl) piperidin-1-yl)ethan-1-one (533);
- 1-(4-(3-isopropyl-2-(2-methylquinolin-4-yl)-1H-indol-5-yl)piperidin-1-yl)-2-(methylamino)ethan-1-one (534);
- 1-(4-(3-isopropyl-2-(8-methylquinolin-6-yl)-1H-indol-5-yl)piperidin-1-yl)-2-(methylamino)ethan-1-one (560);
- 4-(4-(3-isopropyl-2-(2-methylquinolin-4-yl)-1H-indol-5-yl)piperidine-1-carbonyl)-1-methylpyrrolidin-2-one (638);
- N-methyl-2-(4-(3-methyl-2-(quinoxalin-6-yl)-1H-indol-5-yl)piperidin-1-yl)ethan-1-amine (658);
- N-methyl-2-(4-(3-methyl-2-(quinolin-8-yl)-1H-indol-5-yl)piperidin-1-yl)ethan-1-amine (662);
- 2-(4-(2-(isoquinolin-4-yl)-3-methyl-1H-indol-5-yl)piperidin-1-yl)-N-methylethan-1-amine (663);
- N-methyl-2-(4-(3-methyl-2-(quinolin-3-yl)-1H-indol-5-yl) piperidin-1-yl)ethan-1-amine (664);
- 2-(4-(2-(isoquinolin-4-yl)-3-methyl-1H-indol-5-yl) piperidin-1-yl)-N-methylethan-1-amine (665);
- N-methyl-2-(4-(3-methyl-2-(quinolin-6-yl)-1H-indol-5-yl)piperidin-1-yl)ethan-1-amine (666);
- 6-(3-isopropyl-5-(1-(tetrahydro-2H-pyran-4-yl)piperidin-4-yl)-1H-indol-2-yl)-8-methylquinoline (703);
- 6-(3-isopropyl-5-(1-(tetrahydro-2H-pyran-4-yl)piperidin-4-yl)-1H-indol-2-yl)-8-methylquinoline (704);
- 5-(3-isopropyl-5-(1-(oxetan-3-yl)piperidin-4-yl)-1H-indol-2-yl)quinoline-8-carbonitrile (714);
- 6-(3-isopropyl-5-(1-(oxetan-3-yl)piperidin-4-yl)-1H-indol-2-yl)-8-methylquinoline (723);
- 4-(3-isopropyl-5-(1-(oxetan-3-yl) piperidin-4-yl)-1H-indol-2-yl)-2-methylquinoline (725);
- 1-(4-(3-isopropyl-2-(2-methylquinolin-4-yl)-1H-indol-5-yl) piperidin-1-yl)-2-methylpropan-2-ol (752);
- 5-(5-(1-(2-hydroxy-2-methylpropyl)piperidin-4-yl)-3-isopropyl-1H-indol-2-yl) quinoline-8-carbonitrile (766);
- 1-(4-(2-(8-chloroquinolin-6-yl)-3-isopropyl-1H-indol-5-yl)piperidin-1-yl)-2-methylpropan-2-ol (767);
- 1-(4-(3-isopropyl-2-(8-methylquinolin-6-yl)-1H-indol-5-yl) piperidin-1-yl)-2-methylpropan-2-ol (771);
- 5-(3-isopropyl-5-(1-(2-methoxyethyl)piperidin-4-yl)-1H-indol-2-yl)quinoline-8-carbonitrile (778);

5-(3-isopropyl-5-(1-(2-(methylsulfonyl)ethyl)piperidin-4-yl)-1H-indol-2-yl) quinoline-8-carbonitrile (796);

4-(4-(3-isopropyl-2-(8-methylquinolin-6-yl)-1H-indol-5-yl)piperidin-1-yl)tetrahydro-2H-thiopyran 1,1-dioxide (800); and 5-(3-isopropyl-5-(1-isopropylpiperidin-4-yl)-1H-indol-2-yl)quinoline-8-carbonitrile (949).

11. A pharmaceutical composition comprising a compound according to claim 1 or a pharmaceutically-acceptable salt thereof; and a pharmaceutically acceptable carrier.

12. A method of treating an autoimmune disease or a chronic inflammatory disease, comprising administering to a mammalian patient a compound according to claim or a pharmaceutically acceptable salt thereof, wherein said autoimmune disease or chronic inflammatory disease is selected from systemic lupus erythematosus (SLE), rheumatoid arthritis, multiple sclerosis (MS), and Sjögren's syndrome, and wherein said method of treating inhibits, relieves, or inhibits and relieves said autoimmune disease or a chronic inflammatory disease.

\* \* \* \* \*

UNITED STATES PATENT AND TRADEMARK OFFICE
CERTIFICATE OF CORRECTION

| | | |
|---|---|---|
| PATENT NO. | : 11,739,098 B2 | Page 1 of 1 |
| APPLICATION NO. | : 17/699944 | |
| DATED | : August 29, 2023 | |
| INVENTOR(S) | : Alaric Dyckman et al. | |

It is certified that error appears in the above-identified patent and that said Letters Patent is hereby corrected as shown below:

In the Claims

Claim 3, Column 474, Line 60, delete "—$CH_2CH_2NH(S(O)_2CH_3$," and insert -- —$CH_2CH_2NHS(O)_2CH_3$, --.

Claim 3, Column 475, Line 27, delete "—$CH_2H_3$," and insert -- —$CH_2CH_3$, --.

Claim 5, Colum 475, Line 65, delete "—$CH_2H_3$," and insert -- —$CH_2CH_3$, --.

Claim 12, Column 479, Line 13, delete "claim" and insert -- claim 1 --.

Signed and Sealed this
Thirtieth Day of September, 2025

John A. Squires
*Director of the United States Patent and Trademark Office*